United States Patent
Hodges et al.

(10) Patent No.: US 8,614,206 B2
(45) Date of Patent: *Dec. 24, 2013

(54) PYRAZOL-4-YL-HETEROCYCLYL-CARBOXAMIDE COMPOUNDS AND METHODS OF USE

(71) Applicant: Genentech, Inc., South San Francisco, CA (US)

(72) Inventors: Alastair James Hodges, Saffron Walden (GB); Mizio Matteucci, Saffron Walden (GB); Andrew Sharpe, Saffron Walden (GB); Minghua Sun, Burlingame, CA (US); Xiaojing Wang, Foster City, CA (US); Vickie H. Tsui, Burlingame, CA (US)

(73) Assignee: F. Hoffmann-La Roche AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/627,262

(22) Filed: Sep. 26, 2012

(65) Prior Publication Data

US 2013/0079321 A1    Mar. 28, 2013

Related U.S. Application Data

(60) Provisional application No. 61/539,634, filed on Sep. 27, 2011.

(51) Int. Cl.
*A61K 31/4965* (2006.01)
*A61K 31/44* (2006.01)
*A61K 31/415* (2006.01)
*A01N 43/40* (2006.01)
*A01N 43/56* (2006.01)
*C07D 401/00* (2006.01)
*C07D 403/00* (2006.01)
*C07D 403/02* (2006.01)

(52) U.S. Cl.
USPC ............ 514/210.2; 514/255.05; 514/336; 514/406; 514/407; 544/333; 544/405; 546/275.4; 548/364.1

(58) Field of Classification Search
USPC .......... 514/217.09, 403, 406, 407; 548/364.1, 548/362.1, 356.1
See application file for complete search history.

(56) References Cited

U.S. PATENT DOCUMENTS

| | | | |
|---|---|---|---|
| 8,148,411 B2 | 4/2012 | Bothe et al. | |
| 8,163,739 B2 | 4/2012 | Bothe et al. | |
| 8,436,001 B2 * | 5/2013 | Wang | 514/255.05 |
| 2009/0197866 A1 | 8/2009 | Cherrier et al. | |
| 2009/0263398 A1 | 10/2009 | Lyons et al. | |
| 2009/0318430 A1 | 12/2009 | Pike et al. | |
| 2010/0004232 A1 | 1/2010 | Berdini et al. | |
| 2010/0021420 A1 | 1/2010 | Lyons et al. | |
| 2010/0130465 A1 | 5/2010 | Shipps et al. | |
| 2010/0160324 A1 | 6/2010 | Berdini et al. | |
| 2010/0249088 A1 | 9/2010 | Sugasawa et al. | |
| 2011/0059961 A1 | 3/2011 | Wang et al. | |
| 2011/0251176 A1* | 10/2011 | Wang | 514/211.15 |

FOREIGN PATENT DOCUMENTS

| | | |
|---|---|---|
| WO | 2009/077954 A1 | 6/2006 |
| WO | 2008/090382 A1 | 7/2008 |
| WO | 2008/106692 A1 | 9/2008 |
| WO | 2009/074246 A1 | 6/2009 |
| WO | 2009/074247 A1 | 6/2009 |
| WO | 2009/093012 A1 | 7/2009 |
| WO | 2009/109576 A1 | 9/2009 |
| WO | 2011/003065 A2 | 1/2011 |
| WO | 2011/050305 A1 | 4/2011 |
| WO | 2011/089132 A1 | 7/2011 |
| WO | 2011/154327 A1 | 12/2011 |

OTHER PUBLICATIONS

Anizon et al., "Fighting tumor cell survival: advances in the design and evaluation of Pim inhibitors" Curr Med Chem. 17:4114-33 ( 2010).
Velaparthi et al., "5-tert-butyl-N-pyrazol-4-yl-4,5,6,7-tetrahydrobenzo[d]isoxazole-3-carboxamide derivatives as novel potent inhibitors of Mycobacterium tuberculosis pantothenate synthetase: initiating a quest for new antitubercular drugs" J Med Chem. 51:1999-2002 ( 2008).

* cited by examiner

*Primary Examiner* — Paul Zarek
*Assistant Examiner* — George W Kosturko
(74) *Attorney, Agent, or Firm* — Alex Andrus; Genentech, Inc.

(57) ABSTRACT

Pyrazol-4-yl-heterocyclyl-carboxamide compounds of Formula I, including stereoisomers, geometric isomers, tautomers, and pharmaceutically acceptable salts thereof, wherein X is thiazolyl, pyrazinyl, pyridinyl, or pyrimidinyl, are useful for inhibiting Pim kinase, and for treating disorders such as cancer mediated by Pim kinase. Methods of using compounds of Formula I for in vitro, in situ, and in vivo diagnosis, prevention or treatment of such disorders in mammalian cells, or associated pathological conditions, are disclosed.

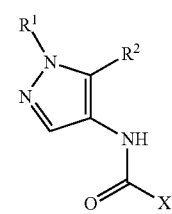

I

8 Claims, 6 Drawing Sheets

PYRAZOL-4-YL-HETEROCYCLYL-CARBOXAMIDE COMPOUNDS AND METHODS OF USE

CROSS REFERENCE TO RELATED APPLICATIONS

This non-provisional application filed under 37 CFR §1.53 (b), claims the benefit under 35 USC §119(e) of U.S. Provisional Application Ser. No. 61/539,634 filed on 27 Sep. 2011, which is incorporated by reference in entirety.

FIELD OF THE INVENTION

The invention relates generally to pyrazol-4-yl-heterocyclyl-carboxamide compounds for treating disorders mediated by Pim kinase (Pim-1, Pim-2, and/or Pim-3) inhibitors, thus useful as cancer therapeutics. The invention also relates to compositions, more specifically pharmaceutical compositions comprising these compounds and methods of using the same, either alone or in combination, to treat various forms of cancer and hyperproliferative disorders, as well as methods of using the compounds for in vitro, in situ, and in vivo diagnosis or treatment of mammalian cells, or associated pathological conditions.

BACKGROUND OF THE INVENTION

Pim kinases are family of three highly-related serine and threonine protein kinases encoded by the genes Pim-1, Pim-2, and Pim-3. The gene names are derived from the phrase Proviral Insertion, Moloney, frequent integration sites for murine moloney virus wherein the insertions lead to overexpression of Pim kinases and either de novo T-cell lymphomas, or dramatic acceleration of tumorigenesis in a transgenic Myc-driven lymphoma model (Cuypers et al. (1984) Cell, vol. 37 (1) pp. 141-50; Selten et al. (1985) EMBO J. vol. 4 (7) pp. 1793-8; van der Lugt et al. (1995) EMBO J. vol. 14 (11) pp. 2536-44; Mikkers et al. (2002) Nature Genetics, vol. 32 (1) pp. 153-9; van Lohuizen et al. (1991) Cell, vol. 65 (5) pp. 737-52). These experiments reveal synergy with the oncogene c-Myc, and suggest that inhibition of the Pim kinases may have therapeutic benefit.

Mouse genetics suggests that antagonizing Pim kinases may have an acceptable safety profile; a Pim 1−/−; Pim-2−/−, Pim-3−/− mouse knockout is viable although slightly smaller than wild type littermates (Mikkers et al. (2004) Mol Cell Biol vol. 24 (13) pp. 6104-154). The three genes give rise to six protein isoforms including a protein kinase domain, and apparently without recognizable regulatory domains. All six isoforms are constitutively active protein kinases that do not require post-translational modification for activity, thus Pim kinases are regulated primarily at the transcriptional level (Qian et al. (2005) J Biol Chem, vol. 280 (7) pp. 6130-7). Pim kinase expression is highly inducible by cytokines and growth factors receptors and Pims are direct transcriptional targets of the Stat proteins, including Stat3 and Stat5. Pim-1, for example, is required for the gp130-mediated Stat3 proliferation signal (Aksoy et al. (2007) Stem Cells, vol. 25 (12) pp. 2996-3004; Hirano et al. (2000) Oncogene vol. 19 (21) pp. 2548-56; Shirogane et al. (1999) Immunity vol. 11 (6) pp. 709-19).

Pim kinases function in cellular proliferation and survival pathways parallel to the PI3k/Akt/mTOR signaling axis (Hammerman et al. (2005) Blood vol. 105 (11) pp. 4477-83). Indeed, several of the phosphorylation targets of the PI3k axis including Bad and eIF4E-BP1 are cell growth and apoptosis regulators and are also phosphorylation targets of the Pim kinases (Fox et al. (2003) Genes Dev vol. 17 (15) pp. 1841-54; Macdonald et al. (2006) Cell Biol vol. 7 pp. 1; Aho et al. (2004) FEBS Letters vol. 571 (1-3) pp. 43-9; Tamburini et al. (2009) Blood vol. 114 (8) pp. 1618-27). Pim kinase may affect cell survival since phosphorylation of Bad increases Bcl-2 activity and therefore promotes cell survival. Likewise, phosphorylation of eIF4E-BP1 by mTOR or Pim kinases causes depression of eIF4E, promoting mRNA translation and cellular growth. In addition, Pim-1 has been recognized to promote cell cycle progression through phosphorylation of CDC25A, p21, and Cdc25C (Mochizuki et al. (1999) J Biol Chem vol. 274 (26) pp. 18659-66; Bachmann et al. (2006) Int J Biochem Cell Biol vol. 38 (3) pp. 430-43; Wang et al. (2002) Biochim Biophys Acta vol. 1593 (1) pp. 45-55.

Pim kinases show synergy in transgenic mouse models with c-Myc-driven and Akt-driven tumors (Verbeek et al. (1991) Mol Cell Biol vol. 11 (2) pp. 1176-9; Allen et al. Oncogene (1997) vol. 15 (10) pp. 1133-41; Hammerman et al. (2005) Blood vol. 105 (11) pp. 4477-83). Pim Kinases are involved in transforming activity of oncogenes identified in acute myeloid leukemia (AML) including Flt3-ITD, BCR-abl, and Tel-Jak2. Expression of these oncogenes in BaF3 cells results in upregulation of Pim-1 and Pim-2 expression, resulting in IL-3 independent growth, and subsequent Pim inhibition results in apoptosis and cell growth arrest (Adam et al. (2006) Cancer Research 66 (7):3828-35). Pim overexpression and dysregulation has also been noted as a frequent event in many hematopoietic cancers, including leukemias and lymphoma (Amson et al. (1989) Proc Natl Acad Sci USA 86 (22):8857-61); Cohen et al. (2004) Leuk Lymphoma 45 (5): 951-5; Hüttmann et al. (2006) Leukemia 20 (10):1774-82) as well as multiple myeloma (Claudio et al. (2002) Blood 100 (6):2175-86. Pim 1 has been shown to be overexpressed and correlated to prostate cancer progression (Cibull et al. (2006) J Clin Pathol 59 (3):285-8; Dhanasekaran et al. (2001) Nature vol. 412 (6849):822-6). Pim 1 expression increases in mouse models with disease progression (Kim et al. (2002) Proc Natl Acad Sci USA 99 (5):2884-9). Pim-1 has been reported to be the most highly overexpressed mRNA in the subset of human prostate tumor samples which have a c-Myc-driven gene signature (Ellwood-Yen et al. (2003) Cancer Cell 4(3):223-38). Pim-3 has been also been shown to be overexpressed and to have a functional role in pancreatic cancer and hepatocellular carcinoma (Li et al. (2006) Cancer Research 66 (13): 6741-7; Fujii et al. (2005) Int J Cancer 114 (2):209-18.

Beyond oncology therapeutic and diagnostic applications, Pim kinases could play an important role in normal immune system function and Pim inhibition could be therapeutic for a number of different immunologic pathologies including tumorigensis (Nawijn et al (2011) Nature Rev. 11:23-34), inflammation, autoimmune conditions, allergy, and immune suppression for organ transplantation (Aho et al. (2005) Immunology 116 (1):82-8).

SUMMARY OF THE INVENTION

The invention relates to pyrazol-4-yl-heterocyclyl-carboxamide compounds for treating disorders mediated by Pim kinase (Pim-1, Pim-2, and/or Pim-3) inhibitors Formula I compounds.

I

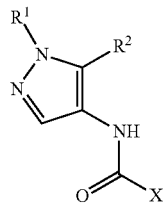

where R² is selected from the structures:

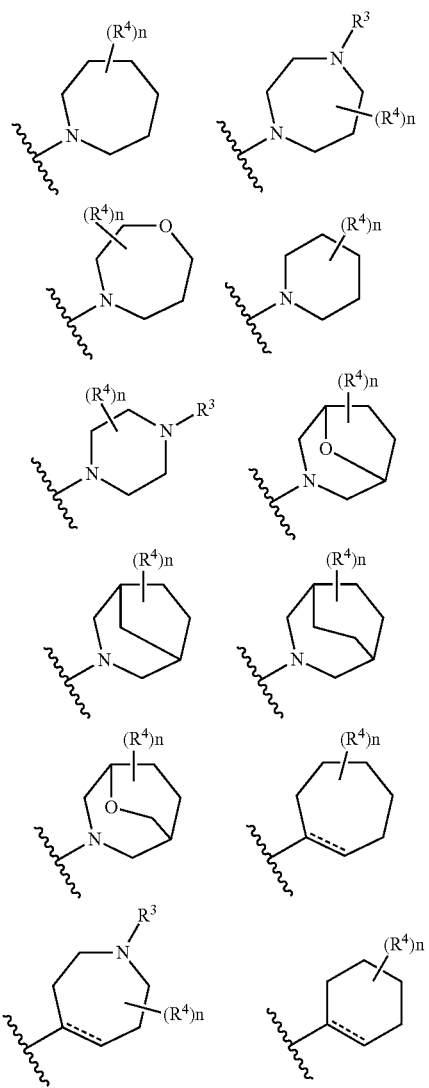

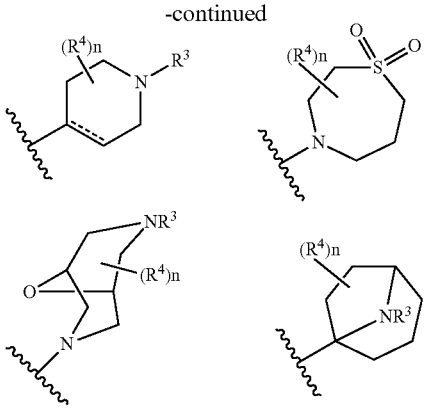

where the wavy line indicates the site of attachment and the dashed line indicates an optional double bond;

X is selected from the structures:

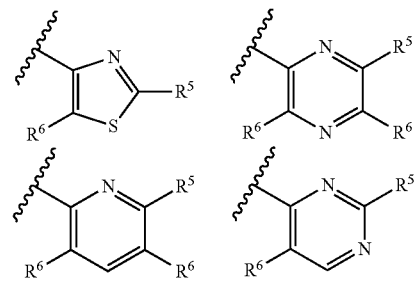

and stereoisomers, geometric isomers, tautomers, and pharmaceutically acceptable salts thereof. The various substituents, including $R^1$, $R^2$, $R^3$, $R^4$, $R^5$, $R^6$, $R^7$, and X are as defined herein.

One aspect of the invention is a pharmaceutical composition comprised of a Formula I compound and a pharmaceutically acceptable carrier, glidant, diluent, or excipient. The pharmaceutical composition may further comprise a chemotherapeutic agent.

The invention includes a method of treating a disease or disorder which method comprises administering a therapeutically effective amount of a Formula I compound to a patient with a disease or disorder selected from cancer, immune disorders, cardiovascular disease, viral infection, inflammation, metabolism/endocrine function disorders and neurological disorders, and mediated by Pim kinase. The method includes further administering an additional therapeutic agent selected from a chemotherapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, and an agent for treating immunodeficiency disorders.

The invention includes use of a Formula I compound in the manufacture of a medicament for the treatment of cancer, immune disorders, cardiovascular disease, viral infection, inflammation, metabolism/endocrine function disorders and neurological disorders, wherein the medicament mediates Pim kinase.

The invention includes a kit for treating a condition mediated by Pim kinase, comprising: a) a first pharmaceutical composition comprising a Formula I compound; and b) instructions for use.

The invention includes a Formula I compound for use as a medicament, and for use in treating a disease or disorder selected from cancer, immune disorders, cardiovascular disease, viral infection, inflammation, metabolism/endocrine function disorders and neurological disorders, and mediated by Pim kinase.

The invention includes methods of making a Formula I compound.

DETAILED DESCRIPTION OF EXEMPLARY EMBODIMENTS

Figure 1:
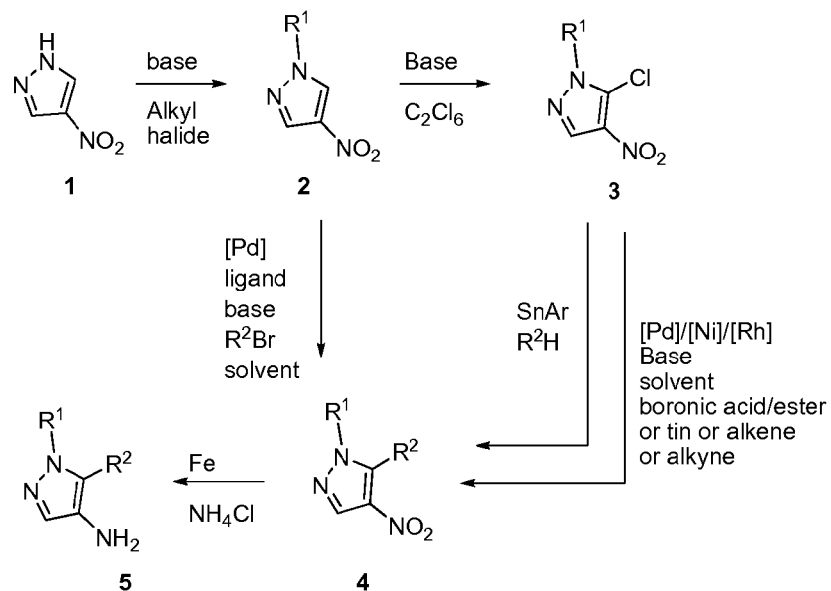
FIG. 1 shows an exemplary synthesis of 4-aminopyrazole compounds 5 from nitro-1H-pyrazole 1.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. The nomenclature used in this application is based on IUPAC systematic nomenclature, unless indicated otherwise.

Definitions

When indicating the number of substituents, the term "one or more" refers to the range from one substituent to the highest possible number of substitution, i.e. replacement of one hydrogen up to replacement of all hydrogens by substituents. The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—CH$_2$—), ethylene (—CH$_2$CH$_2$—), propylene (—CH$_2$CH$_2$CH$_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, $sp^2$ double bond, wherein the alkenylene radical may be optionally substituted substituted independently with one or more substituents described herein, and includes radicals having "cis" and "trans" orientations, or alternatively, "E" and "Z" orientations. Examples include, but are not limited to, ethylenylene or vinylene (—CH=CH—), allyl (—$CH_2$CH=CH—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The term "alkynylene" refers to a linear or branched divalent hydrocarbon radical of two to eight carbon atoms ($C_2$-$C_8$) with at least one site of unsaturation, i.e., a carbon-carbon, sp triple bond, wherein the alkynylene radical may be optionally substituted independently with one or more substituents described herein. Examples include, but are not limited to, ethynylene (—C≡C—), propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Spiro moieties are also included within the scope of this definition. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (MEK inhibitor, Exelixis, WO 2007/044515), ARRY-886 (MEK inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), a rapamycin analog, mTOR inhibitor such as everolimus, a MEK inhibitor (GDC-0973), a Bcl-2 inhibitor such as navitoclax, (ABT-263) or ABT-199), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma 1I, calicheamicin omegaI1 (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (CAMPATH®), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), and tositumomab (BEXXAR®, Corixa, GlaxoSmithKline).

Humanized monoclonal antibodies with therapeutic potential as chemotherapeutic agents in combination with the Formula I compounds of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lebrikizumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a Formula I compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative, and depicted in Table 1 structures for illustrative purposes, while stereochemical determination awaits, such as x-ray crystallographic data.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "pharmaceutically acceptable salts" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid "mesylate", ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The term "$EC_{50}$" is the half maximal effective concentration" and denotes the plasma concentration of a particular compound required for obtaining 50% of the maximum of a particular effect in vivo.

The term "Ki" is the inhibition constant and denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "$IC_{50}$" is the half maximal inhibitory concentration and denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed, and can be converted to an absolute inhibition constant (Ki) using the Cheng-Prusoff equation (Biochem. Pharmacol. (1973) 22:3099).

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

Pyrazol-4-Yl-Heterocyclyl-Carboxamide Compounds

The present invention provides pyrazol-4-yl-heterocyclyl-carboxamide compounds of Formula I, including Formulas Ia-i, and pharmaceutical formulations thereof, which are potentially useful in the treatment of diseases, conditions and/or disorders modulated by Pim kinases.

Formula I compounds have the structure:

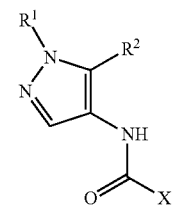

I and stereoisomers, geometric isomers, tautomers, or pharmaceutically acceptable salts thereof, wherein:

$R^1$ is selected from H, $C_1$-$C_{12}$ alkyl, $C_2$-$C_{12}$ alkenyl, $C_2$-$C_{12}$ alkynyl, $C_6$-$C_{20}$ aryl, $C_3$-$C_{12}$ carbocyclyl, $C_2$-$C_{20}$ heterocyclyl, $C_1$-$C_{20}$ heteroaryl, and —($C_1$-$C_{12}$ alkylene)-($C_2$-$C_{20}$ heterocyclyl);

$R^2$ is selected from the structures:

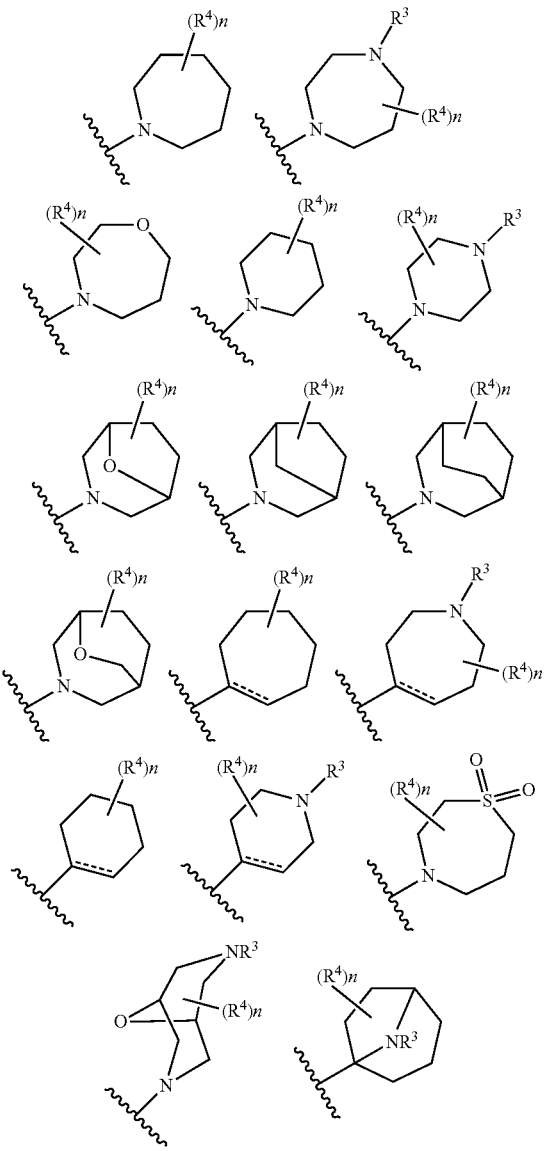

where the wavy line indicates the site of attachment and the dashed line indicates an optional double bond;

$R^3$ is selected from H, —$CH_3$, —$CH_2CH_3$, —$CH(CH_3)_2$, —$CH_2CH(CH_3)_2$, —$CH_2NH_2$, —$CH_2NHCH_3$, —$CH_2CH_2NH_2$, —$CH_2CHCH_2NH_2$, —$CH_2CH(CH_3)NH_2$, —$CH_2OH$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —CN, —$CF_3$, —$CO_2H$, —$COCH_3$, —$CO_2CH_3$, —$CO_2C(CH_3)_3$, —$COCH(OH)CH_3$, —$COCH_2NH_2$, —$CONH_2$, —$CONHCH_3$, —$CON(CH_3)_2$, —$C(CH_3)_2CONH_2$, —$S(O)_2N(CH_3)_2$, —$SCH_3$, —$CH_2OCH_3$, —$S(O)_2CH_3$, cyclopropyl, cyclobutyl, cyclopentyl, cyclohexyl, and cycloheptyl;

$R^4$ is independently selected from F, Cl, Br, I, —$CH_3$, —$CH_2CH_3$, —$CH(CH_3)_2$, —$C(CH_3)_3$, —$CH_2CH(CH_3)_2$, —CH=$CH_2$, —CH=$C(CH_3)_2$, =$CH_2$, —$CH_2F$, —$CHF_2$, —$CF_3$, —$CH_2OH$, —$CH_2OCH_3$, —$CH_2NH_2$, —$CH_2NHCH_3$, —$CH_2CH_2NH_2$, —$CH_2CHCH_2NH_2$, —$CH_2CH(CH_3)NH_2$, —$CH_2OH$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —CN, —$CO_2H$, —$COCH_3$, —$COCH_2NH_2$, —$CO_2CH_3$, —$CO_2C(CH_3)_3$, —$COCH(OH)CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCH_2CHF_2$, —$NHCH_2CF_3$, —$NHCOCH_3$, —$NHCH_2CH_2OH$, —$N(CH_3)COCH_3$, —$NHC(O)OCH_2CH_3$, —$NHC(O)OCH_2Cl_3$, —$NHC(O)OC_6H_5$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$OCHF_2$, —$OCH_2F$, —$OCH_2CH_3$, —$OCH(CH_3)_2$, —$OCH_2CH(CH_3)_2$, —$OC(CH_3)_3$, —$S(O)_2N(CH_3)_2$, —$SCH_3$, —$CH_2OCH_3$, —$S(O)_2CH_3$, cyclopropyl, cyclobutyl, cyclopentyl, cyclohexyl, cycloheptyl, azetidinyl, azepanyl, oxetanyl, oxetan-3-ylmethylamino, (3-methyloxetan-3-yl)methylamino, pyrrolidinyl, piperazinyl, piperidinyl, (piperidin-4-yl)ethyl, pyranyl, (piperidin-4-ylmethyl), morpholinomethyl, and morpholino;

or where two geminal $R^4$ groups form a spiro ring selected from a cyclopropyl, cyclobutyl, cyclopentyl, cyclohexyl, pyrrolidinyl, azetidinyl, azepanyl, oxetanyl, pyrrolidinyl, piperazinyl, or piperidinyl ring, where the spiro ring is optionally substituted with one or more groups independently selected from —F, —OH, =O, —$CH_3$, —$NH_2$, —$CH_2F$, —$CH_2OH$, —$CH_2OCH_3$, —$CH_2NH_2$, and —$CF_3$;

or where two vicinal $R^4$ groups or an $R^4$ group and an $R^3$ group form a five-membered or six-membered heterocyclyl fused ring, where the heterocyclyl fused ring is optionally substituted with one or more groups independently selected from —F, —OH, =O, —$CH_3$, —$NH_2$, —$CH_2F$, —$CH_2OH$, —$CH_2OCH_3$, —$CH_2NH_2$, and —$CF_3$;

n is 0, 1, 2, or 3;

X is selected from the structures:

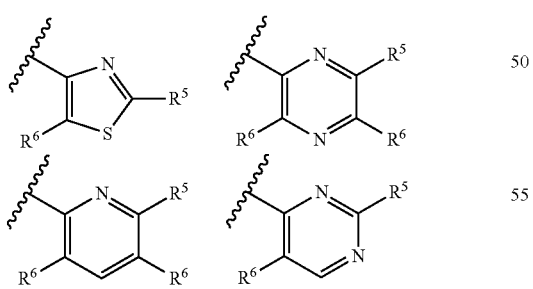

where the wavy line indicates the site of attachment;

$R^5$ is selected from H, Cl, Br, $C_1$-$C_{12}$ alkyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_2$-$C_8$ alkenylene)-($C_3$-$C_{12}$ carbocyclyl), —($C_2$-$C_8$ alkenylene)-($C_2$-$C_{20}$ heterocyclyl), $C_6$-$C_{20}$ aryl, —($C_6$-$C_{20}$ arylene)-($C_2$-$C_{20}$ heterocyclyl), —($C_6$-$C_{20}$ arylene)-($C_1$-$C_{12}$ alkylene)-($C_2$-$C_{20}$ heterocyclyl), $C_3$-$C_{12}$ carbocyclyl, $C_2$-$C_{20}$ heterocyclyl, and $C_1$-$C_{20}$ heteroaryl;

where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2CH_3$, —$CH(CH_3)_2$, —$CH_2CH(CH_3)_2$, —$CH_2NH_2$, —$CH_2CH_2NH_2$, —$CH_2CHCH_2NH_2$, —$CH_2CH(CH_3)NH_2$, —$CH_2OH$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —CN, —$CF_3$, —$CO_2H$, —$COCH_3$, —$CO_2CH_3$, —$CO_2C(CH_3)_3$, —$COCH(OH)CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)$ $CH_2CH_2S(O)_2CH_3$, =O, —OH, —$OCH_3$, —$S(O)_2N(CH_3)_2$, —$SCH_3$, —$CH_2OCH_3$, —$S(O)_2CH_3$, cyclopropyl, cyclobutyl, cyclopentyl, cyclohexyl, cycloheptyl, azetidinyl, azepanyl, oxetanyl, pyrrolidinyl, piperazinyl, piperidinyl, (piperidin-4-yl)ethyl, pyranyl, (piperidin-4-ylmethyl), morpholinomethyl, and morpholino; and $R^6$ is independently H or —$NH_2$.

Exemplary embodiments of Formula I compounds include wherein $R^1$ is H, $C_1$-$C_{12}$ alkyl including —$CH_3$, —$CH_2CH_3$, —$CH_2CHF_2$, and —$CH_2CF_3$, $C_3$-$C_{12}$ carbocyclyl, or —($C_1$-$C_{12}$ alkylene)-($C_2$-$C_{20}$ heterocyclyl) including oxetan-3-ylmethyl.

Exemplary embodiments of Formula I compounds include wherein $R^4$ is independently selected from F, Cl, —OH, —$CH_3$, —$CH_2CH_3$, —$CF_3$, —$NH_2$, —$NHCH_3$, —$N(CH_3)_2$, —$NHCH_2CHF_2$, —$NHCH_2CF_3$, —$CH_2NHCH_3$, and —$OCH_3$; and n is 1, 2, or 3.

Exemplary embodiments of Formula I compounds include wherein $R^5$ is $C_6$-$C_{20}$ aryl including phenyl substituted with one or more F.

Exemplary embodiments of Formula I compounds include wherein $R^6$ is —$NH_2$.

Exemplary embodiments of Formula I compounds include the structures of Formula Ia-i:

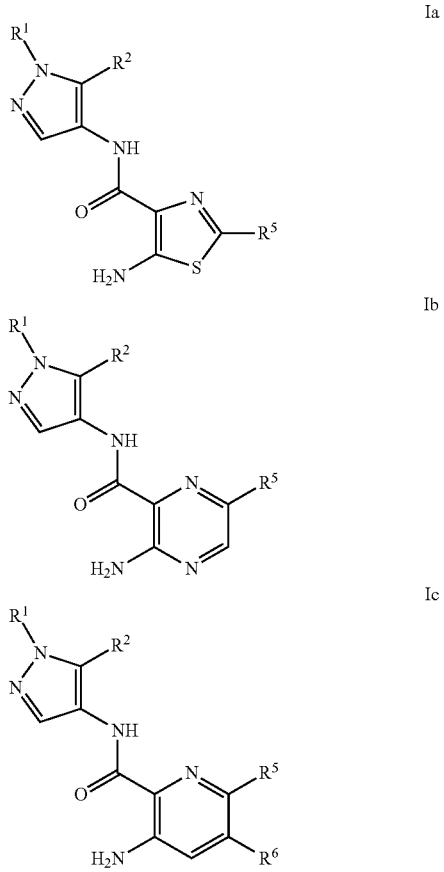

-continued

Id

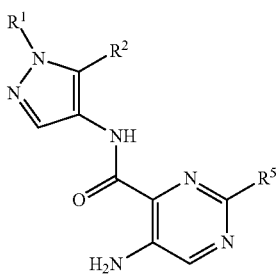

Ie

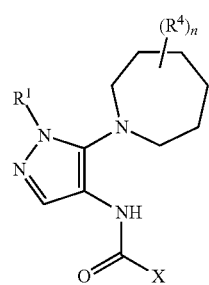

If

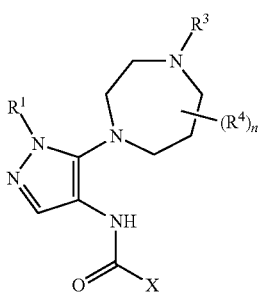

Ig

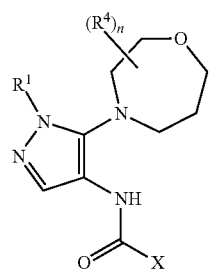

-continued

Ih

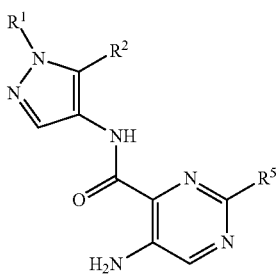

Ii

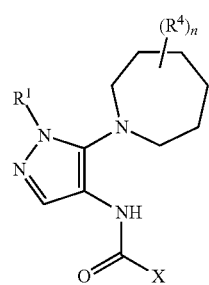

Biological Evaluation

Determination of the Pim kinase activity of a Formula I compound is possible by a number of direct and indirect detection methods. Certain exemplary compounds described herein were assayed for their Pim kinase binding activity, including isoforms Pim-1, Pim-2, and Pim-3, (Example 901) and in vitro activity against tumor cells (Example 902). Certain exemplary compounds of the invention had Pim binding activity $IC_{50}$ values less than about 1 micromolar (µM). Certain compounds of the invention had tumor cell-based activity $EC_{50}$ values less than about 1 micromolar (µM). Formula I compounds having $Ki/IC_{50}/EC_{50}$ of less than 1 µM in assays described in Examples 901 and 902, may be useful therapeutically as Pim kinase inhibitors (Pim-1, Pim-2 and/or Pim-3).

Exemplary Formula I compounds in Tables 1a and 1b were made, characterized, and tested for inhibition of Pim kinase according to the methods of this invention, and have the following structures and corresponding names (ChemBioDraw Ultra, Version 11.0, CambridgeSoft Corp., Cambridge Mass.). Some compounds with chiral atoms in Tables 1a and 1b have not been fully characterized as to stereochemistry. A tentative assignment of stereochemistry or stereochemical relationship to other groups may be depicted in the structures. Means of separation of stereoisomers and characterization data are given in the Examples.

TABLE 1a

| No. | Structure | IUPAC Name | PIM1 LC3K (KI) uM |
|---|---|---|---|
| 101 | 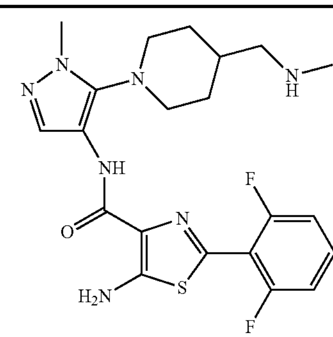 | 5-amino-2-(2,6-difluorophenyl)-N-(1-methyl-5-(4-((methylamino)methyl)piperidin-1-yl)-1H-pyrazol-4-yl)thiazole-4-carboxamide | 0.000048 |

TABLE 1a-continued

| No. | Structure | IUPAC Name | PIM1 LC3K (KI) uM |
|---|---|---|---|
| 102 | 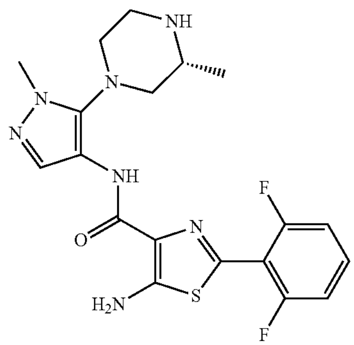 [SMILES: C[C@@H]1CN(c2c(NC(=O)c3nc(-c4c(F)cccc4F)sc3N)cnn2C)CCN1] | (R)-5-amino-2-(2,6-difluorophenyl)-N-(1-methyl-5-(3-methylpiperazin-1-yl)-1H-pyrazol-4-yl)thiazole-4-carboxamide | 0.000958 |
| 103 | 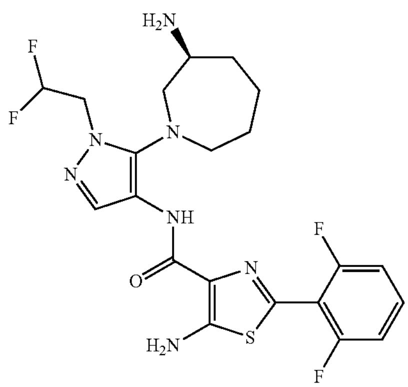 [SMILES: Nc1sc(-c2c(F)cccc2F)nc1C(=O)Nc1cnn(CC(F)F)c1N1CCCC[C@H](N)C1] | (S)-5-amino-N-(5-(3-aminoazepan-1-yl)-1-(2,2-difluoroethyl)-1H-pyrazol-4-yl)-2-(2,6-difluorophenyl)thiazole-4-carboxamide | 0.000083 |
| 104 | 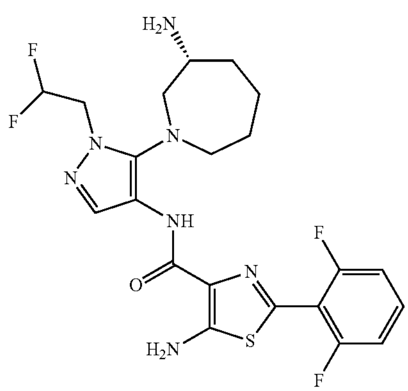 [SMILES: Nc1sc(-c2c(F)cccc2F)nc1C(=O)Nc1cnn(CC(F)F)c1N1CCCC[C@@H](N)C1] | (R)-5-amino-N-(5-(3-aminoazepan-1-yl)-1-(2,2-difluoroethyl)-1H-pyrazol-4-yl)-2-(2,6-difluorophenyl)thiazole-4-carboxamide | 0.000091 |
| 105 | 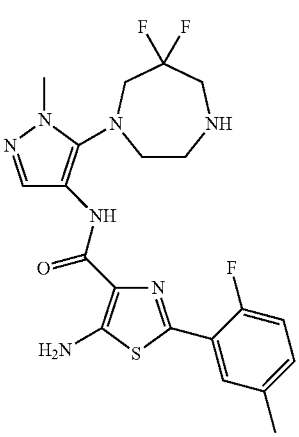 [SMILES: Cc1ccc(F)c(-c2nc(C(=O)Nc3cnn(C)c3N3CCNCC(F)(F)C3)c(N)s2)c1] | 5-amino-N-(5-(6,6-difluoro-1,4-diazepan-1-yl)-1-methyl-1H-pyrazol-4-yl)-2-(2-fluoro-5-methylphenyl)thiazole-4-carboxamide | 0.000019 |

TABLE 1a-continued
| No. | Structure | IUPAC Name | PIM1 LC3K (KI) uM |
|---|---|---|---|
| 106 | 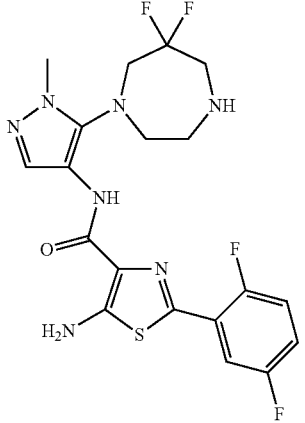 [SMILES: Cn1ncc(NC(=O)c2nc(-c3cc(F)ccc3F)sc2N)c1N1CCNCC(F)(F)C1] | 5-amino-N-(5-(6,6-difluoro-1,4-diazepan-1-yl)-1-methyl-1H-pyrazol-4-yl)-2-(2,5-difluorophenyl)thiazole-4-carboxamide | 0.000030 |
| 107 | 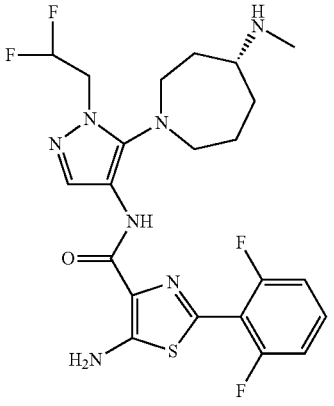 [SMILES: CN[C@@H]1CCCN(c2c(NC(=O)c3nc(-c4c(F)cccc4F)sc3N)cnn2CC(F)F)CC1] | (R)-5-amino-N-(1-(2,2-difluoroethyl)-5-(4-(methylamino)azepan-1-yl)-1H-pyrazol-4-yl)-2-(2,6-difluorophenyl)thiazole-4-carboxamide | 0.000079 |
| 108 | 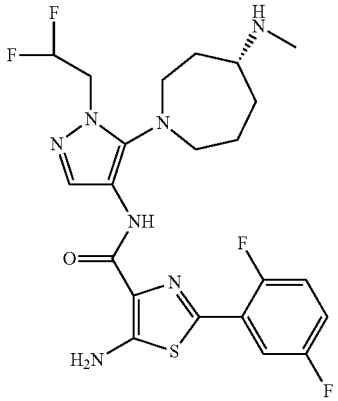 [SMILES: CN[C@@H]1CCCN(c2c(NC(=O)c3nc(-c4cc(F)ccc4F)sc3N)cnn2CC(F)F)CC1] | (R)-5-amino-N-(1-(2,2-difluoroethyl)-5-(4-(methylamino)azepan-1-yl)-1H-pyrazol-4-yl)-2-(2,5-difluorophenyl)thiazole-4-carboxamide | 0.00043 |

TABLE 1a-continued

| No. | Structure | IUPAC Name | PIM1 LC3K (KI) uM |
|-----|-----------|------------|-------------------|
| 109 | 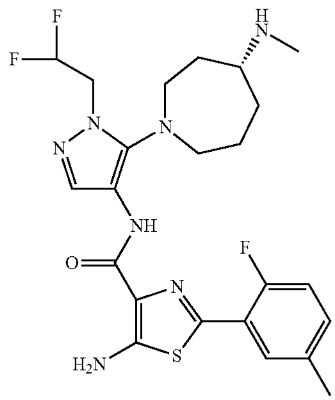 [SMILES: CN[C@@H]1CCCN(c2c(NC(=O)c3nc(-c4cc(C)ccc4F)sc3N)cnn2CC(F)F)CC1] | (R)-5-amino-N-(1-(2,2-difluoroethyl)-5-(4-(methylamino)azepan-1-yl)-1H-pyrazol-4-yl)-2-(2-fluoro-5-methylphenyl)thiazole-4-carboxamide | 0.000097 |
| 110 | 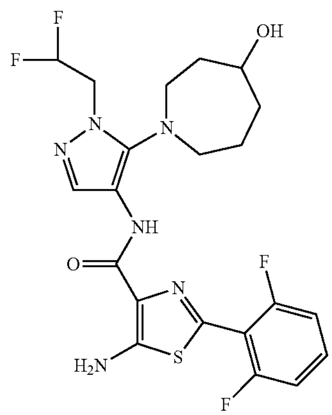 [SMILES: Nc1sc(-c2c(F)cccc2F)nc1C(=O)Nc1cnn(CC(F)F)c1N1CCCC(O)CC1] | 5-amino-N-(1-(2,2-difluoroethyl)-5-(4-hydroxyazepan-1-yl)-1H-pyrazol-4-yl)-2-(2,6-difluorophenyl)thiazole-4-carboxamide | 0.000166 |
| 111 | 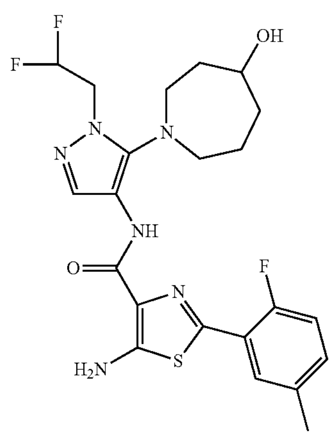 [SMILES: Cc1ccc(F)c(-c2nc(C(=O)Nc3cnn(CC(F)F)c3N3CCCC(O)CC3)c(N)s2)c1] | 5-amino-N-(1-(2,2-difluoroethyl)-5-(4-hydroxyazepan-1-yl)-1H-pyrazol-4-yl)-2-(2-fluoro-5-methylphenyl)thiazole-4-carboxamide | 0.000079 |
| 112 | 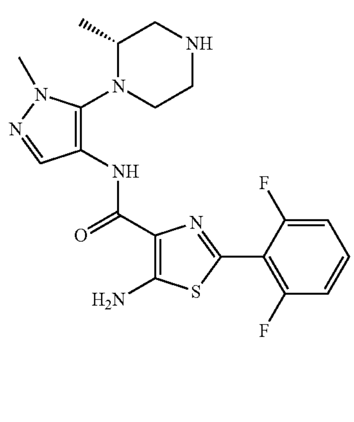 [SMILES: C[C@@H]1CNCCN1c1c(NC(=O)c2nc(-c3c(F)cccc3F)sc2N)cnn1C] | (R)-5-amino-2-(2,6-difluorophenyl)-N-(1-methyl-5-(2-methylpiperazin-1-yl)-1H-pyrazol-4-yl)thiazole-4-carboxamide | 0.00114 |

TABLE 1a-continued

| No. | Structure | IUPAC Name | PIM1 LC3K (KI) uM |
|---|---|---|---|
| 113 | 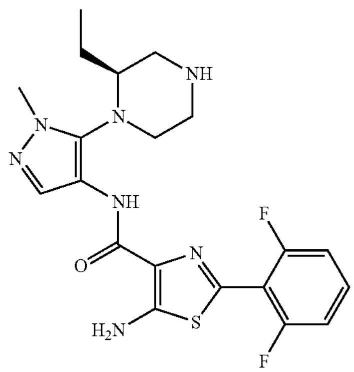 [SMILES: CC[C@H]1CNCCN1c1c(NC(=O)c2nc(-c3c(F)cccc3F)sc2N)cnn1C] | (S)-5-amino-2-(2,6-difluorophenyl)-N-(5-(2-ethylpiperazin-1-yl)-1-methyl-1H-pyrazol-4-yl)thiazole-4-carboxamide | 0.000066 |
| 114 | 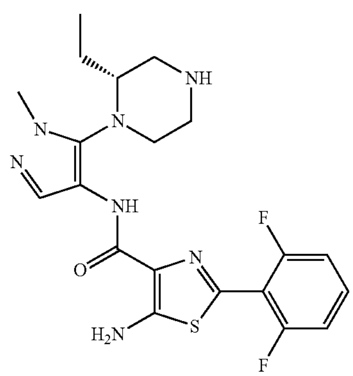 [SMILES: CC[C@@H]1CNCCN1/C(NC)=C(/C=N)NC(=O)c1nc(-c2c(F)cccc2F)sc1N] | (R)-5-amino-2-(2,6-difluorophenyl)-N-(5-(2-ethylpiperazin-1-yl)-1-methyl-1H-pyrazol-4-yl)thiazole-4-carboxamide | 0.000476 |
| 115 | 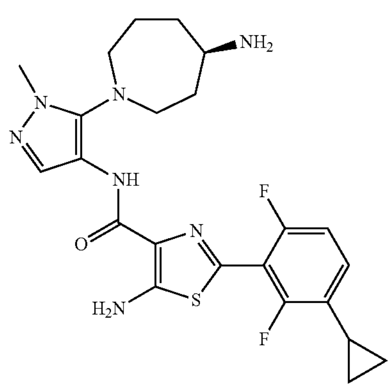 [SMILES: Cn1ncc(NC(=O)c2nc(-c3c(F)ccc(C4CC4)c3F)sc2N)c1N1CCC[C@@H](N)CC1] | (R)-5-amino-N-(5-(4-aminoazepan-1-yl)-1-methyl-1H-pyrazol-4-yl)-2-(3-cyclopropyl-2,6-difluorophenyl)thiazole-4-carboxamide | 0.000015 |
| 116 | 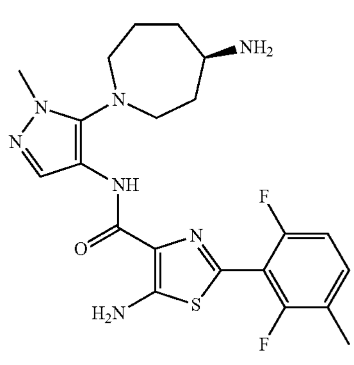 [SMILES: Cc1ccc(F)c(-c2nc(C(=O)Nc3cnn(C)c3N3CCC[C@@H](N)CC3)c(N)s2)c1F] | (R)-5-amino-N-(5-(4-aminoazepan-1-yl)-1-methyl-1H-pyrazol-4-yl)-2-(2,6-difluoro-3-methylphenyl)thiazole-4-carboxamide | 0.000010 |

TABLE 1a-continued

| No. | Structure | IUPAC Name | PIM1 LC3K (KI) uM |
|-----|-----------|------------|-------------------|
| 117 | HCO2H | (S)-5-Amino-2-(2,6-difluorophenyl)-N-(1-methyl-5-(3-methylpiperazin-1-yl)-1H-pyrazol-4-yl)thiazole-4-carboxamide | 0.000876 |
| 118 | 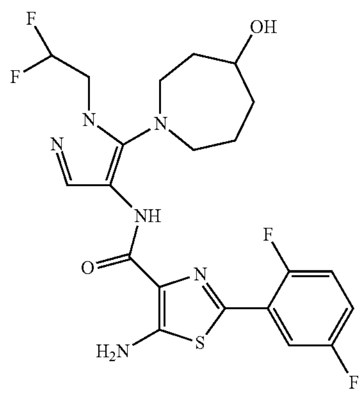 | 5-amino-N-(1-(2,2-difluoroethyl)-5-(4-hydroxyazepan-1-yl)-1H-pyrazol-4-yl)-2-(2,5-difluorophenyl)thiazole-4-carboxamide | 0.000292 |
| 119 | 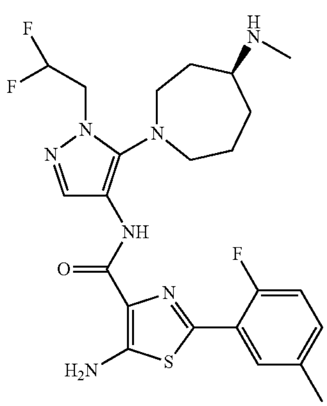 | (S)-5-amino-N-(1-(2,2-difluoroethyl)-5-(4-(methylamino)azepan-1-yl)-1H-pyrazol-4-yl)-2-(2-fluoro-5-methylphenyl)thiazole-4-carboxamide | 0.000044 |
| 120 | 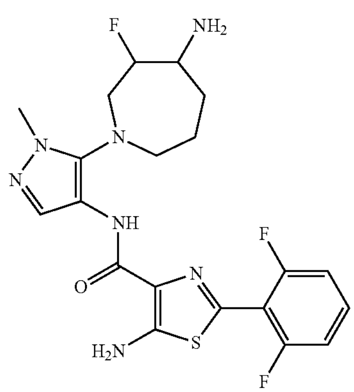 | 5-amino-N-(5-(4-amino-3-fluoroazepan-1-yl)-1-methyl-1H-pyrazol-4-yl)-2-(2,6-difluorophenyl)thiazole-4-carboxamide | 0.00030 |

TABLE 1a-continued

| No. | Structure | IUPAC Name | PIM1 LC3K (KI) uM |
|---|---|---|---|
| 121 | 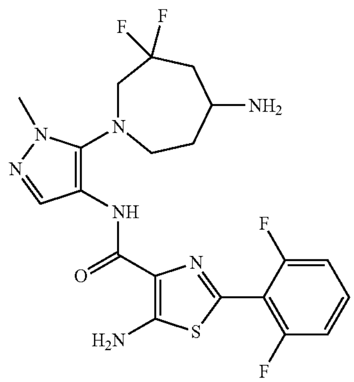 [SMILES: Cn1ncc(NC(=O)c2nc(-c3c(F)cccc3F)sc2N)c1N1CCC(N)CC(F)(F)C1] | 5-amino-N-(5-(5-amino-3,3-difluoroazepan-1-yl)-1-methyl-1H-pyrazol-4-yl)-2-(2,6-difluorophenyl)thiazole-4-carboxamide | 0.000004 |
| 122 | 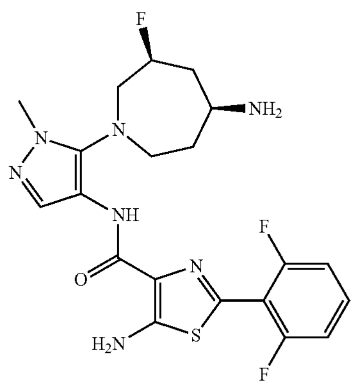 [SMILES: Cn1ncc(NC(=O)c2nc(-c3c(F)cccc3F)sc2N)c1N1CC[C@H](N)C[C@H](F)C1] | 5-amino-N-(5-((3S,5S)-5-amino-3-fluoroazepan-1-yl)-1-methyl-1H-pyrazol-4-yl)-2-(2,6-difluorophenyl)thiazole-4-carboxamide | 0.000158 |
| 123 | 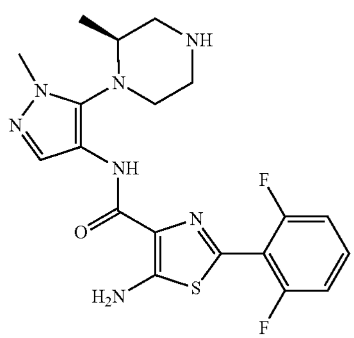 [SMILES: C[C@H]1CNCCN1c1c(NC(=O)c2nc(-c3c(F)cccc3F)sc2N)cnn1C] | (S)-5-amino-2-(2,6-difluorophenyl)-N-(1-methyl-5-(2-methylpiperazin-1-yl)-1H-pyrazol-4-yl)thiazole-4-carboxamide | 0.000158 |
| 124 | 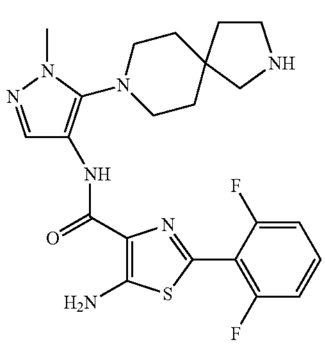 [SMILES: Cn1ncc(NC(=O)c2nc(-c3c(F)cccc3F)sc2N)c1N1CCC2(CCNC2)CC1] | 5-amino-2-(2,6-difluorophenyl)-N-(1-methyl-5-(2,8-diazaspiro[4.5]decan-8-yl)-1H-pyrazol-4-yl)thiazole-4-carboxamide | 0.000056 |

TABLE 1a-continued

| No. | Structure | IUPAC Name | PIM1 LC3K (KI) uM |
|---|---|---|---|
| 125 | 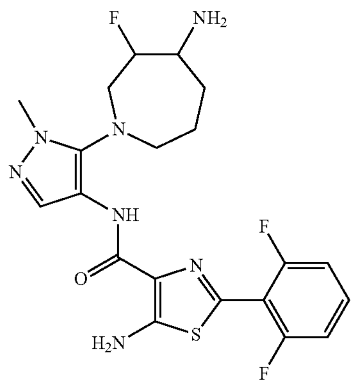 [SMILES: Cn1ncc(NC(=O)c2nc(-c3c(F)cccc3F)sc2N)c1N1CCCC(N)C(F)C1] | 5-amino-N-(5-(4-amino-3-fluoroazepan-1-yl)-1-methyl-1H-pyrazol-4-yl)-2-(2,6-difluorophenyl)thiazole-4-carboxamide | 0.000056 |
| 126 | 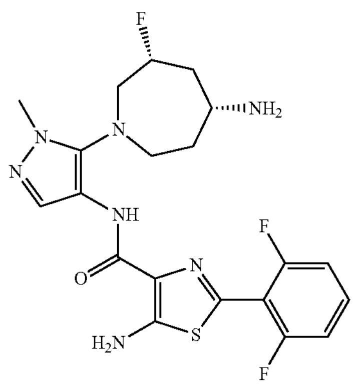 [SMILES: Cn1ncc(NC(=O)c2nc(-c3c(F)cccc3F)sc2N)c1N1CC[C@@H](N)C[C@@H](F)C1] | 5-amino-N-(5-((3R,5R)-5-amino-3-fluoroazepan-1-yl)-1-methyl-1H-pyrazol-4-yl)-2-(2,6-difluorophenyl)thiazole-4-carboxamide | |
| 127 | 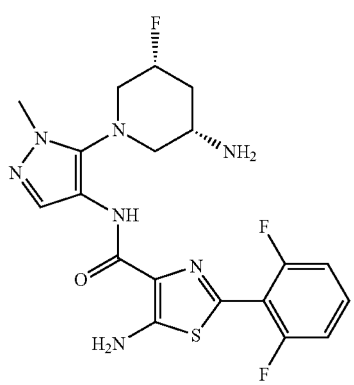 [SMILES: Cn1ncc(NC(=O)c2nc(-c3c(F)cccc3F)sc2N)c1N1C[C@@H](N)C[C@@H](F)C1] | 5-amino-N-(5-((3S,5R)-3-amino-5-fluoropiperidin-1-yl)-1-methyl-1H-pyrazol-4-yl)-2-(2,6-difluorophenyl)thiazole-4-carboxamide | |
| 128 | 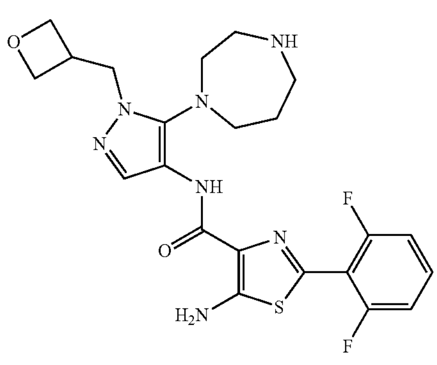 [SMILES: Nc1sc(-c2c(F)cccc2F)nc1C(=O)Nc1cnn(CC2COC2)c1N1CCCNCC1] | N-(5-(1,4-diazepan-1-yl)-1-(oxetan-3-ylmethyl)-1H-pyrazol-4-yl)-5-amino-2-(2,6-difluorophenyl)thiazole-4-carboxamide | |

TABLE 1a-continued

| No. | Structure | IUPAC Name | PIM1 LC3K (KI) uM |
|---|---|---|---|
| 129 | 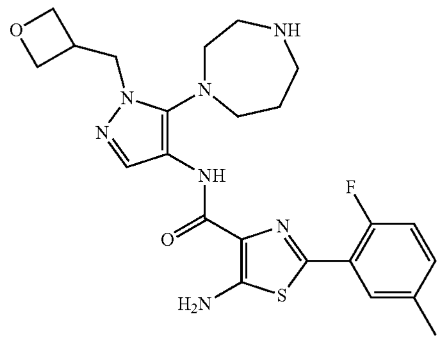 [SMILES: Cc1ccc(F)c(-c2nc(C(=O)Nc3cnn(CC4COC4)c3N3CCCNCC3)c(N)s2)c1] | N-(5-(1,4-diazepan-1-yl)-1-(oxetan-3-ylmethyl)-1H-pyrazol-4-yl)-5-amino-2-(2-fluoro-5-methylphenyl)thiazole-4-carboxamide | |
| 130 | 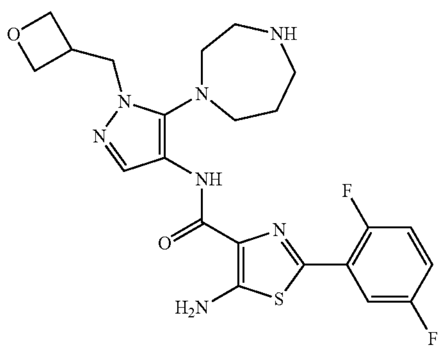 [SMILES: Nc1sc(-c2cc(F)ccc2F)nc1C(=O)Nc1cnn(CC2COC2)c1N1CCCNCC1] | N-(5-(1,4-diazepan-1-yl)-1-(oxetan-3-ylmethyl)-1H-pyrazol-4-yl)-5-amino-2-(2,5-difluorophenyl)thiazole-4-carboxamide | |
| 131 | 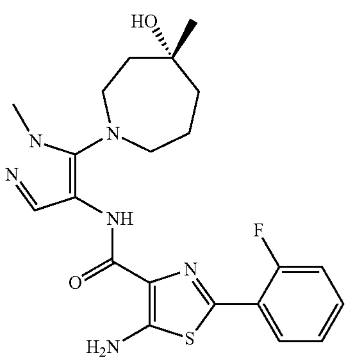 [SMILES: CN/C(=C(\C=N)NC(=O)c1nc(-c2ccccc2F)sc1N)N1CCC[C@@](C)(O)CC1] | (R)-5-amino-2-(2-fluorophenyl)-N-(5-(4-hydroxy-4-methylazepan-1-yl)-1-methyl-1H-pyrazol-4-yl)thiazole-4-carboxamide | |
| 132 | 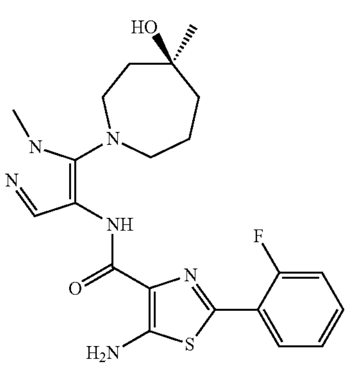 [SMILES: CN/C(=C(\C=N)NC(=O)c1nc(-c2ccccc2F)sc1N)N1CCC[C@](C)(O)CC1] | (S)-5-amino-2-(2-fluorophenyl)-N-(5-(4-hydroxy-4-methylazepan-1-yl)-1-methyl-1H-pyrazol-4-yl)thiazole-4-carboxamide | |

TABLE 1a-continued

| No. | Structure | IUPAC Name | PIM1 LC3K (KI) uM |
|---|---|---|---|
| 133 | 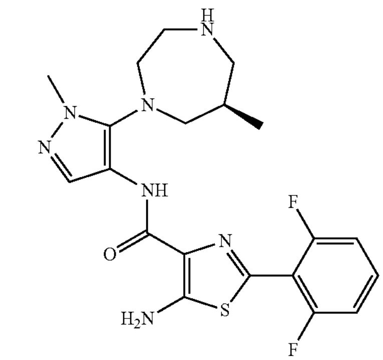 [SMILES: C[C@@H]1CNCCN(c2c(NC(=O)c3nc(-c4c(F)cccc4F)sc3N)cnn2C)C1] | (R)-5-amino-2-(2,6-difluorophenyl)-N-(1-methyl-5-(6-methyl-1,4-diazepan-1-yl)-1H-pyrazol-4-yl)thiazole-4-carboxamide | |
| 134 | 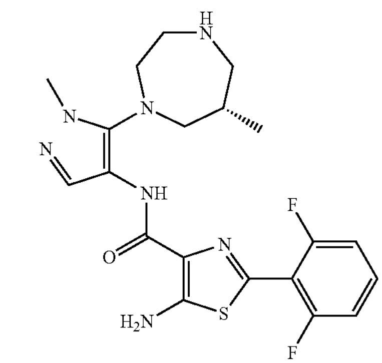 [SMILES: CN/C(=C(\C=N)NC(=O)c1nc(-c2c(F)cccc2F)sc1N)N1CCNC[C@H](C)C1] | (S)-5-amino-2-(2,6-difluorophenyl)-N-(1-methyl-5-(6-methyl-1,4-diazepan-1-yl)-1H-pyrazol-4-yl)thiazole-4-carboxamide | |
| 135 | 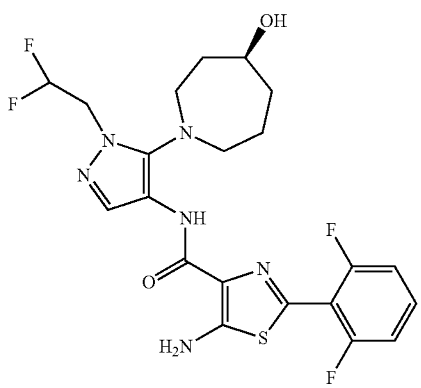 [SMILES: Nc1sc(-c2c(F)cccc2F)nc1C(=O)Nc1cnn(CC(F)F)c1N1CCC[C@H](O)CC1] | (S)-5-amino-N-(1-(2,2-difluoroethyl)-5-(4-hydroxyazepan-1-yl)-1H-pyrazol-4-yl)-2-(2,6-difluorophenyl)thiazole-4-carboxamide | |
| 136 | 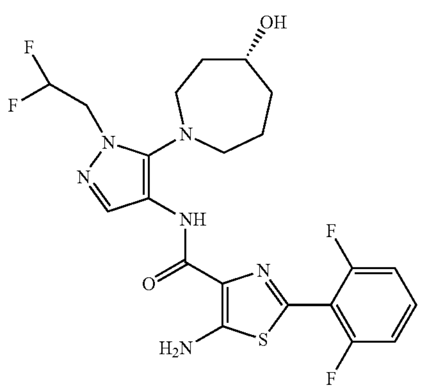 [SMILES: Nc1sc(-c2c(F)cccc2F)nc1C(=O)Nc1cnn(CC(F)F)c1N1CCC[C@@H](O)CC1] | (R)-5-amino-N-(1-(2,2-difluoroethyl)-5-(4-hydroxyazepan-1-yl)-1H-pyrazol-4-yl)-2-(2,6-difluorophenyl)thiazole-4-carboxamide | |

TABLE 1a-continued

| No. | Structure | IUPAC Name | PIM1 LC3K (KI) uM |
|---|---|---|---|
| 137 | 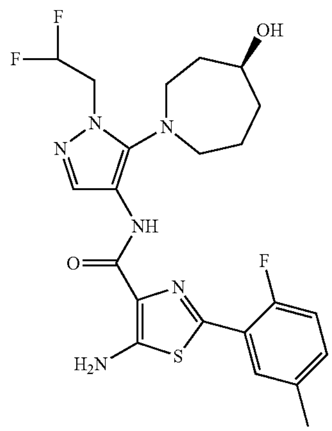 [SMILES: Cc1ccc(F)c(-c2nc(C(=O)Nc3cnn(CC(F)F)c3N3CCC[C@H](O)CC3)c(N)s2)c1] | (S)-5-amino-N-(1-(2,2-difluoroethyl)-5-(4-hydroxyazepan-1-yl)-1H-pyrazol-4-yl)-2-(2-fluoro-5-methylphenyl)thiazole-4-carboxamide | |
| 138 | 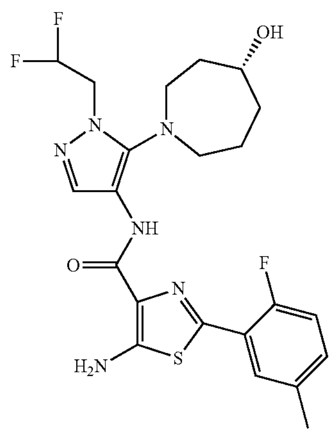 | (R)-5-amino-N-(1-(2,2-difluoroethyl)-5-(4-hydroxyazepan-1-yl)-1H-pyrazol-4-yl)-2-(2-fluoro-5-methylphenyl)thiazole-4-carboxamide | |
| 139 | 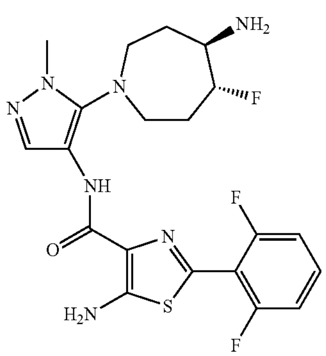 [SMILES: Cn1ncc(NC(=O)c2nc(-c3c(F)cccc3F)sc2N)c1N1CC[C@@H](N)[C@H](F)CC1] | 5-amino-N-(5-((4R,5R)-4-amino-5-fluoroazepan-1-yl)-1-methyl-1H-pyrazol-4-yl)-2-(2,6-difluorophenyl)thiazole-4-carboxamide | 0.000040 |
| 140 | 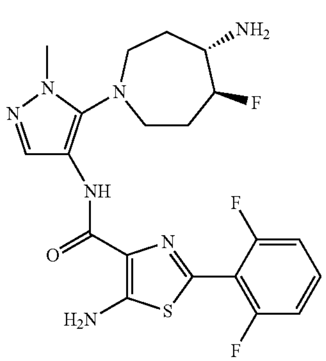 [SMILES: Cn1ncc(NC(=O)c2nc(-c3c(F)cccc3F)sc2N)c1N1CC[C@H](N)[C@@H](F)CC1] | 5-amino-N-(5-((4S,5S)-4-amino-5-fluoroazepan-1-yl)-1-methyl-1H-pyrazol-4-yl)-2-(2,6-difluorophenyl)thiazole-4-carboxamide | 0.000067 |

TABLE 1a-continued

| No. | Structure | IUPAC Name | PIM1 LC3K (KI) uM |
|---|---|---|---|
| 141 | 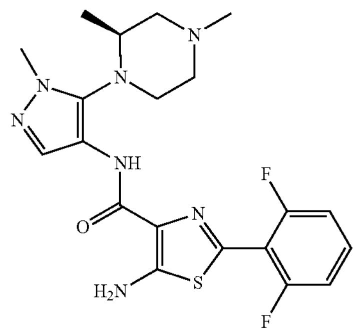 [SMILES: C[C@H]1CN(C)CCN1c1c(NC(=O)c2nc(-c3c(F)cccc3F)sc2N)cnn1C] | (S)-5-amino-2-(2,6-difluorophenyl)-N-(5-(2,4-dimethylpiperazin-1-yl)-1-methyl-1H-pyrazol-4-yl)thiazole-4-carboxamide | |
| 142 | 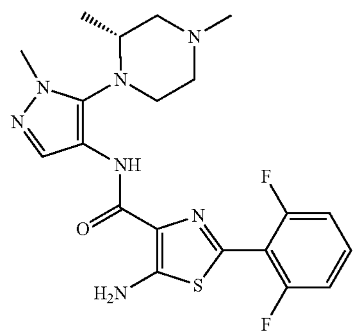 [SMILES: C[C@@H]1CN(C)CCN1c1c(NC(=O)c2nc(-c3c(F)cccc3F)sc2N)cnn1C] | (R)-5-amino-2-(2,6-difluorophenyl)-N-(5-(2,4-dimethylpiperazin-1-yl)-1-methyl-1H-pyrazol-4-yl)thiazole-4-carboxamide | |
| 143 | 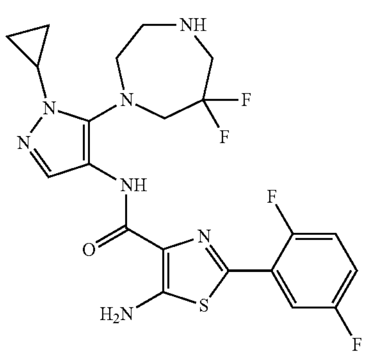 [SMILES: Nc1sc(-c2cc(F)ccc2F)nc1C(=O)Nc1cnn(C2CC2)c1N1CCNCC(F)(F)C1] | 5-amino-N-(1-cyclopropyl-5-(6,6-difluoro-1,4-diazepan-1-yl)-1H-pyrazol-4-yl)-2-(2,5-difluorophenyl)thiazole-4-carboxamide | |
| 144 | 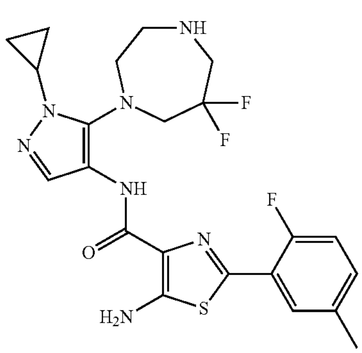 [SMILES: Cc1ccc(F)c(-c2nc(C(=O)Nc3cnn(C4CC4)c3N3CCNCC(F)(F)C3)c(N)s2)c1] | 5-amino-N-(1-cyclopropyl-5-(6,6-difluoro-1,4-diazepan-1-yl)-1H-pyrazol-4-yl)-2-(2-fluoro-5-methylphenyl)thiazole-4-carboxamide | |

TABLE 1a-continued

| No. | Structure | IUPAC Name | PIM1 LC3K (KI) uM |
|---|---|---|---|
| 145 | 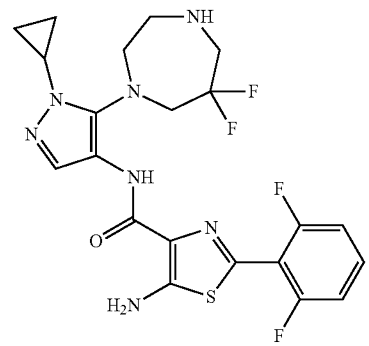 [SMILES: Nc1sc(-c2c(F)cccc2F)nc1C(=O)Nc1cnn(C2CC2)c1N1CCNCC(F)(F)C1] | 5-amino-N-(1-cyclopropyl-5-(6,6-difluoro-1,4-diazepan-1-yl)-1H-pyrazol-4-yl)-2-(2,6-difluorophenyl)thiazole-4-carboxamide | |
| 146 | 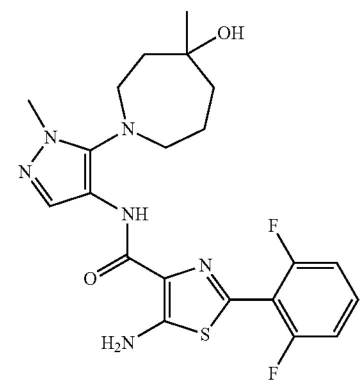 [SMILES: Cn1ncc(NC(=O)c2nc(-c3c(F)cccc3F)sc2N)c1N1CCCC(C)(O)CC1] | 5-amino-2-(2,6-difluorophenyl)-N-(5-(4-hydroxy-4-methylazepan-1-yl)-1-methyl-1H-pyrazol-4-yl)thiazole-4-carboxamide | |
| 147 | 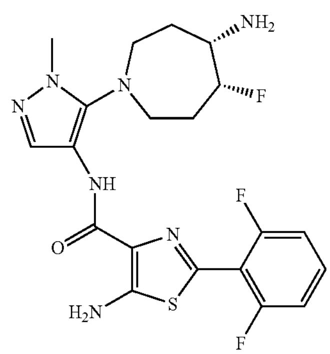 [SMILES: Cn1ncc(NC(=O)c2nc(-c3c(F)cccc3F)sc2N)c1N1CC[C@@H](F)[C@@H](N)CC1] | 5-amino-N-(5-((4S,5R)-4-amino-5-fluoroazepan-1-yl)-1-methyl-1H-pyrazol-4-yl)-2-(2,6-difluorophenyl)thiazole-4-carboxamide | |
| 148 | 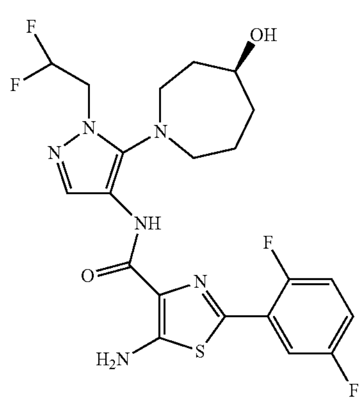 [SMILES: Nc1sc(-c2cc(F)ccc2F)nc1C(=O)Nc1cnn(CC(F)F)c1N1CCC[C@H](O)CC1] | (S)-5-amino-N-(1-(2,2-difluoroethyl)-5-(4-hydroxyazepan-1-yl)-1H-pyrazol-4-yl)-2-(2,5-difluorophenyl)thiazole-4-carboxamide | |

TABLE 1a-continued

| No. | Structure | IUPAC Name | PIM1 LC3K (KI) uM |
|-----|-----------|------------|-------------------|
| 149 | 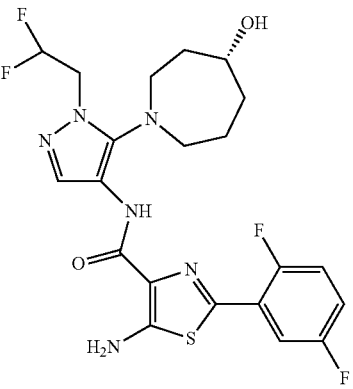 [SMILES: Nc1sc(-c2cc(F)ccc2F)nc1C(=O)Nc1cnn(CC(F)F)c1N1CCC[C@@H](O)CC1] | (R)-5-amino-N-(1-(2,2-difluoroethyl)-5-(4-hydroxyazepan-1-yl)-1H-pyrazol-4-yl)-2-(2,5-difluorophenyl)thiazole-4-carboxamide | |
| 150 | 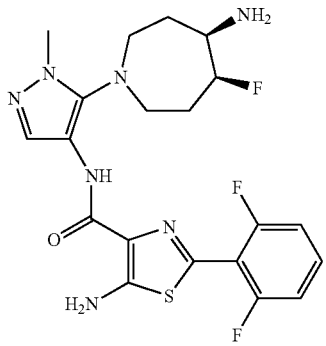 [SMILES: Cn1ncc(NC(=O)c2nc(-c3c(F)cccc3F)sc2N)c1N1CC[C@@H](N)[C@@H](F)CC1] | 5-amino-N-(5-((4R,5S)-4-amino-5-fluoroazepan-1-yl)-1-methyl-1H-pyrazol-4-yl)-2-(2,6-difluorophenyl)thiazole-4-carboxamide | |
| 151 | 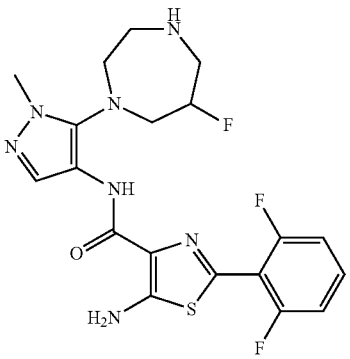 [SMILES: Cn1ncc(NC(=O)c2nc(-c3c(F)cccc3F)sc2N)c1N1CCNCC(F)C1] | 5-amino-2-(2,6-difluorophenyl)-N-(5-(6-fluoro-1,4-diazepan-1-yl)-1-methyl-1H-pyrazol-4-yl)thiazole-4-carboxamide | |
| 152 | 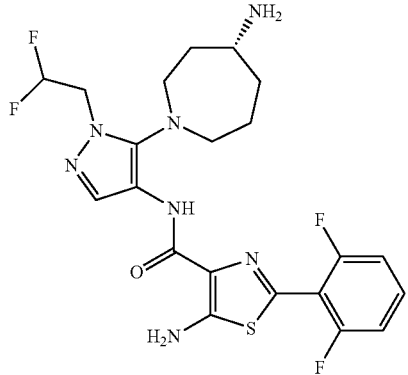 [SMILES: Nc1sc(-c2c(F)cccc2F)nc1C(=O)Nc1cnn(CC(F)F)c1N1CCC[C@@H](N)CC1] | (R)-5-amino-N-(5-(4-aminoazepan-1-yl)-1-(2,2-difluoroethyl)-1H-pyrazol-4-yl)-2-(2,6-difluorophenyl)thiazole-4-carboxamide | |

TABLE 1a-continued

| No. | Structure | IUPAC Name | PIM1 LC3K (KI) uM |
|---|---|---|---|
| 153 | 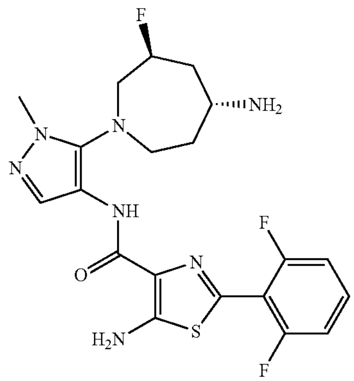 [SMILES: Cn1ncc(NC(=O)c2nc(-c3c(F)cccc3F)sc2N)c1N1CC[C@@H](N)C[C@H](F)C1] | 5-amino-N-(5-((3S,5R)-5-amino-3-fluoroazepan-1-yl)-1-methyl-1H-pyrazol-4-yl)-2-(2,6-difluorophenyl)thiazole-4-carboxamide | |
| 154 | 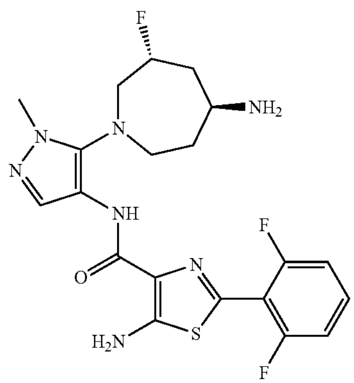 [SMILES: Cn1ncc(NC(=O)c2nc(-c3c(F)cccc3F)sc2N)c1N1CC[C@H](N)C[C@@H](F)C1] | 5-amino-N-(5-((3R,5S)-5-amino-3-fluoroazepan-1-yl)-1-methyl-1H-pyrazol-4-yl)-2-(2,6-difluorophenyl)thiazole-4-carboxamide | 0.000010 |
| 155 | 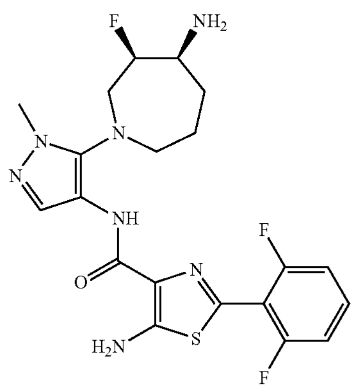 [SMILES: Cn1ncc(NC(=O)c2nc(-c3c(F)cccc3F)sc2N)c1N1CCC[C@H](N)[C@H](F)C1] | 5-amino-N-(5-((3R,4S)-4-amino-3-fluoroazepan-1-yl)-1-methyl-1H-pyrazol-4-yl)-2-(2,6-difluorophenyl)thiazole-4-carboxamide | |
| 156 | 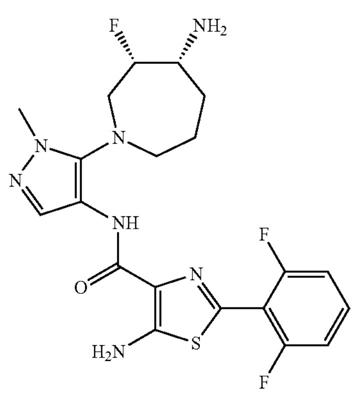 [SMILES: Cn1ncc(NC(=O)c2nc(-c3c(F)cccc3F)sc2N)c1N1CCC[C@@H](N)[C@@H](F)C1] | 5-amino-N-(5-((3S,4R)-4-amino-3-fluoroazepan-1-yl)-1-methyl-1H-pyrazol-4-yl)-2-(2,6-difluorophenyl)thiazole-4-carboxamide | |

TABLE 1a-continued

| No. | Structure | IUPAC Name | PIM1 LC3K (KI) uM |
|-----|-----------|------------|-------------------|
| 157 | 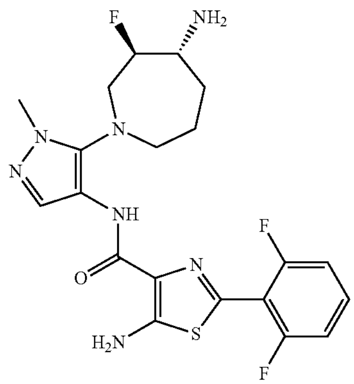 [SMILES: Cn1ncc(NC(=O)c2nc(-c3c(F)cccc3F)sc2N)c1N1CCC[C@@H](N)[C@H](F)C1] | 5-amino-N-(5-((3R,4R)-4-amino-3-fluoroazepan-1-yl)-1-methyl-1H-pyrazol-4-yl)-2-(2,6-difluorophenyl)thiazole-4-carboxamide | |
| 158 | 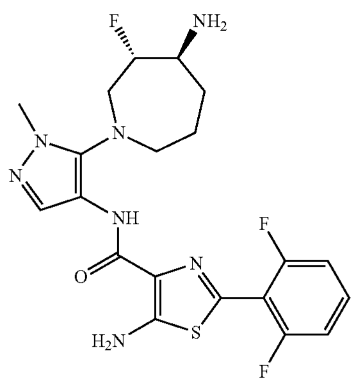 [SMILES: Cn1ncc(NC(=O)c2nc(-c3c(F)cccc3F)sc2N)c1N1CCC[C@H](N)[C@@H](F)C1] | 5-amino-N-(5-((3S,4S)-4-amino-3-fluoroazepan-1-yl)-1-methyl-1H-pyrazol-4-yl)-2-(2,6-difluorophenyl)thiazole-4-carboxamide | 0.000147 |
| 159 | 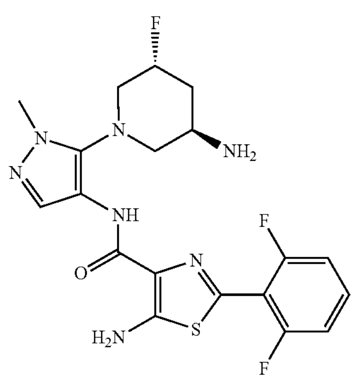 [SMILES: Cn1ncc(NC(=O)c2nc(-c3c(F)cccc3F)sc2N)c1N1C[C@H](N)C[C@@H](F)C1] | 5-amino-N-(5-((3R,5R)-3-amino-5-fluoropiperidin-1-yl)-1-methyl-1H-pyrazol-4-yl)-2-(2,6-difluorophenyl)thiazole-4-carboxamide | |
| 160 | 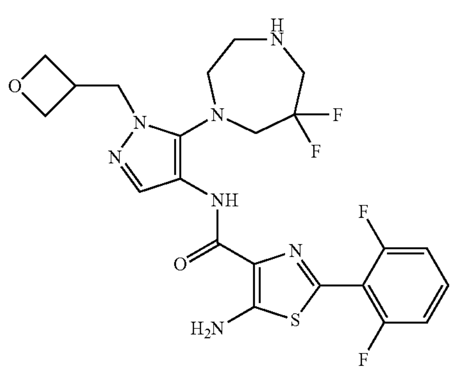 [SMILES: Nc1sc(-c2c(F)cccc2F)nc1C(=O)Nc1cnn(CC2COC2)c1N1CCNCC(F)(F)C1] | 5-amino-N-(5-(6,6-difluoro-1,4-diazepan-1-yl)-1-(oxetan-3-ylmethyl)-1H-pyrazol-4-yl)-2-(2,6-difluorophenyl)thiazole-4-carboxamide | |

TABLE 1a-continued

| No. | Structure | IUPAC Name | PIM1 LC3K (KI) uM |
|---|---|---|---|
| 161 | 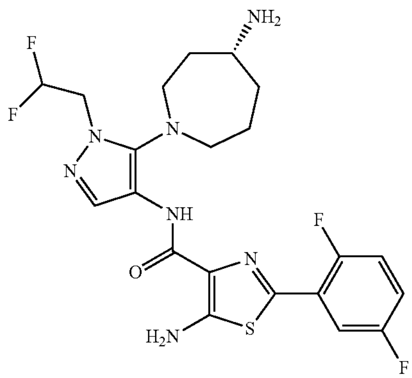 [SMILES: Nc1sc(-c2cc(F)ccc2F)nc1C(=O)Nc1cnn(CC(F)F)c1N1CCC[C@@H](N)CC1] | (R)-5-amino-N-(5-(4-aminoazepan-1-yl)-1-(2,2-difluoroethyl)-1H-pyrazol-4-yl)-2-(2,5-difluorophenyl)thiazole-4-carboxamide | 0.00012 |
| 162 | 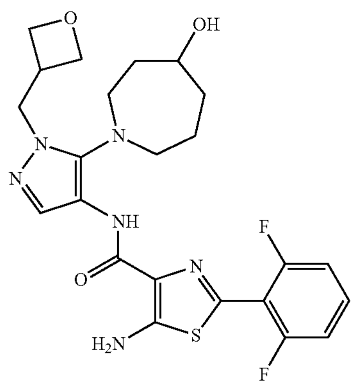 [SMILES: Nc1sc(-c2c(F)cccc2F)nc1C(=O)Nc1cnn(CC2COC2)c1N1CCCC(O)CC1] | 5-amino-2-(2,6-difluorophenyl)-N-(5-(4-hydroxyazepan-1-yl)-1-(oxetan-3-ylmethyl)-1H-pyrazol-4-yl)thiazole-4-carboxamide | |
| 163 | 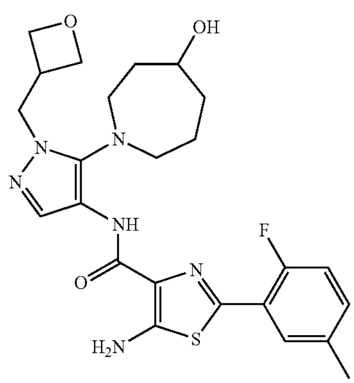 [SMILES: Cc1ccc(F)c(-c2nc(C(=O)Nc3cnn(CC4COC4)c3N3CCCC(O)CC3)c(N)s2)c1] | 5-amino-2-(2-fluoro-5-methylphenyl)-N-(5-(4-hydroxyazepan-1-yl)-1-(oxetan-3-ylmethyl)-1H-pyrazol-4-yl)thiazole-4-carboxamide | |
| 164 | 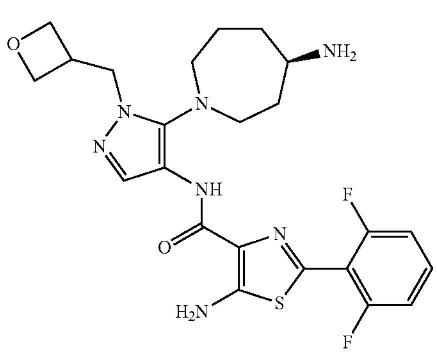 [SMILES: Nc1sc(-c2c(F)cccc2F)nc1C(=O)Nc1cnn(CC2COC2)c1N1CCC[C@@H](N)CC1] | (R)-5-amino-N-(5-(4-aminoazepan-1-yl)-1-(oxetan-3-ylmethyl)-1H-pyrazol-4-yl)-2-(2,6-difluorophenyl)thiazole-4-carboxamide | |

TABLE 1a-continued

| No. | Structure | IUPAC Name | PIM1 LC3K (KI) uM |
|---|---|---|---|
| 165 | 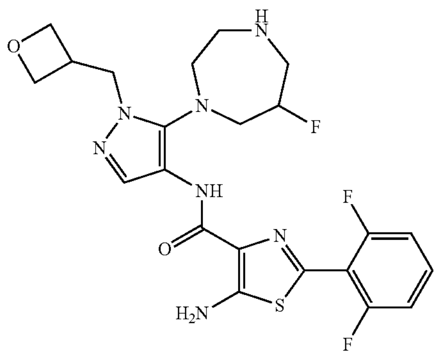 [SMILES: Nc1sc(-c2c(F)cccc2F)nc1C(=O)Nc1cnn(CC2COC2)c1N1CCNCC(F)C1] | 5-amino-2-(2,6-difluorophenyl)-N-(5-(6-fluoro-1,4-diazepan-1-yl)-1-(oxetan-3-ylmethyl)-1H-pyrazol-4-yl)thiazole-4-carboxamide | |
| 166 | 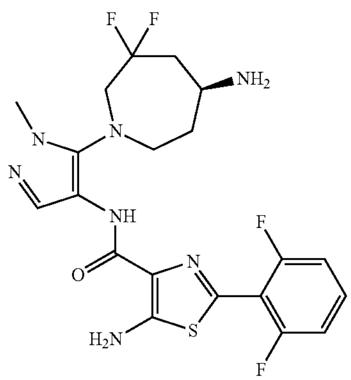 [SMILES: CN/C(=C(\C=N)NC(=O)c1nc(-c2c(F)cccc2F)sc1N)N1CC[C@H](N)CC(F)(F)C1] | (S)-5-amino-N-(5-(5-amino-3,3-difluoroazepan-1-yl)-1-methyl-1H-pyrazol-4-yl)-2-(2,6-difluorophenyl)thiazole-4-carboxamide | 0.000006 |
| 167 | 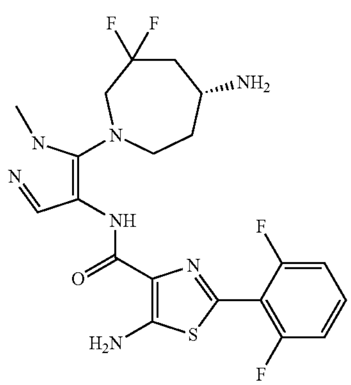 [SMILES: CN/C(=C(\C=N)NC(=O)c1nc(-c2c(F)cccc2F)sc1N)N1CC[C@@H](N)CC(F)(F)C1] | (R)-5-amino-N-(5-(5-amino-3,3-difluoroazepan-1-yl)-1-methyl-1H-pyrazol-4-yl)-2-(2,6-difluorophenyl)thiazole-4-carboxamide | 0.000003 |
| 168 | 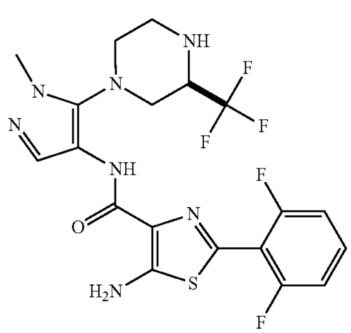 [SMILES: CN/C(=C(\C=N)NC(=O)c1nc(-c2c(F)cccc2F)sc1N)N1CCN[C@@H](C(F)(F)F)C1] | (R)-5-amino-2-(2,6-difluorophenyl)-N-(1-methyl-5-(3-(trifluoromethyl)piperazin-1-yl)-1H-pyrazol-4-yl)thiazole-4-carboxamide | |

TABLE 1a-continued

| No. | Structure | IUPAC Name | PIM1 LC3K (KI) uM |
|---|---|---|---|
| 169 | 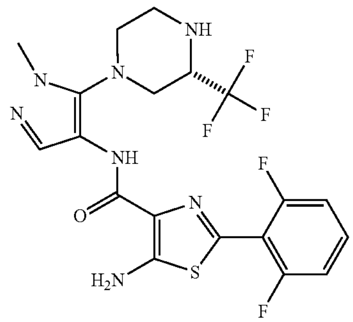 [SMILES: CN/C(=C(\C=N)NC(=O)c1nc(-c2c(F)cccc2F)sc1N)N1CCN[C@H](C(F)(F)F)C1] | (S)-5-amino-2-(2,6-difluorophenyl)-N-(1-methyl-5-(3-(trifluoromethyl)piperazin-1-yl)-1H-pyrazol-4-yl)thiazole-4-carboxamide | |
| 170 | 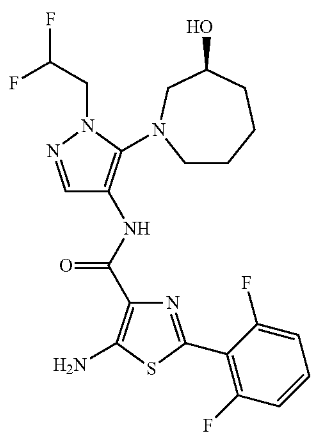 [SMILES: Nc1sc(-c2c(F)cccc2F)nc1C(=O)Nc1cnn(CC(F)F)c1N1CCCC[C@H](O)C1] | (S)-5-amino-N-(1-(2,2-difluoroethyl)-5-(3-hydroxyazepan-1-yl)-1H-pyrazol-4-yl)-2-(2,6-difluorophenyl)thiazole-4-carboxamide | |
| 171 | 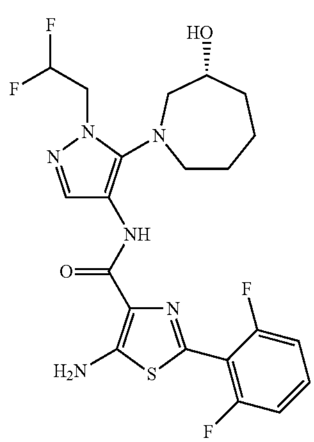 [SMILES: Nc1sc(-c2c(F)cccc2F)nc1C(=O)Nc1cnn(CC(F)F)c1N1CCCC[C@@H](O)C1] | (R)-5-amino-N-(1-(2,2-difluoroethyl)-5-(3-hydroxyazepan-1-yl)-1H-pyrazol-4-yl)-2-(2,6-difluorophenyl)thiazole-4-carboxamide | |

TABLE 1a-continued

| No. | Structure | IUPAC Name | PIM1 LC3K (KI) uM |
|---|---|---|---|
| 172 | 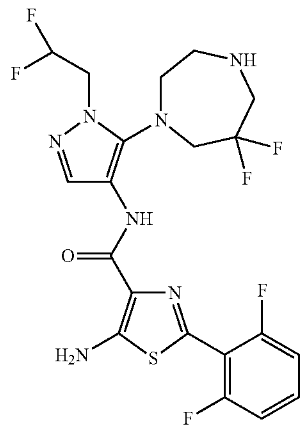 [SMILES: Nc1sc(-c2c(F)cccc2F)nc1C(=O)Nc1cnn(CC(F)F)c1N1CCNCC(F)(F)C1] | 5-amino-N-(5-(6,6-difluoro-1,4-diazepan-1-yl)-1-(2,2-difluoroethyl)-1H-pyrazol-4-yl)-2-(2,6-difluorophenyl)thiazole-4-carboxamide | |
| 173 | 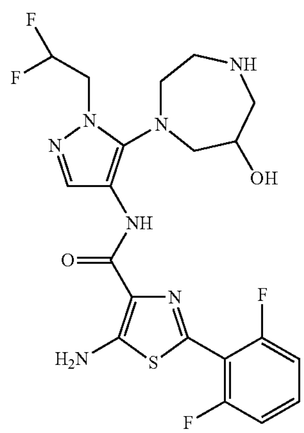 [SMILES: Nc1sc(-c2c(F)cccc2F)nc1C(=O)Nc1cnn(CC(F)F)c1N1CCNCC(O)C1] | 5-amino-N-(1-(2,2-difluoroethyl)-5-(6-hydroxy-1,4-diazepan-1-yl)-1H-pyrazol-4-yl)-2-(2,6-difluorophenyl)thiazole-4-carboxamide | |
| 174 | 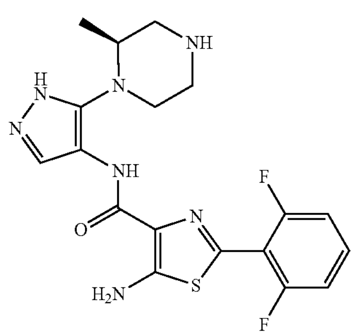 [SMILES: C[C@H]1CNCCN1c1[nH]ncc1NC(=O)c1nc(-c2c(F)cccc2F)sc1N] | (S)-5-amino-2-(2,6-difluorophenyl)-N-(5-(2-methylpiperazin-1-yl)-1H-pyrazol-4-yl)thiazole-4-carboxamide | |
| 175 | 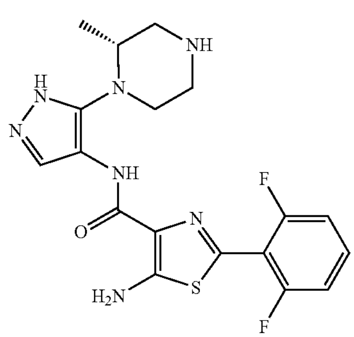 [SMILES: C[C@@H]1CNCCN1c1[nH]ncc1NC(=O)c1nc(-c2c(F)cccc2F)sc1N] | (R)-5-amino-2-(2,6-difluorophenyl)-N-(5-(2-methylpiperazin-1-yl)-1H-pyrazol-4-yl)thiazole-4-carboxamide | |

TABLE 1a-continued

| No. | Structure | IUPAC Name | PIM1 LC3K (KI) uM |
|---|---|---|---|
| 176 | 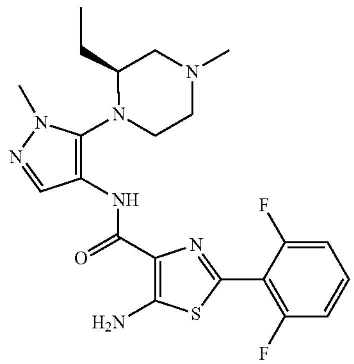 [SMILES: CC[C@H]1CN(C)CCN1c1c(NC(=O)c2nc(-c3c(F)cccc3F)sc2N)cnn1C] | (S)-5-amino-2-(2,6-difluorophenyl)-N-(5-(2-ethyl-4-methylpiperazin-1-yl)-1-methyl-1H-pyrazol-4-yl)thiazole-4-carboxamide | |
| 177 | 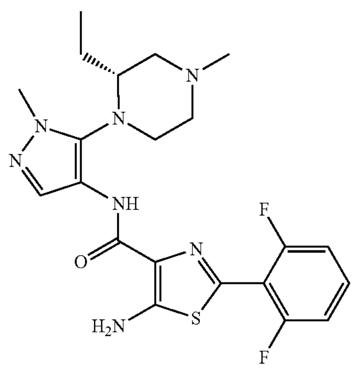 [SMILES: CC[C@@H]1CN(C)CCN1c1c(NC(=O)c2nc(-c3c(F)cccc3F)sc2N)cnn1C] | (R)-5-amino-2-(2,6-difluorophenyl)-N-(5-(2-ethyl-4-methylpiperazin-1-yl)-1-methyl-1H-pyrazol-4-yl)thiazole-4-carboxamide | |
| 178 | 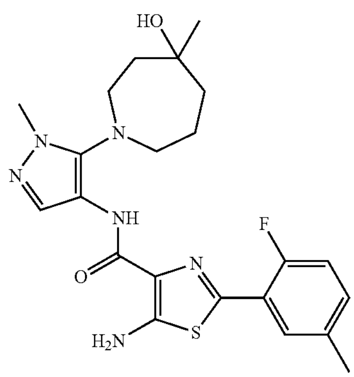 [SMILES: Cc1ccc(F)c(-c2nc(C(=O)Nc3cnn(C)c3N3CCCC(C)(O)CC3)c(N)s2)c1] | 5-amino-2-(2-fluoro-5-methylphenyl)-N-(5-(4-hydroxy-4-methylazepan-1-yl)-1-methyl-1H-pyrazol-4-yl)thiazole-4-carboxamide | |
| 179 | 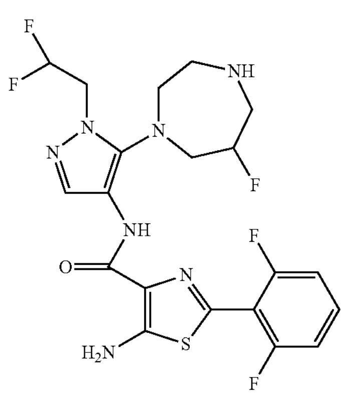 [SMILES: Nc1sc(-c2c(F)cccc2F)nc1C(=O)Nc1cnn(CC(F)F)c1N1CCNCC(F)C1] | 5-amino-N-(1-(2,2-difluoroethyl)-5-(6-fluoro-1,4-diazepan-1-yl)-1H-pyrazol-4-yl)-2-(2,6-difluorophenyl)thiazole-4-carboxamide | |

TABLE 1a-continued

| No. | Structure | IUPAC Name | PIM1 LC3K (KI) uM |
|---|---|---|---|
| 180 | 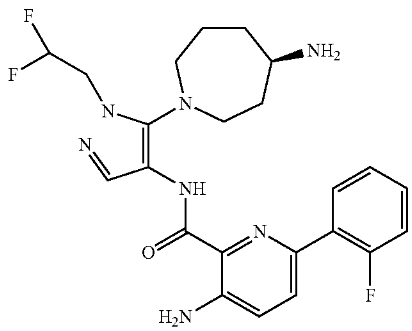 [SMILES: N=C/C(NC(=O)c1nc(-c2ccccc2F)ccc1N)=C(\NCC(F)F)N1CCC[C@@H](N)CC1] | (R)-3-amino-N-(5-(4-aminoazepan-1-yl)-1-(2,2-difluoroethyl)-1H-pyrazol-4-yl)-6-(2-fluorophenyl)picolinamide | |
| 181 | 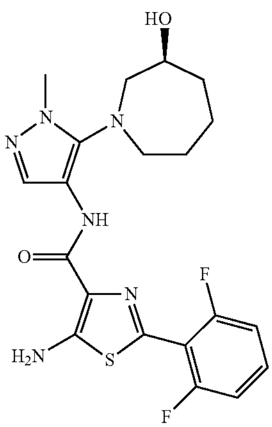 [SMILES: Cn1ncc(NC(=O)c2nc(-c3c(F)cccc3F)sc2N)c1N1CCCC[C@H](O)C1] | (S)-5-amino-2-(2,6-difluorophenyl)-N-(5-(3-hydroxyazepan-1-yl)-1-methyl-1H-pyrazol-4-yl)thiazole-4-carboxamide | |
| 182 | 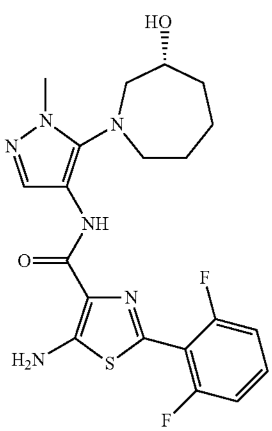 [SMILES: Cn1ncc(NC(=O)c2nc(-c3c(F)cccc3F)sc2N)c1N1CCCC[C@@H](O)C1] | (R)-5-amino-2-(2,6-difluorophenyl)-N-(5-(3-hydroxyazepan-1-yl)-1-methyl-1H-pyrazol-4-yl)thiazole-4-carboxamide | |
| 183 | 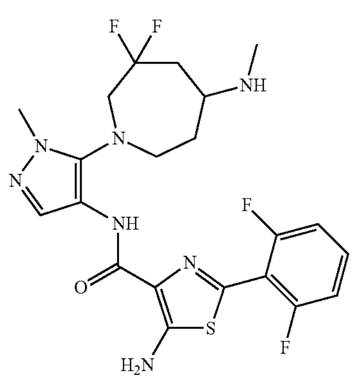 [SMILES: CNC1CCN(c2c(NC(=O)c3nc(-c4c(F)cccc4F)sc3N)cnn2C)CC(F)(F)C1] | 5-amino-N-(5-(3,3-difluoro-5-(methylamino)azepan-1-yl)-1-methyl-1H-pyrazol-4-yl)-2-(2,6-difluorophenyl)thiazole-4-carboxamide | |

TABLE 1a-continued

| No. | Structure | IUPAC Name | PIM1 LC3K (KI) uM |
|---|---|---|---|
| 184 | 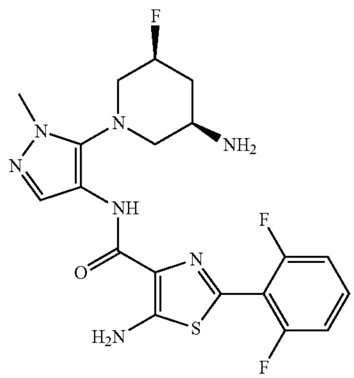 [SMILES: Cn1ncc(NC(=O)c2nc(-c3c(F)cccc3F)sc2N)c1N1C[C@H](N)C[C@H](F)C1] | 5-amino-N-(5-((3R,5S)-3-amino-5-fluoropiperidin-1-yl)-1-methyl-1H-pyrazol-4-yl)-2-(2,6-difluorophenyl)thiazole-4-carboxamide | |
| 185 | 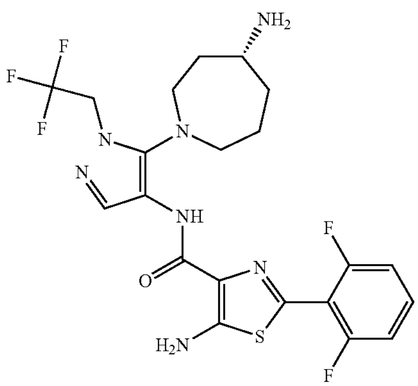 [SMILES: N=C/C(NC(=O)c1nc(-c2c(F)cccc2F)sc1N)=C(\NCC(F)(F)F)N1CCC[C@@H](N)CC1] | (R)-5-amino-N-(5-(4-aminoazepan-1-yl)-1-(2,2,2-trifluoroethyl)-1H-pyrazol-4-yl)-2-(2,6-difluorophenyl)thiazole-4-carboxamide | |
| 186 | 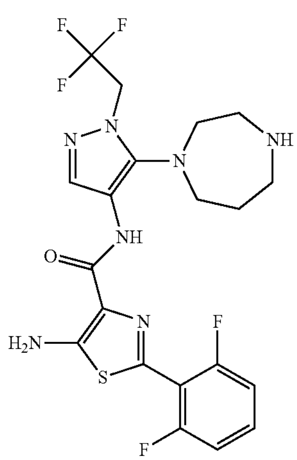 [SMILES: Nc1sc(-c2c(F)cccc2F)nc1C(=O)Nc1cnn(CC(F)(F)F)c1N1CCCNCC1] | N-(5-(1,4-diazepan-1-yl)-1-(2,2,2-trifluoroethyl)-1H-pyrazol-4-yl)-5-amino-2-(2,6-difluorophenyl)thiazole-4-carboxamide | |
| 187 | 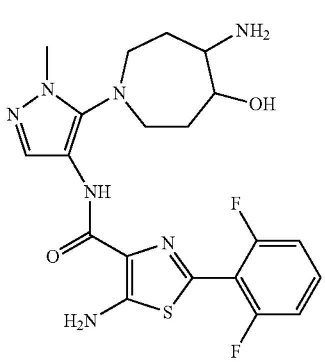 [SMILES: Cn1ncc(NC(=O)c2nc(-c3c(F)cccc3F)sc2N)c1N1CCC(N)C(O)CC1] | 5-amino-N-(5-(4-amino-5-hydroxyazepan-1-yl)-1-methyl-1H-pyrazol-4-yl)-2-(2,6-difluorophenyl)thiazole-4-carboxamide | |

TABLE 1a-continued

| No. | Structure | IUPAC Name | PIM1 LC3K (KI) uM |
|---|---|---|---|
| 188 | 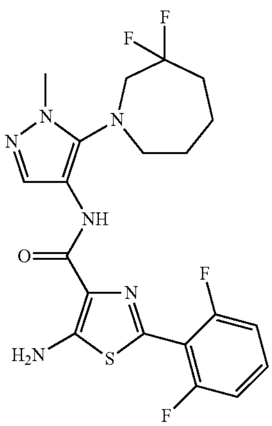 [SMILES: Cn1ncc(NC(=O)c2nc(-c3c(F)cccc3F)sc2N)c1N1CCCCC(F)(F)C1] | 5-amino-N-(5-(3,3-difluoroazepan-1-yl)-1-methyl-1H-pyrazol-4-yl)-2-(2,6-difluorophenyl)thiazole-4-carboxamide | |
| 189 | 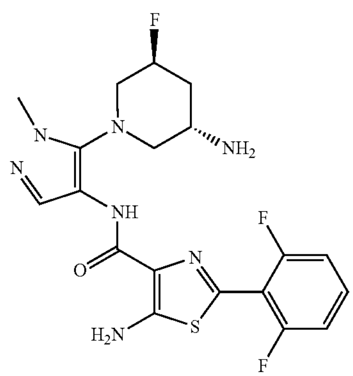 [SMILES: CN/C(=C(\C=N)NC(=O)c1nc(-c2c(F)cccc2F)sc1N)N1C[C@@H](N)C[C@H](F)C1] | 5-amino-N-(5-((3S,5S)-3-amino-5-fluoropiperidin-1-yl)-1-methyl-1H-pyrazol-4-yl)-2-(2,6-difluorophenyl)thiazole-4-carboxamide | |
| 190 | 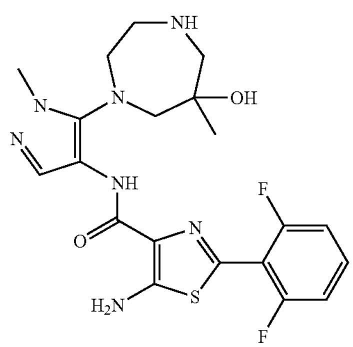 [SMILES: CN/C(=C(\C=N)NC(=O)c1nc(-c2c(F)cccc2F)sc1N)N1CCNCC(C)(O)C1] | 5-amino-2-(2,6-difluorophenyl)-N-(5-(6-hydroxy-6-methyl-1,4-diazepan-1-yl)-1-methyl-1H-pyrazol-4-yl)thiazole-4-carboxamide | |
| 191 | 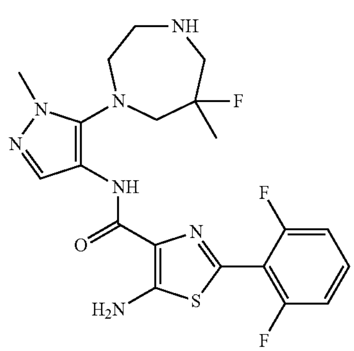 [SMILES: Cn1ncc(NC(=O)c2nc(-c3c(F)cccc3F)sc2N)c1N1CCNCC(C)(F)C1] | 5-amino-2-(2,6-difluorophenyl)-N-(5-(6-fluoro-6-methyl-1,4-diazepan-1-yl)-1-methyl-1H-pyrazol-4-yl)thiazole-4-carboxamide | |

TABLE 1a-continued

| No. | Structure | IUPAC Name | PIM1 LC3K (KI) uM |
|---|---|---|---|
| 192 | 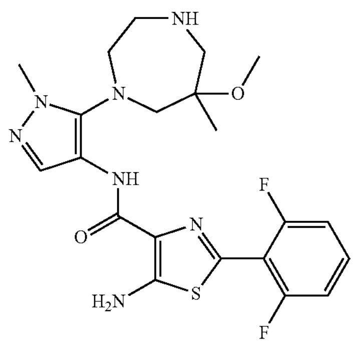 [SMILES: COC1(C)CNCCN(c2c(NC(=O)c3nc(-c4c(F)cccc4F)sc3N)cnn2C)C1] | 5-amino-2-(2,6-difluorophenyl)-N-(5-(6-methoxy-6-methyl-1,4-diazepan-1-yl)-1-methyl-1H-pyrazol-4-yl)thiazole-4-carboxamide | |
| 193 | 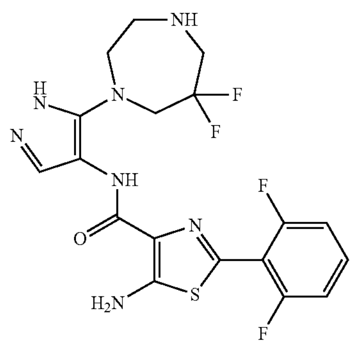 | 5-amino-N-(5-(6,6-difluoro-1,4-diazepan-1-yl)-1H-pyrazol-4-yl)-2-(2,6-difluorophenyl)thiazole-4-carboxamide | |
| 194 | 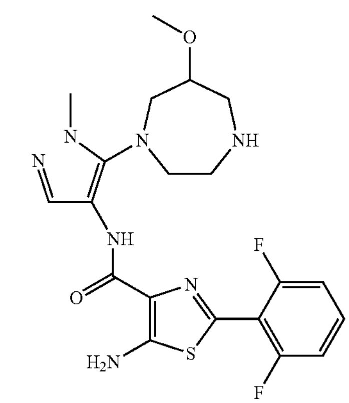 [SMILES: CN/C(=C(\C=N)NC(=O)c1nc(-c2c(F)cccc2F)sc1N)N1CCNCC(OC)C1] | 5-amino-2-(2,6-difluorophenyl)-N-(5-(6-methoxy-1,4-diazepan-1-yl)-1-methyl-1H-pyrazol-4-yl)thiazole-4-carboxamide | |
| 195 | 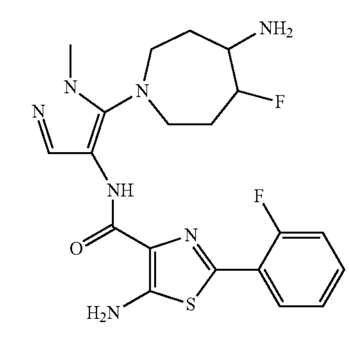 [SMILES: CN/C(=C(\C=N)NC(=O)c1nc(-c2ccccc2F)sc1N)N1CCC(N)C(F)CC1] | 5-amino-N-(5-(4-amino-5-fluoroazepan-1-yl)-1-methyl-1H-pyrazol-4-yl)-2-(2-fluorophenyl)thiazole-4-carboxamide | |

TABLE 1a-continued

| No. | Structure | IUPAC Name | PIM1 LC3K (KI) uM |
|---|---|---|---|
| 196 | 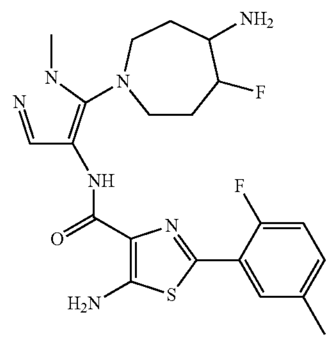 [SMILES: CN/C(=C(\C=N)NC(=O)c1nc(-c2cc(C)ccc2F)sc1N)N1CCC(N)C(F)CC1] | 5-amino-N-(5-(4-amino-5-fluoroazepan-1-yl)-1-methyl-1H-pyrazol-4-yl)-2-(2-fluoro-5-methylphenyl)thiazole-4-carboxamide | |
| 197 | 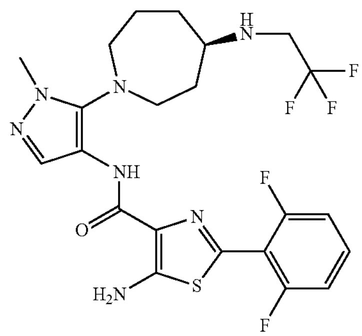 [SMILES: Cn1ncc(NC(=O)c2nc(-c3c(F)cccc3F)sc2N)c1N1CCC[C@@H](NCC(F)(F)F)CC1] | (R)-5-amino-2-(2,6-difluorophenyl)-N-(1-methyl-5-(4-(2,2,2-trifluoroethylamino)azepan-1-yl)-1H-pyrazol-4-yl)thiazole-4-carboxamide | |
| 198 | 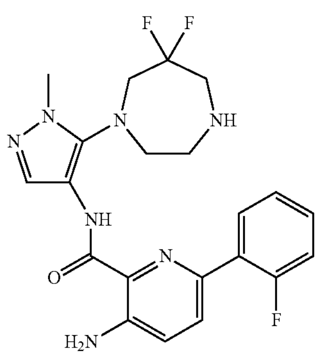 [SMILES: Cn1ncc(NC(=O)c2nc(-c3ccccc3F)ccc2N)c1N1CCNCC(F)(F)C1] | 3-amino-N-(5-(6,6-difluoro-1,4-diazepan-1-yl)-1-methyl-1H-pyrazol-4-yl)-6-(2-fluorophenyl)picolinamide | |
| 199 | 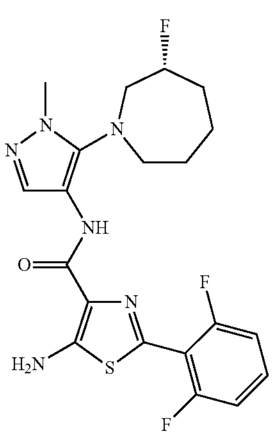 [SMILES: Cn1ncc(NC(=O)c2nc(-c3c(F)cccc3F)sc2N)c1N1CCCC[C@@H](F)C1] | (R)-5-amino-2-(2,6-difluorophenyl)-N-(5-(3-fluoroazepan-1-yl)-1-methyl-1H-pyrazol-4-yl)thiazole-4-carboxamide | |

TABLE 1a-continued

| No. | Structure | IUPAC Name | PIM1 LC3K (KI) uM |
|---|---|---|---|
| 200 | 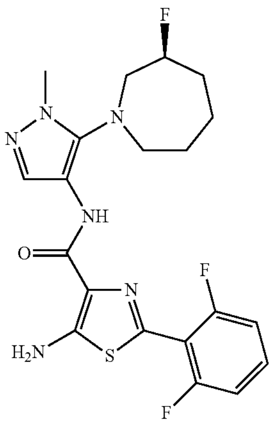 [SMILES: Cn1ncc(NC(=O)c2nc(-c3c(F)cccc3F)sc2N)c1N1CCCC[C@H](F)C1] | (S)-5-amino-2-(2,6-difluorophenyl)-N-(5-(3-fluoroazepan-1-yl)-1-methyl-1H-pyrazol-4-yl)thiazole-4-carboxamide | |
| 201 | 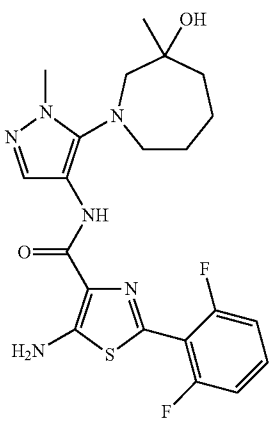 [SMILES: Cn1ncc(NC(=O)c2nc(-c3c(F)cccc3F)sc2N)c1N1CCCCC(C)(O)C1] | 5-amino-2-(2,6-difluorophenyl)-N-(5-(3-hydroxy-3-methylazepan-1-yl)-1-methyl-1H-pyrazol-4-yl)thiazole-4-carboxamide | |
| 202 | 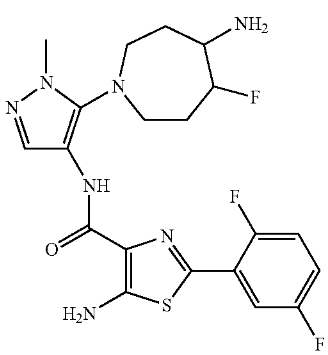 | 5-amino-N-(5-(4-amino-5-fluoroazepan-1-yl)-1-methyl-1H-pyrazol-4-yl)-2-(2,5-difluorophenyl)thiazole-4-carboxamide | |
| 203 | 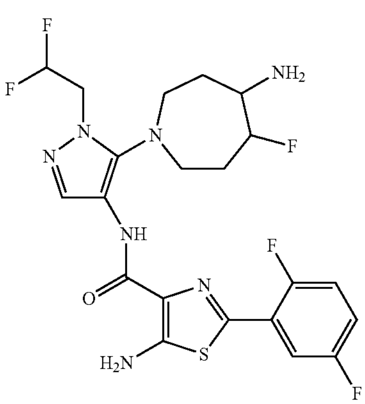 [SMILES: Nc1sc(-c2cc(F)ccc2F)nc1C(=O)Nc1cnn(CC(F)F)c1N1CCC(N)C(F)CC1] | 5-amino-N-(5-(4-amino-5-fluoroazepan-1-yl)-1-(2,2-difluoroethyl)-1H-pyrazol-4-yl)-2-(2,6-difluorophenyl)thiazole-4-carboxamide | |

TABLE 1a-continued

| No. | Structure | IUPAC Name | PIM1 LC3K (KI) uM |
|---|---|---|---|
| 204 | 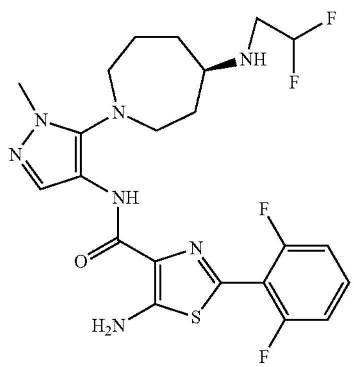 [SMILES: Cn1ncc(NC(=O)c2nc(-c3c(F)cccc3F)sc2N)c1N1CCC[C@@H](NCC(F)F)CC1] | (R)-5-amino-N-(5-(4-(2,2-difluoroethylamino)azepan-1-yl)-1-methyl-1H-pyrazol-4-yl)-2-(2,6-difluorophenyl)thiazole-4-carboxamide | |
| 205 | 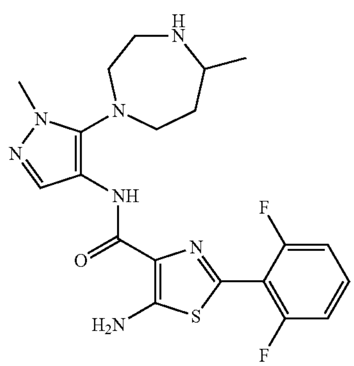 [SMILES: CC1CCN(c2c(NC(=O)c3nc(-c4c(F)cccc4F)sc3N)cnn2C)CCN1] | 5-amino-2-(2,6-difluorophenyl)-N-(1-methyl-5-(5-methyl-1,4-diazepan-1-yl)-1H-pyrazol-4-yl)thiazole-4-carboxamide | |
| 206 | 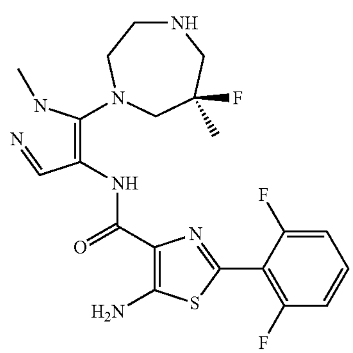 [SMILES: CN/C(=C(\C=N)NC(=O)c1nc(-c2c(F)cccc2F)sc1N)N1CCNC[C@@](C)(F)C1] | (R)-5-amino-2-(2,6-difluorophenyl)-N-(5-(6-fluoro-6-methyl-1,4-diazepan-1-yl)-1-methyl-1H-pyrazol-4-yl)thiazole-4-carboxamide | |
| 207 | 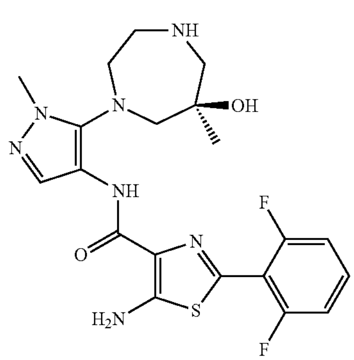 [SMILES: Cn1ncc(NC(=O)c2nc(-c3c(F)cccc3F)sc2N)c1N1CCNC[C@@](C)(O)C1] | (R)-5-amino-2-(2,6-difluorophenyl)-N-(5-(6-hydroxy-6-methyl-1,4-diazepan-1-yl)-1-methyl-1H-pyrazol-4-yl)thiazole-4-carboxamide | |

TABLE 1a-continued

| No. | Structure | IUPAC Name | PIM1 LC3K (KI) uM |
|---|---|---|---|
| 208 | 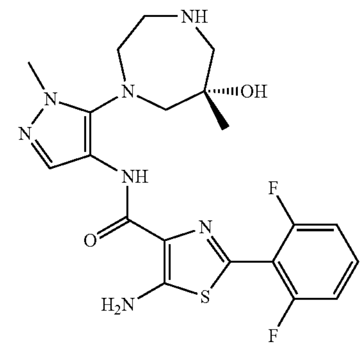 [SMILES: Cn1ncc(NC(=O)c2nc(-c3c(F)cccc3F)sc2N)c1N1CCNC[C@](C)(O)C1] | (S)-5-amino-2-(2,6-difluorophenyl)-N-(5-(6-hydroxy-6-methyl-1,4-diazepan-1-yl)-1-methyl-1H-pyrazol-4-yl)thiazole-4-carboxamide | |
| 209 | 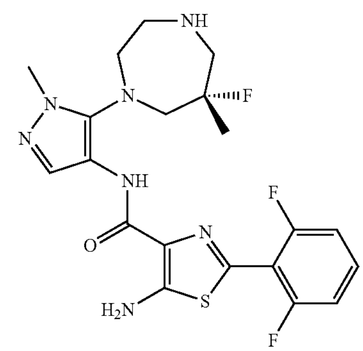 [SMILES: Cn1ncc(NC(=O)c2nc(-c3c(F)cccc3F)sc2N)c1N1CCNC[C@](C)(F)C1] | (S)-5-amino-2-(2,6-difluorophenyl)-N-(5-(6-fluoro-6-methyl-1,4-diazepan-1-yl)-1-methyl-1H-pyrazol-4-yl)thiazole-4-carboxamide | |
| 210 | 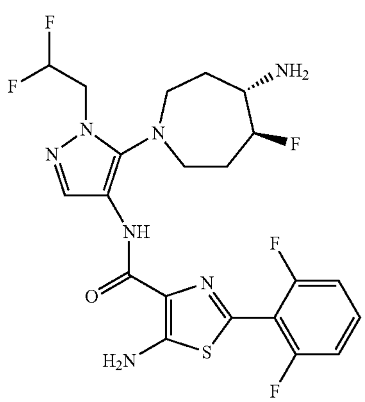 [SMILES: Nc1sc(-c2c(F)cccc2F)nc1C(=O)Nc1cnn(CC(F)F)c1N1CC[C@H](N)[C@@H](F)CC1] | 5-amino-N-(5-((4S,5S)-4-amino-5-fluoroazepan-1-yl)-1-(2,2-difluoroethyl)-1H-pyrazol-4-yl)-2-(2,6-difluorophenyl)thiazole-4-carboxamide | |
| 211 | 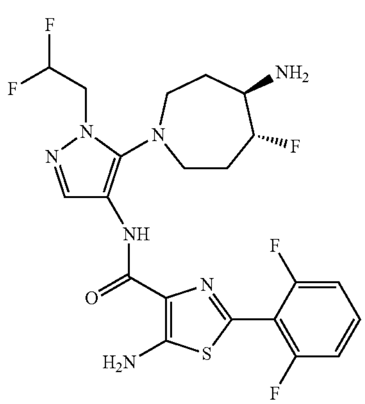 [SMILES: Nc1sc(-c2c(F)cccc2F)nc1C(=O)Nc1cnn(CC(F)F)c1N1CC[C@@H](N)[C@H](F)CC1] | 5-amino-N-(5-((4R,5R)-4-amino-5-fluoroazepan-1-yl)-1-(2,2-difluoroethyl)-1H-pyrazol-4-yl)-2-(2,6-difluorophenyl)thiazole-4-carboxamide | |

TABLE 1a-continued

| No. | Structure | IUPAC Name | PIM1 LC3K (KI) uM |
|---|---|---|---|
| 212 | 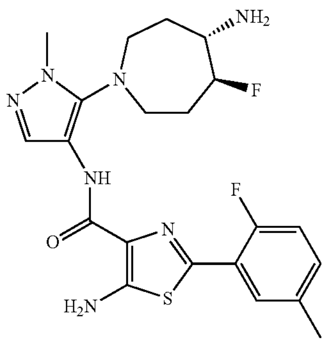 [SMILES: Cc1ccc(F)c(-c2nc(C(=O)Nc3cnn(C)c3N3CC[C@H](N)[C@@H](F)CC3)c(N)s2)c1] | 5-amino-N-(5-((4S,5S)-4-amino-5-fluoroazepan-1-yl)-1-methyl-1H-pyrazol-4-yl)-2-(2-fluoro-5-methylphenyl)thiazole-4-carboxamide | |
| 213 | 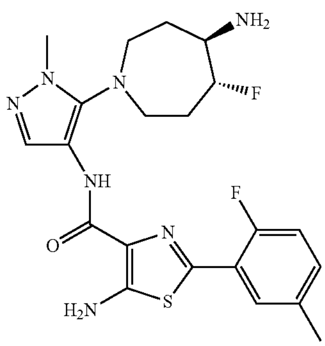 [SMILES: Cc1ccc(F)c(-c2nc(C(=O)Nc3cnn(C)c3N3CC[C@@H](N)[C@H](F)CC3)c(N)s2)c1] | 5-amino-N-(5-((4R,5R)-4-amino-5-fluoroazepan-1-yl)-1-methyl-1H-pyrazol-4-yl)-2-(2-fluoro-5-methylphenyl)thiazole-4-carboxamide | |
| 214 | 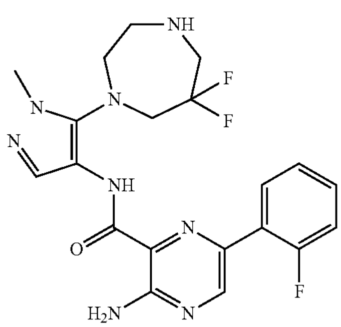 [SMILES: CN/C(=C(\C=N)NC(=O)c1nc(-c2ccccc2F)cnc1N)N1CCNCC(F)(F)C1] | 3-amino-N-(5-(6,6-difluoro-1,4-diazepan-1-yl)-1-methyl-1H-pyrazol-4-yl)-6-(2-fluorophenyl)pyrazine-2-carboxamide | |
| 215 | 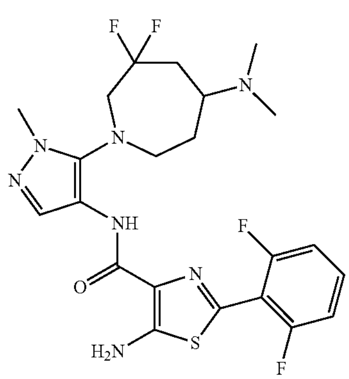 [SMILES: CN(C)C1CCN(c2c(NC(=O)c3nc(-c4c(F)cccc4F)sc3N)cnn2C)CC(F)(F)C1] | 5-amino-2-(2,6-difluorophenyl)-N-(5-(5-(dimethylamino)-3,3-difluoroazepan-1-yl)-1-methyl-1H-pyrazol-4-yl)thiazole-4-carboxamide | |

TABLE 1a-continued

| No. | Structure | IUPAC Name | PIM1 LC3K (KI) uM |
|---|---|---|---|
| 216 | 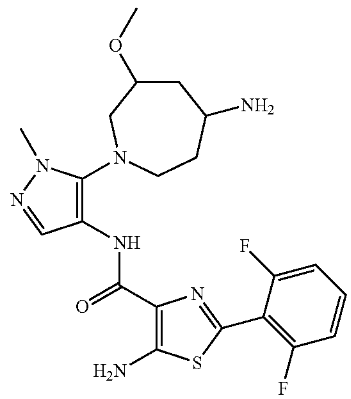 [SMILES: COC1CC(N)CCN(c2c(NC(=O)c3nc(-c4c(F)cccc4F)sc3N)cnn2C)C1] | 5-amino-N-(5-(5-amino-3-methoxyazepan-1-yl)-1-methyl-1H-pyrazol-4-yl)-2-(2,6-difluorophenyl)thiazole-4-carboxamide | |
| 217 | 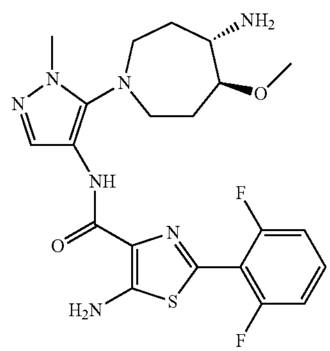 [SMILES: CO[C@H]1CCN(c2c(NC(=O)c3nc(-c4c(F)cccc4F)sc3N)cnn2C)CC[C@@H]1N] | 5-amino-N-(5-((4S,5S)-4-amino-5-methoxyazepan-1-yl)-1-methyl-1H-pyrazol-4-yl)-2-(2,6-difluorophenyl)thiazole-4-carboxamide | 0.000066 |
| 218 | 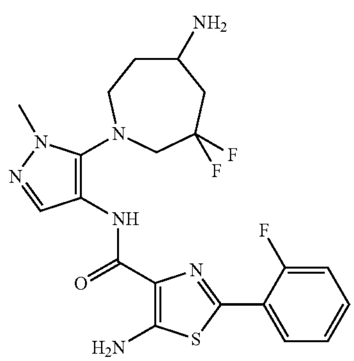 [SMILES: Cn1ncc(NC(=O)c2nc(-c3ccccc3F)sc2N)c1N1CCC(N)CC(F)(F)C1] | 5-amino-N-(5-(5-amino-3,3-difluoroazepan-1-yl)-1-methyl-1H-pyrazol-4-yl)-2-(2-fluorophenyl)thiazole-4-carboxamide | |
| 219 | 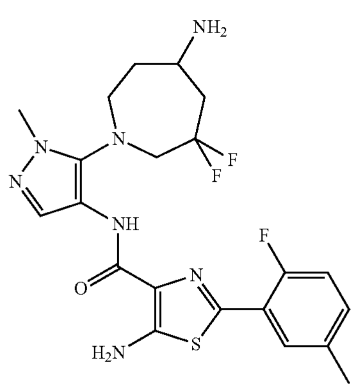 [SMILES: Cc1ccc(F)c(-c2nc(C(=O)Nc3cnn(C)c3N3CCC(N)CC(F)(F)C3)c(N)s2)c1] | 5-amino-N-(5-(5-amino-3,3-difluoroazepan-1-yl)-1-methyl-1H-pyrazol-4-yl)-2-(2-fluoro-5-methylphenyl)thiazole-4-carboxamide | |

TABLE 1a-continued

| No. | Structure | IUPAC Name | PIM1 LC3K (KI) uM |
|---|---|---|---|
| 220 | 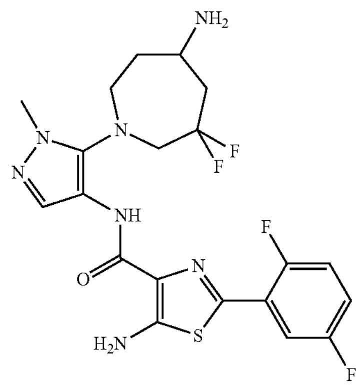 [SMILES: Cn1ncc(NC(=O)c2nc(-c3cc(F)ccc3F)sc2N)c1N1CCC(N)CC(F)(F)C1] | 5-amino-N-(5-(5-amino-3,3-difluoroazepan-1-yl)-1-methyl-1H-pyrazol-4-yl)-2-(2,5-difluorophenyl)thiazole-4-carboxamide | |
| 221 | 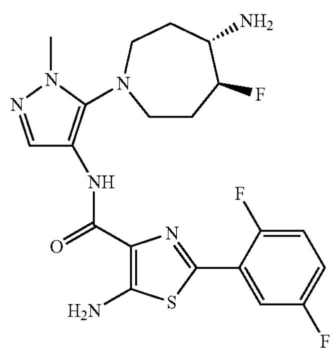 [SMILES: Cn1ncc(NC(=O)c2nc(-c3cc(F)ccc3F)sc2N)c1N1CC[C@H](N)[C@@H](F)CC1] | 5-amino-N-(5-((4S,5S)-4-amino-5-fluoroazepan-1-yl)-1-methyl-1H-pyrazol-4-yl)-2-(2,5-difluorophenyl)thiazole-4-carboxamide | |
| 222 | 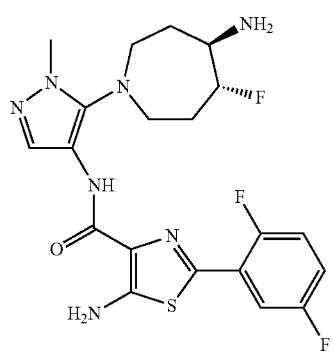 [SMILES: Cn1ncc(NC(=O)c2nc(-c3cc(F)ccc3F)sc2N)c1N1CC[C@@H](N)[C@H](F)CC1] | 5-amino-N-(5-((4R,5R)-4-amino-5-fluoroazepan-1-yl)-1-methyl-1H-pyrazol-4-yl)-2-(2,5-difluorophenyl)thiazole-4-carboxamide | |
| 223 | 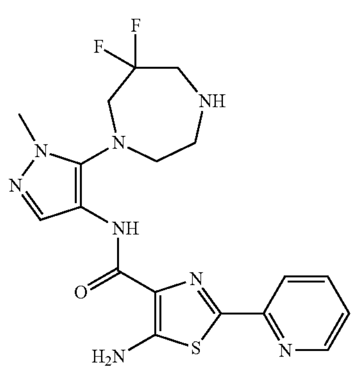 [SMILES: Cn1ncc(NC(=O)c2nc(-c3ccccn3)sc2N)c1N1CCNCC(F)(F)C1] | 5-amino-N-(5-(6,6-difluoro-4-diazepan-1-yl)-1-methyl-1H-pyrazol-4-yl)-2-(pyridin-2-yl)thiazole-4-carboxamide | 0.000206 |

TABLE 1a-continued

| No. | Structure | IUPAC Name | PIM1 LC3K (KI) uM |
|---|---|---|---|
| 224 | 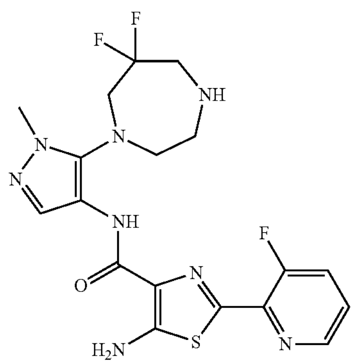 [SMILES: Cn1ncc(NC(=O)c2nc(-c3ncccc3F)sc2N)c1N1CCNCC(F)(F)C1] | 5-amino-N-(5-(6,6-difluoro-1,4-diazepan-1-yl)-1-methyl-1H-pyrazol-4-yl)-2-(3-fluoropyridin-2-yl)thiazole-4-carboxamide | |
| 225 | 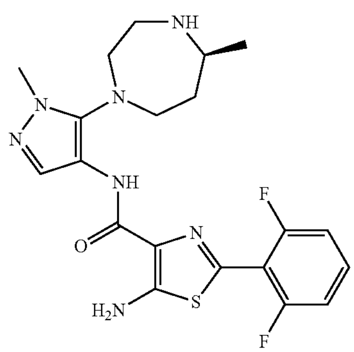 [SMILES: C[C@H]1CCN(c2c(NC(=O)c3nc(-c4c(F)cccc4F)sc3N)cnn2C)CCN1] | (S)-5-amino-2-(2,6-difluorophenyl)-N-(1-methyl-5-(5-methyl-1,4-diazepan-1-yl)-1H-pyrazol-4-yl)thiazole-4-carboxamide | |
| 226 | 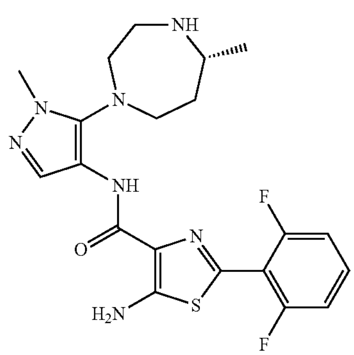 [SMILES: C[C@@H]1CCN(c2c(NC(=O)c3nc(-c4c(F)cccc4F)sc3N)cnn2C)CCN1] | (R)-5-amino-2-(2,6-difluorophenyl)-N-(1-methyl-5-(5-methyl-1,4-diazepan-1-yl)-1H-pyrazol-4-yl)thiazole-4-carboxamide | |
| 227 | 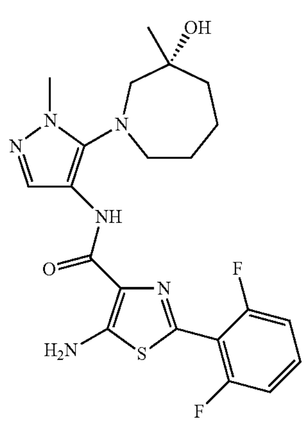 [SMILES: Cn1ncc(NC(=O)c2nc(-c3c(F)cccc3F)sc2N)c1N1CCCC[C@@](C)(O)C1] | (R)-5-amino-2-(2,6-difluorophenyl)-N-(5-(3-hydroxy-3-methylazepan-1-yl)-1-methyl-1H-pyrazol-4-yl)thiazole-4-carboxamide | |

TABLE 1a-continued

| No. | Structure | IUPAC Name | PIM1 LC3K (KI) uM |
|-----|-----------|------------|-------------------|
| 228 | 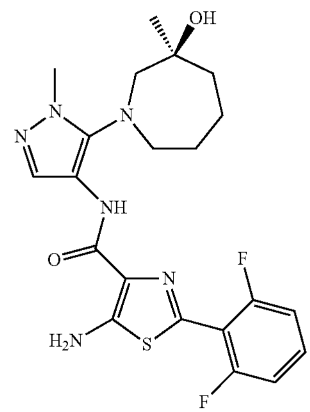 [SMILES: Cn1ncc(NC(=O)c2nc(-c3c(F)cccc3F)sc2N)c1N1CCCC[C@](C)(O)C1] | (S)-5-amino-2-(2,6-difluorophenyl)-N-(5-(3-hydroxy-3-methylazepan-1-yl)-1-methyl-1H-pyrazol-4-yl)thiazole-4-carboxamide | |
| 229 | 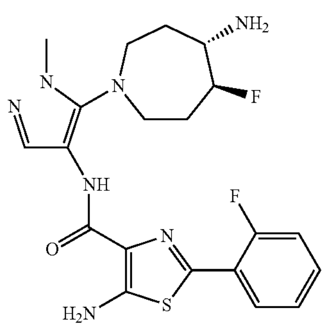 [SMILES: CN/C(=C(\C=N)NC(=O)c1nc(-c2ccccc2F)sc1N)N1CC[C@H](N)[C@@H](F)CC1] | 5-amino-N-(5-((4S,5S)-4-amino-5-fluoroazepan-1-yl)-1-methyl-1H-pyrazol-4-yl)-2-(2-fluorophenyl)thiazole-4-carboxamide | |
| 230 | 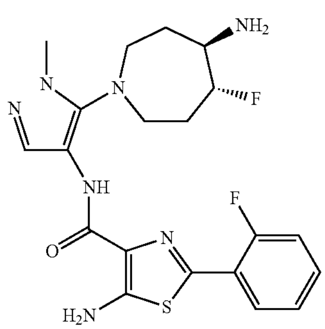 [SMILES: CN/C(=C(\C=N)NC(=O)c1nc(-c2ccccc2F)sc1N)N1CC[C@@H](N)[C@H](F)CC1] | 5-amino-N-(5-((4R,5R)-4-amino-5-fluoroazepan-1-yl)-1-methyl-1H-pyrazol-4-yl)-2-(2-fluorophenyl)thiazole-4-carboxamide | 0.00024 |
| 231 | 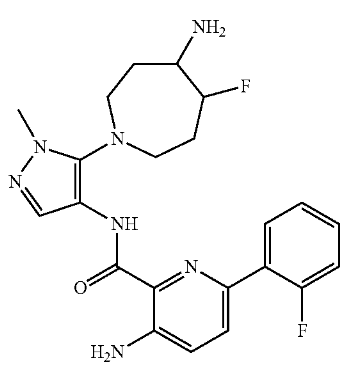 | 3-amino-N-(5-(4-amino-5-fluoroazepan-1-yl)-1-methyl-1H-pyrazol-4-yl)-6-(2-fluorophenyl)picolinamide | |

TABLE 1a-continued

| No. | Structure | IUPAC Name | PIM1 LC3K (KI) uM |
|---|---|---|---|
| 232 | 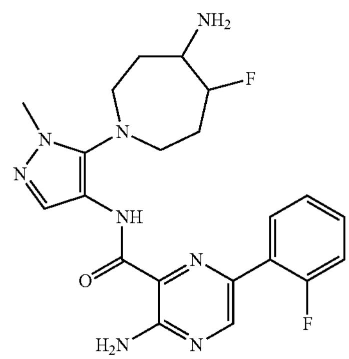 [SMILES: Cn1ncc(NC(=O)c2nc(-c3ccccc3F)cnc2N)c1N1CCC(N)C(F)CC1] | 3-amino-N-(5-(4-amino-5-fluoroazepan-1-yl)-1-methyl-1H-pyrazol-4-yl)-6-(2-fluorophenyl)pyrazine-2-carboxamide | |
| 233 | 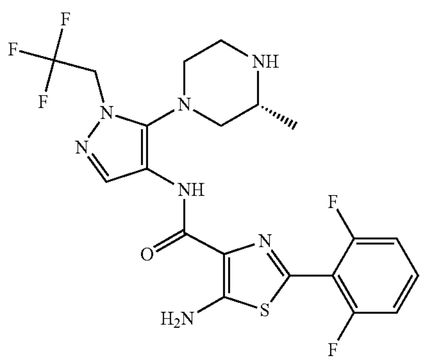 [SMILES: C[C@@H]1CN(c2c(NC(=O)c3nc(-c4c(F)cccc4F)sc3N)cnn2CC(F)(F)F)CCN1] | (R)-5-amino-2-(2,6-difluorophenyl)-N-(5-(3-methylpiperazin-1-yl)-1-(2,2,2-trifluoroethyl)-1H-pyrazol-4-yl)thiazole-4-carboxamide | |
| 234 | 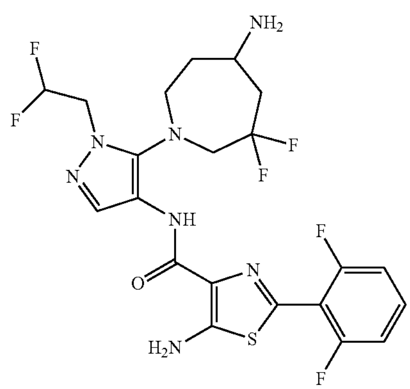 | 5-amino-N-(5-(5-amino-3,3-difluoroazepan-1-yl)-1-(2,2-difluoroethyl)-1H-pyrazol-4-yl)-2-(2,6-difluorophenyl)thiazole-4-carboxamide | |
| 235 | 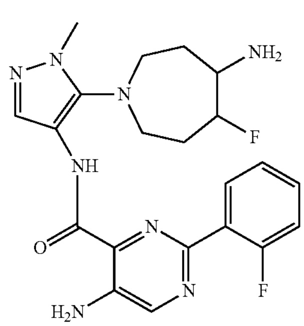 [SMILES: Cn1ncc(NC(=O)c2nc(-c3ccccc3F)ncc2N)c1N1CCC(N)C(F)CC1] | 5-amino-N-(5-(4-amino-5-fluoroazepan-1-yl)-1-methyl-1H-pyrazol-4-yl)-2-(2-fluorophenyl)pyrimidine-4-carboxamide | |

TABLE 1a-continued

| No. | Structure | IUPAC Name | PIM1 LC3K (KI) uM |
|---|---|---|---|
| 236 | 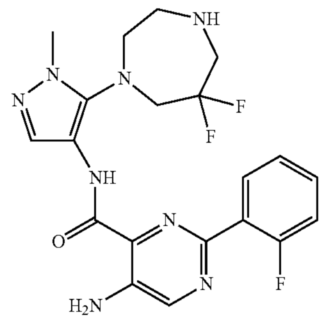 [SMILES: Cn1ncc(NC(=O)c2nc(-c3ccccc3F)ncc2N)c1N1CCNCC(F)(F)C1] | 5-amino-N-(5-(6,6-difluoro-1,4-diazepan-1-yl)-1-methyl-1H-pyrazol-4-yl)-2-(2-fluorophenyl)pyrimidine-4-carboxamide | |
| 237 | 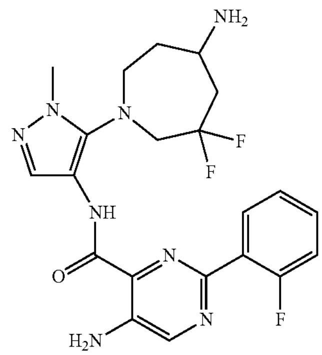 [SMILES: Cn1ncc(NC(=O)c2nc(-c3ccccc3F)ncc2N)c1N1CCC(N)CC(F)(F)C1] | 5-Amino-2-(2-fluoro-phenyl)-pyrimidine-4-carboxylic acid [5-(5-amino-3,3-difluoro-azepan-1-yl)-1-methyl-1H-pyrazol-4-yl]-amide | |
| 238 | | | |
| 239 | | | |
| 240 | | | |
| 241 | 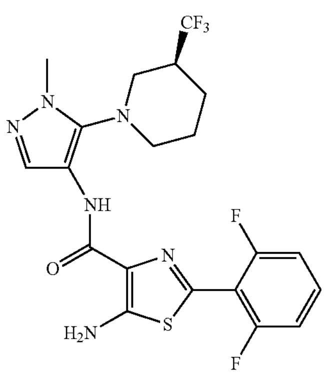 [SMILES: Cn1ncc(NC(=O)c2nc(-c3c(F)cccc3F)sc2N)c1N1CCC[C@H](C(F)(F)F)C1] | (S)-5-amino-2-(2,6-difluorophenyl)-N-(1-methyl-5-(3-(trifluoromethyl)piperidin-1-yl)-1H-pyrazol-4-yl)thiazole-4-carboxamide | |
| 242 | 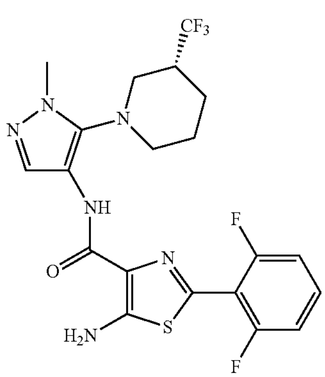 [SMILES: Cn1ncc(NC(=O)c2nc(-c3c(F)cccc3F)sc2N)c1N1CCC[C@@H](C(F)(F)F)C1] | (R)-5-amino-2-(2,6-difluoro-phenyl)-thiazole-4-carboxylic acid [1-methyl-5-(3-trifluoromethyl-piperidin-1-yl)-1H-pyrazol-4-yl]-amide | 0.000268 |

TABLE 1a-continued

| No. | Structure | IUPAC Name | PIM1 LC3K (KI) uM |
|---|---|---|---|
| 243 | 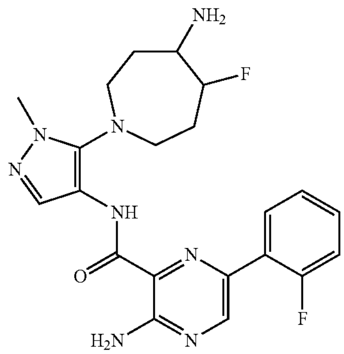 [SMILES: Cn1ncc(NC(=O)c2nc(-c3ccccc3F)cnc2N)c1N1CCC(N)C(F)CC1] | 3-amino-N-(5-(4-amino-5-fluoroazepan-1-yl)-1-methyl-1H-pyrazol-4-yl)-6-(2-fluorophenyl)pyrazine-2-carboxamide | 0.000123 |
| 244 | 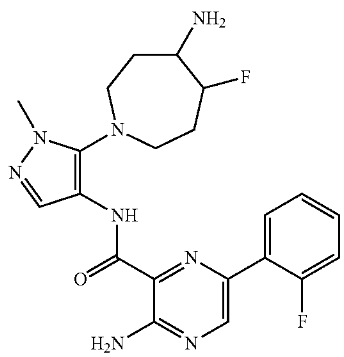 [SMILES: Cn1ncc(NC(=O)c2nc(-c3ccccc3F)cnc2N)c1N1CCC(N)C(F)CC1] | 3-amino-N-(5-(4-amino-5-fluoroazepan-1-yl)-1-methyl-1H-pyrazol-4-yl)-6-(2-fluorophenyl)pyrazine-2-carboxamide | 0.000141 |
| 245 | 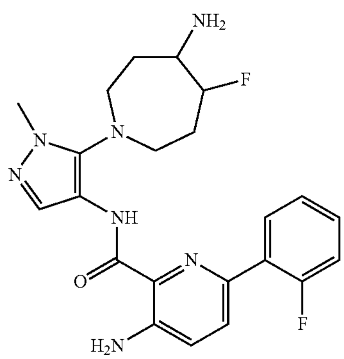 [SMILES: Cn1ncc(NC(=O)c2nc(-c3ccccc3F)ccc2N)c1N1CCC(N)C(F)CC1] | 3-amino-N-(5-(4-amino-5-fluoroazepan-1-yl)-1-methyl-1H-pyrazol-4-yl)-6-(2-fluorophenyl)picolinamide | 0.000173 |
| 246 | 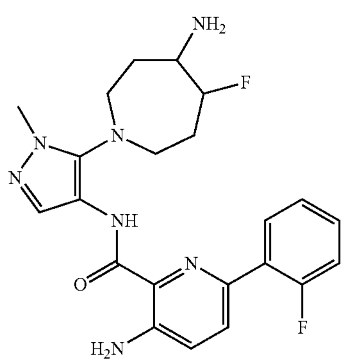 [SMILES: Cn1ncc(NC(=O)c2nc(-c3ccccc3F)ccc2N)c1N1CCC(N)C(F)CC1] | 3-amino-N-(5-(4-amino-5-fluoroazepan-1-yl)-1-methyl-1H-pyrazol-4-yl)-6-(2-fluorophenyl)picolinamide | 0.000149 |

TABLE 1a-continued

| No. | Structure | IUPAC Name | PIM1 LC3K (KI) uM |
|---|---|---|---|
| 247 | 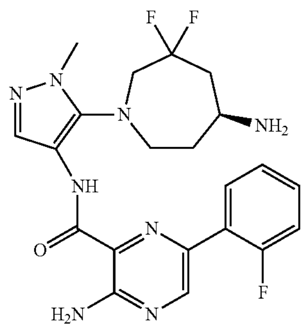 [SMILES: Cn1ncc(NC(=O)c2nc(-c3ccccc3F)cnc2N)c1N1CC[C@H](N)CC(F)(F)C1] | (S)-3-amino-N-(5-(5-amino-3,3-difluoroazepan-1-yl)-1-methyl-1H-pyrazol-4-yl)-6-(2-fluorophenyl)pyrazine-2-carboxamide | 0.00001 |
| 248 | 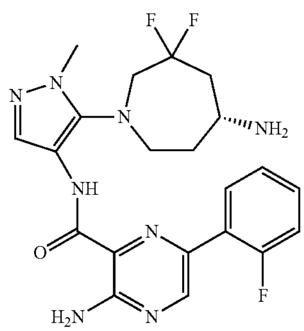 [SMILES: Cn1ncc(NC(=O)c2nc(-c3ccccc3F)cnc2N)c1N1CC[C@@H](N)CC(F)(F)C1] | (R)-3-amino-N-(5-(5-amino-3,3-difluoroazepan-1-yl)-1-methyl-1H-pyrazol-4-yl)-6-(2-fluorophenyl)pyrazine-2-carboxamide | 0.000007 |
| 249 | 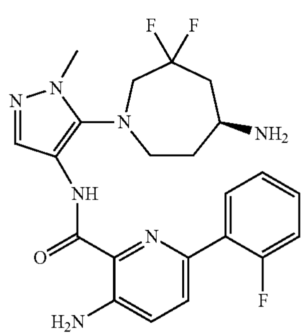 [SMILES: Cn1ncc(NC(=O)c2nc(-c3ccccc3F)ccc2N)c1N1CC[C@H](N)CC(F)(F)C1] | (S)-3-amino-N-(5-(5-amino-3,3-difluoroazepan-1-yl)-1-methyl-1H-pyrazol-4-yl)-6-(2-fluorophenyl)picolinamide | 0.00002 |
| 250 | 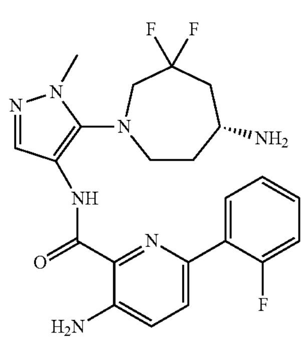 [SMILES: Cn1ncc(NC(=O)c2nc(-c3ccccc3F)ccc2N)c1N1CC[C@@H](N)CC(F)(F)C1] | (R)-3-amino-N-(5-(5-amino-3,3-difluoroazepan-1-yl)-1-methyl-1H-pyrazol-4-yl)-6-(2-fluorophenyl)picolinamide | 0.00003 |

TABLE 1a-continued

| No. | Structure | IUPAC Name | PIM1 LC3K (KI) uM |
|---|---|---|---|
| 251 | 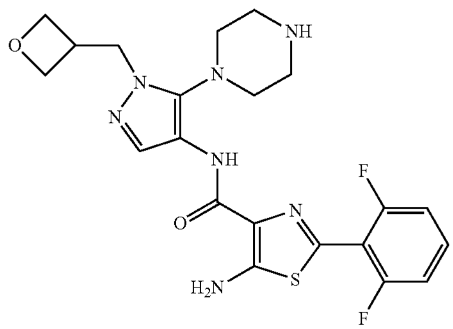 [SMILES: Nc1sc(-c2c(F)cccc2F)nc1C(=O)Nc1cnn(CC2COC2)c1N1CCNCC1] | 5-Amino-2-(2,6-difluoro-phenyl)-thiazole-4-carboxylic acid (1-oxetan-3-ylmethyl-5-piperazin-1-yl-1H-pyrazol-4-yl)-amide | >0.667 |
| 252 | 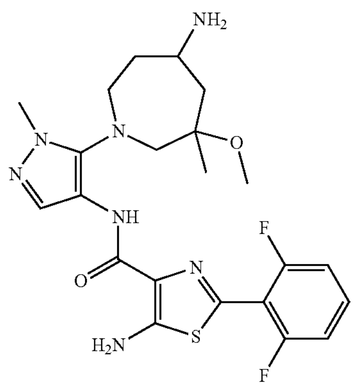 [SMILES: COC1(C)CC(N)CCN(c2c(NC(=O)c3nc(-c4c(F)cccc4F)sc3N)cnn2C)C1] | 5-Amino-2-(2,6-difluoro-phenyl)-thiazole-4-carboxylic acid [5-(5-amino-3-methoxy-3-methyl-azepan-1-yl)-1-methyl-1H-pyrazol-4-yl]-amide | 0.000009 |
| 253 | 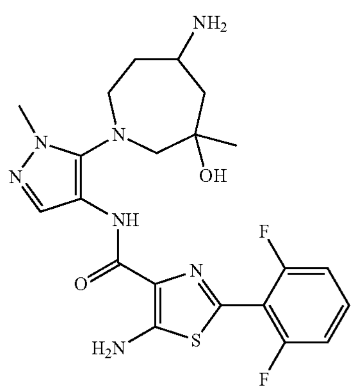 [SMILES: Cn1ncc(NC(=O)c2nc(-c3c(F)cccc3F)sc2N)c1N1CCC(N)CC(C)(O)C1] | 5-Amino-2-(2,6-difluoro-phenyl)-thiazole-4-carboxylic acid [5-(5-amino-3-hydroxy-3-methyl-azepan-1-yl)-1-methyl-1H-pyrazol-4-yl]-amide | 0.000048 |
| 254 | 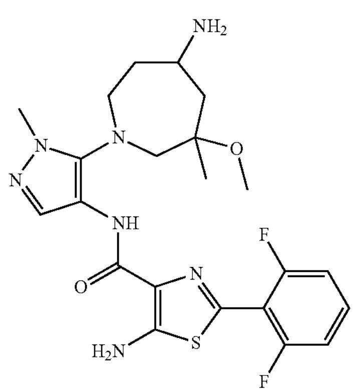 [SMILES: COC1(C)CC(N)CCN(c2c(NC(=O)c3nc(-c4c(F)cccc4F)sc3N)cnn2C)C1] | 5-Amino-2-(2,6-difluoro-phenyl)-thiazole-4-carboxylic acid [5-(5-amino-3-methoxy-3-methyl-azepan-1-yl)-1-methyl-1H-pyrazol-4-yl]-amide | 0.000008 |

TABLE 1a-continued

| No. | Structure | IUPAC Name | PIM1 LC3K (KI) uM |
|---|---|---|---|
| 255 | 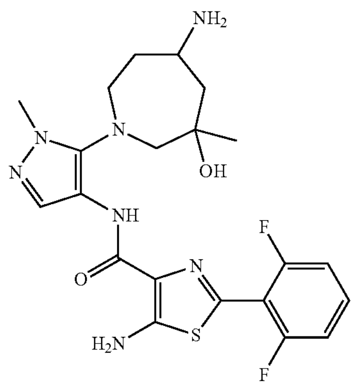 [SMILES: Cn1ncc(NC(=O)c2nc(-c3c(F)cccc3F)sc2N)c1N1CCC(N)CC(C)(O)C1] | 5-Amino-2-(2,6-difluoro-phenyl)-thiazole-4-carboxylic acid [5-(5-amino-3-hydroxy-3-methyl-azepan-1-yl)-1-methyl-1H-pyrazol-4-yl]-amide | 0.000043 |
| 256 | 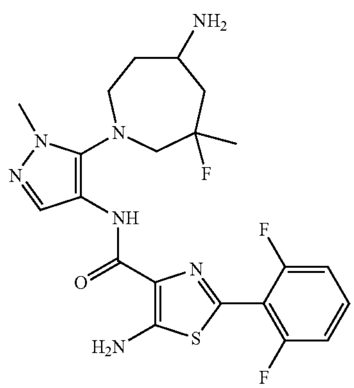 [SMILES: Cn1ncc(NC(=O)c2nc(-c3c(F)cccc3F)sc2N)c1N1CCC(N)CC(C)(F)C1] | 5-Amino-2-(2,6-difluoro-phenyl)-thiazole-4-carboxylic acid [5-(5-amino-3-fluoro-3-methyl-azepan-1-yl)-1-methyl-1H-pyrazol-4-yl]-amide | 0.000009 |
| 257 | 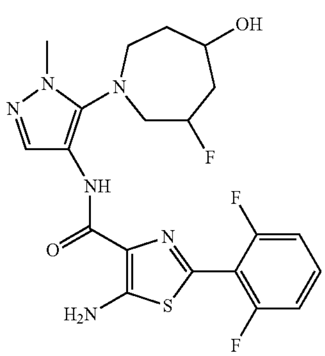 [SMILES: Cn1ncc(NC(=O)c2nc(-c3c(F)cccc3F)sc2N)c1N1CCC(O)CC(F)C1] | 5-Amino-2-(2,6-difluoro-phenyl)-thiazole-4-carboxylic acid [5-(3-fluoro-5-hydroxy-azepan-1-yl)-1-methyl-1H-pyrazol-4-yl]-amide | 0.000043 |
| 258 | 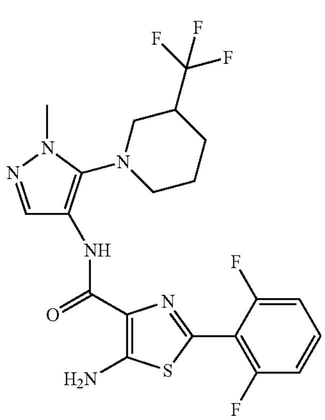 [SMILES: Cn1ncc(NC(=O)c2nc(-c3c(F)cccc3F)sc2N)c1N1CCCC(C(F)(F)F)C1] | 5-Amino-2-(2,6-difluoro-phenyl)-thiazole-4-carboxylic acid [1-methyl-5-(3-trifluoromethyl-piperidin-1-yl)-1H-pyrazol-4-yl]-amide | 0.000353 |
| 259 | | | |
| 260 | | | | ns
TABLE 1a-continued

| No. | Structure | IUPAC Name | PIM1 LC3K (KI) uM |
|---|---|---|---|
| 261 | 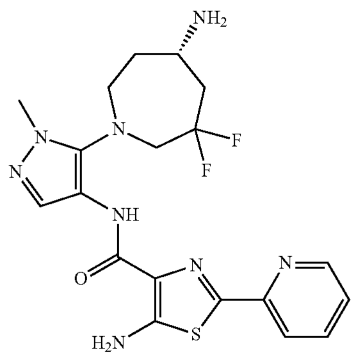 | (S)-5-amino-N-(5-(5-amino-3,3-difluoroazepan-1-yl)-1-methyl-1H-pyrazol-4-yl)-2-(pyridin-2-yl)thiazole-4-carboxamide | 0.000058 |
| 262 | 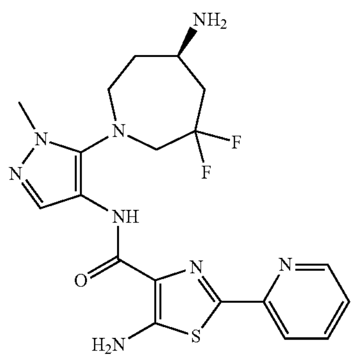 | (R)-5-amino-N-(5-(5-amino-3,3-difluoroazepan-1-yl)-1-methyl-1H-pyrazol-4-yl)-2-(pyridin-2-yl)thiazole-4-carboxamide | 0.000019 |
| 263 | 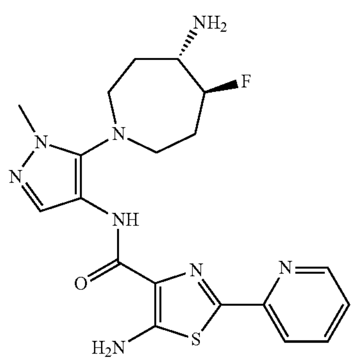 [SMILES: Cn1ncc(NC(=O)c2nc(-c3ccccn3)sc2N)c1N1CC[C@H](N)[C@@H](F)CC1] | 5-amino-N-(5-((4S,5S)-4-amino-5-fluoroazepan-1-yl)-1-methyl-1H-pyrazol-4-yl)-2-(pyridin-2-yl)thiazole-4-carboxamide | 0.000568 |
| 264 | 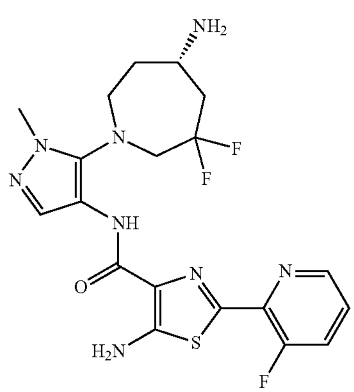 [SMILES: Cn1ncc(NC(=O)c2nc(-c3ncccc3F)sc2N)c1N1CC[C@H](N)CC(F)(F)C1] | (S)-5-amino-N-(5-(5-amino-3,3-difluoroazepan-1-yl)-1-methyl-1H-pyrazol-4-yl)-2-(3-fluoropyridin-2-yl)thiazole-4-carboxamide | 0.000027 |

TABLE 1a-continued

| No. | Structure | IUPAC Name | PIM1 LC3K (KI) uM |
|---|---|---|---|
| 265 | 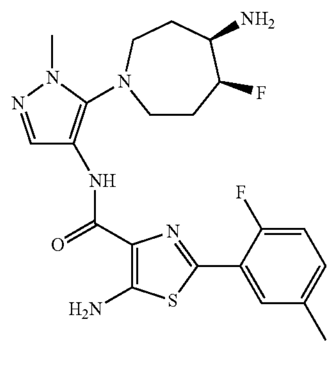 [SMILES: Cc1ccc(F)c(-c2nc(C(=O)Nc3cnn(C)c3N3CC[C@@H](N)[C@@H](F)CC3)c(N)s2)c1] | 5-amino-N-(5-((4R,5S)-4-amino-5-fluoroazepan-1-yl)-1-methyl-1H-pyrazol-4-yl)-2-(2-fluoro-5-methylphenyl)thiazole-4-carboxamide | 0.000038 |
| 266 | 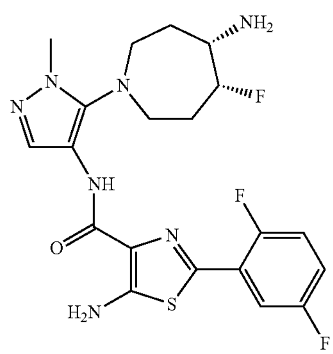 [SMILES: Cn1ncc(NC(=O)c2nc(-c3cc(F)ccc3F)sc2N)c1N1CC[C@@H](F)[C@@H](N)CC1] | 5-amino-N-(5-((4S,5R)-4-amino-5-fluoroazepan-1-yl)-1-methyl-1H-pyrazol-4-yl)-2-(2-fluoro-5-methylphenyl)thiazole-4-carboxamide | 0.000253 |
| 267 | 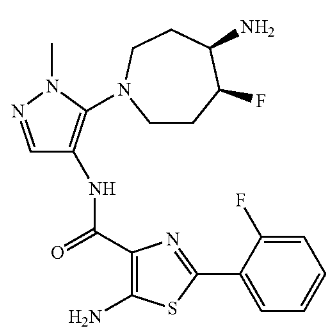 [SMILES: Cn1ncc(NC(=O)c2nc(-c3ccccc3F)sc2N)c1N1CC[C@@H](N)[C@@H](F)CC1] | 5-amino-N-(5-((4R,5S)-4-amino-5-fluoroazepan-1-yl)-1-methyl-1H-pyrazol-4-yl)-2-(2-fluorophenyl)thiazole-4-carboxamide | 0.000064 |
| 268 | 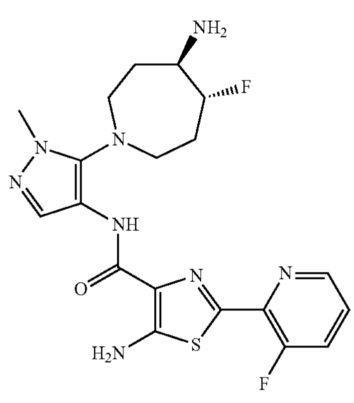 [SMILES: Cn1ncc(NC(=O)c2nc(-c3ncccc3F)sc2N)c1N1CC[C@@H](N)[C@H](F)CC1] | 5-amino-N-(5-((4R,5R)-4-amino-5-fluoroazepan-1-yl)-1-methyl-1H-pyrazol-4-yl)-2-(3-fluoropyridin-2-yl)thiazole-4-carboxamide | 0.000186 |

TABLE 1a-continued

| No. | Structure | IUPAC Name | PIM1 LC3K (KI) uM |
|---|---|---|---|
| 269 | 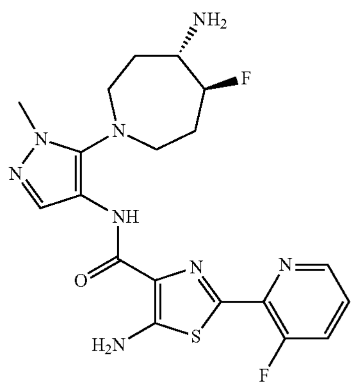 [SMILES: Cn1ncc(NC(=O)c2nc(-c3ncccc3F)sc2N)c1N1CC[C@H](N)[C@@H](F)CC1] | 5-amino-N-(5-((4S,5S)-4-amino-5-fluoroazepan-1-yl)-1-methyl-1H-pyrazol-4-yl)-2-(3-fluoropyridin-2-yl)thiazole-4-carboxamide | 0.000091 |
| 270 | 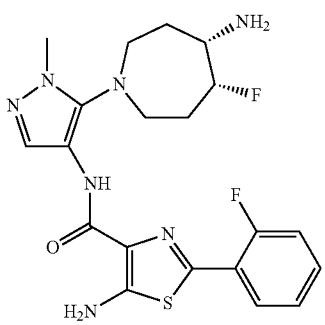 [SMILES: Cn1ncc(NC(=O)c2nc(-c3ccccc3F)sc2N)c1N1CC[C@@H](F)[C@@H](N)CC1] | 5-amino-N-(5-((4S,5R)-4-amino-5-fluoroazepan-1-yl)-1-methyl-1H-pyrazol-4-yl)-2-(2-fluorophenyl)thiazole-4-carboxamide | 0.000091 |
| 271 | 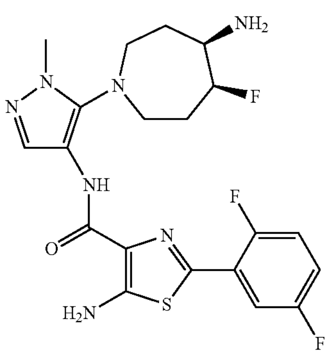 [SMILES: Cn1ncc(NC(=O)c2nc(-c3cc(F)ccc3F)sc2N)c1N1CC[C@@H](N)[C@@H](F)CC1] | 5-amino-N-(5-((4R,5S)-4-amino-5-fluoroazepan-1-yl)-1-methyl-1H-pyrazol-4-yl)-2-(2,5-difluorophenyl)thiazole-4-carboxamide | 0.000058 |
| 272 | 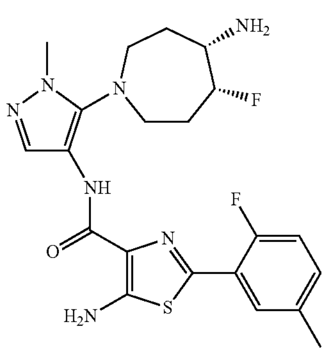 [SMILES: Cc1ccc(F)c(-c2nc(C(=O)Nc3cnn(C)c3N3CC[C@@H](F)[C@@H](N)CC3)c(N)s2)c1] | 5-amino-N-(5-((4S,5R)-4-amino-5-fluoroazepan-1-yl)-1-methyl-1H-pyrazol-4-yl)-2-(2-fluoro-5-methylphenyl)thiazole-4-carboxamide | 0.000147 |

TABLE 1a-continued

| No. | Structure | IUPAC Name | PIM1 LC3K (KI) uM |
|---|---|---|---|
| 273 | 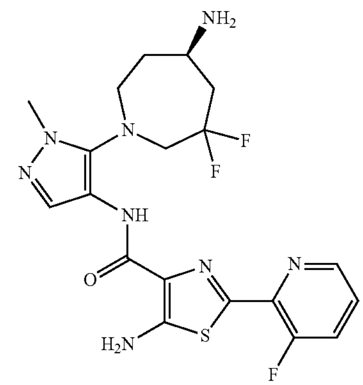 [SMILES: Cn1ncc(NC(=O)c2nc(-c3ncccc3F)sc2N)c1N1CC[C@@H](N)CC(F)(F)C1] | (R)-5-amino-N-(5-(5-amino-3,3-difluoroazepan-1-yl)-1-methyl-1H-pyrazol-4-yl)-2-(3-fluoropyridin-2-yl)thiazole-4-carboxamide | 0.000032 |
| 274 | 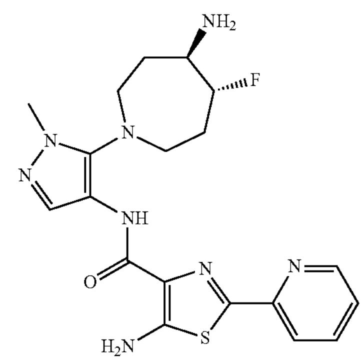 [SMILES: Cn1ncc(NC(=O)c2nc(-c3ccccn3)sc2N)c1N1CC[C@@H](N)[C@H](F)CC1] | 5-amino-N-(5-((4R,5R)-4-amino-5-fluoroazepan-1-yl)-1-methyl-1H-pyrazol-4-yl)-2-(pyridin-2-yl)thiazole-4-carboxamide | 0.00125 |
| 275 | 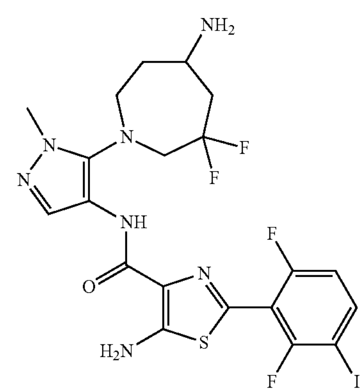 [SMILES: Cn1ncc(NC(=O)c2nc(-c3c(F)ccc(I)c3F)sc2N)c1N1CCC(N)CC(F)(F)C1] | 5-Amino-2-(2,6-difluoro-3-iodo-phenyl)-thiazole-4-carboxylic acid [5-(5-amino-3,3-difluoro-azepan-1-yl)-1-methyl-1H-pyrazol-4-yl]-amide | |
| 276 | 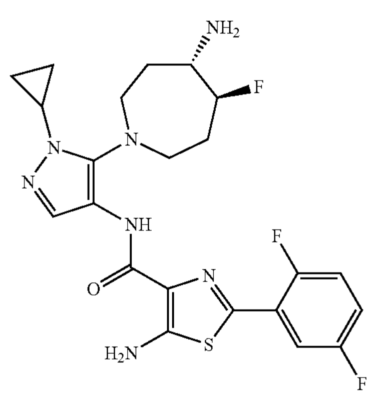 [SMILES: Nc1sc(-c2cc(F)ccc2F)nc1C(=O)Nc1cnn(C2CC2)c1N1CC[C@H](N)[C@@H](F)CC1] | 5-amino-N-(5-((4S,5S)-4-amino-5-fluoroazepan-1-yl)-1-cyclopropyl-1H-pyrazol-4-yl)-2-(2,5-difluorophenyl)thiazole-4-carboxamide | |

TABLE 1a-continued

| No. | Structure | IUPAC Name | PIM1 LC3K (KI) uM |
|---|---|---|---|
| 277 | 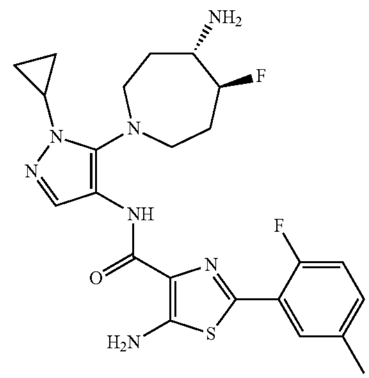 [SMILES: Cc1ccc(F)c(-c2nc(C(=O)Nc3cnn(C4CC4)c3N3CC[C@H](N)[C@@H](F)CC3)c(N)s2)c1] | 5-amino-N-(5-((4S,5S)-4-amino-5-fluoroazepan-1-yl)-1-cyclopropyl-1H-pyrazol-4-yl)-2-(2-fluoro-5-methylphenyl)thiazole-4-carboxamide | |
| 278 | 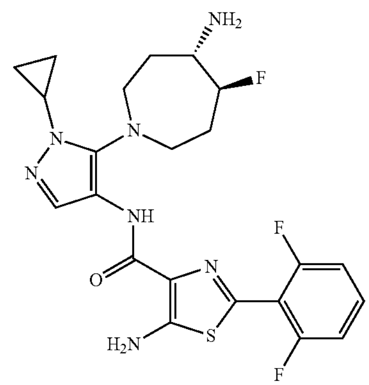 [SMILES: Nc1sc(-c2c(F)cccc2F)nc1C(=O)Nc1cnn(C2CC2)c1N1CC[C@H](N)[C@@H](F)CC1] | 5-amino-N-(5-((4S,5S)-4-amino-5-fluoroazepan-1-yl)-1-cyclopropyl-1H-pyrazol-4-yl)-2-(2,6-difluorophenyl)thiazole-4-carboxamide | |
| 279 | 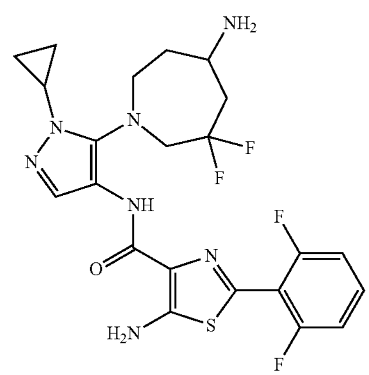 [SMILES: Nc1sc(-c2c(F)cccc2F)nc1C(=O)Nc1cnn(C2CC2)c1N1CCC(N)CC(F)(F)C1] | 5-Amino-2-(2,6-difluoro-phenyl)-thiazole-4-carboxylic acid [5-(5-amino-3,3-difluoro-azepan-1-yl)-1-cyclopropyl-1H-pyrazol-4-yl]-amide | |
| 280 | 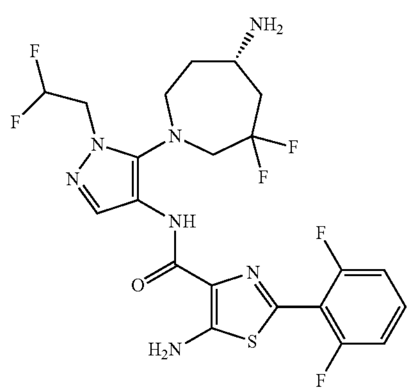 [SMILES: Nc1sc(-c2c(F)cccc2F)nc1C(=O)Nc1cnn(CC(F)F)c1N1CC[C@H](N)CC(F)(F)C1] | (R)-5-amino-N-(5-(5-amino-3,3-difluoroazepan-1-yl)-1-methyl-1H-pyrazol-4-yl)-2-(2,5-difluorophenyl)thiazole-4-carboxamide | 0.00001 |

TABLE 1a-continued

| No. | Structure | IUPAC Name | PIM1 LC3K (KI) uM |
|---|---|---|---|
| 281 | 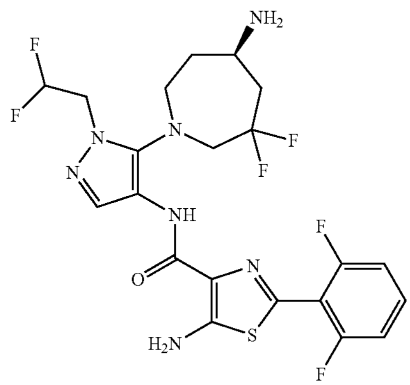 [SMILES: Nc1sc(-c2c(F)cccc2F)nc1C(=O)Nc1cnn(CC(F)F)c1N1CC[C@@H](N)CC(F)(F)C1] | (S)-5-amino-N-(5-(5-amino-3,3-difluoroazepan-1-yl)-1-methyl-1H-pyrazol-4-yl)-2-(2,5-difluorophenyl)thiazole-4-carboxamide | 0.00002 |
| 282 | 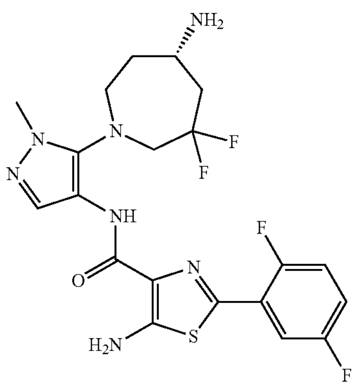 [SMILES: Cn1ncc(NC(=O)c2nc(-c3cc(F)ccc3F)sc2N)c1N1CC[C@H](N)CC(F)(F)C1] | (S)-5-amino-N-(5-(5-amino-3,3-difluoroazepan-1-yl)-1-methyl-1H-pyrazol-4-yl)-2-(2,5-difluorophenyl)thiazole-4-carboxamide | 0.000004 |
| 283 | 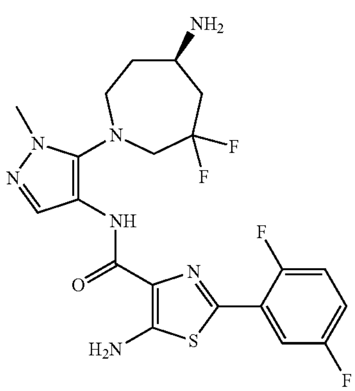 [SMILES: Cn1ncc(NC(=O)c2nc(-c3cc(F)ccc3F)sc2N)c1N1CC[C@@H](N)CC(F)(F)C1] | (R)-5-amino-N-(5-(5-amino-3,3-difluoroazepan-1-yl)-1-methyl-1H-pyrazol-4-yl)-2-(2,5-difluorophenyl)thiazole-4-carboxamide | 0.000008 |
| 284 | 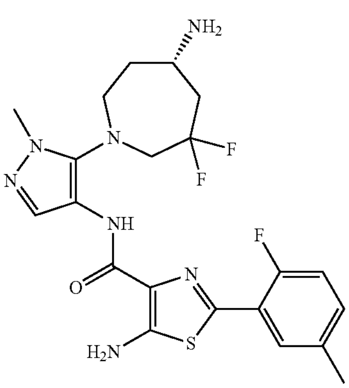 [SMILES: Cc1ccc(F)c(-c2nc(C(=O)Nc3cnn(C)c3N3CC[C@H](N)CC(F)(F)C3)c(N)s2)c1] | (S)-5-amino-N-(5-(5-amino-3,3-difluoroazepan-1-yl)-1-methyl-1H-pyrazol-4-yl)-2-(2-fluoro-5-methylphenyl)thiazole-4-carboxamide | 0.000015 |

TABLE 1a-continued

| No. | Structure | IUPAC Name | PIM1 LC3K (KI) uM |
|---|---|---|---|
| 285 | 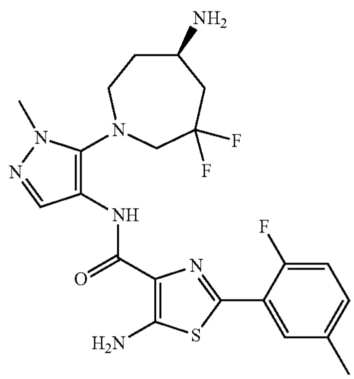 [SMILES: Cc1ccc(F)c(-c2nc(C(=O)Nc3cnn(C)c3N3CC[C@@H](N)CC(F)(F)C3)c(N)s2)c1] | ((R)-5-amino-N-(5-(5-amino-3,3-difluoroazepan-1-yl)-1-methyl-1H-pyrazol-4-yl)-2-(2-fluoro-5-methylphenyl)thiazole-4-carboxamide | 0.000018 |
| 286 | 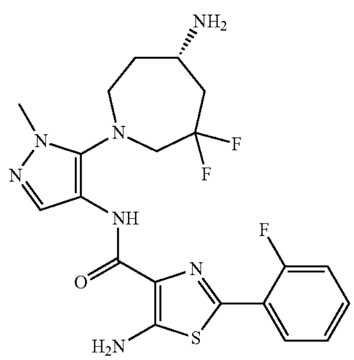 [SMILES: Cn1ncc(NC(=O)c2nc(-c3ccccc3F)sc2N)c1N1CC[C@H](N)CC(F)(F)C1] | (S)-5-amino-N-(5-(5-amino-3,3-difluoroazepan-1-yl)-1-methyl-1H-pyrazol-4-yl)-2-(2-fluorophenyl)thiazole-4-carboxamide | 0.00001 |
| 287 | 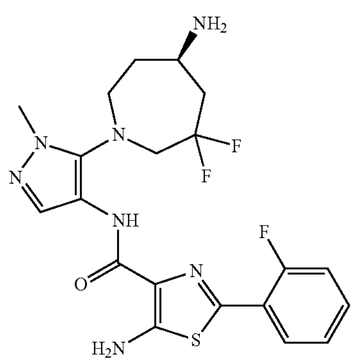 [SMILES: Cn1ncc(NC(=O)c2nc(-c3ccccc3F)sc2N)c1N1CC[C@@H](N)CC(F)(F)C1] | 5-Amino-2-(2-fluoro-phenyl)-thiazole-4-carboxylic acid [5-((R)-5-amino-3,3-difluoro-azepan-1-yl)-1-methyl-1H-pyrazol-4-yl]-amide | 0.000009 |
| 288 | 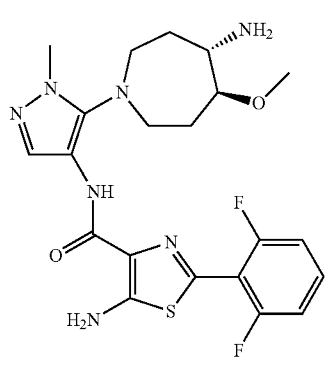 [SMILES: CO[C@H]1CCN(c2c(NC(=O)c3nc(-c4c(F)cccc4F)sc3N)cnn2C)CC[C@@H]1N] | 5-amino-N-(5-((4S,5S)-4-amino-5-methoxyazepan-1-yl)-1-methyl-1H-pyrazol-4-yl)-2-(2,6-difluorophenyl)thiazole-4-carboxamide | 0.000076 |

TABLE 1a-continued

| No. | Structure | IUPAC Name | PIM1 LC3K (KI) uM |
|---|---|---|---|
| 289 | 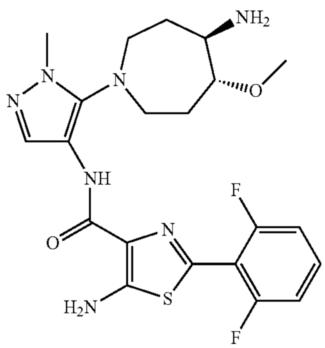 [SMILES: CO[C@@H]1CCN(c2c(NC(=O)c3nc(-c4c(F)cccc4F)sc3N)cnn2C)CC[C@H]1N] | 5-amino-N-(5-((4R,5R)-4-amino-5-methoxyazepan-1-yl)-1-methyl-1H-pyrazol-4-yl)-2-(2,6-difluorophenyl)thiazole-4-carboxamide | 0.000114 |
| 290 | 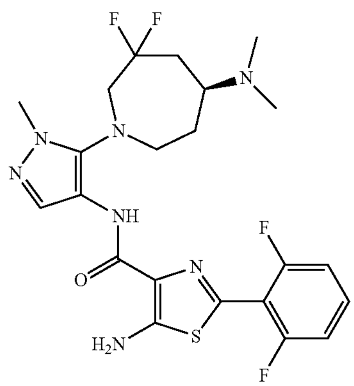 [SMILES: CN(C)[C@H]1CCN(c2c(NC(=O)c3nc(-c4c(F)cccc4F)sc3N)cnn2C)CC(F)(F)C1] | (S)-5-amino-2-(2,6-difluorophenyl)-N-(5-(5-(dimethylamino)-3,3-difluoroazepan-1-yl)-1-methyl-1H-pyrazol-4-yl)thiazole-4-carboxamide | 0.000026 |
| 291 | 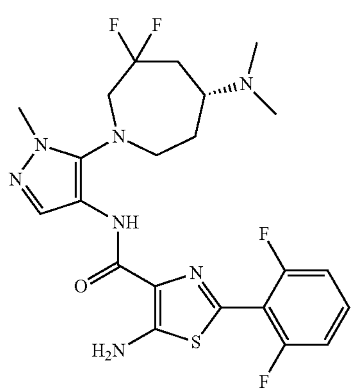 [SMILES: CN(C)[C@@H]1CCN(c2c(NC(=O)c3nc(-c4c(F)cccc4F)sc3N)cnn2C)CC(F)(F)C1] | (R)-5-amino-2-(2,6-difluorophenyl)-N-(5-(5-(dimethylamino)-3,3-difluoroazepan-1-yl)-1-methyl-1H-pyrazol-4-yl)thiazole-4-carboxamide | 0.000066 |
| 292 | 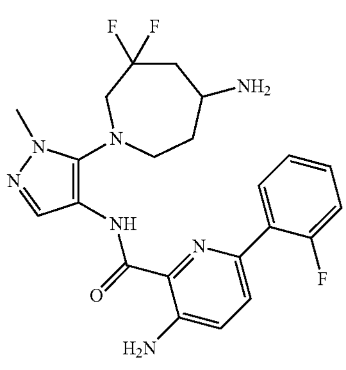 [SMILES: Cn1ncc(NC(=O)c2nc(-c3ccccc3F)ccc2N)c1N1CCC(N)CC(F)(F)C1] | 3-amino-N-(5-(5-amino-3,3-difluoroazepan-1-yl)-1-methyl-1H-pyrazol-4-yl)-6-(2-fluorophenyl)picolinamide | 0.000021 |

TABLE 1a-continued

| No. | Structure | IUPAC Name | PIM1 LC3K (KI) uM |
|---|---|---|---|
| 293 | 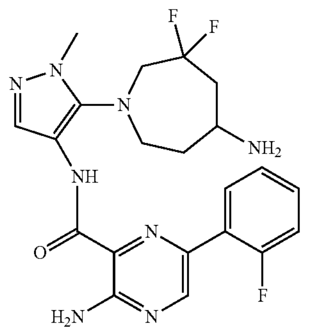 [SMILES: Cn1ncc(NC(=O)c2nc(-c3ccccc3F)cnc2N)c1N1CCC(N)CC(F)(F)C1] | 3-amino-N-(5-(5-amino-3,3-difluoroazepan-1-yl)-1-methyl-1H-pyrazol-4-yl)-6-(2-fluorophenyl)pyrazine-2-carboxamide | 0.000023 |
| 294 | 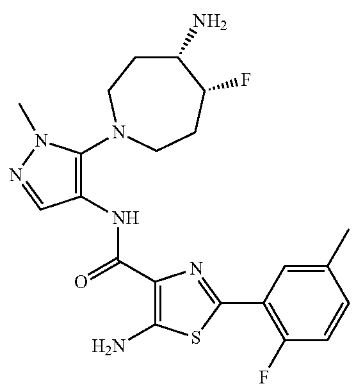 [SMILES: Cc1ccc(F)c(-c2nc(C(=O)Nc3cnn(C)c3N3CC[C@@H](F)[C@@H](N)CC3)c(N)s2)c1] | 5-amino-N-(5-((4S,5R)-4-amino-5-fluoroazepan-1-yl)-1-methyl-1H-pyrazol-4-yl)-2-(2-fluoro-5-methylphenyl)thiazole-4-carboxamide | |
| 295 | 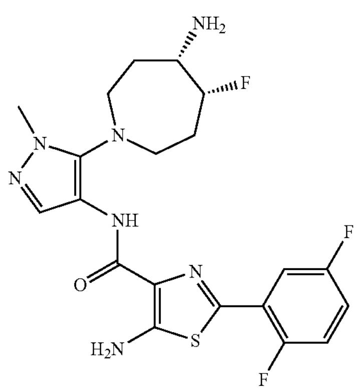 [SMILES: Cn1ncc(NC(=O)c2nc(-c3cc(F)ccc3F)sc2N)c1N1CC[C@@H](F)[C@@H](N)CC1] | 5-amino-N-(5-((4S,5R)-4-amino-5-fluoroazepan-1-yl)-1-methyl-1H-pyrazol-4-yl)-2-(2,5-difluorophenyl)thiazole-4-carboxamide | |
| 296 | 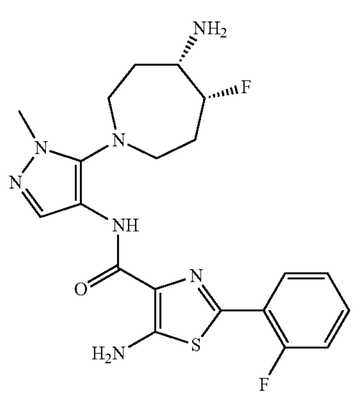 [SMILES: Cn1ncc(NC(=O)c2nc(-c3ccccc3F)sc2N)c1N1CC[C@@H](F)[C@@H](N)CC1] | 5-amino-N-(5-((4S,5R)-4-amino-5-fluoroazepan-1-yl)-1-methyl-1H-pyrazol-4-yl)-2-(2-fluorophenyl)thiazole-4-carboxamide | |

TABLE 1a-continued

| No. | Structure | IUPAC Name | PIM1 LC3K (KI) uM |
|---|---|---|---|
| 297 | 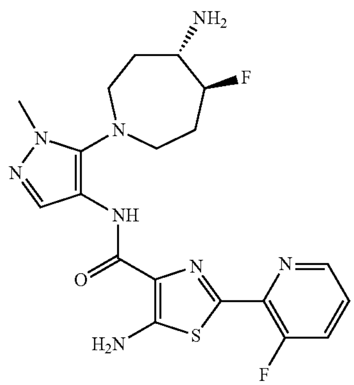 [SMILES: Cn1ncc(NC(=O)c2nc(-c3ncccc3F)sc2N)c1N1CC[C@H](N)[C@@H](F)CC1] | 5-amino-N-(5-((4S,5S)-4-amino-5-fluoroazepan-1-yl)-1-methyl-1H-pyrazol-4-yl)-2-(3-fluoropyridin-2-yl)thiazole-4-carboxamide | |
| 298 | 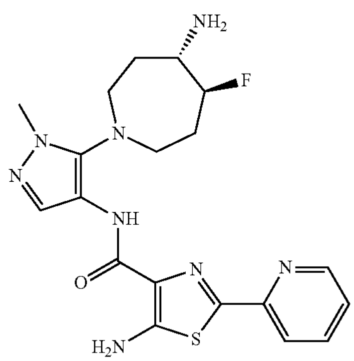 [SMILES: Cn1ncc(NC(=O)c2nc(-c3ccccn3)sc2N)c1N1CC[C@H](N)[C@@H](F)CC1] | 5-amino-N-(5-((4S,5S)-4-amino-5-fluoroazepan-1-yl)-1-methyl-1H-pyrazol-4-yl)-2-(pyridin-2-yl)thiazole-4-carboxamide | |
| 299 | 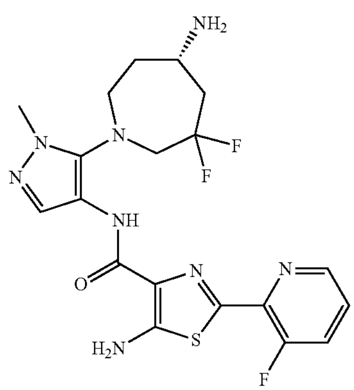 [SMILES: Cn1ncc(NC(=O)c2nc(-c3ncccc3F)sc2N)c1N1CC[C@H](N)CC(F)(F)C1] | 5-Amino-2-(3-fluoro-pyridin-2-yl)-thiazole-4-carboxylic acid [5-(5-amino-3,3-difluoro-azepan-1-yl)-1-methyl-1H-pyrazol-4-yl]-amide | |
| 300 | 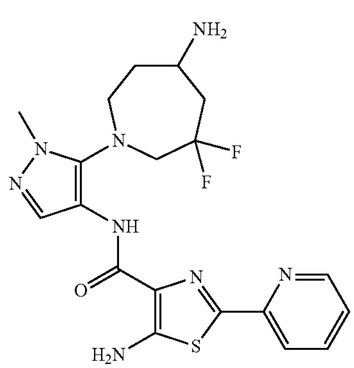 [SMILES: Cn1ncc(NC(=O)c2nc(-c3ccccn3)sc2N)c1N1CCC(N)CC(F)(F)C1] | 5-Amino-2-pyridin-2-yl-thiazole-4-carboxylic acid [5-(5-amino-3,3-difluoro-azepan-1-yl)-1-methyl-1H-pyrazol-4-yl]-amide | |

TABLE 1a-continued

| No. | Structure | IUPAC Name | PIM1 LC3K (KI) uM |
|---|---|---|---|
| 301 | 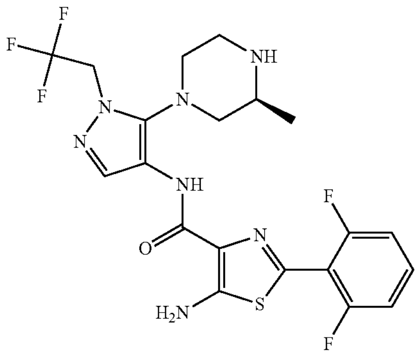 [SMILES: C[C@H]1CN(c2c(NC(=O)c3nc(-c4c(F)cccc4F)sc3N)cnn2CC(F)(F)F)CCN1] | (S)-5-Amino-2-(2,6-difluorophenyl)-N-(5-(3-methylpiperazin-1-yl)-1-(2,2,2-trifluoroethyl)-1H-pyrazol-4-yl)thiazole-4-carboxamide | 0.0021 |
| 302 | 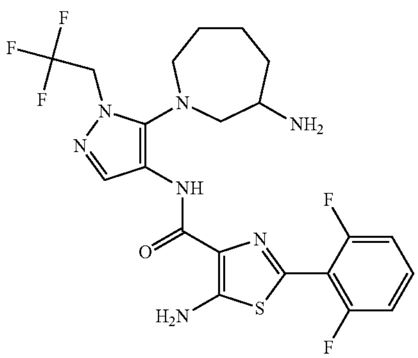 [SMILES: Nc1sc(-c2c(F)cccc2F)nc1C(=O)Nc1cnn(CC(F)(F)F)c1N1CCCCC(N)C1] | 5-Amino-2-(2,6-difluoro-phenyl)-thiazole-4-carboxylic acid [5-(3-amino-azepan-1-yl)-1-(2,2,2-trifluoro-ethyl)-1H-pyrazol-4-yl]-amide | 0.000175 |
| 303 | 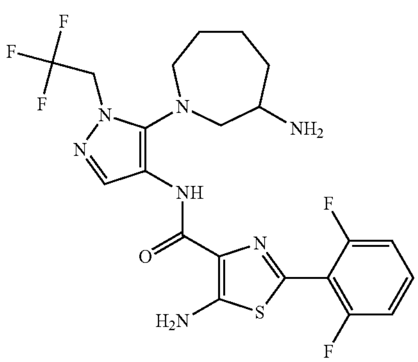 [SMILES: Nc1sc(-c2c(F)cccc2F)nc1C(=O)Nc1cnn(CC(F)(F)F)c1N1CCCCC(N)C1] | 5-Amino-2-(2,6-difluoro-phenyl)-thiazole-4-carboxylic acid [5-(3-amino-azepan-1-yl)-1-(2,2,2-trifluoro-ethyl)-1H-pyrazol-4-yl]-amide | 0.000208 |
| 304 | 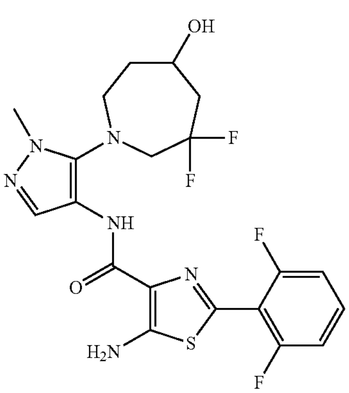 [SMILES: Cn1ncc(NC(=O)c2nc(-c3c(F)cccc3F)sc2N)c1N1CCC(O)CC(F)(F)C1] | 5-Amino-2-(2,6-difluoro-phenyl)-thiazole-4-carboxylic acid [5-(3,3-difluoro-5-hydroxy-azepan-1-yl)-1-methyl-1H-pyrazol-4-yl]-amide | |

TABLE 1a-continued

| No. | Structure | IUPAC Name | PIM1 LC3K (KI) uM |
|---|---|---|---|
| 305 | 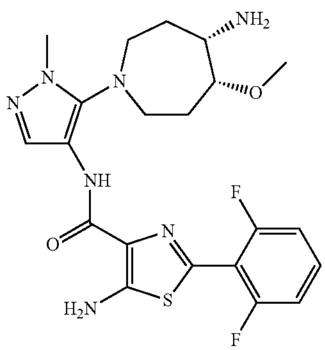 [SMILES: CO[C@@H]1CCN(c2c(NC(=O)c3nc(-c4c(F)cccc4F)sc3N)cnn2C)CC[C@@H]1N] | 5-amino-N-(5-((4S,5R)-4-amino-5-methoxyazepan-1-yl)-1-methyl-1H-pyrazol-4-yl)-2-(2,6-difluorophenyl)thiazole-4-carboxamide | |
| 306 | 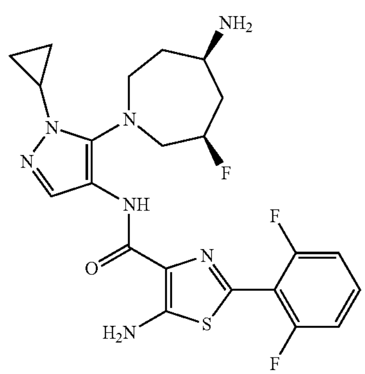 [SMILES: Nc1sc(-c2c(F)cccc2F)nc1C(=O)Nc1cnn(C2CC2)c1N1CC[C@@H](N)C[C@@H](F)C1] | 5-amino-N-(5-((3R,5R)-5-amino-3-fluoroazepan-1-yl)-1-cyclopropyl-1H-pyrazol-4-yl)-2-(2,6-difluorophenyl)thiazole-4-carboxamide | |
| 307 | 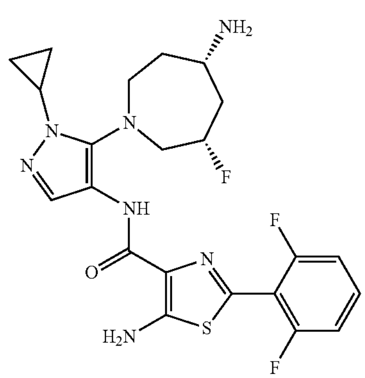 [SMILES: Nc1sc(-c2c(F)cccc2F)nc1C(=O)Nc1cnn(C2CC2)c1N1CC[C@H](N)C[C@H](F)C1] | 5-amino-N-(5-((3S,5S)-5-amino-3-fluoroazepan-1-yl)-1-cyclopropyl-1H-pyrazol-4-yl)-2-(2,6-difluorophenyl)thiazole-4-carboxamide | |
| 308 | 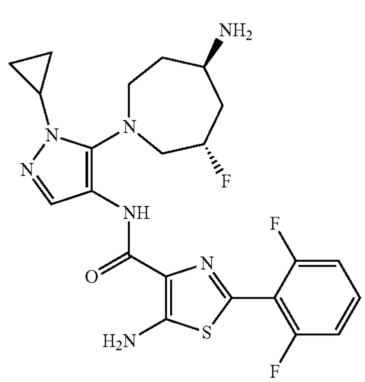 [SMILES: Nc1sc(-c2c(F)cccc2F)nc1C(=O)Nc1cnn(C2CC2)c1N1CC[C@@H](N)C[C@H](F)C1] | 5-amino-N-(5-((3S,5R)-5-amino-3-fluoroazepan-1-yl)-1-cyclopropyl-1H-pyrazol-4-yl)-2-(2,6-difluorophenyl)thiazole-4-carboxamide | |

TABLE 1a-continued

| No. | Structure | IUPAC Name | PIM1 LC3K (KI) uM |
|---|---|---|---|
| 309 | 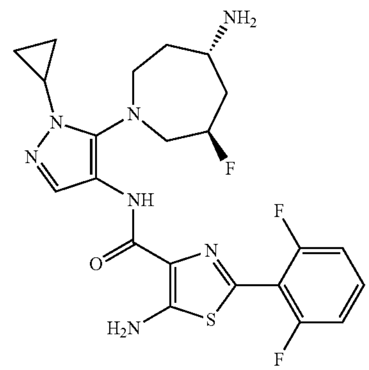 [SMILES: Nc1sc(-c2c(F)cccc2F)nc1C(=O)Nc1cnn(C2CC2)c1N1CC[C@H](N)C[C@@H](F)C1] | 5-amino-N-(5-((3R,5S)-5-amino-3-fluoroazepan-1-yl)-1-cyclopropyl-1H-pyrazol-4-yl)-2-(2,6-difluorophenyl)thiazole-4-carboxamide | |
| 310 | 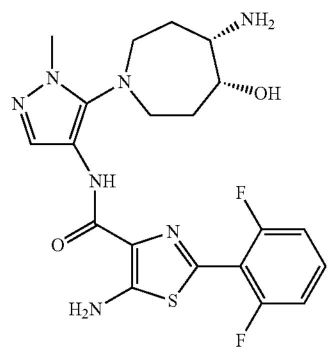 [SMILES: Cn1ncc(NC(=O)c2nc(-c3c(F)cccc3F)sc2N)c1N1CC[C@@H](O)[C@@H](N)CC1] | 5-amino-N-(5-((4S,5R)-4-amino-5-hydroxyazepan-1-yl)-1-methyl-1H-pyrazol-4-yl)-2-(2,6-difluorophenyl)thiazole-4-carboxamide | |
| 311 | 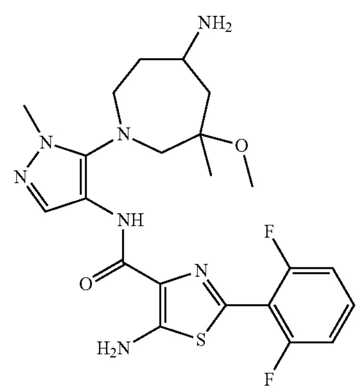 [SMILES: COC1(C)CC(N)CCN(c2c(NC(=O)c3nc(-c4c(F)cccc4F)sc3N)cnn2C)C1] | 5-Amino-2-(2,6-difluoro-phenyl)-thiazole-4-carboxylic acid [5-(5-amino-3-methoxy-3-methyl-azepan-1-yl)-1-methyl-1H-pyrazol-4-yl]-amide | |
| 312 | 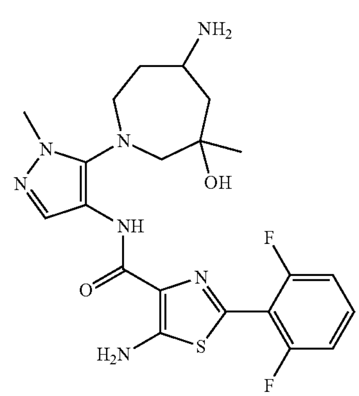 [SMILES: Cn1ncc(NC(=O)c2nc(-c3c(F)cccc3F)sc2N)c1N1CCC(N)CC(C)(O)C1] | 5-Amino-2-(2,6-difluoro-phenyl)-thiazole-4-carboxylic acid [5-(5-amino-3-hydroxy-3-methyl-azepan-1-yl)-1-methyl-1H-pyrazol-4-yl]-amide | |

TABLE 1b

| No. | Structure | IUPAC Name | PIM1 LC3K (KI) uM |
|---|---|---|---|
| 313 | 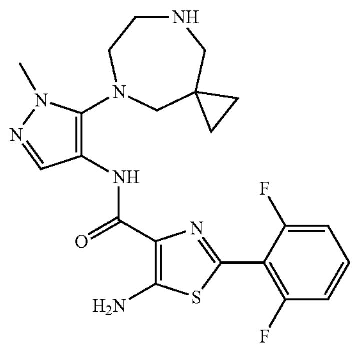 [SMILES: Cn1ncc(NC(=O)c2nc(-c3c(F)cccc3F)sc2N)c1N1CCNCC2(CC2)C1] | 5-amino-N-[5-(5,8-diazaspiro[2.6]nonan-8-yl)-1-methyl-pyrazol-4-yl]-2-(2,6-difluorophenyl)thiazole-4-carboxamide | 0.000025 |
| 314 | 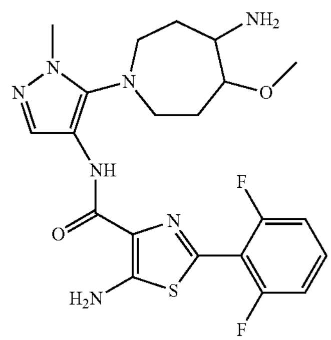 [SMILES: COC1CCN(c2c(NC(=O)c3nc(-c4c(F)cccc4F)sc3N)cnn2C)CCC1N] | 5-amion-N-[5-(4-amino-5-methoxy-azepan-1-yl)-1-methyl-pyrazol-4-yl]-2-(2,6-difluorophenyl)thiazole-4-carboxamide | 0.00007 |
| 315 | 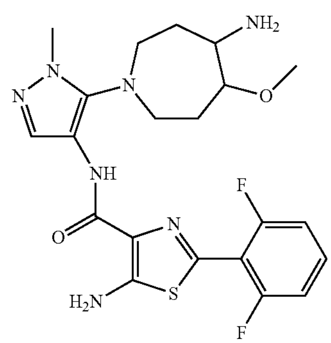 [SMILES: COC1CCN(c2c(NC(=O)c3nc(-c4c(F)cccc4F)sc3N)cnn2C)CCC1N] | 5-amino-N-[5-(4-amino-5-methoxy-azepan-1-yl)-1-methyl-pyrazol-4-yl]-2-(2,6-difluorophenyl)thiazole-4-carboxamide | 0.000052 |
| 316 | 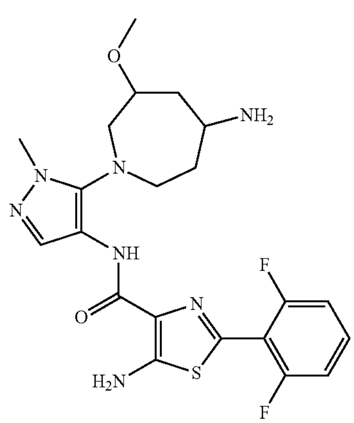 [SMILES: COC1CC(N)CCN(c2c(NC(=O)c3nc(-c4c(F)cccc4F)sc3N)cnn2C)C1] | 5-amino-N-[5-(5-amino-3-methoxy-azepan-1-yl)-1-methyl-pyrazol-4-yl]-2-(2,6-difluorophenyl)thiazole-4-carboxamide | 0.000097 |

TABLE 1b-continued

| No. | Structure | IUPAC Name | PIM1 LC3K (KI) uM |
|---|---|---|---|
| 317 | 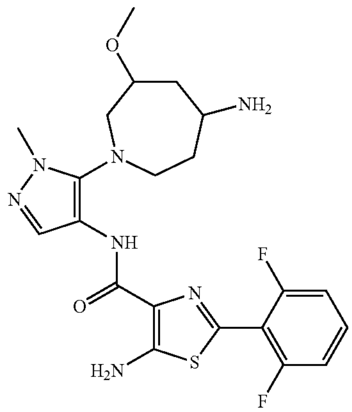 [SMILES: COC1CC(N)CCN(c2c(NC(=O)c3nc(-c4c(F)cccc4F)sc3N)cnn2C)C1] | 5-amino-N-[5-(5-amino-3-methoxy-azepan-1-yl)-1-methyl-pyrazol-4-yl]-2-(2,6-difluorophenyl)thiazole-4-carboxamide | 0.000018 |
| 318 | 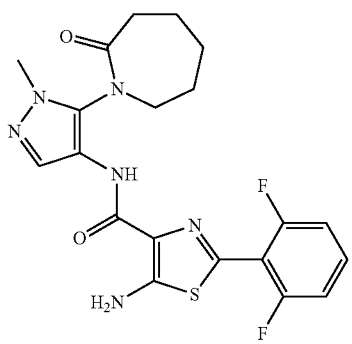 [SMILES: Cn1ncc(NC(=O)c2nc(-c3c(F)cccc3F)sc2N)c1N1CCCCCC1=O] | 5-amino-2-(2,6-difluorophenyl)-N-[1-methyl-5-(2-oxoazepan-1-yl)pyrazol-4-yl]thiazole-4-carboxamide | 0.0189 |
| 319 | 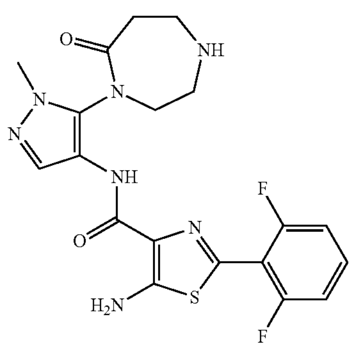 [SMILES: Cn1ncc(NC(=O)c2nc(-c3c(F)cccc3F)sc2N)c1N1CCNCCC1=O] | 5-amino-2-(2,6-difluorophenyl)-N-[1-methyl-5-(7-oxo-1,4-diazepan-1-yl)pyrazol-4-yl]thiazole-4-carboxamide | 0.00102 |
| 320 | 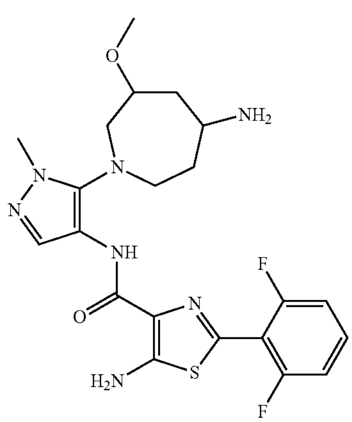 [SMILES: COC1CC(N)CCN(c2c(NC(=O)c3nc(-c4c(F)cccc4F)sc3N)cnn2C)C1] | 5-amino-N-[5-(5-amino-3-methoxy-azepan-1-yl)-1-methyl-pyrazol-4-yl]-2-(2,6-difluorophenyl)thiazole-4-carboxamide | 0.00005 |

TABLE 1b-continued

| No. | Structure | IUPAC Name | PIM1 LC3K (KI) uM |
|---|---|---|---|
| 321 | 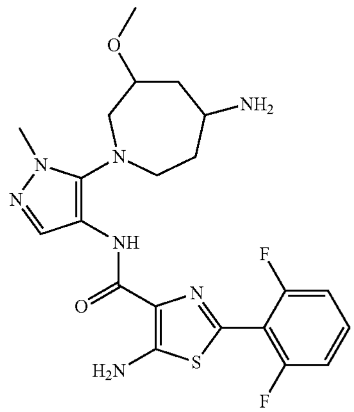 [SMILES: COC1CC(N)CCN(c2c(NC(=O)c3nc(-c4c(F)cccc4F)sc3N)cnn2C)C1] | 5-amino-N-[5-(5-amino-3-methoxy-azepan-1-yl)-1-methyl-pyrazol-4-yl]-2-(2,6-difluorophenyl)thiazole-4-carboxamide | 0.000007 |
| 322 | 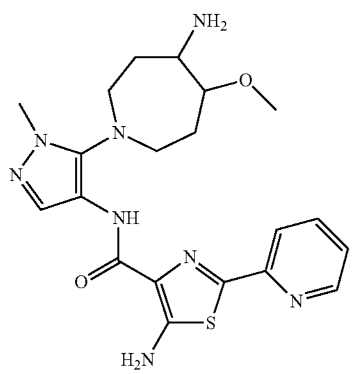 [SMILES: COC1CCN(c2c(NC(=O)c3nc(-c4ccccn4)sc3N)cnn2C)CCC1N] | 5-amino-N-[5-(4-amino-5-methoxy-azepan-1-yl)-1-methyl-pyrazol-4-yl]-2-(2-pyridyl)thiazole-4-carboxamide | 0.000833 |
| 323 | 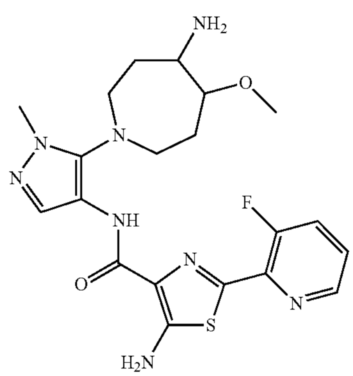 [SMILES: COC1CCN(c2c(NC(=O)c3nc(-c4ncccc4F)sc3N)cnn2C)CCC1N] | 5-amino-N-[5-(4-amino-5-methoxy-azepan-1-yl)-1-methyl-pyrazol-4-yl]-2-(3-fluoro-2-pyridyl)thiazole-4-carboxamide | 0.000266 |
| 324 | 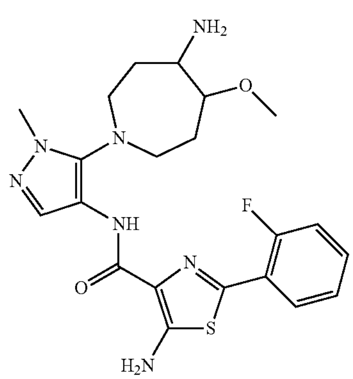 [SMILES: COC1CCN(c2c(NC(=O)c3nc(-c4ccccc4F)sc3N)cnn2C)CCC1N] | 5-amino-N-[5-(4-amino-5-methoxy-azepan-1-yl)-1-methyl-pyrazol-4-yl]-2-(2-fluorophenyl)thiazole-4-carboxamide | 0.0000694 |

TABLE 1b-continued

| No. | Structure | IUPAC Name | PIM1 LC3K (KI) uM |
|---|---|---|---|
| 325 | 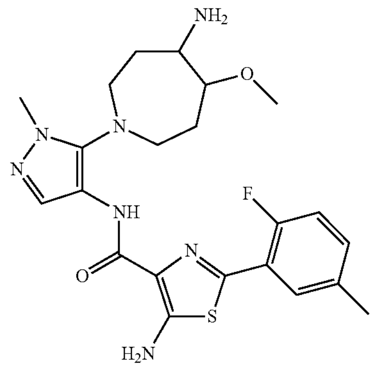 [SMILES: COC1CCN(c2c(NC(=O)c3nc(-c4cc(C)ccc4F)sc3N)cnn2C)CCC1N] | 5-amino-N-[5-(4-amino-5-methoxy-azepan-1-yl)-1-methyl-pyrazol-4-yl]-2-(2-fluoro-5-methyl-phenyl)thiazole-4-carboxamide | 0.000153 |
| 326 | 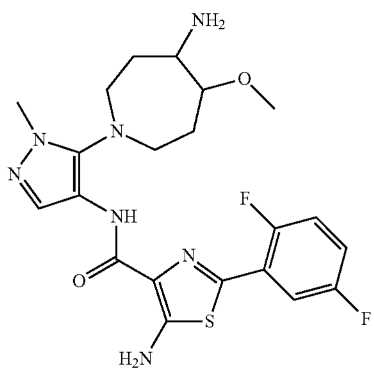 [SMILES: COC1CCN(c2c(NC(=O)c3nc(-c4cc(F)ccc4F)sc3N)cnn2C)CCC1N] | 5-amino-N-[5-(4-amino-5-methoxy-azepan-1-yl)-1-methyl-pyrazol-4-yl]-2-(2,5-difluorophenyl)thiazole-4-carboxamide | 0.000384 |
| 327 | 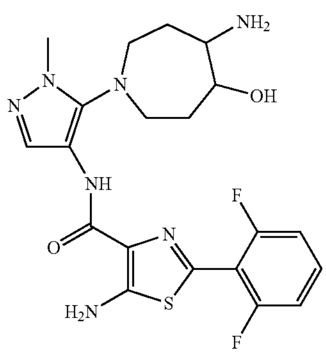 [SMILES: Cn1ncc(NC(=O)c2nc(-c3c(F)cccc3F)sc2N)c1N1CCC(N)C(O)CC1] | 5-amino-N-[5-(4-amino-5-hydroxy-azepan-1-yl)-1-methyl-pyraozl-4-yl]-2-(2,6-difluorophenyl)thiazole-4-carboxamide | 0.000118 |
| 328 | 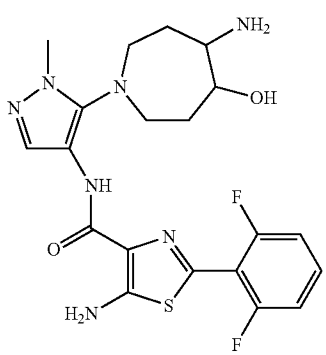 | 5-amino-N-[5-(4-amino-5-hydroxy-azepan-1-yl)-1-methyl-pyraozl-4-yl]-2-(2,6-difluorophenyl)thiazole-4-carboxamide | 0.000128 |

TABLE 1b-continued

| No. | Structure | IUPAC Name | PIM1 LC3K (KI) uM |
|---|---|---|---|
| 329 | 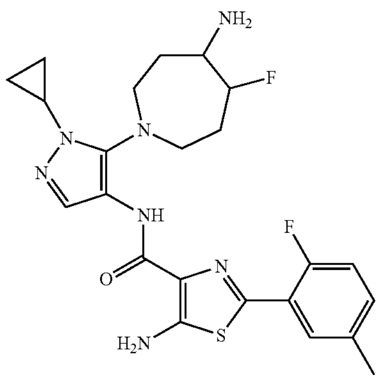 [SMILES: Cc1ccc(F)c(-c2nc(C(=O)Nc3cnn(C4CC4)c3N3CCC(N)C(F)CC3)c(N)s2)c1] | 5-amino-N-[5-(4-amino-5-fluoro-azepan-1-yl)-1-cyclopropyl-pyrazol-4-yl]-2-(2-fluoro-5-methyl-phenyl)thiazole-4-carboxamide | 0.000248 |
| 330 | 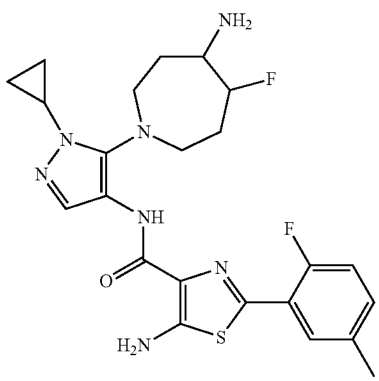 [SMILES: Cc1ccc(F)c(-c2nc(C(=O)Nc3cnn(C4CC4)c3N3CCC(N)C(F)CC3)c(N)s2)c1] | 5-amino-N-[5-(4-amino-5-fluoro-azepan-1-yl)-1-cyclopropyl-pyrazol-4-yl]-2-(2-fluoro-5-methyl-phenyl)thiazole-4-carboxamide | 0.000087 |
| 331 | 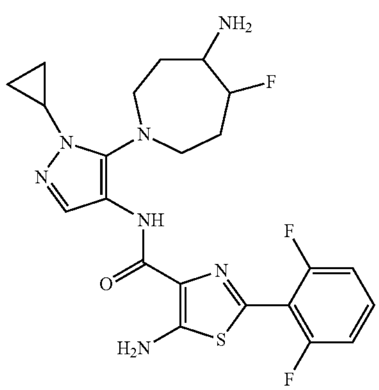 [SMILES: Nc1sc(-c2c(F)cccc2F)nc1C(=O)Nc1cnn(C2CC2)c1N1CCC(N)C(F)CC1] | 5-amino-N-[5-(4-amino-5-fluoro-azepan-1-yl)-1-cyclopropyl-pyrazol-4-yl]-2-(2,6-difluorophenyl)thiazole-4-carboxamide | 0.0000647 |
| 332 | 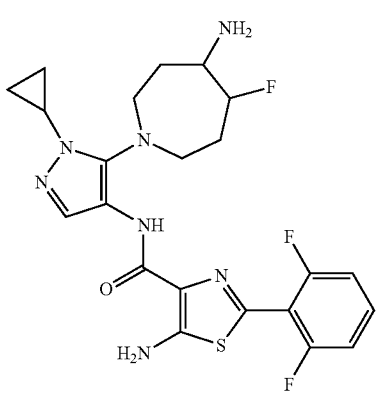 [SMILES: Nc1sc(-c2c(F)cccc2F)nc1C(=O)Nc1cnn(C2CC2)c1N1CCC(N)C(F)CC1] | 5-amino-N-[5-(4-amino-5-fluoro-azepan-1-yl)-1-cyclopropyl-pyrazol-4-yl]-2-(2,6-difluorophenyl)thiazole-4-carboxamide | 0.000148 |

TABLE 1b-continued

| No. | Structure | IUPAC Name | PIM1 LC3K (KI) uM |
|---|---|---|---|
| 333 | 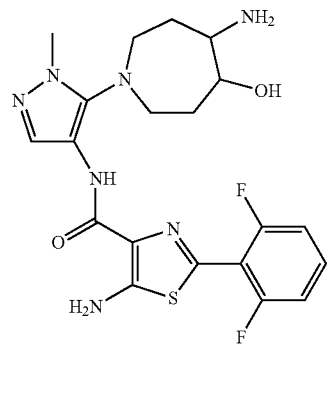 [SMILES: Cn1ncc(NC(=O)c2nc(-c3c(F)cccc3F)sc2N)c1N1CCC(N)C(O)CC1] | 5-amino-N-[5-(4-amino-5-hydroxy-azepan-1-yl)-1-methyl-pyrazol-4-yl]-2-(2,6-difluorophenyl)thiazole-4-carboxamide | 0.000192 |
| 334 | 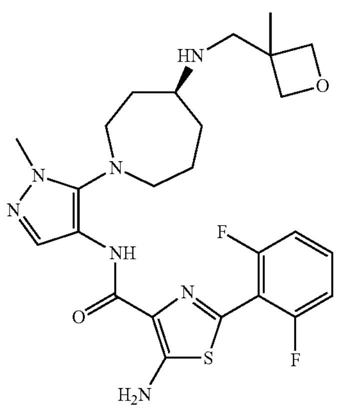 [SMILES: Cn1ncc(NC(=O)c2nc(-c3c(F)cccc3F)sc2N)c1N1CCC[C@H](NCC2(C)COC2)CC1] | 5-amino-2-(2,6-difluorophenyl)-N-[1-methyl-5-[(4S)-4-[(3-methyloxetan-3-yl)methylamino]azepan-1-yl]pyrazol-4-yl]thiazole-4-carboxamide | 0.000295 |
| 335 | 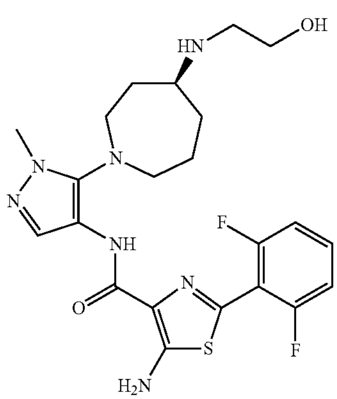 [SMILES: Cn1ncc(NC(=O)c2nc(-c3c(F)cccc3F)sc2N)c1N1CCC[C@H](NCCO)CC1] | 5-amino-2-(2,6-difluorophenyl)-N-[5-[(4S)-4-(2-hydroxyethylamino)azepan-1-yl]-1-methyl-pyrazol-4-yl]thiazole-4-carboxamide | 0.000104 |

TABLE 1b-continued

| No. | Structure | IUPAC Name | PIM1 LC3K (KI) uM |
|---|---|---|---|
| 336 | 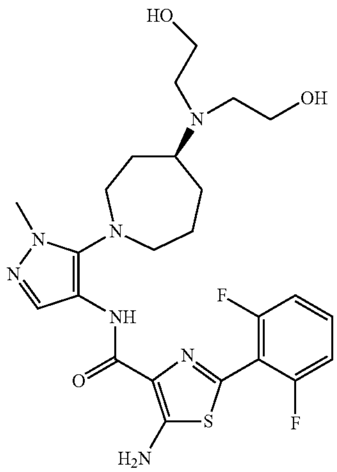 [SMILES: Cn1ncc(NC(=O)c2nc(-c3c(F)cccc3F)sc2N)c1N1CCC[C@H](N(CCO)CCO)CC1] | 5-amino-N-[5-[(4S)-4-[bis(2-hydroxyethyl)amino]azepan-1-yl]-1-methyl-pyrazol-4-yl]-2-(2,6-difluorophenyl)thiazole-4-carboxamide | 0.000199 |
| 337 | 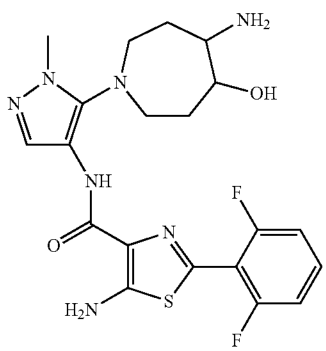 | 5-amino-N-[5-(4-amino-5-hydroxy-azepan-1-yl)-1-methyl-pyrazol-4-yl]-2-(2,6-difluorophenyl)thiazole-4-carboxamide | 0.000026 |
| 338 | 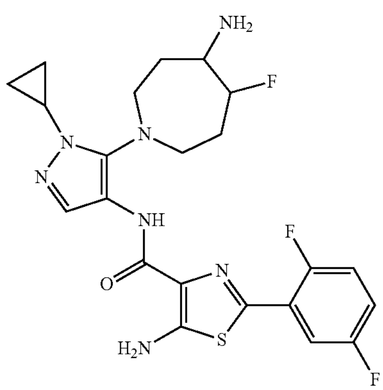 [SMILES: Nc1sc(-c2cc(F)ccc2F)nc1C(=O)Nc1cnn(C2CC2)c1N1CCC(N)C(F)CC1] | 5-amino-N-[5-(4-amino-5-fluoro-azepan-1-yl)-1-cyclopropyl-pyrazol-4-yl]-2-(2,5-difluorophenyl)thiazole-4-carboxamide | 0.000159 |
| 339 | 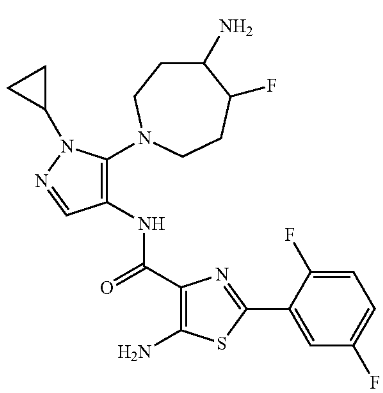 [SMILES: Nc1sc(-c2cc(F)ccc2F)nc1C(=O)Nc1cnn(C2CC2)c1N1CCC(N)C(F)CC1] | 5-amino-N-[5-(4-amino-5-fluoro-azepan-1-yl)-1-cyclopropyl-pyrazol-4-yl]-2-(2,5-difluorophenyl)thiazole-4-carboxamide | 0.000226 |

TABLE 1b-continued

| No. | Structure | IUPAC Name | PIM1 LC3K (KI) uM |
|---|---|---|---|
| 340 | 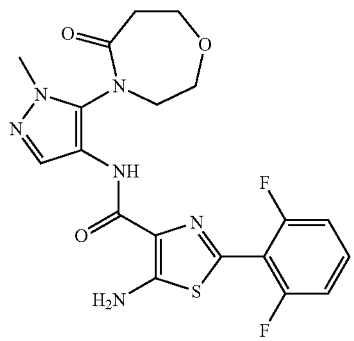 [SMILES: Cn1ncc(NC(=O)c2nc(-c3c(F)cccc3F)sc2N)c1N1CCOCCC1=O] | 5-amino-2-(2,6-difluorophenyl)-N-[1-methyl-5-(5-oxo-1,4-oxazepan-4-yl)pyrazol-4-yl]thiazole-4-carboxamide | 0.0167 |
| 341 | 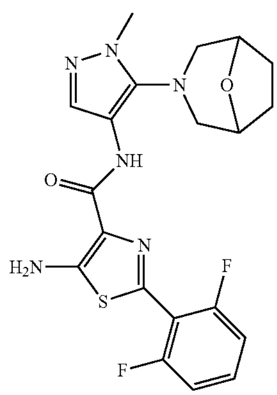 [SMILES: Cn1ncc(NC(=O)c2nc(-c3c(F)cccc3F)sc2N)c1N1CC2CCC(C1)O2] | 5-amino-2-(2,6-difluorophenyl)-N-[1-methyl-5-(8-oxa-3-azabicyclo[3.2.1]octan-3-yl)pyrazol-4-yl]thiazole-4-carboxamide | 0.000678 |
| 342 | 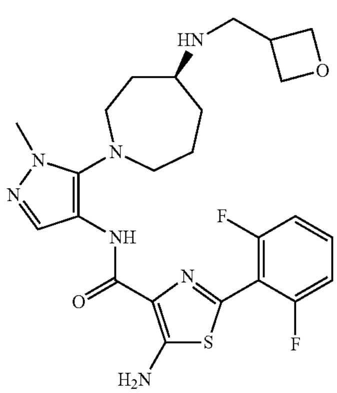 [SMILES: Cn1ncc(NC(=O)c2nc(-c3c(F)cccc3F)sc2N)c1N1CCC[C@H](NCC2COC2)CC1] | 5-amino-2-(2,6-difluorophenyl)-N-[1-methyl-5-[(4S)-4-(oxetan-3-ylmethylamino)azepan-1-yl]pyrazol-4-yl]thiazole-4-carboxamide | 0.000075 |
| 343 | 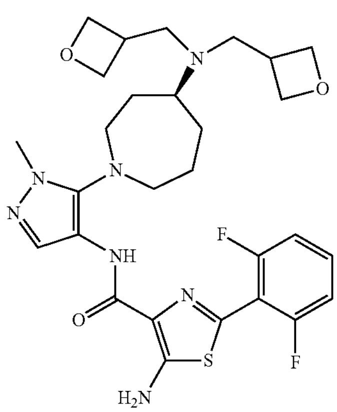 [SMILES: Cn1ncc(NC(=O)c2nc(-c3c(F)cccc3F)sc2N)c1N1CCC[C@H](N(CC2COC2)CC2COC2)CC1] | 5-amino-N-[5-[(4S)-4-[bis(oxetan-3-ylmethyl)amino]azepan-1-yl]-1-methyl-pyrazol-4-yl]-2-(2,6-difluorophenyl)thiazole-4-carboxamide | 0.000962 |

TABLE 1b-continued

| No. | Structure | IUPAC Name | PIM1 LC3K (KI) uM |
|---|---|---|---|
| 344 | 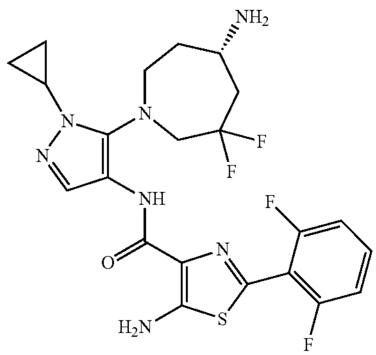 [SMILES: Nc1sc(-c2c(F)cccc2F)nc1C(=O)Nc1cnn(C2CC2)c1N1CC[C@H](N)CC(F)(F)C1] | 5-amino-N-[5-[(5S)-5-amino-3,3-difluoro-azepan-1-yl]-1-cyclopropyl-pyrazol-4-yl]-2-(2,6-difluorophenyl)thiazole-4-carboxamide | 0.00001 |
| 345 | 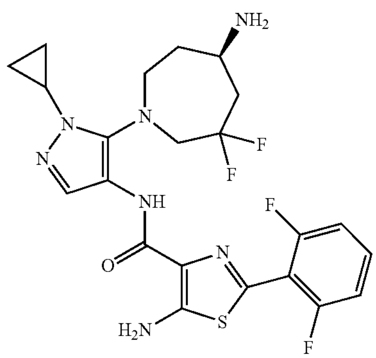 [SMILES: Nc1sc(-c2c(F)cccc2F)nc1C(=O)Nc1cnn(C2CC2)c1N1CC[C@@H](N)CC(F)(F)C1] | 5-amino-N-[5-[(5R)-5-amino-3,3-difluoro-azepan-1-yl]-1-cyclopropyl-pyrazol-4-yl]-2-(2,6-difluorophenyl)thiazole-4-carboxamide | 0.000007 |
| 346 | 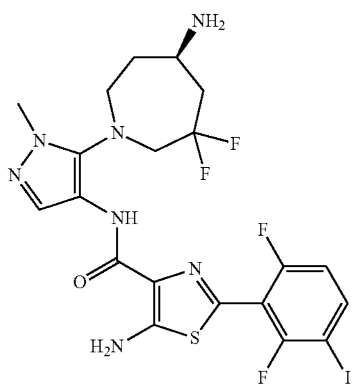 [SMILES: Cn1ncc(NC(=O)c2nc(-c3c(F)ccc(I)c3F)sc2N)c1N1CC[C@@H](N)CC(F)(F)C1] | 5-amino-N-[5-[(5R)-5-amino-3,3-difluoro-azepan-1-yl]-1-methyl-pyrazol-4-yl]-2-(2,6-difluoro-3-iodo-phenyl)thiazole-4-carboxamide | 0.000002 |
| 347 | 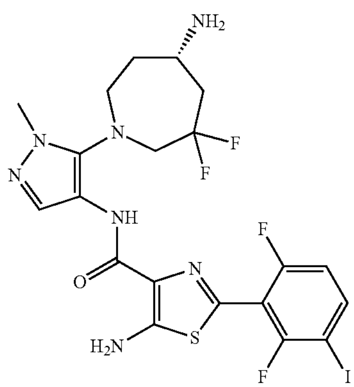 | 5-amino-N-[5-[(5S)-5-amino-3,3-difluoro-azepan-1-yl]-1-methyl-pyrazol-4-yl]-2-(2,6-difluoro-3-iodo-phenyl)thiazole-4-carboxamide | 0.000002 |

TABLE 1b-continued

| No. | Structure | IUPAC Name | PIM1 LC3K (KI) uM |
|---|---|---|---|
| 348 | 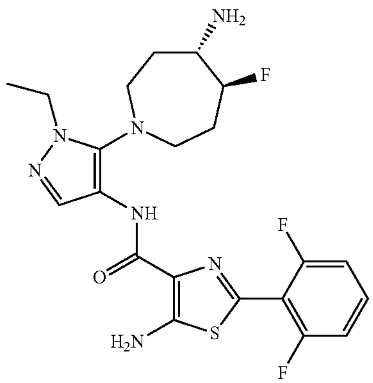 [SMILES: CCn1ncc(NC(=O)c2nc(-c3c(F)cccc3F)sc2N)c1N1CC[C@H](N)[C@@H](F)CC1] | 5-amino-N-(5-((4S,5S)-4-amino-5-fluoroazepan-1-yl)-1-ethyl-1H-pyrazol-4-yl)-2-(2,6-difluorophenyl)thiazole-4-carboxamide | 0.000109 |
| 349 | 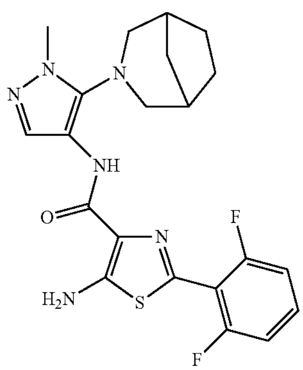 [SMILES: Cn1ncc(NC(=O)c2nc(-c3c(F)cccc3F)sc2N)c1N1CC2CCC(C2)C1] | 5-amino-N-[5-(3-azabicyclo[3.2.1]octan-3-yl)-1-methyl-pyrazol-4-yl]-2-(2,6-difluorophenyl)thiazole-4-carboxamide | 0.000711 |
| 350 | 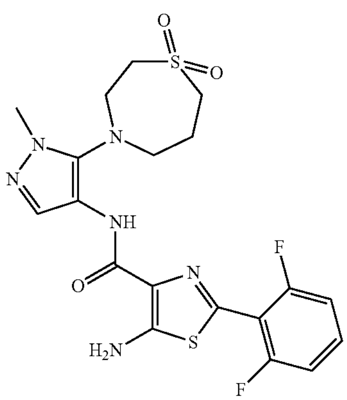 [SMILES: Cn1ncc(NC(=O)c2nc(-c3c(F)cccc3F)sc2N)c1N1CCCS(=O)(=O)CC1] | 5-amino-2-(2,6-difluorophenyl)-N-[5-(1,1-dioxo-1,4-thiazepan-4-yl)-1-methyl-pyrazol-4-yl]thiazole-4-carboxamide | 0.000671 |
| 351 | 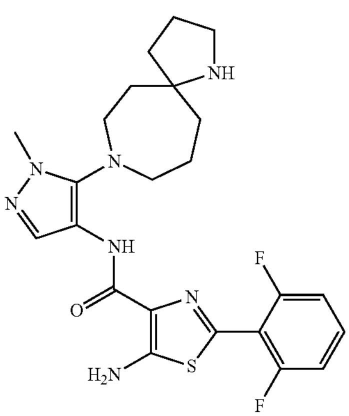 [SMILES: Cn1ncc(NC(=O)c2nc(-c3c(F)cccc3F)sc2N)c1N1CCCC2(CCCN2)CC1] | 5-amino-N-[5-(1,9-diazaspiro[4.6]undecan-9-yl)-1-methyl-pyrazol-4-yl]-2-(2,6-difluorophenyl)thiazole-4-carboxamide | 0.000022 |

TABLE 1b-continued

| No. | Structure | IUPAC Name | PIM1 LC3K (KI) uM |
|---|---|---|---|
| 352 | 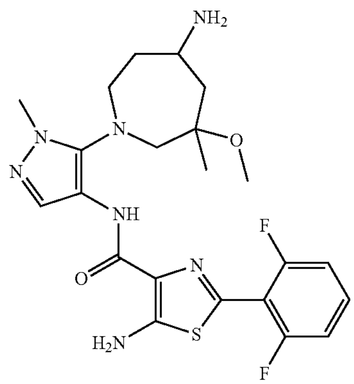 [SMILES: COC1(C)CC(N)CCN(c2c(NC(=O)c3nc(-c4c(F)cccc4F)sc3N)cnn2C)C1] | 5-amino-N-[5-(5-amino-3-methoxy-3-methyl-azepan-1-yl)-1-methyl-pyrazol-4-yl]-2-(2,6-difluorophenyl)thiazole-4-carboxamide | 0.000002 |
| 353 | 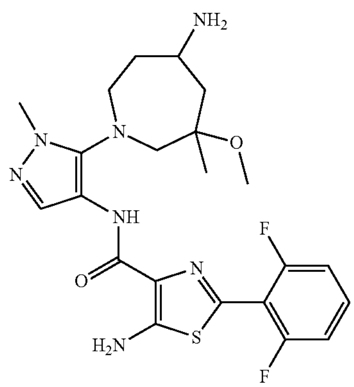 [SMILES: COC1(C)CC(N)CCN(c2c(NC(=O)c3nc(-c4c(F)cccc4F)sc3N)cnn2C)C1] | 5-amino-N-[5-(5-amino-3-methoxy-3-methyl-azepan-1-yl)-1-methyl-pyrazol-4-yl]-2-(2,6-difluorophenyl)thiazole-4-carboxamide | 0.0000511 |
| 354 | 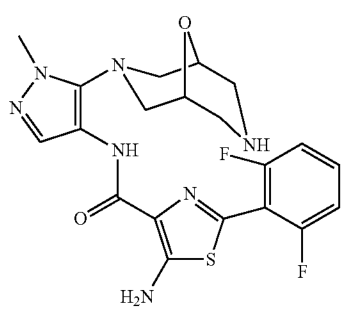 [SMILES: Cn1ncc(NC(=O)c2nc(-c3c(F)cccc3F)sc2N)c1N1CC2CNCC(C1)O2] | 5-amino-2-(2,6-difluorophenyl)-N-[1-methyl-5-(9-oxa-3,7-diazabicyclo[3.3.1]nonan-3-yl)pyrazol-4-yl]thiazole-4-carboxamide | 0.0336 |
| 355 | 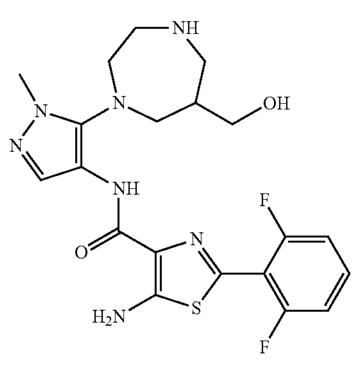 [SMILES: Cn1ncc(NC(=O)c2nc(-c3c(F)cccc3F)sc2N)c1N1CCNCC(CO)C1] | 5-amino-2-(2,6-difluorophenyl)-N-[5-[6-(hydroxymethyl)-1,4-diazepan-1-yl]-1-methyl-pyrazol-4-yl]thiazole-4-carboxamide | 0.000439 |

TABLE 1b-continued

| No. | Structure | IUPAC Name | PIM1 LC3K (KI) uM |
|---|---|---|---|
| 356 | 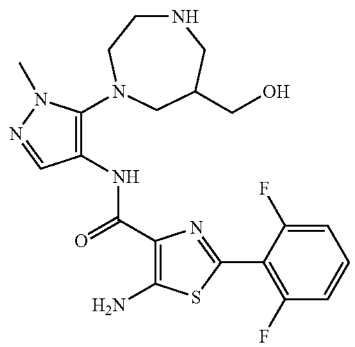 [SMILES: Cn1ncc(NC(=O)c2nc(-c3c(F)cccc3F)sc2N)c1N1CCNCC(CO)C1] | 5-amino-2-(2,6-difluorophenyl)-N-[5-[6-(hydroxymethyl)-1,4-diazepan-1-yl]-1-methyl-pyrazol-4-yl]thiazole-4-carboxamide | 0.00143 |
| 357 | 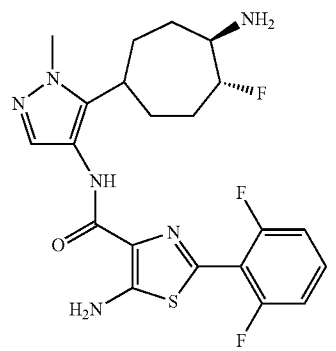 | 5-amino-N-(5-((4R,5R)-4-amino-5-fluorocycloheptyl)-1-methyl-1H-pyrazol-4-yl)-2-(2,6-difluorophenyl)thiazole-4-carboxamide | 0.000522 |
| 358 | 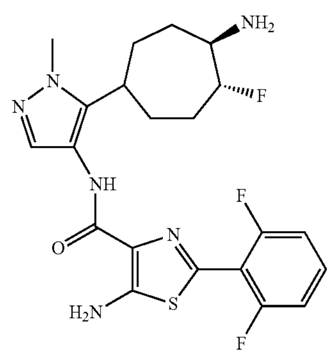 [SMILES: Cn1ncc(NC(=O)c2nc(-c3c(F)cccc3F)sc2N)c1C1CC[C@@H](N)[C@H](F)CC1] | 5-amino-N-(5-((4R,5R)-4-amino-5-fluorocycloheptyl)-1-methyl-1H-pyrazol-4-yl)-2-(2,6-difluorophenyl)thiazole-4-carboxamide | 0.000026 |
| 359 | 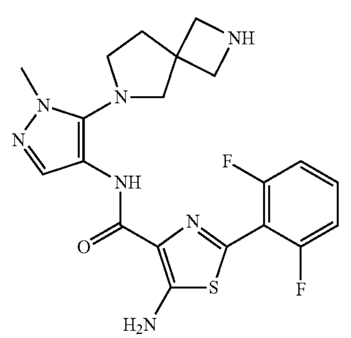 [SMILES: Cn1ncc(NC(=O)c2nc(-c3c(F)cccc3F)sc2N)c1N1CCC2(CNC2)C1] | 5-amino-N-[5-(2,6-diazaspiro[3.4]octan-6-yl)-1-methyl-pyrazol-4-yl]-2-(2,6-difluorophenyl)thiazole-4-carboxamide | 0.000783 |

TABLE 1b-continued

| No. | Structure | IUPAC Name | PIM1 LC3K (KI) uM |
|---|---|---|---|
| 360 | 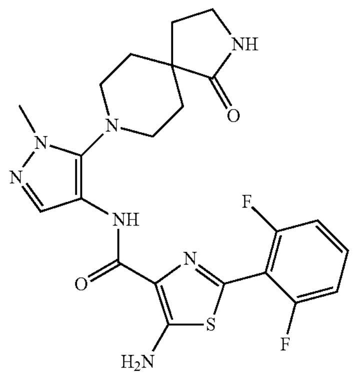 [SMILES: Cn1ncc(NC(=O)c2nc(-c3c(F)cccc3F)sc2N)c1N1CCC2(CCNC2=O)CC1] | 5-amino-2-(2,6-difluorophenyl)-N-[1-methyl-5-(1-oxo-2,8-diazaspiro[4.5]decan-8-yl)pyrazol-4-yl]thiazole-4-carboxamide | 0.000391 |
| 361 | 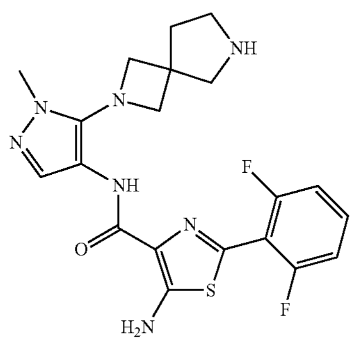 [SMILES: Cn1ncc(NC(=O)c2nc(-c3c(F)cccc3F)sc2N)c1N1CC2(CCNC2)C1] | 5-amino-N-[5-(2,7-diazaspiro[3.4]octan-2-yl)-1-methyl-pyrazol-4-yl]-2-(2,6-difluorophenyl)thiazole-4-carboxamide | 0.00685 |
| 362 | 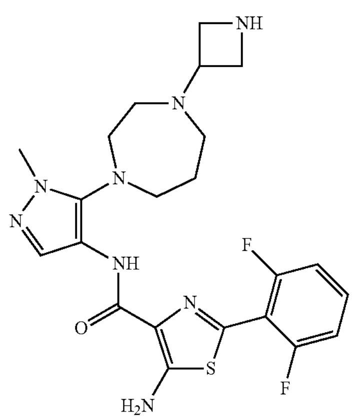 [SMILES: Cn1ncc(NC(=O)c2nc(-c3c(F)cccc3F)sc2N)c1N1CCCN(C2CNC2)CC1] | 5-amino-N-[5-[4-(azetidin-3-yl)-1,4-diazepan-1-yl]-1-methyl-pyrazol-4-yl]-2-(2,6-difluorophenyl)thiazole-4-carboxamide | 0.00025 |
| 363 | 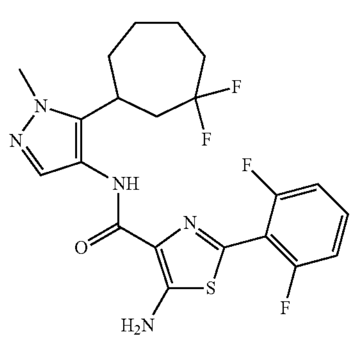 [SMILES: Cn1ncc(NC(=O)c2nc(-c3c(F)cccc3F)sc2N)c1C1CCCCC(F)(F)C1] | 5-amino-N-[5-(3,3-difluorocycloheptyl)-1-methyl-pyraozl-4-yl]-2-(2,6-difluorophenyl)thiazole-4-carboxamide | 0.000678 |

TABLE 1b-continued

| No. | Structure | IUPAC Name | PIM1 LC3K (KI) uM |
|---|---|---|---|
| 364 | 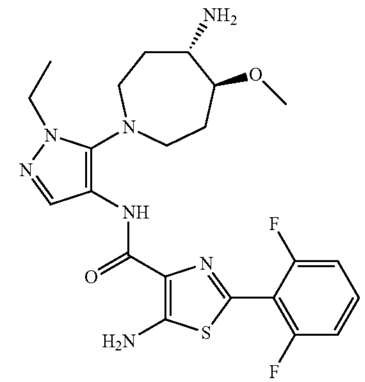 [SMILES: CCn1ncc(NC(=O)c2nc(-c3c(F)cccc3F)sc2N)c1N1CC[C@H](OC)[C@@H](N)CC1] | 5-amino-N-(5-((4S,5S)-4-amino-5-methoxyazepan-1-yl)-1-ethyl-1H-pyrazol-4-yl)-2-(2,6-difluorophenyl)thiazole-4-carboxamide | 0.000247 |
| 365 | 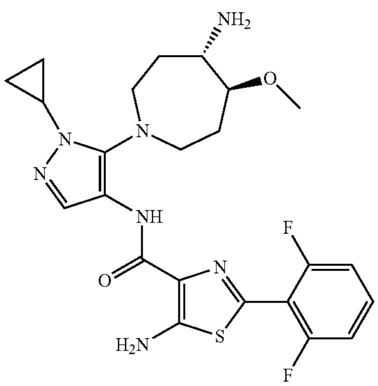 [SMILES: CO[C@H]1CCN(c2c(NC(=O)c3nc(-c4c(F)cccc4F)sc3N)cnn2C2CC2)CC[C@@H]1N] | 5-amino-N-(5-((4S,5S)-4-amino-5-methoxyazepan-1-yl)-1-cyclopropyl-1H-pyrazol-4-yl)-2-(2,6-difluorophenyl)thiazole-4-carboxamide | 0.000219 |
| 366 | 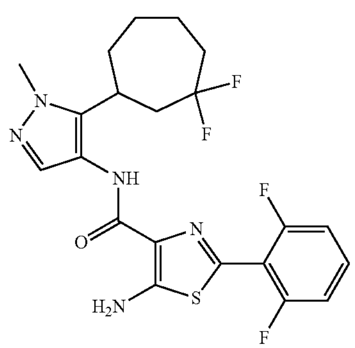 [SMILES: Cn1ncc(NC(=O)c2nc(-c3c(F)cccc3F)sc2N)c1C1CCCCC(F)(F)C1] | 5-amino-N-[5-(3,3-difluorocycloheptyl)-1-methyl-pyrazol-4-yl]-2-(2,6-difluorophenyl)thiazole-4-carboxamide | 0.000483 |
| 367 | 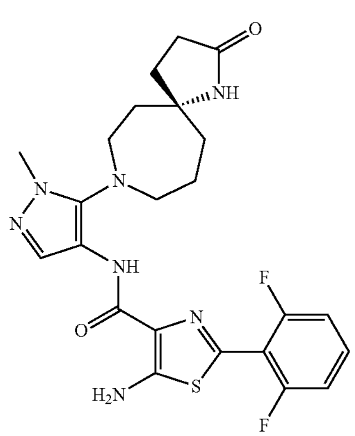 [SMILES: Cn1ncc(NC(=O)c2nc(-c3c(F)cccc3F)sc2N)c1N1CCC[C@]2(CCC(=O)N2)CC1] | (S)-5-amino-2-(2,6-difluorophenyl)-N-(1-methyl-5-(2-oxo-1,8-diazaspiro[4.6]undecan-8-yl)-1H-pyrazol-4-yl)thiazole-4-carboxamide | |

TABLE 1b-continued

| No. | Structure | IUPAC Name | PIM1 LC3K (KI) uM |
|---|---|---|---|
| 368 | 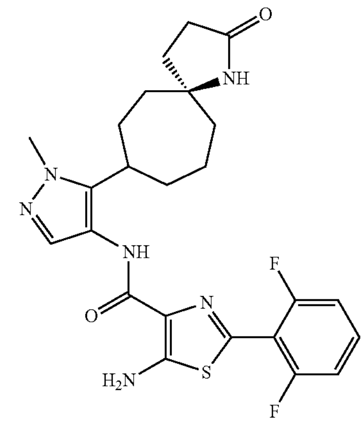 [SMILES: Cn1ncc(NC(=O)c2nc(-c3c(F)cccc3F)sc2N)c1C1CCC[C@@]2(CCC(=O)N2)CC1] | (R)-5-amino-2-(2,6-difluorophenyl)-N-[1-methyl-5-(2-oxo-1,9-diazaspiro[4.6]undecan-9-yl)pyrazol-4-yl]thiazole-4-carboxamide | |
| 369 | 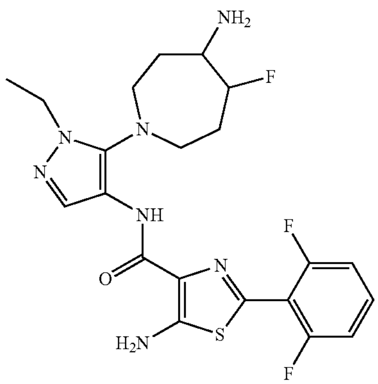 [SMILES: CCn1ncc(NC(=O)c2nc(-c3c(F)cccc3F)sc2N)c1N1CCC(N)C(F)CC1] | 5-amino-N-[5-(4-amino-5-fluoro-azepan-1-yl)-1-ethyl-pyrazol-4-yl]-2-(2,6-difluorophenyl)thiazole-4-carboxamide | 0.000178 |
| 370 | 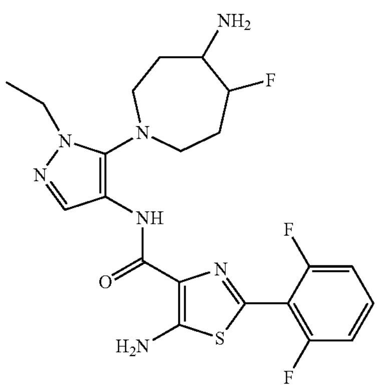 [SMILES: CCn1ncc(NC(=O)c2nc(-c3c(F)cccc3F)sc2N)c1N1CCC(N)C(F)CC1] | 5-amino-N-[5-(4-amino-5-fluoro-azepan-1-yl)-1-ethyl-pyrazol-4-yl]-2-(2,6-difluorophenyl)thiazole-4-carboxamide | 0.000093 |
| 371 | 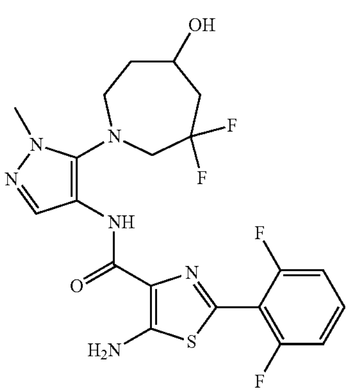 [SMILES: Cn1ncc(NC(=O)c2nc(-c3c(F)cccc3F)sc2N)c1N1CCC(O)CC(F)(F)C1] | 5-amino-N-[5-(3,3-difluoro-5-hydroxy-azepan-1-yl)-1-methyl-pyrazol-4-yl]-2-(2,6-difluorophenyl)thiazole-4-carboxamide | 0.000006 |

TABLE 1b-continued

| No. | Structure | IUPAC Name | PIM1 LC3K (KI) uM |
|---|---|---|---|
| 372 | 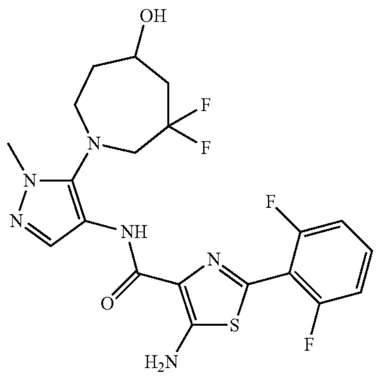 [SMILES: Cn1ncc(NC(=O)c2nc(-c3c(F)cccc3F)sc2N)c1N1CCC(O)CC(F)(F)C1] | 5-amino-N-[5-(3,3-difluoro-5-hydroxy-azepan-1-yl)-1-methyl-pyrazol-4-yl]-2-(2,6-difluorophenyl)thiazole-4-carboxamide | 0.000015 |
| 373 | 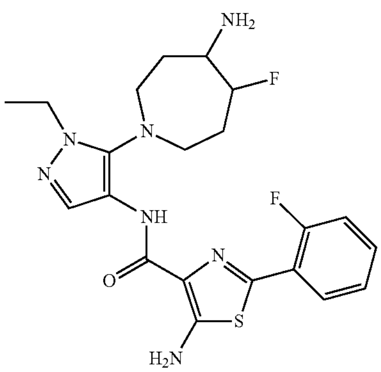 [SMILES: CCn1ncc(NC(=O)c2nc(-c3ccccc3F)sc2N)c1N1CCC(N)C(F)CC1] | 5-amino-N-[5-(4-amino-5-fluoro-azepan-1-yl)-1-ethyl-pyrazol-4-yl]-2-(2-fluorophenyl)thiazole-4-carboxamide | 0.000373 |
| 374 | 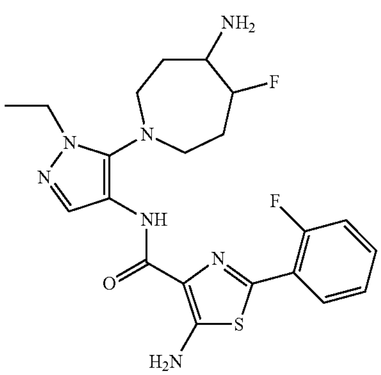 [SMILES: CCn1ncc(NC(=O)c2nc(-c3ccccc3F)sc2N)c1N1CCC(N)C(F)CC1] | 5-amino-N-[5-(4-amino-5-fluoro-azepan-1-yl)-1-ethyl-pyrazol-4-yl]-2-(2-fluorophenyl)thiazole-4-carboxamide | 0.000346 |
| 375 | 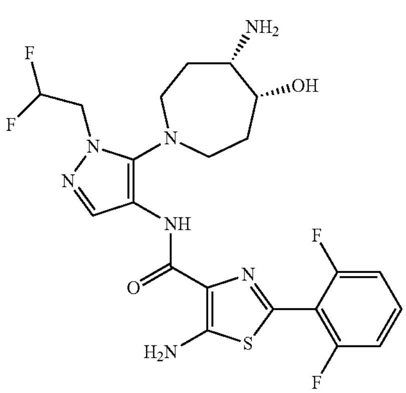 [SMILES: Nc1sc(-c2c(F)cccc2F)nc1C(=O)Nc1cnn(CC(F)F)c1N1CC[C@@H](O)[C@@H](N)CC1] | 5-amino-N-(5-((4S,5R)-4-amino-5-hydroxyazepan-1-yl)-1-(2,2-difluoroethyl)-1H-pyrazol-4-yl)-2-(2,6-difluorophenyl)thiazole-4-carboxamide | 0.000051 |

TABLE 1b-continued

| No. | Structure | IUPAC Name | PIM1 LC3K (KI) uM |
|---|---|---|---|
| 376 | 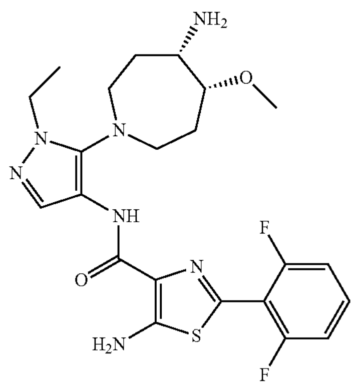 [SMILES: CCn1ncc(NC(=O)c2nc(-c3c(F)cccc3F)sc2N)c1N1CC[C@H](N)[C@H](OC)CC1] | 5-amino-N-(5-((4S,5R)-4-amino-5-methoxyazepan-1-yl)-1-ethyl-1H-pyrazol-4-yl)-2-(2,6-difluorophenyl)thiazole-4-carboxamide | 0.000223 |
| 377 | 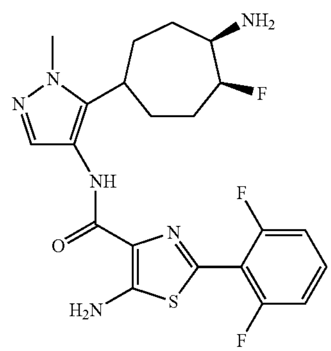 [SMILES: Cn1ncc(NC(=O)c2nc(-c3c(F)cccc3F)sc2N)c1C1CC[C@@H](N)[C@@H](F)CC1] | 5-amino-N-(5-((4R,5S)-4-amino-5-fluorocycloheptyl)-1-methyl-1H-pyrazol-4-yl)-2-(2,6-difluorophenyl)thiazole-4-carboxamide | 0.000428 |
| 378 | 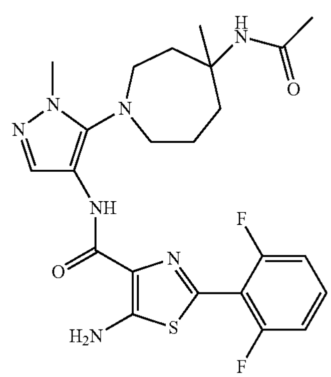 [SMILES: CC(=O)NC1(C)CCCN(c2c(NC(=O)c3nc(-c4c(F)cccc4F)sc3N)cnn2C)CC1] | N-[5-(4-azetamido-4-methyl-azepan-1-yl)-1-methyl-pyrazol-4-yl]-5-amino-2-(2,6-difluorophenyl)thiazole-4-carboxamide | 0.000126 |
| 379 | 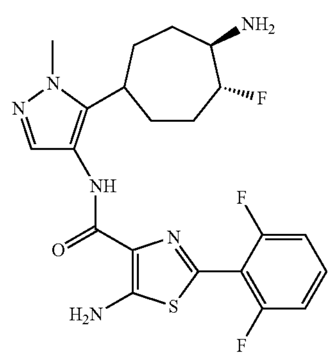 [SMILES: Cn1ncc(NC(=O)c2nc(-c3c(F)cccc3F)sc2N)c1C1CC[C@@H](N)[C@H](F)CC1] | 5-amino-N-(5-((4R,5R)-4-amino-5-fluorocycloheptyl)-1-methyl-1H-pyrazol-4-yl)-2-(2,6-difluorophenyl)thiazole-4-carboxamide | 0.000557 |

TABLE 1b-continued

| No. | Structure | IUPAC Name | PIM1 LC3K (KI) uM |
|---|---|---|---|
| 380 | 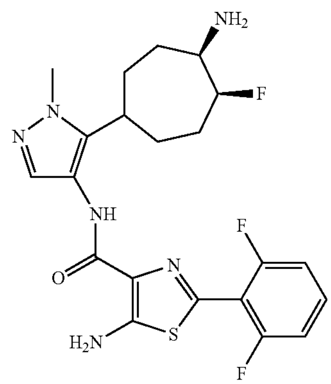 [SMILES: Cn1ncc(NC(=O)c2nc(-c3c(F)cccc3F)sc2N)c1C1CC[C@@H](N)[C@@H](F)CC1] | 5-amino-N-(5-((4R,5S)-4-amino-5-fluorocycloheptyl)-1-methyl-1H-pyrazol-4-yl)-2-(2,6-difluorophenyl)thiazole-4-carboxamide | 0.000252 |
| 381 | 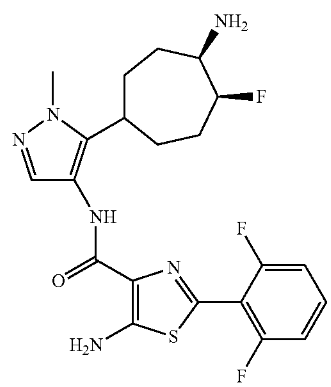 [SMILES: Cn1ncc(NC(=O)c2nc(-c3c(F)cccc3F)sc2N)c1C1CC[C@@H](N)[C@@H](F)CC1] | 5-amino-N-(5-((4R,5S)-4-amino-5-fluorocycloheptyl)-1-methyl-1H-pyrazol-4-yl)-2-(2,6-difluorophenyl)thiazole-4-carboxamide | 0.000272 |
| 382 | 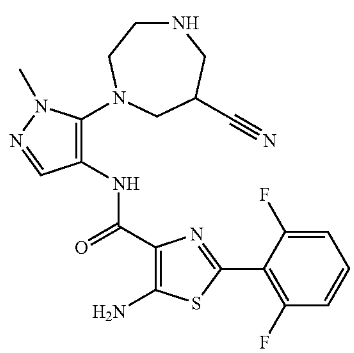 [SMILES: Cn1ncc(NC(=O)c2nc(-c3c(F)cccc3F)sc2N)c1N1CCNCC(C#N)C1] | 5-amino-N-[5-(6-cyano-1,4-diazepan-1-yl)-1-methyl-pyrazol-4-yl]-2-(2,6-difluorophenyl)thiazole-4-carboxamide | 0.00281 |
| 383 | 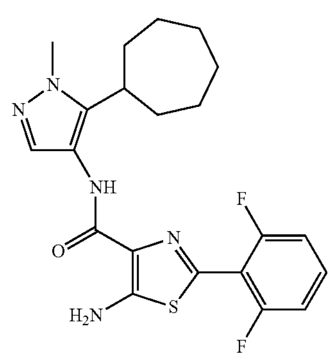 [SMILES: Cn1ncc(NC(=O)c2nc(-c3c(F)cccc3F)sc2N)c1C1CCCCCC1] | 5-amino-N-(5-cycloheptyl-1-methyl-pyrazol-4-yl)-2-(2,6-difluorophenyl)thiazole-4-carboxamide | 0.00373 |

TABLE 1b-continued

| No. | Structure | IUPAC Name | PIM1 LC3K (KI) uM |
|---|---|---|---|
| 384 | 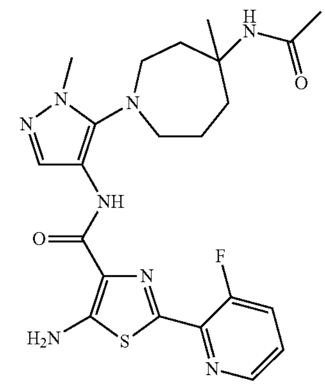 [SMILES: CC(=O)NC1(C)CCCN(c2c(NC(=O)c3nc(-c4ncccc4F)sc3N)cnn2C)CC1] | N-[5-(4-azetamido-4-methyl-azepan-1-yl)-1-methyl-pyrazol-4-yl]-5-amino-2-(3-fluoro-2-pyridyl)thiazole-4-carboxamide | 0.000613 |
| 385 | 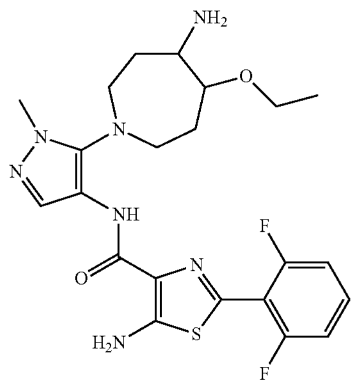 [SMILES: CCOC1CCN(c2c(NC(=O)c3nc(-c4c(F)cccc4F)sc3N)cnn2C)CCC1N] | 5-amino-N-[5-(4-amino-5-ethoxy-azepan-1-yl)-1-methyl-pyrazol-4-yl]-2-(2,6-difluorophenyl)thiazole-4-carboxamide | 0.000145 |
| 386 | 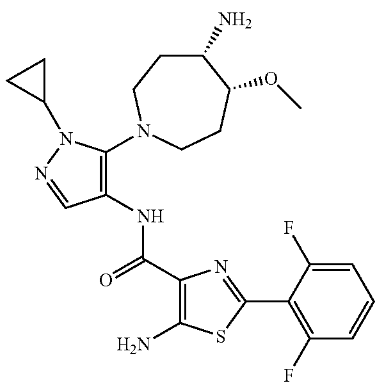 | 5-amino-N-(5-((4S,5R)-4-amino-5-methoxyazepan-1-yl)-1-cyclopropyl-1H-pyrazol-4-yl)-2-(2,6-difluorophenyl)thiazole-4-carboxamide | 0.000103 |
| 387 | 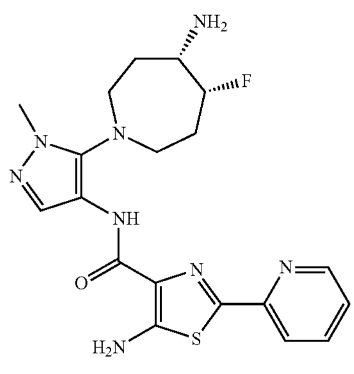 [SMILES: Cn1ncc(NC(=O)c2nc(-c3ccccn3)sc2N)c1N1CC[C@@H](F)[C@@H](N)CC1] | 5-amino-N-(5-((4S,5R)-4-amino-5-fluoroazepan-1-yl)-1-methyl-1H-pyrazol-4-yl)-2-(pyridin-2-yl)thiazole-4-carboxamide | 0.0014 |

TABLE 1b-continued

| No. | Structure | IUPAC Name | PIM1 LC3K (KI) uM |
|---|---|---|---|
| 388 | 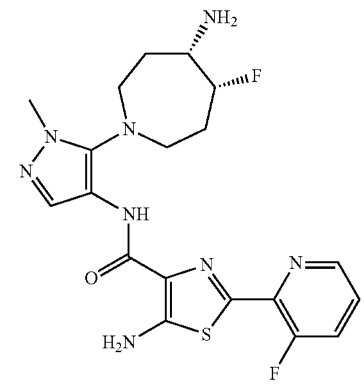 | 5-amino-N-(5-((4S,5R)-4-amino-5-fluoroazepan-1-yl)-1-methyl-1H-pyrazol-4-yl)-2-(3-fluoropyridin-2-yl)thiazole-4-carboxamide | 0.000462 |
| 389 | 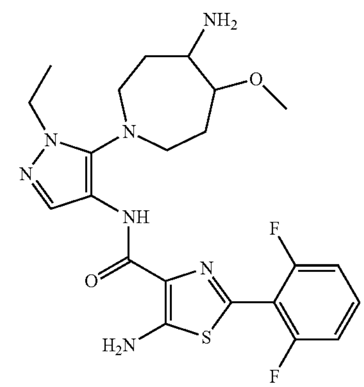 [SMILES: CCn1ncc(NC(=O)c2nc(-c3c(F)cccc3F)sc2N)c1N1CCC(N)C(OC)CC1] | 5-amino-N-[5-(4-amino-5-methoxy-azepan-1-yl)-1-ethyl-pyrazol-4-yl]-2-(2,6-difluorophenyl)thiazole-4-carboxamide | 0.000624 |
| 390 | 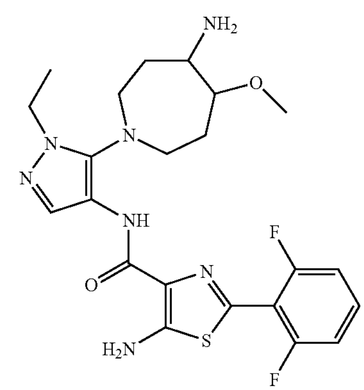 [SMILES: CCn1ncc(NC(=O)c2nc(-c3c(F)cccc3F)sc2N)c1N1CCC(N)C(OC)CC1] | 5-amino-N-[5-(4-amino-5-methoxy-azepan-1-yl)-1-ethyl-pyraozl-4-yl]-2-(2,6-difluorophenyl)thiazole-4-carboxamide | 0.000192 |
| 391 | 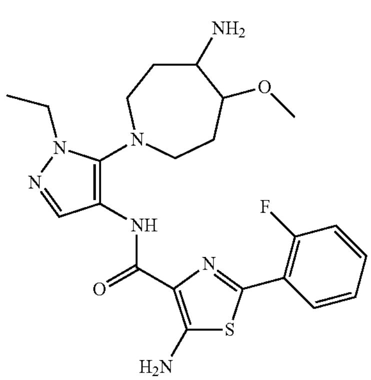 [SMILES: CCn1ncc(NC(=O)c2nc(-c3ccccc3F)sc2N)c1N1CCC(N)C(OC)CC1] | 5-amino-N-[5-(4-amino-5-methoxy-azepan-1-yl)-1-ethyl-pyrazol-4-yl]-2-(2-fluorophenyl)thiazole-4-carboxamide | 0.00216 |

TABLE 1b-continued

| No. | Structure | IUPAC Name | PIM1 LC3K (KI) uM |
|---|---|---|---|
| 392 | 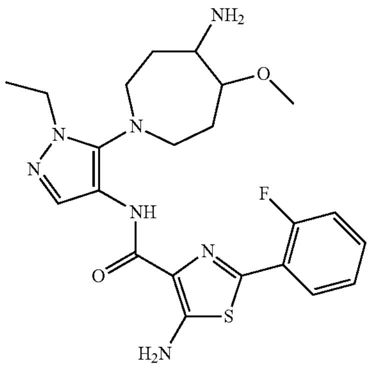 [SMILES: CCn1ncc(NC(=O)c2nc(-c3ccccc3F)sc2N)c1N1CCC(N)C(OC)CC1] | 5-amino-N-[5-(4-amino-5-methoxy-azepan-1-yl)-1-ethyl-pyrazol-4-yl]-2-(2-fluorophenyl)thiazole-4-carboxamide | 0.000668 |
| 393 | 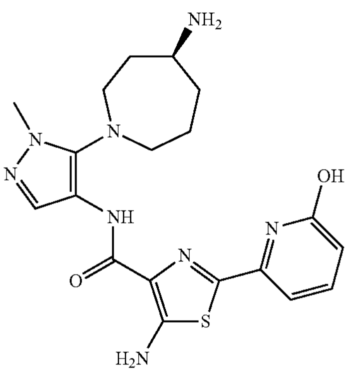 [SMILES: Cn1ncc(NC(=O)c2nc(-c3cccc(O)n3)sc2N)c1N1CCC[C@H](N)CC1] | 5-amino-N-[5-[(4S)-4-aminoazepan-1-yl]-1-methyl-pyrazol-4-yl]-2-(6-hydroxy-2-pyridyl)thiazole-4-carboxamide | 0.014 |
| 394 | 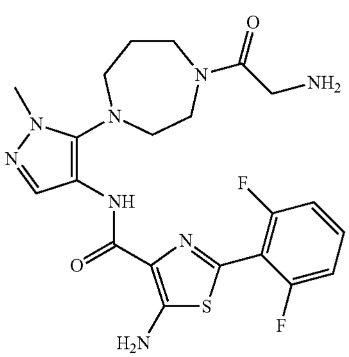 [SMILES: Cn1ncc(NC(=O)c2nc(-c3c(F)cccc3F)sc2N)c1N1CCCN(C(=O)CN)CC1] | 5-amino-N-[5-[4-(2-aminoacetyl)-1,4-diazepan-1-yl]-1-methyl-pyrazol-4-yl]-2-(2,6-difluorophenyl)thiazole-4-carboxamide | 0.000421 |
| 395 | 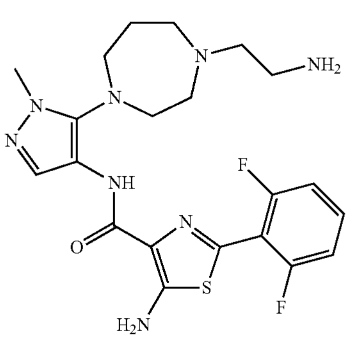 [SMILES: Cn1ncc(NC(=O)c2nc(-c3c(F)cccc3F)sc2N)c1N1CCCN(CCN)CC1] | 5-amino-N-[5-[4-(2-aminoethyl)-1,4-diazepan-1-yl]-1-methyl-pyrazol-4-yl]-2-(2,6-difluorophenyl)thiazole-4-carboxamide | 0.000222 |

TABLE 1b-continued

| No. | Structure | IUPAC Name | PIM1 LC3K (KI) uM |
|---|---|---|---|
| 396 | 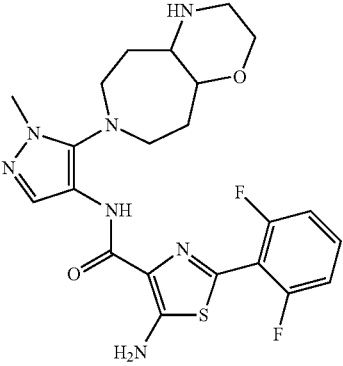 [SMILES: Cn1ncc(NC(=O)c2nc(-c3c(F)cccc3F)sc2N)c1N1CCC2NCCOC2CC1] | N-[5-(3,4,4a,5,6,8,9,9a-octahydro-2H-[1,4]oxazino[2,3-d]azepin-7-yl)-1-methyl-pyrazol-4-yl]-5-amino-2-(2,6-difluorophenyl)thiazole-4-carboxamide | 0.000056 |
| 397 | 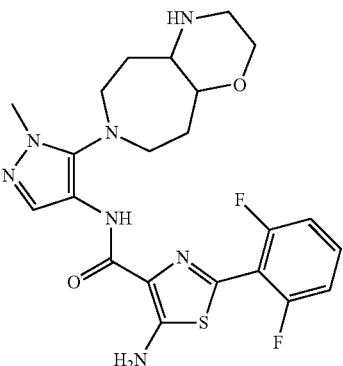 | N-[5-(3,4,4a,5,6,8,9,9a-octahydro-2H-[1,4]oxazino[2,3-d]azepin-7-yl)-1-methyl-pyrazol-4-yl]-5-amino-2-(2,6-difluorophenyl)thiazole-4-carboxamide | 0.000022 |
| 398 | 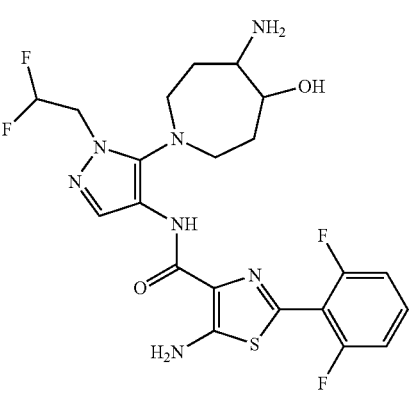 [SMILES: Nc1sc(-c2c(F)cccc2F)nc1C(=O)Nc1cnn(CC(F)F)c1N1CCC(N)C(O)CC1] | 5-amino-N-[5-(4-amino-5-hydroxy-azepan-1-yl)-1-(2,2-difluoroethyl)pyrazol-4-yl]-2-(2,6-difluorophenyl)thiazole-4-carboxamide | 0.000142 |
| 399 | 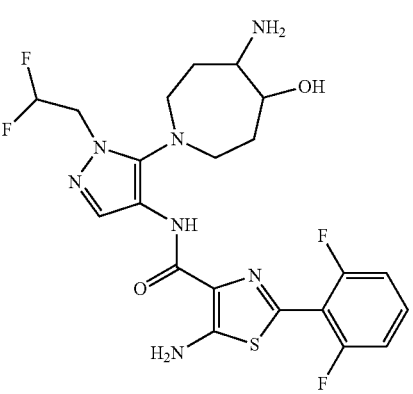 [SMILES: Nc1sc(-c2c(F)cccc2F)nc1C(=O)Nc1cnn(CC(F)F)c1N1CCC(N)C(O)CC1] | 5-amino-N-[5-(4-amino-5-hydroxy-azepan-1-yl)-1-(2,2-difluoroethyl)pyrazol-4-yl]-2-(2,6-difluorophenyl)thiazole-4-carboxamide | 0.000018 |

TABLE 1b-continued

| No. | Structure | IUPAC Name | PIM1 LC3K (KI) uM |
|---|---|---|---|
| 400 | 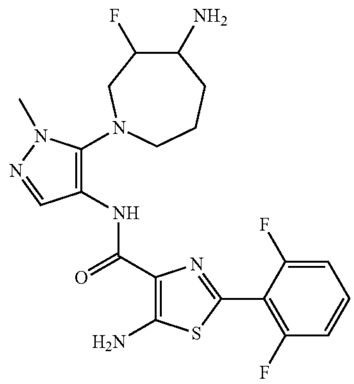 [SMILES: Cn1ncc(NC(=O)c2nc(-c3c(F)cccc3F)sc2N)c1N1CCCC(N)C(F)C1] | 5-amino-N-[5-(4-amino-3-fluoro-azepan-1-yl)-1-methyl-pyrazol-4-yl]-2-(2,6-difluorophenyl)thiazole-4-carboxamide | 0.00015 |
| 401 | 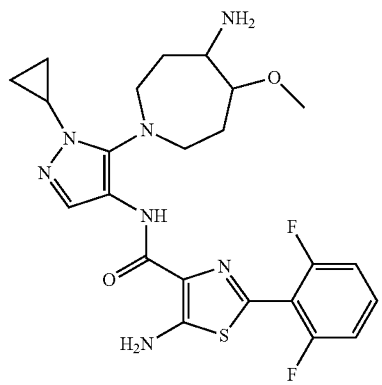 [SMILES: COC1CCN(c2c(NC(=O)c3nc(-c4c(F)cccc4F)sc3N)cnn2C2CC2)CCC1N] | 5-amino-N-[5-(4-amino-5-methoxy-azepan-1-yl)-1-cyclopropyl-pyrazol-4-yl]-2-(2,6-difluorophenyl)thiazole-4-carboxamide | 0.000059 |
| 402 | 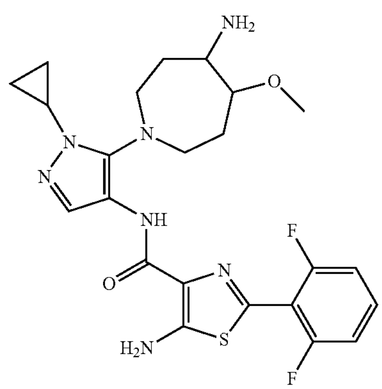 [SMILES: COC1CCN(c2c(NC(=O)c3nc(-c4c(F)cccc4F)sc3N)cnn2C2CC2)CCC1N] | 5-amino-N-[5-(4-amino-5-methoxy-azepan-1-yl)-1-cyclopropyl-pyrazol-4-yl]-2-(2,6-difluorophenyl)thiazole-4-carboxamide | 0.000126 |
| 403 | 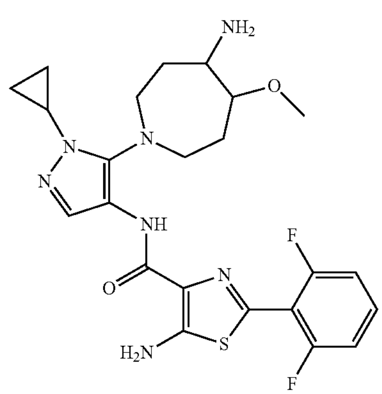 [SMILES: COC1CCN(c2c(NC(=O)c3nc(-c4c(F)cccc4F)sc3N)cnn2C2CC2)CCC1N] | 5-amino-N-[5-(4-amino-5-methoxy-azepan-1-yl)-1-cyclopropyl-pyrazol-4-yl]-2-(2,6-difluorophenyl)thiazole-4-carboxamide | 0.00021 |

TABLE 1b-continued

| No. | Structure | IUPAC Name | PIM1 LC3K (KI) uM |
|---|---|---|---|
| 404 | 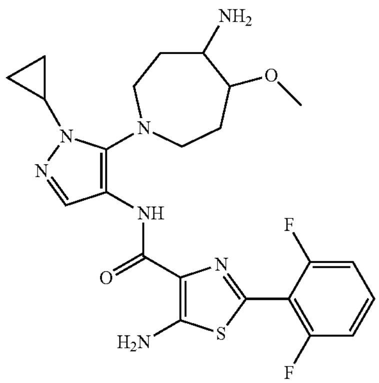 [SMILES: COC1CCN(c2c(NC(=O)c3nc(-c4c(F)cccc4F)sc3N)cnn2C2CC2)CCC1N] | 5-amino-N-[5-(4-amino-5-methoxy-azepan-1-yl)-1-cyclopropyl-pyrazol-4-yl]-2-(2,6-difluroophenyl)thiazole-4-carboxamide | 0.000036 |
| 405 | 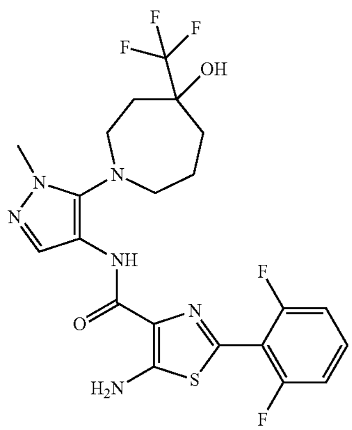 [SMILES: Cn1ncc(NC(=O)c2nc(-c3c(F)cccc3F)sc2N)c1N1CCCC(O)(C(F)(F)F)CC1] | 5-amino-2-(2,6-difluorophenyl)-N-[5-[4-hydroxy-4-(trifluoromethyl)azepan-1-yl]-1-methyl-pyrazol-4-yl]thiazole-4-carboxamide | 0.000055 |
| 406 | 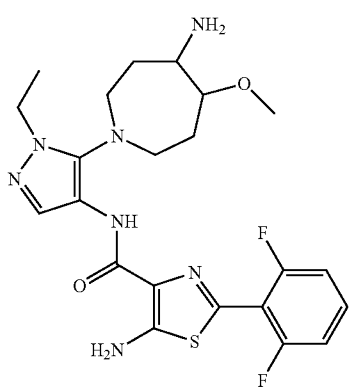 [SMILES: CCn1ncc(NC(=O)c2nc(-c3c(F)cccc3F)sc2N)c1N1CCC(N)C(OC)CC1] | 5-amino-N-[5-(4-amino-5-methoxy-azepan-1-yl)-1-ethyl-pyrazol-4-yl]-2-(2,6-difluorophenyl)thiazole-4-carboxamide | 0.000133 |
| 407 | 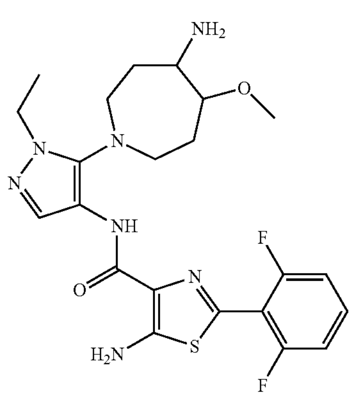 [SMILES: CCn1ncc(NC(=O)c2nc(-c3c(F)cccc3F)sc2N)c1N1CCC(N)C(OC)CC1] | 5-amino-N-[5-(4-amino-5-methoxy-azepan-1-yl)-1-ethyl-pyrazol-4-yl]-2-(2,6-difluorophenyl)thiazole-4-carboxamide | 0.000204 |

TABLE 1b-continued

| No. | Structure | IUPAC Name | PIM1 LC3K (KI) uM |
|---|---|---|---|
| 408 | 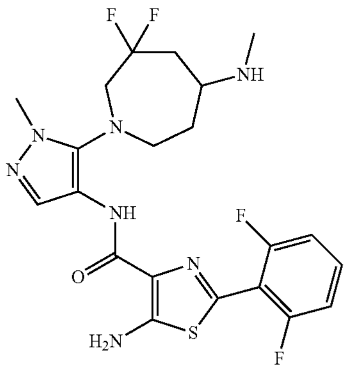 [SMILES: CNC1CCN(c2c(NC(=O)c3nc(-c4c(F)cccc4F)sc3N)cnn2C)CC(F)(F)C1] | 5-amino-N-[5-[3,3-difluoro-5-(methylamino)azepan-1-yl]-1-methyl-pyrazol-4-yl]-2-(2,6-difluorophenyl)thiazole-4-carboxamide | 0.000007 |
| 409 | 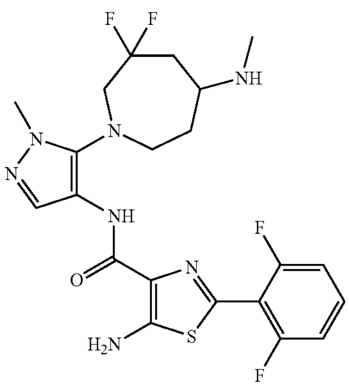 [SMILES: CNC1CCN(c2c(NC(=O)c3nc(-c4c(F)cccc4F)sc3N)cnn2C)CC(F)(F)C1] | 5-amino-N-[5-[3,3-difluoro-5-(methylamino)azepan-1-yl]-1-methyl-pyrazol-4-yl]-2-(2,6-difluorophenyl)thiazole-4-carboxamide | 0.000014 |
| 410 | 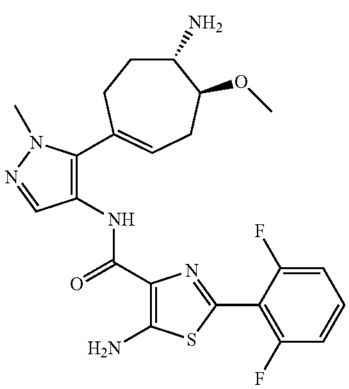 [SMILES: CO[C@H]1CC=C(c2c(NC(=O)c3nc(-c4c(F)cccc4F)sc3N)cnn2C)CC[C@@H]1N] | 5-amino-N-(5-((4S,5S)-5-amino-4-methoxycyclohept-1-enyl)-1-methyl-1H-pyrazol-4-yl)-2-(2,6-difluorophenyl)thiazole-4-carboxamide | 0.000069 |
| 411 | 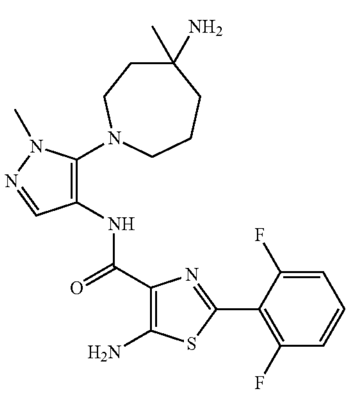 [SMILES: Cn1ncc(NC(=O)c2nc(-c3c(F)cccc3F)sc2N)c1N1CCCC(C)(N)CC1] | 5-amino-N-[5-(4-amino-4-methyl-azepan-1-yl)-1-methyl-pyrazol-4-yl]-2-(2,6-difluorophenyl)thiazole-4-carboxamide | 0.000062 |

TABLE 1b-continued

| No. | Structure | IUPAC Name | PIM1 LC3K (KI) uM |
|---|---|---|---|
| 412 | 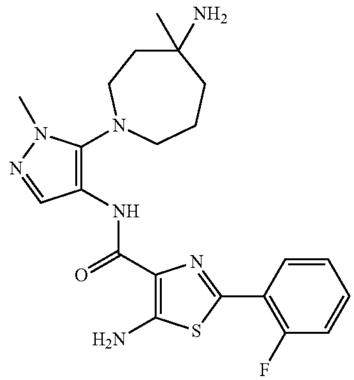 [SMILES: Cn1ncc(NC(=O)c2nc(-c3ccccc3F)sc2N)c1N1CCCC(C)(N)CC1] | 5-amino-N-[5-(4-amino-4-methyl-azepan-1-yl)-1-methyl-pyraozl-4-yl]-2-(2-fluorophenyl)thiazole-4-carboxamide | 0.000057 |
| 413 | 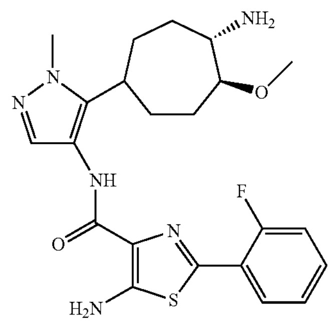 [SMILES: CO[C@H]1CCC(c2c(NC(=O)c3nc(-c4ccccc4F)sc3N)cnn2C)CC[C@@H]1N] | 5-amino-N-(5-((4S,5S)-4-amino-5-methoxycycloheptyl)-1-methyl-1H-pyrazol-4-yl)-2-(2-fluorophenyl)thiazole-4-carboxamide | 0.000822 |
| 414 | 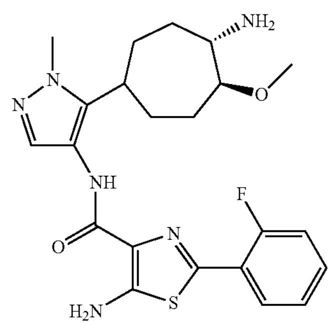 [SMILES: CO[C@H]1CCC(c2c(NC(=O)c3nc(-c4ccccc4F)sc3N)cnn2C)CC[C@@H]1N] | 5-amino-N-(5-((4S,5S)-4-amino-5-methoxycycloheptyl)-1-methyl-1H-pyrazol-4-yl)-2-(2-fluorophenyl)thiazole-4-carboxamide | 0.00012 |
| 415 | 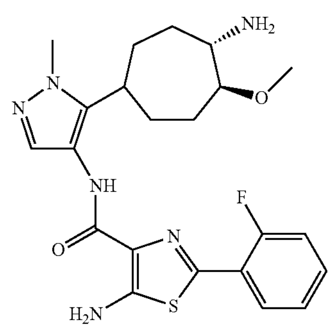 [SMILES: CO[C@H]1CCC(c2c(NC(=O)c3nc(-c4ccccc4F)sc3N)cnn2C)CC[C@@H]1N] | 5-amino-N-(5-((4S,5S)-4-amino-5-methoxycycloheptyl)-1-methyl-1H-pyrazol-4-yl)-2-(2-fluorophenyl)thiazole-4-carboxamide | 0.000461 |

TABLE 1b-continued

| No. | Structure | IUPAC Name | PIM1 LC3K (KI) uM |
|---|---|---|---|
| 416 | 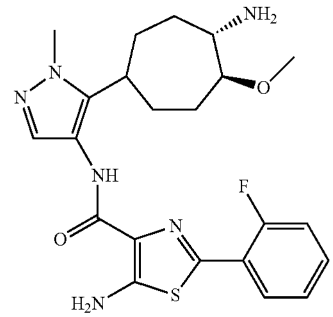 [SMILES: CO[C@H]1CCC(c2c(NC(=O)c3nc(-c4ccccc4F)sc3N)cnn2C)CC[C@@H]1N] | 5-amino-N-(5-((4S,5S)-4-amino-5-methoxycycloheptyl)-1-methyl-1H-pyrazol-4-yl)-2-(2-fluorophenyl)thiazole-4-carboxamide | 0.00158 |
| 417 | 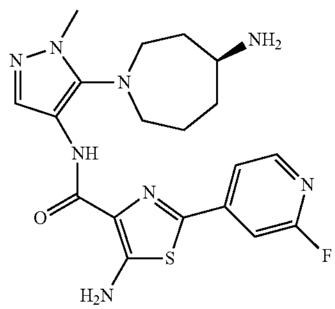 [SMILES: Cn1ncc(NC(=O)c2nc(-c3ccnc(F)c3)sc2N)c1N1CCC[C@H](N)CC1] | 5-amino-N-[5-[(4S)-4-aminoazepan-1-yl]-1-methyl-pyrazol-4-yl]-2-(2-fluoro-4-pyridyl)thiazole-4-carboxamide | 0.00212 |
| 418 | 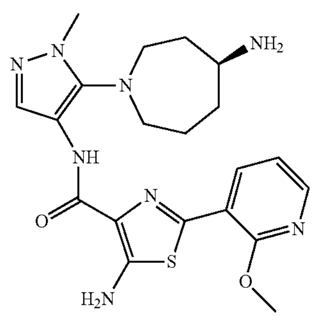 [SMILES: COc1ncccc1-c1nc(C(=O)Nc2cnn(C)c2N2CCC[C@H](N)CC2)c(N)s1] | 5-amino-N-[5-[(4S)-4-aminoazepan-1-yl]-1-methyl-pyrazol-4-yl]-2-(2-methoxy-3-pyridyl)thiazole-4-carboxamide | 0.00108 |
| 419 | 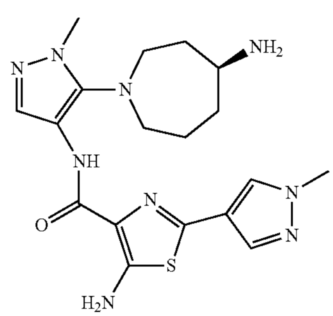 [SMILES: Cn1cc(-c2nc(C(=O)Nc3cnn(C)c3N3CCC[C@H](N)CC3)c(N)s2)cn1] | 5-amino-N-[5-[(4S)-4-aminoazepan-1-yl]-1-methyl-pyrazol-4-yl]-2-(1-methylpyrazol-4-yl)thiazole-4-carboxamide | 0.000785 |
| 420 | 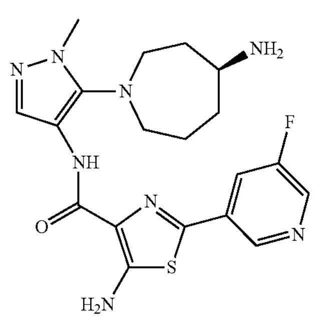 [SMILES: Cn1ncc(NC(=O)c2nc(-c3cncc(F)c3)sc2N)c1N1CCC[C@H](N)CC1] | 5-amino-N-[5-[(4S)-4-aminoazepan-1-yl]-1-methyl-pyrazol-4-yl]-2-(5-fluoro-3-pyridyl)thiazole-4-carboxamide | 0.00425 |

TABLE 1b-continued

| No. | Structure | IUPAC Name | PIM1 LC3K (KI) uM |
|---|---|---|---|
| 421 | 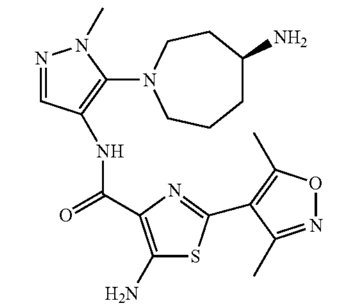 [SMILES: Cc1noc(C)c1-c1nc(C(=O)Nc2cnn(C)c2N2CCC[C@H](N)CC2)c(N)s1] | 5-amino-N-[5-[(4S)-4-aminoazepan-1-yl]-1-methyl-pyrazol-4-yl]-2-(3,5-dimethylisoxazol-4-yl)thiazole-4-carboxamide | 0.00437 |
| 422 | 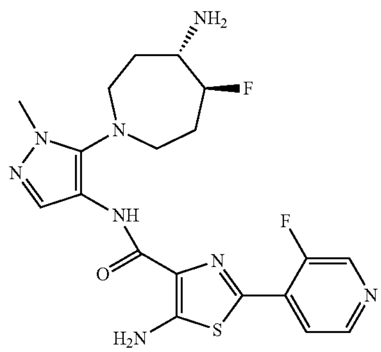 [SMILES: Cn1ncc(NC(=O)c2nc(-c3ccncc3F)sc2N)c1N1CC[C@H](N)[C@@H](F)CC1] | 5-amino-N-(5-((4S,5S)-4-amino-5-fluoroazepan-1-yl)-1-methyl-1H-pyrazol-4-yl)-2-(3-fluoropyridin-4-yl)thiazole-4-carboxamide | 0.00038 |
| 423 | 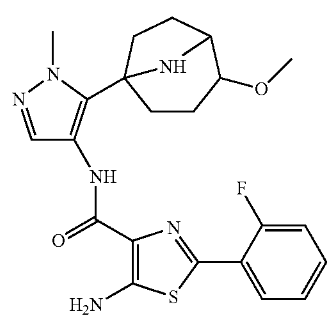 [SMILES: COC1CCC2(c3c(NC(=O)c4nc(-c5ccccc5F)sc4N)cnn3C)CCC1N2] | 5-amino-2-(2-fluorophenyl)-N-[5-(2-methoxy-8-azabicyclo[3.2.1]octan-5-yl)-1-methyl-pyrazol-4-yl]thiazole-4-carboxamide | 0.000362 |
| 424 | 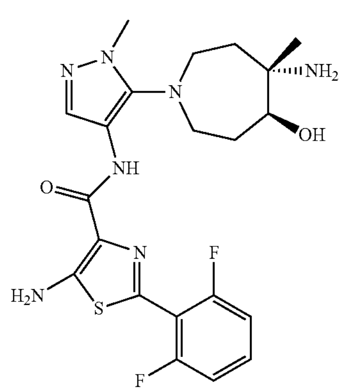 [SMILES: Cn1ncc(NC(=O)c2nc(-c3c(F)cccc3F)sc2N)c1N1CC[C@H](O)[C@@](C)(N)CC1] | 5-amino-N-(5-((4S,5S)-4-amino-5-hydroxy-4-methylazepan-1-yl)-1-methyl-1H-pyrazol-4-yl)-2-(2,6-difluorophenyl)thiazole-4-carboxamide | 0.000199 |

TABLE 1b-continued

| No. | Structure | IUPAC Name | PIM1 LC3K (KI) uM |
|---|---|---|---|
| 425 | 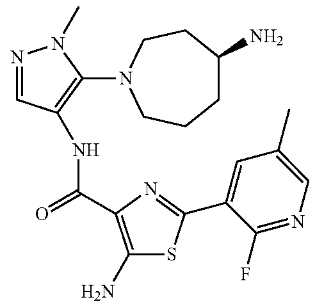 [SMILES: Cc1cnc(F)c(-c2nc(C(=O)Nc3cnn(C)c3N3CCC[C@H](N)CC3)c(N)s2)c1] | 5-amino-N-[5-[(4S)-4-aminoazepan-1-yl]-1-methyl-pyrazol-4-yl]-2-(2-fluoro-5-methyl-3-pyridyl)thiazole-4-carboxamide | 0.000144 |
| 426 | 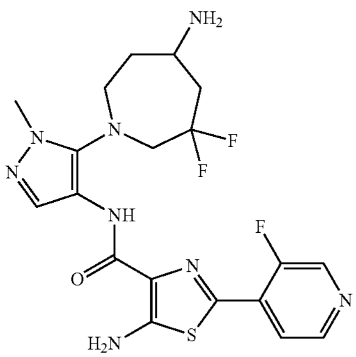 [SMILES: Cn1ncc(NC(=O)c2nc(-c3ccncc3F)sc2N)c1N1CCC(N)CC(F)(F)C1] | 5-amino-N-[5-(5-amino-3,3-difluoro-azepan-1-yl)-1-methyl-pyrazol-4-yl]-2-(3-fluoro-4-pyridyl)thiazole-4-carboxamide | 0.000034 |
| 427 | 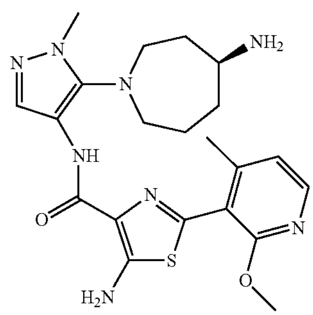 [SMILES: COc1nccc(C)c1-c1nc(C(=O)Nc2cnn(C)c2N2CCC[C@H](N)CC2)c(N)s1] | 5-amino-N-[5-[(4S)-4-aminoazepan-1-yl]-1-methyl-pyrazol-4-yl]-2-(2-methoxy-4-methyl-3-pyridyl)thiazole-4-carboxamide | 0.0037 |
| 428 | 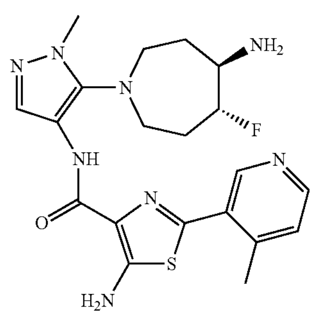 [SMILES: Cc1ccncc1-c1nc(C(=O)Nc2cnn(C)c2N2CC[C@@H](N)[C@H](F)CC2)c(N)s1] | 5-amino-N-[5-[(4R,5R)-4-amino-5-fluoro-azepan-1-yl]-1-methyl-pyrazol-4-yl]-2-(4-methyl-3-pyridyl)thiazole-4-carboxamide | 0.000884 |

TABLE 1b-continued

| No. | Structure | IUPAC Name | PIM1 LC3K (KI) uM |
|---|---|---|---|
| 429 | 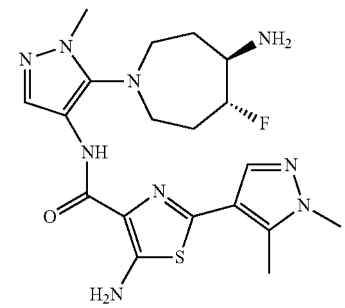 [SMILES: Cc1c(-c2nc(C(=O)Nc3cnn(C)c3N3CC[C@@H](N)[C@H](F)CC3)c(N)s2)cnn1C] | 5-amino-N-[5-[(4R,5R)-4-amino-5-fluoro-azepan-1-yl]-1-methyl-pyrazol-4-yl]-2-(1,5-dimethylpyrazol-4-yl)thiazole-4-carboxamide | 0.000315 |
| 430 | 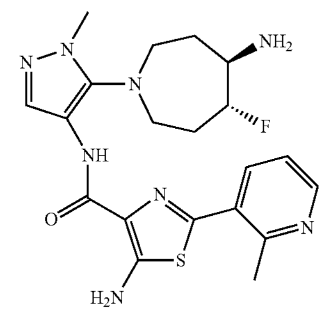 [SMILES: Cc1ncccc1-c1nc(C(=O)Nc2cnn(C)c2N2CC[C@@H](N)[C@H](F)CC2)c(N)s1] | 5-amino-N-[5-[(4R,5R)-4-amino-5-fluoro-azepan-1-yl]-1-methyl-pyrazol-4-yl]-2-(2-methyl-3-pyridyl)thiazole-4-carboxamide | 0.00117 |
| 431 | 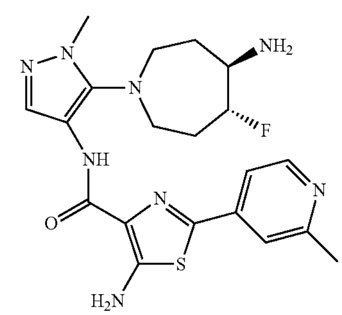 [SMILES: Cc1cc(-c2nc(C(=O)Nc3cnn(C)c3N3CC[C@@H](N)[C@H](F)CC3)c(N)s2)ccn1] | 5-amino-N-[5-[(4R,5R)-4-amino-5-fluoro-azepan-1-yl]-1-methyl-pyrazol-4-yl]-2-(2-methyl-4-pyridyl)thiazole-4-carboxamide | 0.00104 |
| 432 | 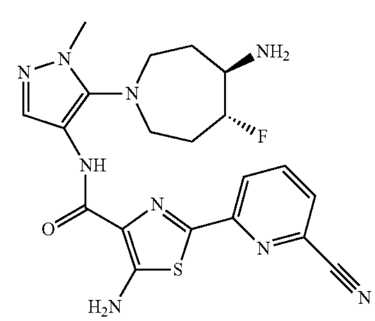 [SMILES: Cn1ncc(NC(=O)c2nc(-c3cccc(C#N)n3)sc2N)c1N1CC[C@@H](N)[C@H](F)CC1] | 5-amino-N-[5-[(4R,5R)-4-amino-5-fluoro-azepan-1-yl]-1-methyl-pyrazol-4-yl]-2-(6-cyano-2-pyridyl)thiazole-4-carboxamide | 0.00144 |

TABLE 1b-continued

| No. | Structure | IUPAC Name | PIM1 LC3K (KI) uM |
|---|---|---|---|
| 433 | 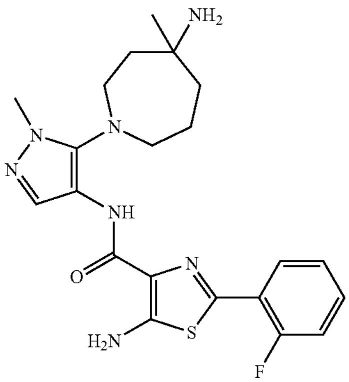 [SMILES: Cn1ncc(NC(=O)c2nc(-c3ccccc3F)sc2N)c1N1CCCC(C)(N)CC1] | 5-amino-N-[5-(4-amino-4-methyl-azepan-1-yl)-1-methyl-pyrazol-4-yl]-2-(2-fluorophenyl)thiazole-4-carboxamide | 0.000024 |
| 434 | 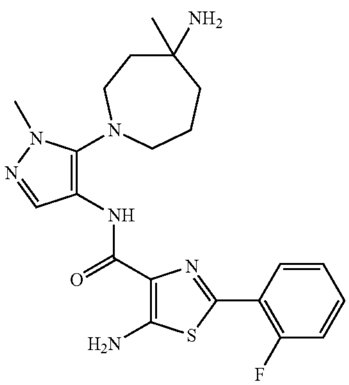 [SMILES: Cn1ncc(NC(=O)c2nc(-c3ccccc3F)sc2N)c1N1CCCC(C)(N)CC1] | 5-amino-N-[5-(4-amino-4-methyl-azepan-1-yl)-1-methyl-pyrazol-4-yl]-2-(2-fluorophenyl)thiazole-4-carboxamide | 0.000093 |
| 435 | 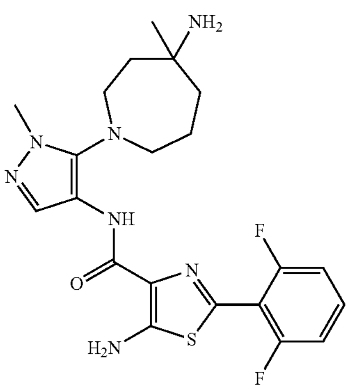 [SMILES: Cn1ncc(NC(=O)c2nc(-c3c(F)cccc3F)sc2N)c1N1CCCC(C)(N)CC1] | 5-amino-N-[5-(4-amino-4-methyl-azepan-1-yl)-1-methyl-pyrazol-4-yl]-2-(2,6-difluorophenyl)thiazole-4-carboxamide | 0.000021 |
| 436 | 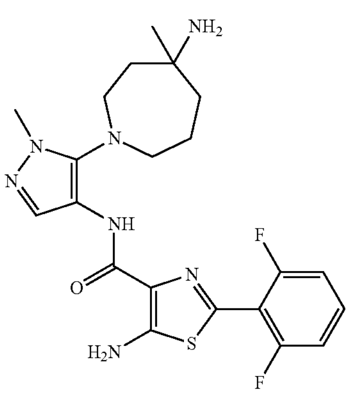 [SMILES: Cn1ncc(NC(=O)c2nc(-c3c(F)cccc3F)sc2N)c1N1CCCC(C)(N)CC1] | 5-amino-N-[5-(4-amino-4-methyl-azepan-1-yl)-1-methyl-pyrazol-4-yl]-2-(2,6-difluorophenyl)thiazole-4-carboxamide | 0.00004 |

TABLE 1b-continued

| No. | Structure | IUPAC Name | PIM1 LC3K (KI) uM |
|---|---|---|---|
| 437 | 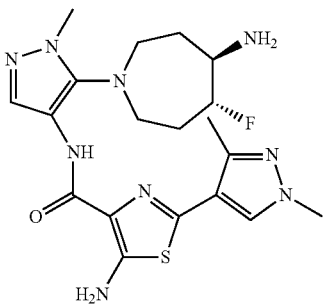 [SMILES: Cc1nn(C)cc1-c1nc(C(=O)Nc2cnn(C)c2N2CC[C@@H](N)[C@H](F)CC2)c(N)s1] | 5-amino-N-[5-[(4R,5R)-4-amino-5-fluoro-azepan-1-yl]-1-methyl-pyrazol-4-yl]-2-(1,3-dimethylpyrazol-4-yl)thiazole-4-carboxamide | 0.000477 |
| 438 | 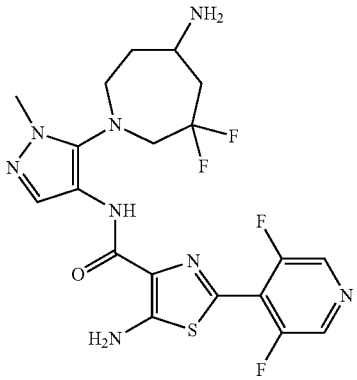 [SMILES: Cn1ncc(NC(=O)c2nc(-c3c(F)cncc3F)sc2N)c1N1CCC(N)CC(F)(F)C1] | 5-amino-N-[5-(5-amino-3,3-difluoro-azepan-1-yl)-1-methyl-pyrazol-4-yl]-2-(3,5-difluoro-4-pyridyl)thiazole-4-carboxamide | 0.000008 |
| 439 | 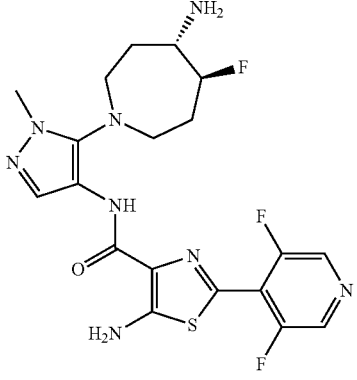 [SMILES: Cn1ncc(NC(=O)c2nc(-c3c(F)cncc3F)sc2N)c1N1CC[C@H](N)[C@@H](F)CC1] | 5-amino-N-(5-((4S,5S)-1-amino-5-fluoroazepan-1-yl)-1-methyl-1H-pyrazol-4-yl)-2-(3,5-difluoropyridin-4-yl)thiazole-carboxamide | 0.000121 |
| 440 | 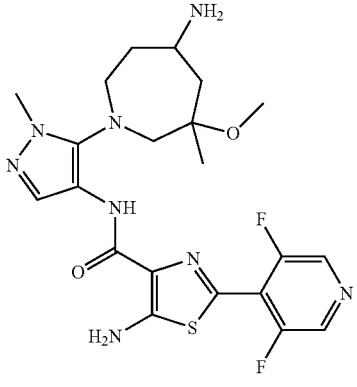 [SMILES: COC1(C)CC(N)CCN(c2c(NC(=O)c3nc(-c4c(F)cncc4F)sc3N)cnn2C)C1] | 5-amino-N-[5-(5-amion-3-methoxy-3-methyl-azepan-1-yl)-1-methyl-pyrazol-4-yl]-2-(3,5-difluoro-4-pyridyl)thiazole-4-carboxamide | 0.000024 |

TABLE 1b-continued

| No. | Structure | IUPAC Name | PIM1 LC3K (KI) uM |
|---|---|---|---|
| 441 | 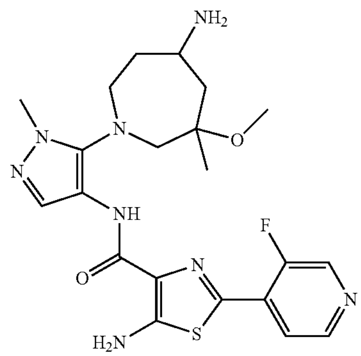 [SMILES: COC1(C)CC(N)CCN(c2c(NC(=O)c3nc(-c4ccncc4F)sc3N)cnn2C)C1] | 5-amino-N-[5-(5-amino-3-methoxy-3-methyl-azepan-1-yl)-1-methyl-pyrazol-4-yl]-2-(3-fluoro-4-pyridyl)thiazole-4-carboxamide | 0.000027 |
| 442 | 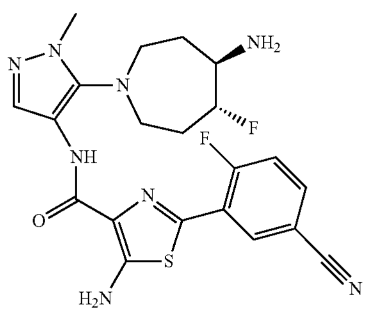 | 5-amino-N-[5-[(4R,5R)-4-amino-5-fluoro-azepan-1-yl]-1-methyl-pyrazol-4-yl]-2-(5-cyano-2-fluoro-phenyl)thiazole-4-carboxamide | 0.00108 |
| 443 | 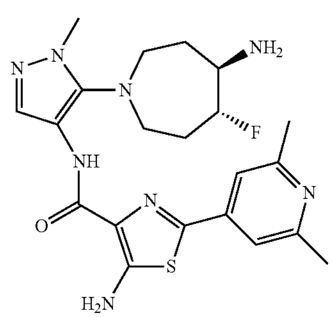 [SMILES: Cc1cc(-c2nc(C(=O)Nc3cnn(C)c3N3CC[C@@H](N)[C@H](F)CC3)c(N)s2)cc(C)n1] | 5-amino-N-[5-[(4R,5R)-4-amino-5-fluoro-azepan-1-yl]-1-methyl-pyrazol-4-yl]-2-(2,6-dimethyl-4-pyridyl)thiazole-4-carboxamide | 0.00254 |
| 444 | 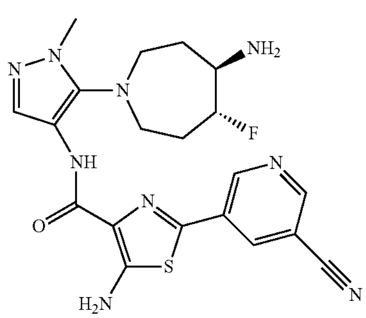 | 5-amino-N-[5-[(4R,5R)-4-amino-5-fluoro-azepan-1-yl]-1-methyl-pyrazol-4-yl]-2-(5-cyano-3-pyridyl)thiazole-4-carboxamide | 0.0354 |

TABLE 1b-continued

| No. | Structure | IUPAC Name | PIM1 LC3K (KI) uM |
|---|---|---|---|
| 445 | 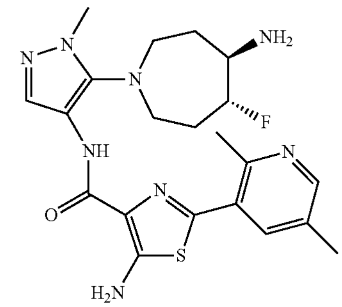 [SMILES: Cc1cnc(C)c(-c2nc(C(=O)Nc3cnn(C)c3N3CC[C@@H](N)[C@H](F)CC3)c(N)s2)c1] | 5-amino-N-[5-[(4R,5R)-4-amino-5-fluoro-azepan-1-yl]-1-methyl-pyrazol-4-yl]-2-(2,5-dimethyl-3-pyridyl)thiazole-4-carboxamide | 0.000446 |
| 446 | 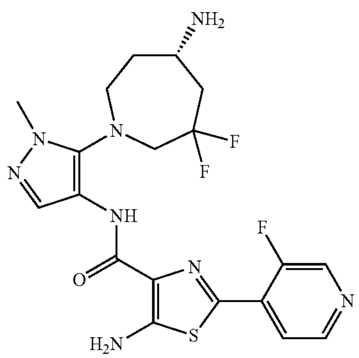 | 5-amino-N-[5-[(5S)-5-amino-3,3-difluoro-azepan-1-yl]-1-methyl-pyrazol-4-yl]-2-(3-fluoro-4-pyridyl)thiazole-4-carboxamide | 0.00001 |
| 447 | 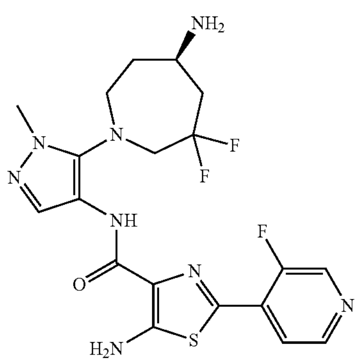 [SMILES: Cn1ncc(NC(=O)c2nc(-c3ccncc3F)sc2N)c1N1CC[C@@H](N)CC(F)(F)C1] | 5-amino-N-[5-[(5R)-5-amino-3,3-difluoro-azepan-1-yl]-1-methyl-pyrazol-4-yl]-2-(3-fluoro-4-pyridyl)thiazole-4-carboxamide | 0.000014 |
| 448 | 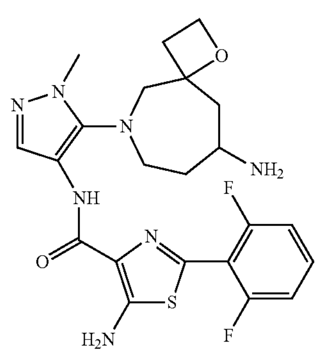 [SMILES: Cn1ncc(NC(=O)c2nc(-c3c(F)cccc3F)sc2N)c1N1CCC(N)CC2(CCO2)C1] | 5-amino-N-[5-(6-amino-1-oxa-9-azaspiro[3.6]decan-9-yl)-1-methyl-pyrazol-4-yl]-2-(2,6-difluorophenyl)thiazole-4-carboxamide | 0.000104 |

TABLE 1b-continued

| No. | Structure | IUPAC Name | PIM1 LC3K (KI) uM |
|---|---|---|---|
| 449 | 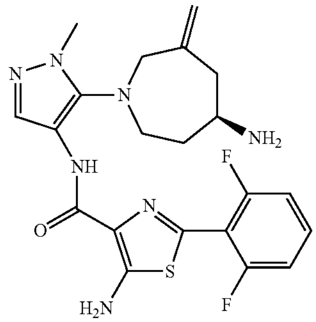 [SMILES: C=C1C[C@@H](N)CCN(c2c(NC(=O)c3nc(-c4c(F)cccc4F)sc3N)cnn2C)C1] | 5-amino-N-[5-[(5R)-5-amino-3-methylene-azepan-1-yl]-1-methyl-pyrazol-4-yl]-2-(2,6-difluorophenyl)thiazole-4-carboxamide | 0.000047 |
| 450 | 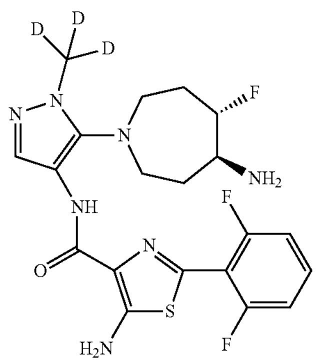 [SMILES: [2H]C([2H])([2H])n1ncc(NC(=O)c2nc(-c3c(F)cccc3F)sc2N)c1N1CC[C@H](N)[C@@H](F)CC1] | 5-amino-N-[5-[(4S,5S)-4-amino-5-fluoro-azepan-1-yl]-1-(trideuteriomethyl)pyrazol-4-yl]-2-(2,6-difluorophenyl)thiazole-4-carboxamide | 0.000101 |
| 451 | 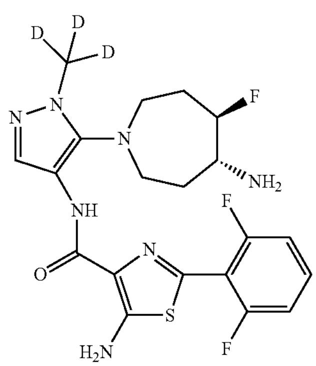 [SMILES: [2H]C([2H])([2H])n1ncc(NC(=O)c2nc(-c3c(F)cccc3F)sc2N)c1N1CC[C@@H](N)[C@H](F)CC1] | 5-amino-N-[5-[(4R,5R)-4-amino-5-fluoro-azepan-1-yl]-1-(trideuteriomethyl)pyrazol-4-yl]-2-(2,6-difluorophenyl)thiazole-4-carboxamide | 0.000017 |
| 452 | 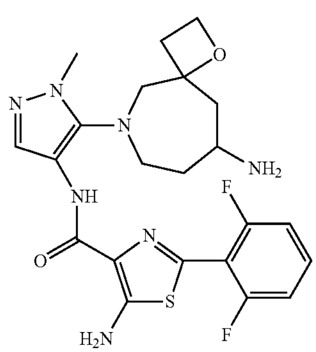 [SMILES: Cn1ncc(NC(=O)c2nc(-c3c(F)cccc3F)sc2N)c1N1CCC(N)CC2(CCO2)C1] | 5-amino-N-[5-(6-amino-1-oxa-9-azaspiro[3.6]decan-9-yl)-1-methyl-pyrazol-4-yl]-2-(2,6-difluorophenyl)thiazole-4-carboxamide | 0.000031 |

TABLE 1b-continued

| No. | Structure | IUPAC Name | PIM1 LC3K (KI) uM |
|---|---|---|---|
| 453 | 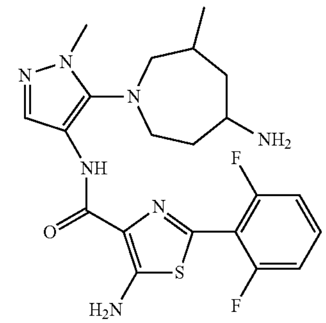 [SMILES: CC1CC(N)CCN(c2c(NC(=O)c3nc(-c4c(F)cccc4F)sc3N)cnn2C)C1] | 5-amino-N-[5-(5-amino-3-methyl-azepan-1-yl)-1-methyl-pyrazol-4-yl]-2-(2,6-difluorophenyl)thiazole-4-carboxamide | 0.000012 |
| 454 | 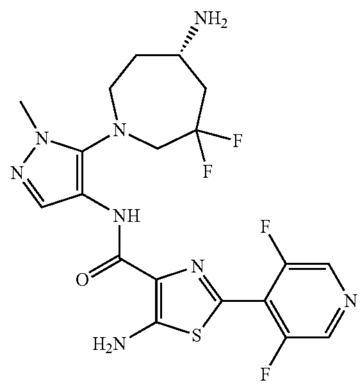 [SMILES: Cn1ncc(NC(=O)c2nc(-c3c(F)cncc3F)sc2N)c1N1CC[C@H](N)CC(F)(F)C1] | 5-amino-N-[5-[(5S)-5-amino-3,3-difluoro-azepan-1-yl]-1-methyl-pyrazol-4-yl]-2-(3,5-difluoro-4-pyridyl)thiazole-4-carboxamide | 0.000023 |
| 455 | 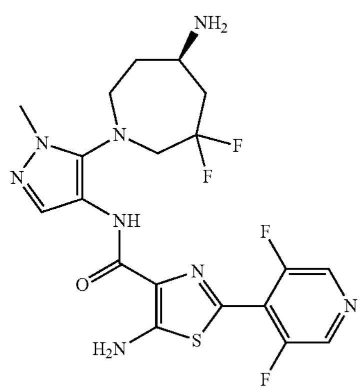 [SMILES: Cn1ncc(NC(=O)c2nc(-c3c(F)cncc3F)sc2N)c1N1CC[C@@H](N)CC(F)(F)C1] | 5-amino-N-[5-[(5R)-5-amino-3,3-difluoro-azepan-1-yl]-1-methyl-pyrazol-4-yl]-2-(3,5-difluoro-4-pyridyl)thiazole-4-carboxamide | 0.000009 |
| 456 | 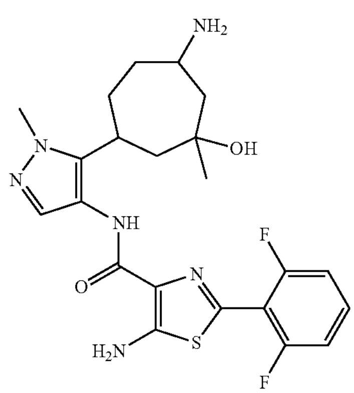 [SMILES: Cn1ncc(NC(=O)c2nc(-c3c(F)cccc3F)sc2N)c1C1CCC(N)CC(C)(O)C1] | 5-amino-N-[5-(5-amino-3-hydroxy-3-methyl-cycloheptyl)-1-methyl-pyrazol-4-yl]-2-(2,6-difluorophenyl)thiazole-4-carboxamide | 0.00007 |

TABLE 1b-continued

| No. | Structure | IUPAC Name | PIM1 LC3K (KI) uM |
|---|---|---|---|
| 457 | 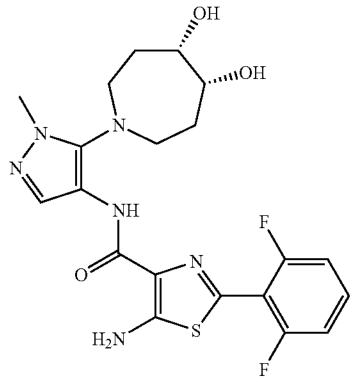 [SMILES: Cn1ncc(NC(=O)c2nc(-c3c(F)cccc3F)sc2N)c1N1CC[C@@H](O)[C@@H](O)CC1] | 5-amino-2-(2,6-difluorophenyl)-N-(5-((4R,5S)-4,5-dihydroxyazepan-1-yl)-1-methyl-1H-pyrazol-4-yl)thiazole-4-carboxamide | 0.00016 |
| 458 | 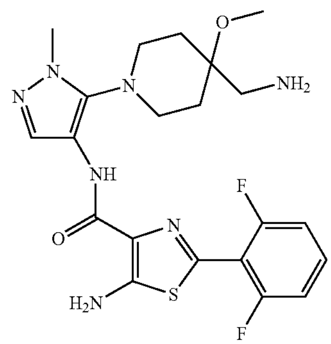 [SMILES: COC1(CN)CCN(c2c(NC(=O)c3nc(-c4c(F)cccc4F)sc3N)cnn2C)CC1] | 5-amino-N-[5-[4-(aminomethyl)-4-methoxy-1-piperidyl]-1-methyl-pyrazol-4-yl]-2-(2,6-difluorophenyl)thiazole-4-carboxamide | 0.000257 |
| 459 | 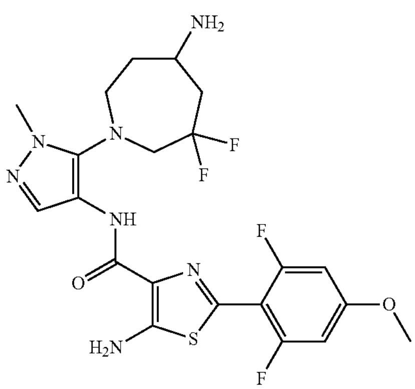 [SMILES: COc1cc(F)c(-c2nc(C(=O)Nc3cnn(C)c3N3CCC(N)CC(F)(F)C3)c(N)s2)c(F)c1] | 5-amino-N-[5-(5-amino-3,4-difluoro-azepan-1-yl)-1-methyl-pyrazol-4-yl]-2-(2,6-difluoro-4-methoxy-phenyl)thiazole-4-carboxamide | 0.000006 |
| 460 | 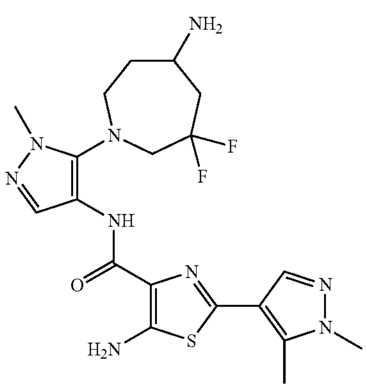 [SMILES: Cc1c(-c2nc(C(=O)Nc3cnn(C)c3N3CCC(N)CC(F)(F)C3)c(N)s2)cnn1C] | 5-amino-N-[5-(5-amino-3,3-difluoro-azepan-1-yl)-1-methyl-pyrazol-4-yl]-2-(1,5-dimethylpyrazol-4-yl)thiazole-4-carboxamide | 0.000026 |

TABLE 1b-continued

| No. | Structure | IUPAC Name | PIM1 LC3K (KI) uM |
|---|---|---|---|
| 461 | 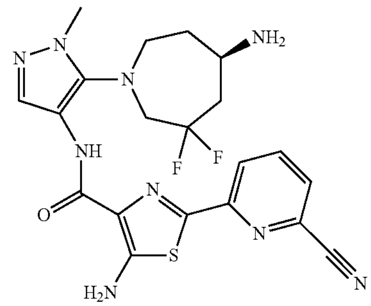 [SMILES: Cn1ncc(NC(=O)c2nc(-c3cccc(C#N)n3)sc2N)c1N1CC[C@@H](N)CC(F)(F)C1] | 5-amino-N-[5-[(5R)-5-amino-3,3-difluoro-azepan-1-yl]-1-methyl-pyrazol-4-yl]-2-(6-cyano-2-pyridyl)thiazole-4-carboxamide | 0.00008 |
| 462 | 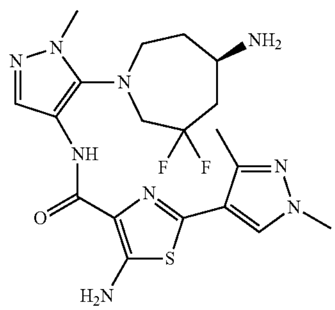 [SMILES: Cc1nn(C)cc1-c1nc(C(=O)Nc2cnn(C)c2N2CC[C@@H](N)CC(F)(F)C2)c(N)s1] | 5-amino-N-[5-[(5R)-5-amino-3,3-difluoro-azepan-1-yl]-1-methyl-pyrazol-4-yl]-2-(1,3-dimethylpyrazol-4-yl)thiazole-4-carboxamide | 0.00003 |
| 463 | 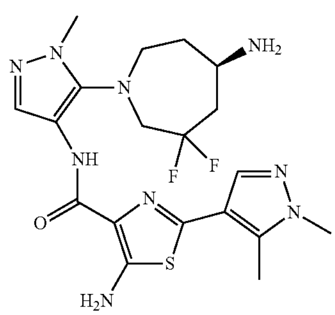 [SMILES: Cc1c(-c2nc(C(=O)Nc3cnn(C)c3N3CC[C@@H](N)CC(F)(F)C3)c(N)s2)cnn1C] | 5-amino-N-[5-[(5R)-5-amino-3,3-difluoro-azepan-1-yl]-1-methyl-pyrazol-4-yl]-2-(1,5-dimethylpyrazol-4-yl)thiazole-4-carboxamide | 0.000018 |
| 464 | 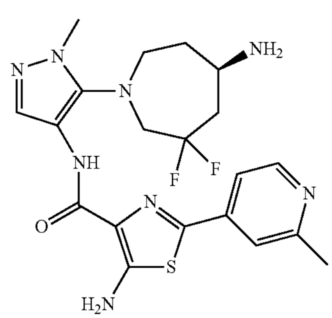 [SMILES: Cc1cc(-c2nc(C(=O)Nc3cnn(C)c3N3CC[C@@H](N)CC(F)(F)C3)c(N)s2)ccn1] | 5-amino-N-[5-[(5R)-5-amino-3,3-difluoro-azepan-1-yl]-1-methyl-pyrazol-4-yl]-2-(2-methyl-4-pyridyl)thiazole-4-carboxamide | 0.00006 |

TABLE 1b-continued

| No. | Structure | IUPAC Name | PIM1 LC3K (KI) uM |
|---|---|---|---|
| 465 | 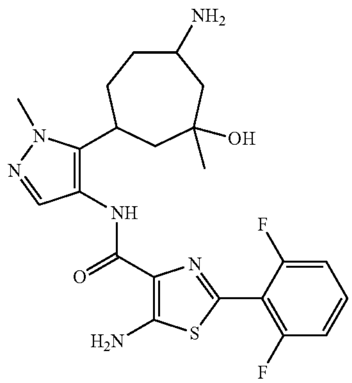 [SMILES: Cn1ncc(NC(=O)c2nc(-c3c(F)cccc3F)sc2N)c1C1CCC(N)CC(C)(O)C1] | 5-amino-N-[5-(5-amino-3-hydroxy-3-methyl-cycloheptyl)-1-methyl-pyrazol-4-yl]-2-(2,6-difluorophenyl)thiazole-4-carboxamide | 0.000559 |
| 466 | 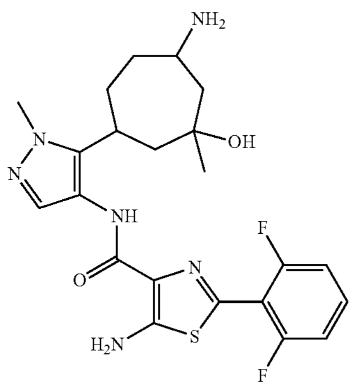 [SMILES: Cn1ncc(NC(=O)c2nc(-c3c(F)cccc3F)sc2N)c1C1CCC(N)CC(C)(O)C1] | 5-amino-N-[5-(5-amino-3-hydroxy-3-methyl-cycloheptyl)-1-methyl-pyrazol-4-yl]-2-(2,6-difluorophenyl)thiazole-4-carboxamide | 0.000222 |
| 467 | 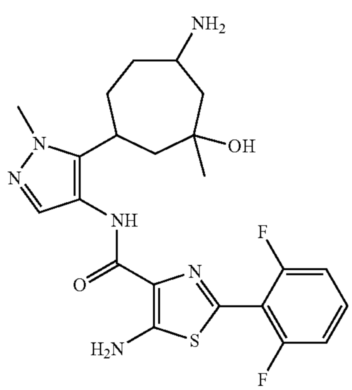 [SMILES: Cn1ncc(NC(=O)c2nc(-c3c(F)cccc3F)sc2N)c1C1CCC(N)CC(C)(O)C1] | 5-amino-N-[5-(5-amino-3-hydroxy-3-methyl-cycloheptyl)-1-methyl-pyrazol-4-yl]-2-(2,6-difluorophenyl)thiazole-4-carboxamide | 0.000126 |
| 468 | 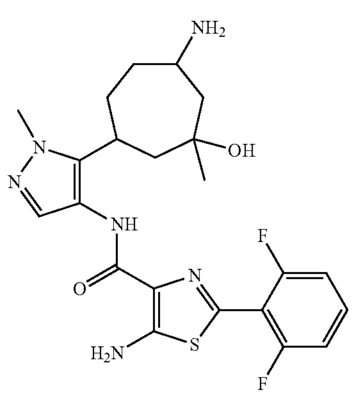 [SMILES: Cn1ncc(NC(=O)c2nc(-c3c(F)cccc3F)sc2N)c1C1CCC(N)CC(C)(O)C1] | 5-amino-N-[5-(5-amino-3-hydroxy-3-methyl-cycloheptyl)-1-methyl-pyrazol-4-yl]-2-(2,6-difluorophenyl)thiazole-4-carboxamide | 0.000139 |

TABLE 1b-continued

| No. | Structure | IUPAC Name | PIM1 LC3K (KI) uM |
|---|---|---|---|
| 469 | 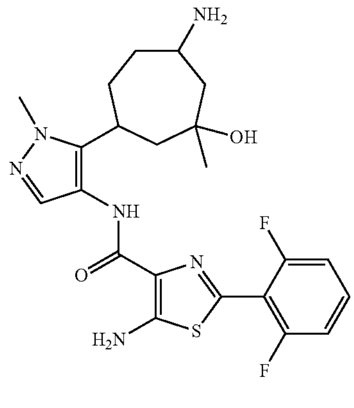 [SMILES: Cn1ncc(NC(=O)c2nc(-c3c(F)cccc3F)sc2N)c1C1CCC(N)CC(C)(O)C1] | 5-amino-N-[5-(5-amino-3-hydroxy-3-methyl-cycloheptyl)-1-methyl-pyrazol-4-yl]-2-(2,6-difluorophenyl)thiazole-4-carboxamide | 0.00155 |
| 470 | 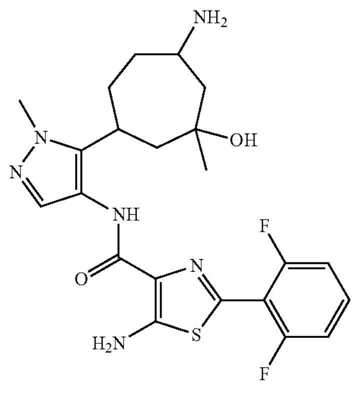 [SMILES: Cn1ncc(NC(=O)c2nc(-c3c(F)cccc3F)sc2N)c1C1CCC(N)CC(C)(O)C1] | 5-amino-N-[5-(5-amino-3-hydroxy-3-methyl-cycloheptyl)-1-methyl-pyrazol-4-yl]-2-(2,6-difluorophenyl)thiazole-4-carboxamide | 0.000108 |
| 471 | 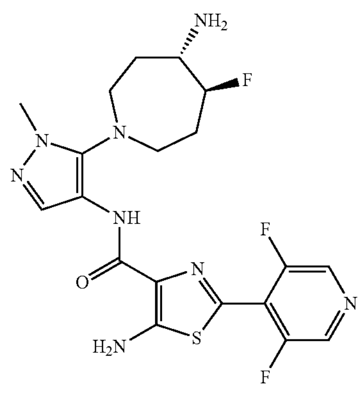 [SMILES: Cn1ncc(NC(=O)c2nc(-c3c(F)cncc3F)sc2N)c1N1CC[C@H](N)[C@@H](F)CC1] | 5-amino-N-[5-[(4S,5S)-4-amino-5-fluoro-azepan-1-yl]-1-methyl-pyrazol-4-yl]-2-(3,5-difluoro-4-pyridyl)thiazole-4-carboxamide | 0.000242 |
| 472 | 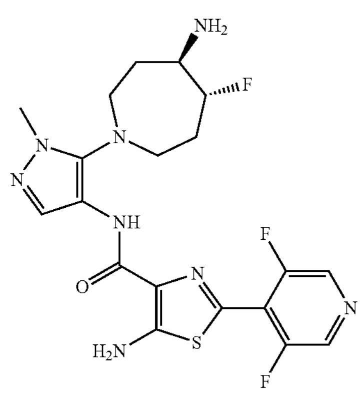 [SMILES: Cn1ncc(NC(=O)c2nc(-c3c(F)cncc3F)sc2N)c1N1CC[C@@H](N)[C@H](F)CC1] | 5-amino-N-[5-[(4R,5R)-4-amino-5-fluoro-azepan-1-yl]-1-methyl-pyrazol-4-yl]-2-(3,5-difluoro-4-pyridyl)thiazole-4-carboxamide | 0.000086 |

TABLE 1b-continued

| No. | Structure | IUPAC Name | PIM1 LC3K (KI) uM |
|---|---|---|---|
| 473 | 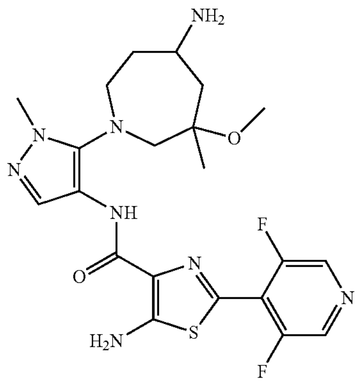 [SMILES: COC1(C)CC(N)CCN(c2c(NC(=O)c3nc(-c4c(F)cncc4F)sc3N)cnn2C)C1] | 5-amino-N-[5-(5-amino-3-methoxy-3-methyl-azepan-1-yl)-1-methyl-pyrazol-4-yl]-2-(3,5-difluoro-4-pyridyl)thiazole-4-carboxamide | 0.000009 |
| 474 | 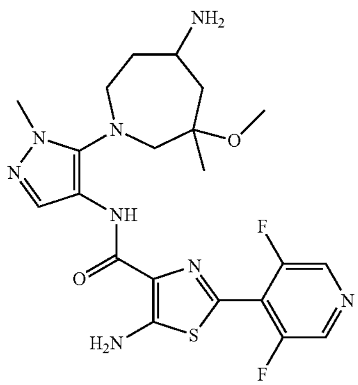 [SMILES: COC1(C)CC(N)CCN(c2c(NC(=O)c3nc(-c4c(F)cncc4F)sc3N)cnn2C)C1] | 5-amino-N-[5-(5-amino-3-methoxy-3-methyl-azepan-1-yl)-1-methyl-pyrazol-4-yl]-2-(3,5-difluoro-4-pyridyl)thiazole-4-carboxamide | 0.000425 |
| 475 | 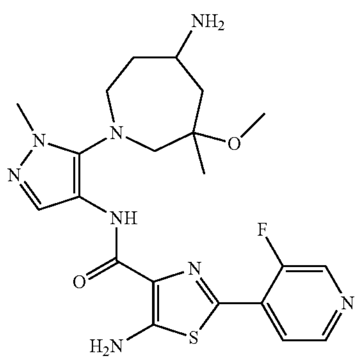 [SMILES: COC1(C)CC(N)CCN(c2c(NC(=O)c3nc(-c4ccncc4F)sc3N)cnn2C)C1] | 5-amino-N-[5-(5-amino-3-methoxy-3-methyl-azepan-1-yl)-1-methyl-pyrazol-4-yl]-2-(3-fluoro-4-pyridyl)thiazole-4-carboxamide | 0.000212 |
| 476 | 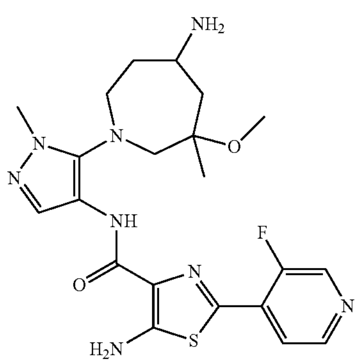 [SMILES: COC1(C)CC(N)CCN(c2c(NC(=O)c3nc(-c4ccncc4F)sc3N)cnn2C)C1] | 5-amino-N-[5-(5-amino-3-methoxy-3-methyl-azepan-1-yl)-1-methyl-pyrazol-4-yl]-2-(3-fluoro-4-pyridyl)thiazole-4-carboxamide | 0.000013 |

TABLE 1b-continued

| No. | Structure | IUPAC Name | PIM1 LC3K (KI) uM |
|---|---|---|---|
| 477 | 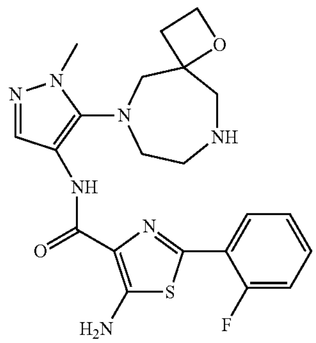 [SMILES: Cn1ncc(NC(=O)c2nc(-c3ccccc3F)sc2N)c1N1CCNCC2(CCO2)C1] | 5-amino-2-(2-fluorophenyl)-N-[1-methyl-5-(1-oxa-6,9-diazaspiro[3.6]decan-6-yl)pyrazol-4-yl]thiazole-4-carboxamide | 0.000188 |
| 478 | 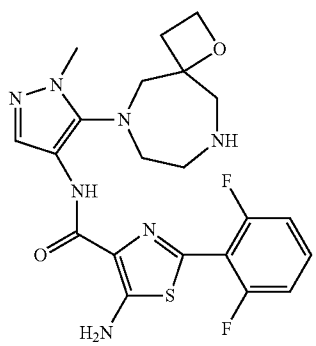 [SMILES: Cn1ncc(NC(=O)c2nc(-c3c(F)cccc3F)sc2N)c1N1CCNCC2(CCO2)C1] | 5-amino-2-(2,6-difluorophenyl)-N-[1-methyl-5-(1-oxa-6,9-diazaspiro[3.6]decan-6-yl)pyrazol-4-yl]thiazole-4-carboxamide | 0.000251 |
| 479 | 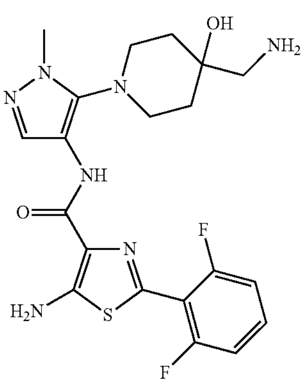 [SMILES: Cn1ncc(NC(=O)c2nc(-c3c(F)cccc3F)sc2N)c1N1CCC(O)(CN)CC1] | 5-amino-N-[5-[4-(aminomethyl)-4-hydroxy-1-piperidyl]-1-methyl-pyrazol-4-yl]-2-(2,6-difluorophenyl)thiazole-4-carboxamide | 0.000033 |
| 480 | 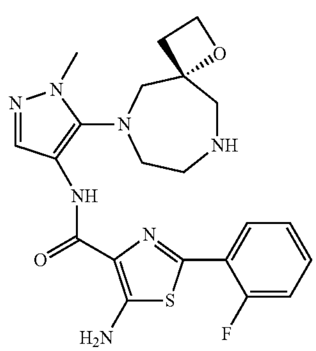 [SMILES: Cn1ncc(NC(=O)c2nc(-c3ccccc3F)sc2N)c1N1CCNC[C@]2(CCO2)C1] | (R)-5-amino-2-(2-fluorophenyl)-N-(1-methyl-5-(1-oxa-6,9-diazaspiro[3.6]decan-6-yl)-1H-pyrazol-4-yl)thiazole-4-carboxamide | 0.000045 |

TABLE 1b-continued

| No. | Structure | IUPAC Name | PIM1 LC3K (KI) uM |
|---|---|---|---|
| 481 | 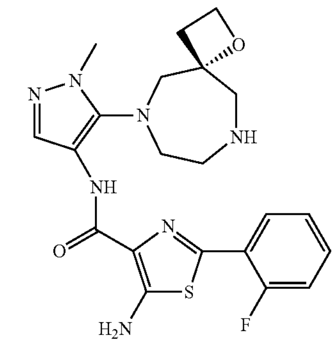 [SMILES: Cn1ncc(NC(=O)c2nc(-c3ccccc3F)sc2N)c1N1CCNC[C@]2(CCO2)C1] | (S)-5-amino-2-(2-fluorophenyl)-N-(1-methyl-5-(1-oxa-6,9-diazaspiro[3.6]decan-6-yl)-1H-pyrazol-4-yl)thiazole-4-carboxamide | 0.000496 |
| 482 | 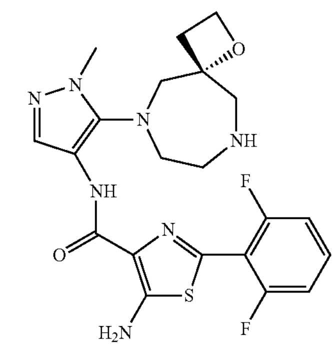 [SMILES: Cn1ncc(NC(=O)c2nc(-c3c(F)cccc3F)sc2N)c1N1CCNC[C@]2(CCO2)C1] | (R)-5-amino-2-(2,6-difluorophenyl)-N-(1-methyl-5-(1-oxa-6,9-diazaspiro[3.6]decan-6-yl)-1H-pyrazol-4-yl)thiazole-4-carboxamide | 0.000383 |
| 483 | 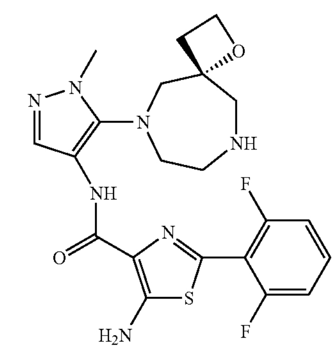 [SMILES: Cn1ncc(NC(=O)c2nc(-c3c(F)cccc3F)sc2N)c1N1CCNC[C@]2(CCO2)C1] | (S)-5-amino-2-(2,6-difluroophenyl)-N-(1-methyl-5-(1-oxa-6,9-diazaspiro[3.6]decan-6-yl)-1H-pyrazol-4-yl)thiazole-4-carboxamide | 0.000131 |
| 484 | 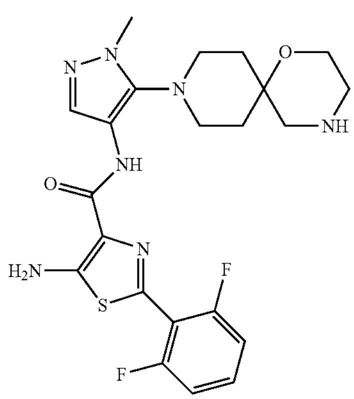 [SMILES: Cn1ncc(NC(=O)c2nc(-c3c(F)cccc3F)sc2N)c1N1CCC2(CC1)CNCCO2] | 5-amino-2-(2,6-difluorophenyl)-N-[1-methyl-5-(1-oxa-4,9-diazaspiro[5.5]undecan-9-yl)pyrazol-4-yl]thiazole-4-carboxamide | 0.000049 |

TABLE 1b-continued

| No. | Structure | IUPAC Name | PIM1 LC3K (KI) uM |
|---|---|---|---|
| 485 | 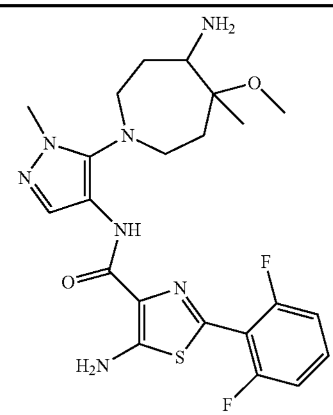 | 5-amino-N-[5-(5-amino-4-methoxy-4-methyl-azepan-1-yl)-1-methyl-pyrazol-4-yl]-2-(2,6-difluorophenyl)thiazole-4-carboxamide | 0.000035 |
| 486 | 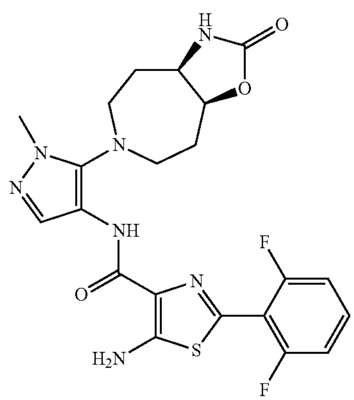 [SMILES: Cn1ncc(NC(=O)c2nc(-c3c(F)cccc3F)sc2N)c1N1CC[C@@H]2OC(=O)N[C@@H]2CC1] | N-[5-[(3aR,8aS)-2-oxo-3a,4,5,7,8,8a-hexahydro-3H-oxazolo[4,5-d]azepin-6-yl]-1-methyl-pyrazol-4-yl]-5-amino-2-(2,6-difluorophenyl)thiazole-4-carboxamide | 0.000058 |
| 487 | 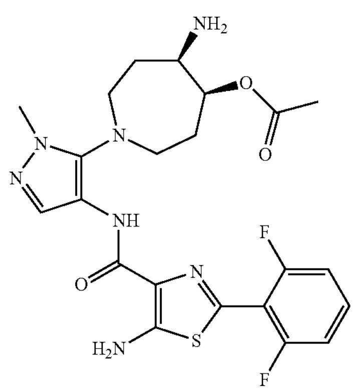 [SMILES: CC(=O)O[C@H]1CCN(c2c(NC(=O)c3nc(-c4c(F)cccc4F)sc3N)cnn2C)CC[C@H]1N] | [(4S,5R)-5-amino-1-[4-[[5-amino-2-(2,6-difluorophenyl)thiazole-4-carbonyl]amino]-2-methyl-pyrazol-3-yl]azepan-4-yl] acetate | 0.000498 |
| 488 | 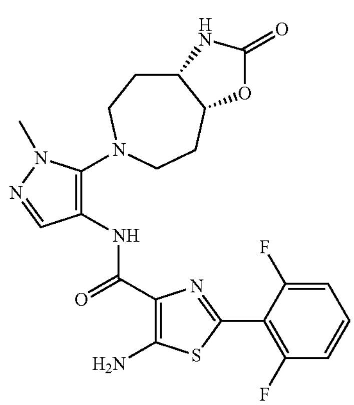 [SMILES: Cn1ncc(NC(=O)c2nc(-c3c(F)cccc3F)sc2N)c1N1CC[C@@H]2NC(=O)O[C@@H]2CC1] | N-[5-[(3aS,8aR)-2-oxo-3a,4,5,7,8,8a-hexahydro-3H-oxazolo[4,5-d]azepin-6-yl]-1-methyl-pyrazol-4-yl]-5-amino-2-(2,6-difluorophenyl)thiazole-4-carboxamide | 0.000353 |

TABLE 1b-continued

| No. | Structure | IUPAC Name | PIM1 LC3K (KI) uM |
|---|---|---|---|
| 489 | 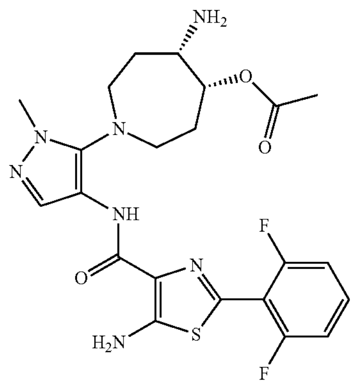 [SMILES: CC(=O)O[C@@H]1CCN(c2c(NC(=O)c3nc(-c4c(F)cccc4F)sc3N)cnn2C)CC[C@@H]1N] | [(4R,5S)-5-amino-1-[5-[[5-amino-2-(2,6-difluorophenyl)thiazole-4-carbonyl]amino]-2-methyl-pyrazol-3-yl]azepan-4-yl] acetate | 0.000846 |
| 490 | 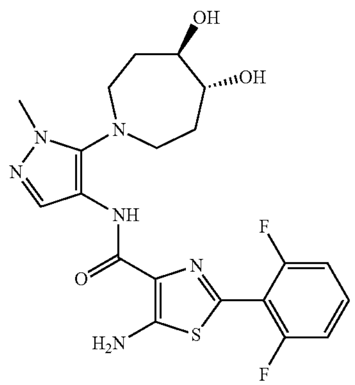 [SMILES: Cn1ncc(NC(=O)c2nc(-c3c(F)cccc3F)sc2N)c1N1CC[C@@H](O)[C@H](O)CC1] | 5-amino-2-(2,6-difluorophenyl)-N-(5-((4R,5R)-4,5-dihydroxyazepan-1-yl)-1-methyl-1H-pyrazol-4-yl)thiazole-4-carboxamide | 0.000179 |
| 491 | 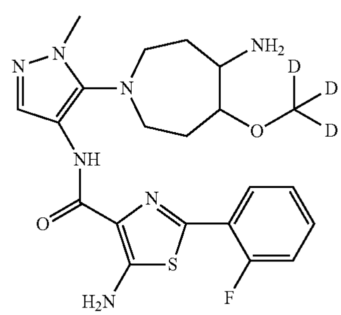 [SMILES: [2H]C([2H])([2H])OC1CCN(c2c(NC(=O)c3nc(-c4ccccc4F)sc3N)cnn2C)CCC1N] | 5-amino-N-[5-[4-amino-5-(trideuteriomethoxy)azepan-1-yl]-1-methyl-pyrazol-4-yl]-2-(2-fluorophenyl)thiazole-4-carboxamide | 0.000055 |
| 492 | 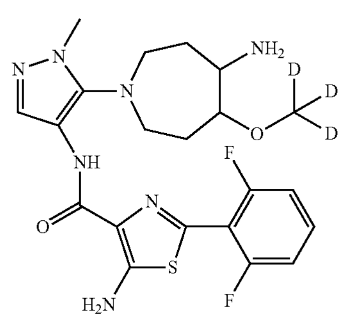 [SMILES: [2H]C([2H])([2H])OC1CCN(c2c(NC(=O)c3nc(-c4c(F)cccc4F)sc3N)cnn2C)CCC1N] | 5-amino-N-[5-[4-amino-5-(trideuteriomethoxy)azepan-1-yl]-1-methyl-pyrazol-4-yl]-2-(2,6-difluorophenyl)thiazole-4-carboxamide | 0.000035 |

TABLE 1b-continued

| No. | Structure | IUPAC Name | PIM1 LC3K (KI) uM |
|---|---|---|---|
| 493 | 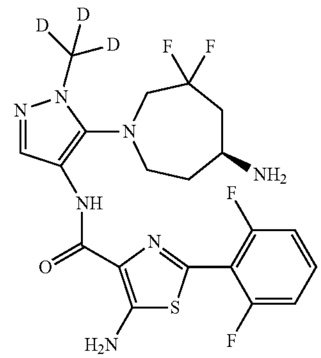 [SMILES: [2H]C([2H])([2H])n1ncc(NC(=O)c2nc(-c3c(F)cccc3F)sc2N)c1N1CC[C@H](N)CC(F)(F)C1] | 5-amino-N-[5-[(5S)-5-amino-3,3-difluoro-azepan-1-yl]-1-(trideuteriomethyl)pyrazol-4-yl]-2-(2,6-difluorophenyl)thiazole-4-carboxamide | 0.000002 |
| 494 | 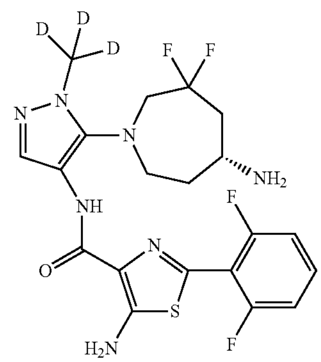 [SMILES: [2H]C([2H])([2H])n1ncc(NC(=O)c2nc(-c3c(F)cccc3F)sc2N)c1N1CC[C@@H](N)CC(F)(F)C1] | 5-amino-N-[5-[(5R)-5-amino-3,3-difluoro-azepan-1-yl]-1-(trideuteriomethyl)pyrazol-4-yl]-2-(2,6-difluorophenyl)thiazole-4-carboxamide | 0.000006 |
| 495 | 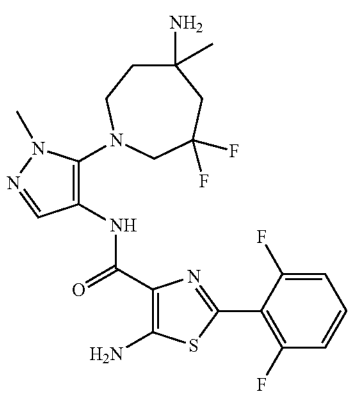 [SMILES: Cn1ncc(NC(=O)c2nc(-c3c(F)cccc3F)sc2N)c1N1CCC(C)(N)CC(F)(F)C1] | 5-amino-N-[5-(5-amino-3,3-difluoro-5-methyl-azepan-1-yl)-1-methyl-pyrazol-4-yl]-2-(2,6-difluorophenyl)thiazole-4-carboxamide | 0.000003 |
| 496 | 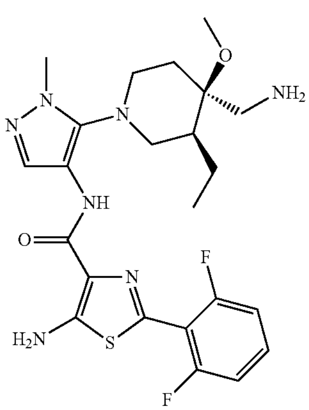 [SMILES: CC[C@H]1CN(c2c(NC(=O)c3nc(-c4c(F)cccc4F)sc3N)cnn2C)CC[C@@]1(CN)OC] | 5-amino-N-(5-((3S,4R)-4-(aminomethyl)-3-ethyl-4-methoxypiperidin-1-yl)-1-methyl-1H-pyrazol-4-yl)-2-(2,6-difluorophenyl)thiazole-4-carboxamide | 0.000042 |

TABLE 1b-continued

| No. | Structure | IUPAC Name | PIM1 LC3K (KI) uM |
|---|---|---|---|
| 497 | 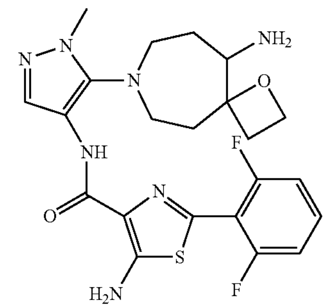 [SMILES: Cn1ncc(NC(=O)c2nc(-c3c(F)cccc3F)sc2N)c1N1CCC(N)C2(CCO2)CC1] | 5-amino-N-[5-(5-amino-1-oxa-8-azaspiro[3.6]decan-8-yl)-1-methyl-pyrazol-4-yl]-2-(2,6-difluorophenyl)thiazole-4-carboxamide | 0.000268 |
| 498 | 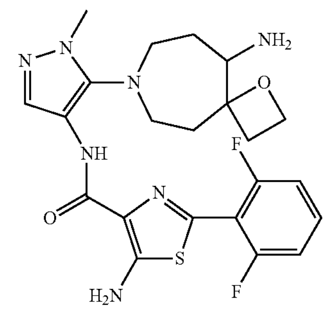 [SMILES: Cn1ncc(NC(=O)c2nc(-c3c(F)cccc3F)sc2N)c1N1CCC(N)C2(CCO2)CC1] | 5-amino-N-[5-(5-amino-1-oxa-8-azaspiro[3.6]decan-8-yl)-1-methyl-pyrazol-4-yl]-2-(2,6-difluorophenyl)thiazole-4-carboxamide | 0.000038 |
| 499 | 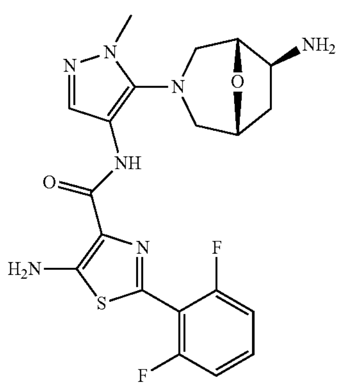 [SMILES: Cn1ncc(NC(=O)c2nc(-c3c(F)cccc3F)sc2N)c1N1C[C@H]2C[C@H](N)[C@@H](C1)O2] | 5-amino-N-(5-((1R,5R,6S)-6-amino-8-oxa-3-azabicyclo[3.2.1]octan-3-yl)-1-methyl-1H-pyrazol-4-yl)-2-(2,6-difluorophenyl)thiazole-4-carboxamide | 0.000888 |
| 500 | 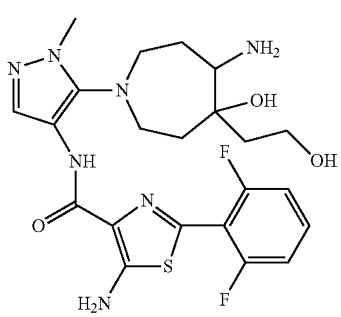 [SMILES: Cn1ncc(NC(=O)c2nc(-c3c(F)cccc3F)sc2N)c1N1CCC(N)C(O)(CCO)CC1] | 5-amino-N-[5-[5-amino-4-hydroxy-4-(2-hydroxyethyl)azepan-1-yl]-1-methyl-pyrazol-4-yl]-2-(2,6-difluorophenyl)thiazole-4-carboxamide | 0.000038 |

TABLE 1b-continued

| No. | Structure | IUPAC Name | PIM1 LC3K (KI) uM |
|---|---|---|---|
| 501 | 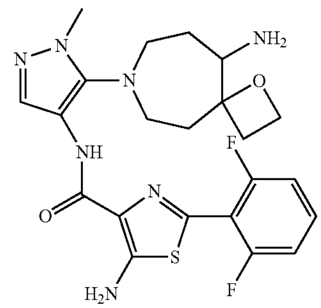 [SMILES: Cn1ncc(NC(=O)c2nc(-c3c(F)cccc3F)sc2N)c1N1CCC(N)C2(CCO2)CC1] | 5-amino-N-[5-(5-amino-1-oxa-8-azaspiro[3.6]decan-8-yl)-1-methyl-pyrazol-4-yl]-2-(2,6-difluorophenyl)thiazole-4-carboxamide | 0.000025 |
| 502 | 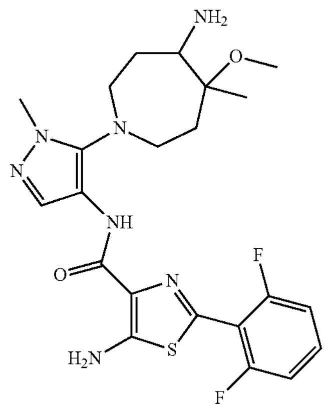 [SMILES: COC1(C)CCN(c2c(NC(=O)c3nc(-c4c(F)cccc4F)sc3N)cnn2C)CCC1N] | 5-amino-N-[5-(5-amino-4-methoxy-4-methyl-azepan-1-yl)-1-methyl-pyrazol-4-yl]-2-(2,6-difluorophenyl)thiazole-4-carboxamide | 0.00004 |
| 503 | 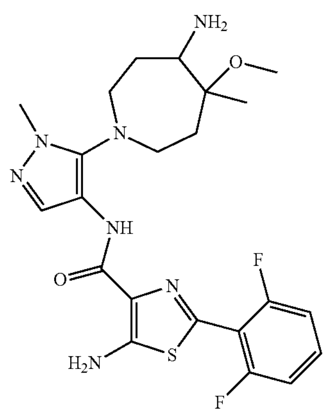 [SMILES: COC1(C)CCN(c2c(NC(=O)c3nc(-c4c(F)cccc4F)sc3N)cnn2C)CCC1N] | 5-amino-N-[5-(5-amino-4-methoxy-4-methyl-azepan-1-yl)-1-methyl-pyrazol-4-yl]-2-(2,6-difluorophenyl)thiazole-4-carboxamide | 0.000047 |
| 504 | 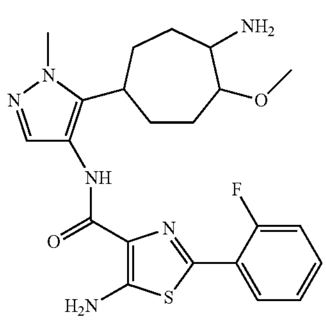 [SMILES: COC1CCC(c2c(NC(=O)c3nc(-c4ccccc4F)sc3N)cnn2C)CCC1N] | 5-amino-N-[5-(4-amino-5-methoxy-cycloheptyl)-1-methyl-pyrazol-4-yl]-2-(2-fluorophenyl)thiazole-4-carboxamide | 0.000055 |

TABLE 1b-continued

| No. | Structure | IUPAC Name | PIM1 LC3K (KI) uM |
|---|---|---|---|
| 505 | 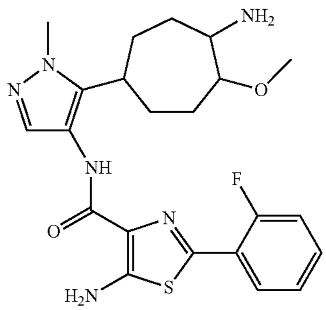 [SMILES: COC1CCC(c2c(NC(=O)c3nc(-c4ccccc4F)sc3N)cnn2C)CCC1N] | 5-amino-N-[5-(4-amino-5-methoxy-cycloheptyl)-1-methyl-pyrazol-4-yl]-2-(2-fluorophenyl)thiazole-4-carboxamide | 0.000197 |
| 506 | 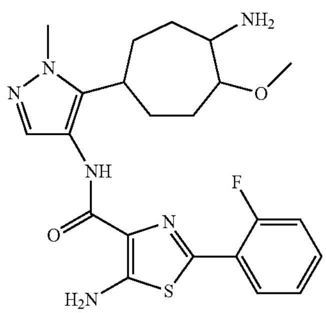 [SMILES: COC1CCC(c2c(NC(=O)c3nc(-c4ccccc4F)sc3N)cnn2C)CCC1N] | 5-amino-N-[5-(4-amino-5-methoxy-cycloheptyl)-1-methyl-pyrazol-4-yl]-2-(2-fluorophenyl)thiazole-4-carboxamide | 0.000392 |
| 507 | 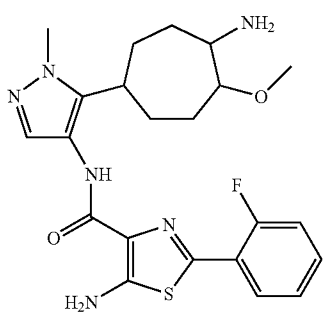 [SMILES: COC1CCC(c2c(NC(=O)c3nc(-c4ccccc4F)sc3N)cnn2C)CCC1N] | 5-amino-N-[5-(4-amino-5-methoxy-cycloheptyl)-1-methyl-pyrazol-4-yl]-2-(2-fluorophenyl)thiazole-4-carboxamide | 0.000976 |
| 508 | 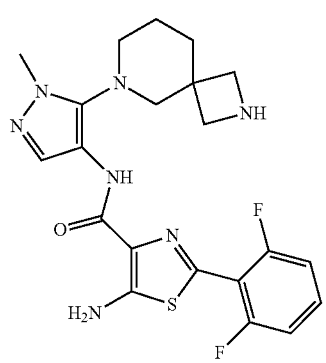 [SMILES: Cn1ncc(NC(=O)c2nc(-c3c(F)cccc3F)sc2N)c1N1CCCC2(CNC2)C1] | 5-amino-N-[5-(2,6-diazaspiro[3.5]nonan-6-yl)-1-methyl-pyrazol-4-yl]-2-(2,6-difluorophenyl)thiazole-4-carboxamide | 0.000129 |

TABLE 1b-continued

| No. | Structure | IUPAC Name | PIM1 LC3K (KI) uM |
|---|---|---|---|
| 509 | 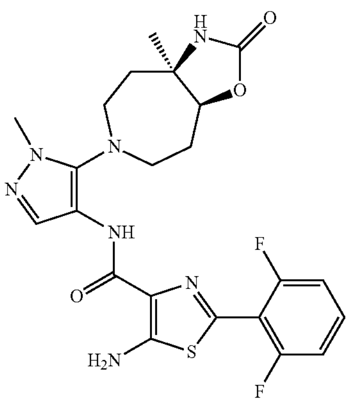 [SMILES: Cn1ncc(NC(=O)c2nc(-c3c(F)cccc3F)sc2N)c1N1CC[C@@H]2OC(=O)N[C@]2(C)CC1] | 5-amino-2-(2,6-difluorophenyl)-N-(1-methyl-5-((3aR,8aS)-3a-methyl-2-oxotetrahydro-2H-oxazolo[5,4-d]azepin-6(7H,8H,8aH)-yl)-1H-pyrazol-4-yl)thiazole-4-carboxamide | 0.000084 |
| 510 | 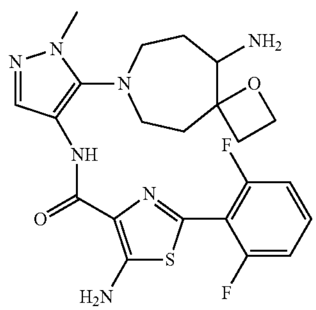 [SMILES: Cn1ncc(NC(=O)c2nc(-c3c(F)cccc3F)sc2N)c1N1CCC(N)C2(CCO2)CC1] | 5-amino-N-[5-(5-amino-1-oxa-8-azaspiro[3.6]decan-8-yl)-1-methyl-pyrazol-4-yl]-2-(2,6-difluorophenyl)thiazole-4-carboxamide | 0.000095 |
| 511 | 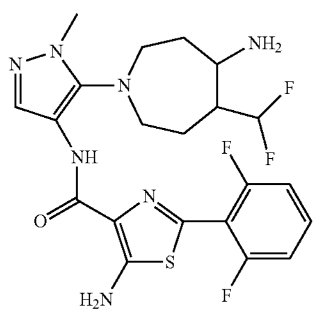 [SMILES: Cn1ncc(NC(=O)c2nc(-c3c(F)cccc3F)sc2N)c1N1CCC(N)C(C(F)F)CC1] | 5-amino-N-[5-[4-amino-5-(difluoromethyl)azepan-1-yl]-1-methyl-pyrazol-4-yl]-2-(2,6-difluorophenyl)thiazole-4-carboxamide | 0.000556 |
| 512 | 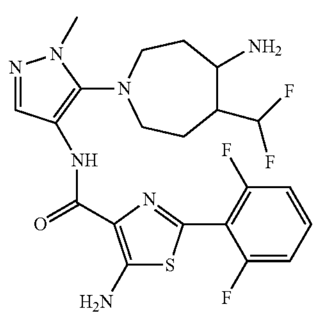 [SMILES: Cn1ncc(NC(=O)c2nc(-c3c(F)cccc3F)sc2N)c1N1CCC(N)C(C(F)F)CC1] | 5-amino-N-[5-[4-amino-5-(difluoromethyl)azepan-1-yl]-1-methyl-pyrazol-4-yl]-2-(2,6-difluorophenyl)thiazole-4-carboxamide | 0.000036 |

TABLE 1b-continued

| No. | Structure | IUPAC Name | PIM1 LC3K (KI) uM |
|---|---|---|---|
| 513 | 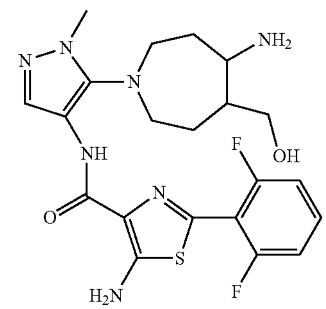 [SMILES: Cn1ncc(NC(=O)c2nc(-c3c(F)cccc3F)sc2N)c1N1CCC(N)C(CO)CC1] | 5-amino-N-[5-[4-amino-5-(hydroxymethyl)azepan-1-yl]-1-methyl-pyrazol-4-yl]-2-(2,6-difluorophenyl)thiazole-4-carboxamide | 0.000058 |
| 514 | 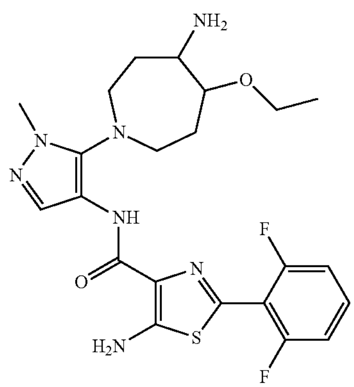 [SMILES: CCOC1CCN(c2c(NC(=O)c3nc(-c4c(F)cccc4F)sc3N)cnn2C)CCC1N] | 5-amino-N-[5-(4-amino-5-ethoxy-azepan-1-yl)-1-methyl-pyrazol-4-yl]-2-(2,6-difluorophenyl)thiazole-4-carboxamide | 0.000115 |
| 515 | 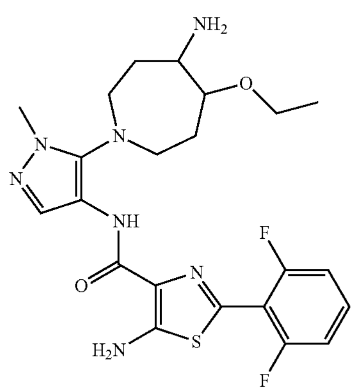 [SMILES: CCOC1CCN(c2c(NC(=O)c3nc(-c4c(F)cccc4F)sc3N)cnn2C)CCC1N] | 5-amino-N-[5-(4-amino-5-ethoxy-azepan-1-yl)-1-methyl-pyrazol-4-yl]-2-(2,6-difluorophenyl)thiazole-4-carboxamide | 0.000035 |
| 516 | 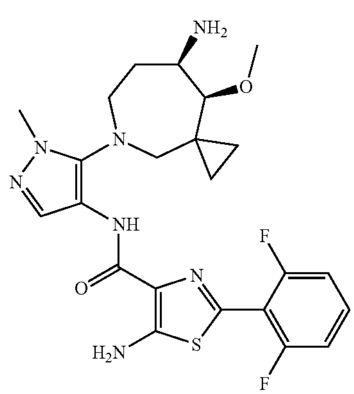 [SMILES: CO[C@@H]1[C@H](N)CCN(c2c(NC(=O)c3nc(-c4c(F)cccc4F)sc3N)cnn2C)CC12CC2] | 5-amino-N-(5-((8R,9S)-8-amino-9-methoxy-5-azaspiro[2.6]nonan-5-yl)-1-methyl-1H-pyrazol-4-yl)-2-(2,6-difluorophenyl)thiazole-4-carboxamide | 0.000019 |

TABLE 1b-continued

| No. | Structure | IUPAC Name | PIM1 LC3K (KI) uM |
|---|---|---|---|
| 517 | 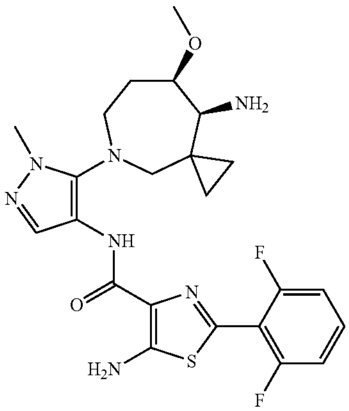 [SMILES: CO[C@@H]1CCN(c2c(NC(=O)c3nc(-c4c(F)cccc4F)sc3N)cnn2C)CC2(CC2)[C@@H]1N] | 5-amino-N-(5-((8R,9S)-9-amino-8-methoxy-5-azaspiro[2.6]nonan-5-yl)-1-methyl-1H-pyrazol-4-yl)-2-(2,6-difluorophenyl)thiazole-4-carboxamide | 0.000047 |
| 518 | 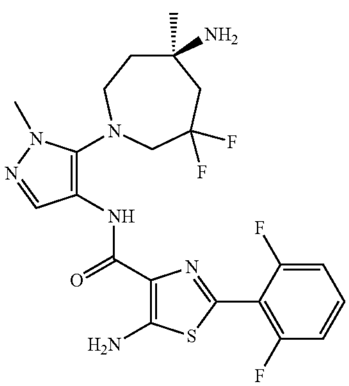 [SMILES: Cn1ncc(NC(=O)c2nc(-c3c(F)cccc3F)sc2N)c1N1CC[C@@](C)(N)CC(F)(F)C1] | (R)-5-amino-N-(5-(5-amino-3,3-difluoro-5-methylazepan-1-yl)-1-methyl-1H-pyrazol-4-yl)-2-(2,6-difluorophenyl)thiazole-4-carboxamide | 0.0050 |
| 519 | 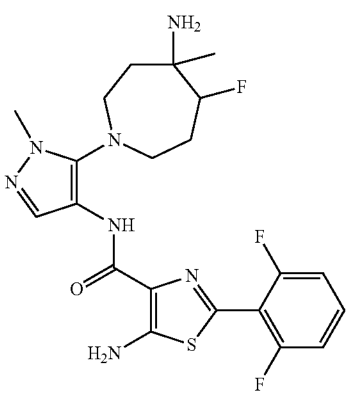 [SMILES: Cn1ncc(NC(=O)c2nc(-c3c(F)cccc3F)sc2N)c1N1CCC(F)C(C)(N)CC1] | 5-amino-N-(5-(4-amino-5-fluoro-4-methylazepan-1-yl)-1-methyl-1H-pyrazol-4-yl)-2-(2,6-difluorophenyl)thiazole-4-carboxamide | 0.000050 |
| 520 | 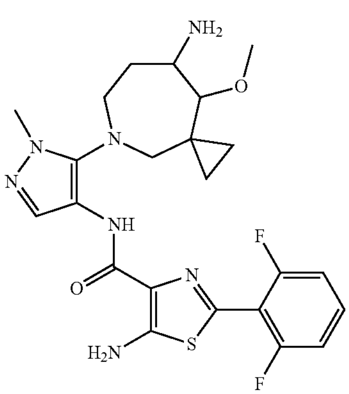 [SMILES: COC1C(N)CCN(c2c(NC(=O)c3nc(-c4c(F)cccc4F)sc3N)cnn2C)CC12CC2] | 5-amino-N-(5-(8-amino-9-methoxy-5-azaspiro[2.6]nonan-5-yl)-1-methyl-1H-pyrazol-4-yl)-2-(2,6-difluorophenyl)thiazole-4-carboxamide | 0.0000040 |

TABLE 1b-continued

| No. | Structure | IUPAC Name | PIM1 LC3K (KI) uM |
|---|---|---|---|
| 521 | 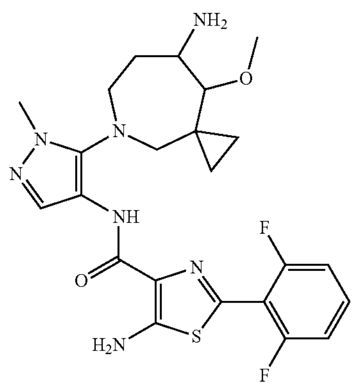 [SMILES: COC1C(N)CCN(c2c(NC(=O)c3nc(-c4c(F)cccc4F)sc3N)cnn2C)CC12CC2] | 5-amino-N-(5-(8-amino-9-methoxy-5-azaspiro[2.6]nonan-5-yl)-1-methyl-1H-pyrazol-4-yl)-2-(2,6-difluorophenyl)thiazole-4-carboxamide | 0.000016 |
| 522 | 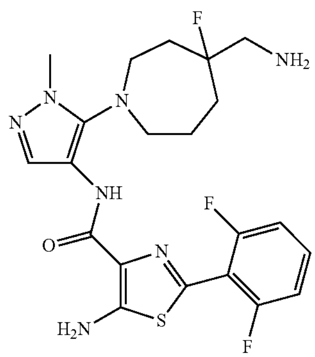 [SMILES: Cn1ncc(NC(=O)c2nc(-c3c(F)cccc3F)sc2N)c1N1CCCC(F)(CN)CC1] | 5-amino-N-(5-(4-(aminomethyl)-4-fluoroazepan-1-yl)-1-methyl-1H-pyrazol-4-yl)-2-(2,6-difluorophenyl)thiazole-4-carboxamide | 0.000068 |
| 523 | 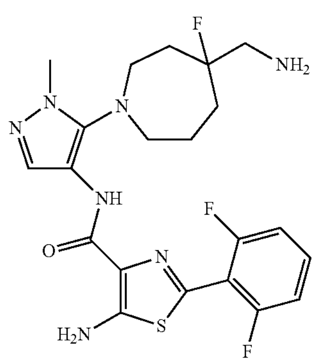 [SMILES: Cn1ncc(NC(=O)c2nc(-c3c(F)cccc3F)sc2N)c1N1CCCC(F)(CN)CC1] | 5-amino-N-(5-(4-(aminomethyl)-4-fluoroazepan-1-yl)-1-methyl-1H-pyrazol-4-yl)-2-(2,6-difluorophenyl)thiazole-4-carboxamide | 0.000035 |
| 524 | 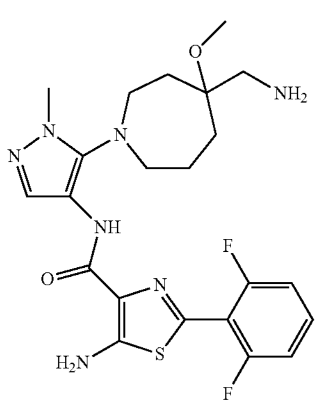 [SMILES: COC1(CN)CCCN(c2c(NC(=O)c3nc(-c4c(F)cccc4F)sc3N)cnn2C)CC1] | 5-amino-N-(5-(4-(aminomethyl)-4-methoxyazepan-1-yl)-1-methyl-1H-pyrazol-4-yl)-2-(2,6-difluorophenyl)thiazole-4-carboxamide | 0.000103 |

TABLE 1b-continued

| No. | Structure | IUPAC Name | PIM1 LC3K (KI) uM |
|-----|-----------|------------|-------------------|
| 525 | 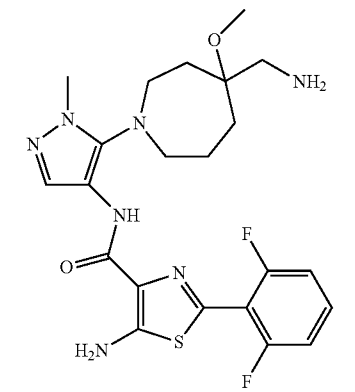 [SMILES: COC1(CN)CCCN(c2c(NC(=O)c3nc(-c4c(F)cccc4F)sc3N)cnn2C)CC1] | 5-amino-N-(5-(4-(aminomethyl)-4-methoxyazepan-1-yl)-1-methyl-1H-pyrazol-4-yl)-2-(2,6-difluorophenyl)thiazole-4-carboxamide | 0.000039 |
| 526 | 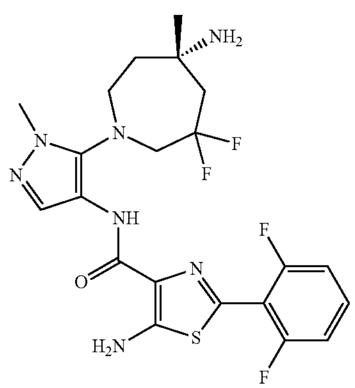 [SMILES: Cn1ncc(NC(=O)c2nc(-c3c(F)cccc3F)sc2N)c1N1CC[C@](C)(N)CC(F)(F)C1] | (S)-5-amino-N-(4-(4-amino-3,3-difluoro-5-methylazepan-1-yl)-1-methyl-1H-pyrazol-4-yl)-2-(2,6-difluorophenyl)thiazole-4-carboxamide | 0.000026 |
| 527 | 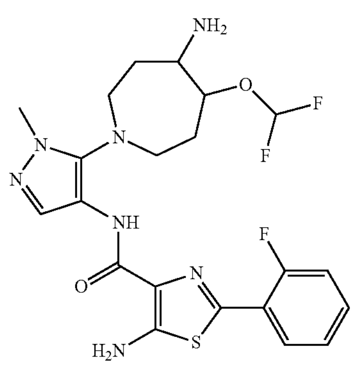 [SMILES: Cn1ncc(NC(=O)c2nc(-c3ccccc3F)sc2N)c1N1CCC(N)C(OC(F)F)CC1] | 5-amino-N-(5-(4-amino-5-(difluoromethoxy)azepan-1-yl)-1-methyl-1H-pyrazol-4-yl)-2-(2-fluorophenyl)thiazole-4-carboxamide | |
| 528 | 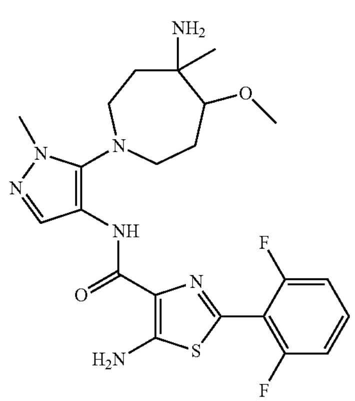 [SMILES: COC1CCN(c2c(NC(=O)c3nc(-c4c(F)cccc4F)sc3N)cnn2C)CCC1(C)N] | 5-amino-N-(5-(4-amino-5-methoxy-4-methylazepan-1-yl)-1-methyl-1H-pyrazol-4-yl)-2-(2,6-difluorophenyl)thiazole-4-carboxamide | |

TABLE 1b-continued

| No. | Structure | IUPAC Name | PIM1 LC3K (KI) uM |
|---|---|---|---|
| 529 | 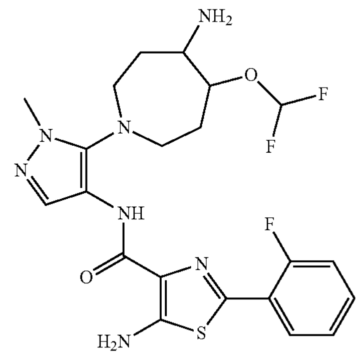 [SMILES: Cn1ncc(NC(=O)c2nc(-c3ccccc3F)sc2N)c1N1CCC(N)C(OC(F)F)CC1] | 5-amino-N-(5-(4-amino-5-(difluoromethoxy)azepan-1-yl)-1-methyl-1H-pyrazol-4-yl)-2-(2-fluorophenyl)thiazole-4-carboxamide | |

The present invention includes a composition (e.g., a pharmaceutical composition) comprising a compound of Formula I, and/or solvates, hydrates and/or salts thereof, and a carrier (a pharmaceutically acceptable carrier). The present invention also includes a composition (e.g., a pharmaceutical composition) comprising a compound of Formula I and/or solvates, hydrates and/or salts thereof, and a carrier (a pharmaceutically acceptable carrier), further comprising a second chemotherapeutic agent such as those described herein. The present compositions are useful for inhibiting abnormal cell growth or treating a hyperproliferative disorder such as cancer in a mammal (e.g., human). For example, the present compounds and compositions are useful for treating multiple myeloma, lymphoma, acute myeloid leukemia, prostate cancer, breast cancer, hepatocellular carcinoma, pancreatic cancer, and/or colorectal cancer in a mammal (e.g., human).

The present invention includes a method of inhibiting abnormal cell growth or treating a hyperproliferative disorder such as cancer in a mammal (e.g., human) comprising administering to said mammal a therapeutically effective amount of a compound of Formula I, and/or solvates, hydrates and/or salts thereof, or a composition thereof. For example, the present invention includes a method of treating multiple myeloma, lymphoma, acute myeloid leukemia, prostate cancer, breast cancer, hepatocellular carcinoma, pancreatic cancer, and/or colorectal cancer in a mammal (e.g., human), comprising administering to said mammal a therapeutically effective amount of a compound of Formula I, and/or solvates, hydrates and/or salts thereof) or a composition thereof.

The present invention includes a method of inhibiting abnormal cell growth or treating a hyperproliferative disorder such as cancer in a mammal (e.g., human) comprising administering to said mammal a therapeutically effective amount of a compound of Formula I, and/or solvates, hydrates and/or salts thereof, or a composition thereof, in combination with a second chemotherapeutic agent such as those described herein. For example, the present invention includes a method of treating multiple myeloma, lymphoma, acute myeloid leukemia, prostate cancer, breast cancer, hepatocellular carcinoma, pancreatic cancer, and/or colorectal cancer in a mammal (e.g., human), comprising administering to said mammal a therapeutically effective amount of a compound of Formula I, and/or solvates, hydrates and/or salts thereof, or a composition thereof, in combination with a second chemotherapeutic agent such as those described herein.

The present invention includes a method of treating lymphoma in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as an anti-B-cell antibody therapeutic (e.g., Rituxan and/or Dacetuzumab), gemcitabine, corticosteroids (e.g., prednisolone and/or dexamethasone), chemotherapy cocktails (e.g., CHOP (cyclophosphamide, doxorubicin, vincristine, prednisolone) and/or ICE (isfosfamide, cytoxan, etoposide)), a combination of biologics and chemotherapy (e.g., Rituxan-ICE, Dacetuzumab-Rituxan-ICE, R-Gem, and/or D-R-Gem), an Akt inhibitor, a PI3K inhibitor (e.g, GDC-0941 (Genentech) and/or GDC-0980 (Genentech)), rapamycin, a rapamycin analog, mTOR inhibitor such as everolimus or sirolimus, a MEK inhibitor (GDC-0973), and a Bcl-2 inhibitor (ABT-263 or ABT-199).

The present invention includes a method of treating multiple myeloma in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as melphalan, "Imids" (immuno-modulators, e.g., thalidomide, lenalidomide, and/or pomolidamide), corticosteroids (e.g., dexamethasone and/or prednisolone), and bortezomib or other proteasome inhibitor.

The present invention includes a method of treating multiple myeloma, chronic lymphocytic leukemia (CLL), or acute myeloid leukemia (AML) in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as cytarabine (araC), anthracyclines (e.g., daunorubicin and/or idarubicin), anti-myeloid antibody therapeutics (e.g., SGN-33), anti-myeloid antibody-drug conjugates (e.g., MYLOTARG®).

The present invention includes a method of treating chronic lymphocytic leukemia (CLL) in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as fludarabine, cyclophosphamide, anti-B-cell antibody therapeutics (e.g., Rituxan and/or Dacetuzumab).

The present invention includes a method of treating chronic myeloid leukemia (CML) in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as a BCR-abl inhibitor (e.g., imatinib, nilotinib, and/or dasatinib).

The present invention includes a method of treating myelodysplastic diseases (MDS) and myeloproliferative disorders including polycythemia vera (PV), essential thrombocytosis (ET) or myelofibrosis (MF), in a mammal (e.g., human) comprising administering to said mammal a therapeutically effective amount of a compound of Formula I, and/or solvates, hydrates and/or salts thereof, or a composition thereof, either alone or in combination.

The present invention includes a method of using the present compounds for in vitro, in situ, and in vivo diagnosis or treatment of mammalian cells, organisms, or associated pathological conditions.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, inhalation and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or in combination with one or more chemotherapeutic agents, for example those described herein. Such conjoint treatment may be achieved by way of the simultaneous, sequential or separate dosing of the individual components of treatment.

The pharmaceutical composition may, for example, be in a form suitable for oral administration as a tablet, capsule, pill, powder, sustained release formulations, solution, suspension for parenteral injection as a sterile solution, suspension or emulsion for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of Formula I compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tabletting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 15.sup.th Edition (1975).

Administration of Formula I Compounds

The Formula I compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Compounds of the present invention are useful for treating hyperproliferative diseases, conditions and/or disorders including, but not limited to, those characterized by over expression of Pim kinases, e.g. Pim-1, Pim-2 and Pim-3 kinases. Accordingly, another aspect of this invention includes methods of treating or preventing diseases or conditions that can be treated or prevented by inhibiting Pim kinase. In one embodiment, the method comprises administering to a mammal in need thereof a therapeutically effective amount of a compound of Formula I, or a stereoisomer, geometric isomer, tautomer, or pharmaceutically acceptable salt thereof. In one embodiment, a human patient is treated with a compound of Formula I and a pharmaceutically acceptable carrier, adjuvant, or vehicle, wherein said compound of Formula I is present in an amount to detectably inhibit Pim kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Another aspect of this invention provides a compound of this invention for use in the treatment of the diseases or conditions described herein in a mammal, for example, a human, suffering from such disease or condition. Also provided is the use of a compound of this invention in the preparation of a medicament for the treatment of the diseases and conditions described herein in a warm-blooded animal, such as a mammal, for example a human, suffering from such disorder.

Pharmaceutical Formulations

In order to use a Formula I compound for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a Formula I compound and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the Formula I compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16$^{th}$ edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound of this invention for use herein is preferably sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution.

The pharmaceutical compositions of the invention comprising a Formula I compound will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the Formula I compound administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences $16^{th}$ edition, Osol, A. Ed. (1980).

Sustained-release preparations of Formula I compounds may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier, it desirably comprises a mixture of at least one emulsifier with a fat or oil, or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein, such as a hyperproliferative disorder (e.g., cancer). In certain embodiments, a compound of Formula I is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of anti-cancer therapy, a compound of Formula I, or a stereoisomer, geometric isomer, tautomer, solvate, metabolite, or pharmaceutically acceptable salt or prodrug thereof, may be combined with other chemotherapeutic, hormonal or antibody agents such as those described herein, as well as combined with surgical therapy and radiotherapy. Combination therapies according to the present invention thus comprise the administration of at least one compound of Formula I, or a stereoisomer, geometric isomer, tautomer, solvate, metabolite, or pharmaceutically acceptable salt or prodrug thereof, and the use of at least one other cancer treatment method. The amounts of the compound(s) of Formula I and the other pharmaceutically active chemotherapeutic agent(s) and the relative timings of administration will be selected in order to achieve the desired combined therapeutic effect.

Metabolites of Formula I Compounds

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, may be useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. The kit comprises a container comprising a compound of Formula I. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or II or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I, and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Compounds of Formula I may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

The General Procedures and Examples provide exemplary methods for preparing Formula I compounds. Those skilled in the art will appreciate that other synthetic routes may be used to synthesize the Formula I compounds. Although specific starting materials and reagents are depicted and discussed in the Figures, General Procedures, and Examples, other starting materials and reagents can be easily substituted to provide a variety of derivatives and/or reaction conditions.

In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

In the methods of preparing Formula I compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions, such as on a chiral adsorbent by HPLC or SFC (Supercritical Fluid Chromatography), see White and Burnett (2005) Jour. of Chrom. A1074:175-185; and "Drug Stereochemistry, Analytical Methods and Pharmacology," (1993) Irving W. Wainer, Ed., Marcel Dekker, Inc., New York).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

General Preparative Procedures

FIG. 1 shows an exemplary synthesis of 4-aminopyrazole compounds 5. 4-Nitro-1H-pyrazole 1 is converted to 2 by treatment with a base in a suitable solvent or neat, followed by the addition of an alkylation reagent such as dimethyl sulfate. Compound 2 may be converted to 5-chloro-4-nitro-1H-pyrazole 3 by treatment with a base such as lithium hexamethyldisilazide, or nBuLi in a suitable solvent at an appropriate temperature, such as THF at −78° C. Compound 3 may be converted to compound 4 by direct SnAr, or transition metal catalyzed cross coupling reactions, e.g. Suzuki, Sonogashira, Heck, Buchwald, Goldberg conditions under known methods. 4-Aminopyrazole 5 may be synthesized from 4 by a suitable reduction method, such as treatment with zinc powder and ammonium formate in tetrahydrofuran, or hydrogenation with $H_2$ and transitional metal catalysts such as palladium on carbon.

Figure 2:
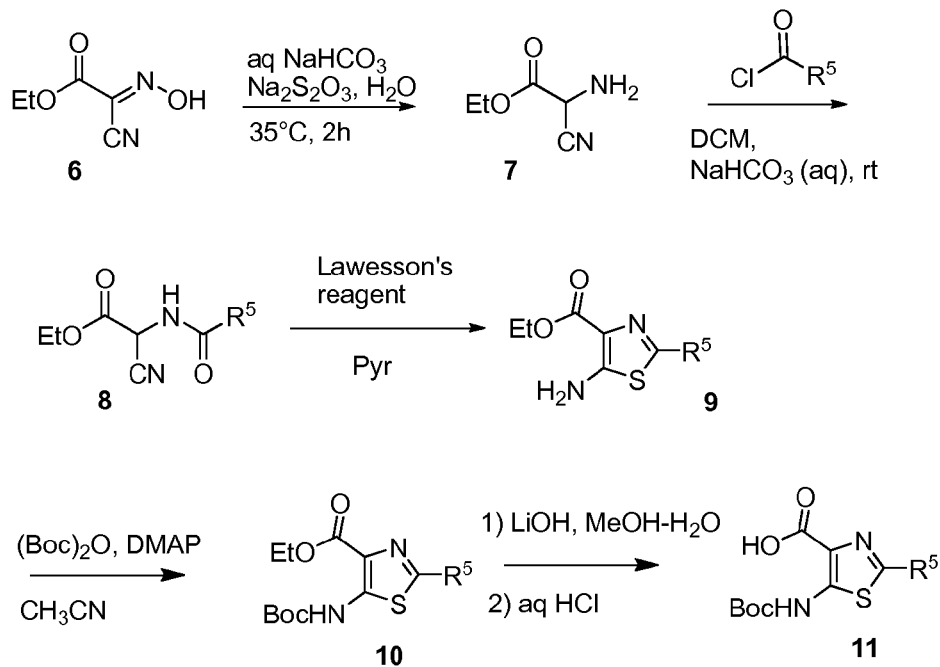
FIG. 2 shows an exemplary synthesis of 4-carboxy-thiazoles 11 from hydroxamide compounds 6.

FIG. 2 shows an exemplary synthesis of 4-carboxy-thiazoles 11 from hydroxamide compounds 6. Reduction of 6 by a reducing reagent in a suitable solvent such as $Na_2S_2O_3$ in water gives 7, which may be converted to 8 by an acylating reagent in a suitable solvent with a suitable base such as benzoyl chloride in dichloromethane with sodium bicarbonate. Compound 8 may be converted to 9 by a sulfur containing reagent in a suitable reagent such as Lawesson's reagent in pyridine, and protected to 10 by a suitable Boc-protecting group. Ester hydrolysis of 10 using a suitable base and solvent, such as LiOH in methanol and water gives 11.

Figure 3:
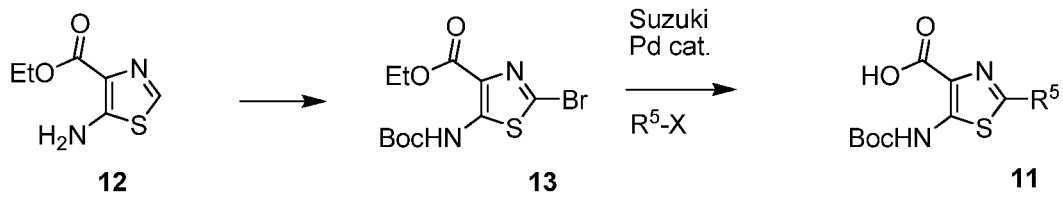
FIG. 3 shows an exemplary synthesis of 2-substituted, 4-carboxy-5-aminothiazoles 11 by C-2 bromination of 12 followed by Suzuki reaction of 13.

FIG. 3 shows an exemplary synthesis of 2-substituted, 4-carboxy-5-aminothiazoles 11 by C-2 bromination of 12 followed by Suzuki reaction of 13. The Suzuki-type coupling reaction is useful to attach a heterocycle or a heteroaryl by displacing a halide at the 2-position of the thiazole, pyridyl, pyrazinyl, or pyrimidinyl ring in the synthesis of a Formula I compound. For example, 2-bromo (or chloro) thiazole 11 may be reacted with about 1.5 equivalents of a aryl, heterocyclyl or heteroaryl boronic acid or ester reagent and an excess of aqueous sodium carbonate in acetonitrile. A catalytic amount, or more, of a low valent palladium reagent, such as bis(triphenylphosphine)palladium(II) dichloride, is added. A variety of boronic acids or boronic esters can be used. Boronic esters include pinacol esters (4,4,5,5-tetramethyl-1,3,2-dioxaborolan-2-yl). Also, a nitrogen of a heterocycle or heteroaryl may be protected, for example as N-THP. In some cases potassium acetate is used in place of sodium carbonate to adjust the pH of the aqueous layer. The reaction may be heated to about 140-150° C. under pressure in a microwave reactor such as the Biotage Optimizer (Biotage, Inc.) for 10 to 30 minutes. The contents are extracted with ethyl acetate, or another organic solvent. After evaporation of the organic layer the Suzuki coupling product may be purified on silica or by reverse phase HPLC.

A variety of palladium catalysts can be used during the Suzuki coupling step to form exemplary Formula I compounds. Low valent, Pd(II) and Pd(0) catalysts may be used in the Suzuki coupling reaction, including $PdCl2(PPh_3)_2$, Pd(t-Bu)$_3$, $PdCl_2$ dppf $CH_2Cl_2$, Pd(PPh$_3$)$_4$, Pd(Oac)/PPh$_3$, Cl$_2$Pd[(Pet$_3$)]$_2$, Pd(DIPHOS)$_2$, Cl$_2$Pd(Bipy), [PdCl(Ph$_2$PCH$_2$PPh$_2$)]$_2$, Cl$_2$Pd[P(o-tol)$_3$]$_2$, Pd$_2$(dba)$_3$/P(o-tol)$_3$, Pd$_2$(dba)/P(furyl)$_3$, Cl$_2$Pd[P(furyl)$_3$]$_2$, Cl$_2$Pd(PmePh$_2$)$_2$, Cl$_2$Pd[P(4-F-Ph)$_3$]$_2$, Cl$_2$Pd[P(C$_6$F$_6$)$_3$]$_2$, Cl$_2$Pd[P(2-COOH-Ph)(Ph)$_2$]$_2$, Cl$_2$Pd[P(4-COOH-Ph)(Ph)$_2$]$_2$, and encapsulated catalysts Pd EnCat™ 30, Pd EnCat™ TPP30, and Pd(II) EnCat™ BINAP30 (US 2004/0254066).

Figure 4:
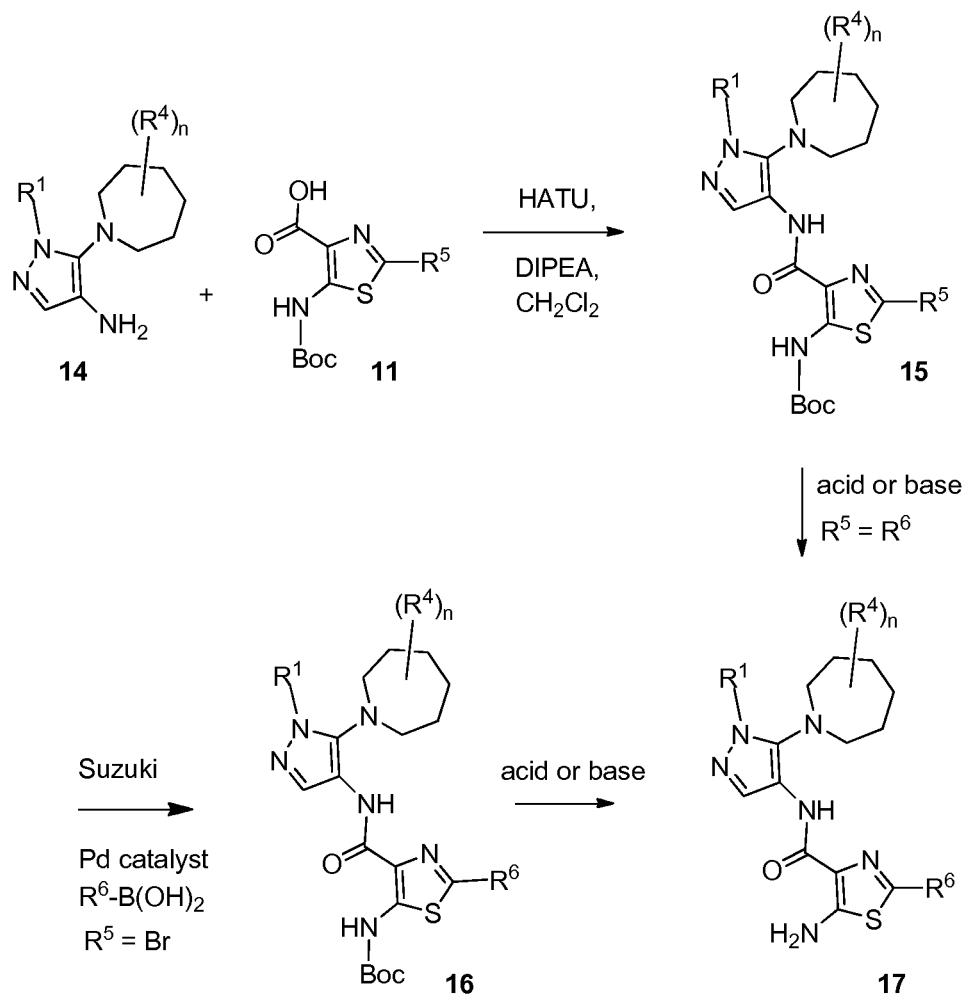
FIG. 4 shows an exemplary synthesis of 5-azepanyl-N-(pyrazol-4-yl)thiazole-carboxamide compounds 17 made from coupling of 4-amino,5-azepanyl pyrazole compounds 14 and 2-bromo, 4-carboxy-5-aminothiazoles 11.

FIG. 4 shows an exemplary synthesis of 5-azepanyl-N-(pyrazol-4-yl)thiazole-carboxamide compounds 17 made from coupling of 4-amino,5-azepanyl pyrazole compounds 14 and 2-bromo, 4-carboxy-5-aminothiazoles 11. Compounds 14 and 11 may be coupled using an amide coupling reagent such as HATU, HBTU with a suitable solvent such as dichloromethane or DMF. The coupled intermediate 15 may be then converted to compounds 17 by deprotection using a suitable acid or base in a solvent such as HCl in dioxane and water or trifluoroacetic acid in dichloromethane or $K_2CO_3$ in acetonitrile. In addition, when $R^5$ is a halogen group, eg bromine, compounds 15 may be subjected to a Suzuki or Stille condition to yield compounds 16. Removal of protecting groups of compounds of formula 16 either under acidic or basic condition with a suitable acid or base in a suitable solvent, such as HCl in dioxane and water or trifluoroacetic acid in dichloromethane or K$_2$CO$_3$ in acetonitrile, may yield compounds 17.

Figure 5:
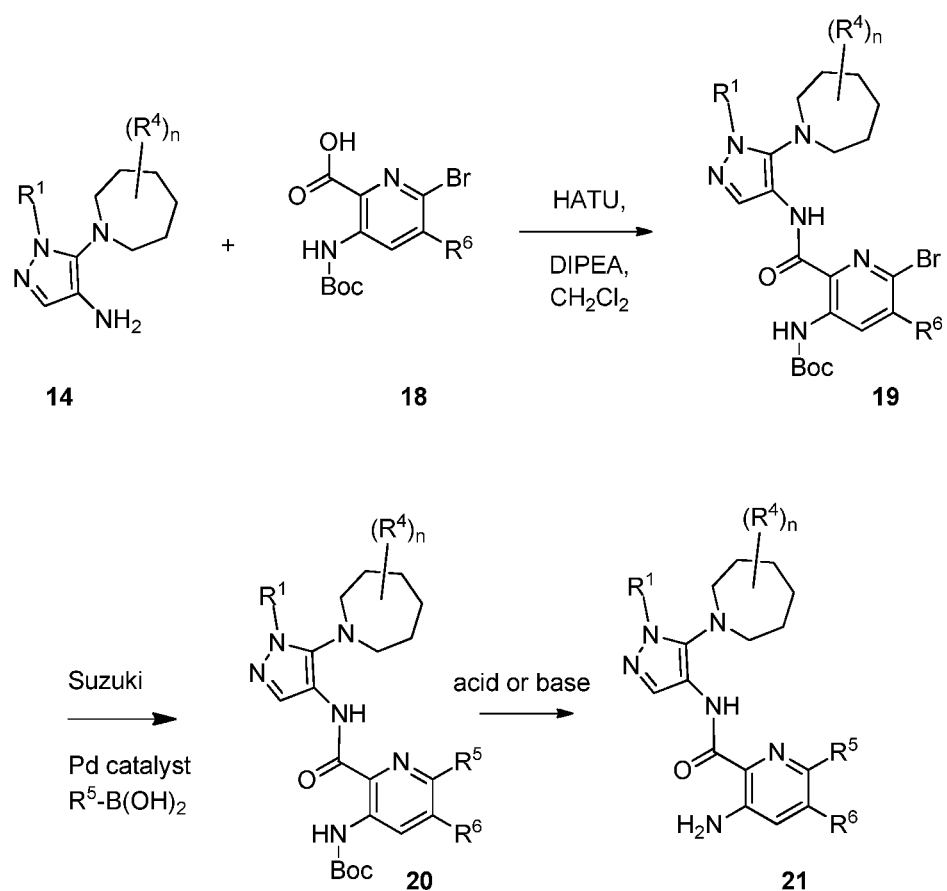
FIG. 5 shows an exemplary synthesis of 6-amino-N-(pyrazol-4-yl)pyridyl-carboxamide compounds 21 made from coupling of 4-amino,5-azepanyl pyrazole compounds 14 and 2-bromo, 3-Boc-amino,6-carboxy-pyridyl compounds 18.

FIG. 5 shows an exemplary synthesis of 6-amino-N-(pyrazol-4-yl)pyridyl-carboxamide compounds 21 made from coupling of 4-amino,5-azepanyl pyrazole compounds 14 and 2-bromo, 3-Boc-amino,6-carboxy-pyridyl compounds 18. Compounds 14 and 18 may be coupled using an amide coupling reagent such as HATU, HBTU with a suitable solvent such as dichloromethane or DMF. The coupled intermediate 19 may be subjected to a Suzuki or Stille condition to yield compounds 20. Removal of protecting groups of compounds 20 either under acidic or basic condition with a suitable acid or base in a suitable solvent, such as HCl in dioxane and water or trifluoroacetic acid in dichloromethane or K$_2$CO$_3$ in acetonitrile, may yield compounds 21.

Figure 6:
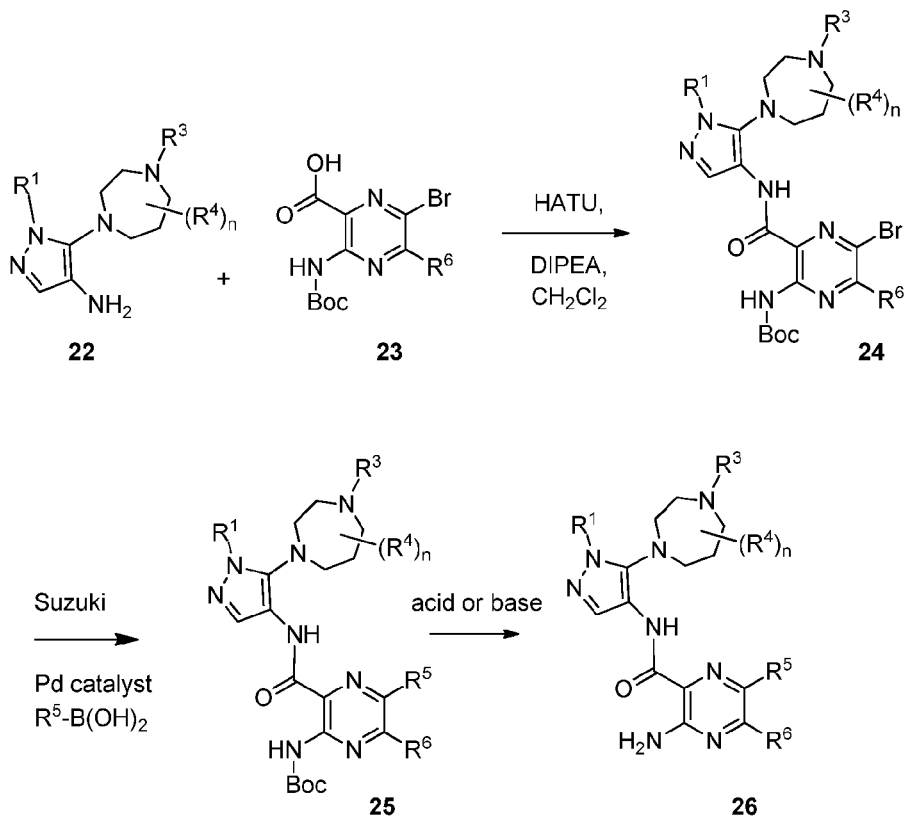
FIG. 6 shows an exemplary synthesis of 6-amino-N-(pyrazol-4-yl)pyrazine-carboxamide compounds 26 from coupling of 4-amino,5-diazepanyl pyrazole compounds 22 and 2-bromo,3-substituted, 6-carboxy-5-aminopyrazinyl compounds 23.

FIG. 6 shows an exemplary synthesis of 6-amino-N-(pyrazol-4-yl)pyrazine-carboxamide compounds 26 from coupling of 4-amino,5-diazepanyl pyrazole compounds 22 and 2-bromo,3-substituted, 6-carboxy-5-aminopyrazinyl compounds 23. Compounds 22 and 23 may be coupled using an amide coupling reagent such as HATU, HBTU with a suitable solvent such as dichloromethane or DMF. The coupled intermediate 24 may be subjected to a Suzuki or Stille condition to yield compounds 25. Removal of protecting groups of compounds 25 either under acidic or basic condition with a suitable acid or base in a suitable solvent, such as HCl in dioxane and water or trifluoroacetic acid in dichloromethane or K$_2$CO$_3$ in acetonitrile, may yield compounds 26.

Figure 7:
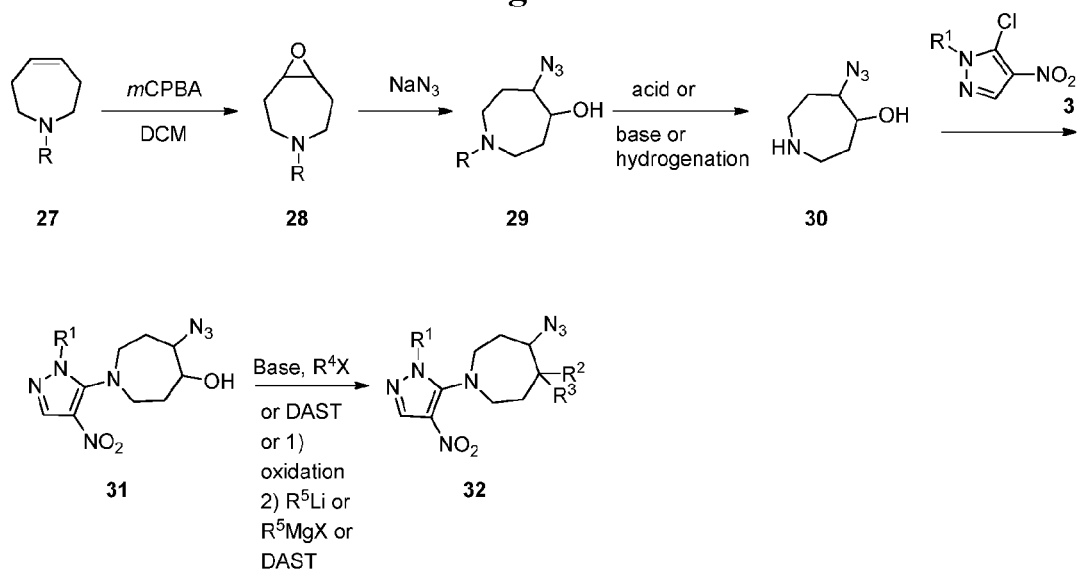
FIG. 7 shows an exemplary synthesis of 5-azido-(4-nitro-1H-pyrazol-5-yl)azepane 32 from 2,3,6,7-tetrahydro-1H-azepine 27.

FIG. 7 shows an exemplary synthesis of 5-azido-(4-nitro-1H-pyrazol-5-yl)azepane 32 from 2,3,6,7-tetrahydro-1H-azepine 27. Compounds 27 may be converted to compounds 28 by treatment with m-CPBA or similar methods described in the literature. Compounds 29 may be synthesized from compounds 28 by opening of the epoxide with sodium azide according to literature methods. Removal of the R protecting group of compounds 29 may be effected by suitable acidic or basic or hydrogenation condition or other known literature methods. Compounds 30 may be reacted with compounds 3 by heating with potassium fluoride in a suitable solvent such as dimethylsulfoxide to give compounds 31. Compounds 31 may be O-alkylated using sodium hydride and iodomethane or by other methylation methods described in the literature to give 5-azido-(4-nitro-1H-pyrazol-5-yl)azepane compounds 32. Compounds 31 may be converted to 32 by nucleophilic fluorination reagent such as DAST. Compounds 31 may be converted to 32 by oxidation to the ketone followed by nucleophilic addition with organometallic reagents such as lithium or Grignard reagents or followed by nucleophilic fluorination reagent such as DAST.

Figure 8:
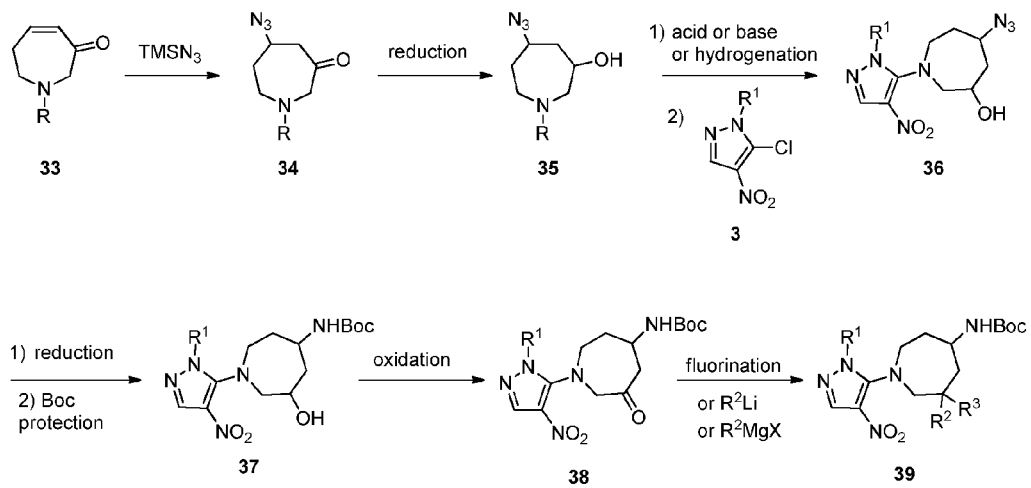
FIG. 8 shows an exemplary synthesis of 5-Boc-amino-(4-nitro-1H-pyrazol-5-yl)azepane 39 from 6,7-dihydro-1H-azepin-3(2H)-one 33.

FIG. 8 shows an exemplary synthesis of 5-Boc-amino-(4-nitro-1H-pyrazol-5-yl)azepane 39 from 6,7-dihydro-1H-azepin-3(2H)-one 33. Compounds 33 may be converted to 5-azido-azepan-3-one 34 by heating with TMS-azide and Amberlite IRA 900F resin in a suitable solvent such as acetonitrile. Reduction of the ketone of 34 using sodium borohydride in THF and water or by methods described in the literature gives 5-azido-azepan-3-ol 35. Removal of the R protecting group of 35 may be effected by acidic or basic or hydrogenation condition or by literature methods. The resulting amine may be converted to 5-azido-1-(4-nitro-1H-pyrazol-5-yl)azepan-3-ol 36 by heating with 5-chloro-4-nitro-1H-pyrazole 3 with potassium fluoride in a solvent such as dimethylsulfoxide. Compounds 36 may be converted to 5-(N-Boc)-1-(1-methyl-4-nitro-1H-pyrazol-5-yl)azepan-3-ol 37 using Staudinger azide reduction of heating with triphenylphosphine in THF and water followed by protection of the resulting amine with a suitable protecting group such as a Boc-protecting group using the methods described or those described in the literature. Oxidation of 37 by a method such as treatment with the Dess-Martin reagent or as described in the literature gives tert-butyl 1-(4-nitro-1H-pyrazol-5-yl)-6-oxoazepan-4-ylcarbamate 38. Compounds 38 may be converted to 39 by treatment with Bis(2-methoxyethyl)aminosulfur trifluoride (deoxo-Fluor®, Sigma-Aldrich) in a suitable solvent such as dichloromethane or by methods described in the literature. Compounds 38 may be converted to 39 by treatment with organometallic reagent such lithium or Grignard reagent or by methods described in the literature.

Figure 9:
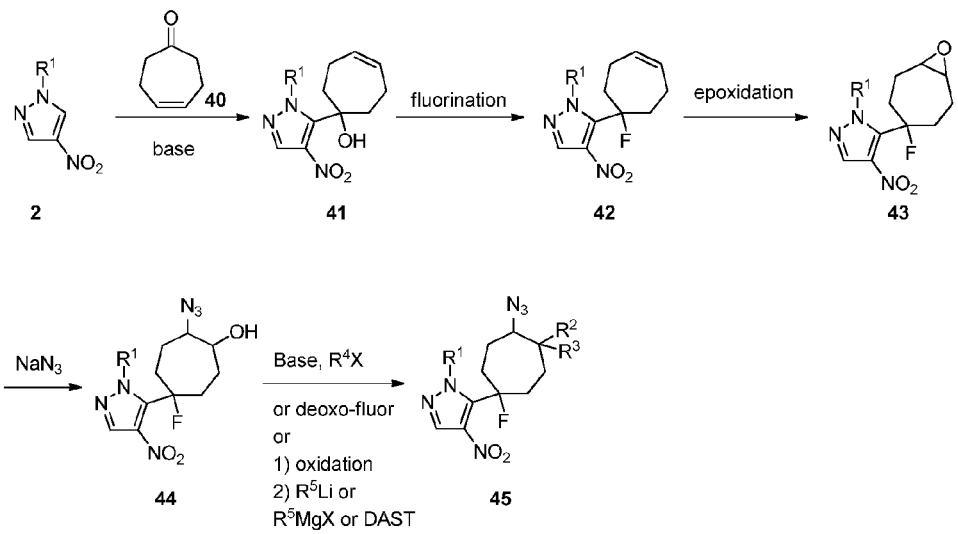
FIG. 9 shows an exemplary synthesis of 5-(4-azido-1-fluorocycloheptyl)-4-nitro-1H-pyrazole 45 from 4-nitro-1H-pyrazole 2.

FIG. 9 shows an exemplary synthesis of 5-(4-azido-1-fluorocycloheptyl)-4-nitro-1H-pyrazole 45 from 4-nitro-1H-pyrazole 2. Treatment of 4-nitro-1H-pyrazole 2 with (Z)-cyclohept-4-enone 40 and a base such as lithium hexamethyldisilazide at an appropriate temperature in a suitable solvent such as THF or by methods described in the literature yields 1-(4-nitro-1H-pyrazol-5-yl)cyclohept-4-enol 41. Treatment of 41 with deoxo-Fluor® in a suitable solvent such as DCM or methods described in the literature yields 5-(1-fluorocyclohept-4-enyl)-4-nitro-1H-pyrazole 42. Epoxidation of 42 with m-CPBA or by similar procedures reported in the literature yields 5-(4-fluoro-8-oxabicyclo[5.1.0]octan-4-yl)-4-nitro-1H-pyrazole 43. Opening of the epoxide of 43 with sodium azide according to literature methods, such as sodium azide, gives 2-azido-5-fluoro-5-(4-nitro-1H-pyrazol-5-yl)cycloheptanol 44. O-Alkylation of 44 using sodium hydride and iodomethane, or by other methylation methods described in the literature, gives 45 where $R^2$ is O-alkyl and $R^3$ is H. Compounds 44 may be converted to 45 where $R^2$ and $R^3$ are F by nucleophilic fluorination with a reagent such as DAST. Compounds 44 may be converted to 45 where $R^2$ ($R^5$) is alkyl and $R^3$ is F by being oxidized into ketone followed by nucleophilic addition with organometallic reagents such as lithium or Grignard reagents or followed by nucleophilic fluorination with a reagent such as DAST.

Figure 10:
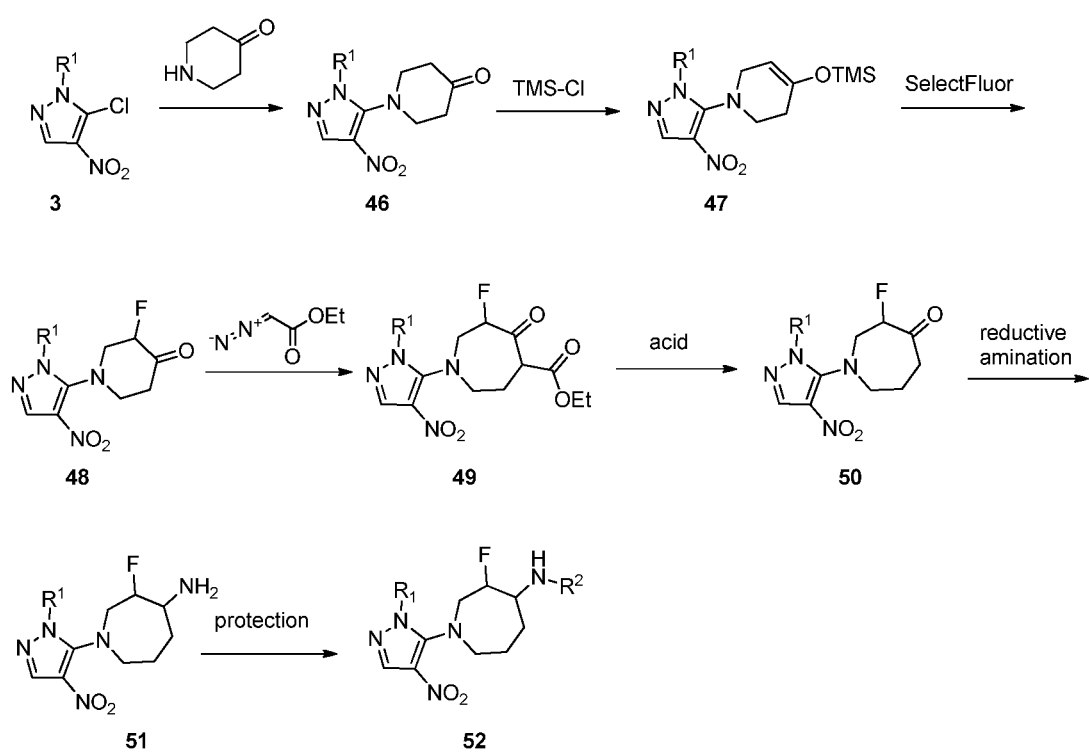
FIG. 10 shows an exemplary synthesis of 3-fluoro-1-(4-nitro-1H-pyrazol-5-yl)azepan-4-amine 52 from 5-chloro-4-nitro-1H-pyrazole 3.

FIG. 10 shows an exemplary synthesis of 3-fluoro-1-(4-nitro-1H-pyrazol-5-yl)azepan-4-amine 52 from 5-chloro-4-nitro-1H-pyrazole 3. Heating 3 with piperidin-4-one hydrochloride hydrate and potassium fluoride in a suitable solvent such as dimethylsulfoxide or using methods described in the literature gives 1-(4-nitro-1H-pyrazol-5-yl)piperidin-4-one 46. Heating 46 with trimethylsilyl chloride and triethylamine in a suitable solvent such as DMF or using methods described in the literature gives 1-(4-nitro-1H-pyrazol-5-yl)-4-(trimethylsilyloxy)-1,2,3,6-tetrahydropyridine 47. Fluorination of 47 using SelectFluor® in acetonitrile at a suitable temperature or using methods described in the literature gives 3-fluoro-1-(4-nitro-1H-pyrazol-5-yl)piperidin-4-one 48. Ring expansion of 48 to ethyl 6-fluoro-1-(4-nitro-1H-pyrazol-5-yl)-5-oxoazepane-4-carboxylate 49 may be achieved using ethyl diazoacetate and boron trifluoride diethyl etherate in a suitable solvent such as dichloromethane at suitable temperatures or using methods described in the literature. Decarboxylation of 49 by heating with hydrochloric acid at a suitable temperature or by methods described in the literature to give 3-fluoro-1-(4-nitro-1H-pyrazol-5-yl)azepan-4-one 50. Reductive amination of 50 by methods described in the literature gives 3-fluoro-1-(4-nitro-1H-pyrazol-5-yl)azepan-4-amine 51. The amine of 51 can be protected with a suitable protecting group such as trifluoroacetamide using trifluoroacetic anhydride with diisopropylethylamine in a suitable solvent such as dichloromethane, or using other methods described in the literature, to give amine-protected 52.

EXAMPLES

Example 1

5-chloro-1-methyl-4-nitro-1H-pyrazole

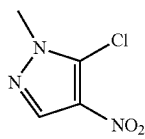

To a 500 mL round bottom flask containing 4-nitro-1-H-pyrazole (5 g, 44.2 mmol) was added sodium hydroxide (1M, 200 mL) and dimethyl sulfate (31 mL, 330 mmol). The mixture was stirred at room temperature for 72 h and the mixture was extracted with $CH_2Cl_2$ (2×150 mL). The organic layer was separated and the solvent was distilled off to yield 1-methyl-4-nitro-1H-pyrazole as a white solid (4.30 g, 76%).

Following WO 2007/99326, to a 500 mL 3-neck-round bottom flask was added 1-methyl-4-nitro-1H-pyrazole (4.30 g, 33.8 mmol) and THF (12 mL). The mixture was cooled to −78° C. and lithium hexamethyldisilazide in THF (1M, 88.4 mL, 90 mmol) was added dropwise via an addition funnel over 20 min. The brown mixture was stirred for 30 min and warmed to −45° C. over 30 min. The mixture was cooled back down to −78° C. and hexachloroethane (10.5 g, 44.2 mmol) dissolved in THF (20 mL) was added via an addition funnel over 15 min. The mixture was stirred for 2.5 h, warmed from −78° C. to −40° C. and the reaction was monitored by LCMS. Upon completion of the reaction, the reaction was quenched with a solution of saturated $NH_4Cl$ (150 mL), and ethyl acetate (100 mL) was added. The organic layer was separated and the aqueous layer was extracted with ethyl acetate (100 mL). The combined organic layer was washed with water (150 mL), dried over $Na_2SO_4$ and the organic solvent was distilled off. The crude product was purified via flash chromatography ($CH_2Cl_2$/7% MeOH) to yield 5-chloro-1-methyl-4-nitro-1H-pyrazole as a white solid (1.40 g, 20%). $^1H$ NMR (400 MHz, $CDCl_3$) δ 8.13 (s, 1H), 3.92 (s, 3H); ESIMS m/z=162.0 (M+1)

Example 2 tert-butyl 1-(4-amino-1-methyl-1H-pyrazol-5-yl)azepan-4-ylcarbamate

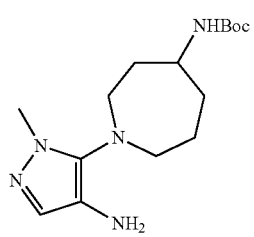 [SMILES: Cn1ncc(N)c1N1CCCC(NC(=O)OC(C)(C)C)CC1]

To a 10 mL microwave vial was added 5-chloro-1-methyl-4-nitro-1H-pyrazole from Example 1 (150 mg, 0.93 mmol), tert-butyl azepan-4-ylcarbamate (220 mg, 1.02 mmol). Ethanol (4 mL) and diisopropylethylamine (1.00 mL, 8.00 mmol) were added and the mixture was irradiated with a microwave for 60 min at 130° C. The mixture was cooled, concentrated and purified via flash chromatography, heptane/ethyl acetate 20% to 80% to afford yellow oil (306 mg, 97%).

To a 50 mL round bottom flask was added the nitro compound (306 mg, 0.90 mmol), iron (202 mg, 3.61 mmol), ammonium chloride (241 mg, 4.5 mmol), ethanol (10 mL) and water (1.5 mL). The mixture was stirred for 1 h at 60° C. and the reaction was monitored by LCMS. Upon completion of the reaction, the mixture was filtered through a pad of Celite and was washed with ethyl acetate (30 mL) and a 10% aqueous solution of $K_3PO_4$ (30 mL). The organic layer was washed with water (30 mL), dried over $Na_2SO_4$ and the organic solvent was distilled off to yield tert-butyl 1-(4-amino-1-methyl-1H-pyrazol-5-yl)azepan-4-ylcarbamate as a brown oil with a purity of >98% (264 mg, 95%). ESIMS m/z=310.1 (M+1).

Example 3 tert-butyl 1-(1-methyl-4-amino-1H-pyrazol-5-yl)piperidin-4-ylcarbamate

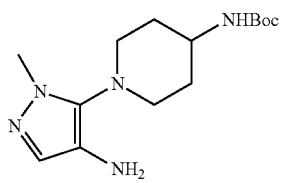 [SMILES: Cn1ncc(N)c1N1CCC(NC(=O)OC(C)(C)C)CC1]

Following the procedures as described in Example 2 and starting with tert-butyl piperidin-4-ylcarbamate, tert-butyl 1-(1-methyl-4-amino-1H-pyrazol-5-yl)piperidin-4-ylcarbamate was obtained as a brown oil (173 mg, 70%) over two steps. ESIMS m/z=296.1 (M+1).

Example 4

(S)-tert-butyl 1-(1-methyl-4-amino-1H-pyrazol-5-yl)piperidin-3-ylcarbamate

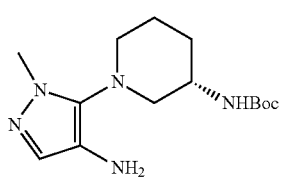

Following the procedures as described in Example 2 and starting with (S)-tert-butyl piperidin-3-ylcarbamate, (S)-tert-butyl 1-(1-methyl-4-amino-1H-pyrazol-5-yl)piperidin-3-ylcarbamate was obtained as a brown oil (206 mg, 75%) over two steps. ESIMS m/z=296.1 (M+1).

Example 4a 1-(1-Methyl-4-nitro-1H-pyrazol-5-yl)-3-(trifluoromethyl)piperidine

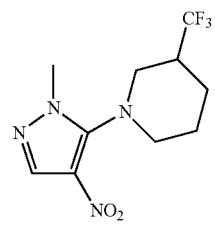 [SMILES: Cn1ncc([N+](=O)[O-])c1N1CCCC(C(F)(F)F)C1]

Following the procedure for Intermediate 22 starting from 5-chloro-1-methyl-4-nitro-1H-pyrazole and 3-(trifluoromethyl)piperidine gave 107 as a yellow oil (499 mg, 97%). ¹H NMR (400 MHz, CDCl₃) δ 8.03 (s, 1H), 3.77 (s, 3H), 3.41-3.32 (m, 1H), 3.31-3.18 (m, 2H), 3.07-2.97 (m, 1H), 2.54-2.40 (m, 1H), 2.13-2.06 (m, 1H), 1.97-1.90 (m, 1H), 1.80-1.60 (m, 2H).

Example 5

(S)-tert-butyl 1-(4-amino-1-methyl-1H-pyrazol-5-yl)pyrrolidin-3-ylcarbamate

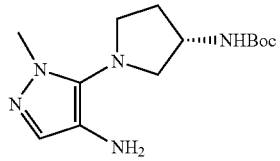

Following the procedures as described in Example 2 and starting with (S)-tert-butyl pyrrolidin-3-ylcarbamate, (S)-tert-butyl 1-(4-amino-1-methyl-1H-pyrazol-5-yl)pyrrolidin-3-ylcarbamate was obtained as a brown oil (162 mg, 62%) over two steps. ESIMS m/z=282.1 (M+1).

Example 6 tert-butyl 4-((4-amino-1-methyl-1H-pyrazol-5-yloxy)methyl)piperidine-1-carboxylate

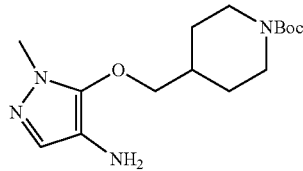 [SMILES: Cn1ncc(N)c1OCC1CCN(C(=O)OC(C)(C)C)CC1]

To a 50 mL round bottom flask was added 5-chloro-1-methyl-4-nitro-1H-pyrazole from Example 1 (100 mg, 0.60 mmol), tert-butyl 4-(hydroxymethyl)piperidine-1-carboxylate (200 mg, 0.93 mmol) and DMF (10 mL). NaH (37 mg, 1.55 mmol) was added slowly and the mixture was stirred for 1 h. The mixture concentrated and purified via flash chromatography, heptane/ethyl acetate 20% to 80% to afford an oil (150 mg, 70%).

To a 50 mL round bottom flask was added the nitro compound (150 mg, 0.44 mmol), iron (173 mg, 3.10 mmol), ammonium chloride (199 mg, 3.71 mmol), ethanol (10 mL) and water (1.5 mL). The mixture was stirred for 1 h at 60° C. and the reaction was monitored by LCMS. Upon completion of the reaction, the mixture was filtered through a pad of Celite and was washed with ethyl acetate (30 mL) and a 10% aqueous solution of K₃PO₄ (30 mL). The organic layer was washed with water (30 mL), dried over Na₂SO₄ and the organic solvent was distilled off to yield tert-butyl 4-((4-amino-1-methyl-1H-pyrazol-5-yloxy)methyl)piperidine-1-carboxylate as a brown oil with a purity of >98% (135 mg, 99%). ESIMS m/z=311.1 (M+1).

Example 7

(R)-tert-butyl 1-(1-methyl-4-amino-1H-pyrazol-5-yl)piperidin-3-ylcarbamate

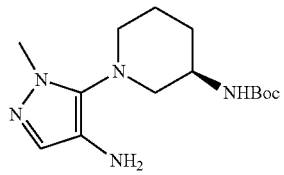 [SMILES: Cn1ncc(N)c1N1CCC[C@@H](NC(=O)OC(C)(C)C)C1]

Following the procedures as described in Example 2 and starting with (R)-tert-butyl piperidin-3-ylcarbamate, (R)-tert-butyl 1-(1-methyl-4-amino-1H-pyrazol-5-yl)piperidin-3-ylcarbamate was obtained as a brown oil (187 mg, 68%) over two steps. ESIMS m/z=296.1 (M+1).

Example 8 tert-butyl 4-(4-amino-1-methyl-1H-pyrazol-5-yloxy)piperidine-1-carboxylate

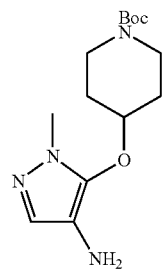

Following the procedures as described in Example 6 and starting with tert-butyl 4-hydroxypiperidine-1-carboxylate, tert-butyl 4-(4-amino-1-methyl-1H-pyrazol-5-yloxy)piperidine-1-carboxylate was obtained as a brown oil (102 mg, 50%) over two steps. ESIMS m/z=297.1 (M+1)

Example 9

(R)-tert-butyl 1-(4-amino-1-methyl-1H-pyrazol-5-yl)pyrrolidin-3-ylcarbamate

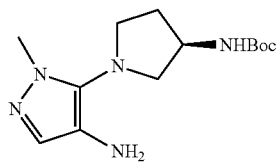

Following the procedures as described in Example 2 and starting with (R)-tert-butyl pyrrolidin-3-ylcarbamate, (R)-tert-butyl 1-(4-amino-1-methyl-1H-pyrazol-5-yl)pyrrolidin-3-ylcarbamate was obtained as a brown oil (159 mg, 61%) over two steps. ESIMS m/z=282.1 (M+1).

Example 10 tert-butyl 4-((4-amino-1-methyl-1H-pyrazol-5-ylamino)methyl)piperidine-1-carboxylate

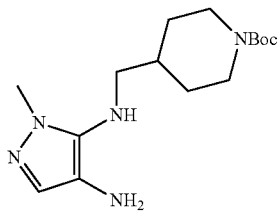 [SMILES: Cn1ncc(N)c1NCC1CCN(C(=O)OC(C)(C)C)CC1]

Following the procedures as described in Example 2 and starting with tert-butyl 4-(aminomethyl)piperidine-1-carboxylate, tert-butyl 4-((4-amino-1-methyl-1H-pyrazol-5-ylamino)methyl)piperidine-1-carboxylate was obtained as a brown oil (124 mg, 43%) over two steps. ESIMS m/z=310.1 (M+1).

Example 11

(S)-tert-butyl (1-(4-amino-1-methyl-1H-pyrazol-5-yl)pyrrolidin-3-yl)methylcarbamate

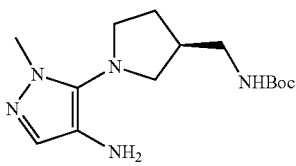 [SMILES: Cn1ncc(N)c1N1CC[C@@H](CNC(=O)OC(C)(C)C)C1]

Following the procedures as described in Example 2 and starting with (R)-tert-butyl pyrrolidin-3-ylmethylcarbamate, (S)-tert-butyl (1-(4-amino-1-methyl-1H-pyrazol-5-yl)pyrrolidin-3-yl)methylcarbamate was obtained as a brown oil (230 mg, 84%) over two steps. ESIMS m/z=296.1 (M+1)

Example 12

(R)-tert-butyl (1-(4-amino-1-methyl-1H-pyrazol-5-yl)pyrrolidin-3-yl)methylcarbamate

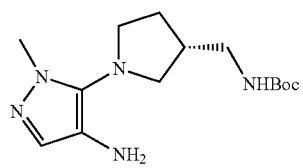 [SMILES: Cn1ncc(N)c1N1CC[C@H](CNC(=O)OC(C)(C)C)C1]

Following the procedures as described in Example 2 and starting with (S)-tert-butyl pyrrolidin-3-ylmethylcarbamate, (R)-tert-butyl (1-(4-amino-1-methyl-1H-pyrazol-5-yl)pyrrolidin-3-yl)methylcarbamate was obtained as a brown oil (200 mg, 73%) over two steps. ESIMS m/z=296.1 (M+1).

Example 13 tert-butyl (1-(4-amino-1H-pyrazol-5-yl)piperidin-4-yl)methylcarbamate

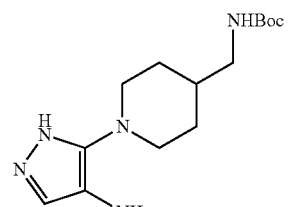

Following the procedures as described in Example 2 and starting with tert-butyl piperidin-4-ylmethylcarbamate, tert-butyl (1-(4-amino-1H-pyrazol-5-yl)piperidin-4-yl)methylcarbamate was obtained as a brown oil (270 mg, 98%) over two steps. ESIMS m/z=310.1 (M+1).

Example 14

(S)-tert-butyl (1-(4-amino-1-methyl-1H-pyrazol-5-yl)piperidin-3-yl)methylcarbamate

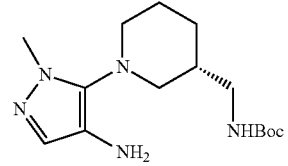

Following the procedures as described in Example 2 and starting with (R)-tert-butyl piperidin-3-ylmethylcarbamate, (S)-tert-butyl (1-(4-amino-1-methyl-1H-pyrazol-5-yl)piperidin-3-yl)methylcarbamate was obtained as a brown oil (270 mg, 98%) over two steps. ESIMS m/z=310.1 (M+1).

Example 15

(R)-tert-butyl (1-(4-amino-1-methyl-1H-pyrazol-5-yl)piperidin-3-yl)methylcarbamate

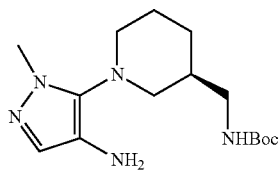 [SMILES: Cn1ncc(N)c1N1CCC[C@@H](CNC(=O)OC(C)(C)C)C1]

Following the procedures as described in Example 2 and starting with (S)-tert-butyl piperidin-3-ylmethylcarbamate, (R)-tert-butyl (1-(4-amino-1-methyl-1H-pyrazol-5-yl)piperidin-3-yl)methylcarbamate was obtained as a brown oil (268 mg, 98%) over two steps.

ESIMS m/z=310.1 (M+1)

Example 16

(R)-benzyl 1-(4-amino-1-methyl-1H-pyrazol-5-yl)azepan-4-ylcarbamate

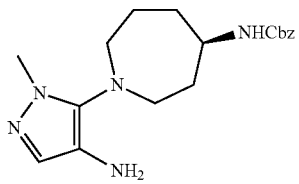 [SMILES: Cn1ncc(N)c1N1CCC[C@@H](NC(=O)OCc2ccccc2)CC1]

Following the procedures as described in Example 2 and starting with (R)-benzyl azepan-4-ylcarbamate, (R)-benzyl 1-(4-amino-1-methyl-1H-pyrazol-5-yl)azepan-4-ylcarbamate was obtained as a brown oil (191 mg, 60%) over two steps. ESIMS m/z=344.1 (M+1).

Example 17

(S)-benzyl 1-(4-amino-1-methyl-1H-pyrazol-5-yl)azepan-4-ylcarbamate

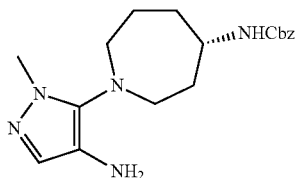

Following the procedures as described in Example 2 and starting with (S)-benzyl azepan-4-ylcarbamate, (S)-benzyl 1-(4-amino-1-methyl-1H-pyrazol-5-yl)azepan-4-ylcarbamate was obtained as a brown oil (220 mg, 63%) over two steps. ESIMS m/z=344.1 (M+1).

Example 18 tert-butyl 3-(4-amino-1-methyl-1H-pyrazol-5-yl)-3-azabicyclo[3.1.0]hexan-6-ylcarbamate

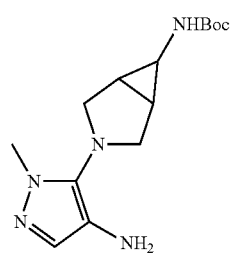 [SMILES: Cn1ncc(N)c1N1CC2C(C1)C2NC(=O)OC(C)(C)C]

Following the procedures as described in Example 2 and starting tert-butyl 3-azabicyclo[3.1.0]hexan-6-ylcarbamate, tert-butyl 3-(4-amino-1-methyl-1H-pyrazol-5-yl)-3-azabicyclo[3.1.0]hexan-6-ylcarbamate was obtained as a brown oil (130 mg, 48%) over two steps. ESIMS m/z=294.1 (M+1).

Example 19 ethyl 2-amino-2-cyanoacetate

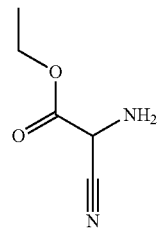

To a stirred solution of (E)-ethyl 2-cyano-2-(hydroxyimino)acetate (20 g, 0.14 mol) in water (250 mL) was added a saturated solution of NaHCO$_3$ in water (160 mL), followed by the addition of Na$_2$S$_2$O$_4$ (60 g, 0.423 mol). The reaction mixture was warmed up to 35° C. and stirred for additional 2 hr. It was then saturated with NaCl (150 g) and extracted with DCM (3×350 mL). Combined organic layers were washed with brine, dried over Na$_2$SO$_4$, filtered and concentrated in vacuo to give ethyl 2-amino-2-cyanoacetate as a red oil (7.8 g, 43%) that was used at the next step without additional purification. $^1$H-NMR (CDCl$_3$, 500 MHz) δ (ppm): 4.45 (s, 1H), 4.34 (q, J=7.0 Hz, 2H), 1.36 (t, J=7.0 Hz, 3H); MS (ESI) m/z: 129 [M+H$^+$].

Example 20 ethyl 2-benzamido-2-cyanoacetate

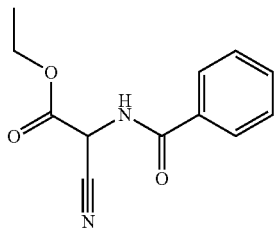 [SMILES: CCOC(=O)C(C#N)NC(=O)c1ccccc1]

To a stirred solution of compound ethyl 2-amino-2-cyanoacetate (0.64 g, 5 mmol) in DCM (15 mL) was added a saturate solution of NaHCO$_3$ in water (15 mL). With vigorously stirring, benzoyl chloride (0.84 g, 6 mmol) was added. The reaction mixture was stirred at ambient temperature for additional 30 min at which time it was extracted with DCM (3×15 mL). Combined organic layers were washed with brine (20 mL) and dried over Na$_2$SO$_4$, filtered, concentrated in vacuo. Resulted residue was purified by silica gel column chromatography (5:1 PE/EtOAc) to afford ethyl 2-benzamido-2-cyanoacetate (0.25 g, 22%) as white solid: $^1$H-NMR (CDCl$_3$, 500 MHz) δ (ppm): 7.83-7.85 (m, 2H), 7.59 (t, J=7.5 Hz, 1H), 7.49 (t, J=7.5 Hz, 2H), 7.02 (d, J=7.0 Hz, 1H), 5.72 (d, J=7.5 Hz, 1H), 4.40 (q, J=7.5 Hz, 2H), 1.39 (t, J=7.0 Hz, 3H); MS (ESI) m/z: 233 [M+H$^+$].

Example 21 ethyl 5-amino-2-phenylthiazole-4-carboxylate

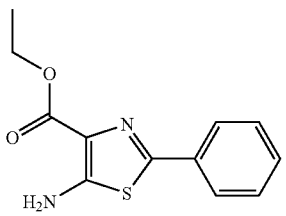 [SMILES: CCOC(=O)c1nc(-c2ccccc2)sc1N]

To a stirred solution of compound ethyl 2-benzamido-2-cyanoacetate (0.46 g, 2 mmol) in pyridine (20 mL) was added Lawesson's reagent (0.81 g, 2 mmol). The reaction mixture was heated at reflux for 15 hr. It was then concentrated and diluted with EtOAc (40 mL). The diluted mixture was washed with water (3×20 mL), brine (10 mL), dried over Na$_2$SO$_4$, filtered, and concentrated in vacuo. The residue was purified by silica gel column chromatography (10:1 PE/EtOAc) to afford ethyl 5-amino-2-phenylthiazole-4-carboxylate (0.2 g, 40%) as yellow solid: $^1$H-NMR (CDCl$_3$, 500 MHz) δ (ppm): 7.80 (d, J=6.5 Hz, 1H), 7.36-7.41 (m, 3H), 4.43 (q, J=7.0 Hz, 2H), 1.44 (t, J=7.0 Hz, 3H); MS (ESI) m/z: 249 [M+H$^+$].

Example 22 ethyl 5-(tert-butoxycarbonylamino)-2-phenylthiazole-4-carboxylate

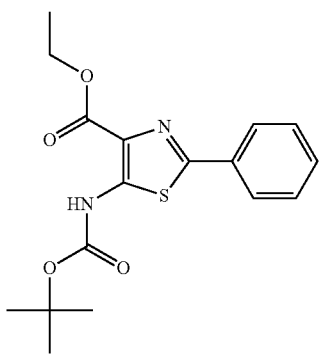 [SMILES: CCOC(=O)c1nc(-c2ccccc2)sc1NC(=O)OC(C)(C)C]

To a solution of compound ethyl 5-amino-2-phenylthiazole-4-carboxylate (248 mg, 1 mmol) in CH$_3$CN (10 mL) was added DMAP (6 mg, 0.05 mmol) followed by (Boc)$_2$O (262 mg, 1.2 mmol). The reaction mixture was maintained at ambient temperature for additional 30 min. The mixture was then evaporated in vacuo to give ethyl 5-(tert-butoxycarbonylamino)-2-phenylthiazole-4-carboxylate as a red solid (340 mg, 95%) that was used at the next step without further purification.

Example 23

5-(tert-butoxycarbonylamino)-2-phenylthiazole-4-carboxylic acid

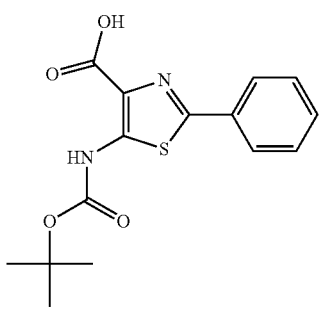 [SMILES: CC(C)(C)OC(=O)Nc1sc(-c2ccccc2)nc1C(=O)O]

To a solution of compound ethyl 5-(tert-butoxycarbonylamino)-2-phenylthiazole-4-carboxylate (348 mg, 1 mmol) in MeOH/H$_2$O (10 mL, 1:1) was added LiOH.H$_2$O (20 mg, 5 mmol). The reaction mixture was heated at 50-55° C. until starting material disappeared from TLC. It was cooled at about 0-4° C. and conc. HCl added dropwise until pH of about 5. The resulted mixture was then extracted with DCM (3×20 mL). Combined organic layers were washed with brine (2×20 mL), dried over Na$_2$SO$_4$, filtered, and concentrated in vacuo. The residue was purified by silica gel column chromatography (50:1 DCM:MeOH) to give the 5-(tert-butoxycarbonylamino)-2-phenylthiazole-4-carboxylic acid (0.22 g, 68%) as white solid: ¹H-NMR (CDCl₃, 500 MHz) δ (ppm): 9.69 (s, 1H), 7.89-7.91 (m, 2H), 7.46-7.47 (m, 3H), 1.57 (s, 9H); MS (ESI) m/z: 321 [M+H⁺]

Example 24

5-(tert-butoxycarbonylamino)-2-(2-fluorophenyl)thiazole-4-carboxylic acid

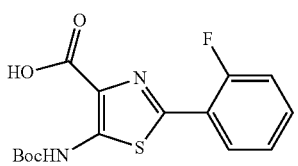 [SMILES: CC(C)(C)OC(=O)Nc1sc(-c2ccccc2F)nc1C(=O)O]

Following procedures from Examples 19-23 and shown in FIG. 2, 2-fluorobenzoyl chloride was converted to 5-(tert-butoxycarbonylamino)-2-(2-fluorophenyl)thiazole-4-carboxylic acid: ¹H-NMR (CDCl₃, 500 MHz) δ (ppm): 9.70 (s, 1H), 8.19-8.23 (m, 1H), 7.42-7.45 (m, 1H), 7.20-7.30 (m, 2H), 1.57 (s, 9H); MS (ESI) m/z: 339 [M+H⁺]

Example 25

5-(tert-butoxycarbonylamino)-2-(2,6-difluorophenyl)thiazole-4-carboxylic acid

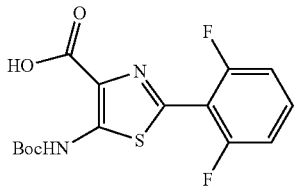 [SMILES: CC(C)(C)OC(=O)Nc1sc(-c2c(F)cccc2F)nc1C(=O)O]

Following procedures from Examples 19-23 and shown in FIG. 2, 2,6-difluorobenzoyl chloride was converted to 5-(tert-butoxycarbonylamino)-2-(2,6-difluorophenyl)thiazole-4-carboxylic acid: ¹H-NMR (CD₃OD, 500 MHz) δ (ppm): 7.42-7.46 (m, 1H), 7.06 (t, J=8.5 Hz, 2H), 1.47 (s, 9H); MS (ESI) m/z: 355 [M+H⁺].

Example 26

5-(tert-butoxycarbonylamino)-2-(2-chlorophenyl)thiazole-4-carboxylic acid

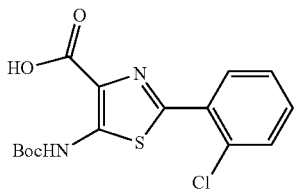 [SMILES: CC(C)(C)OC(=O)Nc1sc(-c2ccccc2Cl)nc1C(=O)O]

Following procedures from Examples 19-23 and shown in FIG. 2, 2-chlorobenzoyl chloride was converted to 5-(tert-butoxycarbonylamino)-2-(2-chlorophenyl)thiazole-4-carboxylic acid: ¹H-NMR (DMSO, 500 MHz) δ (ppm): 13.57 (s, 1H), 10.05 (s, 1H), 8.14-8.17 (m, 1H), 7.63-7.65 (m, 1H), 7.49-7.51 (m, 2H), 1.53 (s, 9H); MS (ESI) m/z: 355 [M+H⁺].

Example 27

2-(5-bromo-2-fluorophenyl)-5-(tert-butoxycarbonylamino)thiazole-4-carboxylic acid

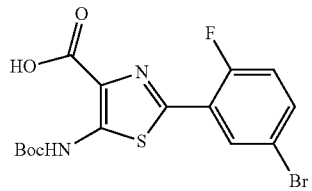 [SMILES: CC(C)(C)OC(=O)Nc1sc(-c2cc(Br)ccc2F)nc1C(=O)O]

Following procedures from Examples 19-23 and shown in FIG. 2, 5-bromo-2-fluorobenzoyl chloride was converted to 2-(5-bromo-2-fluorophenyl)-5-(tert-butoxycarbonylamino)thiazole-4-carboxylic acid: ¹H-NMR (CDCl₃, 500 MHz) δ (ppm): 9.70 (s, 1H), 8.32-8.34 (m, 1H), 7.49-7.52 (m, 1H), 7.09-7.13 (m, 1H), 1.57 (s, 9H); MS (ESI) m/z: 418 [M+H⁺].

Example 28

2-(5-bromo-2-chlorophenyl)-5-(tert-butoxycarbonylamino)thiazole-4-carboxylic acid

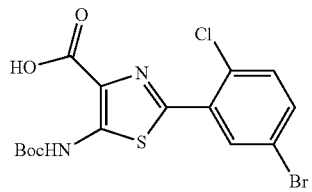 [SMILES: CC(C)(C)OC(=O)Nc1sc(-c2cc(Br)ccc2Cl)nc1C(=O)O]

Following procedures from Examples 19-23 and shown in FIG. 2, 5-bromo-2-chlorobenzoyl chloride was converted to 2-(5-bromo-2-chlorophenyl)-5-(tert-butoxycarbonylamino)thiazole-4-carboxylic acid: ¹H-NMR (CDCl₃, 500 MHz) δ (ppm): 9.70 (s, 1H), 8.31 (d, J=2.5 Hz, 1H), 7.47 (dd, J=2.5 Hz, J=8.5 Hz, 1H), 7.35 (d, J=9.0 Hz, 1H), 1.57 (s, 9H); MS (ESI) m/z: 433 [M+H⁺].

Example 29

2-(3-bromophenyl)-5-(tert-butoxycarbonylamino)thiazole-4-carboxylic acid

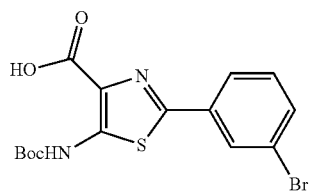 [SMILES: CC(C)(C)OC(=O)Nc1sc(-c2cccc(Br)c2)nc1C(=O)O]

Following procedures from Examples 19-23 and shown in FIG. 2, 3-bromobenzoyl chloride was converted to 2-(3-bromophenyl)-5-(tert-butoxycarbonylamino)thiazole-4-carboxylic acid: ¹H-NMR (CDCl₃, 500 MHz) δ (ppm): 9.68 (s, 1H), 8.08 (s, 1H), 7.78 (d, J=8.0 Hz, 1H), 7.56 (d, J=8.0 Hz, 1H), 7.32 (t, J=8.0 Hz, 1H), 1.57 (s, 9H); MS (ESI) m/z: 399 [M+H⁺]

Example 30

2-(4-bromo-2-fluorophenyl)-5-(tert-butoxycarbonylamino)thiazole-4-carboxylic acid

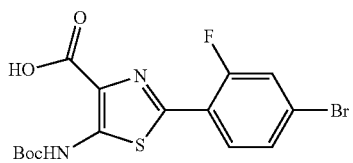 [SMILES: CC(C)(C)OC(=O)Nc1sc(-c2ccc(Br)cc2F)nc1C(=O)O]

Following procedures from Examples 19-23 and shown in FIG. 2, 4-bromo-2-fluorobenzoyl chloride was converted to 2-(4-bromo-2-fluorophenyl)-5-(tert-butoxycarbonylamino) thiazole-4-carboxylic acid: $^1$H-NMR (CDCl$_3$, 500 MHz) δ (ppm): 9.67 (s, 1H), 8.07 (t, J=8.0 Hz, 1H), 7.42 (d, J=9.5 Hz, 1H), 1.57 (s, 9H); MS (ESI) m/z: 417 [M+H$^+$]

Example 31

5-(tert-butoxycarbonylamino)-2-(yridine-2-yl)thiazole-4-carboxylic acid

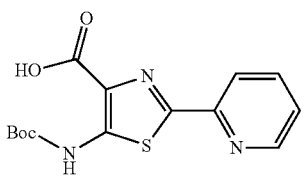 [SMILES: CC(C)(C)OC(=O)Nc1sc(-c2ccccn2)nc1C(=O)O]

To a solution of picolinic acid (1.23 g, 10 mmol), EDC.HCl (1.91 g, 10 mmol) and HOBT (1.35 g, 10 mmol) in THF (80 mL) was added DIPEA (3.6 g, 30 mmol) at ambient temperature. The reaction mixture was maintained at the same temperature for 1 hr at which time a solution of ethyl 2-amino-2-cyanoacetate (1.28 g, 10 mmol) in THF (5 mL) was added. The reaction mixture was stirred at ambient temperature for additional 6 hr. It was then concentrated, and the residue was purified by silica gel column chromatography (5:1 PE/EtOAc) to give ethyl 2-cyano-2-(picolinamido)acetate (0.7 g, 30%) as yellow solid.

Following procedures from Examples 19-23 and shown in FIG. 2, ethyl 2-cyano-2-(picolinamido)acetate was converted to 5-(tert-butoxycarbonylamino)-2-(pyridine-2-yl)thiazole-4-carboxylic acid: $^1$H-NMR (CDCl$_3$, 500 MHz) δ (ppm): 9.72 (s, 1H), 8.61 (d, J=4.5 Hz, 1H), 8.09 (d, J=8.0 Hz, 1H), 7.81 (t, J=7.5 Hz, 1H), 7.34 (dd, J=5.5 Hz, J=7.0 Hz, 1H), 1.57 (s, 9H); MS (ESI) m/z: 322 [M+H$^+$].

Example 32

5-(tert-butoxycarbonylamino)-2-isopropylthiazole-4-carboxylic acid

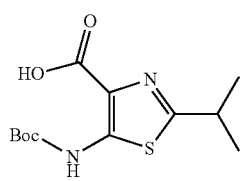 [SMILES: CC(C)c1nc(C(=O)O)c(NC(=O)OC(C)(C)C)s1]

Following procedures from Examples 19-23 and shown in FIG. 2, isobutyryl chloride was converted to 5-(tert-butoxycarbonylamino)-2-isopropylthiazole-4-carboxylic acid: $^1$H-NMR (CDCl$_3$, 500 MHz) δ (ppm): 9.54 (s, 1H), 3.16-3.21 (m, 1H), 1.54 (s, 9H), 1.37 (d, J=7.0 Hz, 6H); MS (ESI) m/z: 287 [M+H$^+$].

Example 33

5-(tert-butoxycarbonylamino)-2-cyclohexylthiazole-4-carboxylic acid

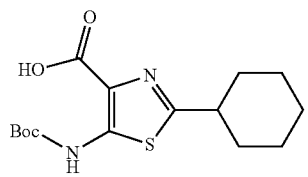 [SMILES: CC(C)(C)OC(=O)Nc1sc(C2CCCCC2)nc1C(=O)O]

Following procedures from Examples 19-23 and shown in FIG. 2, cyclohexanecarboxylic acid chloride was converted to 5-(tert-butoxycarbonylamino)-2-cyclohexylthiazole-4-carboxylic acid: $^1$H-NMR (CDCl$_3$, 500 MHz) δ (ppm): 9.53 (s, 1H), 2.84-2.89 (m, 1H), 2.08-2.12 (m, 2H), 1.84 (dd, J=3.5 Hz, J=10.0 Hz, 2H), 1.73 (d, J=13.0 Hz, 1H), 1.53 (s, 9H), 1.35-1.50 (m, 4H), 1.25-1.27 (m, 1H); MS (ESI) m/z: 327 [M+H$^+$].

Example 34

5-(tert-butoxycarbonylamino)-2-o-tolylthiazole-4-carboxylic acid

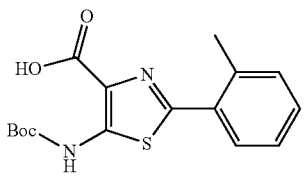 [SMILES: Cc1ccccc1-c1nc(C(=O)O)c(NC(=O)OC(C)(C)C)s1]

Following procedures from Examples 19-23 and shown in FIG. 2, 2-methylbenzoyl chloride was converted to 5-(tert-butoxycarbonylamino)-2-o-tolylthiazole-4-carboxylic acid: $^1$H-NMR (CD$_3$OD, 500 MHz) δ (ppm): 7.34 (s, 1H), 7.13-7.22 (m, 3H), 2.32 (s, 3H), 1.43 (s, 9H); MS (ESI) m/z: 335 [M+H$^+$].

Example 35

5-(tert-butoxycarbonylamino)-2-(2-methoxyphenyl)thiazole-4-carboxylic acid

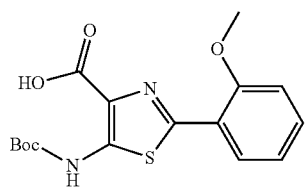 [SMILES: COc1ccccc1-c1nc(C(=O)O)c(NC(=O)OC(C)(C)C)s1]

Following procedures from Examples 19-23 and shown in FIG. 2, 2-methoxybenzoyl chloride was converted to 5-(tert-butoxycarbonylamino)-2-(2-methoxyphenyl)thiazole-4-carboxylic acid: $^1$H-NMR (CD$_3$OD, 500 MHz) δ (ppm): 9.63 (s, 1H), 8.27 (d, J=7.5 Hz, 1H), 7.42 (t, J=8.0 Hz, 1H), 7.09 (t, J=7.5 Hz, 1H), 7.04 (d, J=9.0 Hz, 1H), 1.57 (s, 9H); MS (ESI) m/z: 351 [M+H$^+$]

Example 36

5-(tert-butoxycarbonylamino)-2-(2-(trifluoromethyl)phenyl)thiazole-4-carboxylic acid

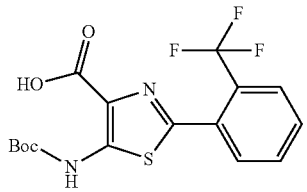 [SMILES: CC(C)(C)OC(=O)Nc1sc(-c2ccccc2C(F)(F)F)nc1C(=O)O]

Following procedures from Examples 19-23 and shown in FIG. 2, 2-(trifluoromethyl)benzoyl chloride was converted to 5-(tert-butoxycarbonylamino)-2-(2-(trifluoromethyl)phenyl)thiazole-4-carboxylic acid: $^1$H-NMR (CD$_3$OD, 500 MHz) δ (ppm): 7.76 (d, J=7.5 Hz, 1H), 7.58-7.64 (m, 3H), 1.46 (s, 9H); MS (ESI) m/z: 389 [M+H$^+$].

Example 37

5-(tert-butoxycarbonylamino)-2-methylthiazole-4-carboxylic acid

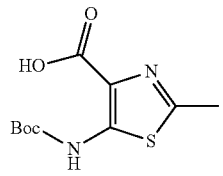

Following procedures from Examples 19-23 and shown in FIG. 2, acetyl chloride was converted to 5-(tert-butoxycarbonylamino)-2-methylthiazole-4-carboxylic acid: $^1$H-NMR (CDCl$_3$, 500 MHz) δ (ppm): 9.62 (s, 1H), 2.62 (s, 3H), 1.54 (s, 9H); MS (ESI) m/z: 259 [M+H$^+$]

Example 38

5-(tert-butoxycarbonylamino)thiazole-4-carboxylic acid

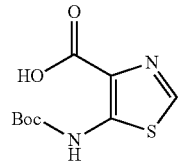

Under a nitrogen atmosphere (N$_2$), HCOOH (2.44 g, 53 mmol) was added to Ac$_2$O (6.48 g, 63.6 mmol) at 0° C. After it was allowed to warm to ambient temperature the reaction was heated at 50° C. for 15 hr. It was allowed to cool to ambient temperature. This mixed acid anhydride was then added dropwise to a solution of ethyl 2-amino-2-cyanoacetate (128 mg, 1 mmol) in dry THF (5 mL) at 0° C. After the cooling bath was removed, the reaction was maintained at ambient temperature for additional 1 hr. The reaction mixture was concentrated and purified by silica gel column chromatography (5:1 PE/EtOAc) to afford ethyl 2-cyano-2-formamidoacetate (110 mg, 70%) as a white solid.

Following procedures from Examples 19-23 and shown in FIG. 2, ethyl 2-cyano-2-formamidoacetate was converted to 5-(tert-butoxycarbonylamino)thiazole-4-carboxylic acid: $^1$H-NMR (CDCl$_3$, 500 MHz) δ (ppm): 9.70 (s, 1H), 8.29 (s, 1H), 1.55 (s, 9H); MS (ESI) m/z: 245 [M+H$^+$]

Example 39

2-bromo-5-(tert-butoxycarbonylamino)thiazole-4-carboxylic acid

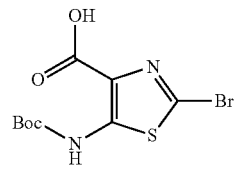

To a solution of 5-(tert-butoxycarbonylamino)thiazole-4-carboxylic acid (1.72 g, 10 mmol) in DCM (50 mL) was added in three portions NBS (1.95 g, 11 mmol); the reaction mixture was stirred at ambient temperature for 1 h. Reaction was concentrated in vacuo; resulted residue was purified by silica gel column chromatography (6:1 Pet-ether-EtOAc) to afford 2-bromo-5-(tert-butoxycarbonylamino)thiazole-4-carboxylic acid (1.75 g, 70%) as white solid: $^1$H-NMR (CDCl$_3$, 500 MHz) δ (ppm): 13.65 (s, 1H), 10.03 (s, 1H), 1.49 (s, 9H). MS (ESI) m/z: 324 [M+H$^+$]

Example 40

5-(tert-butoxycarbonylamino)-2-(2,5-difluorophenyl)thiazole-4-carboxylic acid

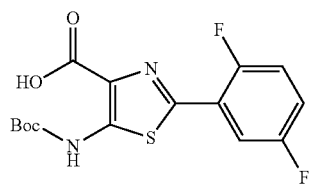 [SMILES: CC(C)(C)OC(=O)Nc1sc(-c2cc(F)ccc2F)nc1C(=O)O]

Following procedures from Examples 19-23 and shown in FIG. 2, 2,5-difluorobenzoyl chloride was converted to 5-(tert-butoxycarbonylamino)-2-(2,5-difluorophenyl)thiazole-4-carboxylic acid: $^1$H-NMR (CDCl$_3$, 500 MHz) δ (ppm): 9.68

(s, 1H), 7.87-7.91 (m, 1H), 7.15-7.26 (m, 1H), 7.08-7.13 (m, 1H), 1.57 (s, 9H); MS (ESI) m/z: 357 [M+H$^+$]

Example 41

5-(tert-butoxycarbonylamino)-2-(2,4-difluorophenyl)thiazole-4-carboxylic acid

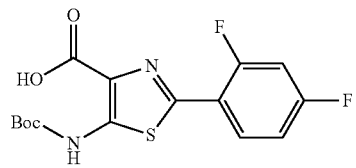 [SMILES: CC(C)(C)OC(=O)Nc1sc(-c2ccc(F)cc2F)nc1C(=O)O]

Following procedures from Examples 19-23 and shown in FIG. 2, 2,4-difluorobenzoyl chloride was converted to 5-(tert-butoxycarbonylamino)-2-(2,4-difluorophenyl)thiazole-4-carboxylic acid: $^1$H-NMR (CDCl$_3$, 500 MHz) δ (ppm): 9.66 (s, 1H), 8.16-8.21 (m, 1H), 6.95-7.04 (m, 2H), 1.62 (s, 9H); MS (ESI) m/z: 357 [M+H$^+$]

Example 42

5-(tert-butoxycarbonylamino)-2-(2,3-difluorophenyl)thiazole-4-carboxylic acid

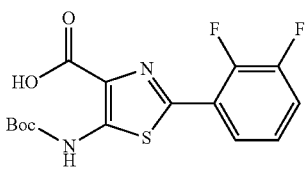 [SMILES: CC(C)(C)OC(=O)Nc1sc(-c2cccc(F)c2F)nc1C(=O)O]

Following procedures from Examples 19-23 and shown in FIG. 2, 2,3-difluorobenzoyl chloride was converted to 5-(tert-butoxycarbonylamino)-2-(2,3-difluorophenyl)thiazole-4-carboxylic acid: $^1$H-NMR (CD$_3$OD, 400 MHz) δ (ppm): 7.45 (s, 1H), 7.07-7.16 (m, 2H), 1.42 (s, 9H); MS (ESI) m/z: 357 [M+H$^+$].

Example 43

2-benzyl-5-(tert-butoxycarbonylamino)thiazole-4-carboxylic acid

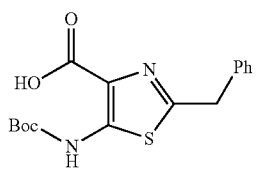 [SMILES: CC(C)(C)OC(=O)Nc1sc(Cc2ccccc2)nc1C(=O)O]

Following procedures from Examples 19-23 and shown in FIG. 2, 2-phenylacetyl chloride was converted to 2-benzyl-5-(tert-butoxycarbonylamino)thiazole-4-carboxylic acid:

$^1$H-NMR (CDCl$_3$, 500 MHz) δ (ppm): 9.63 (s, 1H), 7.27-7.35 (m, 5H), 4.25 (s, 2H), 1.50 (s, 9H); MS (ESI) m/z: 335 [M+H$^+$].

Example 44

5-(tert-butoxycarbonylamino)-2-(quinolin-7-yl)thiazole-4-carboxylic acid

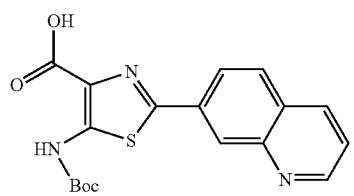 [SMILES: CC(C)(C)OC(=O)Nc1sc(-c2ccc3cccnc3c2)nc1C(=O)O]

Following procedures from Examples 19-23 and shown in FIG. 2, quinoline-7-carbonyl chloride was converted to 5-(tert-butoxycarbonylamino)-2-(quinolin-7-yl)thiazole-4-carboxylic acid: $^1$H-NMR (DMSO, 500 MHz) δ (ppm): 10.14 (s, 1H), 9.11 (d, J=5 Hz, 1 h), 8.68 (s, 1H), 8.55 (s, 1H), 8.21-8.25 (m, 2H), 7.75-7.77 (m, 1H), 1.54 (s, 9H); MS (ESI) m/z: 372 [M+H$^+$]

Example 45

5-(tert-butoxycarbonylamino)-2-(imidazo[1,2-a]yridine-2-yl)thiazole-4-carboxylic acid

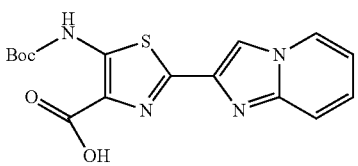 [SMILES: CC(C)(C)OC(=O)Nc1sc(-c2cn3ccccc3n2)nc1C(=O)O]

Following procedures from Examples 19-23 and shown in FIG. 2, imidazo[1,2-a]pyridine-2-carbonyl chloride was converted to 5-(tert-butoxycarbonylamino)-2-(imidazo[1,2-a]yridine-2-yl)thiazole-4-carboxylic acid: $^1$H-NMR (DMSO, 500 MHz) δ (ppm): 10.12 (s, 1H), 8.58 (d, 5 Hz, 1H), 8.45 (s, 1H), 7.61 (d, 5 Hz, 1H), 7.31-7.34 (m, 1H), 6.97-6.99 (m, 1H), 1.53 (s, 9H); MS (ESI) m/z: 361 [M+H$^+$].

Example 46

5-(tert-butoxycarbonylamino)-2-tert-butylthiazole-4-carboxylic acid

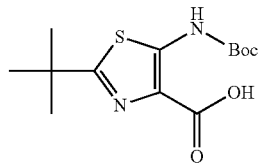 [SMILES: CC(C)(C)OC(=O)Nc1sc(C(C)(C)C)nc1C(=O)O]

Following procedures from Examples 19-23 and shown in FIG. 2, pivaloyl chloride was converted to 5-(tert-butoxycarbonylamino)-2-tert-butylthiazole-4-carboxylic acid:

¹H-NMR (CDCl₃, 500 MHz) δ (ppm): 9.55 (s, 1H), 1.55 (s, 9H), 1.42 (s, 9H); MS (ESI) m/z: 301 [M+H⁺].

Example 47

5-(tert-butoxycarbonylamino)-2-(3-chlorophenyl)thiazole-4-carboxylic acid

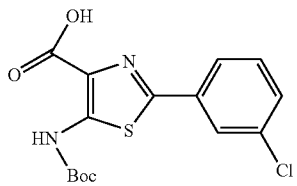 [SMILES: CC(C)(C)OC(=O)Nc1sc(-c2cccc(Cl)c2)nc1C(=O)O]

Following procedures from Examples 19-23 and shown in FIG. 2, 3-chlorobenzoyl chloride was converted to 5-(tert-butoxycarbonylamino)-2-(3-chlorophenyl)thiazole-4-carboxylic acid: ¹H-NMR (DMSO, 500 MHz) δ (ppm): 9.67 (s, 1H), 7.91 (s, 1H), 7.72 (d, J=7 Hz, 1H), 7.38-7.40 (m, 2H), 1.56 s, 9H); MS (ESI) m/z: 355 [M+H⁺].

Example 48

5-(tert-butoxycarbonylamino)-2-(4-chlorophenyl)thiazole-4-carboxylic acid

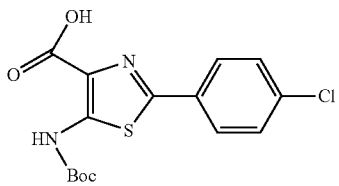 [SMILES: CC(C)(C)OC(=O)Nc1sc(-c2ccc(Cl)cc2)nc1C(=O)O]

Following procedures from Examples 19-23 and shown in FIG. 2, 4-chlorobenzoyl chloride was converted to 5-(tert-butoxycarbonylamino)-2-(4-chlorophenyl)thiazole-4-carboxylic acid: ¹H-NMR (DMSO, 500 MHz) δ (ppm): 9.66 (s, 1H), 7.81 (d, J=8.5 Hz, 2H), 7.42 (d, J=8.5 Hz, 2H), 1.56 (s, 9H); MS (ESI) m/z: 355 [M+H⁺].

Example 49

5-amino-N-(1-methyl-1H-pyrazol-4-yl)thiazole-4-carboxamide

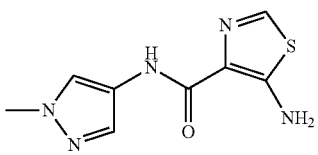

Following the procedures as described in Example 113, 1-methyl-1H-pyrazol-4-amine, 5-(tert-butoxycarbonylamino)thiazole-4-carboxylic acid were reacted to give 5-amino-N-(1-methyl-1H-pyrazol-4-yl)thiazole-4-carboxamide as a white solid (13 mg, 32%) over two steps. ESIMS m/z=336.1 (M+1)

Example 50 tert-butyl 3-(4-amino-1-methyl-1H-pyrazol-5-yl)phenylcarbamate

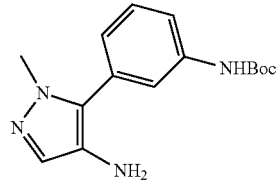 [SMILES: Cn1ncc(N)c1-c1cccc(NC(=O)OC(C)(C)C)c1]

To a 10 mL microwave vial was added 5-chloro-1-methyl-4-nitro-1H-pyrazole from Example 1 (150 mg, 0.93 mmol), 3-(tert-butoxycarbonylamino)phenylboronic acid (440 mg, 1.86 mmol), dichloro[1,1'-bis(diphenylphosphino)ferrocene]palladium(II) (152 mg, 0.019 mmol), a 1:1 M solution of Na₂CO₃/KOAc (1 mL) and acetonitrile (4 mL). The mixture was irradiated to 130° C. with a microwave for 40 min and the mixture was cooled, concentrated and purified via flash chromatography, heptane/ethyl acetate 20% to 95% to afford a yellow oil. To a 50 mL round bottom flask was added the nitro compound (120 mg, 0.90 mmol), iron (156 mg, 2.8 mmol), ammonium chloride (200 mg, 3.7 mmol), ethanol (10 mL) and water (1.5 mL). The mixture was stirred for 1 h and the reaction was monitored by LCMS. Upon completion of the reaction, the mixture was filtered through a pad of Celite and was washed with ethyl acetate (30 mL) and a 10% aqueous solution of K₃PO₄ (30 mL). The organic layer was washed with water (30 mL), dried over Na₂SO₄ and the organic solvent was distilled off to yield tert-butyl 3-(4-amino-1-methyl-1H-pyrazol-5-yl)phenylcarbamate as a brown oil with a purity of >98% (120 mg, 45%) over two steps. ESIMS m/z=289.1 (M+1)

Example 51

1-methyl-5-o-tolyl-1H-pyrazol-4-amine

Following the procedures as described in Example 2 and starting with o-tolylboronic acid, 1-methyl-5-o-tolyl-1H-pyrazol-4-amine was obtained as a brown oil (148 mg, 85%) over two steps. ESIMS m/z=188.1 (M+1)

Example 52

2-(4-Cyclopropyl-2-fluorophenyl)-4,4,5,5-tetramethyl-1,3,2-dioxaborolane

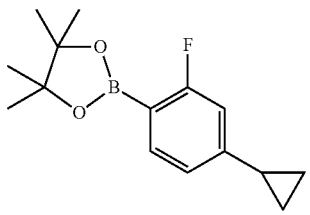 [SMILES: CC1(C)OB(c2ccc(C3CC3)cc2F)OC1(C)C]

Step 1: 3-fluoro-4-nitrophenyl trifluoromethanesulfonate

To a stirred solution of 3-fluoro-4-nitrophenol (10.00 g, 63.65 mmol) and trifluoromethanesulfonic anhydride (20.0 mL, 119 mmol, 1.87 eq.) in anhydrous DCM (100.0 mL) at 0° C. was added dropwise triethylamine (33.27 mL, 238.7 mmol, 3.75 eq.). The resultant brown reaction mixture was stirred at 0° C. for 2 h and then stirred at ambient temperature for 16 h. The reaction mixture was slowly quenched with water and extracted with DCM (3×100 mL). The combined organic layers were washed with brine (1×), dried over $Na_2SO_4$, filtered, and concentrated under reduced pressure. The crude oil was purified via flash column chromatography eluted with 0 to 65% DCM/hexane to give 15.67 g (85.1%) of 3-fluoro-4-nitrophenyl trifluoromethanesulfonate as an oil. $^1H$ NMR (500 MHz, $CDCl_3$) δ 8.23 (t, J=8.52 Hz, 1H), 7.34-7.27 (m, 2H).

Step 2: 4-cyclopropyl-2-fluoro-1-nitrobenzene

A mixture of 3-fluoro-4-nitrophenyl trifluoromethanesulfonate (7.15 g, 24.73 mmol), cyclopropylboronic acid (2.55 g, 29.67 mmol), [1,1'-bis(diphenylphosphino)-ferrocene]dichloropalladium(II), complexed with dichloromethane (1:1) (1.62 g, 1.98 mmol), and 2M cesium carbonate in water (19.8 mL, 39.56 mmol) in toluene (39.5 mL) was degassed for 20 min. The reaction mixture was stirred at 90° C. under $N_2$ for 2.5 h. The reaction was cooled to RT, diluted with ethyl acetate (200 mL), and filtered through a pad of Celite. The filtrate was washed with brine, dried over $Na_2SO_4$, filtered, and concentrated under reduced pressure. The crude residue was purified via flash column chromatography eluted with 0 to 75% DCM/hexane to give 4.11 g (91.7%) of 4-cyclopropyl-2-fluoro-1-nitrobenzene as an oil. $^1H$ NMR (400 MHz, MeOD) δ 7.98 (dd, J=10.2, 6.6 Hz, 1H), 7.12-7.02 (m, 2H), 2.11-1.97 (m, 1H), 1.20-1.11 (m, 2H), 0.89-0.82 (m, 2H).

Step 3: 4-cyclopropyl-2-fluoroaniline

A mixture of 4-cyclopropyl-2-fluoro-1-nitrobenzene (3.36 g, 18.55 mmol), powdered iron (4.35 g, 77.9 mmol), and 2M ammonium chloride in water (19.8 mL) and 3:2:1 v/v EtOH:THF:$H_2O$ (86 mL) was stirred at reflux under $N_2$ for 17 h. The reaction mixture was cooled to RT and filtered through a pad of Celite. The Celite pad was rinsed well with ethyl acetate (~50 mL). Saturated aqueous $NaHCO_3$ solution was slowly added to the filtrate to neutralize the reaction mixture. The reaction mixture was extracted with ethyl acetate (3×200 mL). The combined organic layers were washed with water and brine, dried over $Na_2SO_4$, filtered, and concentrated under reduced pressure. The crude residue was purified via flash column chromatography eluted with 0 to 75% ethyl acetate/hexane to give 2.80 g (99%) of an orange oil, which solidified at 20° C. $^1H$ NMR (400 MHz, $CDCl_3$) δ 6.75-6.63 (m, 3H), 3.57 (s, 2H), 1.87-1.72 (m, 1H), 0.93-0.83 (m, 2H), 0.64-0.51 (m, 2H); MS (ESI) m/z: 152.3 [M+H]$^+$.

Step 4: 4-cyclopropyl-2-fluoro-1-iodobenzene

To a stirred mixture of 4-cyclopropyl-2-fluoroaniline (1.63 g, 10.78 mmol) in water (20 mL) at 0° C. was added concentrated sulfuric acid (8.6 mL, 15.0 eq.) dropwise, while keeping the temperature constant at 0° C. A solution of sodium nitrite (781.0 mg, 11.32 mmol, 1.05 eq.) in water (2.7 mL) was added and stirred for 5 minutes. This resulting reaction mixture was then added to a solution of potassium iodide (3.76 g, 22.64 mmol, 2.1 eq.) in water (9.7 mL), and the reaction mixture was stirred at 60° C. for 3 h. DCM (400 mL) was added to the cooled reaction. The biphasic layers were separated, and the aqueous layer was extracted with DCM (2×150 mL). The combined organic layers were washed with saturated aqueous $Na_2S_2O_4$, water, and brine, dried over $Na_2SO_4$, filtered, and concentrated under reduced pressure. The crude residue was purified via flash column chromatography eluted with 100% heptane to give 2.01 g (71.28%) of 4-cyclopropyl-2-fluoro-1-iodobenzene as a clear oil. $^1H$ NMR (400 MHz, $CDCl_3$) δ 7.57 (dd, J=8.0, 6.9 Hz, 1H), 6.76 (dd, J=9.4, 1.9 Hz, 1H), 6.64 (dd, J=8.2, 1.9 Hz, 1H), 1.94-1.77 (m, 1H), 1.09-0.95 (m, 2H), 0.79-0.56 (m, 2H).

Step 5: In a high pressure tube was placed 4-cyclopropyl-2-fluoro-1-iodo-benzene (1.32 g, 5.04 mmol), bispinacol ester boronate (1.53 g, 6.04 mmol), potassium acetate (1.98 g, 20.15 mmol), [1,1'-bis(diphenylphosphino)ferrocene]dichloropalladium(II) (368.5 mg, 0.50 mmol), and N,N-dimethylformamide (35 mL). The reaction mixture was degassed with $N_2$ for 15 minutes. The vessel was sealed and the reaction mixture was stirred at 90° C. for 16 h. The cooled reaction mixture was diluted with ethyl acetate (75 mL) and water (25 mL) and then filtered through a pad of Celite. The biphasic layers were separated and the organic layer was washed with water and brine, dried over $Na_2SO_4$, filtered, and concentrated under reduced pressure. The crude residue was purified via flash column chromatography eluted with 0 to 75% EA/heptane to give 859.0 mg (65.1%) of 2-(4-cyclopropyl-2-fluorophenyl)-4,4,5,5-tetramethyl-1,3,2-dioxaborolane as a clear oil. $^1H$ NMR (400 MHz, $CDCl_3$) δ 7.58 (s, 1H), 6.83 (d, J=7.7 Hz, 1H), 6.68 (d, J=10.8 Hz, 1H), 1.91-1.81 (m, 1H), 1.33 (s, 12H), 0.98 (dd, J=8.3, 2.0 Hz, 2H), 0.74-0.66 (m, 2H)

Example 53

((R)-1-{4-[(2-Bromo-5-tert-butoxycarbonylamino-thiazole-4-carbonyl)-amino]-2-methyl-2H-pyrazol-3-yl}-perhydro-azepin-4-yl)-carbamic acid benzyl ester

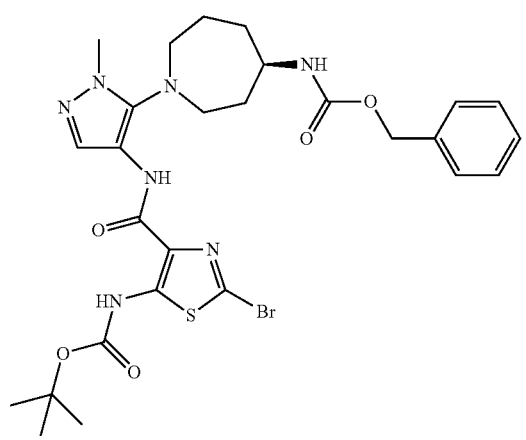 [SMILES: Cn1ncc(NC(=O)c2nc(Br)sc2NC(=O)OC(C)(C)C)c1N1CCC[C@@H](NC(=O)OCc2ccccc2)CC1]

To a stirred solution of 2-bromo-5-(isopropoxycarbonylamino)-thiazole-4-carboxylic acid (650.0 mg, 2.01 mmol) and [(R)-1-(4-amino-2-methyl-2H-pyrazol-3-yl)-azepan-4-yl]-carbamic acid benzyl ester (828.9 mg, 2.41 mmol, 1.2 eq.) in anhydrous N,N-dimethylformamide (22 mL) was added HATU (1.07 g, 2.81 mmol, 1.4 eq.) followed by N,N-diisopropylethylamine (0.88 mL, 5.03 mmol, 2.5 eq.), and the reaction mixture was stirred at RT under $N_2$ for 7 days. The reaction mixture was diluted with ethyl acetate (150 mL). The organic layer was washed with 50% brine/water, water and brine, dried over $Na_2SO_4$, filtered, and concentrated under reduced pressure. The crude was purified via flash column chromatography eluted with 45 to 100% ethyl acetate/heptane to give 1.30 g (79.7%) of ((R)-1-{4-[(2-Bromo-5-tert-butoxycarbonylamino-thiazole-4-carbonyl)-amino]-2-methyl-2H-pyrazol-3-yl}-perhydro-azepin-4-yl)-carbamic acid benzyl ester as a tacky gel. $^1$H NMR (400 MHz, $CDCl_3$) δ 10.28 (s, 1H), 8.39 (s, 1H), 7.74 (s, 1H), 7.33 (s, 5H), 5.09 (s, 2H), 4.98 (s, 1H), 3.89 (s, 1H), 3.72 (s, 3H), 3.36-3.21 (m, 2H), 3.16-3.03 (m, 2H), 2.19-2.01 (m, 2H), 2.00-1.61 (m, 4H), 1.51 (s, 9H)

Example 54

N-(5,5-Difluoro-1-(1-methyl-4-nitro-1H-pyrazol-5-yl)azepan-4-yl)-2,2,2-trifluoroacetamide

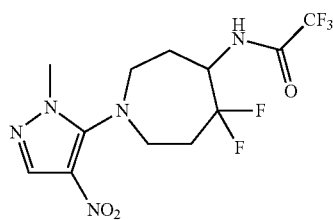 [SMILES: Cn1ncc([N+](=O)[O-])c1N1CCC(NC(=O)C(F)(F)F)C(F)(F)CC1]

Dess-Martin periodinane (2.3 g, 5.4 mmol) was added by portions to a solution of benzyl 4-azido-5-hydroxyazepane-1-carboxylate (1.3 g, 4.5 mmol) in DCM (25 mL). After stirring at room temperature for 18 hr, the mixture was diluted with DCM and quenched with aqueous $NaHCO_3$ (40 mL) followed by aqueous $Na_2S_2O_3$ (20%, 40 mL). The resulting mixture was stirred for 20 min. The organic layer was separated, dried over $Na_2SO_4$ and the solvent removed under reduced pressure. Purification via silica gel column chromatography (0-50% EtOAc/isohexane) gave benzyl 4-azido-5-oxoazepane-1-carboxylate (1.10 g, 84%) as a clear oil. To a solution of this oil (1.10 g, 3.8 mmol) in DCM (10 mL) was added Bis(2-methoxyethyl)aminosulfur trifluoride (deoxoFluor®, Sigma-Aldrich) (50% in THF, 3.5 mL, 9.5 mmol) and the mixture was stirred at room temperature for 18 hr. The mixture was diluted with DCM, cooled in an ice/water bath and quenched by dropwise addition of saturated aqueous $NaHCO_3$ (20 mL). Effervescence was observed. The resulting mixture was stirred for 10 min. The organic layer was separated, dried over $Na_2SO_4$ and the solvent removed under reduced pressure. The crude product was purified via silica gel column chromatography (0-40% EtOAc/isohexane) to give benzyl 5-azido-4,4-difluoroazepane-1-carboxylate (0.65 g, 56%) as a clear oil. This oil was dissolved in THF (10 mL) and water (2 mL) and triphenylphosphine (0.58 g, 2.2 mmol) added. After stirring and heating at 60° C. for 18 hr, the mixture was concentrated under reduced pressure. The crude product was dissolved in DCM and the organic layer was washed with water, separated, dried over $Na_2SO_4$ and the solvent removed under reduced pressure. To the crude product in DCM (20 mL), cooled in a water/ice bath, was added DIPEA (1.1 mL, 6.36 mmol) followed by trifluoroacetic anhydride (0.75 mL, 5.3 mmol) dropwise. The mixture was allowed to warm to room temperature, stirred for 18 hr and diluted with DCM. Water was added and the organic layer was separated, dried over $Na_2SO_4$ and the solvent was removed under reduced pressure. The residue was purified via silica gel column chromatography (0-60% EtOAc/isohexane) to yield benzyl 4,4-difluoro5-(2,2,2-trifluoroacetamido) azepane-1-carboxylate (0.59 g, 73%) as a clear oil. This trifluoroacetamide (0.57 g, 1.5 mmol) was dissolved in MeOH (50 mL) and passed through the H-Cube® (Full $H_2$ Mode, 70° C., flow rate: 1 mL/min, 30 mm 10% Pd/C cartridge). The solvent was removed under reduced pressure to give crude N-(5,5-difluoroazepan-4-yl)-2,2,2-trifluoroacetamide. To a solution of the azepane (0.37 g, 1.5 mmol) in EtOH (4 mL) was added 5-chloro-1-methyl-4-nitro-1H-pyrazole from Example 1 (0.73 g, 4.5 mmol) and DIPEA (0.65 mL, 3.8 mmol). The mixture was heated at 130° C. in a microwave for 6 hr. The solvent was removed under reduced pressure and the crude product was purified via silica gel column chromatography (0-50% EtOAc/isohexane) to yield N-(5,5-difluoro-1-(1-methyl-4-nitro-1H-pyrazol-5-yl)azepan-4-yl)-2,2,2-trifluoroacetamide as a pale yellow oil (0.31 g, 56%). $^1$H NMR (400 MHz, $CDCl_3$) δ 8.05 (s, 1H), 6.77 (d, J=9.0 Hz, 1H), 4.72-4.58 (m, 1H), 3.80 (s, 3H), 3.55-3.39 (m, 2H), 3.33-3.18 (m, 2H), 2.52-2.17 (m, 3H), 2.14-2.04 (m, 1H).

Example 55 tert-Butyl 4-(5-(4,4-difluoro-5-(2,2,2-trifluoroacetamido)azepan-1-yl)-1-methyl-1H-pyrazol-4-ylcarbamoyl)-2-(2,6-difluorophenyl)thiazol-5-ylcarbamate

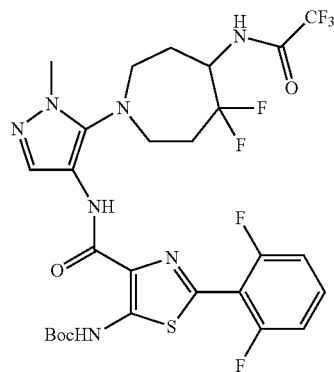 [SMILES: Cn1ncc(NC(=O)c2nc(-c3c(F)cccc3F)sc2NC(=O)OC(C)(C)C)c1N1CCC(NC(=O)C(F)(F)F)C(F)(F)CC1]

A solution of N-(5,5-difluoro-1-(1-methyl-4-nitro-1H-pyrazol-5-yl)azepan-4-yl)-2,2,2-trifluoroacetamide (0.29 g, 0.78 mmol) in MeOH (20 mL) was passed through the H-Cube® (Full $H_2$ Mode, 70° C., flow rate: 1 mL/min, 30 mm 10% Pd/C cartridge). The solvent was removed under reduced pressure to give the crude amine. To a solution of this amine (0.26 g, 0.78 mmol) in DCM (15 mL) was added DIPEA (0.68 mL, 3.9 mmol), PyBOP (0.61 g, 1.17 mmol) and 5-(tert-butoxycarbonylamino)-2-(2,6-difluorophenyl) thiazole-4-carboxylic acid from Example 25 (0.30 g, 0.86 mmol) and the mixture was stirred at room temperature for 18 hr. The mixture was diluted with DCM and washed with water. The organic layer was separated, dried over $Na_2SO_4$ and the solvent removed under reduced pressure. Purification via silica gel column chromatography (0-80% EtOAc/isohexane) gave tert-butyl 4-(5-(4,4-difluoro-5-(2,2,2-trifluoroacetamido)-azepan-1-yl)-1-methyl-1H-pyrazol-4-ylcarbamoyl)-2-(2,6-difluorophenyl)thiazol-5-ylcarbamate as a white solid (0.37 g, 69%). $^1$H NMR (400 MHz, $CDCl_3$) δ 10.28 (s, 1H), 8.71 (s, 1H), 7.82 (s, 1H), 7.42-7.33 (m, 1H), 7.11-7.01 (m, 2H), 6.72 (d, J=9.0 Hz, 1H), 4.73-4.57 (m, 1H), 3.77 (s, 3H), 3.51-3.37 (m, 2H), 3.36-3.25 (m, 2H), 2.49-2.36 (m, 2H), 2.25-2.03 (m, 2H), 1.55 (s, 9H).

Example 56

3,3-Difluoro-1-(1-methyl-4-nitro-1H-pyrazol-5-yl)piperidine

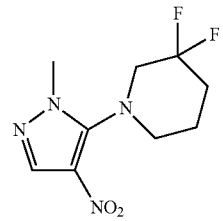 [SMILES: Cn1ncc([N+](=O)[O-])c1N1CCCC(F)(F)C1]

A mixture of 5-chloro-1-methyl-4-nitro-1H-pyrazole from Example 1 (0.1 g, 4.5 mmol), 3,3-difluoropiperidine hydrochloride (0.14 g, 0.93 mmol) and DIPEA (0.5 mL, 2.8 mmol) in EtOH (3 mL) was heated at 130° C. in a microwave for 1 hr. Additional DIPEA (0.5 mL, 2.8 mmol) and 3,3-difluoropiperidine hydrochloride (0.29 g, 1.8 mmol) were added and the mixture was heated at 130° C. in a microwave for 2 hr. The solvent was removed under reduced pressure and the crude product was purified via silica gel column chromatography (0-60% EtOAc/isohexane) to yield 3,3-difluoro-1-(1-methyl-4-nitro-1H-pyrazol-5-yl)piperidine as a yellow oil (127 mg, 83%). $^1$H NMR (400 MHz, CDCl$_3$) δ 8.04 (s, 1H), 3.80 (s, 3H), 3.41-3.29 (m, 2H), 3.26-3.04 (m, 2H), 2.17-2.03 (m, 2H), 1.97-1.88 (m, 2H).

Example 57 tert-Butyl 2-(2,6-difluorophenyl)-4-(5-(3,3-difluoropiperidin-1-yl)-1-methyl-1H-pyrazol-4-ylcarbamoyl)thiazol-5-ylcarbamate

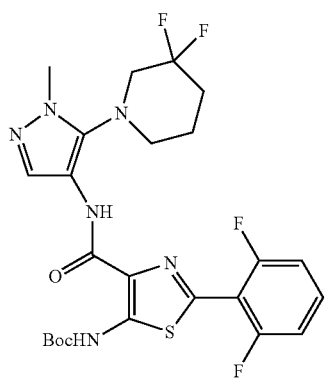 [SMILES: Cn1ncc(NC(=O)c2nc(-c3c(F)cccc3F)sc2NC(=O)OC(C)(C)C)c1N1CCCC(F)(F)C1]

Following the procedure for Example 55, starting with 3,3-difluoro-1-(1-methyl-4-nitro-1H-pyrazol-5-yl)piperidine and 5-(tert-butoxycarbonylamino)-2-(2,6-difluorophenyl)thiazole-4-carboxylic acid from Example 25, gave tert-butyl 2-(2,6-difluorophenyl)-4-(5-(3,3-difluoropiperidin-1-yl)-1-methyl-1H-pyrazol-4-ylcarbamoyl)thiazol-5-ylcarbamate as a cream solid (57 mg, 20%). $^1$H NMR (400 MHz, CDCl$_3$) δ 10.33 (s, 1H), 8.67 (s, 1H), 7.71 (s, 1H), 7.41-7.32 (m, 1H), 7.11-7.01 (m, 2H), 3.76 (s, 3H), 3.32 (t, J=11.0 Hz, 2H), 3.19-3.13 (m, 2H), 2.10-1.97 (m, 2H), 1.94-1.85 (m, 2H), 1.53 (s, 9H).

Example 58 tert-Butyl 3-(methyl(1-methyl-4-nitro-1H-pyrazol-5-yl)amino)propylcarbamate

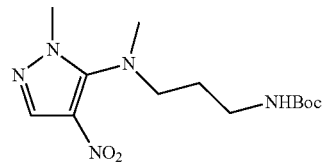 [SMILES: CN(CCCNC(=O)OC(C)(C)C)c1c([N+](=O)[O-])cnn1C]

A mixture of 5-chloro-1-methyl-4-nitro-1H-pyrazole from Example 1 (0.81 g, 5 mmol), tert-butyl 3-aminopropylcarbamate (0.85 g, 4.88 mmol) and DIPEA (1.8 mL, 10.5 mmol) in EtOH (5 mL) was heated at 130° C. in the microwave for 90 min. On cooling the reaction mixture was concentrated under reduced pressure and the residue purified via silica gel column chromatography (0-100% EtOAc/isohexane) to afford tert-butyl 3-(1-methyl-4-nitro-1H-pyrazol-5-ylamino)propylcarbamate as a yellow gum (1.27 g, 85%). A mixture of this gum (0.3 g, 1 mmol), K$_2$CO$_3$ (0.41 g, 3 mmol) and methyl iodide (0.1 mL, 1.58 mmol) in DMF (5 mL) was stirred at 60° C. for 18 hr. More methyl iodide (0.1 mL, 1.58 mmol) was added and stirring at 60° C. was continued for 24 hr. The reaction mixture was cooled and concentrated under reduced pressure. The residue was triturated in DCM (100 mL), filtered and the filtrate concentrated under reduced pressure. Purification via silica gel column chromatography (0-100% EtOAc/isohexane) gave tert-butyl 3-(methyl(1-methyl-4-nitro-1H-pyrazol-5-yl)amino)propylcarbamate as a pale yellow gum (0.122 g, 38%). $^1$H-NMR (400 MHz, CDCl$_3$) δ 8.03 (s, 1H), 4.60 (s, 1H), 3.77 (s, 3H), 3.20-3.14 (m, 4H), 2.86 (s, 3H), 1.72-1.61 (m, 2H), 1.42 (s, 9H).

Example 59 tert-Butyl 2-(2,6-difluorophenyl)-4-(5-(tert-butyl-(3-methylamino)propylcarbamoyl-3-yl)-1-methyl-1H-pyrazol-4-ylcarbamoyl)thiazol-5-ylcarbamate

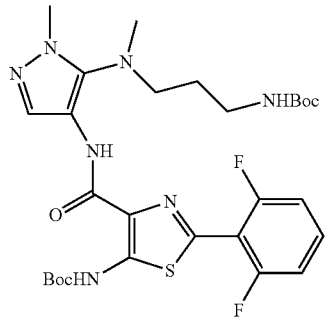 [SMILES: CN(CCCNC(=O)OC(C)(C)C)c1c(NC(=O)c2nc(-c3c(F)cccc3F)sc2NC(=O)OC(C)(C)C)cnn1C]

A solution of tert-butyl 3-(methyl(1-methyl-4-nitro-1H-pyrazol-5-yl)amino)propylcarbamate (122 mg, 0.39 mmol) in MeOH (15 mL) was passed through the H-Cube® (Full H$_2$ Mode, 50° C., flow rate: 1 mL/min, 30 mm 10% Pd/C cartridge). The solvent was removed under reduced pressure to afford a red oil (0.12 g). To a solution of this oil in DCM (10 mL) was added 5-(tert-butoxycarbonylamino)-2-(2,6-difluorophenyl)thiazole-4-carboxylic acid from Example 25 (166 mg, 0.47 mmol), PyBOP (0.33 g, 0.64 mmol) and DIPEA (0.5 mL, 2.86 mmol) and the mixture was stirred at room temperature for 66 hr. Water (20 ml) was added and stirring continued for 30 min. The layers were separated and the aqueous layer extracted with DCM. The combined organic layers were passed through a phase separation cartridge and the solvent removed under reduced pressure. Purification via silica gel column chromatography (0-100% EtOAc/isohexane) gave tert-butyl 2-(2,6-difluorophenyl)-4-(5-(tert-butyl-(3-methylamino)propylcarbamoyl-3-yl)-1-methyl-1H-pyrazol-4-yl-carbamoyl)thiazol-5-ylcarbamate as a white solid (207 mg, 90%). $^1$H-NMR (400 MHz, CDCl$_3$) δ 10.37 (s, 1H), 8.74 (s, 1H), 7.87 (s, 1H), 7.42-7.32 (m, 1H), 7.10-7.02 (m, 2H), 4.65 (s, 1H), 3.75 (s, 3H), 3.20-3.14 (m, 2H), 3.10 (t, J=7 Hz, 2H), 2.85 (s, 3H), 1.76-1.66 (m, 2H), 1.55 (s, 9H), 1.39 (s, 9H).

Example 60

5-Chloro-1-ethyl-4-nitro-1H-pyrazole

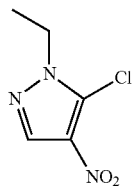

Following the procedure for Example 1 starting with 1-ethyl-4-nitropyrazole gave 5-chloro-1-ethyl-4-nitro-1H-pyrazole as a colorless solid (1.3 g, 74%). $^1$H-NMR (400 MHz, CDCl$_3$) δ 8.16 (s, 1H), 4.26 (q, J=7 Hz, 2H), 1.50 (t, J=7 Hz, 3H).

Example 61

5-Chloro-1-cyclopropylmethyl-4-nitro-1H-pyrazole

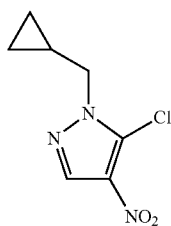

Following the procedure for Example 1 starting with 1-cyclopropylmethyl-4-nitropyrazole gave 5-chloro-1-cyclopropylmethyl-4-nitro-1H-pyrazole as a colorless oil (1.16 g, 56%). $^1$H-NMR (400 MHz, CDCl$_3$) δ 8.17 (s, 1H), 4.07 (d, J=7 Hz, 2H), 1.39-1.28 (m, 1H), 0.66-0.59 (m, 2H), 0.50-0.40 (m, 2H).

Example 62

5-Chloro-1-cyclopropyl-4-nitro-1H-pyrazole

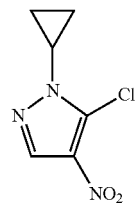

Following the procedure for Example 1 starting with 1-cyclopropyl-4-nitropyrazole gave 5-chloro-1-cyclopropyl-4-nitro-1H-pyrazole as a colorless solid (0.23 g, 63%). $^1$H-NMR (400 MHz, CDCl$_3$) δ 8.09 (s, 1H), 3.62-3.54 (m, 1H), 1.38-1.28 (m, 2H), 1.25-1.13 (m, 2H).

Example 63

(R)—N-(Azepan-4-yl)-2,2,2-trifluoroacetamide

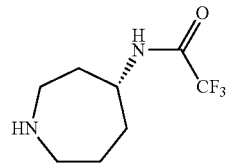

A solution of (R)-tert-butyl 4-(benzyloxycarbonylamino)azepane-1-carboxylate (3.25 g, 0.33 mmol) in MeOH (100 mL) was stirred at room temperature under an atmospheric pressure of hydrogen gas in the presence of 10% Pd/C (1 g) for 1.5 hr. The mixture was filtered through celite and the solvent removed under reduced pressure to afford (R)-tert-butyl 4-(2,2,2-trifluoroacetamido)azepane-1-carboxylate as a pale grey oil (2 g, 100%). To a stirred solution of this oil (1.8 g, 8.4 mmol) and DIPEA (3 mL, 17.18 mmol) in DCM (100 mL) at room temperature was added trifluoroacetic anhydride (1.31 mL, 9.27 mmol) dropwise over 5 min and the resultant pale yellow solution was stirred for 18 hr. Saturated aqueous sodium hydrogen carbonate (150 mL) was added and stirring continued for 1 hr. The layers were separated, the organics passed through a phase separation cartridge and the solvent removed under reduced pressure to give (R)-tert-butyl 4-(2,2,2-trifluoroacetamido)azepane-1-carboxylate as a pale yellow oil (2.61 g, 100%). To a solution of this oil (2.6 g, 8.38 mmol) in DCM (50 mL) at room temperature was added trifluoroacetic acid (25 mL) and the mixture stirred for 2 hr. The solvent was removed under reduced pressure and the residue dissolved in DCM and passed through an SCX column washing with DCM and MeOH and eluting with 1 N ammonia in MeOH. The solvent was removed under reduced pressure to afford (R)—N-(azepan-4-yl)-2,2,2-trifluoroacetamide as a pale yellow oil (1.3 g, 74%). $^1$H-NMR (400 MHz, CDCl$_3$) δ 7.83 (s, 1H), 4.44-4.37 (m, 1H), 3.13-3.03

(m, 2H), 2.88 (dt, J=13.2, 6.6 Hz, 1H), 2.65-2.55 (m, 1H), 2.03-1.79 (m, 3H), 1.75 (s, 1H), 1.69-1.58 (m, 3H).

Example 64

(S)—N-(Azepan-4-yl)-2,2,2-trifluoroacetamide

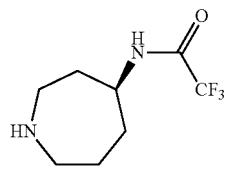

Following the procedure for Example 510 starting with (S)-tert-butyl 4-(benzyloxycarbonylamino)azepane-1-carboxylate gave (S)—N-(azepan-4-yl)-2,2,2-trifluoroacetamide as a pale yellow oil (1.35 g, 75% over three steps). $^1$H-NMR (400 MHz, CDCl$_3$) δ 7.86 (s, 1H), 4.44-4.37 (m, 1H), 3.15-3.03 (m, 2H), 2.92-2.81 (m, 1H), 2.67-2.55 (m, 1H), 2.02-1.81 (m, 4H), 1.76-1.56 (m, 3H).

Example 64a tert-Butyl 3-fluoro-5-(4-methoxybenzyloxy)azepane-1-carboxylate

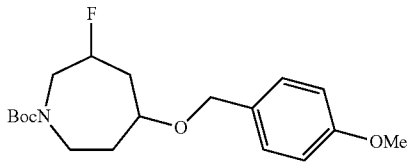 [SMILES: COc1ccc(COC2CCN(C(=O)OC(C)(C)C)CC(F)C2)cc1]

A solution of (Z)-tert-Butyl 3-oxo-2,3,6,7-tetrahydro-1H-azepine-1-carboxylate (2 g, 9.48 mmol), (4-methoxyphenyl)methanol (6.55 g, 47.4 mmol) and DBU (0.14 mL, 0.95 mmol) in acetonitrile (10 mL) was heated at 60° C. for 23 hr. The solvents were removed under reduced pressure. Purification by silica gel column chromatography (0-40% EtOAc/isohexane) gave tert-butyl 5-(4-methoxybenzyloxy)-3-oxoazepane-1-carboxylate as a clear oil (1.99 g). To a solution of this oil (1.33 g, 3.8 mmol) in water/THF (20 mL/20 mL) was added NaBH$_4$ and the mixture was stirred for 1.5 h. The THF was removed under reduced pressure and the aqueous phase was extracted with EtOAc (3×20 mL). The combined organic layers were concentrated under reduced pressure. Purification via silica gel column chromatography (0-60% EtOAc/isohexane) gave tert-butyl 3-hydroxy-5-(4-methoxybenzyloxy)azepane-1-carboxylate (1.30 g) as a clear oil. This oil (1.15 g, 3.28 mmol) was dissolved in DCM (20 mL) and deoxo-Fluor® was added (50% in THF, 5.93 mL, 16.4 mmol). The mixture was stirred at room temperature for 18 hr, diluted with DCM (30 mL), cooled in an ice/water bath and quenched by dropwise addition of saturated aqueous NaHCO$_3$ solution (50 mL). The resulting mixture was stirred for 10 min. The organic layer was separated, dried over Na$_2$SO$_4$ and the solvent removed under reduced pressure. Purification via silica gel column chromatography (0-30% EtOAc/isohexane) gave tert-butyl 3-fluoro-5-(4-methoxybenzyloxy)azepane-1-carboxylate (746 mg, 39% over three steps) as a clear oil. $^1$H NMR (400 MHz, CDCl$_3$) δ 7.36-7.30 (m, 2H), 6.95 (d, J=8.2 Hz, 2H), 5.19-4.64 (m, 1H), 4.65-4.43 (m, 2H), 4.06-3.20 (m, 8H), 2.35-1.67 (m, 4H), 1.55-1.50 (m, 9H).

Example 64b

3-Fluoro-5-(4-methoxybenzyloxy)-1-(1-methyl-4-nitro-1H-pyrazol-5-yl)azepane

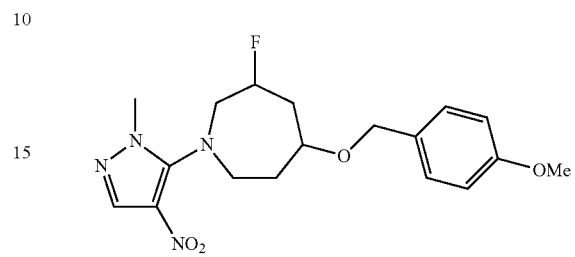

To a solution of tert-butyl 3-fluoro-5-(4-methoxybenzyloxy)azepane-1-carboxylate (740 mg, 0.21 mmol) in MeOH (5 mL) was added HCl (4 M in 1,4-dioxane, 5.3 mL, 21 mmol) and the solution was stirred at room temperature for 16 hr. The solvents were removed under reduced pressure and the residue was dissolved in MeOH and loaded onto an SCX column. The column was washed with MeOH and eluted with 7 N ammonia in MeOH. The solvents were removed under reduced pressure to afford a yellow oil. To a solution of this oil in dry DMSO (15 mL) was added potassium fluoride (0.32 g, 8.4 mmol) and 5-chloro-1-methyl-4-nitro-1H-pyrazole (372 mg, 2.31 mmol) and the mixture was heated at 65° C. for 16 hr. After cooling to room temperature, the mixture was diluted with water (300 mL) and extracted with EtOAc (2×50 mL). The combined organic layers were washed with water (3×50 mL) and the solvent was removed under reduced pressure. Purification via silica gel column chromatography (20-100% EtOAc/isohexane) gave 3-fluoro-5-(4-methoxybenzyloxy)-1-(1-methyl-4-nitro-1H-pyrazol-5-yl)azepane as a yellow oil (300 g, 55% over two steps). $^1$H NMR (400 MHz, CDCl$_3$) δ 7.33-7.23 (m, 3H), 6.89-6.86 (m, 2H), 4.82-4.66 (m, 2H), 4.49-3.93 (m, 1H), 3.81 (s, 3H), 3.30-2.99 (m, 4H), 2.95-2.74 (m, 4H), 2.35-2.03 (m, 2H), 1.98-1.83 (m, 2H).

Example 65

N-(1-(1-Ethyl-4-nitro-1H-pyrazol-5-yl)azepan-4-yl)-2,2,2-trifluoroacetamide

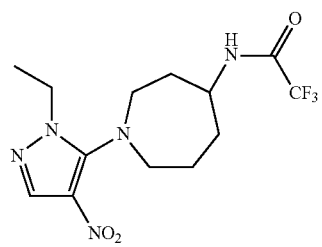 [SMILES: CCn1ncc([N+](=O)[O-])c1N1CCCC(NC(=O)C(F)(F)F)CC1]

Following the procedure for Example 503 starting with 5-chloro-1-ethyl-4-nitro-1H-pyrazole and 2,2,2-trifluoro-N-(hexahydro-1H-azepin-4-yl)-acetamide gave N-(1-(1-ethyl-4-nitro-1H-pyrazol-5-yl)azepan-4-yl)-2,2,2-trifluoroacetamide as a pale yellow gum (0.136 g, 55%). $^1$H-NMR (400 MHz, CDCl$_3$) δ 8.07 (s, 1H), 6.39-6.37 (m, 1H), 4.22-4.19 (m, 1H), 4.12 (q, J=7 Hz, 2H), 3.42-3.35 (m, 1H), 3.27-3.18 (m, 3H), 2.25-2.05 (m, 2H), 2.00-1.75 (m, 4H), 1.47 (t, J=7 Hz, 3H).

Example 66

(R)—N-(1-(1-Ethyl-4-nitro-1H-pyrazol-5-yl)azepan-4-yl)-2,2,2-trifluoroacetamide

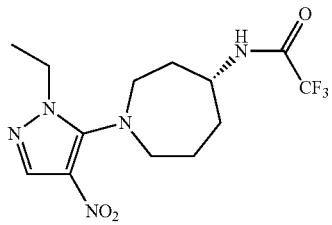 [SMILES: CCn1ncc([N+](=O)[O-])c1N1CCC[C@@H](NC(=O)C(F)(F)F)CC1]

Following the procedure for Example 503 starting with 5-chloro-1-ethyl-4-nitro-1H-pyrazole and (R)-2,2,2-trifluoro-N-(hexahydro-1H-azepin-4-yl)-acetamide (0.1 g, 0.476 mmol) gave (R)—N-(1-(1-ethyl-4-nitro-1H-pyrazol-5-yl)azepan-4-yl)-2,2,2-trifluoroacetamide as a pale yellow gum (0.1 g, 60%). $^1$H-NMR (400 MHz, CDCl$_3$) δ 8.07 (s, 1H), 6.39-6.36 (m, 1H), 4.23-4.19 (m, 1H), 4.12 (q, J=7 Hz, 2H), 3.42-3.35 (m, 1H), 3.27-3.18 (m, 3H), 2.25-2.05 (m, 2H), 2.00-1.75 (m, 4H), 1.47 (t, J=7 Hz, 3H).

Example 67

(S)—N-(1-(1-Ethyl-4-nitro-1H-pyrazol-5-yl)azepan-4-yl)-2,2,2-trifluoroacetamide

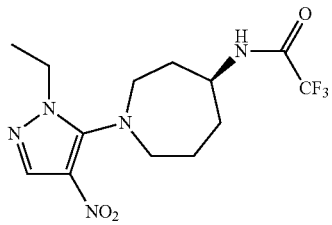 [SMILES: CCn1ncc([N+](=O)[O-])c1N1CCC[C@H](NC(=O)C(F)(F)F)CC1]

Following the procedure for Example 503 starting with 5-chloro-1-ethyl-4-nitro-1H-pyrazole and (S)-2,2,2-trifluoro-N-(hexahydro-1H-azepin-4-yl)-acetamide gave (S)—N-(1-(1-ethyl-4-nitro-1H-pyrazol-5-yl)azepan-4-yl)-2,2,2-trifluoroacetamide as a pale yellow gum (0.12 g, 44%). $^1$H-NMR (400 MHz, CDCl$_3$) δ 8.07 (s, 1H), 6.42-6.40 (m, 1H), 4.22-4.18 (m, 1H), 4.12 (q, J=7 Hz, 2H), 3.42-3.35 (m, 1H), 3.27-3.18 (m, 3H), 2.25-2.05 (m, 2H), 2.00-1.75 (m, 4H), 1.47 (t, J=7 Hz, 3H).

Example 68

(R)—N-(1-(1-Cyclopropylmethyl-4-nitro-1H-pyrazol-5-yl)azepan-4-yl)-2,2,2-trifluoroacetamide

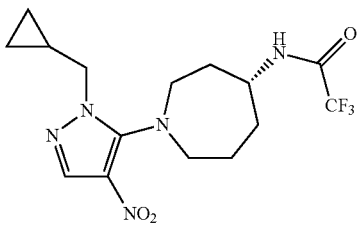 [SMILES: O=C(N[C@@H]1CCCN(c2c([N+](=O)[O-])cnn2CC2CC2)CC1)C(F)(F)F]

Following the procedure for Example 503 starting with 5-chloro-1-cyclopropylmethyl-4-nitro-1H-pyrazole and (R)-2,2,2-trifluoro-N-(hexahydro-1H-azepin-4-yl)-acetamide gave (R)—N-(1-(1-cyclopropylmethyl-4-nitro-1H-pyrazol-5-yl)azepan-4-yl)-2,2,2-trifluoroacetamide as a pale yellow gum (0.98 g, 55%). $^1$H-NMR (400 MHz, CDCl$_3$) δ 8.08 (s, 1H), 6.42-6.39 (m, 1H), 4.22-4.14 (m, 1H), 4.00-3.85 (m, 2H), 3.44-3.32 (m, 1H), 3.30-3.15 (m, 3H), 2.25-2.05 (m, 2H), 2.00-1.75 (m, 4H), 1.30-1.20 (m, 1H), 0.70-0.62 (m, 2H), 0.50-0.35 (m, 2H).

Example 69

(R)—N-(1-(1-Cyclopropyl-4-nitro-1H-pyrazol-5-yl)azepan-4-yl)-2,2,2-trifluoroacetamide

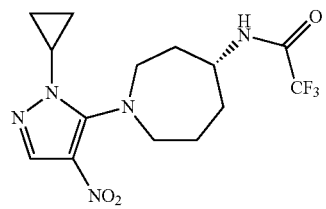 [SMILES: O=C(N[C@@H]1CCCN(c2c([N+](=O)[O-])cnn2C2CC2)CC1)C(F)(F)F]

Following the procedure for Example 503 starting with 5-chloro-1-cyclopropyl-4-nitro-1H-pyrazole and (R)-2,2,2-trifluoro-N-(hexahydro-1H-azepin-4-yl)-acetamide gave (R)—N-(1-(1-cyclopropyl-4-nitro-1H-pyrazol-5-yl)azepan-4-yl)-2,2,2-trifluoroacetamide as a pale yellow gum (0.105 g, 61%). $^1$H-NMR (400 MHz, CDCl$_3$) δ 7.96 (s, 1H), 6.55-6.38 (m, 1H), 4.30-4.15 (m, 1H), 3.65-3.53 (m, 1H), 3.55-3.25 (m, 4H), 2.25-2.05 (m, 6H), 1.35-1.05 (m, 4H).

Example 70 tert-Butyl 2-(2,6-difluorophenyl)-4-(1-ethyl-5-(4-(2,2,2-trifluoroacetamido)azepan-1-yl)-1H-pyrazol-4-ylcarbamoyl)thiazol-5-ylcarbamate

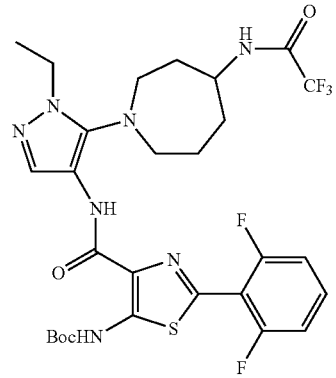 [SMILES: CCn1ncc(NC(=O)c2nc(-c3c(F)cccc3F)sc2NC(=O)OC(C)(C)C)c1N1CCCC(NC(=O)C(F)(F)F)CC1]

A solution of N-(1-(1-ethyl-4-nitro-1H-pyrazol-5-yl)azepan-4-yl)-2,2,2-trifluoroacetamide (136 mg, 0.39 mmol) in MeOH (15 mL) was passed through the H-Cube® (70 bar, 25° C., flow rate: 1 mL/min, 30 mm 10% Pd/C cartridge). The solvent was removed under reduced pressure to afford the crude amine as a purple gum (121 mg). To a solution of this amine in DCM (10 mL) was added 5-(tert-butoxycarbonylamino)-2-(2,6-difluorophenyl)thiazole-4-carboxylic acid from Example 25 (149 mg, 0.42 mmol), HATU (0.43 g, 1.14 mmol) and DIPEA (1 mL, 5.72 mmol). The mixture was stirred at room temperature for 18 hr. Water (30 ml) was added and stirring continued for 15 min. The layers were separated and the aqueous extracted with DCM. The combined organics were passed through a phase separation cartridge and the solvent removed under reduced pressure. Purification of the residue via silica gel column chromatography (0-100% EtOAc/isohexane) gave tert-butyl 2-(2,6-difluorophenyl)-4-(1-ethyl-5-(4-(2,2,2-trifluoroacetamido)azepan-1-yl)-1H-pyrazol-4-ylcarbamoyl)thiazol-5-ylcarbamate as a colorless solid (170 mg, 68%). $^1$H-NMR (400 MHz, CDCl$_3$) δ 10.39 (s, 1H), 8.75 (s, 1H), 7.95 (s, 1H), 7.42-7.33 (m, 1H), 7.12-7.02 (m, 2H), 6.35 (d, J=8 Hz, 1H), 4.25-4.13 (m, 1H), 4.05 (q, J=7 Hz, 2H), 3.45-3.25 (m, 2H), 3.23-3.10 (m, 2H), 2.25-1.65 (m, 6H), 1.56 (s, 9H), 1.45 (t, J=7 Hz, 3H).

Example 71

(R)-tert-Butyl 2-(2,6-difluorophenyl)-4-(1-ethyl-5-(4-(2,2,2-trifluoroacetamido)azepan-1-yl)-1H-pyrazol-4-ylcarbamoyl)thiazol-5-ylcarbamate

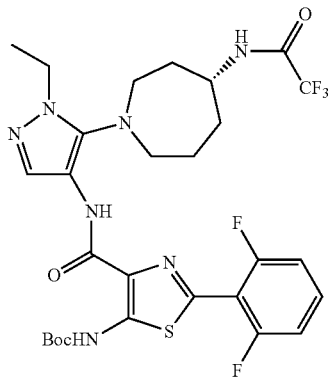 [SMILES: CCn1ncc(NC(=O)c2nc(-c3c(F)cccc3F)sc2NC(=O)OC(C)(C)C)c1N1CCC[C@@H](NC(=O)C(F)(F)F)CC1]

Following the procedure for Example 517 starting with (R)—N-(1-(1-ethyl-4-nitro-1H-pyrazol-5-yl)azepan-4-yl)-2,2,2-trifluoroacetamide and 5-(tert-butoxycarbonylamino)-2-(2,6-difluorophenyl)thiazole-4-carboxylic acid from Example 25 gave (R)-tert-butyl 2-(2,6-difluorophenyl)-4-(1-ethyl-5-(4-(2,2,2-trifluoroacetamido)azepan-1-yl)-1H-pyrazol-4-ylcarbamoyl)thiazol-5-ylcarbamate as a cream solid (0.148 g, 76%). $^1$H-NMR (400 MHz, CDCl$_3$) δ 10.40 (s, 1H), 8.76 (s, 1H), 7.95 (s, 1H), 7.43-7.34 (m, 1H), 7.12-7.02 (m, 2H), 6.37 (d, J=8 Hz, 1H), 4.23-4.16 (m, 1H), 4.05 (q, J=7 Hz, 2H), 3.43-3.31 (m, 2H), 3.25-3.15 (m, 2H), 2.22-2.05 (m, 2H), 2.03-1.89 (m, 2H), 1.89-1.72 (m, 2H), 1.57 (m, 12H).

Example 72

(S)-tert-Butyl 2-(2,6-difluorophenyl)-4-(1-ethyl-5-(4-(2,2,2-trifluoroacetamido)azepan-1-yl)-1H-pyrazol-4-ylcarbamoyl)thiazol-5-ylcarbamate

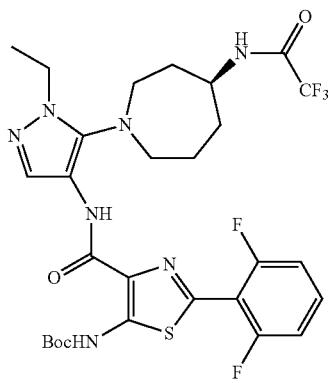 [SMILES: CCn1ncc(NC(=O)c2nc(-c3c(F)cccc3F)sc2NC(=O)OC(C)(C)C)c1N1CCC[C@H](NC(=O)C(F)(F)F)CC1]

Following the procedure for Example 517 starting with (S)—N-(1-(1-ethyl-4-nitro-1H-pyrazol-5-yl)azepan-4-yl)-2,2,2-trifluoroacetamide and 5-(tert-butoxycarbonylamino)-2-(2,6-difluorophenyl)thiazole-4-carboxylic acid from Example 25 gave (S)-tert-butyl 2-(2,6-difluorophenyl)-4-(1-ethyl-5-(4-(2,2,2-trifluoroacetamido)azepan-1-yl)-1H-pyrazol-4-ylcarbamoyl)thiazol-5-ylcarbamate as a cream solid (151 mg, 66%). $^1$H-NMR (400 MHz, CDCl$_3$) δ 10.40 (s, 1H), 8.75 (s, 1H), 7.95 (s, 1H), 7.45-7.34 (m, 1H), 7.12-7.02 (m, 2H), 6.37 (d, J=8 Hz, 1H), 4.23-4.16 (m, 1H), 4.05 (q, J=7 Hz, 2H), 3.43-3.31 (m, 2H), 3.25-3.15 (m, 2H), 2.22-2.05 (m, 2H), 2.03-1.89 (m, 2H), 1.89-1.72 (m, 2H), 1.55 (s, 9H), 1.46 (t, J=7 Hz, 3H).

Example 73

(R)-tert-Butyl 2-(2,6-difluorophenyl)-4-(1-cyclopropylmethyl-5-(4-(2,2,2-trifluoroacetamido)azepan-1-yl)-1H-pyrazol-4-ylcarbamoyl)thiazol-5-ylcarbamate

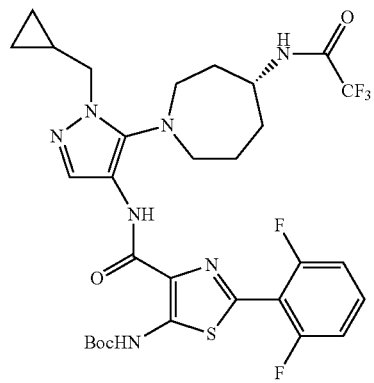 [SMILES: CC(C)(C)OC(=O)Nc1sc(-c2c(F)cccc2F)nc1C(=O)Nc1cnn(CC2CC2)c1N1CCC[C@@H](NC(=O)C(F)(F)F)CC1]

(R)—N-(1-(1-cyclopropylmethyl-4-nitro-1H-pyrazol-5-yl)azepan-4-yl)-2,2,2-trifluoroacetamide and 5-(tert-butoxycarbonylamino)-2-(2,6-difluorophenyl)thiazole-4-carboxylic acid were reacted to give (R)-tert-butyl 2-(2,6-difluorophenyl)-4-(1-cyclopropylmethyl-5-(4-(2,2,2-trifluoroacetamido)azepan-1-yl)-1H-pyrazol-4-ylcarbamoyl)thiazol-5-ylcarbamate as a cream solid (136 mg, 77%). $^1$H-NMR (400 MHz, CDCl$_3$) δ 10.39 (s, 1H), 8.75 (s, 1H), 7.95 (s, 1H), 7.41-7.36 (m, 1H), 7.10-7.02 (m, 2H), 6.37 (d, J=8 Hz, 1H), 4.25-4.10 (m, 1H), 3.90-3.83 (m, 2H), 3.43-3.31 (m, 2H), 3.30-3.15 (m, 2H), 2.25-2.05 (m, 2H), 2.03-1.70 (m, 4H), 1.57 (s, 9H) 1.35-1.20 (m, 1H), 0.64-0.59 (m, 2H), 0.43-0.38 (m, 2H).

Example 74

(R)-tert-Butyl 2-(2,6-difluorophenyl)-4-(1-cyclopropyl-5-(4-(2,2,2-trifluoroacetamido)azepan-1-yl)-1H-pyrazol-4-ylcarbamoyl)thiazol-5-ylcarbamate

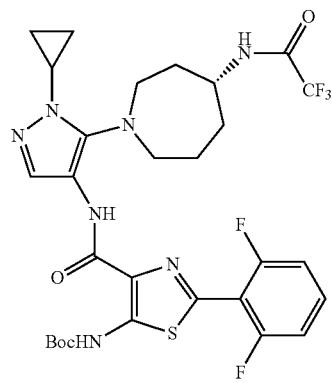 [SMILES: CC(C)(C)OC(=O)Nc1sc(-c2c(F)cccc2F)nc1C(=O)Nc1cnn(C2CC2)c1N1CCC[C@@H](NC(=O)C(F)(F)F)CC1]

(R)—N-(1-(1-cyclopropyl-4-nitro-1H-pyrazol-5-yl)azepan-4-yl)-2,2,2-trifluoroacetamide and 5-(tert-butoxycarbonylamino)-2-(2,6-difluorophenyl)thiazole-4-carboxylic acid from Example 25 were reacted to give (R)-tert-butyl 2-(2,6-difluorophenyl)-4-(1-cyclopropyl-5-(4-(2,2,2-trifluoroacetamido)azepan-1-yl)-1H-pyrazol-4-ylcarbamoyl)thiazol-5-ylcarbamate as a cream solid (142 mg, 73%). $^1$H-NMR (400 MHz, CDCl$_3$) δ 10.40 (s, 1H), 8.76 (s, 1H), 7.87 (s, 1H), 7.41-7.34 (m, 1H), 7.10-7.00 (m, 2H), 6.39 (d, J=8 Hz, 1H), 4.25-4.15 (m, 1H), 3.45-3.36 (m, 3H), 3.35-3.15 (m, 2H), 2.25-2.12 (m, 1H), 2.10-1.70 (m, 5H), 1.55 (s, 9H), 1.35-1.15 (m, 2H), 1.10-1.00 (m, 2H).

Example 75

(R)-tert-Butyl 2-(2-fluorophenyl)-4-(1-ethyl-5-(4-(2,2,2-trifluoroacetamido)azepan-1-yl)-1H-pyrazol-4-ylcarbamoyl)thiazol-5-ylcarbamate

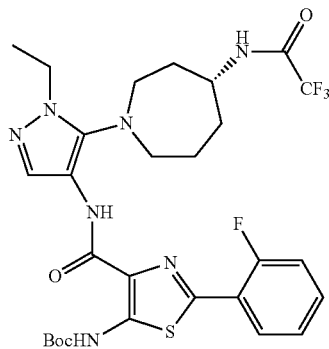 [SMILES: CCn1ncc(NC(=O)c2nc(-c3ccccc3F)sc2NC(=O)OC(C)(C)C)c1N1CCC[C@@H](NC(=O)C(F)(F)F)CC1]

Following the procedure for Example 506 starting with (R)—N-(1-(1-ethyl-4-nitro-1H-pyrazol-5-yl)azepan-4-yl)-2,2,2-trifluoroacetamide and 5-(tert-butoxycarbonylamino)-2-(2-fluorophenyl)thiazole-4-carboxylic acid gave (R)-tert-butyl 2-(2-fluorophenyl)-4-(1-ethyl-5-(4-(2,2,2-trifluoroacetamido)azepan-1-yl)-1H-pyrazol-4-ylcarbamoyl)thiazol-5-ylcarbamate as a cream solid (330 mg, 72%). $^1$H-NMR (400 MHz, CDCl$_3$) δ 10.37 (s, 1H), 8.66 (s, 1H), 8.15-8.05 (m, 1H), 7.45-7.35 (m, 1H), 7.30-7.15 (m, 3H), 6.31 (d, J=8 Hz, 1H), 4.25-4.15 (m, 1H), 4.07 (q, J=7 Hz, 2H), 3.43-3.31 (m, 2H), 3.25-3.15 (m, 2H), 2.25-2.10 (m, 2H), 2.10-1.70 (m, 4H), 1.57 (s, 9H) 1.47 (t, J=7 Hz, 3H).

Example 76

(R)-tert-Butyl 2-(2-fluorophenyl)-4-(1-cyclopropylmethyl-5-(4-(2,2,2-trifluoroacetamido)azepan-1-yl)-1H-pyrazol-4-ylcarbamoyl)thiazol-5-ylcarbamate

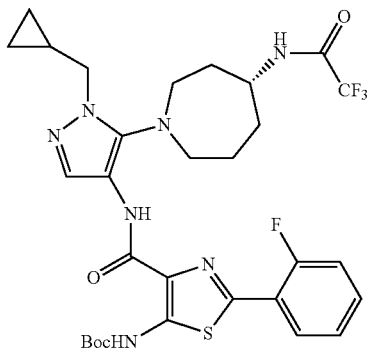 [SMILES: CC(C)(C)OC(=O)Nc1sc(-c2ccccc2F)nc1C(=O)Nc1cnn(CC2CC2)c1N1CCC[C@@H](NC(=O)C(F)(F)F)CC1]

Following the procedure for Example 506 starting with (R)—N-(1-(1-cyclopropylmethyl-4-nitro-1H-pyrazol-5-yl)azepan-4-yl)-2,2,2-trifluoroacetamide 5-(tert-butoxycarbonylamino)-2-(2-fluorophenyl)thiazole-4-carboxylic acid gave (R)-tert-butyl 2-(2-fluorophenyl)-4-(1-cyclopropylmethyl-5-(4-(2,2,2-trifluoroacetamido)azepan-1-yl)-1H-pyrazol-4-ylcarbamoyl)thiazol-5-ylcarbamate as a cream solid (350 mg, 70%). $^1$H-NMR (400 MHz, CDCl$_3$) δ 10.36 (s, 1H), 8.66 (s, 1H), 8.15-8.05 (m, 1H), 7.45-7.35 (m, 1H), 7.28-7.15 (m, 3H), 6.31 (d, J=7.5 Hz, 1H), 4.25-4.15 (m, 1H), 3.95-3.85 (m, 2H), 3.43-3.30 (m, 2H), 3.28-3.15 (m, 2H), 2.25-2.08 (m, 2H), 2.08-1.70 (m, 4H), 1.55 (s, 9H), 1.35-1.20 (m, 1H), 0.70-0.60 (m, 2H), 0.50-0.35 (m, 2H).

Example 77

(R)-tert-Butyl 2-(2-fluorophenyl)-4-(1-cyclopropyl-5-(4-(2,2,2-trifluoroacetamido)azepan-1-yl)-1H-pyrazol-4-ylcarbamoyl)thiazol-5-ylcarbamate

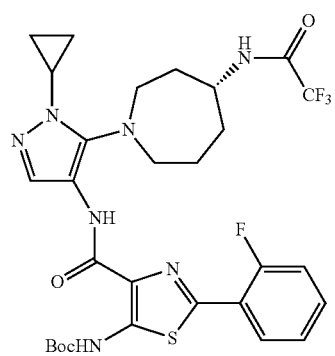 [SMILES: CC(C)(C)OC(=O)Nc1sc(-c2ccccc2F)nc1C(=O)Nc1cnn(C2CC2)c1N1CCC[C@@H](NC(=O)C(F)(F)F)CC1]

Following the procedure for Example 506 starting with (R)—N-(1-(1-cyclopropyl-4-nitro-1H-pyrazol-5-yl)azepan-4-yl)-2,2,2-trifluoroacetamide and 5-(tert-butoxycarbonylamino)-2-(2-fluorophenyl)thiazole-4-carboxylic acid gave (R)-tert-butyl 2-(2-fluorophenyl)-4-(1-cyclopropyl-5-(4-(2,2,2-trifluoroacetamido)azepan-1-yl)-1H-pyrazol-4-ylcarbamoyl)thiazol-5-ylcarbamate as a cream solid (370 mg, 76%). $^1$H-NMR (400 MHz, CDCl$_3$) δ 10.36 (s, 1H), 8.69 (s, 1H), 8.12-8.00 (m, 1H), 7.45-7.30 (m, 1H), 7.28-7.15 (m, 3H), 6.40-6.27 (m, 1H), 4.30-4.15 (m, 1H), 3.43-3.15 (m, 5H), 2.25-1.75 (m, 6H), 1.55 (s, 9H), 1.35-1.15 (m, 2H), 1.10-0.95 (m, 2H).

Example 78 tert-Butyl (1-(4-amino-1-methyl-1H-pyrazol-5-yl)piperidin-4-yl)methylcarbamate

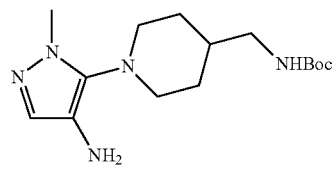 [SMILES: Cn1ncc(N)c1N1CCC(CNC(=O)OC(C)(C)C)CC1]

A solution of 5-chloro-1-methyl-4-nitro-1H-pyrazole from Example 1 (1.9 g, 11.77 mmol), 4-(boc-aminomethyl)piperidine (3.78 g, 17.66 mmol) and DIPEA (6.15 mL, 35.31 mmol) in EtOH (20 mL) was heated in a microwave at 130° C. for 1 hr. The solvent was removed under reduced pressure and the residue re-dissolved in DCM. The organic layer was washed with water, passed through a phase separation cartridge and concentrated under reduced pressure. The residue was purified via silica gel column chromatography (0-100% EtOAc/isohexane) to yield tert-butyl (1-(1-methyl-4-nitro-1H-pyrazol-5-yl)piperidin-4-yl)methylcarbamate as a yellow solid (3.95 g, 98%). To a solution of this solid (3.84 g, 11.30 mmol) in MeOH (125 mL) was added 10% Pd/C (0.42 g, 3.96 mmol) and ammonium formate (2.85 g, 45.2 mmol). The mixture was heated at 80° C. for 2.5 hr. The mixture was concentrated under reduced pressure and the residue was re-dissolved in EtOAc and washed with water. The organic layer was passed through a phase separation cartridge and concentrated under reduced pressure to give tert-butyl (1-(4-amino-1-methyl-1H-pyrazol-5-yl)piperidin-4-yl)methylcarbamate as a brown oil (3.49 g, 99%). $^1$H NMR (400 MHz, CDCl$_3$) δ 7.04 (s, 1H), 4.63 (s, 1H), 3.64 (s, 3H), 3.11-3.07 (m, 6H), 2.67 (s, 2H), 1.77 (d, J=12.8 Hz, 2H), 1.45 (s, 9H), 1.39-1.26 (m, 2H). 1H hidden by water peak.

Example 79 tert-Butyl 4-(5-(4-(butyloxycarbonylaminomethyl)piperidin-1-yl)-1-methyl-1H-pyrazol-4-ylcarbamoyl)-2-bromothiazol-5-ylcarbamate

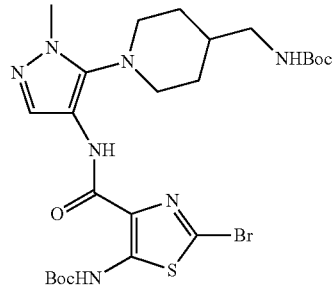 [SMILES: Cn1ncc(NC(=O)c2nc(Br)sc2NC(=O)OC(C)(C)C)c1N1CCC(CNC(=O)OC(C)(C)C)CC1]

A solution of PyBOP (2.84 g, 5.46 mmol) and 2-bromo-5-(tert-butoxycarbonylamino)thiazole-4-carboxylic acid (1.39 g, 4.29 mmol) in DCM (10 mL) was stirred at room temperature for 30 min. A solution of tert-butyl (1-(4-amino-1-methyl-1H-pyrazol-5-yl)piperidin-4-yl)methylcarbamate (1.2 g, 3.90 mmol) and DIPEA (1.1 mL, 6.24 mmol) in DCM (20 mL) was added and the mixture stirred at room temperature for 16 hr. The mixture was diluted with DCM and washed with water. The organic layer was separated, passed through a phase separation cartridge and concentrated under reduced pressure. The residue was purified via silica gel column chromatography (0-100% EtOAc/isohexane) to yield tert-butyl 4-(5-(4-(butyloxycarbonylaminomethyl)piperidin-1-yl)-1-methyl-1H-pyrazol-4-ylcarbamoyl)-2-bromothiazol-5-ylcarbamate as a pink solid (2.32 g, 96%). $^1$H NMR (400 MHz, d$_6$-DMSO) δ 10.62 (s, 1H), 9.64 (s, 1H), 7.23 (s, 1H), 6.86 (t, J=5.8 Hz, 1H), 3.62 (s, 3H), 3.07 (d, J=11.4 Hz, 2H), 2.95 (t, J=11.5 Hz, 2H), 2.87 (t, J=6.3 Hz, 2H), 1.67 (d, J=12.3 Hz, 2H), 1.52 (s, 9H), 1.45 (s, 1H), 1.40 (s, 9H), 1.27-1.16 (m, 2H).

Example 80

5-(tert-Butoxycarbonylamino)-2-(2,6-difluoro-3-methoxyphenyl)thiazole-4-carboxylic acid

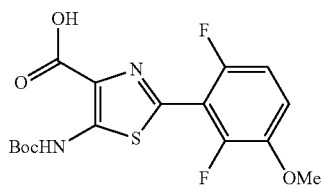 [SMILES: COc1ccc(F)c(-c2nc(C(=O)O)c(NC(=O)OC(C)(C)C)s2)c1F]

Following the procedure for Examples 19-23 starting with 2,6-difluoro-3-methoxybenzoyl chloride gave 5-(tert-butoxycarbonylamino)-2-(2,6-difluoro-3-methoxyphenyl)thiazole-4-carboxylic acid as a pale yellow solid (120 mg, 70%). $^1$H NMR (400 MHz, d$_6$-DMSO) δ 7.32-7.23 (m, 1H), 7.22-7.15 (m, 1H), 3.88 (s, 3H), 1.49 (s, 9H).

Example 81

(R)-Benzyl 1-(4-(5-tert-butoxycarbonyl-amino-2-bromothiazole-4-carboxamido)-1-methyl-1H-pyrazol-5-yl)azepan-4-ylcarbamate

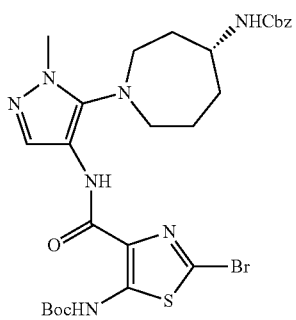 [SMILES: Cn1ncc(NC(=O)c2nc(Br)sc2NC(=O)OC(C)(C)C)c1N1CCC[C@@H](NC(=O)OCc2ccccc2)CC1]

A solution of PyBOP (1.31 g, 2.52 mmol) and 2-bromo-5-(tert-butoxycarbonylamino)thiazole-4-carboxylic acid (0.61 g, 1.89 mmol) in DCM (20 mL) was stirred at room temperature for 30 min. A solution of (R)-benzyl azepan-4-ylcarbamate (0.62 g, 1.80 mmol) and DIPEA (0.5 mL, 2.88 mmol) in DCM (20 mL) was added and the mixture stirred at room temperature for 16 hr. The mixture was diluted with DCM and washed with water. The organic layer was separated, passed through a phase separation cartridge and concentrated under reduced pressure. The residue was purified via silica gel column chromatography (0-100% EtOAc/hexane) to yield (R)-benzyl 1-(4-(5-tert-butoxycarbonyl-amino-2-bromothiazole-4-carboxamido)-1-methyl-1H-pyrazol-5-yl)azepan-4-ylcarbamate as a pink solid (1.04 g, 89%). $^1$H NMR (400 MHz, CDCl$_3$) δ 10.28 (s, 1H), 8.40 (s, 1H), 7.75 (s, 1H), 7.38-7.27 (m, 5H), 5.09 (s, 2H), 5.00-4.92 (m, 1H), 3.91-3.84

(m, 1H), 3.73 (s, 3H), 3.36-3.24 (m, 2H), 3.15-3.04 (m, 2H), 2.19-2.03 (m, 2H), 1.96-1.79 (m, 3H), 1.75-1.63 (m, 1H), 1.52 (s, 9H).

Example 82

(R)-tert-Butyl 2-bromo-4-(1-methyl-5-(4-(2,2,2-trifluoroacetamido)azepan-1-yl)-1H-pyrazol-4-ylcarbamoyl)thiazol-5-ylcarbamate

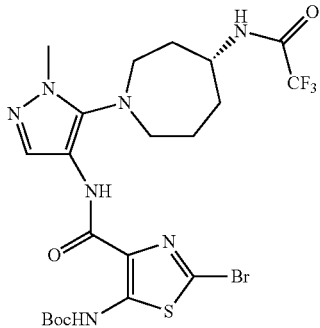 [SMILES: Cn1ncc(NC(=O)c2nc(Br)sc2NC(=O)OC(C)(C)C)c1N1CCC[C@@H](NC(=O)C(F)(F)F)CC1]

2-Bromo-5-(tert-butoxycarbonylamino)thiazole-4-carboxylic acid and (R)—N-(azepan-4-yl)-2,2,2-trifluoroacetamide were coupled to give (R)-tert-butyl 2-bromo-4-(1-methyl-5-(4-(2,2,2-trifluoroacetamido)azepan-1-yl)-1H-pyrazol-4-ylcarbamoyl)thiazol-5-ylcarbamate as a salmon solid (500 mg, 74%). $^1$H NMR (400 MHz, CDCl$_3$) δ 10.27 (s, 1H), 8.38 (s, 1H), 7.74 (s, 1H), 6.41 (d, J=8.2 Hz, 1H), 4.23-4.15 (m, 1H), 3.75 (s, 3H), 3.38-3.29 (m, 2H), 3.22-3.08 (m, 2H), 2.22-2.08 (m, 2H), 2.03-1.93 (m, 2H), 1.88-1.69 (m, 2H), 1.52 (s, 9H).

Example 83

(R)-4-(benzyloxycarbonylamino)azepane or (S) 4-(benzyloxycarbonylamino)azepane

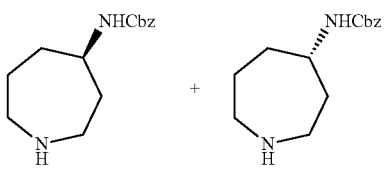 [SMILES: O=C(N[C@@H]1CCCNCC1)OCc1ccccc1 ; O=C(N[C@H]1CCCNCC1)OCc1ccccc1]

To a 250 mL 3-neck-round bottom flask was added tert-butyl 4-aminoazepane-1-carboxylate (8.80 g, 41.0 mmol), triethylamine (29 mL, 0.21 mol) and methylene chloride (20 mL). The mixture was cooled to −20° C. and benzyl chloroformate (8.4 g, 49 mmol) was added dropwise via a syringe over 10 min. The heterogeneous mixture was warmed to room temperature and stirred for 2 h. The reaction was monitored by LCMS and upon completion of the reaction, the solvent was distilled off and the crude product was purified via flash chromatography, heptane/ethyl acetate 10% to 30% to afford a white solid (6.0 g, 42%).

The racemic azepine was resolved using chiral SFC (Supercritical Fluid Chromatography, see White and Burnett (2005) Jour. of Chrom. A1074:175-185) under pressurized carbon dioxide with a Chiralpak OJ-H (100×4.6 mm, 5 micron) column, 15% Methanol/CO$_2$, with a flow rate of 200 ml/min, pressure at 100 bars and at 40° C. for 5 min. to afford the two enantiomers ((R)-tert-butyl 4-(benzyloxycarbonylamino)azepane-1-carboxylate and (S)-tert-butyl 4-(benzyloxycarbonylamino)azepane-1-carboxylate).

To a 100 mL round bottom flask was added one of the enantiomers, dioxane (20 mL) and 12N HCl (4 mL). The mixture was stirred for 2 h and the solvent was distilled off. The product, an HCl salt, (2.2 g, 37%) of isomer 1 and (2.4 g, 40%) of isomer 2 was used directly in the next step.

Example 84 tert-Butyl 5-azido-3-hydroxy-3-methylazepane-1-carboxylate

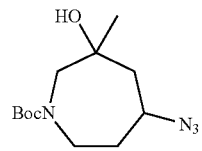 [SMILES: CC1(O)CC(N=[N+]=[N-])CCN(C(=O)OC(C)(C)C)C1]

To a stirred solution of (Z)-tert-butyl 3-oxo-2,3,6,7-tetrahydro-1H-azepine-1-carboxylate (15 g, 71.1 mmol) in acetonitrile (25 mL) was added trimethylsilylazide (28.2 mL, 213 mmol) followed by Amberlite IRA 900F resin (loading: 2-3 mmol/g, 18 g) and the mixture was heated at 60° C. for 4 hr. After standing at room temperature for 16 hr, the resin was filtered off, washed with acetonitrile and the solvent removed under reduced pressure to give a yellow oil. To a solution of this oil (813 mg, 3.2 mmol) in dry Et$_2$O (20 ml) cooled in an ice-salt bath was added a solution of methyl lithium (1.6 M in Et$_2$O, 2.1 mL, 3.36 mmol) dropwise over 10 mins. After stirring for a further 1.5 hr, saturated NaHCO$_3$ (10 mL) was added and the mixture was extracted with EtOAc (2×20 mL). The combined organic layers were dried over MgSO$_4$ and the solvent removed under reduced pressure to afford a green oil (0.8 g, 81% over four steps). $^1$H NMR (400 MHz, CDCl$_3$) δ 4.00-2.65 (m, 6H), 2.30-1.60 (m, 4H), 1.55-1.20 (m, 12H).

Example 84a

5-Azido-3-methyl-1-(1-methyl-4-nitro-1H-pyrazol-5-yl)azepan-3-ol

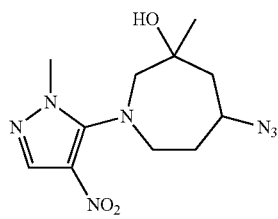 [SMILES: Cn1ncc([N+](=O)[O-])c1N1CCC(N=[N+]=[N-])CC(C)(O)C1]

A solution of tert-butyl 5-azido-3-hydroxy-3-methylazepane-1-carboxylate (0.8 g, 3 mmol) in DCM (15 mL) and trifluoroacetic acid (5 mL) was stirred at room temperature for 1.5 hr and then concentrated under reduced pressure. The residue was dissolved in the minimum volume of DCM, loaded onto an SCX column, washed with DCM and MeOH and eluted with 1 N ammonia in MeOH. The solvent was removed under reduced pressure. To a solution of the residue in anhydrous DMSO (10 mL) was added 5-chloro-1-methyl- 4-nitro-1H-pyrazole (574 mg, 3.56 mmol) and potassium fluoride (675 mg, 12.7 mmol). The mixture was heated at 70° C. for 16 hr under nitrogen, then cooled and poured into water (300 mL). The mixture was extracted with EtOAc (3×150 mL) and the combined organic layers were washed with water (100 mL) and brine (50 mL), separated, dried over MgSO$_4$ and concentrated to give a brown gum. Purification via silica gel column chromatography (0-100% EtOAc/isohexane) gave 5-azido-3-methyl-1-(1-methyl-4-nitro-1H-pyrazol-5-yl)azepan-3-ol as a mixture of four diastereoisomers (0.38 g, 47% over 2 steps). $^1$H NMR (400 MHz, CDCl$_3$) δ 8.04 (s, 1H), 4.12-3.90 (m, 1H), 3.85 and 3.74 (2s, 3H), 3.60-3.40 (m, 1H), 3.40-3.30 (m, 1H), 3.25-3.10 (m, 1H), 3.00-2.60 (m, 2H), 2.30-2.10 (m, 2H), 2.00-1.70 (m, 2H), 1.35-1.15 (m, 3H). LCMS (ES+) m/z 296 (M+1).

This mixture was separated into two pairs of diastereoisomers via silica gel column chromatography (0-50% EtOAc/isohexane) to afford:

Less polar pair of diastereoisomers (111A) $^1$H NMR (400 MHz, CDCl$_3$) δ 8.04 (s, 1H), 4.12-3.95 (m, 1H), 3.83 (s, 3H), 3.60-3.50 (m, 1H), 3.45-3.30 (m, 1H), 3.25-3.10 (m, 1H), 2.95-2.85 (m, 1H), 2.55 (br s, 1H), 2.30-2.10 (m, 2H), 2.00-1.70 (m, 2H), 1.25 (s, 3H). LCMS (ES+) m/z 296 (M+1).

More polar pair of diastereoisomers (111B) $^1$H NMR (400 MHz, CDCl$_3$) δ 8.04 (s, 1H), 4.00-3.92 (m, 1H), 3.90 (s, 3H), 3.55-3.45 (m, 1H), 3.40-3.30 (m, 1H), 3.25-3.15 (m, 1H), 3.00-2.85 (m, 1H), 2.83 (s, 1H), 2.30-2.10 (m, 3H), 1.95-1.85 (m, 1H), 1.20 (s, 3H). LCMS (ES+) m/z 296 (M+1).

Example 84b tert-Butyl 6-fluoro-6-methyl-1-(1-methyl-4-nitro-1H-pyrazol-5-yl)azepan-4-ylcarbamate

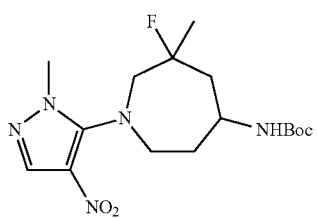 [SMILES: Cn1ncc([N+](=O)[O-])c1N1CCC(NC(=O)OC(C)(C)C)CC(C)(F)C1]

Triphenylphosphine (338 mg, 1.29 mmol) was added to a stirred solution of 5-azido-3-methyl-1-(1-methyl-4-nitro-1H-pyrazol-5-yl)azepan-3-ol (380 mg, 1.29 mmol) in THF (15 mL) and water (3 mL) and the mixture was heated at 60° C. for 16 hr. The reaction mixture was concentrated under reduced pressure. The residue was dissolved in DCM (20 mL) and DIPEA (0.67 mL, 3.86 mmol) and di-tert-butyldicarbonate (565 mg, 3.58 mmol) were added. The mixture was stirred at room temperature for 20 hr, concentrated under reduced pressure and the residue purified via silica gel column chromatography (0-100% EtOAc/isohexane) to afford a pale orange solid (0.4 g). To a solution of this solid (0.4 g, 1.29 mmol) in DCM (10 mL) was added deoxo-Fluor® (1.2 mL, 3.31 mmol, 50% in THF) and the mixture was stirred at room temperature for 20 hr. Saturated NaHCO$_3$ (30 mL) was added and stirring continued for 15 mins. The aqueous layer was extracted with DCM (30 mL) and the combined organic layers were dried over MgSO$_4$ and concentrated under reduced pressure. Purification via silica gel column chromatography (0-100% EtOAc/isohexane) gave tert-butyl 6-fluoro-6-methyl-1-(1-methyl-4-nitro-1H-pyrazol-5-yl)azepan-4-ylcarbamate as a pale orange gum (315 mg, 64% over three steps). $^1$H NMR (400 MHz, CDCl$_3$) δ 8.04 (s, 1H), 5.30-4.90 (m, 1H), 4.75-4.15 (m, 1H), 3.90-3.75 (m, 3H), 3.65-3.00 (m, 4H), 2.55-1.75 (m, 4H), 1.48 (s, 9H), 1.45-1.25 (m, 3H). LCMS (ES+) m/z 394 (M+Na).

Example 84c tert-Butyl 6-hydroxy-6-methyl-1-(1-methyl-4-nitro-1H-pyrazol-5-yl)azepan-4-ylcarbamate (Less Polar Pair of Diastereomers)

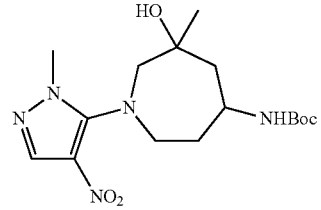 [SMILES: Cn1ncc([N+](=O)[O-])c1N1CCC(NC(=O)OC(C)(C)C)CC(C)(O)C1]

Triphenylphosphine (113 mg, 0.43 mmol) was added to a stirred solution of 5-azido-3-methyl-1-(1-methyl-4-nitro-1H-pyrazol-5-yl)azepan-3-ol (less polar pair of diastereomers) (103 mg, 0.35 mmol) in THF (5 mL) and water (1 mL) and the mixture was heated at 60° C. for 16 hr. The reaction mixture was concentrated under reduced pressure and the residue was dissolved in DCM (10 mL) and DIPEA (0.19 mL, 1.09 mmol) before di-tert-butyldicarbonate (153 mg, 0.70 mmol) was added. The mixture was stirred at room temperature for 3 hr and then washed with saturated NaHCO$_3$ (15 mL). The organic layer was passed through a phase separation cartridge and the solvent removed under reduced pressure. The residue was purified via silica gel column chromatography (0-100% EtOAc/isohexane) to afford a pale orange gum (110 mg, 86% over two steps). $^1$H NMR (400 MHz, CDCl$_3$) δ 8.02 (s, 1H), 4.62 (br s, 1H), 4.2-4.10 (m, 1H), 3.87 (s, 3H), 3.60-3.45 (m, 1H), 3.35-3.10 (m, 2H), 2.90-2.80 (m, 1H), 2.73 (br s, 1H), 2.25-2.10 (m, 1H), 2.05-1.90 (m, 1H), 1.80-1.65 (m, 2H), 1.45 (s, 9H), 1.19 (s, 3H). LCMS (ES+) m/z 370 (M+1).

Example 84d tert-Butyl 6-hydroxy-6-methyl-1-(1-methyl-4-nitro-1H-pyrazol-5-yl)azepan-4-ylcarbamate (More Polar Pair of Diastereoisomers)

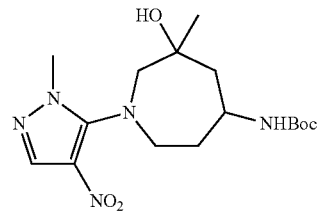 [SMILES: Cn1ncc([N+](=O)[O-])c1N1CCC(NC(=O)OC(C)(C)C)CC(C)(O)C1]

Following the procedure for Intermediate 113 starting from 5-azido-3-methyl-1-(1-methyl-4-nitro-1H-pyrazol-5-yl)azepan-3-ol (more polar pair of diastereoisomers) gave tert-butyl 6-hydroxy-6-methyl-1-(1-methyl-4-nitro-1H-pyrazol-5-yl)azepan-4-ylcarbamate (more polar pair of diastereoisomers) as a pale orange gum (100 mg, 97%). $^1$H NMR (400 MHz, CDCl$_3$) δ 8.03 (s, 1H), 4.70 (br s, 1H), 4.05-3.90 (m, 1H), 3.88 (s, 3H), 3.60-3.50 (m, 1H), 3.35-3.25 (m, 1H), 3.15-3.05 (m, 1H), 2.95-2.85 (m, 1H), 2.30-2.10 (m, 1H), 2.10-1.80 (m, 4H), 1.45 (s, 9H), 1.26 (s, 3H). LCMS (ES+) m/z 370 (M+1).

Example 84e tert-Butyl 6-methoxy-6-methyl-1-(1-methyl-4-nitro-1H-pyrazol-5-yl)azepan-4-ylcarbamate (Less Polar Pair of Diastereoisomers)

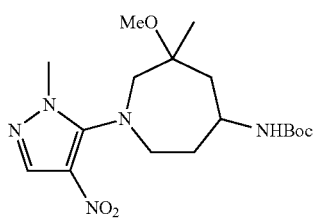 [SMILES: COC1(C)CC(NC(=O)OC(C)(C)C)CCN(c2c([N+](=O)[O-])cnn2C)C1]

To a solution of 5-azido-3-methyl-1-(1-methyl-4-nitro-1H-pyrazol-5-yl)azepan-3-ol (less polar pair of diastereoisomers) (115 mg, 0.53 mmol) in dry DMF (2 mL) at room temperature under nitrogen was added sodium hydride (25 mg, 0.63 mmol, 60% dispersion in oil) and the mixture was stirred at room temperature for 10 mins. Methyl iodide (0.05 mL, 0.80 mmol) was added and the mixture was stirred at room temperature for 1 hr. Ice-water (50 mL) was added and the mixture was extracted with EtOAc (2×25 mL). The combined organic layers were washed with brine (20 mL), separated, dried over $MgSO_4$ and the solvent removed under reduced pressure. The residue was dissolved in THF (5 mL) and water (1 mL) and triphenylphosphine (102 mg, 0.39 mmol) was added. The reaction mixture was heated at 60° C. for 16 hr. The mixture was concentrated under reduced pressure. The residue was dissolved in DCM (10 mL) and DIPEA (0.2 mL, 1.15 mmol) and di-tert-butyldicarbonate (170 mg, 0.78 mmol) were added. The mixture was stirred at room temperature for 3 hr then washed with saturated $NaHCO_3$ (15 mL). The organic layer was passed through a phase separation cartridge and the solvent removed under reduced pressure. Purification via silica gel column chromatography (0-100% EtOAc/isohexane) gave tert-butyl 6-methoxy-6-methyl-1-(1-methyl-4-nitro-1H-pyrazol-5-yl)azepan-4-ylcarbamate (less polar pair of diastereoisomers) as a pale orange gum (118 mg, 79% over three steps). $^1$H NMR (400 MHz, $CDCl_3$) δ 8.02 (s, 1H), 4.55 (br s, 1H), 4.20-4.10 (m, 1H), 3.88 (s, 3H), 3.45-3.25 (m, 2H), 3.20 (s, 3H), 3.20-2.95 (m, 2H), 2.30-2.10 (m, 2H), 1.80-1.50 (m, 2H), 1.45 (s, 9H), 1.08 (s, 3H). LCMS (ES+) m/z 384 (M+1).

Example 84f tert-Butyl 6-methoxy-6-methyl-1-(1-methyl-4-nitro-1H-pyrazol-5-yl)azepan-4-ylcarbamate (Diastereomer B)

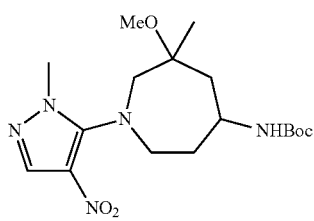

Following the procedure for Intermediate 115 starting from 5-azido-3-methyl-1-(1-methyl-4-nitro-1H-pyrazol-5-yl)azepan-3-ol (more polar pair of diastereoisomers) gave tert-butyl 6-methoxy-6-methyl-1-(1-methyl-4-nitro-1H-pyrazol-5-yl)azepan-4-ylcarbamate (more polar pair of diastereoisomers) as a pale orange gum (110 mg, 68% over three steps). $^1$H NMR (400 MHz, $CDCl_3$) δ 8.03 (s, 1H), 5.70 (br s, 1H), 4.05-3.90 (m, 1H), 3.88 (s, 3H), 3.50-3.25 (m, 2H), 3.15 (s, 3H), 3.10-2.90 (m, 2H), 2.25-2.05 (m, 2H), 2.00-1.85 (m, 1H), 1.75-1.60 (m, 1H), 1.45 (s, 9H), 1.14 (s, 3H). LCMS (ES+) m/z 384 (M+1).

Example 85 tert-Butyl 5-(benzylideneaminooxy)-3,3-difluoro-azepane-1-carboxylate

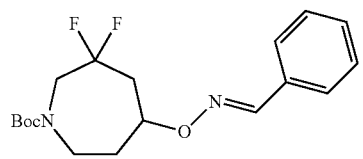 [SMILES: CC(C)(C)OC(=O)N1CCC(O/N=C/c2ccccc2)CC(F)(F)C1]

(Z)-tert-butyl 3-oxo-2,3,6,7-tetrahydro-1H-azepine-1-carboxylate (330 mg, 1.56 mmol), (E)-benzaldehyde oxime (286 mg, 2.36 mmol) and DBU (0.007 mL, 0.05 mmol) were combined in MeCN (0.5 mL) and the mixture was stirred at room temperature for 48 hr. The solvent was removed under reduced pressure and the residue purified via preparative HPLC to give tert-butyl 5-(benzylideneaminooxy)-3-oxoazepane-1-carboxylate as a brown oil (127 mg).

A solution of this oil (125 mg, 0.37 mmol) in DCM (20 mL) was treated with deoxo-Fluor® (50% in THF, 0.67 mL, 1.86 mmol) and the mixture was stirred at room temperature for 18 hr. The mixture was diluted with DCM (20 mL), cooled in an ice/water bath and quenched by dropwise addition of saturated aqueous $NaHCO_3$ (30 mL). The resulting mixture was stirred for 10 min. The organic layer was separated, dried over $Na_2SO_4$ and the solvent removed under reduced pressure. Purification via silica gel column chromatography (0-30% EtOAc/isohexane) gave tert-butyl 5-(benzylideneaminooxy)-3,3-difluoroazepane-1-carboxylate (101 mg, 18% over two steps) as a clear oil. $^1$H NMR (400 MHz, $CDCl_3$) δ 8.11-8.03 (m, 1H), 7.61-7.55 (m, 2H), 7.40-7.36 (m, 3H), 4.52-4.42 (m, 1H), 4.02-3.56 (m, 3H), 3.51-3.27 (m, 1H), 2.67-2.51 (m, 1H), 2.42-2.21 (m, 2H), 2.09-1.91 (m, 1H), 1.50-1.45 (m, 9H).

Example 85a

Benzaldehyde O-6,6-difluoro-1-(1-methyl-4-nitro-1H-pyrazol-5-yl)azepan-4-yl oxime

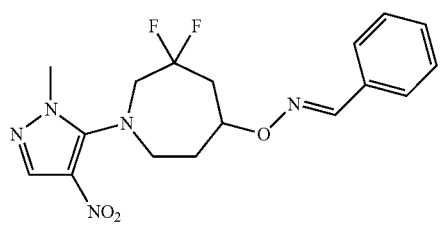 [SMILES: Cn1ncc([N+](=O)[O-])c1N1CCC(O/N=C/c2ccccc2)CC(F)(F)C1]

Following the procedure for Intermediate 109 starting from tert-butyl 5-(benzylideneaminooxy)-3,3-difluoroazepane-1-carboxylate gave benzaldehyde O-6,6-difluoro-1-(1-methyl-4-nitro-1H-pyrazol-5-yl)azepan-4-yl oxime as a yellow oil (52 mg, 33%). $^1$H NMR (400 MHz, CDCl$_3$) δ 8.21-7.98 (m, 1H), 8.05 (s, 1H), 7.63-7.58 (m, 2H), 7.41-7.36 (m, 3H), 4.71-4.62 (m, 1H), 3.85 (s, 3H), 3.80-3.65 (m, 1H), 3.47-3.39 (m, 2H), 3.26-3.23 (m, 1H), 2.77 (q, J=13.2 Hz, 1H), 2.58-2.29 (m, 2H), 2.23-2.10 (m, 1H).

INTERMEDIATES

Intermediate 1 tert-Butyl methyl((1-(1-methyl-4-nitro-1H-pyrazol-5-yl)piperidin-4-yl)methyl)carbamate

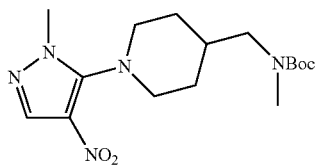

A solution of 5-chloro-1-methyl-4-nitro-1H-pyrazole from Example 1 (0.2 g, 1.23 mmol), tert-butyl methyl(piperidin-4-ylmethyl)carbamate (0.29 g, 1.36 mmol) and DIPEA (1 mL, 5.7 mmol) in EtOH (3 mL) was heated at 130° C. in a microwave for 2 hr. The solvent was removed under reduced pressure and the residue was purified by silica gel column chromatography (40% EtOAc/isohexane) to give tert-butyl (1-(1-methyl-4-nitro-1H-pyrazol-5-yl)piperidin-4-yl)methylcarbamate as a yellow oil (0.34 g, 80%). To a solution of this oil (0.15 mg, 0.44 mmol) in DMF (5 mL) cooled to 0° C. was added sodium hydride (27 mg, 0.66 mmol, 60% in mineral oil) and the mixture was stirred at 0° C. for 15 min. Iodomethane (0.03 mL, 0.53 mmol) was added and the mixture was stirred at 0° C. for 30 min. Additional sodium hydride (14 mg, 0.33 mmol) and iodomethane (0.02 mL, 0.78 mmol) were added, the reaction mixture was allowed to warm to 10° C. and stirred for 1 hr. Water (10 mL) was added and the mixture was extracted with EtOAc (60 mL). The organic layer was washed with water (7×10 mL), washed with brine (10 mL), separated, dried over MgSO$_4$ and the solvent removed under reduced pressure. Purification of the residue by silica gel column chromatography (30% EtOAc/isohexane) afforded tert-butyl methyl((1-(1-methyl-4-nitro-1H-pyrazol-5-yl)piperidin-4-yl)methyl)carbamate as a yellow oil (148 mg, 95%). $^1$H NMR (400 MHz, CDCl$_3$) δ 8.01 (s, 1H), 3.74 (s, 3H), 3.38-3.26 (m, 2H), 3.25-3.15 (m, 2H), 3.12-2.95 (m, 2H), 2.89 (s, 3H), 1.90-1.71 (m, 3H), 1.60-1.32 (m, 2H), 1.47 (s, 9H).

Intermediate 2 tert-Butyl 6,6-difluoro-4-(1-methyl-4-nitro-1H-pyrazol-5-yl)-1,4-diazepane-1-carboxylate

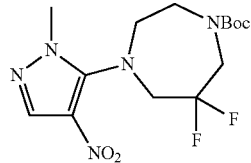 [SMILES: Cn1ncc([N+](=O)[O-])c1N1CCN(C(=O)OC(C)(C)C)CC(F)(F)C1]

A solution of 5-chloro-1-methyl-4-nitro-1H-pyrazole (1.62 g, 10.0 mmol), 1,4-diazepan-6-ol (4.18 g, 15.0 mmol) and DIPEA (6.6 mL) in EtOH (6 mL) was heated at 130° C. in a microwave for 3 hr. The solvent was removed under reduced pressure and the residue dissolved in DCM (60 mL) and DMF (10 mL). Di-tert-butyl dicarbonate (8.73 g, 40 mmol) and DIPEA (3.48 mL) were added and the mixture stirred at room temperature for 16 hr. The solvent was removed under reduced pressure and the residue purified by silica gel column chromatography (0-100% EtOAc/isohexane) to give tert-butyl 6-hydroxy-4-(1-methyl-4-nitro-1H-pyrazol-5-yl)-1,4-diazepane-1-carboxylate (2.13 g) as a yellow oil. To a solution of this oil (2.13 g, 6.2 mmol) in DCM (20 mL), Dess-Martin periodinane (3.18 g, 7.49 mmol) was added portionwise. After stirring at room temperature for 18 hr, the mixture was diluted with DCM (20 mL) and quenched with saturated aqueous NaHCO$_3$ (40 mL) followed by 20% aqueous sodium thiosulphate (40 mL). The resulting mixture was stirred for 20 min. The organic layer was separated, dried over Na$_2$SO$_4$ and the solvent removed under reduced pressure. Purification via silica gel column chromatography (0-100% EtOAc/isohexane) gave tert-butyl 4-(1-methyl-4-nitro-1H-pyrazol-5-yl)-6-oxo-1,4-diazepane-1-carboxylate (1.6 g) as a viscous yellow oil. To a solution of this oil (0.49 g, 1.43 mmol) in DCM (10 mL) was added deoxo-Fluor® (50% in THF, 1.3 mL, 3.6 mmol) and the mixture was stirred at room temperature for 18 hr. The mixture was diluted with DCM (30 mL), cooled in an ice/water bath and quenched by dropwise addition of saturated aqueous NaHCO$_3$ (50 mL). The resulting mixture was stirred for 10 min. The organic layer was separated, dried over Na$_2$SO$_4$ and the solvent removed under reduced pressure. The crude product was purified via silica gel column chromatography (0-60% EtOAc/isohexane) to give tert-butyl 6,6-difluoro-4-(1-methyl-4-nitro-1H-pyrazol-5-yl)-1,4-diazepane-1-carboxylate (467 mg, 42% over four steps) as a clear oil. $^1$H NMR (400 MHz, CDCl$_3$) δ 8.04 (s, 1H), 4.05-3.27 (m, 11H), 1.50 (s, 9H).

Intermediate 3 tert-Butyl 4-(4-(2-bromo-5-(tert-butoxycarbonylamino)thiazole-4-carboxamido)-1-methyl-1H-pyrazol-5-yl)-6,6-difluoro-1,4-diazepane-1-carboxylate

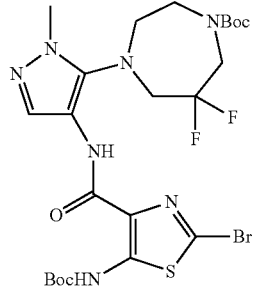 [SMILES: Cn1ncc(NC(=O)c2nc(Br)sc2NC(=O)OC(C)(C)C)c1N1CCN(C(=O)OC(C)(C)C)CC(F)(F)C1]

A solution of tert-butyl 6,6-difluoro-4-(1-methyl-4-nitro-1H-pyrazol-5-yl)-1,4-diazepane-1-carboxylate (467 mg, 1.29 mmol) in MeOH (30 mL) was passed through the H-Cube® (70 bar, 60° C., flow rate: 1 mL/min, 30 mm 10% Pd/C cartridge). The solvent was removed under reduced pressure to afford a red oil (428 mg). To a solution of this oil in DCM (15 mL) was added 2-bromo-5-(tert-butoxycarbonylamino)thiazole-4-carboxylic acid (459 mg, 1.42 mmol), PyBOP (1.0 g, 1.94 mmol) and DIPEA (0.57 mL, 3.22 mmol) and the mixture was stirred at room temperature for 16 hr. Water (20 ml) was added and the mixture was diluted with DCM (100 mL). The organic layer was washed with water (20 mL), separated, dried over MgSO$_4$ and the solvent removed under reduced pressure. Purification via silica gel column chromatography (0-80% EtOAc/isohexane) gave tert-butyl 4-(4-(2-bromo-5-(tert-butoxycarbonylamino)thiazole-4-carboxamido)-1-methyl-1H-pyrazol-5-yl)-6,6-difluoro-1,4-diazepane-1-carboxylate as a beige foam (565 mg, 69% over two steps). ¹H NMR (400 MHz, CDCl₃) δ 10.23 (s, 1H), 8.31 (s, 1H), 7.62 (s, 1H), 4.07-3.95 (m, 2H), 3.76 (s, 3H), 3.64 (s, 2H), 3.56-3.42 (m, 2H), 3.38-3.28 (m, 2H), 1.53 (s, 9H), 1.49 (s, 9H).

Intermediate 4

(R)—N-(Azepan-4-yl)-2,2,2-trifluoroacetamide

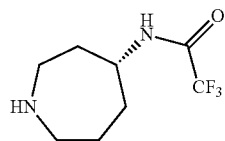

A solution of (R)-tert-butyl 4-(benzyloxycarbonylamino) azepane-1-carboxylate (3.25 g, 0.33 mmol) in MeOH (100 mL) was stirred at room temperature under an atmospheric pressure of hydrogen gas in the presence of 10% palladium on carbon (1 g) for 1.5 hr. The mixture was filtered through Celite® and the solvent removed under reduced pressure to afford (R)-tert-butyl 4-(2,2,2-trifluoroacetamido)azepane-1-carboxylate as a pale grey oil (2 g, 100%). To a stirred solution of this oil (1.8 g, 8.4 mmol) and DIPEA (3 mL, 17.2 mmol) in DCM (100 mL) at room temperature was added trifluoroacetic anhydride (1.31 mL, 9.3 mmol) dropwise over 5 min and the resultant pale yellow solution was stirred for 18 hr. Saturated aqueous NaHCO₃ solution (150 mL) was added and stirring continued for 1 hr. The layers were separated, the organics passed through a phase separation cartridge and the solvent removed under reduced pressure to give (R)-tert-butyl 4-(2,2,2-trifluoroacetamido)azepane-1-carboxylate as a pale yellow oil (2.61 g, 100%). To a solution of this oil (2.6 g, 8.38 mmol) in DCM (50 mL) at room temperature was added trifluoroacetic acid (25 mL) and the mixture stirred for 2 hr. The solvent was removed under reduced pressure and the residue dissolved in DCM and passed through an SCX column washing with DCM and MeOH and eluting with 1 N ammonia in MeOH. The solvent was removed under reduced pressure to afford (R)—N-(azepan-4-yl)-2,2,2-trifluoroacetamide as a pale yellow oil (1.3 g, 74%). ¹H-NMR (400 MHz, CDCl₃) δ 7.83 (s, 1H), 4.44-4.37 (m, 1H), 3.13-3.03 (m, 2H), 2.88 (dt, J=13.2, 6.6 Hz, 1H), 2.65-2.55 (m, 1H), 2.03-1.79 (m, 3H), 1.75 (s, 1H), 1.69-1.58 (m, 3H).

Intermediate 5

5-Chloro-1-(2,2-difluoroethyl)-4-nitro-1H-pyrazole

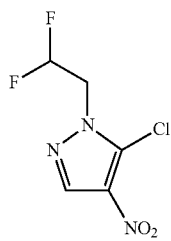

To a stirred solution of 1-(2,2-difluoroethyl)-4-nitro-1H-pyrazole (1.0 g, 5.13 mmol) in dry THF (20 mL) cooled to −70° C. was added dropwise a solution of lithium hexamethyldisilazide (1 M in THF, 8.47 mL, 8.47 mmol). After stirring at −70° C. for 40 min, the reaction mixture was allowed to warm to −55° C. over 20 min. After recooling to −70° C., a solution of perchloroethane (1.74 g, 7.34 mmol) in THF (10 mL) was added slowly and the reaction mixture was stirred at −70° C. for 1.5 hr. Saturated aqueous ammonium chloride solution (30 mL) was added followed by water (15 mL) and the mixture was extracted with EtOAc (3×100 mL). The combined organic layers were dried over MgSO₄ and the solvent removed under reduced pressure. Purification of the residue by silica gel column chromatography (0-100% EtOAc/isohexane) gave 5-chloro-1-(2,2-difluoroethyl)-4-nitro-1H-pyrazole as an off-white solid (438 mg, 37%). ¹H NMR (400 MHz, CDCl₃) δ 8.24 (s, 1H), 6.18 (tt, J=54.8, 4.2 Hz, 1H), 4.58 (td, J=12.8, 4.2 Hz, 2H).

Intermediate 6

(R)—N-(1-(4-Amino-1-(2,2-difluoroethyl)-1H-pyrazol-5-yl)azepan-4-yl)-2,2,2-trifluoro-N-methylacetamide

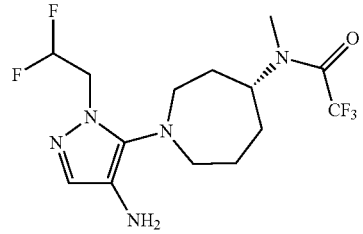 [SMILES: CN(C(=O)C(F)(F)F)[C@@H]1CCCN(c2c(N)cnn2CC(F)F)CC1]

A solution of 5-chloro-1-(2,2-difluoroethyl)-4-nitro-1H-pyrazole (438 mg, 2.07 mmol), (R)—N-(azepan-4-yl)-2,2,2-trifluoroacetamide (438 mg, 2.07 mmol) and DIPEA (1 mL) in EtOH (4 mL) was heated at 155° C. in the microwave for 5 hr. The solvent was removed under reduced pressure and the residue purified by silica gel column chromatography (0-100% EtOAc/isohexane) to give (R)—N-(1-(1-(2,2-difluoroethyl)-4-nitro-1H-pyrazol-5-yl)azepan-4-yl)-2,2,2-trifluoroacetamide as a pale orange gum (518 mg). A portion of this gum (39 mg, 0.10 mmol) in dry THF (2 mL) was treated with sodium hydride (60% in mineral oil, 5 mg, 0.12 mmol). After stirring at room temperature for 10 min, iodomethane (0.01 mL, 0.20 mmol) was added and the reaction mixture was stirred at room temperature for 2 hr. The reaction was repeated on the remaining (R)—N-(1-(1-(2,2-difluoroethyl)-4-nitro-1H-pyrazol-5-yl)azepan-4-yl)-2,2,2-trifluoroacetamide. Water (50 mL) was added carefully and the mixture was extracted with EtOAc (2×100 mL). The organic layers were combined, dried over MgSO₄ and the solvent was removed under reduced pressure to give (R)—N-(1-(1-(2,2-difluoroethyl)-4-nitro-1H-pyrazol-5-yl)azepan-4-yl)-2,2,2-trifluoro-N-methylacetamide as a pale yellow gum (518 mg). This gum (514 mg, 1.29 mmol) was dissolved in MeOH (20 mL) and treated with ammonium formate (325 mg, 6.15 mmol) and 10% palladium on carbon (50 mg). The mixture was heated at 85° C. for 2 hr. After cooling to room temperature the catalyst was filtered off and the filtrate was concentrated under reduced pressure. The residue was partitioned between DCM (50 mL) and water (30 mL) and the aqueous layer was extracted with DCM (2×50 mL). The combined organic layers were passed through a phase separation cartridge and the solvent was removed under reduced pressure to afford (R)—N-(1-(4-amino-1-(2,2-difluoroethyl)-1H-pyrazol-5-yl) azepan-4-yl)-2,2,2-trifluoro-N-methylacetamide as a pale yellow gum (348 mg, 46% over three steps). ¹H NMR (400 MHz, CDCl₃) δ 7.13 (s, 1H), 6.19 (tq, J=55.4, 4.4 Hz, 1H), 4.65-4.15 (m, 3H), 3.40-3.10 (m, 4H), 3.10 and 2.97 (2s, 3H), 2.80 (br s, 2H), 2.10-1.70 (m, 6H).

Intermediate 7

(R)-tert-Butyl 2-bromo-4-(1-(2,2-difluoroethyl)-5-(4-(2,2,2-trifluoro-N-methylacetamido)azepan-1-yl)-1H-pyrazol-4-ylcarbamoyl)thiazol-5-ylcarbamate

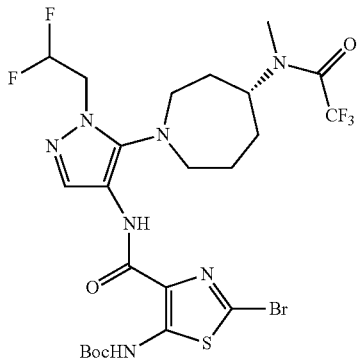 [SMILES: CN(C(=O)C(F)(F)F)[C@@H]1CCCN(c2c(NC(=O)c3nc(Br)sc3NC(=O)OC(C)(C)C)cnn2CC(F)F)CC1]

To a solution of (R)—N-(1-(4-amino-1-(2,2-difluoroethyl)-1H-pyrazol-5-yl)azepan-4-yl)-2,2,2-trifluoro-N-methylacetamide (248 mg, 0.67 mmol) in DCM (20 mL) was added DIPEA (1.0 mL, 5.7 mmol), PyBOP (700 mg, 1.34 mmol) and 2-bromo-5-(tert-butoxycarbonylamino)-thiazole-4-carboxylic acid (282 mg, 0.87 mmol) and the mixture was stirred at room temperature for 20 hr. Water (50 mL) was added and stirring continued for 1 hr. The mixture was extracted with DCM (50 mL), the combined organic layers were passed through a phase separation cartridge and the solvent removed under reduced pressure. Purification via silica gel column chromatography (0-100% EtOAc/isohexane) gave (R)-tert-butyl 2-bromo-4-(1-(2,2-difluoroethyl)-5-(4-(2,2,2-trifluoro-N-methylacetamido)azepan-1-yl)-1H-pyrazol-4-ylcarbamoyl)thiazol-5-ylcarbamate as a pale yellow gum (405 mg, 90%). $^1$H NMR (400 MHz, CDCl$_3$) δ 10.27 and 10.26 (2s, 1H), 8.32 and 8.27 (2s, 1H), 7.88 and 7.85 (2s, 1H), 6.36-6.02 (m, 1H), 4.67-4.11 (m, 2H), 3.41-3.08 (m, 5H), 3.08 and 2.95 (2s, 3H), 2.22-1.71 (m, 4H), 1.31-1.18 (m, 2H).

Intermediate 8

1-(4-Amino-1-(2,2-difluoroethyl)-1H-pyrazol-5-yl)azepan-4-ol

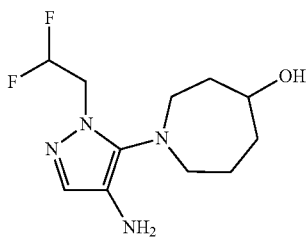 [SMILES: Nc1cnn(CC(F)F)c1N1CCCC(O)CC1]

A solution of 5-chloro-1-(2,2-difluoroethyl)-4-nitro-1H-pyrazole (470 mg, 2.22 mmol), azepan-4-ol (281 mg, 2.44 mmol) and DIPEA (1 mL) in EtOH (3 mL) was heated at 155° C. in the microwave for 5 hr. The solvent was removed under reduced pressure and the residue purified by silica gel column chromatography (0-100% EtOAc/isohexane) to give 1-(1-(2,2-difluoroethyl)-4-nitro-1H-pyrazol-5-yl)azepan-4-ol as a pale orange gum (400 mg). This gum (390 mg, 1.35 mmol) was dissolved in MeOH (25 mL) and treated with ammonium formate (340 mg, 5.38 mmol) and 10% palladium on carbon (50 mg). The mixture was heated at 85° C. for 4 hr. After standing at room temperature overnight more ammonium formate (205 mg, 3.25 mmol) and 10% palladium on carbon (50 mg) were added to the reaction mixture which was then heated at 85° C. for 1 hr. The catalyst was filtered off and the filtrate was concentrated under reduced pressure. The residue was partitioned between DCM (30 mL) and water (20 mL). The organic layer was passed through a phase separation cartridge and the solvent was removed under reduced pressure to afford 1-(4-amino-1-(2,2-difluoroethyl)-1H-pyrazol-5-yl)azepan-4-ol as an orange oil (265 mg, 42% over two steps). $^1$H NMR (400 MHz, CDCl$_3$) δ 7.17 (s, 1H), 6.27-5.91 (m, 1H), 4.39-4.23 (m, 2H), 4.16-4.04 (m, 1H), 3.30-3.11 (m, 4H), 2.60 (br s, 3H), 2.55 (s, 2H), 2.08-1.81 (m, 3H), 1.80-1.71 (m, 1H).

Intermediate 9 tert-Butyl 2-bromo-4-(1-(2,2-difluoroethyl)-5-(4-hydroxyazepan-1-yl)-1H-pyrazol-4-ylcarbamoyl)thiazol-5-ylcarbamate

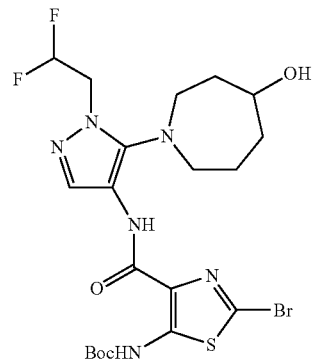 [SMILES: CC(C)(C)OC(=O)Nc1sc(Br)nc1C(=O)Nc1cnn(CC(F)F)c1N1CCCC(O)CC1]

Following the procedure for Intermediate 7 starting with 1-(4-amino-1-(2,2-difluoroethyl)-1H-pyrazol-5-yl)azepan-4-ol and 2-bromo-5-(tert-butoxycarbonylamino)-thiazole-4-carboxylic acid afforded tert-butyl 2-bromo-4-(1-(2,2-difluoroethyl)-5-(4-hydroxyazepan-1-yl)-1H-pyrazol-4-ylcarbamoyl)thiazol-5-ylcarbamate as a colorless solid (265 mg, 69%). $^1$H NMR (400 MHz, CDCl$_3$) δ 10.39 (s, 1H), 9.14 (s, 1H), 8.02 (s, 1H), 6.18 (tt, J=55.9, 4.5 Hz, 1H), 4.38-4.27 (m, 2H), 3.33-3.12 (m, 5H), 2.20 (br s, 1H), 2.35-1.58 (m, 4H), 1.70-1.48 (m, 2H).

Intermediate 10

(R)-tert-Butyl 4-(4-amino-1-methyl-1H-pyrazol-5-yl)-3-methylpiperazine-1-carboxylate

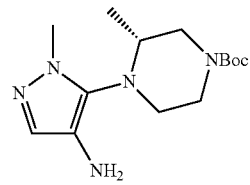 [SMILES: C[C@@H]1CN(C(=O)OC(C)(C)C)CCN1c1c(N)cnn1C]

To a solution of 5-chloro-1-methyl-4-nitro-1H-pyrazole from Example 1 (355 mg, 2.2 mmol) and potassium fluoride (511 mg, 8.8 mmol) in dry DMSO (20 mL) was added (R)-tert-butyl 3-methylpiperazine-1-carboxylate (507 mg, 2.53 mmol) and the mixture was heated in the microwave at 100° C. for 10 hr. The mixture was partitioned between water (40 mL) and EtOAc (100 mL) and the organic layer passed through a phase separation cartridge and concentrated under reduced pressure. Purification via silica gel column chromatography (0-100% EtOAc/isohexane) gave (R)-tert-butyl 3-methyl-4-(1-methyl-4-nitro-1H-pyrazol-5-yl)piperazine-1-carboxylate as an orange gum (627 mg). To a solution of this gum (179 mg, 0.55 mmol) and ammonium formate (256 mg, 4.4 mmol) in MeOH (10 mL) under nitrogen was added 10% palladium on carbon (59 mg, 0.55 mmol). The mixture was heated at 70° C. for 4 hr before being cooled, filtered and concentrated under reduced pressure. The residue was partitioned between water (20 mL) and DCM (60 mL) and the organic layer separated, passed through a phase separation cartridge and concentrated under reduced pressure to give (R)-tert-butyl 4-(4-amino-1-methyl-1H-pyrazol-5-yl)-3-methylpiperazine-1-carboxylate as a brown gum (150 mg, 80% over two steps). LCMS (ES+) m/z 296 (M+1).

Intermediate 11

(S)-tert-Butyl 4-(4-amino-1-methyl-1H-pyrazol-5-yl)-3-ethylpiperazine-1-carboxylate

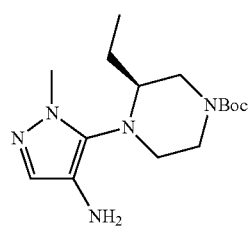 [SMILES: CC[C@H]1CN(C(=O)OC(C)(C)C)CCN1c1c(N)cnn1C]

Following the procedure for Intermediate 10 starting from 5-chloro-1-methyl-4-nitro-1H-pyrazole from Example 1 and (S)-tert-butyl 3-ethylpiperazine-1-carboxylate gave (S)-tert-butyl 4-(4-amino-1-methyl-1H-pyrazol-5-yl)-3-ethylpiperazine-1-carboxylate as an orange gum (110 mg, 65% over two steps). LCMS (ES+) m/z 310 (M+1).

Intermediate 12

(R)-tert-Butyl 4-(4-amino-1-methyl-1H-pyrazol-5-yl)-3-ethylpiperazine-1-carboxylate

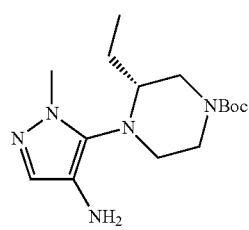 [SMILES: CC[C@@H]1CN(C(=O)OC(C)(C)C)CCN1c1c(N)cnn1C]

Following the procedure for Intermediate 10 starting from 5-chloro-1-methyl-4-nitro-1H-pyrazole from Example 1 and (R)-tert-butyl 3-ethylpiperazine-1-carboxylate gave (R)-tert-butyl 4-(4-amino-1-methyl-1H-pyrazol-5-yl)-3-ethylpiperazine-1-carboxylate as an orange gum (118 mg, 67% over two steps). LCMS (ES+) m/z 310 (M+1).

Intermediate 13

(S)—N-(Azepan-4-yl)-2,2,2-trifluoroacetamide

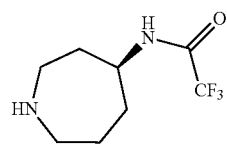

Following the procedure for Intermediate 4 starting with (S)-tert-butyl 4-(benzyloxycarbonylamino)azepane-1-carboxylate gave (S)—N-(azepan-4-yl)-2,2,2-trifluoroacetamide as a pale yellow oil (1.35 g, 75% over three steps). $^1$H-NMR (400 MHz, CDCl$_3$) δ 7.86 (s, 1H), 4.44-4.37 (m, 1H), 3.15-3.03 (m, 2H), 2.92-2.81 (m, 1H), 2.67-2.55 (m, 1H), 2.02-1.81 (m, 4H), 1.76-1.56 (m, 3H).

Intermediate 14

(S)—N-(1-(4-Amino-1-(2,2-difluoroethyl)-1H-pyrazol-5-yl)azepan-4-yl)-2,2,2-trifluoro-N-methylacetamide

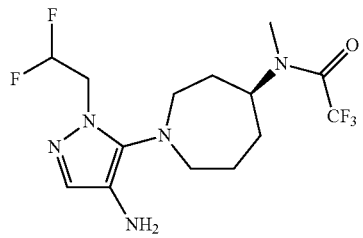 [SMILES: CN(C(=O)C(F)(F)F)[C@H]1CCCN(c2c(N)cnn2CC(F)F)CC1]

Following the procedure for Intermediate 6 starting from (S)—N-(azepan-4-yl)-2,2,2-trifluoroacetamide and 5-chloro-1-(2,2-difluoroethyl)-4-nitro-1H-pyrazole gave (S)—N-(1-(4-amino-1-(2,2-difluoroethyl)-1H-pyrazol-5-yl)azepan-4-yl)-2,2,2-trifluoro-N-methylacetamide as a pale red gum (100 mg, 32% over three steps). $^1$H NMR (400 MHz, CDCl$_3$) δ 7.13 (s, 1H), 6.19 (tq, J=55.4, 4.4 Hz, 1H), 4.65-4.15 (m, 3H), 3.40-3.10 (m, 4H), 3.10 and 2.97 (2s, 3H), 2.80 (br s, 2H), 2.10-1.70 (m, 6H).

Intermediate 15

(S)-tert-Butyl 2-bromo-4-(1-(2,2-difluoroethyl)-5-(4-(2,2,2-trifluoro-N-methylacetamido)azepan-1-yl)-1H-pyrazol-4-ylcarbamoyl)thiazol-5-ylcarbamate

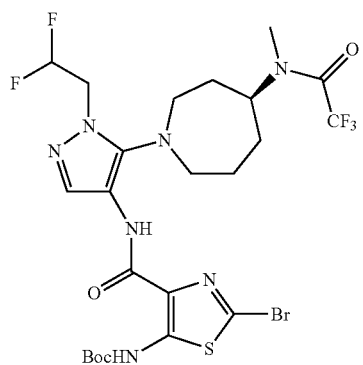 [SMILES: CN(C(=O)C(F)(F)F)[C@H]1CCCN(c2c(NC(=O)c3nc(Br)sc3NC(=O)OC(C)(C)C)cnn2CC(F)F)CC1]

Following the procedure for Intermediate 7 starting from (S)—N-(1-(4-amino-1-(2,2-difluoroethyl)-1H-pyrazol-5-yl)azepan-4-yl)-2,2,2-trifluoro-N-methylacetamide and 2-bromo-5-(tert-butoxycarbonylamino)-thiazole-4-carboxylic acid afforded (S)-tert-butyl 2-bromo-4-(1-(2,2-difluoroethyl)-5-(4-(2,2,2-trifluoro-N-methylacetamido)azepan-1-yl)-1H-pyrazol-4-ylcarbamoyl)thiazol-5-ylcarbamate as a pale pink gum (80 mg 57%). $^1$H NMR (400 MHz, CDCl$_3$) δ 10.27 (s, 1H), 8.31 and 8.27 (2s, 1H), 7.88 and 7.85 (2s, 1H), 6.34-6.05 (m, 1H), 4.41-4.31 (m, 2H), 3.42-3.29 (m, 5H), 3.10 and 2.95 (2s, 3H), 2.08-1.75 (m, 4H), 1.40-1.15 (m, 2H).

Intermediate 16

3-Fluoro-1-(1-methyl-4-nitro-1H-pyrazol-5-yl)piperidin-4-one

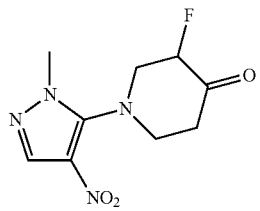 [SMILES: Cn1ncc([N+](=O)[O-])c1N1CCC(=O)C(F)C1]

Three identical solutions of piperidin-4-one hydrochloride hydrate (1.84 g, 12.0 mmol), 5-chloro-1-methyl-4-nitro-1H-pyrazole from Example 1 (1.3 g, 8.0 mmol) and potassium fluoride (1.86 g, 32 mmol) in dry DMSO (20 mL) were heated in a microwave at 100° C. for 12 hr. The mixtures were combined, poured into water (700 mL) and extracted into EtOAc (3×100 mL). The combined organic layers were passed through a phase separation cartridge and concentrated under reduced pressure. Purification via silica gel column chromatography (0-5% MeOH/DCM) gave 1-(1-methyl-4-nitro-1H-pyrazol-5-yl)piperidin-4-one as a yellow solid (1.97 g, 36%). To a solution of this ketone in DMF (40 mL) was added NEt$_3$ (3.05 mL, 21.9 mmol) and chlorotrimethylsilane (1.55 mL, 12.3 mmol). The reaction vessel was sealed and the mixture heated at 90° C. for 16 hr. The mixture was cooled and the product extracted into EtOAc (2×50 mL). The combined organic layers were passed through a phase separation cartridge and concentrated under reduced pressure. Purification via silica gel column chromatography (0-100% Et$_2$O/isohexane) gave 1-(1-methyl-4-nitro-1H-pyrazol-5-yl)-4-(trimethylsilyloxy)-1,2,3,6-tetrahydropyridine as a yellow gum (1.53 g, 59%). This gum was dissolved in MeCN (130 mL) and cooled to 0° C. A solution of SelectFluor® (1.99 g, 5.61 mmol) in 2:1 MeCN:DMF (10 mL) was added dropwise over 20 min and the mixture stirred at between −5° C. and 0° C. for 2 hr. The solvent was removed under reduced pressure and the residue was partitioned between EtOAc (50 mL) and water (40 mL). The product was extracted into EtOAc (50 mL) and DCM (50 mL), and the combined organic layers passed through a phase separation cartridge and concentrated under reduced pressure. Purification via silica gel column chromatography (0-100% EtOAc/isohexane) gave 3-fluoro-1-(1-methyl-4-nitro-1H-pyrazol-5-yl)piperidin-4-one as a pale yellow solid (1.23 g, 99%). $^1$H NMR (400 MHz, CDCl$_3$) δ 8.07 (s, 1H), 5.04 (ddd, J=48.3, 8.2, 5.7 Hz, 1H), 3.89 (s, 3H), 3.77-3.64 (m, 2H), 3.64-3.51 (m, 1H), 3.50-3.43 (m, 1H), 2.88-2.72 (m, 2H).

Intermediate 17

2,2,2-trifluoro-N-(3-fluoro-1-(1-methyl-4-nitro-1H-pyrazol-5-yl)azepan-4-yl)acetamide

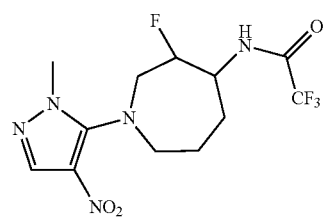 [SMILES: Cn1ncc([N+](=O)[O-])c1N1CCCC(NC(=O)C(F)(F)F)C(F)C1]

To a solution of 3-fluoro-1-(1-methyl-4-nitro-1H-pyrazol-5-yl)piperidin-4-one (1.07 g, 4.40 mmol) in DCM (10 mL) at −5° C. was added dropwise a solution of boron trifluoride diethyl etherate (0.71 ml, 5.72 mmol) in DCM (1 mL). The mixture was stirred for 30 min before a solution of ethyl diazoacetate (0.60 ml, 5.72 mmol) in DCM (1 mL) was added. The mixture was stirred at −5° C. for 1 hr before being allowed to warm to room temperature. Water (5 mL) was added and the mixture stirred for 30 min. The organic layer was passed through a phase separation cartridge and concentrated under reduced pressure. Purification via silica gel column chromatography (0-100% EtOAc/isohexane) gave ethyl 6-fluoro-1-(1-methyl-4-nitro-1H-pyrazol-5-yl)-5-oxoazepane-4-carboxylate as a yellow gum (0.85 g, 58%). This gum was re-dissolved in 3 M hydrochloric acid (30 mL) and heated at 100° C. for 4 hr. The mixture was concentrated under reduced pressure, re-dissolved in DCM (30 mL) and washed with water (20 mL). The organic phase was passed through a phase separation cartridge and concentrated under reduced pressure. Purification via silica gel column chromatography (0-100% EtOAc/isohexane) gave 3-fluoro-1-(1-methyl-4-nitro-1H-pyrazol-5-yl)azepan-4-one as a pale yellow solid (0.30 g, 45%). To a solution of this solid (0.30 g, 1.15 mmol) in anhydrous MeOH (6 mL) and DCM (6 mL) was added ammonium acetate (0.709 g, 9.20 mmol) and crushed activated 4 Å molecular sieves. The mixture was heated at 55° C. for 4 hr before being cooled to room temperature. Sodium cyanoborohydride (80 mg, 1.27 mmol) was added portionwise and the mixture stirred at room temperature for 1 hr. The mixture was filtered and concentrated under reduced pressure. The residue was re-dissolved in DCM (10 mL) and washed with 10% aqueous NaOH (10 mL). The aqueous washings were extracted with EtOAc (3×20 mL) and the combined organic layers were passed through a phase separation cartridge and concentrated under reduced pressure. Purification via amine-functionalized silica gel column chromatography (0-100% EtOAc/isohexane) gave 3-fluoro-1-(1-methyl-4-nitro-1H-pyrazol-5-yl)azepan-4-amine as a yellow gum (0.205 g, 69%). To solution of this gum (0.20 g, 0.79 mmol) and DIPEA (0.37 mL, 2.13 mmol) in DCM (5 mL) was added dropwise trifluoroacetic anhydride (0.11 mL, 0.78 mmol). The mixture was stirred at room temperature for 16 hr before being washed with water (10 mL). The organic layer was separated, passed through a phase separation cartridge and concentrated under reduced pressure. Purification via silica gel column chromatography (0-100% EtOAc/isohexane) gave tert-butyl 3-fluoro-1-(1-methyl-4-nitro-1H-pyrazol-5-yl)azepan-4-ylcarbamate as a pale yellow solid (140 mg, 55%). LCMS (ES+) m/z 354 (M+1).

Intermediate 18

5-Azido-1-(1-methyl-4-nitro-1H-pyrazol-5-yl)azepan-3-ol

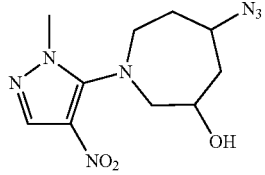 [SMILES: Cn1ncc([N+](=O)[O-])c1N1CCC(N=[N+]=[N-])CC(O)C1]

To as solution of (Z)-tert-butyl 3-oxo-2,3,6,7-tetrahydro-1H-azepine-1-carboxylate (2.0 g, 9.5 mmol) in acetonitrile (3 mL), was added trimethylsilyl azide (3.76 mL, 28.4 mmol) followed by AMBERLITE® IRA 900F resin (loading: 2-3 mmolg-1, 2.4 g) and the resulting mixture was heated at 60° C. behind a blast shield for 16 hr. After cooling to room temperature, the solution was filtered washing the resin with acetonitrile and the filtrate was concentrated under reduced pressure (temperature of bath<40° C.) to give tert-butyl 5-azido-3-oxoazepane-1-carboxylate as a yellow liquid (2.21 g). To a solution of the azide (2.2 g, 8.70 mmol) in THF/water (1/1, 40 mL), was added portionwise NaBH$_4$ (0.82 mg, 21.8 mmol) and the mixture was stirred at room temperature for 2 hr. The mixture was diluted with water (100 mL) and extracted with EtOAc (100 mL). The organic layer was separated, dried over MgSO$_4$ and the solvent removed under reduced pressure. Purification via silica gel column chromatography (0-60% EtOAc/isohexane) gave tert-butyl 5-azido-3-hydroxyazepane-1-carboxylate as an oil (2.01 g). To a solution of this oil (2.0 g, 7.8 mmol) in MeOH (20 mL), was added HCl (4 M in 1,4-dioxane, 43 mL, 173 mmol) and the solution was stirred at room temperature for 16 hr. The solvents were removed under reduced pressure and the crude residue was dissolved in MeOH and passed through an SCX column, washing with MeOH and eluting with 7 N ammonia in MeOH to give 5-azidoazepan-3-ol as a yellow oil. To this oil in dry DMSO (20 mL) was added potassium fluoride (1.68 g, 28.9 mmol) and 5-chloro-1-methyl-4-nitro-1H-pyrazole from Example 1 (1.17 g, 7.2 mmol) and the mixture heated at 65° C. for 16 hr. The mixture was diluted with water (300 mL) and extracted with EtOAc (2×50 mL). The combined organic layers were washed with water (3×20 mL), separated, dried over MgSO$_4$ and the solvents removed under reduced pressure. Purification via silica gel column chromatography (0-30% EtOAc/isohexane) gave 5-azido-1-(1-methyl-4-nitro-1H-pyrazol-5-yl)azepan-3-ol as a viscous yellow oil (1.9 g, 72% over four steps). $^1$H NMR (400 MHz, CDCl$_3$) δ 8.06 and 8.02 (2s, 1H), 4.15-3.97 (m, 2H), 3.95-3.83 (m, 4H), 3.58-3.46 (m, 1H), 3.39-3.16 (m, 3H), 2.29-1.91 (m, 4H).

Intermediate 19 tert-Butyl 6,6-difluoro-1-(1-methyl-4-nitro-1H-pyrazol-5-yl)azepan-4-ylcarbamate

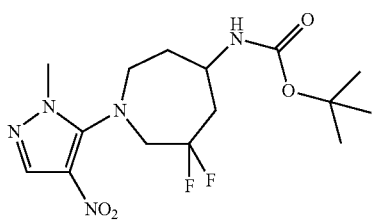 [SMILES: Cn1ncc([N+](=O)[O-])c1N1CCC(NC(=O)OC(C)(C)C)CC(F)(F)C1]

To a solution of 5-azido-1-(1-methyl-4-nitro-1H-pyrazol-5-yl)azepan-3-ol, Intermediate 18 (3.4 g, 16 mmol) in THF (40 mL) and water (8 mL) was added triphenylphosphine (1.89 g, 7.2 mmol) and the mixture was heated at 65° C. behind a blast screen for 16 hr. The solvents were removed under reduced pressure to afford 5-amino-1-(1-methyl-4-nitro-1H-pyrazol-5-yl)azepan-3-ol (contaminated with triphenylphosphine oxide) as a viscous oil. To this amine in DCM (40 mL) was added di-tert-butyl dicarbonate (4.49 g, 20.6 mmol) and DIPEA (4.78 mL, 27.4 mmol) and the mixture was stirred at room temperature for 60 hr. The solvent was removed under reduced pressure and the residue purified via silica gel column chromatography (0-100% EtOAc/isohexane) to give tert-butyl 6-hydroxy-1-(1-methyl-4-nitro-1H-pyrazol-5-yl)azepan-4-ylcarbamate as a yellow oil (1.2 g). To a solution of this oil (1.2 g) in DCM (25 mL) was added portionwise Dess-Martin periodinane (1.72 g, 1.51 mmol). After stirring at room temperature for 16 hr, the mixture was diluted with DCM (25 mL) and quenched with saturated aqueous NaHCO$_3$ (40 mL) followed by 20% aqueous sodium thiosulphate (40 mL). The resulting mixture was stirred for 20 min. The organic layer was separated, dried over Na$_2$SO$_4$ and the solvent removed under reduced pressure. Purification via silica gel column chromatography (0-60% EtOAc/isohexane) gave tert-butyl 1-(1-methyl-4-nitro-1H-pyrazol-5-yl)-6-oxoazepan-4-ylcarbamate (0.56 g) as a yellow oil. To a solution of this oil (0.51 g, 1.46 mmol) in DCM (15 mL) was added deoxo-Fluor® (50% in THF, 1.85 mL, 5.1 mmol) and the mixture was stirred at room temperature for 16 hr. The mixture was diluted with DCM (30 mL), cooled in an ice/water bath and quenched by dropwise addition of saturated aqueous NaHCO$_3$ (30 mL). The resulting mixture was stirred for 10 min. The organic layer was separated, dried over Na$_2$SO$_4$ and the solvent removed under reduced pressure. Purification via silica gel column chromatography (0-50% EtOAc/isohexane) gave tert-butyl 6,6-difluoro-1-(1-methyl-4-nitro-1H-pyrazol-5-yl)azepan-4-ylcarbamate (510 mg, 64% over four steps) as an oil. $^1$H NMR (400 MHz, CDCl$_3$) δ 8.04 (s, 1H), 4.18-4.01 (m, 1H), 3.84 (s, 3H), 3.79-3.19 (m, 4H), 2.56-2.42 (m, 1H), 2.38-1.99 (m, 4H), 1.46 (s, 9H).

Intermediate 20 tert-Butyl 6-fluoro-1-(1-methyl-4-nitro-1H-pyrazol-5-yl)azepan-4-ylcarbamate

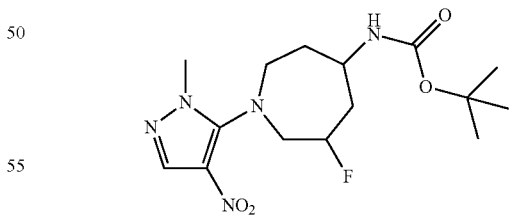

To a solution of 5-azido-1-(1-methyl-4-nitro-1H-pyrazol-5-yl)azepan-3-ol, Intermediate 18 (3.4 g, 16 mmol) in THF (40 mL) and water (8 mL), was added triphenylphosphine (1.89 g, 7.2 mmol) and the mixture was heated at 65° C. for 16 hr. The solvents were removed under reduced pressure to afford 5-amino-1-(1-methyl-4-nitro-1H-pyrazol-5-yl)azepan-3-ol (contaminated with triphenylphosphine oxide) as a viscous oil. To this amine in DCM (40 mL), di-tert-butyl dicarbonate (4.49 g, 20.6 mmol) and DIPEA (4.78 mL, 27.4 mmol) were added and the mixture stirred at room temperature for 60 hr. The solvent was removed under reduced pressure and the residue purified by silica gel column chromatography (0-100% EtOAc/isohexane) to give tert-butyl 6-hydroxy-1-(1-methyl-4-nitro-1H-pyrazol-5-yl)azepan-4-ylcarbamate as a yellow oil (2.6 g). To a solution of this oil (2.6 g, 10.2 mmol) in DCM (50 mL) was added deoxo-Fluor® (50% in THF, 6.7 mL, 18.6 mmol) and the mixture was stirred at room temperature for 16 hr. The mixture was diluted with DCM (30 mL), cooled in an ice/water bath and quenched by the dropwise addition of saturated aqueous NaHCO₃ (30 mL). The resulting mixture was stirred for 10 min. The organic layer was separated, dried over Na₂SO₄ and the solvent removed under reduced pressure. Purification via silica gel column chromatography (0-50% EtOAc/isohexane) gave tert-butyl 6-fluoro-1-(1-methyl-4-nitro-1H-pyrazol-5-yl)azepan-4-ylcarbamate (1.07 g, 66% over three steps) as a pale yellow oil. ¹H NMR (400 MHz, CDCl₃) δ 8.14-7.97 (m, 1H), 5.04-4.46 (m, 3H), 3.96-2.99 (m, 6H), 2.42-1.64 (m, 5H), 1.70-1.22 (m, 9H).

Intermediate 21

(S)-tert-Butyl 4-(4-amino-1-methyl-1H-pyrazol-5-yl)-3-methylpiperazine-1-carboxylate

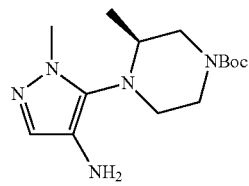

Following the procedure for Intermediate 10 starting from 5-chloro-1-methyl-4-nitro-1H-pyrazole from Example 1 and (S)-tert-butyl 3-methylpiperazine-1-carboxylate gave (S)-tert-butyl 4-(4-amino-1-methyl-1H-pyrazol-5-yl)-3-methylpiperazine-1-carboxylate as an orange gum (134 mg, 73% over two steps). LCMS (ES+) m/z 296 (M+1).

Intermediate 22 tert-Butyl 8-(1-methyl-4-nitro-1H-pyrazol-5-yl)-2,8-diazaspiro[4.5]decane-2-carboxylate

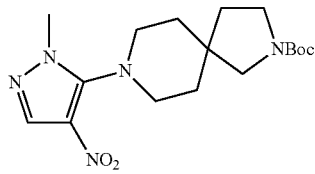

A mixture of 5-chloro-1-methyl-4-nitro-1H-pyrazole from Example 1 (150 mg, 0.93 mmol), tert-butyl 2,8-diazaspiro[4.5]decane-2-carboxylate (244 mg, 1.02 mmol) and DIPEA (1 mL) in EtOH (3 mL) was heated at 130° C. in a microwave for 2 hr. The solvent was removed under reduced pressure and the crude product was purified via silica gel column chromatography (50% EtOAc/isohexane) to give tert-butyl 8-(1-methyl-4-nitro-1H-pyrazol-5-yl)-2,8-diazaspiro[4.5]decane-2-carboxylate as a yellow oil (245 mg, 72%). ¹H NMR (400 MHz, CDCl₃) δ 8.02 (s, 1H), 3.76 (s, 3H), 3.49-3.39 (m, 2H), 3.30-3.00 (m, 6H), 1.90-1.60 (m, 6H), 1.55 (s, 9H).

Intermediate 23

(S)-5-(2,4-Dimethylpiperazin-1-yl)-1-methyl-1H-pyrazol-4-amine

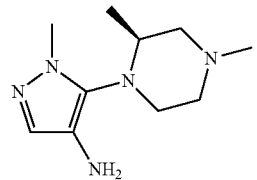

To a solution of 5-chloro-1-methyl-4-nitro-1H-pyrazole from Example 1 (355 mg, 2.2 mmol) and potassium fluoride (511 mg, 8.8 mmol) in dry DMSO (20 mL) was added (R)-tert-butyl 3-methylpiperazine-1-carboxylate (1.15 eq, 2.53 mmol) and the mixture was heated in the microwave at 100° C. for 10 hr. The mixture was partitioned between water (40 mL) and EtOAc (100 mL), the organic layer passed through a phase separation cartridge and concentrated under reduced pressure. Purification via silica gel column chromatography (0-100% EtOAc/isohexane) gave (S)-tert-butyl 3-methyl-4-(1-methyl-4-nitro-1H-pyrazol-5-yl)piperazine-1-carboxylate as an orange gum (627 mg). To a solution of this gum (212 mg, 0.65 mmol) in DCM (9 mL) was added trifluoroacetic acid (3 mL) and the mixture stirred at room temperature for 4 hr. The mixture was concentrated under reduced pressure and the residue was partitioned between water (20 mL) and DCM (30 mL). The organic layer was passed through a phase separation cartridge and concentrated under reduced pressure to give (S)-2-methyl-1-(1-methyl-4-nitro-1H-pyrazol-5-yl)piperazine as a yellow gum (120 mg). To a solution of this gum (119 mg, 0.53 mmol) and acetic acid (0.12 mL, 2.12 mmol) in MeOH (10 mL) was added aqueous formaldehyde (37 wt % in water, 0.17 mL, 2.12 mmol) and the mixture stirred at room temperature for 1 hr. Sodium cyanoborohydride (83 mg, 1.33 mmol) was then added and the mixture stirred at room temperature for 70 hr. The mixture was concentrated under reduced pressure and the residue was partitioned between water (20 mL) and DCM (30 mL). The organic layer was passed through a phase separation cartridge and concentrated under reduced pressure to give (S)-2,4-dimethyl-1-(1-methyl-4-nitro-1H-pyrazol-5-yl)piperazine as a yellow gum (109 mg). To a solution of this gum (108 mg, 0.45 mmol) and ammonium formate (209 mg, 3.6 mmol) in MeOH (10 mL) under nitrogen was added 10% palladium on carbon (48 mg, 0.45 mmol). The mixture was heated at 70° C. for 4 hr before being cooled, filtered and concentrated under reduced pressure. The residue was partitioned between water (20 mL) and DCM (50 mL) and the organic layer was separated, passed through a phase separation cartridge and concentrated under reduced pressure to give (S)-5-(2,4-dimethylpiperazin-1-yl)-1-methyl-1H-pyrazol-4-amine as a brown gum (94 mg, 62% over four steps). ¹H NMR (400 MHz, CDCl₃) δ 7.07 (s, 1H), 3.66 (s, 3H), 3.51-3.41 (m, 1H), 3.36 (td, J=5.7, 2.6 Hz, 1H), 2.94-2.84 (m, 3H), 2.36 (s, 3H), 2.28 (td, J=5.6, 3.0 Hz, 1H), 1.92 (dd, J=11.2, 9.8 Hz, 1H), 0.86 (d, J=6.3 Hz, 3H). Exchangeable NH$_2$ not observed.

Intermediate 24

(R)-5-(2,4-Dimethylpiperazin-1-yl)-1-methyl-1H-pyrazol-4-amine

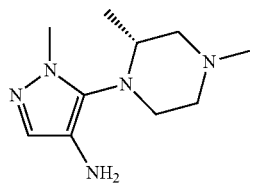

Following the procedure for Intermediate 23 starting with 5-chloro-1-methyl-4-nitro-1H-pyrazole from Example 1 and (R)-tert-butyl 3-methyl-piperazine-1-carboxylate gave (R)-5-(2,4-dimethylpiperazin-1-yl)-1-methyl-1H-pyrazol-4-amine as a brown solid (94 mg, 62% over four steps). $^1$H NMR (400 MHz, CDCl$_3$) δ 7.07 (s, 1H), 3.66 (s, 3H), 3.59-3.44 (m, 2H), 2.99-2.86 (m, 3H), 2.46-2.31 (m, 4H), 2.03 (t, J=10.7 Hz, 1H), 0.87 (d, J=6.3 Hz, 3H). Exchangeable NH$_2$ not observed.

Intermediate 25

5-Chloro-1-cyclopropyl-4-nitro-1H-pyrazole

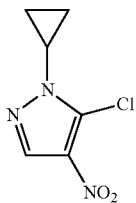 [SMILES: O=[N+]([O-])c1cnn(C2CC2)c1Cl]

Following the procedure for Intermediate 5 starting with 1-cyclopropyl-4-nitropyrazole gave 5-chloro-1-cyclopropyl-4-nitro-1H-pyrazole as a colorless solid (0.23 g, 63%). $^1$H-NMR (400 MHz, CDCl$_3$) δ 8.09 (s, 1H), 3.62-3.54 (m, 1H), 1.38-1.28 (m, 2H), 1.25-1.13 (m, 2H).

Intermediate 26 tert-Butyl 4-(1-cyclopropyl-4-nitro-1H-pyrazol-5-yl)-6,6-difluoro-1,4-diazepane-1-carboxylate

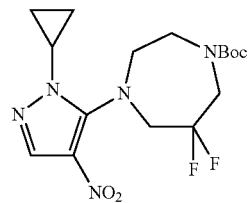 [SMILES: CC(C)(C)OC(=O)N1CCN(c2c([N+](=O)[O-])cnn2C2CC2)CC(F)(F)C1]

Following the procedure for Intermediate 2 starting with 5-chloro-1-cyclopropyl-4-nitro-1H-pyrazole gave, after silica gel column chromatography (0-100% EtOAc/isohexane) gave tert-butyl 4-(1-cyclopropyl-4-nitro-1H-pyrazol-5-yl)-6,6-difluoro-1,4-diazepane-1-carboxylate as a yellow oil (520 mg, 9% over four steps). $^1$H NMR (400 MHz, CDCl$_3$) δ 7.96 (s, 1H), 4.07-3.34 (m, 9H), 1.49 (s, 9H), 1.34-1.17 (m, 2H), 1.08-1.01 (m, 2H).

Intermediate 27 tert-Butyl 4-(4-(2-bromo-5-(tert-butoxycarbonylamino)thiazole-4-carboxamido)-1-cyclopropyl-1H-pyrazol-5-yl)-6,6-difluoro-1,4-diazepane-1-carboxylate

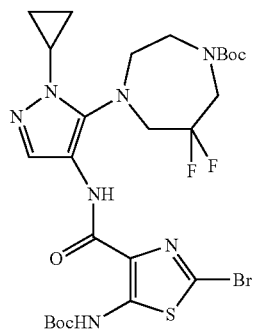 [SMILES: CC(C)(C)OC(=O)Nc1sc(Br)nc1C(=O)Nc1cnn(C2CC2)c1N1CCN(C(=O)OC(C)(C)C)CC(F)(F)C1]

Following the procedure for Intermediate 3 starting with tert-butyl 4-(1-cyclopropyl-4-nitro-1H-pyrazol-5-yl)-6,6-difluoro-1,4-diazepane-1-carboxylate gave, after silica gel column chromatography, (0-50% EtOAc/isohexane) gave tert-butyl 4-(4-(2-bromo-5-(tert-butoxycarbonylamino)thiazole-4-carboxamido)-1-cyclopropyl-1H-pyrazol-5-yl)-6,6-difluoro-1,4-diazepane-1-carboxylate as an off-white foam (573 mg, 62% over four steps). $^1$H NMR (400 MHz, CDCl$_3$) δ 10.23 (s, 1H), 8.43 (s, 1H), 7.65 (s, 1H), 3.71-3.63 (m, 4H), 3.45-3.10 (m, 5H), 1.49 (s, 9H), 1.44 (s, 9H), 1.27-1.18 (m, 2H), 1.06-0.99 (m, 2H).

Intermediate 28

4-Methyl-1-(1-methyl-4-nitro-1H-pyrazol-5-yl)azepan-4-ol

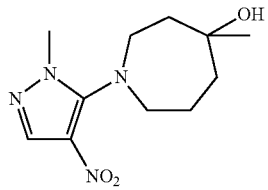 [SMILES: Cn1ncc([N+](=O)[O-])c1N1CCCC(C)(O)CC1]

To a solution of 5-chloro-1-methyl-4-nitro-1H-pyrazole from Example 1 (390 mg, 2.4 mmol) and 4-hydroxy-4-methylazepane hydrochloride (0.48 g, 2.9 mmol) in EtOH (9.5 mL) was added DIPEA (1.9 ml, 10.9 mmol). The reaction mixture was heated at 130° C. in a microwave for 1 hr. The solvent was removed under reduced pressure and the residue was purified via silica gel column chromatography (0-5% MeOH/DCM) to give 4-methyl-1-(1-methyl-4-nitro-1H-pyrazol-5-yl)azepan-4-ol as a colorless oil (410 mg, 66%). $^1$H NMR (400 MHz, CDCl$_3$) δ 8.03 (s, 1H), 3.77 (s, 3H), 3.56-3.47 (m, 1H), 3.28-3.20 (m, 2H), 3.08-3.04 (m, 1H), 2.17-2.03 (m, 1H), 1.95-1.81 (m, 4H), 1.78-1.67 (m, 1H), 1.56 (br s, 1H), 1.25 (s, 3H).

Intermediate 29 tert-Butyl 2-bromo-4-(5-(4-hydroxy-4-methylazepan-1-yl)-1-methyl-1H-pyrazol-4-ylcarbamoyl)thiazol-5-ylcarbamate

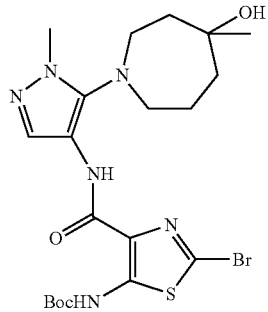 [SMILES: Cn1ncc(NC(=O)c2nc(Br)sc2NC(=O)OC(C)(C)C)c1N1CCCC(C)(O)CC1]

To a solution of 4-methyl-1-(1-methyl-4-nitro-1H-pyrazol-5-yl)azepan-4-ol (212 mg, 0.83 mmol) in MeOH (15 mL) was added ammonium formate (386 mg, 5.63 mmol) and 10% palladium on carbon (88 mg, 0.83 mmol) and the mixture was heated at 80° C. for 18 hr. The mixture was filtered through Celite® and the filtrate concentrated under reduced pressure. The residue was partitioned between DCM (20 mL) and water (20 mL) and the aqueous layer was re-extracted with DCM (3×20 mL). The combined organic layers were passed through a phase separation cartridge and concentrated under reduced pressure to give 1-(4-amino-1-methyl-1H-pyrazol-5-yl)-4-methylazepan-4-ol as a red oil. To a solution of this oil (140 mg, 0.623 mmol) in DCM (25 mL) was added 2-bromo-5-(tert-butoxycarbonylamino)thiazole-4-carboxylic acid (241 mg, 0.75 mmol), PyBOP (454 mg, 1.94 mmol) and DIPEA (0.17 mL, 1.0 mmol) and the mixture was stirred at room temperature for 16 hr. Water (20 ml) was added and the mixture was diluted with DCM (100 mL). The organic layer was washed with water (20 mL), separated, dried over MgSO$_4$ and the solvent removed under reduced pressure. Purification via silica gel column chromatography (0-100% EtOAc/isohexane) gave tert-butyl 2-bromo-4-(5-(4-hydroxy-4-methylazepan-1-yl)-1-methyl-1H-pyrazol-4-ylcarbamoyl)thiazol-5-ylcarbamate as an off-white solid (280 mg, 63% over two steps). $^1$H NMR (400 MHz, CDCl$_3$) δ 10.49 (s, 1H), 9.41 (s, 1H), 7.95 (s, 1H), 3.71 (s, 3H), 3.41-3.30 (m, 1H), 3.24-3.11 (m, 3H), 2.39 (br s, 1H), 2.07-1.75 (m, 5H), 1.84-1.78 (m, 1H), 1.52 (s, 9H), 1.43 (s, 3H).

Intermediate 30 tert-Butyl 4-(1-(2,2-difluoroethyl)-4-nitro-1H-pyrazol-5-yl)-6,6-difluoro-1,4-diazepane-1-carboxylate

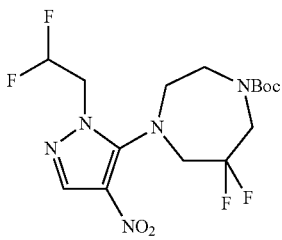

Following the procedure for Intermediate 2 starting with 5-chloro-1-(2,2-difluoroethyl)-4-nitro-1H-pyrazole gave tert-butyl 4-(1-(2,2-difluoroethyl)-4-nitro-1H-pyrazol-5-yl)-6,6-difluoro-1,4-diazepane-1-carboxylate as a pale green gum (11% over four steps). $^1$H NMR (400 MHz, CDCl$_3$) δ 8.13 and 8.12 (2s, 1H), 6.33-6.02 (m, 1H), 4.60-4.40 (m, 2H), 4.10-3.30 (m, 8H), 1.48 (s, 9H).

Intermediate 31 tert-Butyl 4-(1-(2,2-difluoroethyl)-4-nitro-1H-pyrazol-5-yl)-6-hydroxy-1,4-diazepane-1-carboxylate

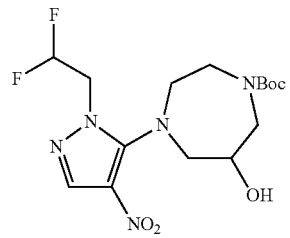 [SMILES: CC(C)(C)OC(=O)N1CCN(c2c([N+](=O)[O-])cnn2CC(F)F)CC(O)C1]

A mixture of 5-chloro-1-(2,2-difluoroethyl)-4-nitro-1H-pyrazole (800 mg, 3.78 mmol), 1,4-diazepan-6-ol dihydrobromide (1.58 g, 5.67 mmol) and DIPEA (2.5 mL, 14.35 mmol) in EtOH (6 mL) was heated at 130° C. in a microwave for 3 hr. The solvent was removed under reduced pressure and the residue was passed through an SCX column washing with DCM and 1:1 MeOH:DCM and MeOH and eluting with 1N ammonia in MeOH to give 1-(1-(2,2-difluoroethyl)-4-nitro-1H-pyrazol-5-yl)-1,4-diazepan-6-ol as a pale yellow gum (1.0 g). This gum (1.0 g, 3.44 mmol) was dissolved in DCM (100 mL) and treated with di-tert-butyl dicarbonate (2.25 g, 10.31 mmol) and DIPEA (2.4 mL, 13.75 mmol). The reaction mixture was stirred at room temperature for 1.5 hr and washed with saturated aqueous NaHCO$_3$ solution (100 mL). The organic layer was separated, passed through a phase separation cartridge and the solvent removed under reduced pressure. Purification via silica gel column chromatography (0-100%) EtOAc/isohexane gave tert-butyl 4-(1-(2,2-difluoroethyl)-4-nitro-1H-pyrazol-5-yl)-6-hydroxy-1,4-diazepane-1-carboxylate as a pale green gum (46% over two steps). $^1$H NMR (400 MHz, CDCl$_3$) δ 8.11 (s, 1H), 6.18 (tdd, J=55.6, 5.6, 3.2 Hz, 1H), 4.49-4.31 (m, 2H), 4.19-2.95 (m, 10H), 1.60-1.40 (m, 9H).

Intermediate 32

5-Chloro-1-(4-methoxybenzyl)-4-nitro-1H-pyrazole

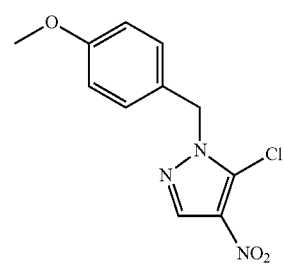 [SMILES: COc1ccc(Cn2ncc([N+](=O)[O-])c2Cl)cc1]

Following the procedure for Intermediate 5 starting with 1-(4-methoxybenzyl)-4-nitro-1H-pyrazole gave 5-chloro-1-(4-methoxybenzyl)-4-nitro-1H-pyrazole as a yellow solid (536 mg, 46%). $^1$H NMR (400 MHz, CDCl$_3$) δ 8.17 (s, 1H), 7.25 (d, J=8.3 Hz, 2H), 6.89 (d, J=8.3 Hz, 2H), 5.30 (s, 2H), 3.80 (s, 3H).

Intermediate 33

(S)-tert-Butyl 4-(4-amino-1-(4-methoxybenzyl)-1H-pyrazol-5-yl)-3-methylpiperazine-1-carboxylate

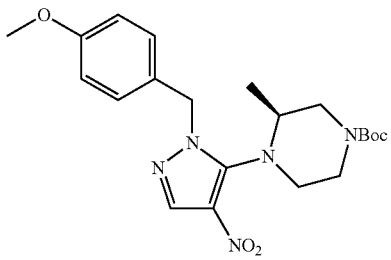 [SMILES: COc1ccc(Cn2ncc([N+](=O)[O-])c2N2CCN(C(=O)OC(C)(C)C)C[C@@H]2C)cc1]

To a solution of 5-chloro-1-(4-methoxybenzyl)-4-nitro-1H-pyrazole (268 mg, 1.0 mmol) and potassium fluoride (232 mg, 4.0 mmol) in dry DMSO (20 mL) was added (S)-tert-butyl 3-methylpiperazine-1-carboxylate (230 mg, 1.15 mmol) and the mixture heated in the microwave at 100° C. for 8 hr. The mixture was partitioned between water (30 mL) and EtOAc (50 mL) and the organic layer was passed through a phase separation cartridge and concentrated under reduced pressure. Purification via silica gel column chromatography (0-100% EtOAc/isohexane) gave (S)-tert-butyl 4-(1-(4-methoxybenzyl)-4-nitro-1H-pyrazol-5-yl)-3-methylpiperazine-1-carboxylate as a yellow gum (380 mg). To a solution of this gum (371 mg, 0.86 mmol) in ethanol/water (20 mL/2 mL) was added ammonium chloride (230 mg, 4.3 mmol) and iron powder (192 mg, 3.44 mmol.) and the mixture heated at 80° C. for 1.5 hr. The mixture was cooled, filtered through Celite® and concentrated under reduced pressure. The residue was partitioned between water (30 mL) and DCM (40 mL) and the organic layer was separated, passed through a phase separation cartridge and the solvent removed under reduced pressure. Purification via silica gel column chromatography (0-5% MeOH/DCM) gave (S)-tert-butyl 4-(4-amino-1-(4-methoxybenzyl)-1H-pyrazol-5-yl)-3-methylpiperazine-1-carboxylate as a red gum (330 mg, 84% over two steps). $^1$H NMR (400 MHz, CDCl$_3$) δ 7.17-7.11 (m, 3H), 6.82 (d, J=8.6 Hz, 2H), 5.34 (d, J=14.4 Hz, 1H), 5.17 (d, J=14.4 Hz, 1H), 3.98-3.80 (m, 2H), 3.78 (s, 3H), 3.23 (ddd, J=9.9, 6.4, 3.3 Hz, 1H), 3.01 (td, J=11.4, 3.0 Hz, 1H), 2.92-2.83 (m, 1H), 2.66 (s, 1H), 2.57 (s, 1H), 1.47 (s, 9H), 0.81 (d, J=6.3 Hz, 3H).

Intermediate 34 tert-Butyl 4-(4-amino-1-(4-methoxybenzyl)-1H-pyrazol-5-yl)piperazine-1-carboxylate

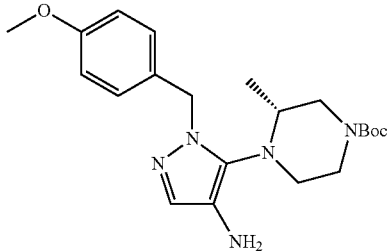 [SMILES: COc1ccc(Cn2ncc(N)c2N2CCN(C(=O)OC(C)(C)C)C[C@H]2C)cc1]

Following the procedure for Intermediate 33 starting with 5-chloro-1-(4-methoxybenzyl)-4-nitro-1H-pyrazole and (R)-tert-butyl 3-methylpiperazine-1-carboxylate gave (R)-tert-butyl 4-(4-amino-1-(4-methoxybenzyl)-1H-pyrazol-5-yl)-3-methylpiperazine-1-carboxylate as a red gum (325 mg, 81% over two steps). $^1$H NMR (400 MHz, CDCl$_3$) δ 7.16-7.11 (m, 3H), 6.82 (d, J=8.6 Hz, 2H), 5.16 (d, J=14.8 Hz, 1H), 5.05 (d, J=14.8 Hz, 1H), 4.10-3.80 (m, 2H), 3.78 (s, 3H), 3.26-3.19 (m, 1H), 3.01 (td, J=11.4, 3.0 Hz, 1H), 2.86 (t, J=13.2 Hz, 1H), 2.66 (s, 2H), 2.57 (s, 2H), 1.47 (s, 9H), 0.81 (d, J=6.3 Hz, 3H).

Intermediate 35

(S)-5-(2-Ethyl-4-methylpiperazin-1-yl)-1-methyl-1H-pyrazol-4-amine

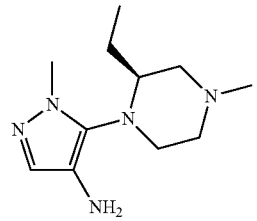 [SMILES: CC[C@H]1CN(C)CCN1c1c(N)cnn1C]

Following the procedure for Intermediate 24 starting with (S)-tert-butyl 3-ethyl-piperazine-1-carboxylate gave (S)-5-(2-ethyl-4-methylpiperazin-1-yl)-1-methyl-1H-pyrazol-4-amine as a brown solid (100 mg, 86% over four steps). $^1$H NMR (400 MHz, CDCl$_3$) δ 8.38 (s, 1H), 7.08 (s, 1H), 3.75-3.55 (m, 5H), 3.29 (dt, J=11.4, 2.4 Hz, 1H), 3.22 (ddd, J=6.0, 5.5, 2.6 Hz, 1H), 2.95 (dt, J=12.5, 2.8 Hz, 1H), 2.64 (dd, J=11.8, 3.6 Hz, 1H), 2.61 (s, 3H), 2.29 (t, J=10.9 Hz, 1H), 1.48-1.31 (m, 1H), 1.26-1.11 (m, 1H), 0.82 (t, J=7.6 Hz, 3H). NH$_2$ partially exchanged.

Intermediate 36

(R)-5-(2-Ethyl-4-methylpiperazin-1-yl)-1-methyl-1H-pyrazol-4-amine

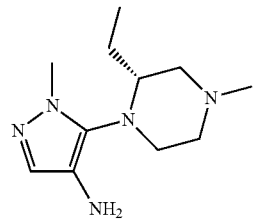 [SMILES: CC[C@@H]1CN(C)CCN1c1c(N)cnn1C]

Following the procedure for Intermediate 24 starting with (R)-tert-butyl 3-ethyl-piperazine-1-carboxylate gave (R)-5-(2-ethyl-4-methylpiperazin-1-yl)-1-methyl-1H-pyrazol-4-amine as a brown solid (100 mg, 86% over four steps). $^1$H NMR (400 MHz, CDCl$_3$) δ 8.40 (s, 1H), 7.07 (s, 1H), 3.65 (s, 3H), 3.66-3.46 (m, 2H), 3.24 (dt, J=11.3, 2.4 Hz, 1H), 3.16 (ddd, J=5.8, 5.6, 2.7 Hz, 1H), 2.94 (dt, J=12.3, 2.8 Hz, 1H), 2.77-2.34 (m, 4H), 2.21 (t, J=10.8 Hz, 1H), 1.47-1.32 (m, 1H), 1.27-1.10 (m, 1H), 0.81 (t, J=7.5 Hz, 3H). NH$_2$ partially exchanged.

Intermediate 37 tert-Butyl 4-(1-(2,2-difluoroethyl)-4-nitro-1H-pyrazol-5-yl)-6-fluoro-1,4-diazepane-1-carboxylate

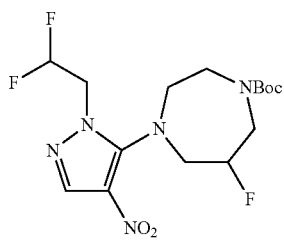

To a solution of tert-butyl 4-(1-(2,2-difluoroethyl)-4-nitro-1H-pyrazol-5-yl)-6-hydroxy-1,4-diazepane-1-carboxylate (370 mg, 0.95 mmol) in DCM (10 mL) was added deoxo-Fluor® (50% solution in THF, 1.0 mL, 2.37 mmol) and the mixture was stirred at room temperature for 18 hr. Saturated aqueous NaHCO$_3$ solution (10 mL) was added slowly and the mixture was stirred for 15 min. The aqueous layer was extracted with DCM (10 mL), the combined organic layers were passed through a phase separation cartridge and the solvent was removed under reduced pressure. Purification via silica gel column chromatography gave tert-butyl 4-(1-(2,2-difluoroethyl)-4-nitro-1H-pyrazol-5-yl)-6-fluoro-1,4-diazepane-1-carboxylate as a pale green gum (366 mg, 74%). $^1$H NMR (400 MHz, CDCl$_3$) δ 8.12 (s, 1H), 6.34-6.00 (m, 1H), 5.08-2.75 (m, 11H), 1.48 (s, 9H).

Intermediate 38 tert-Butyl 6,6-difluoro-1-(1-methyl-4-nitro-1H-pyrazol-5-yl)azepan-4-yl(methyl)carbamate

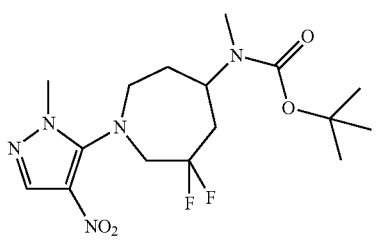 [SMILES: CN(C(=O)OC(C)(C)C)C1CCN(c2c([N+](=O)[O-])cnn2C)CC(F)(F)C1]

To a cooled (ice-water bath) solution of tert-butyl 6,6-difluoro-1-(1-methyl-4-nitro-1H-pyrazol-5-yl)azepan-4-yl-carbamate (190 mg, 0.51 mmol) in THF (10 mL) was added lithium hexamethyldisilazide (1M in THF, 0.8 mL, 0.8 mmol) and the mixture stirred for 30 min. Iodomethane (0.06 mL, 1.02 mmol) was added and the mixture stirred at room temperature for 16 hr. Water (2 mL) was added and the mixture extracted with EtOAc (30 mL). The organic layer was separated, dried over Na$_2$SO$_4$ and the solvent removed under reduced pressure. Purification via silica gel column chromatography (0-70% EtOAc/isohexane) gave tert-butyl 6,6-difluoro-1-(1-methyl-4-nitro-1H-pyrazol-5-yl)azepan-4-yl(methyl)carbamate (180 mg, 90%) as a yellow oil. $^1$H NMR (400 MHz, CDCl$_3$) δ 8.09-7.99 (m, 1H), 4.57-4.38 (m, 1H), 3.85 (s, 3H), 3.84-3.53 (m, 1H), 3.45-3.15 (m, 3H), 2.81 (s, 3H), 2.53-2.29 (m, 2H), 2.16-2.01 (m, 2H), 1.48 (s, 9H).

Intermediate 39

5-Bromo-4-nitro-1-(2,2,2-trifluoroethyl)-1H-pyrazole

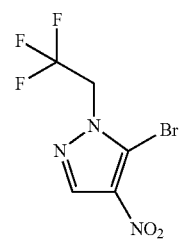

To a stirred solution of 1-(2,2,2-trifluoroethyl)-1H-pyrazol-5-amine (990 mg, 6.0 mmol) in acetic acid (5 mL) was added dropwise acetic anhydride (0.57 mL, 6.0 mmol) and the mixture was stirred at room temperature for 16 hr. More acetic anhydride (0.57 mL, 6.0 mmol) was added to the reaction mixture which was cooled in an ice bath for the addition of fuming nitric acid (0.28 mL, 6 mmol) to take place dropwise. The reaction mixture was stirred at room temperature for 7 hr and the solvent was removed under reduced pressure. The residue was dissolved in EtOH (15 mL) and concentrated hydrochloric acid (10 mL) was added. The mixture was heated at reflux for 16 hr. After concentrating under reduced pressure the residue was partitioned between DCM (50 mL) and 5% aqueous NaHCO$_3$ solution (100 mL). The mixture was filtered and the aqueous layer was extracted with DCM (100 mL). The organic layers were combined, dried over MgSO$_4$ and the solvent removed under reduced pressure to give a pale orange solid (540 mg). This solid (540 mg, 2.57 mmol) was dissolved in bromoform (2.9 mL, 33 mmol) and to the solution was added dropwise tert-butyl nitrite (0.92 mL, 7.71 mmol). The reaction mixture was stirred at room temperature for 15 min and then heated at 145° C. for 1.5 hr. The solvent was removed under reduced pressure and the residue purified by silica gel column chromatography (0-100% EtOAc/isohexane) to give 5-bromo-4-nitro-1-(2,2,2-trifluoroethyl)-1H-pyrazole as a pale yellow solid (536 mg, 33% over four steps). $^1$H NMR (400 MHz, CDCl$_3$) δ 8.30 (s, 1H), 4.86 (q, J=7.8 Hz, 2H).

Intermediate 40

(R)—N-(1-(4-Amino-1-(2,2,2-trifluoroethyl)-1H-pyrazol-5-yl)azepan-4-yl)-2,2,2-trifluoroacetamide

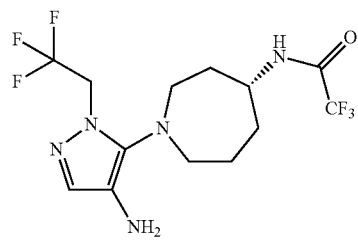 [SMILES: Nc1cnn(CC(F)(F)F)c1N1CCC[C@@H](NC(=O)C(F)(F)F)CC1]

Following the procedure for Intermediate 8 starting from 5-bromo-4-nitro-1-(2,2,2-trifluoroethyl)-1H-pyrazole (150 mg, 0.55 mmol) and (R)—N-(azepan-4-yl)-2,2,2-trifluoroacetamide (115 mg, 0.55 mmol) gave (R)—N-(1-(4-amino-1-(2,2,2-trifluoroethyl)-1H-pyrazol-5-yl)azepan-4-yl)-2,2,2-trifluoroacetamide as a colourless gum (110 mg, 53%). $^1$H NMR (400 MHz, CDCl$_3$) δ 7.25 (s, 1H), 7.11 (br s, 1H), 4.54 (q, J=8.5 Hz, 2H), 4.35-4.22 (m, 1H), 3.40-3.23 (m, 2H), 3.21-3.08 (m, 2H), 2.62 (br s, 2H), 2.17-2.08 (m, 1H), 2.06-1.91 (m, 1H), 1.92-1.71 (m, 4H).

Intermediate 41 tert-Butyl 4-(4-nitro-1-(2,2,2-trifluoroethyl)-1H-pyrazol-5-yl)-1,4-diazepane-1-carboxylate

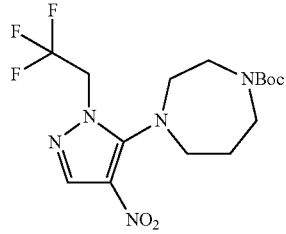 [SMILES: CC(C)(C)OC(=O)N1CCCN(c2c([N+](=O)[O-])cnn2CC(F)(F)F)CC1]

Following the procedure for Intermediate 22 starting from 5-bromo-4-nitro-1-(2,2,2-trifluoroethyl)-1H-pyrazole and tert-butyl 1,4-diazepane-1-carboxylate gave tert-butyl 4-(4-nitro-1-(2,2,2-trifluoroethyl)-1H-pyrazol-5-yl)-1,4-diazepane-1-carboxylate as a pale yellow gum (197 mg, 91%). $^1$H NMR (400 MHz, CDCl$_3$) δ 8.19-8.12 (m, 1H), 4.76-4.66 (m, 2H), 3.65-3.49 (m, 4H), 3.32-3.23 (m, 4H), 1.92-1.78 (m, 2H), 1.52-1.47 (m, 9H).

Intermediate 42

Benzyl 4-hydroxy-5-(2,2,2-trifluoroacetamido)azepane-1-carboxylate

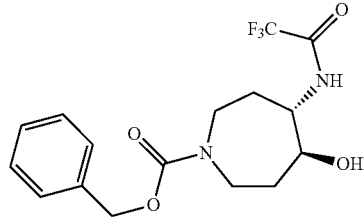 [SMILES: O=C(OCc1ccccc1)N1CC[C@H](NC(=O)C(F)(F)F)[C@@H](O)CC1]

To a solution of benzyl 4-azido-5-hydroxyazepane-1-carboxylate (1.4 g, 4.83 mmol) in THF/water (30 mL/6 mL) was added triphenylphosphine (1.26 g, 4.83 mmol) and the reaction mixture was heated at 60° C. for 16 hr. EtOAc (100 mL) was added and the mixture was washed with water (20 mL). The organic layer was separated, dried over MgSO$_4$ and concentrated under reduced pressure. The resulting oil was triturated in Et$_2$O, the resulting solid was filtered off and the filtrate concentrated under reduced pressure to give a yellow oil. To a solution of this oil in dry DCM (20 mL) at 0° C. was added DIPEA (2.5 mL, 14.4 mmol) and trifluoroacetic anhydride (1.0 mL, 7.22 mmol) took place. The reaction mixture was allowed to warm to room temperature and stirred for 16 hr. Water (20 mL) was added and the mixture extracted with DCM (100 mL). The organic layer was separated, dried over MgSO$_4$ and concentrated under reduced pressure. Purification via silica gel column chromatography (50% EtOAc/isohexane) gave benzyl 4-hydroxy-5-(2,2,2-trifluoroacetamido)azepane-1-carboxylate as a golden-yellow viscous oil (934 mg, 54% over 2 steps). $^1$H NMR (400 MHz, CDCl$_3$) δ 7.40-7.29 (m, 5H), 6.49 (s, 1H), 5.20-5.11 (m, 2H), 3.94-3.25 (m, 6H), 2.35-1.65 (m, 5H).

Intermediate 43

N-(1-(4-Amino-1-methyl-1H-pyrazol-5-yl)-5-hydroxyazepan-4-yl)-2,2,2-trifluoroacetamide

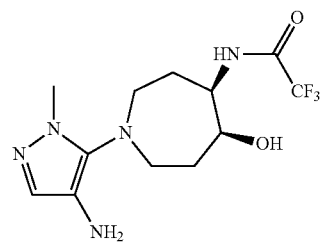 [SMILES: Cn1ncc(N)c1N1CC[C@H](O)[C@H](NC(=O)C(F)(F)F)CC1]

A solution of benzyl 4-hydroxy-5-(2,2,2-trifluoroacetamido)azepane-1-carboxylate (935 mg, 3.0 mmol) in MeOH (100 mL) was passed through the H-Cube® (full H$_2$, 50° C., flow rate: 1 mL/min, 30 mm 10% Pd/C cartridge). The solvent was removed under reduced pressure to give 4-hydroxy-5-(2,2,2-trifluoroacetamido)azepane as a pale yellow solid (514 mg). To a solution of this solid (500 mg, 2.21 mmol) in dry DMSO (10 mL) was added 5-chloro-1-methyl-4-nitro-1H-pyrazole from Example 1 (150 mg, 0.93 mmol) and potassium fluoride (513 mg, 8.85 mmol). The reaction mixture was heated at 65° C. for 16 hr. The mixture was poured into water (200 mL) and extracted with EtOAc (5×50 mL). The combined organic layers were dried over MgSO$_4$ and concentrated under reduced pressure. Purification of the residue by silica gel column chromatography (70% EtOAc/isohexane) gave 2,2,2-trifluoro-N-(5-hydroxy-1-(1-methyl-4-nitro-1H-pyrazol-5-yl)azepan-4-yl)acetamide as a yellow solid (640 mg). A portion of this solid (200 mg, 0.57 mmol) was dissolved in MeOH (25 mL) and passed through the H-Cube® (full H$_2$, 50° C., flow rate: 1 mL/min, 30 mm 10% Pd/C cartridge). The solvent was removed under reduced pressure to give N-(1-(4-amino-1-methyl-1H-pyrazol-5-yl)-5-hydroxyazepan-4-yl)-2,2,2-trifluoroacetamide as an orange foam (172 mg, 68% over 3 steps). $^1$H NMR (400 MHz, DMSO) δ 9.22 (d, J=8.1 Hz, 1H), 6.83 (s, 1H), 4.84 (d, J=5.0 Hz, 1H), 3.91-3.73 (m, 2H), 3.32 (s, 3H), 3.28-2.96 (m, 4H), 2.00-1.75 (m, 4H). Exchangeable NH$_2$ not observed.

Intermediate 44 tert-Butyl 6-hydroxy-6-methyl-4-(1-methyl-4-nitro-1H-pyrazol-5-yl)-1,4-diazepane-1-carboxylate

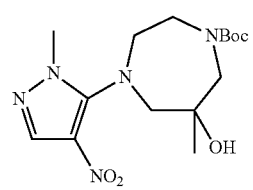 [SMILES: Cn1ncc([N+](=O)[O-])c1N1CCN(C(=O)OC(C)(C)C)CC(C)(O)C1]

To a cooled solution (ice water bath) of di-tert-butyl 6-oxo-1,4-diazepane-1,4-dicarboxylate (570 mg, 1.82 mmol) in THF (10 mL), was added dropwise a solution of methylmagnesium bromide (3 M in Et$_2$O, 0.79 mL, 2.36 mmol). The mixture was allowed to warm to room temperature and stirred for 16 hr. Aqueous saturated ammonium chloride solution (5 mL) was added and the mixture diluted with EtOAc (30 mL) and water (30 mL). The layers were separated and the organic layer was passed through a phase separation cartridge and concentrated under reduced pressure. Purification via silica gel column chromatography (0-70% EtOAc/isohexane) gave di-tert-butyl 6-hydroxy-6-methyl-1,4-diazepane-1,4-dicarboxylate as an oil (0.45 g). To a solution of this oil (0.45 g, 1.36 mmol) in MeOH (2 mL), was added HCl in 1,4-dioxane (4 M, 6.8 mL, 27.3 mmol) and the solution was stirred at room temperature for 16 hr. The solvents were removed under reduced pressure. The residue was dissolved in MeOH and passed through an SCX column washing with MeOH and eluting with 1 N ammonia in MeOH. The solvent was removed under reduced pressure to afford 6-methyl-1,4-diazepan-6-ol as an oil. To this amine in EtOH (3 mL) was added 5-chloro-1-methyl-4-nitro-1H-pyrazole from Example 1 (209 mg, 1.29 mmol) and DIPEA (0.9 mL, 5.44 mmol) and the mixture was heated in the microwave at 130° C. for 3 hr. The solvent was removed under reduced pressure. To the crude tert-butyl 6-hydroxy-6-methyl-4-(1-methyl-4-nitro-1H-pyrazol-5-yl)-1,4-diazepane-1-carboxylate in DCM (10 mL) was added di-tert-butyl dicarbonate (1.18 g, 5.44 mmol) and DIPEA (0.9 mL, 5.44 mmol). The mixture was stirred at room temperature for 16 hr, the solvent was removed under reduced pressure and the residue dissolved in DCM (30 mL). Water (20 mL) was added and the organic layer was separated, dried over Na$_2$SO$_4$ and the solvent removed under reduced pressure. Purification via silica gel column chromatography (0-80% EtOAc/isohexane) gave tert-butyl 6-hydroxy-6-methyl-4-(1-methyl-4-nitro-1H-pyrazol-5-yl)-1,4-diazepane-1-carboxylate (235 mg, 22% over four steps) as yellow oil. $^1$H NMR (400 MHz, CDCl$_3$) δ 8.03 (s, 1H), 4.16-3.79 (m, 7H), 3.52-2.81 (m, 4H), 1.70-1.80 (br s, 1H), 1.51 (s, 9H), 1.16 (s, 3H).

Intermediate 45 tert-Butyl 6-fluoro-6-methyl-4-(1-methyl-4-nitro-1H-pyrazol-5-yl)-1,4-diazepane-1-carboxylate

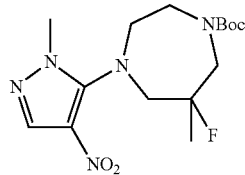

To a solution of tert-butyl 6-hydroxy-6-methyl-4-(1-methyl-4-nitro-1H-pyrazol-5-yl)-1,4-diazepane-1-carboxylate (100 mg, 0.28 mmol) in DCM (5 mL) was added deoxo-Fluor® (50% in THF, 0.26 mL, 0.7 mmol) and the mixture was stirred at room temperature for 18 hr. The mixture was diluted with DCM (30 mL), cooled in an ice water bath and quenched by dropwise addition of saturated aqueous NaHCO$_3$ (40 mL). The resulting mixture was stirred for 10 min. The organic layer was separated, dried over Na$_2$SO$_4$ and the solvent removed under reduced pressure. The crude product was purified via silica gel column chromatography (0-50% EtOAc/isohexane) to give tert-butyl 6-fluoro-6-methyl-4-(1-methyl-4-nitro-1H-pyrazol-5-yl)-1,4-diazepane-1-carboxylate (70 mg, 70%) as a clear colorless oil. $^1$H NMR (400 MHz, CDCl$_3$) δ 8.03 (s, 1H), 3.80 (s, 3H), 3.73-3.32 (m, 6H), 3.26-3.03 (m, 2H), 1.50 (s, 9H), 1.32 (d, J=20.1 Hz, 3H).

Intermediate 46 tert-Butyl 6,6-difluoro-4-(4-nitro-1-((2-(trimethylsilyl)ethoxy)methyl)-1H-pyrazol-5-yl)-1,4-diazepane-1-carboxylate

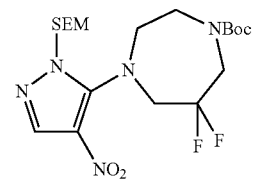 [SMILES: CC(C)(C)OC(=O)N1CCN(c2c([N+](=O)[O-])cnn2COCC[Si](C)(C)C)CC(F)(F)C1]

5-Chloro-4-nitro-1-(2-(trimethylsilyl)ethoxy)methyl)-1H-pyrazole (815 mg, 2.93 mmol), 1,4-diazepan-6-ol (510 mg, 4.39 mmol) and DIPEA (2.55 mL, 14.6 mmol) were combined in EtOH (10 mL) and heated in the microwave at 130° C. for 1 hr and the solvents were removed under reduced pressure to give 1-(4-nitro-1-((2-(trimethylsilyl)ethoxy)methyl)-1H-pyrazol-5-yl)-1,4-diazepan-6-ol. To this amine was added di-tert-butyl dicarbonate (2.56 g, 11.7 mmol) and DIPEA (2.55 mL, 14.6 mmol). After stirring at room temperature for 16 hr, the solvent was removed under reduced pressure and the residue dissolved in DCM (30 mL). Water (20 mL) was added and the organic layer was separated, dried over Na$_2$SO$_4$ and the solvent removed under reduced pressure. Purification via silica gel column chromatography (0-50% EtOAc/isohexane) gave tert-butyl 6-hydroxy-4-(4-nitro-1-((2-(trimethylsilyl)ethoxy)methyl)-1H-pyrazol-5-yl)-1,4-diazepane-1-carboxylate as an oil (590 mg). To a solution of this oil (570 mg, 1.26 mmol) in DCM (10 mL) was added portionwise Dess-Martin periodinane (0.68 g, 1.51 mmol). After stirring at room temperature for 16 hr, the mixture was diluted with DCM and quenched with saturated aqueous NaHCO$_3$ (40 mL) followed by 20% aqueous sodium thiosulphate (30 mL). The resulting mixture was stirred for 20 min. The organic layer was separated, dried over Na$_2$SO$_4$ and the solvent removed under reduced pressure. Purification via silica gel column chromatography (0-50% EtOAc/isohexane) gave tert-butyl 4-(4-nitro-1-(2-(trimethylsilyl)ethoxy)methyl)-1H-pyrazol-5-yl)-6-oxo-1,4-diazepane-1-carboxylate (0.36 g) as an oil. To a solution of this oil (0.35 g, 0.76 mmol) in DCM (5 mL) was added deoxo-Fluor® (50% in THF, 0.69 mL, 1.91 mmol) and the mixture was stirred at room temperature for 16 hr. The mixture was diluted with DCM (30 mL), cooled in an ice/water bath and quenched by dropwise addition of saturated aqueous NaHCO$_3$ (30 mL). The resulting mixture was stirred for 10 min. The organic layer was separated, dried over Na$_2$SO$_4$ and the solvent removed under reduced pressure. The crude product was purified via silica gel column chromatography (0-50% EtOAc/isohexane) to give tert-butyl 6,6-difluoro-4-(4-nitro-1-((2-(trimethylsilyl)ethoxy)methyl)-1H-pyrazol-5-yl)-1,4-diazepane-1-carboxylate (280 mg, 19% over four steps) as a yellow oil. $^1$H NMR (400 MHz, CDCl$_3$) δ 8.12-8.03 (m, 1H), 5.61-5.34 (m, 2H), 4.01-3.41 (m, 6H), 3.59-3.09 (m, 4H), 1.67-1.34 (m, 9H), 0.94-0.86 (m, 2H), SiMe₃ masked by internal standard TMS peak.

Intermediate 47 tert-Butyl 6-methoxy-4-(1-methyl-4-nitro-1H-pyrazol-5-yl)-1,4-diazepane-1-carboxylate

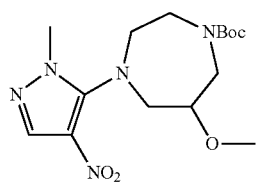

A solution of 5-chloro-1-methyl-4-nitro-1H-pyrazole from Example 1 (1.62 g, 10.0 mmol), 1,4-diazepan-6-ol (4.18 g, 15.0 mmol) and DIPEA (6.6 mL) in EtOH (6 mL) was heated at 130° C. in a microwave for 3 hr. The solvent was removed under reduced pressure and the residue dissolved in DCM (60 mL) and DMF (10 mL). Di-tert-butyl dicarbonate (8.73 g, 40 mmol) and DIPEA (3.48 mL) were added and the mixture stirred at room temperature for 16 hr. The solvent was removed under reduced pressure and the residue purified by silica gel column chromatography (0-100% EtOAc/isohexane) to give tert-butyl 6-hydroxy-4-(1-methyl-4-nitro-1H-pyrazol-5-yl)-1,4-diazepane-1-carboxylate as a yellow oil (2.13 g). To a solution of this oil (205 mg, 0.6 mmol) in THF (5 ml) at 0° C. was added sodium hydride (60% in mineral oil, 24 mg, 0.6 mmol). After 30 min, iodomethane (0.04 mL, 0.6 mmol) was added and the resulting mixture allowed to warm to room temperature over 1.5 hr. The mixture was diluted with DCM (20 mL) and washed with water (20 ml) and saturated aqueous NaHCO₃ (20 mL). The organic layer was separated, passed through a phase separation cartridge and concentrated under reduced pressure. Purification via silica gel column chromatography (0-100% EtOAc/isohexane) gave tert-butyl 6-methoxy-4-(1-methyl-4-nitro-1H-pyrazol-5-yl)-1,4-diazepane-1-carboxylate as a yellow gum (116 mg, 33% over two steps). LCMS (ES+) m/z 356 (M+1).

Intermediate 48

5-Azido-1-(1-methyl-4-nitro-1H-pyrazol-5-yl)azepan-4-ol

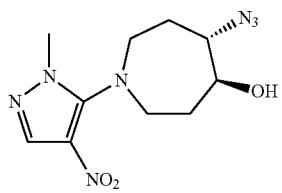 [SMILES: Cn1ncc([N+](=O)[O-])c1N1CC[C@H](N=[N+]=[N-])[C@@H](O)CC1]

Trifluoroacetic acid (20 mL) was added to a solution of tert-butyl 4-azido-5-hydroxyazepane-1-carboxylate (7.43 g, 29.0 mmol) in DCM (70 mL) and the mixture heated behind a blast shield at 35° C. for 4 hr. The solvents were removed under reduced pressure and the residue re-dissolved in MeOH and passed through an SCX column, washing with DCM and MeOH and eluting with 3-10% 7 N ammonia in MeOH/DCM to give 5-azidoazepan-4-ol as a yellow oil (4.38 g, 28.0 mmol) which was dissolved in dry DMSO (100 mL). 5-Chloro-1-methyl-4-nitro-1H-pyrazole from Example 1 (5.20 g, 32.2 mmol) and potassium fluoride (6.51 g, 112 mmol) were added. The mixture was heated at 70° C. for 16 hr, allowed to cool to room temperature, poured into water (1000 mL) and extracted into EtOAc (4×250 mL). The combined organic layers were passed through a phase separation cartridge and concentrated under reduced pressure. Purification via silica gel column chromatography (0-100% EtOAc/isohexane) gave 5-azido-1-(1-methyl-4-nitro-1H-pyrazol-5-yl)azepan-4-ol as a yellow gum (7.27 g, 77% over two steps). ¹H NMR (400 MHz, CDCl₃) δ 8.04 (s, 1H), 3.94-3.66 (m, 4H), 3.65 (td, J=9.7, 3.8 Hz, 1H), 3.44-3.18 (m, 4H), 2.50 (d, J=2.8 Hz, 1H), 2.24-2.12 (m, 2H), 2.02-1.89 (m, 2H).

Intermediate 48a

4-Azido-5-fluoro-1-(1-methyl-4-nitro-1H-pyrazol-5-yl)azepane

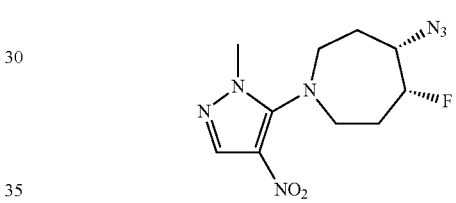

To a solution of 5-azido-1-(1-methyl-4-nitro-1H-pyrazol-5-yl)azepan-4-ol (4.0 g, 14.2 mmol) in dry DCM (100 mL) cooled to 0° C. was added slowly triethylamine (4.0 mL, 28.5 mmol) followed by DMAP (175 mg, 1.42 mmol) and 4-methylbenzene-1-sulfonyl chloride (4.1 g, 21.4 mmol) portionwise. The reaction mixture was allowed to warm to room temperature and stirred for 18 hr. More 4-methylbenzene-1-sulfonyl chloride (1.4 g, 7.12 mmol) was added to the reaction mixture, which was stirred at room temperature for a further 24 hr. Water (40 mL) was added and the mixture was extracted with DCM (100 mL). The organic layer was separated, dried over MgSO₄ and the solvent removed under reduced pressure. Purification via silica gel column chromatography (30-70% EtOAc/isohexane) gave 5-azido-1-(1-methyl-4-nitro-1H-pyrazol-5-yl)azepan-4-yl 4-methylbenzenesulfonate as a dark cream solid (2.81 g). This solid (2.3 g, 5.29 mmol) was treated with a solution of TBAF (1.0 M in THF, 21 mL, 21.1 mmol) and the reaction mixture was heated at 60° C. for 2 hr. After cooling to room temperature, water (30 mL) was added and the mixture was extracted with EtOAc (2×150 mL). The combined organic layers were dried over MgSO₄ and concentrated under reduced pressure. Purification via silica gel column chromatography (30-40% EtOAc/isohexane) gave 4-azido-5-fluoro-1-(1-methyl-4-nitro-1H-pyrazol-5-yl)azepane as a yellow viscous oil (804 mg, 20% over two steps) ¹H NMR (400 MHz, CDCl₃) δ 8.04 (s, 1H), 5.06 (ddt, J=46.2, 8.1, 2.5 Hz, 1H), 4.00 (dd, J=20.8, 8.1 Hz, 1H), 3.79 (s, 3H), 3.43-3.34 (m, 2H), 3.26-3.11 (m, 2H), 2.43-2.30 (m, 1H), 2.30-2.18 (m, 1H), 2.12-1.92 (m, 2H).

Intermediate 49

N-((4S,5S)-1-(4-amino-1-methyl-1H-pyrazol-5-yl)-5-fluoroazepan-4-yl)-2,2,2-trifluoroacetamide

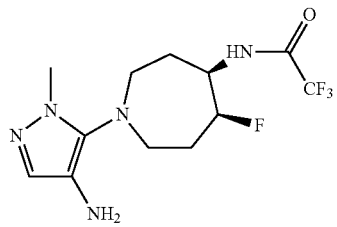 [SMILES: Cn1ncc(N)c1N1CC[C@H](F)[C@H](NC(=O)C(F)(F)F)CC1]

To a solution of 5-azido-1-(1-methyl-4-nitro-1H-pyrazol-5-yl)azepan-4-ol (7.26 g, 25.8 mmol) in dry DCM (100 ml) was added dropwise deoxo-Fluor® (12.1 mL, 32.84 mmol, 50% in THF) and the mixture was stirred at room temperature for 16 hr. The mixture was cooled in an ice bath and saturated aqueous NaHCO₃ solution (40 mL) was added slowly (effervescence observed) and the mixture was extracted with DCM (150 mL). The organic layer was washed with saturated aqueous NaHCO₃ solution (2×30 mL), separated, passed through a phase separation cartridge and concentrated under reduced pressure. The residue was purified via silica gel column chromatography (0-100% EtOAc/isohexane) to give 4-azido-5-fluoro-1-(1-methyl-4-nitro-1H-pyrazol-5-yl)azepane as a yellow gum (5.55 g). The reaction was repeated to provide additional material. A solution of this gum (6.40 g, 22.6 mmol) in THF/water (120 mL/24 mL) was treated with triphenylphosphine (5.93 g, 22.6 mmol) and the mixture was heated at 60° C. for 16 hr. The mixture was partitioned between EtOAc (150 mL) and water (20 mL) and the organic layer was separated, washed with brine (20 mL), passed through a phase separation cartridge and concentrated under reduced pressure. The residue was re-dissolved in MeOH and passed through an SCX column, washing with MeOH and eluting with 3-10% 7 N ammonia in MeOH/DCM to give 5-fluoro-1-(1-methyl-4-nitro-1H-pyrazol-5-yl)azepan-4-amine as a yellow oil (5.70 g). To a solution of this oil (5.7 g, 22.1 mmol) and DIPEA (11.5 mL, 66.3 mmol) in DCM (50 mL) was added dropwise trifluoroacetic anhydride (3.38 mL, 24.3 mmol) and the mixture stirred at room temperature for 16 hr. Water (15 mL) was added and the organic phase separated, passed through a phase separation cartridge and concentrated under reduced pressure to give 2,2,2-trifluoro-N-(5-fluoro-1-(1-methyl-4-nitro-1H-pyrazol-5-yl)azepan-4-yl)acetamide as a yellow gum (7.8 g). To a solution of this gum (7.8 g, 22.0 mmol) and ammonium formate (10.23 g, 176.0 mmol) in MeOH (100 mL) under nitrogen was added 10% palladium on carbon (585 mg, 5.5 mmol). The mixture was heated at 70° C. for 4 hr before being cooled, filtered and concentrated under reduced pressure. The residue was partitioned between water (20 mL) and DCM (100 mL) and the organic layer was separated, passed through a phase separation cartridge and concentrated under reduced pressure to give N-((4S,5S)-1-(4-amino-1-methyl-1H-pyrazol-5-yl)-5-fluoroazepan-4-yl)-2,2,2-trifluoroacetamide as a brown solid (4.72 g, 49% over four steps). ¹H NMR (400 MHz, CDCl₃) δ 9.03 (s, 1H), 7.19 (s, 1H), 4.90-4.76 (m, 2H), 3.66 (s, 3H), 3.52-3.43 (m, 2H), 3.12 (td, J=11.9, 5.4 Hz, 1H), 2.96 (dt, J=14.8, 4.2 Hz, 1H), 2.43-2.31 (m, 1H), 2.13-1.85 (m, 3H). Exchangeable NH₂ not observed.

Intermediate 49a

N-((4S,5R)-1-(4-amino-1-methyl-1H-pyrazol-5-yl)-5-fluoroazepan-4-yl)-2,2,2-trifluoroacetamide

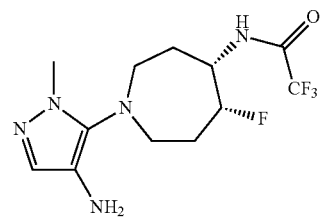 [SMILES: Cn1ncc(N)c1N1CC[C@@H](F)[C@@H](NC(=O)C(F)(F)F)CC1]

A solution of 4-azido-5-fluoro-1-(1-methyl-4-nitro-1H-pyrazol-5-yl)azepane (1.4 g, 4.95 mmol) in THF/water (30 mL/6 mL) was treated with triphenylphosphine (1.3 g, 4.95 mmol) and the mixture was heated at 60° C. behind a blast screen for 4 hr. The mixture was partitioned between EtOAc (200 mL) and saturated aqueous NaHCO₃ solution (30 mL). The aqueous layer was extracted with EtOAc (50 mL) and the combined organic layers were dried over MgSO₄ and concentrated under reduced pressure. The resulting oil was triturated with diethyl ether, the resulting solid was filtered off and the filtrate concentrated under reduced pressure to give 5-fluoro-1-(1-methyl-4-nitro-1H-pyrazol-5-yl)azepan-4-amine contaminated with triphenylphosphine oxide as a yellow oil. To a solution of this oil (1.27 g, 4.95 mmol) in dry DCM (40 mL) at 0° C. was added slowly DIPEA (2.6 mL, 14.8 mmol) followed by trifluoroacetic anhydride (0.83 ml, 5.94 mmol) dropwise. The reaction mixture was allowed to warm to room temperature and stirred for 18 hr. Water (40 mL) was added and the mixture was extracted with DCM (150 mL). The organic layer was separated, dried over MgSO₄ and concentrated under reduced pressure. Purification via silica gel column chromatography (40% EtOAc/isohexane) gave 2,2,2-trifluoro-N-(5-fluoro-1-(1-methyl-4-nitro-1H-pyrazol-5-yl)azepan-4-yl)acetamide as a yellow viscous oil (1.4 g). To a solution of this oil (1.4 g, 3.97 mmol) and ammonium formate (2.5 g, 39.7 mmol) in MeOH (40 mL) under nitrogen was added 10% palladium on carbon (140 mg). The mixture was heated at 70° C. for 30 min before being cooled, filtered and concentrated under reduced pressure. The residue was partitioned between water (30 mL) and DCM (75 mL). The aqueous layer was extracted with DCM (2×75 mL) and the combined organic layers were separated, dried over MgSO₄ and concentrated under reduced pressure to give N-((4S,5R)-1-(4-amino-1-methyl-1H-pyrazol-5-yl)-5-fluoroazepan-4-yl)-2,2,2-trifluoroacetamide as an orange-yellow glass (1.1 g, 69% over three steps). ¹H NMR (400 MHz, CDCl₃) δ 7.47 (s, 1H), 7.12 (s, 1H), 5.02-4.85 (m, 1H), 4.69-4.55 (m, 1H), 3.66 (s, 3H), 3.42-3.20 (m, 3H), 3.11 (ddd, J=14.4, 6.7, 3.3 Hz, 1H), 2.36-2.22 (m, 1H), 2.23-1.94 (m, 2H), 1.90-1.82 (m, 1H). NH₂ not observed.

Intermediate 49b

5-Azido-1-(1-methyl-4-nitro-1H-pyrazol-5-yl)azepan-4-ol

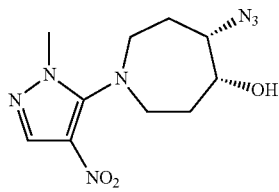 [SMILES: Cn1ncc([N+](=O)[O-])c1N1CC[C@@H](O)[C@@H](N=[N+]=[N-])CC1]

To a solution of anti-5-azido-1-(1-methyl-4-nitro-1H-pyrazol-5-yl)azepan-4-ol (1.75 g, 6.23 mmol) in DCM (40 mL) was added by portions Dess-Martin periodinane (3.2 g, 7.47 mmol). An exotherm was observed so the mixture was cooled in a cold water bath. The reaction mixture was stirred at room temperature for 18 hr. Saturated aqueous NaHCO$_3$ solution (50 mL) was added and the mixture was extracted with DCM (200 mL). The organic layer was washed sequentially with saturated aqueous sodium thiosulfate solution (2×50 mL) and saturated aqueous NaHCO$_3$ solution (2×50 mL). The organic layer was separated, dried over MgSO$_4$ and the solvent removed under reduced pressure. Purification via silica gel column chromatography (30-60% EtOAc/isohexane) gave 5-azido-1-(1-methyl-4-nitro-1H-pyrazol-5-yl)azepan-4-one as a yellow solid (1.55 g). To a solution of this solid (1.5 g, 5.38 mmol) in dry THF (40 mL) under nitrogen cooled to −78° C. was added dropwise a solution of L-SELECTRIDE® (1 M in THF, 6.5 mL, 6.45 mmol) and the reaction mixture was stirred at −78° C. for 90 min. The mixture was allowed to warm to room temperature and water (30 mL) was added. The mixture was extracted with EtOAc (2×100 mL) and the combined organic layers were dried over MgSO$_4$ and concentrated under reduced pressure. Purification via silica gel column chromatography (50-70% EtOAc/isohexane) gave syn-5-azido-1-(1-methyl-4-nitro-1H-pyrazol-5-yl)azepan-4-ol as an orange-yellow oil (845 mg, 50% over two steps). $^1$H NMR (400 MHz, CDCl$_3$) δ 8.07-8.01 (m, 1H), 4.21-4.16 (m, 1H), 3.98-3.92 (m, 1H), 3.80 (s, 2H), 3.44-3.30 (m, 2H), 3.28-3.19 (m, 1H), 3.14 (ddd, J=13.3, 7.4, 4.0 Hz, 1H), 2.33-2.22 (m, 1H), 2.21-2.09 (m, 1H), 2.07 (d, J=5.1 Hz, 1H), 2.01-1.86 (m, 2H). OH not observed.

Intermediate 49c tert-Butyl 5-methoxy-1-(1-methyl-4-nitro-1H-pyrazol-5-yl)azepan-4-ylcarbamate

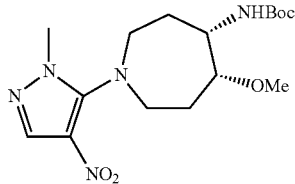

To a solution of 5-azido-1-(1-methyl-4-nitro-1H-pyrazol-5-yl)azepan-4-ol (420 mg, 1.49 mmol) in dry DMF (15 mL) cooled to 0° C. was added sodium hydride (60% in mineral oil, 90 mg, 2.24 mmol). After stirring for 15 min, iodomethane (0.14 mL, 2.24 mmol) was added and the reaction mixture was allowed to warm to room temperature and stirred for 1 hr. Water (20 mL) was added and the mixture was extracted with EtOAc (150 mL). The organic layer was washed with water (6×30 mL) and brine (20 mL), separated, dried over MgSO$_4$, and concentrated under reduced pressure. Purification via silica gel column chromatography gave 4-azido-5-methoxy-1-(1-methyl-4-nitro-1H-pyrazol-5-yl)azepane as a yellow oil (350 mg). A solution of this oil (350 mg, 1.19 mmol) in THF/water (15 mL/3 mL) was treated with triphenylphosphine (311 mg, 1.19 mmol) and the reaction mixture was heated at 60° C. behind a blast screen for 18 hr. Water (2 mL) was added and the mixture was extracted with EtOAc (2×50 mL) The combined organic layers were dried over MgSO$_4$ and concentrated under reduced pressure. The resulting oil was triturated in Et$_2$O, the resulting solid was filtered off and the filtrate concentrated under reduced pressure to give a yellow oil. To a solution of this oil (319 mg, 1.19 mmol) in dry DCM (10 mL) at 0° C. was added a solution of di-tert-butyl-dicarbonate (310 mg, 1.42 mmol) in DCM (10 mL) and DIPEA (1.0 mL, 5.93 mmol). The reaction mixture was allowed to warm to room temperature and stirred for 72 hr. Water (20 mL) was added and the mixture extracted with DCM (100 mL). The organic layer was separated, dried over MgSO$_4$ and concentrated under reduced pressure. Purification via silica gel column chromatography (40-50% EtOAc/isohexane) gave tert-butyl 5-methoxy-1-(1-methyl-4-nitro-1H-pyrazol-5-yl)azepan-4-ylcarbamate as a yellow oil (355 mg, 64% over three steps). $^1$H NMR (400 MHz, CDCl$_3$) δ 8.02 (s, 1H), 5.14 (d, J=8.9 Hz, 1H), 4.00-3.90 (m, 1H), 3.78 (s, 3H), 3.68-3.60 (m, 1H), 3.48 (t, J=12.6 Hz, 1H), 3.39 (s, 3H), 3.33-3.23 (m, 1H), 3.19-3.11 (m, 1H), 3.04-2.95 (m, 1H), 2.25-2.06 (m, 2H), 1.88-1.76 (m, 2H), 1.45 (s, 9H).

Intermediate 49d tert-Butyl 5-hydroxy-1-(1-methyl-4-nitro-1H-pyrazol-5-yl)azepan-4-ylcarbamate

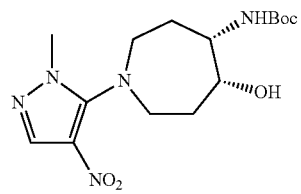 [SMILES: Cn1ncc([N+](=O)[O-])c1N1CC[C@@H](O)[C@@H](NC(=O)OC(C)(C)C)CC1]

A solution of syn-5-azido-1-(1-methyl-4-nitro-1H-pyrazol-5-yl)azepan-4-ol (420 mg, 1.49 mmol) in THF/water (15 mL/3 mL) was treated with triphenylphosphine (392 mg, 1.49 mmol) and the reaction mixture was heated at 60° C. for 9 hr. Brine (5 mL) was added and the mixture was extracted with EtOAc (2×75 mL) The combined organic layers were dried over MgSO$_4$ and concentrated under reduced pressure. The resulting oil was triturated with Et$_2$O, the resulting solid was filtered off and the filtrate concentrated under reduced pressure to give a yellow solid. To a solution of this solid in dry DCM (10 mL) was added a solution of di-tert-butyl-dicarbonate (391 mg, 1.79 mmol) in DCM (10 mL) and DIPEA (1.3 mL, 7.47 mmol). The reaction mixture was allowed to warm to room temperature and stirred for 18 hr. Water (10 mL) was added and the mixture extracted with DCM (100 mL). The organic layer was separated, dried over MgSO$_4$ and concentrated under reduced pressure. Purification via silica gel column chromatography (60-75% EtOAc/isohexane) gave tert-butyl 5-hydroxy-1-(1-methyl-4-nitro-1H-pyrazol-5-yl)azepan-4-ylcarbamate contaminated with triphenylphosphine oxide as a yellow oil (172 mg). ¹H NMR (400 MHz, CDCl₃) δ 8.03 (s, 1H), 5.20 (br s, 1H), 4.19 (br s, 1H), 3.98-3.90 (m, 1H), 3.79 (s, 3H), 3.52-3.42 (m, 1H), 3.34-3.05 (m, 3H), 2.72 (br s, 1H), 2.23-2.10 (m, 1H), 2.04-1.95 (m, 2H), 1.92-1.80 (m, 1H), 1.46 (s, 9H).

Intermediate 50

5-Azido-1-(1-(2,2-difluoroethyl)-4-nitro-1H-pyrazol-5-yl)azepan-4-ol

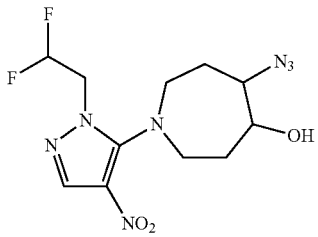 [SMILES: [N-]=[N+]=NC1CCN(c2c([N+](=O)[O-])cnn2CC(F)F)CCC1O]

Following the procedure for Intermediate 48 starting from tert-butyl 4-azido-5-hydroxyazepane-1-carboxylate and 5-chloro-1-(2,2-difluoroethyl)-4-nitro-1H-pyrazole gave 5-azido-1-(1-(2,2-difluoroethyl)-4-nitro-1H-pyrazol-5-yl)azepan-4-ol as a yellow gum (1.16 g, 50% over two steps). ¹H NMR (400 MHz, CDCl₃) δ 8.14-8.09 (m, 1H), 6.11 (tt, J=27.8, 4.4 Hz, 1H), 4.50-4.39 (m, 2H), 3.83 (tt, J=8.8, 3.1 Hz, 1H), 3.67 (td, J=4.7, 3.6 Hz, 1H), 3.45-3.21 (m, 4H), 2.37 (d, J=2.9 Hz, 1H), 2.25-2.12 (m, 2H), 2.03-1.91 (m, 2H).

Intermediate 51

N-(1-(4-amino-1-(2,2-difluoroethyl)-1H-pyrazol-5-yl)-5-fluoroazepan-4-yl)-2,2,2-trifluoroacetamide

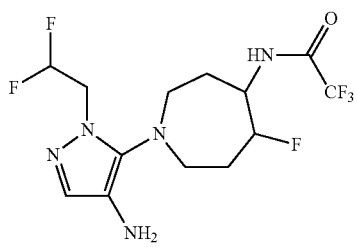 [SMILES: Nc1cnn(CC(F)F)c1N1CCC(F)C(NC(=O)C(F)(F)F)CC1]

Following the procedure for Intermediate 49 starting from 5-azido-1-(1-(2,2-difluoroethyl)-4-nitro-1H-pyrazol-5-yl)azepan-4-ol gave N-(1-(4-amino-1-(2,2-difluoroethyl)-1H-pyrazol-5-yl)-5-fluoroazepan-4-yl)-2,2,2-trifluoroacetamide as a red gum (720 mg, 50% over four steps). LCMS (ES+) m/z 374 (M+1).

Intermediate 52

6,6-Difluoro-N,N-dimethyl-1-(1-methyl-4-nitro-1H-pyrazol-5-yl)azepan-4-amine

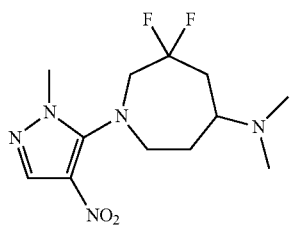 [SMILES: CN(C)C1CCN(c2c([N+](=O)[O-])cnn2C)CC(F)(F)C1]

To a solution of tert-butyl 6,6-difluoro-1-(1-methyl-4-nitro-1H-pyrazol-5-yl)azepan-4-ylcarbamate (0.96 g, 2.56 mmol) in MeOH (3 mL) was added HCl in 1,4-dioxane (4 M, 12.8 mL, 51.2 mmol) and the solution was stirred at room temperature for 16 hr. The solvents were removed under reduced pressure and the residue was dissolved in DCM (30 mL). The organic layer was washed with saturated aqueous NaHCO₃ solution (30 mL), dried over Na₂SO₄ and the solvent removed under reduced pressure to give 6,6-difluoro-1-(1-methyl-4-nitro-1H-pyrazol-5-yl)azepan-4-amine. This amine was dissolved in MeOH/THF (1:1, 50 mL) and treated with formaldehyde (38% in water, 0.45 mL, 6.21 mmol). After 5 min, sodium cyanoborohydride (0.39 g, 6.21 mmol) was added portionwise and the resulting mixture stirred for 5 hr. Additional formaldehyde (38% in water, 0.45 mL, 6.21 mmol) and sodium cyanoborohydride (0.39 g, 6.21 mmol) were added and the resulting mixture was stirred for 60 hr. The solvents were removed under reduced pressure and the crude was purified via silica gel column chromatography (0-10% MeOH/DCM) to give 6,6-difluoro-N,N-dimethyl-1-(1-methyl-4-nitro-1H-pyrazol-5-yl)azepan-4-amine as a yellow oil (0.64 g, 82% over two steps). ¹H NMR (400 MHz, CDCl₃) δ 8.07-8.03 (m, 1H), 3.82 (s, 3H), 3.70-3.57 (m, 2H), 3.42-3.29 (m, 1H), 3.24-3.05 (m, 1H), 3.04-2.98 (m, 1H), 2.51-2.40 (m, 1H), 2.35-2.29 (m, 6H), 2.20-2.01 (m, 2H), 1.97-1.82 (m, 1H).

Intermediate 53 tert-Butyl 6-methoxy-1-(1-methyl-4-nitro-1H-pyrazol-5-yl)azepan-4-ylcarbamate

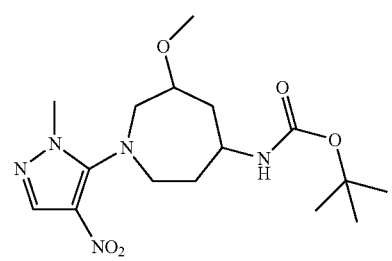 [SMILES: COC1CC(NC(=O)OC(C)(C)C)CCN(c2c([N+](=O)[O-])cnn2C)C1]

To a solution of 5-azido-1-(1-methyl-4-nitro-1H-pyrazol-5-yl)azepan-3-ol, Intermediate 18 (0.85 g, 3.0 mmol) in DMF (5 mL) cooled to 0° C. under nitrogen, was added sodium hydride (60% in mineral oil, 133 mg, 3.3 mmol) and the resulting mixture was stirred for 10 min. Iodomethane (0.37 mL, 6.0 mmol) was added and the mixture stirred at room temperature for 16 hr. Water (200 mL) was added and the mixture extracted with EtOAc (2×50 mL). The combined organic layers were dried over $Na_2SO_4$ and the solvent removed under reduced pressure. Purification via silica gel column chromatography (0-50% EtOAc/isohexane) gave 5-azido-3-methoxy-1-(1-methyl-4-nitro-1H-pyrazol-5-yl)azepane as an oil (0.76 g). This azide (0.76 g, 2.6 mmol) in THF (15 mL) and water (3 mL) was treated with triphenylphosphine (0.71 g, 2.7 mmol). The mixture was heated at 65° C. for 16 hr and the solvents were removed under reduced pressure to afford 6-methoxy-1-(1-methyl-4-nitro-1H-pyrazol-5-yl)azepan-4-amine. This amine was suspended in DCM (40 mL) and di-tert-butyl dicarbonate (1.13 g, 5.2 mmol) and DIPEA (1.36 mL, 7.8 mmol) were added. After stirring at room temperature for 16 hr the solvent was removed under reduced pressure and the residue dissolved in DCM (40 mL). Water (20 ml) was added and the organic layer was separated, dried over $Na_2SO_4$ and the solvent removed under reduced pressure. Purification via silica gel column chromatography (0-50% EtOAc/isohexane) gave tert-butyl 6-methoxy-1-(1-methyl-4-nitro-1H-pyrazol-5-yl)azepan-4-ylcarbamate (0.84 g, 74% over three steps) as an oil. $^1$H NMR (400 MHz, $CDCl_3$) δ 8.03 (d, J=4.3 Hz, 1H), 5.39 (d, J=7.9 Hz, 1H), 4.21-3.94 (m, 1H), 3.84 (s, 3H), 3.56-3.42 (m, 2H), 3.35-3.03 (m, 6H), 2.28-1.89 (m, 4H), 1.46 (s, 9H).

Intermediate 53a

N-(1-(4-Amino-1-cyclopropyl-1H-pyrazol-5-yl)-6-fluoroazepan-4-yl)-2,2,2-trifluoroacetamide

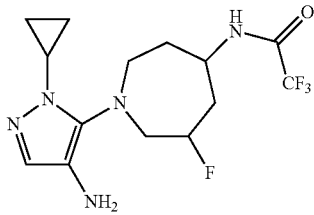 [SMILES: Nc1cnn(C2CC2)c1N1CCC(NC(=O)C(F)(F)F)CC(F)C1]

To a solution of 5-azido-1-(1-cyclopropyl-4-nitro-1H-pyrazol-5-yl)azepan-3-ol (0.69 g, 2.25 mmol) in DCM (30 mL) was added deoxo-Fluor® (50% in THF, 1.06 mL, 2.86 mmol) and the mixture was stirred at room temperature for 62 hr. The mixture was diluted with DCM (30 mL), cooled in an ice/water bath and quenched by dropwise addition of saturated aqueous $NaHCO_3$ (100 mL). The resulting mixture was stirred for 10 min. The organic layer was separated, passed through a phase separation cartridge and the solvent removed under reduced pressure. Purification via silica gel column chromatography (0-100% EtOAc/isohexane) gave 5-azido-1-(1-cyclopropyl-4-nitro-1H-pyrazol-5-yl)-3,3-difluoroazepane (410 mg) as a viscous yellow oil. To a solution of this oil (400 mg, 1.3 mmol) in THF (10 mL) and water (2 mL) was added triphenylphosphine (341 mg, 1.3 mmol) and the mixture was heated at 60° C. behind a blast screen for 16 hr. The mixture was diluted with EtOAc (30 mL) and washed with water (3×20 mL). The organic layer was separated, passed through a phase separation cartridge and the solvents removed under reduced pressure. The residue was passed through an SCX column washing with DCM and MeOH and eluting with 3-10% 1 N ammonia in MeOH/DCM to afford 1-(1-cyclopropyl-4-nitro-1H-pyrazol-5-yl)-6,6-difluoroazepan-4-amine (555 mg) contaminated with triphenylphosphine oxide) as a viscous yellow oil. To a solution of this oil (360 mg, 1.28 mmol) and DIPEA (0.67 mL, 3.84 mmol) in DCM (20 mL) was added trifluoroacetic anhydride (0.2 mL, 1.41 mmol) and the mixture stirred at room temperature for 16 hr. The organic layer was washed with water (2×20 mL), separated and passed through a phase separation cartridge. The solvent was removed under reduced pressure and the residue purified via silica gel column chromatography (0-100% EtOAc/isohexane) to give N-(1-(1-cyclopropyl-4-nitro-1H-pyrazol-5-yl)-6-fluoroazepan-4-yl)-2,2,2-trifluoroacetamide (280 mg) as a viscous yellow oil.

To a solution of this oil (276 mg, 0.73 mmol) and ammonium formate (340 mg, 5.84 mmol) in MeOH (15 mL) under nitrogen was added 10% palladium on carbon (31 mg, 0.29 mmol). The mixture was heated at 80° C. for 4 hr before being cooled, filtered and concentrated under reduced pressure. The residue was partitioned between water (10 mL) and DCM (50 mL). The organic layer was separated, passed through a phase separation cartridge and concentrated under reduced pressure to give N-(1-(4-amino-1-cyclopropyl-1H-pyrazol-5-yl)-6-fluoroazepan-4-yl)-2,2,2-trifluoroacetamide (210 mg, 28% over 4 steps) as a viscous red oil. LCMS (ES+) m/z 350 (M+1).

Intermediate 54

N-(1-(4-Amino-1-methyl-1H-pyrazol-5-yl)-5-methoxyazepan-4-yl)-2,2,2-trifluoroacetamide

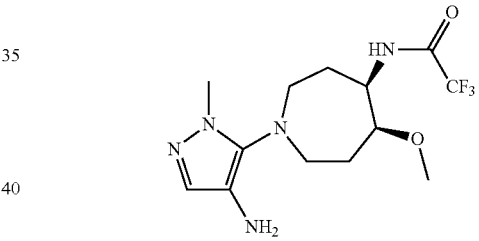

To a solution of 5-azido-1-(1-methyl-4-nitro-1H-pyrazol-5-yl)azepan-4-ol (500 mg, 1.78 mmol) in dry DMF (15 mL) cooled to 0° C. was added sodium hydride (60% in mineral oil, 107 mg, 2.67 mmol). After stirring for 15 min, iodomethane (0.17 mL, 2.67 mmol) was added and the reaction mixture was allowed to warm to room temperature and stirred for 90 min. Water (20 mL) was added and the mixture was extracted with EtOAc (200 mL), washed with water (6×20 mL) and brine (20 mL). The organic layer was separated, dried over $MgSO_4$, and concentrated under reduced pressure to give 4-azido-5-methoxy-1-(1-methyl-4-nitro-1H-pyrazol-5-yl)azepane as a yellow oil (484 mg). A solution of this oil (480 mg, 1.63 mmol) in THF/water (15 mL/3 mL) was treated with triphenylphosphine (426 mg, 1.63 mmol) and the reaction mixture was heated at 60° C. for 5 hr. EtOAc (100 mL) was added and the mixture was washed with saturated aqueous $NaHCO_3$ solution (20 mL). The aqueous layer was extracted with EtOAc (50 mL) and the combined organic layers were dried over $MgSO_4$ and concentrated under reduced pressure. The resulting oil was triturated in $Et_2O$, the resulting solid was filtered off and the filtrate concentrated under reduced pressure to give a yellow oil. To a solution of this oil in dry DCM (20 mL) at 0° C. was added DIPEA (0.85 mL, 4.88 mmol) and trifluoroacetic anhydride (0.27 mL, 1.95 mmol) took place. The reaction mixture was allowed to warm to room temperature and stirred for 4 hr. Water (20 mL) was added and the mixture extracted with DCM (100 mL). The organic layer was separated, dried over MgSO₄ and concentrated under reduced pressure. Purification via silica gel column chromatography (40-50% EtOAc/isohexane) gave 2,2,2-trifluoro-N-(5-methoxy-1-(1-methyl-4-nitro-1H-pyrazol-5-yl)azepan-4-yl)acetamide as a yellow oil (530 mg). A solution of this oil (520 mg, 1.42 mmol) in MeOH (20 mL) was treated with ammonium formate (900 mg, 14.2 mmol) and 10% palladium on carbon (50 mg). The mixture was heated at 65° C. for 1 hr. After cooling to room temperature the catalyst was filtered off and the filtrate concentrated under reduced pressure. The residue was partitioned between saturated aqueous NaHCO₃ solution (20 mL) and DCM (50 mL). The aqueous layer was extracted with DCM (3×50 mL) and the combined organic layers were dried over MgSO₄ and concentrated under reduced pressure to give N-(1-(4-amino-1-methyl-1H-pyrazol-5-yl)-5-methoxyazepan-4-yl)-2,2,2-trifluoroacetamide as an orange foam (486 mg, 82% over 4 steps). ¹H NMR (400 MHz, CDCl₃) δ 8.85 (br s, 1H), 7.17 (s, 1H), 4.64 (dd, J=14.5, 7.2 Hz, 1H), 3.65 (s, 3H), 3.57-3.36 (m, 2H), 3.41 (s, 3H), 3.15-3.05 (m, 1H), 2.93-2.85 (m, 1H), 2.61 (br s, 2H), 2.43-2.33 (m, 1H), 1.92-1.77 (m, 4H).

Intermediate 55

5-Azido-1-(1-(2,2-difluoroethyl)-4-nitro-1H-pyrazol-5-yl)azepan-3-ol

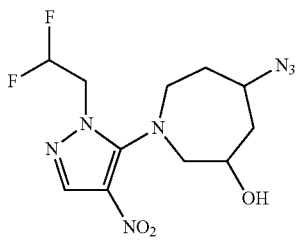

Following the procedure for Intermediate 18 starting from (Z)-tert-butyl 3-oxo-2,3,6,7-tetrahydro-1H-azepine-1-carboxylate gave 5-azido-1-(1-(2,2-difluoroethyl)-4-nitro-1H-pyrazol-5-yl)azepan-3-ol as a pale brown gum (88% over four steps). ¹H NMR (400 MHz, CDCl₃) δ 8.11 (s, 1H), 6.36-5.99 (m, 1H), 4.89-4.70 (m, 1H), 4.55-4.23 (m, 1H), 4.18-4.00 (m, 1H), 3.96-3.76 (m, 1H), 3.73-3.44 (m, 2H), 3.42-3.12 (m, 2H), 2.32-1.95 (m, 5H).

Intermediate 56 tert-Butyl 1-(1-(2,2-difluoroethyl)-4-nitro-1H-pyrazol-5-yl)-6,6-difluoroazepan-4-ylcarbamate

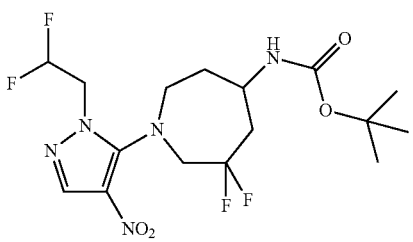 [SMILES: CC(C)(C)OC(=O)NC1CCN(c2c([N+](=O)[O-])cnn2CC(F)F)CC(F)(F)C1]

Following the procedure for Intermediate 19 starting from 5-azido-1-(1-(2,2-difluoroethyl)-4-nitro-1H-pyrazol-5-yl)azepan-3-ol gave tert-butyl 1-(1-(2,2-difluoroethyl)-4-nitro-1H-pyrazol-5-yl)-6,6-difluoroazepan-4-ylcarbamate as a pale green gum (1.34 g, 46% over four steps). ¹H NMR (400 MHz, CDCl₃) δ 8.17-8.06 (m, 1H), 6.34-6.00 (m, 1H), 4.72-4.30 (m, 3H), 4.12-3.95 (m, 1H), 3.66-3.10 (m, 4H), 2.59-2.03 (m, 4H), 1.45-1.41 (m, 9H).

Intermediate 57

(R)—N-(1-(1-Cyclopropyl-4-nitro-1H-pyrazol-5-yl)azepan-4-yl)-2,2,2-trifluoroacetamide

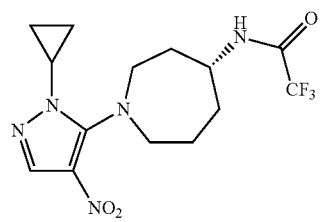 [SMILES: O=C(N[C@@H]1CCCN(c2c([N+](=O)[O-])cnn2C2CC2)CC1)C(F)(F)F]

Following the procedure for Intermediate 28 starting with 5-chloro-1-cyclopropyl-4-nitro-1H-pyrazole and (R)-2,2,2-trifluoro-N-(hexahydro-1H-azepin-4-yl)-acetamide gave (R)—N-(1-(1-cyclopropyl-4-nitro-1H-pyrazol-5-yl)azepan-4-yl)-2,2,2-trifluoroacetamide as a pale yellow gum (105 mg, 61%). ¹H-NMR (400 MHz, CDCl₃) δ 7.96 (s, 1H), 6.55-6.38 (m, 1H), 4.30-4.15 (m, 1H), 3.65-3.53 (m, 1H), 3.55-3.25 (m, 4H), 2.25-2.05 (m, 6H), 1.35-1.05 (m, 4H).

Intermediate 57a

5-Azido-1-(1-cyclopropyl-4-nitro-1H-pyrazol-5-yl)azepan-3-ol

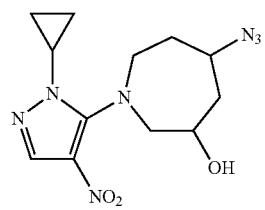 [SMILES: [N-]=[N+]=NC1CCN(c2c([N+](=O)[O-])cnn2C2CC2)CC(O)C1]

To as solution of (Z)-tert-butyl 3-oxo-2,3,6,7-tetrahydro-1H-azepine-1-carboxylate (15.0 g, 71.1 mmol) in acetonitrile (25 mL) was added trimethylsilyl azide (28.2 mL, 213 mmol) followed by Amberlite IRA 900F resin (loading: 2-3 mmol/g, 18 g) and the resulting mixture was heated at 60° C. behind a blast shield for 16 hr. After cooling to room temperature, the solution was filtered, washing the resin with acetonitrile and the filtrate was concentrated under reduced pressure (temperature of bath<40° C.) to give tert-butyl 5-azido-3-oxoazepane-1-carboxylate as a pale orange oil. To a solution of this oil in THF/water (150 mL/150 mL) cooled in an ice bath was added portion wise over 15 mins NaBH₄ (6.73 g, 178 mmol) and the mixture was stirred at room temperature for 3 hr. The mixture was extracted with EtOAc (2×400 mL), the combined organic layers were washed with water (2×250 mL) and brine (150 mL), separated, dried over MgSO₄, and the solvent removed under reduced pressure to give tert-butyl 5-azido-3-hydroxyazepane-1-carboxylate as a colorless oil (19.2 g). To a solution of this oil (4.0 g, 15.6 mmol) in DCM (60 mL) was added TFA (30 mL) and the solution was stirred at room temperature for 2 hr. The solvents were removed under reduced pressure and the crude residue was dissolved in DCM and passed through an SCX column, washing with DCM, 1:1 MeOH/DCM and MeOH and eluting with 1 N ammonia in MeOH to give 5-azidoazepan-3-ol as a pale yellow gum (2.36 g). To this gum (1.17 g, 7.48 mmol) in dry DMSO (25 mL) was added potassium fluoride (1.74 g, 29.9 mmol) and 5-chloro-1-cyclopropyl-4-nitro-1H-pyrazole (1.61 g, 8.6 mmol) and the mixture heated at 70° C. for 16 hr. The mixture was diluted with water (100 mL) and extracted with EtOAc (3×30 mL). The combined organic layers were washed with water (3×20 mL), separated, passed through a phase separation cartridge and the solvents removed under reduced pressure. Purification via silica gel column chromatography (0-100% EtOAc/isohexane) gave 5-azido-1-(1-cyclopropyl-4-nitro-1H-pyrazol-5-yl)azepan-3-ol as a viscous yellow oil (2.24 g, 81% over four steps). LCMS (ES+) m/z 308 (M+1).

Intermediate 57b

N-(1-(1-Cyclopropyl-4-nitro-1H-pyrazol-5-yl)-6,6-difluoroazepan-4-yl)-2,2,2-trifluoroacetamide

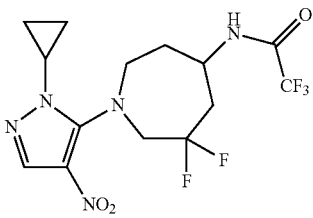 [SMILES: O=C(NC1CCN(c2c([N+](=O)[O-])cnn2C2CC2)CC(F)(F)C1)C(F)(F)F]

To a solution of 5-azido-1-(1-cyclopropyl-4-nitro-1H-pyrazol-5-yl)azepan-3-ol (1.54 g, 5.0 mmol) in DCM (50 mL) was added by portions Dess-Martin periodinane (2.54 g, 6.0 mmol). After stirring at room temperature for 3 hr, the mixture was diluted with DCM (25 mL) and quenched with saturated aqueous NaHCO$_3$ (50 mL) followed by saturated aqueous sodium thiosulfate (50 mL). The resulting mixture was stirred for 20 min. The organic layer was separated and the aqueous extracted with more EtOAc (3×30 mL). The combined organic layers were passed through a phase separation cartridge and the solvents removed under reduced pressure. Purification via silica gel column chromatography (0-100% EtOAc/isohexane) gave 5-azido-1-(1-cyclopropyl-4-nitro-1H-pyrazol-5-yl)azepan-3-one (1.22 g) as a pale yellow solid. To a solution of this solid (1.22 g, 4.0 mmol) in DCM (60 mL) was added deoxo-Fluor® (50% in THF, 2.68 mL, 7.3 mmol) and the mixture was stirred at room temperature for 62 hr. The mixture was diluted with DCM (30 mL), cooled in an ice/water bath and quenched by dropwise addition of saturated aqueous NaHCO$_3$ (100 mL). The resulting mixture was stirred for 10 min. The organic layer was separated, passed through a phase separation cartridge and the solvent removed under reduced pressure. Purification via silica gel column chromatography (0-100% EtOAc/isohexane) gave 5-azido-1-(1-cyclopropyl-4-nitro-1H-pyrazol-5-yl)-3,3-difluoroazepane (860 mg) as a viscous yellow oil. To a solution of this oil (0.85 g, 2.6 mmol) in THF (20 mL) and water (4 mL) was added triphenylphosphine (682 mg, 2.6 mmol) and the mixture was heated at 60° C. behind a blast screen for 16 hr. The mixture was diluted with EtOAc (30 mL) and washed with water (3×20 mL). The organic layer was separated, passed through a phase separation cartridge and the solvents removed under reduced pressure. The residue was passed through an SCX column washing with DCM and 1:1 MeOH:DCM and MeOH and eluting with 1 N ammonia in MeOH to afford 1-(1-cyclopropyl-4-nitro-1H-pyrazol-5-yl)-6,6-difluoroazepan-4-amine (783 mg) contaminated with triphenylphosphine oxide) as a viscous dark yellow oil. To a solution of this oil (0.78 g, 2.60 mmol) and DIPEA (1.36 mL, 7.80 mmol) in DCM (20 mL) was added trifluoroacetic anhydride (0.4 mL, 2.86 mmol) and the mixture stirred at room temperature for 16 hr. The organic layer was washed with water (2×20 mL), separated and passed through a phase separation cartridge. The solvent was removed under reduced pressure and the residue purified via silica gel column chromatography (0-100% EtOAc/isohexane) to give N-(1-(1-cyclopropyl-4-nitro-1H-pyrazol-5-yl)-6,6-difluoroazepan-4-yl)-2,2,2-trifluoroacetamide as a yellow solid (880 mg, 44% over 4 steps). $^1$H NMR (400 MHz, CDCl$_3$) δ 7.99-7.95 (m, 1H), 6.55 (d, J=8.0 Hz, 1H), 4.59-4.50 (m, 1H), 3.74-3.62 (m, 3H), 3.44-3.34 (m, 2H), 2.55-2.44 (m, 2H), 2.31-2.14 (m, 2H), 1.39-1.07 (m, 4H).

Intermediate 58

(R)-tert-Butyl 2-bromo-4-(1-cyclopropyl-5-(4-(2,2,2-trifluoroacetamido)azepan-1-yl)-1H-pyrazol-4-ylcarbamoyl)thiazol-5-ylcarbamate

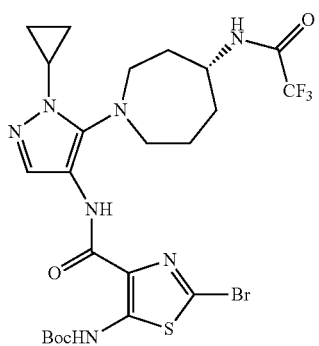 [SMILES: CC(C)(C)OC(=O)Nc1sc(Br)nc1C(=O)Nc1cnn(C2CC2)c1N1CCC[C@@H](NC(=O)C(F)(F)F)CC1]

To a solution of (R)—N-(1-(1-cyclopropyl-4-nitro-1H-pyrazol-5-yl)azepan-4-yl)-2,2,2-trifluoroacetamide (0.725 g, 2.00 mmol) in MeOH (20 mL) was added 10% palladium on carbon (0.75 g, 7.07 mmol) and ammonium formate (0.507 g, 8.03 mmol). The mixture was heated at 80° C. for 3 hr. The mixture was filtered through Celite® and the filtrate concentrated under reduced pressure. The residue was re-dissolved in DCM (20 mL) and 2-bromo-5-(tert-butoxycarbonylamino)thiazole-4-carboxylic acid (0.74 g, 2.29 mmol), PyBOP (1.57 g, 3.01 mmol) and DIPEA (1 mL, 5.6 mmol) were added. The reaction mixture was stirred at room temperature for 18 hr. Water (20 mL) was added and stirring continued for 10 min. The layers were separated and the aqueous extracted with DCM (2×20 mL). The combined organic layers were passed through a phase separation cartridge and the solvent removed under reduced pressure. The residue was purified by silica gel column chromatography (0-100% EtOAc/isohexane) to afford (R)-tert-butyl 2-bromo-4-(1-cyclopropyl-5-(4-(2,2,2-trifluoroacetamido)azepan-1-yl)-1H-pyrazol-4-ylcarbamoyl)thiazol-5-ylcarbamate as a pale brown solid (0.98 g, 77% over two steps). $^1$H NMR (400 MHz, CDCl$_3$) δ 10.26 (s, 1H), 8.43 (s, 1H), 7.71 (s, 1H), 6.47 (d, J=8.3 Hz, 1H), 4.25-4.15 (m, 1H), 3.47-3.35 (m, 3H), 3.29-3.13 (m, 2H), 2.46-1.57 (m, 6H), 1.52 (s, 9H), 1.23-1.17 (m, 2H), 1.12-0.96 (m, 2H).

Intermediate 58a

5-Azido-1-(1-cyclopropyl-4-nitro-1H-pyrazol-5-yl)azepan-4-ol

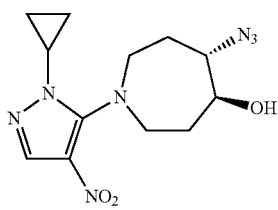 [SMILES: [N-]=[N+]=N[C@H]1CCN(c2c([N+](=O)[O-])cnn2C2CC2)CC[C@@H]1O]

Following the procedure for Intermediate 48 starting from tert-butyl 4-azido-5-hydroxyazepane-1-carboxylate gave 5-azido-1-(1-cyclopropyl-4-nitro-1H-pyrazol-5-yl)azepan-4-ol as a yellow gum (1.2 g, 72%). $^1$H NMR (400 MHz, CDCl$_3$) δ 7.96 (s, 1H), 3.82 (tt, J=8.5, 4.8 Hz, 1H), 3.65 (ddd, J=10.0, 8.5, 3.8 Hz, 1H), 3.62-3.54 (m, 1H), 3.52-3.37 (m, 2H), 3.31 (tdd, J=14.1, 5.7, 3.8 Hz, 2H), 2.50 (d, J=3.1 Hz, 1H), 2.24-2.13 (m, 2H), 2.04-1.92 (m, 2H), 1.31-1.20 (m, 2H), 1.14-1.05 (m, 2H).

Intermediate 58b

N-(1-(4-Amino-1-cyclopropyl-1H-pyrazol-5-yl)-5-fluoroazepan-4-yl)-2,2,2-trifluoroacetamide

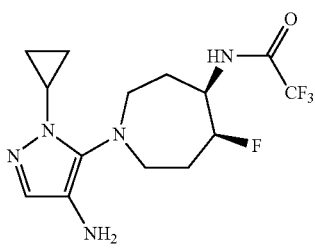 [SMILES: Nc1cnn(C2CC2)c1N1CC[C@H](F)[C@H](NC(=O)C(F)(F)F)CC1]

Following the procedure for Intermediate 49 starting from 5-azido-1-(1-cyclopropyl-4-nitro-1H-pyrazol-5-yl)azepan-4-ol gave N-(1-(4-amino-1-cyclopropyl-1H-pyrazol-5-yl)-5-fluoroazepan-4-yl)-2,2,2-trifluoroacetamide as an orange gum (900 mg, 67% over 4 steps). LCMS (ES+) m/z 350 (M+1).

Intermediate 59

5-Chloro-1-ethyl-4-nitro-1H-pyrazole

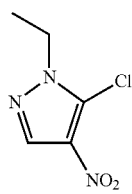

Following the procedure for Intermediate 5 starting with 1-ethyl-4-nitropyrazole gave 5-chloro-1-ethyl-4-nitro-1H-pyrazole as a colorless solid (1.3 g, 74%). $^1$H-NMR (400 MHz, CDCl$_3$) δ 8.16 (s, 1H), 4.26 (q, J=7 Hz, 2H), 1.50 (t, J=7 Hz, 3H).

Intermediate 60

N-(1-(1-Ethyl-4-nitro-1H-pyrazol-5-yl)azepan-4-yl)-2,2,2-trifluoroacetamide

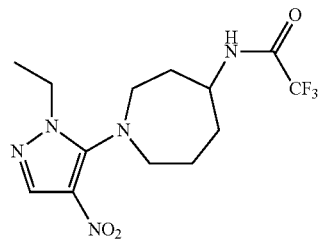 [SMILES: CCn1ncc([N+](=O)[O-])c1N1CCCC(NC(=O)C(F)(F)F)CC1]

Following the procedure for Intermediate 28 starting with 5-chloro-1-ethyl-4-nitro-1H-pyrazole and 2,2,2-trifluoro-N-(hexahydro-1H-azepin-4-yl)-acetamide gave N-(1-(1-ethyl-4-nitro-1H-pyrazol-5-yl)azepan-4-yl)-2,2,2-trifluoroacetamide as a pale yellow gum (136 mg, 55%). $^1$H-NMR (400 MHz, CDCl$_3$) δ 8.07 (s, 1H), 6.39-6.37 (m, 1H), 4.22-4.19 (m, 1H), 4.12 (q, J=7 Hz, 2H), 3.42-3.35 (m, 1H), 3.27-3.18 (m, 3H), 2.25-2.05 (m, 2H), 2.00-1.75 (m, 4H), 1.47 (t, J=7 Hz, 3H).

Intermediate 61

(R)-tert-Butyl 2-bromo-4-(1-ethyl-5-(4-(2,2,2-trifluoroacetamido)azepan-1-yl)-1H-pyrazol-4-ylcarbamoyl)thiazol-5-ylcarbamate

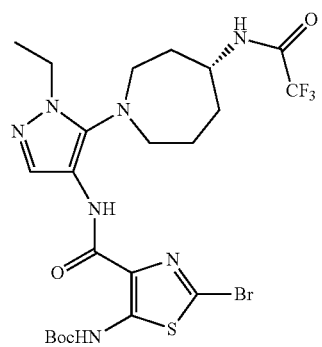 [SMILES: CCn1ncc(NC(=O)c2nc(Br)sc2NC(=O)OC(C)(C)C)c1N1CCC[C@@H](NC(=O)C(F)(F)F)CC1]

Following the procedure for Intermediate 58 starting with (R)—N-(1-(1-ethyl-4-nitro-1H-pyrazol-5-yl)azepan-4-yl)-2,2,2-trifluoroacetamide gave (R)-tert-butyl 2-bromo-4-(1-ethyl-5-(4-(2,2,2-trifluoroacetamido)azepan-1-yl)-1H-pyrazol-4-ylcarbamoyl)thiazol-5-ylcarbamate as a pale brown solid (186 mg, 31% over two steps). $^1$H NMR (400 MHz, CDCl$_3$) δ 10.30 (s, 1H), 8.41 (s, 1H), 7.81 (s, 1H), 6.44 (d, J=8.2 Hz, 1H), 4.25-4.17 (m, 1H), 4.06 (q, J=7.2 Hz, 2H), 3.40-3.32 (m, 2H), 3.23-3.10 (m, 2H), 2.23-2.09 (m, 2H), 2.06-1.94 (m, 2H), 1.91-1.68 (m, 2H), 1.54 (s, 9H), 1.48 (t, J=7.2 Hz, 3H).

Intermediate 62

1-((3-Methyloxetan-3-yl)methyl)-1H-pyrazol-4-amine

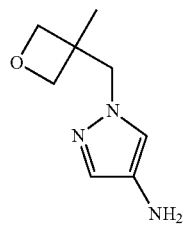

A mixture of 4-nitropyrazole (1.13 g, 10 mmol) and $K_2CO_3$ (3.4 g, 25 mmol) in MeCN (50 mL) was stirred at room temperature for 15 min prior to addition of 3-(bromomethyl)-3-methyloxetane (1.8 g, 11 mmol). The reaction mixture was stirred at room temperature for 18 hr, filtered and the filter cake washed with MeCN. The filtrate was concentrated under reduced pressure and the residue purified by silica gel column chromatography (0-100% EtOAc/isohexane) gradient to afford 1-((3-methyloxetan-3-yl)methyl)-4-nitro-1H-pyrazole as a colorless solid (1.43 g, 73%). A portion of this solid (206 mg, 1.04 mmol) dissolved in MeOH (20 mL) was treated with ammonium formate (260 mg, 4.13 mmol) and 10% palladium on carbon (50 mg). The mixture was heated at 80° C. for 1.5 hr, cooled, filtered through Celite® and the filtrate concentrated under reduced pressure to afford 1-((3-methyloxetan-3-yl)methyl)-1H-pyrazol-4-amine as a pale pink gum (160 mg, 92%). $^1$H NMR (400 MHz, $CDCl_3$) δ 7.15 (s, 1H), 6.97 (s, 1H), 4.66 (d, J=6.1 Hz, 2H), 4.37 (d, J=6.1 Hz, 2H), 4.19 (s, 2H), 2.91 (s, 2H), 1.23 (s, 3H).

Intermediate 63 tert-Butyl 4-(1-methyl-4-nitro-1H-pyrazol-5-yl)but-3-ynylcarbamate

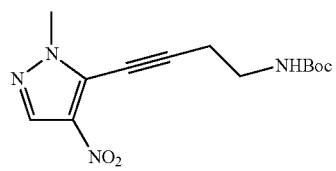 [SMILES: Cn1ncc([N+](=O)[O-])c1C#CCCNC(=O)OC(C)(C)C]

A solution of tert-butyl 3-butyn-1-ylcarbamate (123 mg, 0.728 mmol) in $NEt_3$ (4 mL) was treated with 5-bromo-1-methyl-4-nitro-1H-pyrazole (100 mg, 0.485 mmol) and copper(I) bromide dimethyl sulfide complex (10 mg, 0.049 mmol). The mixture was degassed four times by evacuating and refilling with nitrogen gas before tetrakis(triphenylphosphine)-palladium(0) (28 mg, 0.024 mmol) was added. Degassing was repeated twice and the reaction mixture was stirred at room temperature for 20 hr. More tert-butyl 3-butyn-1-ylcarbamate (123 mg, 0.728 mmol) and copper(I) bromide dimethyl sulfide complex (10 mg, 0.049 mmol) were added and the mixture was degassed three times. Tetrakis(triphenylphosphine)palladium(0) (28 mg, 0.024 mmol) was added and the reaction mixture was stirred at room temperature for 48 hr. The mixture was diluted with EtOAc (100 mL) and washed with water (20 mL) and brine (20 mL). The organic layer was separated, dried over $MgSO_4$ and the solvent removed under reduced pressure. Purification of the residue via silica gel column chromatography (30-40% EtOAc/isohexane) gave tert-butyl 4-(1-methyl-4-nitro-1H-pyrazol-5-yl)but-3-ynylcarbamate as a yellow oil (112 mg, 78%). $^1$H NMR (400 MHz, $CDCl_3$) δ 8.05 (s, 1H), 5.03 (s, 1H), 3.94 (s, 3H), 3.46 (q, J=6.4 Hz, 2H), 2.79 (t, J=6.4 Hz, 2H), 1.67-1.27 (m, 9H).

Intermediate 64

5-Chloro-1-cyclopropylmethyl-4-nitro-1H-pyrazole

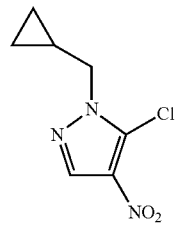 [SMILES: O=[N+]([O-])c1cnn(CC2CC2)c1Cl]

Following the procedure for Intermediate 5 starting with 1-cyclopropylmethyl-4-nitropyrazole gave 5-chloro-1-cyclopropylmethyl-4-nitro-1H-pyrazole as a colorless oil (1.16 g, 56%). $^1$H-NMR (400 MHz, $CDCl_3$) δ 8.17 (s, 1H), 4.07 (d, J=7 Hz, 2H), 1.39-1.28 (m, 1H), 0.66-0.59 (m, 2H), 0.50-0.40 (m, 2H).

Intermediate 65

(R)—N-(1-(1-Cyclopropylmethyl-4-nitro-1H-pyrazol-5-yl)azepan-4-yl)-2,2,2-trifluoroacetamide

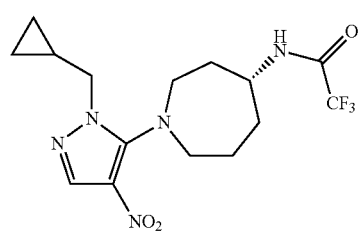

Following the procedure for Intermediate 28 starting with 5-chloro-1-cyclopropylmethyl-4-nitro-1H-pyrazole and (R)-2,2,2-trifluoro-N-(hexahydro-1H-azepin-4-yl)-acetamide gave (R)—N-(1-(1-cyclopropylmethyl-4-nitro-1H-pyrazol-5-yl)azepan-4-yl)-2,2,2-trifluoroacetamide as a pale yellow gum (0.98 g, 55%). $^1$H-NMR (400 MHz, $CDCl_3$) δ 8.08 (s, 1H), 6.42-6.39 (m, 1H), 4.22-4.14 (m, 1H), 4.00-3.85 (m, 2H), 3.44-3.32 (m, 1H), 3.30-3.15 (m, 3H), 2.25-2.05 (m, 2H), 2.00-1.75 (m, 4H), 1.30-1.20 (m, 1H), 0.70-0.62 (m, 2H), 0.50-0.35 (m, 2H).

Intermediate 66

(R)-tert-Butyl 2-bromo-4-(1-(cyclopropylmethyl)-5-(4-(2,2,2-trifluoroacetamido)azepan-1-yl)-1H-pyrazol-4-ylcarbamoyl)thiazol-5-ylcarbamate

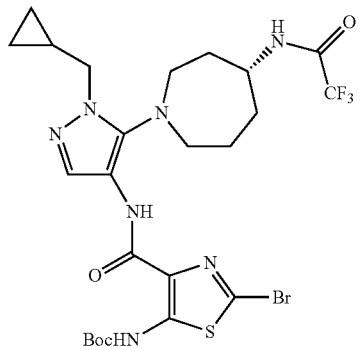 [SMILES: CC(C)(C)OC(=O)Nc1sc(Br)nc1C(=O)Nc1cnn(CC2CC2)c1N1CCC[C@@H](NC(=O)C(F)(F)F)CC1]

Following the procedure for Intermediate 58 starting with (R)—N-(1-(1-cyclopropylmethyl-4-nitro-1H-pyrazol-5-yl) azepan-4-yl)-2,2,2-trifluoroacetamide gave (R)-tert-butyl 2-bromo-4-(1-(cyclopropylmethyl-5-(4-(2,2,2-trifluoroacetamido)azepan-1-yl)-1H-pyrazol-4-ylcarbamoyl)thiazol-5-ylcarbamate as a pale brown solid (310 mg, 57% over two steps). $^1$H NMR (400 MHz, CDCl$_3$) δ 10.28 (s, 1H), 8.39 (s, 1H), 7.83-7.75 (m, 1H), 6.40 (d, J=8.2 Hz, 1H), 4.22-4.14 (m, 1H), 3.90-3.80 (m, 2H), 3.39-3.30 (m, 2H), 3.23-3.11 (m, 2H), 2.02-1.91 (m, 3H), 1.89-1.67 (m, 4H), 1.52 (s, 9H), 0.65-0.59 (m, 2H), 0.47-0.37 (m, 2H).

Intermediate 67

5-Amino-N-(5-chloro-1-methyl-1H-pyrazol-4-yl)-2-(2,6-difluorophenyl)thiazole-4-carboxamide

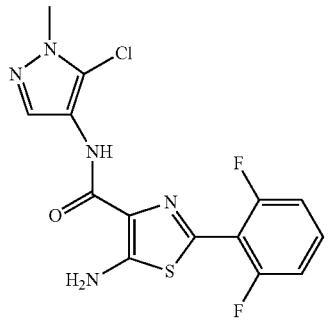 [SMILES: Cn1ncc(NC(=O)c2nc(-c3c(F)cccc3F)sc2N)c1Cl]

Following the procedure for Example 110 starting from 3-chloro-1-methyl-1H-pyrazol-4-amine gave 5-Amino-N-(5-chloro-1-methyl-1H-pyrazol-4-yl)-2-(2,6-difluorophenyl)thiazole-4-carboxamide as an off-white solid (146 mg, 46% over 3 steps). $^1$H NMR (400 MHz, d$_6$-DMSO) δ 8.89 (s, 1H), 7.74 (s, 1H), 7.60-7.50 (m, 3H), 7.28 (t, J=8.6 Hz, 2H), 3.80 (s, 3H). LCMS (ES+) m/z 370 (M+1).

Intermediate 68

5-Amino-2-(2,6-difluorophenyl)-N-(1-(3-methoxypropyl)-1H-pyrazol-4-yl)thiazole-4-carboxamide

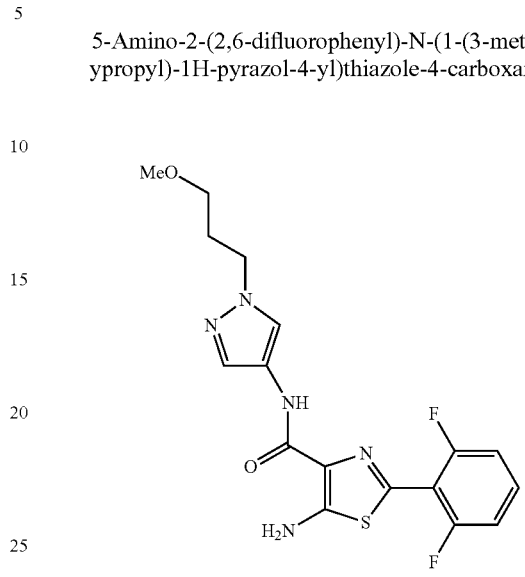

Following the procedure for Example 107 gave, after purification via preparative HPLC, 5-Amino-2-(2,6-difluorophenyl)-N-(1-(3-methoxypropyl)-1H-pyrazol-4-yl)thiazole-4-carboxamide (0.14 g, 28% over two steps) as a cream solid. $^1$H (400 MHz, d$_6$-DMSO) δ 9.75 (s, 1H), 7.97 (s, 1H), 7.67 (s, 1H), 7.58-7.52 (m, 3H), 7.30-7.25 (m, 2H), 4.09 (t, J=17.0 Hz, 2H), 3.27 (s, 3H), 3.23 (t, J=15.4 Hz, 2H), 1.98-1.93 (m, 2H). LCMS (ES+) m/z 394 (M+1)

Intermediate 69

5-Amino-2-(2,6-difluorophenyl)-N-(1-(tetrahydro-2H-pyran-4-yl)-1H-pyrazol-4-yl)thiazole-4-carboxamide

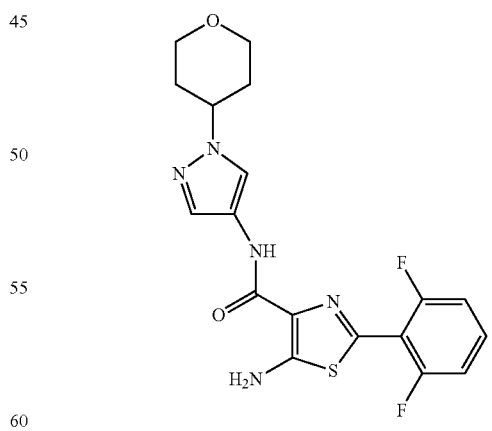

Following the procedure for Example 107 gave, after purification via preparative HPLC, 5-Amino-2-(2,6-difluorophenyl)-N-(1-(tetrahydro-2H-pyran-4-yl)-1H-pyrazol-4-yl)thiazole-4-carboxamide (0.17 g, 43% over two steps) as a light brown solid. $^1$H (400 MHz, d$_6$-DMSO) δ 9.75 (s, 1H), 8.03 (s, 1H), 7.70 (s, 1H), 7.58-7.52 (m, 3H), 7.29-7.25 (m, 2H), 4.40-4.36 (m, 1H), 3.97-3.93 (m, 2H), 3.49-3.43 (m, 2H), 1.97-1.87 (m, 4H) LCMS (ES+) m/z 406 (M+1).

Intermediate 201 tert-Butyl 8-(1-methyl-4-nitro-1H-pyrazol-5-yl)-5,8-diazaspiro[2.6]nonane-5-carboxylate

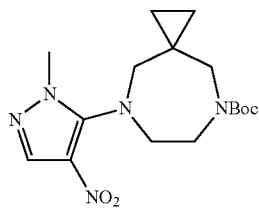 [SMILES: Cn1ncc([N+](=O)[O-])c1N1CCN(C(=O)OC(C)(C)C)CC2(CC2)C1]

To a solution of 5-chloro-1-methyl-4-nitro-1H-pyrazole (323 mg, 2.0 mmol), triethylamine (0.7 mL, 5.0 mmol) and potassium fluoride (581 mg, 10.0 mmol) in dry DMSO (20 mL) was added 5,8-diazaspiro[2.6]nonane dihydrobromide (686 mg, 2.4 mmol) and the mixture was heated in the microwave at 65° C. for 4 hr. The mixture was diluted with EtOAc (30 mL) and washed with saturated aqueous NaHCO$_3$ (3×20 mL). The aqueous layer was further extracted with DCM (3×20 mL) and the combined organic layers passed through a phase separation cartridge and concentrated under reduced pressure. The residue was loaded onto an SCX-2 column which was washed with MeOH and eluted with 3% 7M ammonia in MeOH/DCM and concentrated under reduced pressure to give 5-(1-methyl-4-nitro-1H-pyrazol-5-yl)-5,8-diazaspiro[2.6]nonane as a yellow gum (153 mg). To a solution of this intermediate in DCM (10 mL) was added di-tert-butyl dicarbonate (157 mg, 0.72 mmol) and DMAP (4 mg, 0.03 mmol) and the mixture stirred at room temperature for 2 hr. The mixture was washed with water (3×10 mL) and the organic layer separated, passed through a phase separation cartridge and concentrated under reduced pressure to give tert-butyl 8-(1-methyl-4-nitro-1H-pyrazol-5-yl)-5,8-diazaspiro[2.6]nonane-5-carboxylate as a yellow gum (200 mg, 28% over two steps). $^1$H NMR (400 MHz, CDCl$_3$) δ 8.02 and 8.00 (2s, 1H), 3.85-3.77 (m, 3H), 3.75-3.67 (m, 2H), 3.47-3.27 (m, 4H), 3.29-2.97 (m, 2H), 1.49 (s, 9H), 0.73-0.55 (m, 2H), 0.47-0.38 (m, 2H).

Intermediate 202

1-(1-Methyl-4-nitro-1H-pyrazol-5-yl)azepan-2-one

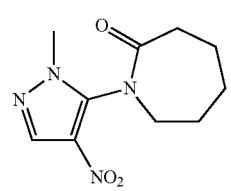 [SMILES: Cn1ncc([N+](=O)[O-])c1N1CCCCCC1=O]

A mixture of azepan-2-one (136 mg, 1.2 mmol), 5-bromo-1-methyl-4-nitro-1H-pyrazole (206 mg, 1.0 mmol), Xantphos (116 mg, 0.20 mmol) and caesium carbonate (456 mg, 1.40 mmol) in dioxane (4 mL) was degassed by bubbling nitrogen through it for 15 min. Tris(dibenzylideneacetone)dipalladium(0) (46 mg, 0.05 mmol) was then added and the mixture degassed for a further 10 min before being heated in the microwave at 140° C. for 3 hours. Water (10 mL) was added and the mixture extracted into EtOAc (3×10 mL). The combined organic layers were passed through a phase separation cartridge and concentrated under reduced pressure.

The residue was purified via silica gel chromatography (0-100% EtOAc/isohexane) to give 1-(1-methyl-4-nitro-1H-pyrazol-5-yl)azepan-2-one as a brown gum (107 mg, 44%). $^1$H NMR (400 MHz, CDCl$_3$) δ 8.11 (s, 1H), 3.96 (dd, J=15.2, 10.0 Hz, 1H), 3.76 (s, 3H), 3.53 (dd, J=15.2, 7.2 Hz, 1H), 2.82-2.74 (m, 2H), 2.13-1.96 (m, 3H), 1.83-1.67 (m, 3H).

Intermediate 203 tert-Butyl 4-(1-methyl-4-nitro-1H-pyrazol-5-yl)-5-oxo-1,4-diazepane-1-carboxylate

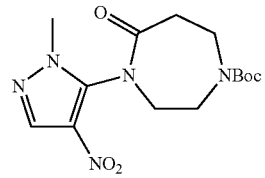 [SMILES: Cn1ncc([N+](=O)[O-])c1N1CCN(C(=O)OC(C)(C)C)CCC1=O]

Following the procedure for Intermediate 202 starting from 5-bromo-1-methyl-4-nitro-1H-pyrazole and tert-butyl 5-oxo-1,4-diazepane-1-carboxylate gave tert-butyl 4-(1-methyl-4-nitro-1H-pyrazol-5-yl)-5-oxo-1,4-diazepane-1-carboxylate as a brown gum (136 mg, 33%). $^1$H NMR (400 MHz, d$_4$-MeOD) δ 8.18 (s, 1H), 4.04-3.72 (m, 5H), 3.90-3.62 (m, 4H), 3.02-2.86 (m, 2H), 1.52 (s, 9H).

Intermediate 204

4-(1-Methyl-4-nitro-1H-pyrazol-5-yl)-1,4-oxazepan-5-one

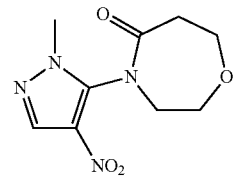 [SMILES: Cn1ncc([N+](=O)[O-])c1N1CCOCCC1=O]

Following the procedure for Intermediate 202 starting from 5-bromo-1-methyl-4-nitro-1H-pyrazole and 1,4-oxazepan-5-one gave 4-(1-methyl-4-nitro-1H-pyrazol-5-yl)-1,4-oxazepan-5-one as an orange solid (40 mg, 13%). $^1$H NMR (400 MHz, CDCl$_3$) δ 8.11 (s, 1H), 4.18 (dd, J=13.3, 6.4 Hz, 1H), 4.12-3.99 (m, 2H), 3.96-3.82 (m, 2H), 3.77 (s, 3H), 3.64 (dd, J=15.7, 6.4 Hz, 1H), 3.08 (ddd, J=15.6, 8.5, 2.1 Hz, 1H), 2.94 (ddd, J=15.6, 7.5, 1.8 Hz, 1H).

Intermediate 205

5-Azido-1-(1-ethyl-4-nitro-1H-pyrazol-5-yl)azepan-4-ol

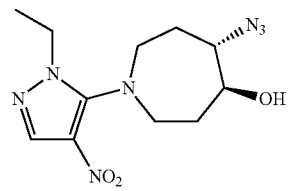 [SMILES: CCn1ncc([N+](=O)[O-])c1N1CC[C@H](N=[N+]=[N-])[C@@H](O)CC1]

A solution of 5-azidoazepan-4-ol (2.5 g, 16.0 mmol) was dissolved in dry DMSO (20 mL) and 5-chloro-1-methyl-4-nitro-1H-pyrazole (2.70 g, 15.4 mmol) and potassium fluoride (3.71 g, 64 mmol) were added. The mixture was heated at 60° C. for 16 hr, allowed to cool to room temperature, poured into water (300 mL) and extracted into EtOAc (2×50 mL). The combined organic layers were passed through a phase separation cartridge and concentrated under reduced pressure. Purification via silica gel column chromatography (0-100% EtOAc/isohexane) gave 5-azido-1-(1-ethyl-4-nitro-1H-pyrazol-5-yl)azepan-4-ol as a yellow gum (2.5 g, 53%). $^1$H NMR (400 MHz, CDCl$_3$) δ 8.18-7.95 (m, 1H), 4.16-4.07 (m, 2H), 3.80 (tt, J=9.1, 3.1 Hz, 1H), 3.67-3.59 (m, 1H), 3.42-3.18 (m, 4H), 2.51 (d, J=2.9 Hz, 1H), 2.24-2.12 (m, 2H), 2.07-1.87 (m, 2H), 1.46 (t, J=7.3 Hz, 3H).

Intermediate 206 tert-Butyl 1-(1-ethyl-4-nitro-1H-pyrazol-5-yl)-5-fluoroazepan-4-ylcarbamate

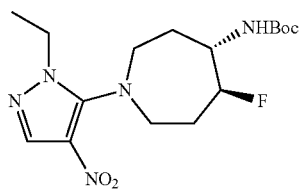 [SMILES: CCn1ncc([N+](=O)[O-])c1N1CC[C@H](NC(=O)OC(C)(C)C)[C@@H](F)CC1]

To a solution of 5-azido-1-(1-ethyl-4-nitro-1H-pyrazol-5-yl)azepan-4-ol (1.25 g, 4.2 mmol) in dry DCM (20 ml) was added dropwise deoxo-Fluor® (3.8 mL, 10.6 mmol, 50% in THF) and the mixture was stirred at room temperature for 16 hr. The mixture was cooled in an ice bath, saturated aqueous NaHCO$_3$ solution (40 mL) was added slowly (effervescence observed) and the mixture was extracted with DCM (2×20 mL). The organic layer was washed with saturated aqueous NaHCO$_3$ solution (2×10 mL), passed through a phase separation cartridge and concentrated under reduced pressure. The residue was purified via silica gel column chromatography (0-100% EtOAc/isohexane) to give 4-azido-5-fluoro-1-(1-ethyl-4-nitro-1H-pyrazol-5-yl)azepane as a yellow gum (0.91 g). A solution of this gum (0.9 g, 3.0 mmol) in THF/water (20 mL/4 mL) was treated with triphenylphosphine (0.8 g, 3.0 mmol) and the mixture was heated at 60° C. for 16 hr. The mixture was cooled and concentrated to 4 mL under reduced pressure, diluted with EtOAc (30 mL) and extracted with 1M HCl (4×10 mL). The combined aqueous extracts were washed with EtOAc (20 mL) and then basified with 6N NaOH and extracted with DCM (3×20 mL) The combined organic layers were separated, dried over MgSO$_4$ and concentrated under reduced pressure to give 5-fluoro-1-(1-methyl-4-nitro-1H-pyrazol-5-yl)azepan-4-amine as a yellow oil (0.82 g). To a solution of this oil (0.8 g, 2.9 mmol) and DIPEA (0.77 mL, 4.4 mmol) in DCM (25 mL) was added di-tert-butyl-dicarbonate (0.97 g, 4.4 mmol) and the mixture stirred at room temperature for 16 hr. Water (15 mL) was added and the organic phase separated, dried over MgSO$_4$ and concentrated under reduced pressure. Purification via silica gel column chromatography (0-100% EtOAc/isohexane) gave tert-butyl 1-(1-ethyl-4-nitro-1H-pyrazol-5-yl)-5-fluoroazepan-4-ylcarbamate as a yellow solid (1.1 g, 70% over three steps). $^1$H NMR (400 MHz, CDCl$_3$) δ 8.07 (s, 1H), 4.96 (s, 1H), 4.74 (td, J=7.4, 3.6 Hz, 1H), 4.65-4.58 (m, 1H), 4.16-4.05 (m, 3H), 3.42-3.29 (m, 2H), 3.16 (d, J=11.4 Hz, 2H), 2.31-2.18 (m, 2H), 2.20-2.06 (m, 2H), 1.94-1.82 (m, 1H), 1.60-1.45 (m, 10H).

Intermediate 207 tert-Butyl 1-(1-ethyl-4-nitro-1H-pyrazol-5-yl)-5-methoxyazepan-4-ylcarbamate

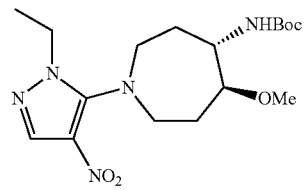 [SMILES: CCn1ncc([N+](=O)[O-])c1N1CC[C@H](NC(=O)OC(C)(C)C)[C@@H](OC)CC1]

Following the procedure for Intermediate 120 starting from 5-azido-1-(1-ethyl-4-nitro-1H-pyrazol-5-yl)azepan-4-ol gave tert-butyl 1-(1-ethyl-4-nitro-1H-pyrazol-5-yl)-5-methoxyazepan-4-ylcarbamate as a yellow gum (0.59 g, 70% over three steps). $^1$H NMR (400 MHz, CDCl$_3$) δ 8.09-8.03 (m, 1H), 4.21-3.99 (m, 4H), 3.54-3.30 (m, 4H), 3.33-3.05 (m, 4H), 2.40-2.30 (m, 1H), 2.08-1.98 (m, 1H), 1.95-1.78 (m, 2H), 1.50-1.40 (m, 12H).

Intermediate 208 tert-Butyl 1-(1-cyclopropyl-4-nitro-1H-pyrazol-5-yl)-5-methoxyazepan-4-ylcarbamate

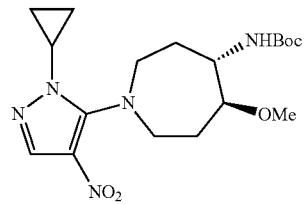 [SMILES: CO[C@H]1CCN(c2c([N+](=O)[O-])cnn2C2CC2)CC[C@@H]1NC(=O)OC(C)(C)C]

Following the procedure for Intermediate 120 starting from 5-azido-1-(1-cyclopropyl-4-nitro-1H-pyrazol-5-yl)azepan-4-ol gave tert-butyl 1-(1-cyclopropyl-4-nitro-1H-pyrazol-5-yl)-5-methoxyazepan-4-ylcarbamate as a yellow gum (0.67 g, 70% over three steps). $^1$H NMR (400 MHz, CDCl$_3$) δ 7.96 (s, 1H), 5.38 (m, 1H), 4.15-4.08 (m, 1H), 3.68-3.31 (m, 7H), 3.28-3.18 (m, 1 H), 3.07 (ddd, J=14.1, 6.2, 3.1 Hz, 1H), 2.42-2.32 (m, 1 H), 2.05-1.92 (m, 2 H), 1.93-1.80 (m, 1 H), 1.48 (s, 9H), 1.26-1.13 (m, 4 H).

Intermediate 209 syn-5-Azido-1-(1-(2,2-difluoroethyl)-4-nitro-1H-pyrazol-5-yl)azepan-4-ol

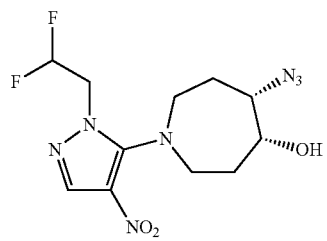 [SMILES: [N-]=[N+]=N[C@H]1CCN(c2c([N+](=O)[O-])cnn2CC(F)F)CC[C@H]1O]

Following the procedure for Intermediate 119 starting from anti-5-azido-1-(1-(2,2-difluoroethyl)-4-nitro-1H-pyrazol-5-yl)azepan-4-ol gave syn-5-azido-1-(1-(2,2-difluoroethyl)-4-nitro-1H-pyrazol-5-yl)azepan-4-ol as a brown gum (0.57 g, 92% over two steps). $^1$H NMR (400 MHz, CDCl$_3$) δ 8.15-8.07 (m, 1H), 6.35-6.02 (m, 1H), 4.55-4.35 (m, 2H), 3.83 (tt, J=8.8, 2.9 Hz, 1H), 3.70-3.62 (m, 1H), 3.37 (t, J=11.8 Hz, 1H), 3.32-3.18 (m, 3H), 2.46 (d, J=2.9 Hz, 1H), 2.25-2.12 (m, 2 H), 2.11-1.85 (m, 2H).

Intermediate 210 tert-Butyl 1-(1-(2,2-difluoroethyl)-4-nitro-1H-pyrazol-5-yl)-5-hydroxyazepan-4-ylcarbamate

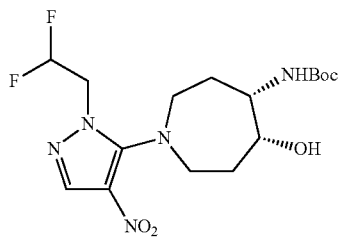

Following the procedure for Intermediate 122 starting from 5-azido-1-(1-(2,2-difluoroethyl)-4-nitro-1H-pyrazol-5-yl)azepan-4-ol gave tert-butyl 1-(1-(2,2-difluoroethyl)-4-nitro-1H-pyrazol-5-yl)-5-hydroxyazepan-4-ylcarbamate as a yellow gum (0.33 g, 47% over two steps). $^1$H NMR (400 MHz, CDCl$_3$) δ 8.12 (s, 1H), 6.32-6.05 (m, 1H), 5.06 (d, J=7.9 Hz, 1H), 4.64-4.40 (m, 2H), 4.23 (m, 1H), 3.89 (m, 1H), 3.45-3.29 (m, 2H), 3.18-3.09 (m, 2H), 2.60 (m, 1H), 2.20-1.93 (m, 3H), 1.86 (dd, J=14.1, 5.4 Hz, 1H), 1.44 (s, 9H).

Intermediate 211 syn-5-Azido-1-(1-ethyl-4-nitro-1H-pyrazol-5-yl)azepan-4-ol

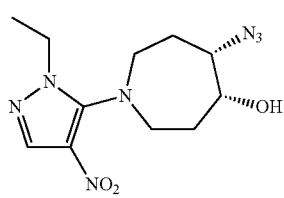 [SMILES: CCn1ncc([N+](=O)[O-])c1N1CC[C@@H](O)[C@@H](N=[N+]=[N-])CC1]

Following the procedure for Intermediate 119 starting from anti-5-azido-1-(1-ethyl-4-nitro-1H-pyrazol-5-yl)azepan-4-ol gave syn-5-azido-1-(1-ethyl-4-nitro-1H-pyrazol-5-yl)azepan-4-ol as a brown gum (0.5 g, 81% over two steps). $^1$H NMR (400 MHz, CDCl$_3$) δ 8.08-8.04 (m, 1H), 4.25-4.07 (m, 2H), 3.44-3.28 (m, 1H), 3.27-3.09 (m, 1H), 2.32-2.21 (m, 1H), 2.23-2.09 (m, 1H), 1.99-1.84 (m, 2H), 1.42-1.14 (m, 5H), 1.10-0.84 (m, 3H).

Intermediate 212 tert-Butyl 1-(1-ethyl-4-nitro-1H-pyrazol-5-yl)-5-methoxyazepan-4-ylcarbamate

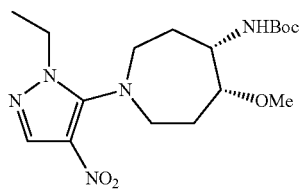 [SMILES: CCn1ncc([N+](=O)[O-])c1N1CC[C@H](NC(=O)OC(C)(C)C)[C@H](OC)CC1]

Following the procedure for Intermediate 120 starting from syn-5-azido-1-(1-ethyl-4-nitro-1H-pyrazol-5-yl)azepan-4-ol gave tert-butyl 1-(1-ethyl-4-nitro-1H-pyrazol-5-yl)-5-methoxyazepan-4-ylcarbamate as a yellow gum (0.46 g, 70% over three steps). $^1$H NMR (400 MHz, CDCl$_3$) δ 8.06 (s, 1H), 5.11 (t, J=8.8 Hz, 1H), 4.14 (q, J=7.3 Hz, 2H), 3.94 (m, 1 H), 3.65-3.61 (m, 1H), 3.59-3.18 (m, 4H), 3.31-3.20 (m, 1H), 3.18-3.10 (m, 1H), 2.99 (d, J=13.4 Hz, 1H), 2.26-2.02 (m, 2H), 1.88-1.76 (m, 2H), 1.45-1.35 (m, 12H).

Intermediate 213

3-(1-Methyl-4-nitro-1H-pyrazol-5-yl)-8-oxa-3-azabicyclo[3.2.1]octane

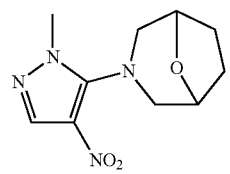 [SMILES: Cn1ncc([N+](=O)[O-])c1N1CC2CCC(C1)O2]

8-Oxa-3-azabyclo[3.2.1]octane hydrochloride (150 mg, 1.0 mmol) and DIPEA (0.26 mL, 1.5 mmol) were stirred in DMSO (4 mL) for 15 min at room temperature. 5-Chloro-1-methyl-4-nitro-1H-pyrazole (150 mg, 0.95 mmol) and potassium fluoride (170 mg, 3 mmol) were then added and the reaction mixture was heated at 70° C. for 18 hr. The mixture was allowed to cool to room temperature and poured into water (4 mL). The aqueous was extracted with EtOAc (3×10 mL) and the combined organic layers were washed with brine (10 mL), separated, dried over MgSO$_4$ and concentrated under reduced pressure to give 3-(1-methyl-4-nitro-1H-pyrazol-5-yl)-8-oxa-3-azabicyclo[3.2.1]octane (220 mg, 92%). $^1$H NMR (400 MHz CDCl$_3$) δ 8.04 (s, 1H), 4.43 (s, 2H), 3.86 (s, 3H), 3.73-3.70 (m, 2H), 2.61-2.58 (m 2H), 2.09-2.07 (m, 4H).

Intermediate 214

3-(1-Methyl-4-nitro-1H-pyrazol-5-yl)-3-azabicyclo[3.2.1]octane

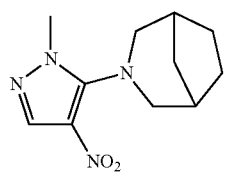

Following the procedure for Intermediate 213 starting from (1R,5S)-3-azabyclo[3.2.1]octane hydrochloride gave 3-(1-methyl-4-nitro-1H-pyrazol-5-yl)-3-azabicyclo[3.2.1]octane as an off-white solid (290 mg, 99%). $^1$H NMR (400 MHz CDCl$_3$) δ 8.03 (s, 1H), 3.81 (s, 3H), 3.44 (d, J=10.1 Hz, 2H), 2.66-2.59 (m, 2H), 2.29 (br s, 2H), 1.78-1.71 (m, 4H), 1.64-1.59 (m, 2H).

Intermediate 215

4-(1-Methyl-4-nitro-1H-pyrazol-5-yl)-1,4-thiazepane 1,1-dioxide

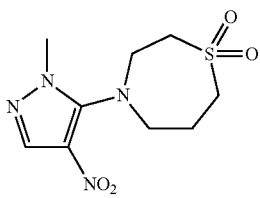 [SMILES: Cn1ncc([N+](=O)[O-])c1N1CCCS(=O)(=O)CC1]

1,4-Thiazepane hydrochloride (153 mg, 1 mmol) and DIPEA (0.26 mL, 1.5 mmol) were stirred in DMSO (4 mL) for 15 min at room temperature. 5-Chloro-1-methyl-4-nitro-1H-pyrazole (150 mg, 0.95 mmol) and potassium fluoride (170 mg, 3 mmol) were then added and the reaction mixture was heated at 70° C. for 18 h. The mixture was allowed to cool to room temperature and poured into water (4 mL). The aqueous was extracted with EtOAc (3×10 mL) and the combined organic layers were washed with brine (10 mL), separated, dried over MgSO$_4$ and concentrated under reduced pressure to give 3-(1-methyl-4-nitro-1H-pyrazol-5-yl)-8-oxa-3-azabicyclo[3.2.1]octane (220 mg, 92%). This intermediate was dissolved in DCM (10 mL), cooled to 0° C., treated with m-chloroperbenzoic acid (400 mg, 1.9 mmol) and the resulting mixture stirred at room temperature for 16 hr. The resulting precipitate was filtered off washing with cold DCM (5 mL). The filtrate was washed with 2M NaOH (5 mL) and brine (5 mL), passed through a phase separation cartridge and concentrated under reduced pressure to give 4-(1-methyl-4-nitro-1H-pyrazol-5-yl)-1,4-thiazepane 1,1-dioxide (280 mg, 97% over two steps) as a yellow solid. $^1$H NMR (400 MHz, CDCl$_3$) δ 8.14 (s, 1H), 3.87 (s, 3H), 3.59-3.55 (m, 2H), 3.41-3.36 (m, 6H), 2.29-2.24 (m, 2H).

Intermediate 218

(Z)-1-(1-Methyl-4-nitro-1H-pyrazol-5-yl)cyclohept-4-enol

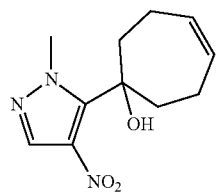 [SMILES: Cn1ncc([N+](=O)[O-])c1C1(O)CCC=CCC1]

To a solution of 1-methyl-4-nitro-1H-pyrazole (1.5 g, 11.8 mmol) and (Z)-cyclohept-4-enone (1.4 g, 13.0 mmol) in dry THF (30 mL) under nitrogen cooled to −78° C. was added dropwise a solution of lithium hexamethyldisilazide (1.0 M in THF, 30 mL, 29.5 mmol). The reaction mixture was allowed to warm to −40° C. and stirred for 90 min. Saturated aqueous ammonium chloride solution (30 mL) was added (dropwise initially) and the mixture was allowed to warm to room temperature and extracted with EtOAc (150 mL). The organic layer was washed with water (30 mL), washed with brine (20 mL), separated, dried over MgSO$_4$ and concentrated under reduced pressure. Purification via silica gel column chromatography (20-25% EtOAc) gave (Z)-1-(1-methyl-4-nitro-1H-pyrazol-5-yl)cyclohept-4-enol as a tan oil (1.37 g, 49%). $^1$H NMR (400 MHz, CDCl$_3$) δ 8.03 (s, 1H), 5.96-5.86 (m, 2H), 4.13 (s, 3H), 3.70 (s, 1H), 2.63-2.54 (m, 2H), 2.41-2.31 (m, 2H), 2.16-2.03 (m, 2H), 2.00-1.92 (m, 2H).

Intermediate 219

5-((1E,4Z)-Cyclohepta-1,4-dienyl)-1-methyl-4-nitro-1H-pyrazole

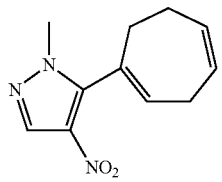 [SMILES: Cn1ncc([N+](=O)[O-])c1C1=CCC=CCC1]

To a solution of (Z)-1-(1-methyl-4-nitro-1H-pyrazol-5-yl)cyclohept-4-enol (1.35 g, 5.70 mmol) in dry DCM (60 mL) was added dropwise a solution of deoxo-Fluor® (50% in THF, 6.2 mL, 17.1 mmol) and the reaction mixture was stirred at room temperature for 90 min. The mixture was cooled to 0° C. and saturated aqueous NaHCO$_3$ solution (70 mL) was added, dropwise initially, and extracted with DCM (100 mL). The organic layer was separated, dried over MgSO$_4$, and concentrated under reduced pressure. Purification via silica gel column chromatography (15-20% EtOAc/hexane) gave 5-((1E,4Z)-cyclohepta-1,4-dienyl)-1-methyl-4-nitro-1H-pyrazole as a pale yellow oil (523 mg, 42%). $^1$H NMR (400 MHz, CDCl$_3$) δ 8.06 (s, 1H), 5.90 (t, J=5.6 Hz, 1H), 5.88-5.79

(m, 1H), 5.71-5.63 (m, 1H), 3.82 (s, 3H), 3.14-3.08 (m, 2H), 2.62-2.55 (m, 2H), 2.44-2.37 (m, 2H).

Intermediate 220

(Z)-5-(1-Fluorocyclohept-4-enyl)-1-methyl-4-nitro-1H-pyrazole

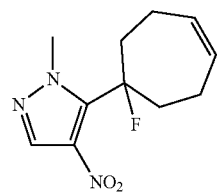 [SMILES: Cn1ncc([N+](=O)[O-])c1C1(F)CCC=CCC1]

Following the procedure for Intermediate 219 gave (Z)-5-(1-fluorocyclohept-4-enyl)-1-methyl-4-nitro-1H-pyrazole as an off-white solid (615 mg, 45%). $^1$H NMR (400 MHz, CDCl$_3$) δ 8.03 and 8.02 (2s, 1H), 5.98-5.94 (m, 2H), 4.10 and 4.08 (2s, 3H), 2.67-2.54 (m, 3H), 2.49 (t, J=13.6 Hz, 1H), 2.10-1.93 (m, 4H).

Intermediate 221

(E)-2-Azido-5-(1-methyl-4-nitro-1H-pyrazol-5-yl)cyclohept-4-enol

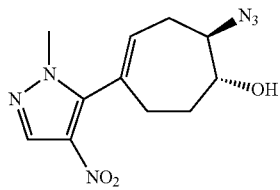 [SMILES: Cn1ncc([N+](=O)[O-])c1C1=CC[C@@H](N=[N+]=[N-])[C@H](O)CC1]

To a solution of 5-((1E,4Z)-cyclohepta-1,4-dienyl)-1-methyl-4-nitro-1H-pyrazole (520 mg, 2.37 mmol) in DCM (20 mL) cooled to 0° C. was added portionwise m-CPBA (70%, 646 mg, 2.61 mmol). The reaction mixture was allowed to warm to room temperature and stirred for 90 min. Saturated aqueous NaHCO$_3$ solution (30 mL) was added and the mixture was extracted with DCM (100 mL). The organic layer was washed with 2M NaOH solution (3×30 mL), separated, dried over MgSO$_4$, and concentrated under reduced pressure to give a pale yellow solid (595 mg). A suspension of this solid (590 mg, 2.51 mmol) in MeOH/water (16 mL/4 mL) was treated with ammonium chloride (333 mg, 6.28 mmol) and sodium azide (816 mg, 12.6 mmol). The reaction mixture was heated at 70° C. for 18 hrs. The MeOH was removed under reduced pressure, the residue diluted with water (20 mL) and extracted with EtOAc (100 mL). The organic layer was washed with brine (20 mL), separated, dried over MgSO$_4$, and concentrated under reduced pressure. Purification via silica gel column chromatography (50-60% EtOAc/isohexane) gave (E)-2-azido-5-(1-methyl-4-nitro-1H-pyrazol-5-yl)cyclohept-4-enol as a pale yellow oil (294 mg, 42% over two steps). $^1$H NMR (400 MHz, CDCl$_3$) δ 8.06 (s, 1H), 5.96 (dd, J=8.3, 4.9 Hz, 1H), 3.84-3.70 (m, 4H), 3.56-3.47 (m, 1H), 2.71 (ddd, J=15.5, 8.3, 2.3 Hz, 1H), 2.61-2.36 (m, 4H), 2.23-2.14 (m, 1H), 1.89-1.76 (m, 1H).

Intermediate 222 tert-Butyl 2-(2,6-difluorophenyl)-4-(5-(4-fluoro-5-(2,2,2-trifluoroacetamido)cycloheptyl)-1-methyl-1H-pyrazol-4-ylcarbamoyl)thiazol-5-ylcarbamate (Diastereomer 1)

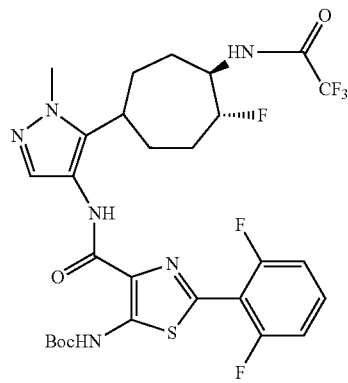 [SMILES: Cn1ncc(NC(=O)c2nc(-c3c(F)cccc3F)sc2NC(=O)OC(C)(C)C)c1C1CC[C@@H](F)[C@H](NC(=O)C(F)(F)F)CC1]

To a solution of (E)-2-azido-5-(1-methyl-4-nitro-1H-pyrazol-5-yl)cyclohept-4-enol (450 mg, 1.62 mmol) in dry DCM (20 mL) under nitrogen was added dropwise a solution of deoxo-Fluor® (50% in THF, 1.5 mL, 4.05 mmol) and the mixture stirred at room temperature for 2 hr. Saturated aqueous NaHCO$_3$ solution (20 mL) was added and the mixture was extracted with DCM (75 mL). The organic layer was washed with NaHCO$_3$ solution (20 mL), separated, dried over MgSO$_4$, and concentrated under reduced pressure. Purification of the residue via silica gel column chromatography (20-40% EtOAc/isohexane) gave a pale yellow oil (260 mg). A solution of this oil (250 mg, 0.89 mmol) in THF/water (10 mL/2 mL) was treated with triphenylphosphine (234 mg, 0.89 mmol) and the mixture was heated at 60° C. for 6 hr. More triphenylphosphine (24 mg, 0.09 mmol) was added to the reaction mixture, which was heated at 60° C. for 1 hr. The mixture was partitioned between EtOAc (75 mL) and saturated aqueous NaHCO$_3$ solution (10 mL) and the organic layer was separated, dried over MgSO$_4$ and concentrated under reduced pressure to give a yellow oil. To a solution of this oil (227 mg, 0.89 mmol) and DIPEA (0.47 mL, 2.69 mmol) in DCM (10 mL) was added dropwise trifluoroacetic anhydride (0.15 mL, 1.07 mmol) and the mixture stirred at room temperature for 72 hr. Water (20 mL) was added and the mixture extracted with DCM (100 ml). The organic layer was separated, dried over MgSO$_4$, and concentrated under reduced pressure to give a pale yellow viscous oil (240 mg). A solution of this oil (240 mg, 0.69 mmol) in MeOH (50 mL) was passed through the H-Cube® (full H$_2$, 70° C., flow rate: 1 mL/min, 10% Pd/C cartridge). The solvent was removed under reduced pressure to give a pale yellow foam (195 mg). To a solution of this foam (190 mg, 0.59 mmol) in DCM (20 mL) was added DIPEA (1.0 mL), PyBOP (767 mg, 1.48 mmol) and 5-(tert-butoxycarbonylamino)-2-(2,6-difluorophenyl)thiazole-4-carboxylic acid (231 mg, 0.65 mmol) and the mixture was stirred at room temperature for 18 hr. Water (30 mL) was added and the mixture extracted with DCM (100 mL and 30 mL). The organic layers were combined, dried over MgSO$_4$ and the solvent removed under reduced pressure. Purification via silica gel column chromatography (60-70% EtOAc/isohexane) followed by chiral preparative HPLC gave tert-butyl 2-(2,6-difluorophenyl)-4-(5-(4-fluoro-5-(2,2,2-trifluoroacetamido)cycloheptyl)-1-methyl-1H-pyrazol-4-ylcarbamoyl)thiazol-5-ylcarbamate (Diastereomer 1) as an off-white solid (53 mg, 5% over five steps). $^1$H NMR (400 MHz, CDCl$_3$) δ 10.31 (s, 1H), 8.70 (s, 1H), 7.79 (s, 1H), 7.40-7.33 (m, 1H), 7.10-7.01 (m, 2H), 6.41 (d, J=7.3 Hz, 1H), 4.81-4.62 (m, 1H), 4.17-4.06 (m, 1H), 3.86 (s, 3H), 2.90-2.79 (m, 1H), 2.40-2.28 (m, 1H), 2.22-1.89 (m, 5H), 1.79-1.67 (m, 1 H), 1.60-1.48 (m, 10 H).

Intermediate 223 tert-Butyl 2-(2,6-difluorophenyl)-4-(5-(4-fluoro-5-(2,2,2-trifluoroacetamido)cycloheptyl)-1-methyl-1H-pyrazol-4-ylcarbamoyl)thiazol-5-ylcarbamate (Diastereomer 2)

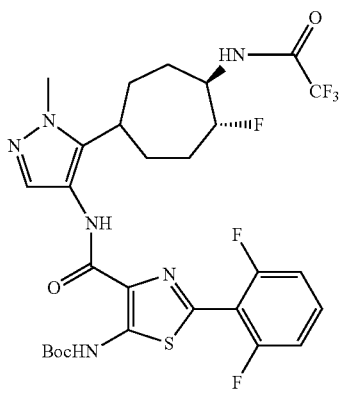 [SMILES: Cn1ncc(NC(=O)c2nc(-c3c(F)cccc3F)sc2NC(=O)OC(C)(C)C)c1C1CC[C@@H](F)[C@H](NC(=O)C(F)(F)F)CC1]

Following the procedure for Intermediate 222 gave tert-butyl 2-(2,6-difluorophenyl)-4-(5-(4-fluoro-5-(2,2,2-trifluoroacetamido)cycloheptyl)-1-methyl-1H-pyrazol-4-ylcarbamoyl)thiazol-5-ylcarbamate (Diastereomer 2) as a white solid (28 mg, 3% over five steps). $^1$H NMR (400 MHz, CDCl$_3$) δ 10.31 (s, 1H), 8.70 (s, 1H), 7.79 (s, 1H), 7.41-7.32 (m, 1H), 7.12-7.02 (m, 2H), 6.50 (d, J=7.4 Hz, 1H), 4.81-4.63 (m, 1H), 4.18-4.05 (m, 1H), 3.86 (s, 3H), 2.87-2.79 (m, 1H), 2.38-2.25 (m, 1H), 2.21-1.91 (m, 5H), 1.68-1.50 (m, 2 H), 1.54 (s, 9H).

Intermediate 224 tert-Butyl 2-(2,6-difluorophenyl)-4-(5-(4-fluoro-5-(2,2-trifluoroacetamido)cycloheptyl)-1-methyl-1H-pyrazol-4-ylcarbamoyl)thiazol-5-ylcarbamate (Diastereomer 3 and Diastereomer 4)

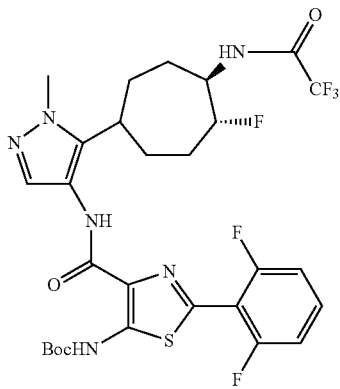 [SMILES: Cn1ncc(NC(=O)c2nc(-c3c(F)cccc3F)sc2NC(=O)OC(C)(C)C)c1C1CC[C@@H](F)[C@H](NC(=O)C(F)(F)F)CC1]

Following the procedure for Intermediate 222 gave, after purification via silica gel column chromatography, tert-butyl 2-(2,6-difluorophenyl)-4-(5-(4-fluoro-5-(2,2,2-trifluoroacetamido)cycloheptyl)-1-methyl-1H-pyrazol-4-ylcarbamoyl)thiazol-5-ylcarbamate (Diastereomer 3 and Diastereomer 4) as a racemic mixture of enantiomers as an off-white solid (82 mg, 8% over five steps). $^1$H NMR (400 MHz, CDCl$_3$) δ 10.35 (s, 1H), 8.56 (s, 1H), 7.78 (s, 1H), 7.44-7.35 (m, 1H), 7.11-7.01 (m, 2H), 6.46 (d, J=8.0 Hz, 1H), 4.64-4.44 (m, 1H), 4.26-4.19 (s, 1H), 3.85 (s, 3H), 3.05-2.95 (s, 1H), 2.36-2.27 (m, 1H), 2.09-1.84 (m, 7H), 1.54 (s, 9H).

Intermediate 225 tert-Butyl 2-(2,6-difluorophenyl)-4-(5-(4-fluoro-5-(2,2,2-trifluoroacetamido)cycloheptyl)-1-methyl-1H-pyrazol-4-ylcarbamoyl)thiazol-5-ylcarbamate (Diastereomer 5)

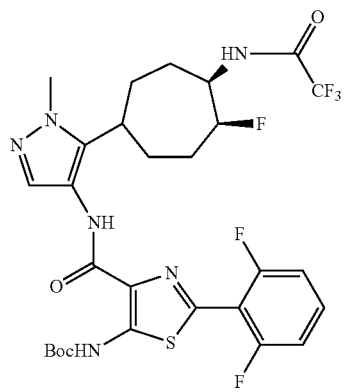 [SMILES: Cn1ncc(NC(=O)c2nc(-c3c(F)cccc3F)sc2NC(=O)OC(C)(C)C)c1C1CC[C@H](F)[C@H](NC(=O)C(F)(F)F)CC1]

Following the procedure for Intermediate 222 gave tert-butyl 2-(2,6-difluorophenyl)-4-(5-(4-fluoro-5-(2,2,2-trifluoroacetamido)cycloheptyl)-1-methyl-1H-pyrazol-4-ylcarbamoyl)thiazol-5-ylcarbamate (Diastereomer 5) as a white solid (28 mg, 3% over five steps). $^1$H NMR (400 MHz, CDCl$_3$) δ 10.31 (s, 1H), 8.74 (s, 1H), 7.84 (s, 1H), 7.40-7.33 (m, 1H), 7.14-7.04 (m, 2H), 6.63 (d, J=8.5 Hz, 1H), 5.06-4.88 (m, 1H), 4.30-4.16 (m, 1H), 3.85 (s, 3H), 3.09-2.99 (m, 1H), 2.35-1.88 (m, 8H), 1.54 (s, 9H).

Intermediate 226 tert-Butyl 2-(2,6-difluorophenyl)-4-(5-(4-fluoro-5-(2,2-trifluoroacetamido)cycloheptyl)-1-methyl-1H-pyrazol-4-ylcarbamoyl)thiazol-5-ylcarbamate (Diastereomer 6, Diastereomer 7 and Diastereomer 8)

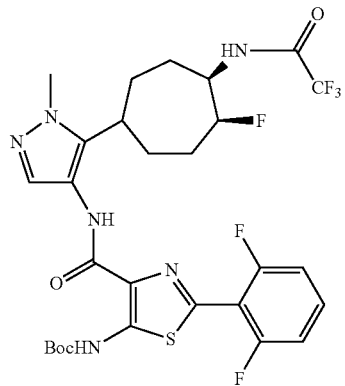 [SMILES: Cn1ncc(NC(=O)c2nc(-c3c(F)cccc3F)sc2NC(=O)OC(C)(C)C)c1C1CC[C@H](F)[C@H](NC(=O)C(F)(F)F)CC1]

Following the procedure for Intermediate 222 gave tert-butyl 2-(2,6-difluorophenyl)-4-(5-(4-fluoro-5-(2,2,2-trifluoroacetamido)cycloheptyl)-1-methyl-1H-pyrazol-4-ylcarbamoyl)thiazol-5-ylcarbamate (Diastereomer 6, Diastereomer 7 and Diastereomer 8) as a white solid (76 mg, 7% over five steps). $^1$H NMR (400 MHz, CDCl$_3$) δ 10.35 and 10.31 (2s, 1H), 8.74 and 8.61 (2s, 1H), 7.84 and 7.75 (2s, 1H), 7.41-7.34 (m, 1H), 7.12-7.02 (m, 2H), 6.73-6.58 (m, 1H), 4.31-4.11 (m, 1H), 3.86 and 3.85 (2s, 3H), 3.08-2.97 (m, 1H), 2.44-1.71 (m, 9H), 1.55 (s, 9H).

Intermediate 227

(E)-5-(6,6-Difluorocyclohept-1-enyl)-1-methyl-4-nitro-1H-pyrazole

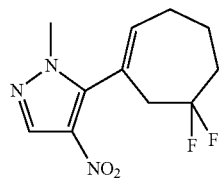 [SMILES: Cn1ncc([N+](=O)[O-])c1C1=CCCCC(F)(F)C1]

(E)-3-Oxocyclohept-1-enyl trifluoromethanesulfonate (1.8 g, 6.98 mmol), 4,4,4',4',5,5,5',5'-octamethyl-2,2'-bi(1,3,2-dioxaborolane) (2.42 g, 9.52 mmol), potassium acetate (1.56 g, 15.8 mmol) and Pd(dppf)Cl$_2$ DCM complex (0.32 g, 0.39 mmol) were suspended in degassed dioxane (20 mL) and the mixture was heated to 80° C. for 16 hr. After cooling, the mixture was filtered and the filter cake washed with dioxane (3×20 mL). This solution was degassed by bubbling nitrogen through it for 10 min and to it was added a degassed aqueous potassium acetate/sodium carbonate solution (1 M, 1:1, 20.9 mL, 20.9 mmol), Pd(dppf)Cl$_2$ DCM complex (0.32 g, 0.39 mmol) and 5-chloro-1-methyl-4-nitro-1H-pyrazole (1.54 g, 9.51 mmol). The mixture was heated to 110° C. for 24 hr, allowed to cool to room temperature and filtered through Celite®. The filtrate was concentrated under reduced pressure and the residue dissolved in EtOAC (30 mL) and washed with water (3×20 mL). The organic layer was passed through a phase separation cartridge and the solvent removed under reduced pressure. Purification via silica gel column chromatography (0-100% EtOAc/isohexane) gave an oil (460 mg). A solution of this oil (440 mg, 1.86 mmol) in DCM (8 mL) was treated with deoxo-Fluor® (50% solution in THF, 1.57 mL, 4.34 mmol) and the reaction mixture was stirred at room temperature for 16 hr. The mixture was diluted with DCM (20 mL), cooled in an ice-water bath and carefully quenched with saturated aqueous NaHCO$_3$ (50 mL). The organic layer was washed with water (2×20 mL), passed through a phase separation cartridge and the solvent removed under reduced pressure. Purification via silica gel column chromatography (0-40% EtOAc/isohexane) gave (E)-5-(6,6-difluorocyclohept-1-enyl)-1-methyl-4-nitro-1H-pyrazole as an oil (0.16 g, 33% over three steps). $^1$H NMR (400 MHz, CDCl$_3$) δ 8.06 (s, 1H), 6.24-6.16 (m, 1H), 3.84 (s, 3H), 2.49-2.31 (m, 4H), 1.88-1.75 (m, 3H), 1.60 (d, J=6.5 Hz, 1H).

Intermediate 228

N-(4-Methyl-1-(1-methyl-4-nitro-1H-pyrazol-5-yl)azepan-4-yl)acetamide

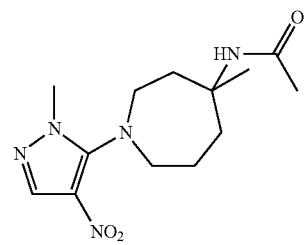 [SMILES: CC(=O)NC1(C)CCCN(c2c([N+](=O)[O-])cnn2C)CC1]

4-Methyl-1-(1-methyl-4-nitro-1H-pyrazol-5-yl)azepan-4-ol (610 mg, 2.40 mmol) was dissolved in acetonitrile (4 mL) and cooled to 0° C. before concentrated sulphuric acid (2.1 mL) was added dropwise. The reaction was allowed to warm to room temperature and stirred for 1 hr before being poured onto ice (150 g), basified with KOH and extracted with DCM (2×30 mL). The combined organic layers were washed with brine (20 mL), passed through a phase separation cartridge and concentrated under reduced pressure to give N-(4-methyl-1-(1-methyl-4-nitro-1H-pyrazol-5-yl)azepan-4-yl)acetamide as a yellow solid (660 mg, 93%). $^1$H NMR (400 MHz, CDCl$_3$) δ 8.05-7.98 (m, 1H), 5.31 (s, 1H), 3.81-3.73 (m, 3H), 3.35 (ddd, J=14.2, 9.3, 2.2 Hz, 1H), 3.22 (t, J=5.9 Hz, 2H), 3.09 (ddd, J=14.2, 7.6, 2.5 Hz, 1H), 2.43-2.31 (m, 2H), 2.05-1.95 (m, 3H), 1.89-1.74 (m, 4H), 1.53-1.36 (m, 3H).

Intermediate 229

N-(1-(4-Amino-1-methyl-1H-pyrazol-5-yl)-5-ethoxyazepan-4-yl)-2,2,2-trifluoroacetamide

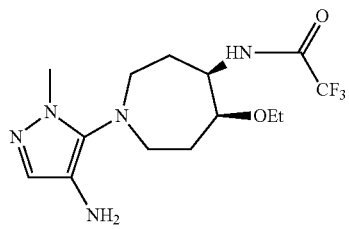 [SMILES: CCO[C@H]1CCN(c2c(N)cnn2C)CC[C@H]1NC(=O)C(F)(F)F]

Following the procedure for Intermediate 54 starting from 5-azido-1-(1-methyl-4-nitro-1H-pyrazol-5-yl)azepan-4-ol and iodoethane gave N-(1-(4-amino-1-methyl-1H-pyrazol-5-yl)-5-ethoxyazepan-4-yl)-2,2,2-trifluoroacetamide as a pink gum (151 mg, 60% over four steps). $^1$H NMR (400 MHz, CDCl$_3$) δ 8.73 (s, 1H), 7.16 (s, 1H), 4.60-4.53 (m, 1H), 3.69-3.36 (m, 8H), 3.16-3.05 (m, 1H), 2.90 (dt, J=14.4, 4.4 Hz, 1H), 2.64-2.27 (m, 3H), 1.89-1.76 (m, 3H), 1.22 (t, J=7.0 Hz, 3H).

Intermediate 230 syn-5-Azido-1-(1-cyclopropyl-4-nitro-1H-pyrazol-5-yl)azepan-4-ol

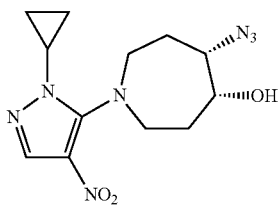 [SMILES: [N-]=[N+]=N[C@H]1CCN(c2c([N+](=O)[O-])cnn2C2CC2)CC[C@H]1O]

Following the procedure for Intermediate 119 starting from anti-5-azido-1-(1-cyclopropyl-4-nitro-1H-pyrazol-5-yl)azepan-4-ol gave syn-5-azido-1-(1-cyclopropyl-4-nitro-1H-pyrazol-5-yl)azepan-4-ol as a brown oil (560 mg, 78% over two steps). $^1$H NMR (400 MHz, CDCl$_3$) δ 7.97-7.92 (m, 1H), 3.94 (dt, J=9.0, 2.7 Hz, 1H), 3.73-3.62 (m, 1H), 3.53-3.22 (m, 5H), 2.24-2.12 (m, 2H), 2.02-1.88 (m, 2H), 1.28-1.23 (m, 2H), 1.15-1.05 (m, 2H). OH not observed.

Intermediate 231 tert-Butyl 1-(1-cyclopropyl-4-nitro-1H-pyrazol-5-yl)-5-methoxyazepan-4-ylcarbamate

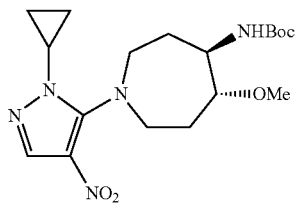 [SMILES: CO[C@@H]1CCN(c2c([N+](=O)[O-])cnn2C2CC2)CC[C@H]1NC(=O)OC(C)(C)C]

Following the procedure for Intermediate 120 starting from syn-5-azido-1-(1-cyclopropyl-4-nitro-1H-pyrazol-5-yl)azepan-4-ol gave tert-butyl 1-(1-cyclopropyl-4-nitro-1H-pyrazol-5-yl)-5-methoxyazepan-4-ylcarbamate as a yellow oil (440 mg, 61% over three steps). $^1$H NMR (400 MHz, CDCl$_3$) δ 7.95 (s, 1H), 5.21 (d, J=9.0 Hz, 1H), 4.00 (d, J=10.3 Hz, 1H), 3.73-3.51 (m, 3H), 3.56-3.27 (m, 4H), 3.26-3.18 (m, 1H), 3.10 (d, J=13.5 Hz, 1H), 2.28-2.16 (m, 1H), 2.15-2.06 (m, 1H), 1.93-1.79 (m, 2H), 1.46 (s, 9H), 1.37-1.03 (m, 4H).

Intermediate 232

1-(1-Methyl-4-nitro-1H-pyrazol-5-yl)-4-(trifluoromethyl)azepan-4-ol

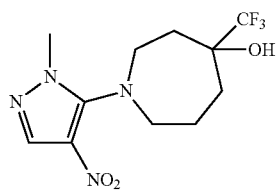

To a solution of benzyl 4-oxoazepane-1-carboxylate (2.0 g, 8.08 mmol) in trifluoromethyltrimethylsilane (1.42 mL, 9.70 mmol) was added caesium fluoride (70.4 mg, 0.40 mmol). The reaction mixture was stirred at room temperature until complete consumption of trifluoromethyltrimethylsilane was observed by $^{19}$F NMR and quenched with a 1 M HCl solution (50 mL). The mixture was extracted with EtOAc (3×50 mL) and the combined organic layers were washed with brine (50 mL), separated, dried over MgSO$_4$ and the solvent removed under reduced pressure. Purification via silica gel column chromatography (0-100% EtOAc/isohexane) gave benzyl 4-hydroxy-4-(trifluoromethyl)azepane-1-carboxylate as a yellow oil (1.48 g). To a solution of this oil (1.3 g, 4.1 mmol) in ethanol (20 mL) was added methylcyclohexadiene (4.6 mL) and 10% palladium on carbon (0.13 g). The reaction mixture was heated at reflux for 30 min before being cooled down to room temperature, filtered through Celite®, washed with MeOH and concentrated under reduced pressure. The residue was dissolved in DMSO (10 mL) and 5-chloro-1-methyl-4-nitro-1H-pyrazole (637 mg, 3.94 mmol) and potassium fluoride (916 mg, 15.76 mmol) were added. The reaction mixture was heated at 70° C. for 16 hr, quenched with water (50 mL) and extracted with EtOAc (3×50 mL). The combined organic layers were washed with water (100 mL) and brine (100 mL), separated, dried over MgSO$_4$ and the solvent removed under reduced pressure. Purification via silica gel column chromatography (0-100% EtOAc/isohexane) gave 1-(1-methyl-4-nitro-1H-pyrazol-5-yl)-4-(trifluoromethyl)azepan-4-ol as a yellow solid (1.06 g, 40% over three steps). $^1$H NMR (400 MHz, CDCl$_3$) δ 8.04 (s, 1H), 3.78 (s, 3H), 3.71 (ddd, J=14.7, 10.5, 2.0 Hz, 1H), 3.31 (dt, J=11.8, 4.4 Hz, 1H), 3.14 (td, J=11.3, 4.6 Hz, 1H), 3.06 (ddd, J=14.7, 5.7, 2.9 Hz, 1H), 2.31-2.13 (m, 1H), 2.14-1.94 (m, 5H), 1.92-1.83 (m, 1H).

Intermediate 233

(E)-7-Azido-4-(1-methyl-4-nitro-1H-pyrazol-5-yl)cyclohept-3-enol

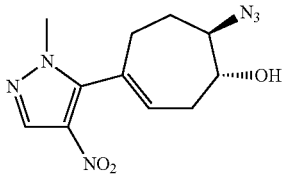

Following the procedure for Intermediate 221 gave (E)-7-azido-4-(1-methyl-4-nitro-1H-pyrazol-5-yl)cyclohept-3-enol as a pale yellow oil (244 mg, 35% over two steps). $^1$H NMR (400 MHz, CDCl$_3$) δ 8.06 (s, 1H), 5.95 (dd, J=8.2, 5.1 Hz, 1H), 3.80 (s, 3H), 3.69-3.61 (m, 2H), 2.74-2.63 (m, 1H), 2.61-2.41 (m, 3H), 2.28-2.19 (m, 1H), 1.97-1.86 (m, 1 H). OH not observed.

Intermediate 234 tert-butyl (E)-2-methoxy-5-(1-methyl-4-nitro-1H-pyrazol-5-yl)cyclohept-4-enylcarbamate

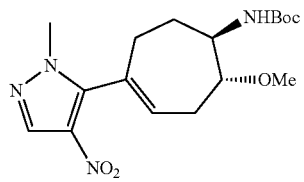 [SMILES: CO[C@@H]1CC=C(c2c([N+](=O)[O-])cnn2C)CC[C@H]1NC(=O)OC(C)(C)C]

Following the procedure for Intermediate 120 starting from (E)-7-azido-4-(1-methyl-4-nitro-1H-pyrazol-5-yl)cyclohept-3-enol gave tert-butyl (E)-2-methoxy-5-(1-methyl-4-nitro-1H-pyrazol-5-yl)cyclohept-4-enylcarbamate as a pale yellow solid (360 mg, 62% over three steps). $^1$H NMR (400 MHz, CDCl$_3$) δ 8.05 (s, 1H), 5.82 (t, J=6.5 Hz, 1H), 4.77 (s, 1H), 3.93 (s, 1H), 3.82 (s, 3H), 3.42 (s, 3H), 3.37 (t, J=7.6 Hz, 1H), 2.71-2.44 (m, 3H), 2.34 (t, J=11.7 Hz, 1H), 2.22-2.11 (m, 1H), 1.86-1.74 (m, 1H), 1.47 (s, 9H).

Intermediate 235 tert-Butyl 4-methyl-1-(1-methyl-4-nitro-1H-pyrazol-5-yl)azepan-4-ylcarbamate

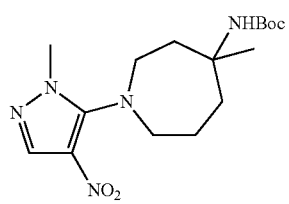 [SMILES: Cn1ncc([N+](=O)[O-])c1N1CCCC(C)(NC(=O)OC(C)(C)C)CC1]

To a solution of benzyl 4-oxoazepane-1-carboxylate (2.0 g, 8.09 mmol) in diethyl ether (18 mL) cooled to −78° C. was added dropwise a solution of methyllithium lithium bromide complex (1.5 M in Et$_2$O, 10.8 mL, 16.17 mmol). The reaction mixture was stirred at −78° C. for 30 min before being quenched with a saturated solution of ammonium chloride (50 mL). The reaction was allowed to warm to room temperature and extracted with EtOAc (3×50 mL). The combined organic layers were dried over MgSO$_4$ and the solvent removed under reduced pressure. Purification via silica gel column chromatography (0-50% EtOAc/isohexane) gave benzyl 4-hydroxy-4-methylazepane-1-carboxylate as a light yellow oil (1.94 g). A solution of this oil (884 mg, 3.36 mmol) in MeOH (10 mL) was passed through the H-Cube® (full H$_2$, 50° C., flow rate: 1 mL/min, 30 mm 10% Pd/C cartridge) and the solvent removed under reduced pressure. The residue was dissolved in DMSO (10 mL) and 5-chloro-1-methyl-4-nitro-1H-pyrazole (521 mg, 3.23 mmol) and potassium fluoride (750 mg, 12.91 mmol) were added. The reaction mixture was heated at 75° C. for 16 hr before being quenched with water (30 mL). The mixture was extracted with EtOAc (3×30 mL) and the combined organic layers were washed with water (20 mL), separated, dried over MgSO$_4$ and the solvent removed under reduced pressure. Purification via silica gel column chromatography (0-100% EtOAc/isohexane) gave 4-methyl-1-(1-methyl-4-nitro-1H-pyrazol-5-yl)azepan-4-ol as a yellow oil (290 mg). To a solution of this oil (260 mg, 1.04 mmol) and chloroacetonitrile (139 mL, 2.09 mmol) in acetic acid (1.0 mL) at 0° C. was added dropwise concentrated sulphuric acid (308 mL, 3.15 mmol). The reaction mixture was allowed to warm to room temperature and stirred for an additional 2 hr before being quenched with aqueous 2 M NaOH (10 mL) and extracted with EtOAc (3×10 mL). The combined organic layers were separated, dried over MgSO$_4$ and the solvent removed under reduced pressure. Purification via silica gel column chromatography (0-50% EtOAc/isohexane) gave 2-chloro-N-(4-methyl-1-(1-methyl-4-nitro-1H-pyrazol-5-yl)azepan-4-yl)acetamide as a yellow oil (264 mg). To a solution of this oil (264 mg, 0.80 mmol) in ethanol (1.4 mL) and acetic acid (0.6 mL) was added thiourea (73 mg, 0.96 mmol). The reaction mixture was heated at reflux for 16 hr, quenched with 1M NaOH solution (5 mL) and extracted with EtOAc (10 mL). The organic layer was separated, dried over MgSO$_4$ and the solvent removed under reduced pressure. The residue was passed through an SCX column eluting with 1M NH$_3$ in MeOH to give 4-methyl-1-(1-methyl-4-nitro-1H-pyrazol-5-yl)azepan-4-amine as a gum (172 mg). To a solution of this gum (166 mg, 0.65 mmol) in DCM (5 mL) was added DIPEA (0.57 mL, 3.27 mmol) followed by di-tert-butyl dicarbonate (171 mg, 0.78 mmol). The reaction mixture was left stirring at room temperature for 16 hr, quenched with water (10 mL) and extracted with DCM (3×10 mL). The combined organic layers were passed through a phase separator and concentrated under reduced pressure. Purification via silica gel column chromatography (0-100% EtOAc/isohexane) gave tert-butyl 4-methyl-1-(1-methyl-4-nitro-1H-pyrazol-5-yl)azepan-4-ylcarbamate as a yellow oil (188 mg, 14% over six steps). $^1$H NMR (400 MHz, CDCl$_3$) δ 8.03 (s, 1H), 4.53 (s, 1H), 3.78 (s, 3H), 3.38-3.28 (m, 1H), 3.28-3.16 (m, 2H), 3.11-3.03 (m, 1H), 2.28-2.12 (m, 2H), 1.90-1.69 (m, 4H), 1.44 (d, J=7.2 Hz, 12H).

Intermediate 236

5-(4-Fluoro-8-oxabicyclo[5.1.0]octan-4-yl)-1-methyl-4-nitro-1H-pyrazole

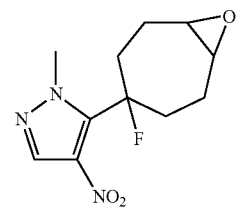 [SMILES: Cn1ncc([N+](=O)[O-])c1C1(F)CCC2OC2CC1]

To a solution of (7)-5-(1-fluorocyclohept-4-enyl)-1-methyl-4-nitro-1H-pyrazole (900 mg, 3.77 mmol) in DCM (30 mL) at 0° C. was added portionwise meta-chloroperoxybenzoic acid (1.0 g, 4.14 mmol). The reaction mixture was allowed to warm to room temperature and stirred for 90 min before being quenched with a saturated solution of sodium hydrogencarbonate (30 mL). The mixture was extracted with DCM (100 mL), washed with aqueous 2 M (2×50 mL) and brine (30 mL). The organic layer was separated, dried over MgSO$_4$ and concentrated under reduced pressure to give 5-(4-fluoro-8-oxabicyclo[5.1.0]octan-4-yl)-1-methyl-4-nitro-1H-pyrazole as a colourless solid (982 mg, quantitative) as a 2:5 ratio of diastereomers. $^1$H NMR (400 MHz, CDCl$_3$) δ 8.07 and 8.01 (2s, 1H), 4.12-4.00 (m, 3H), 3.27-3.11 (m, 2H), 2.90-2.63 (m, 2H), 2.24-1.74 (m, 6H).

Intermediate 237

2-Azido-5-fluoro-5-(1-methyl-4-nitro-1H-pyrazol-5-yl)cycloheptanol

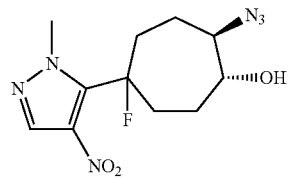 [SMILES: Cn1ncc([N+](=O)[O-])c1C1(F)CC[C@@H](O)[C@H](N=[N+]=[N-])CC1]

A solution of 5-(4-fluoro-8-oxabicyclo[5.1.0]octan-4-yl)-1-methyl-4-nitro-1H-pyrazole (260 mg, 1.02 mmol) in DMF/water (10 mL/1 mL) was treated with ammonium chloride (135 mg, 2.55 mmol) and sodium azide (332 mg, 5.1 mmol) and the mixture was heated at 100° C. for 48 hrs. The reaction mixture was extracted with EtOAc (100 mL) and the organic layer was washed with water (7×20 mL), washed with brine (20 mL), separated, dried over MgSO$_4$, and concentrated under reduced pressure. Purification via silica gel column chromatography (40% EtOAc/isohexane) gave 2-azido-5-fluoro-5-(1-methyl-4-nitro-1H-pyrazol-5-yl)cycloheptanol as a white solid (145 mg, 48%). $^1$H NMR (400 MHz, CDCl$_3$) δ 8.06 and 8.05 (2s, 1H), 4.08 and 4.06 (2s, 3H), 3.83 (dd, J=10.7, 8.2 Hz, 1H), 3.65-3.58 (m, 1H), 2.87-2.55 (m, 2H), 2.33-2.21 (m, 2H), 2.17-1.98 (m, 3H), 1.98-1.84 (m, 2H).

Intermediate 238 tert-Butyl 5-fluoro-2-methoxy-5-(1-methyl-4-nitro-1H-pyrazol-5-yl)cycloheptylcarbamate

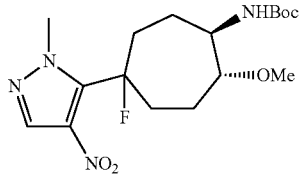 [SMILES: CO[C@@H]1CCC(F)(c2c([N+](=O)[O-])cnn2C)CC[C@H]1NC(=O)OC(C)(C)C]

Following the procedure for Intermediate 120 starting from 2-azido-5-fluoro-5-(1-methyl-4-nitro-1H-pyrazol-5-yl)cycloheptanol gave tert-butyl 5-fluoro-2-methoxy-5-(1-methyl-4-nitro-1H-pyrazol-5-yl)cycloheptylcarbamate as an off-white solid (155 mg, 53% over three steps). $^1$H NMR (400 MHz, CDCl$_3$) δ 8.06 (s, 1H), 4.08 and 4.06 (2s, 3H), 3.82 (d, J=8.8 Hz, 1H), 3.39 (s, 3H), 2.98-2.62 (m, 1H), 2.16-1.84 (m, 7H), 1.61-1.49 (m, 2H), 1.47 (s, 9H).

Intermediate 239 tert-Butyl 1-(4-amino-1-methyl-1H-pyrazol-5-yl)-5-fluoroazepan-4-ylcarbamate

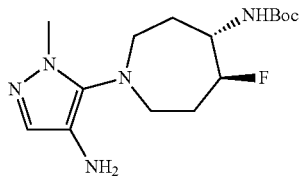

To a solution of 5-azido-1-(1-methyl-4-nitro-1H-pyrazol-5-yl)azepan-4-ol (5.4 g, 19.2 mmol) in DCM (150 mL) at 0° C. was added dropwise a solution of Deoxofluor® in THF (18.5 mL, 51.1 mmol) over a period of 15 min. The reaction was allowed to warm to room temperature over 18 hr. The mixture was then cooled down to 0° C. before a saturated solution of sodium hydrogen carbonate (300 mL) was added dropwise. The reaction mixture was stirred for 1 hr before the layers were separated and the aqueous layer extracted with DCM (200 mL). The combined organic layers were dried over MgSO$_4$ and the solvent removed under reduced pressure. Purification via silica gel column chromatography (0-100% EtOAc/isohexane) gave 4-azido-5-fluoro-1-(1-methyl-4-nitro-1H-pyrazol-5-yl)azepane as a pale green gum (3.66 g). To a solution of this gum (3.66 g, 12.9 mmol) in THF (200 mL) and water (20 mL) was added triphenylphosphine (3.38 g, 12.9 mmol). The reaction mixture was heated at 60° C. for 18 hr before being cooled to room temperature and concentrated under reduced pressure. The residue was then diluted with EtOAc (500 mL), quenched with a 1 N HCl aqueous solution (100 mL) and washed with water (2×100 mL). The combined aqueous layers were washed with EtOAc (300 mL) before being basified to pH 14 with solid sodium hydroxide and extracted with DCM (3×250 mL). The combined organic layers were dried over MgSO$_4$ and the solvent removed under reduced pressure to give 5-fluoro-1-(1-methyl-4-nitro-1H-pyrazol-5-yl)azepan-4-amine as a pale green gum (3.1 g). To a solution of this gum (3.1 g, 12.0 mmol) in DCM (150 mL) was added triethylamine (4 mL, 28.6 mmol) followed by di-tert-butyl dicarbonate (3.95 g, 18.0 mmol). The reaction mixture was left stirring at room temperature for 2 hr, before being concentrated under reduced pressure. Purification via silica gel column chromatography (0-100% EtOAc/isohexane) gave tert-butyl-5-fluoro-1-(1-methyl-4-nitro-1H-pyrazol-5-yl)azepan-4-ylcarbamate as a pale yellow solid (3.7 g, 86%). To a solution of this solid (1.5 g, 4.19 mmol) in MeOH (100 mL) was added ammonium formate (1.95 g, 33.58 mmol) followed by 10% palladium on carbon (178 mg, 1.68 mmol) and the mixture was heated at 75° C. for 2 hr. The mixture was filtered through Celite® and the solvents concentrated under reduced pressure. The residue was dissolved in water (100 mL) and extracted with DCM (3×100 mL). The combined organic layers were passed through a phase separation cartridge and concentrated under reduced pressure to give tert-butyl 1-(4-amino-1-methyl-1H-pyrazol-5-yl)-5-fluoroazepan-4-ylcarbamate as a purple solid (1.37 g, 54% over four steps). $^1$H NMR (400 MHz, CDCl$_3$) δ 7.13 (s, 1H), 6.28 (s, 1H), 4.75 (d, J=46.1 Hz, 1H), 4.26 (s, 1H), 3.66 (s, 3H), 3.49-3.30 (m, 2H), 3.13-2.88 (m, 2H), 2.62 (s, 2H), 2.29-2.15 (m, 1H), 2.10-1.97 (m, 1H), 1.89-1.80 (m, 1H), 1.75-1.54 (m, 1H), 1.45 (s, 9H).

Intermediate 240 tert-Butyl 1-(4-(5-(tert-butoxy-carbonyl)-amino-2-bromothiazole-4-carboxamido)-1-methyl-1H-pyrazol-5-yl)-5-fluoroazepan-4-ylcarbamate

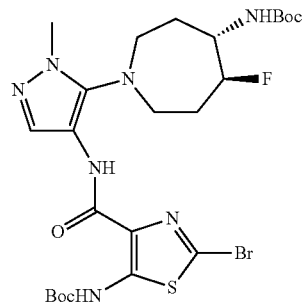 [SMILES: Cn1ncc(NC(=O)c2nc(Br)sc2NC(=O)OC(C)(C)C)c1N1CC[C@H](NC(=O)OC(C)(C)C)[C@@H](F)CC1]

A solution of PyBOP (3.06 g, 5.03 mmol) and 2-bromo-5-(tert-butoxycarbonyl-amino)thiazole-4-carboxylic acid (1.63 g, 5.04 mmol) in DCM (50 mL) was stirred at room temperature for 15 min. tert-Butyl 1-(4-amino-1-methyl-1H-pyrazol-5-yl)-5-fluoroazepan-4-ylcarbamate (1.37 g, 4.20 mmol) and DIPEA (1.17 mL, 6.71 mmol) were added and the mixture stirred at room temperature for 2 days. The reaction mixture was diluted with DCM (50 mL) and washed with water (3×50 mL). The organic layers was passed through a phase separation cartridge and concentrated under reduced pressure. Purification of the residue via silica gel column chromatography (0-100% EtOAc/isohexane) gave tert-butyl 1-(4-(5-amino-2-bromothiazole-4-carboxamido)-1-methyl-1H-pyrazol-5-yl)-5-fluoroazepan-4-ylcarbamate as a pink solid (2.50 g, 94%). $^1$H NMR (400 MHz, CDCl$_3$) δ 10.27 (s, 1H), 8.27 (s, 1H), 7.64 (s, 1H), 5.01 (s, 1H), 4.86-4.60 (m, 1H), 3.81-3.64 (m, 3H), 3.44-3.27 (m, 2H), 3.15-3.07 (m, 2H), 2.28-2.10 (m, 3H), 1.92-1.70 (m, 2H), 1.52 (s, 9H), 1.44 (s, 9H).

Intermediate 240a 6-azido-6-methyl-cyclohex-3-en-1-ol

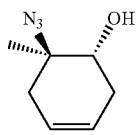

Sodium hydrogencarbonate (7.5 g, 89 mmol) and m-chloroperbenzoic acid (20 g, 89 mmol) were added portionwise to a solution of 1-methylcyclohexa-1,4-diene (8.4 g, 89 mmol) in DCM (250 mL) cooled to −15° C. and the mixture was stirred for 30 min. The reaction was quenched with a 20% solution of sodium sulphite (100 mL) and warmed to room temperature. The aqueous layer was extracted with DCM (3×100 mL) and the combined organic layers were washed with aqueous sodium sulphite solution (100 mL), aqueous NaHCO$_3$ (100 mL), water (100 mL) and brine (100 mL), passed through a phase separation cartridge and concentrated under reduced pressure to give an epoxide as colourless oil. The epoxide (2.1 g, 19.1 mmol) was added slowly to a mixture of sodium azide (6.2 g, 95 mmol) in acetic acid (5 mL) and water (25 mL) stirring at 30° C. and the resulting mixture stirred for 16 hr blowing any hydrazoic acid generated in situ above the condenser into a solution of bleach. The mixture was cooled to room temperature and quenched with aqueous NaHCO$_3$ (20 mL). The mixture was extracted with ether (3×50 mL) and the combined organics washed with 2 N aqueous NaOH (50 mL), separated, dried over MgSO$_4$ and concentrated under reduced pressure to give 6-azido-6-methyl-cyclohex-3-en-1-ol as yellow oil (1.8 g, 82% over two steps). $^1$H NMR (400 MHz, CDCl$_3$) δ 5.58-5.55 (m, 2H), 3.77-3.73 (m, 1H), 2.46 (d, J=6.5 Hz, 1H), 2.30-2.27 (m, 2H), 2.10 (s, 3H), 2.06-2.03 (m, 2H).

Intermediate 241

5-Azido-1-benzyl-5-methylazepan-4-ol

A solution of 6-azido-6-methylcyclohex-3-enol (3.9 g, 25 mmol) in MeOH/DCM (100 mL/20 mL) cooled to −78° C. was degassed by bubbling nitrogen through it for 5 min. Ozone was then bubbled through the reaction mixture until a greyish-blue colour persisted. Nitrogen was again bubbled through the cold reaction mixture until only a pale colour persisted. A solution of benzylamine (2.7 g, 25 mmol) dissolved in MeOH (5 mL) was added followed by NaCNBH$_3$ (6.4 g, 101.5 mmol) in MeOH (10 mL). The mixture was allowed to warm to room temperature and stirred for 16 hr. The solvents were removed under reduced pressure and the residue partitioned between EtOAc (50 mL) and water (50 mL). The aqueous layer was further extracted with EtOAc (3×50 mL) and the combined organic layers were washed with brine (40 mL), separated, dried over MgSO$_4$ and concentrated under reduced pressure. Purification of the residue via silica gel column chromatography (1-10% 7 M NH$_3$ in MeOH/DCM) gave 5-azido-1-benzyl-5-methylazepan-4-ol as a viscous yellow oil (4.8 g, 73%). $^1$H NMR (400 MHz, CDCl$_3$) δ 7.25-7.34 (m, 5H), 3.69-3.62 (m, 2H), 3.51-3.47 (m, 2H), 2.96-2.89 (m, 1H), 2.69-2.62 (m, 3H), 2.19-2.11 (m, 1H), 1.99-1.85 (m, 1H), 1.78-1.68 (m, 1H), 1.61-1.57 (m, 1H), 1.43 (s, 3H).

Intermediate 242

5-Amino-1-benzyl-5-methylazepan-4-ol

To a solution of 5-azido-1-benzyl-5-methylazepan-4-ol (1.5 g, 5.76 mmol) in THF (12 mL) and water (4 mL) was added slowly a solution of trimethylphosphine (1 M in toluene, 28 mL, 28.9 mmol) and the reaction was stirred at 65° C. for 18 hr. The mixture was allowed to cool to room temperature and concentrated under reduced pressure. The residue was dissolved in 1 M HCl (30 mL) and extracted with EtOAc (2×25 mL). The aqueous layer was basified to pH14 with aqueous 6 M NaOH and extracted with DCM (3×30 mL). The combined organic layers were passed through a phase separation cartridge concentrated under reduced pressure. Purification via silica gel column chromatography (1-10% 7 M NH$_3$ in MeOH/DCM) gave 5-amino-1-benzyl-5-methylazepan-4-ol as a viscous yellow oil (1.2 g, 89%). $^1$H NMR (400 MHz, CDCl$_3$) δ 7.34-7.20 (m, 5H), 3.60-3.52 (m, 2H), 3.50-3.46 (m, 2H), 2.80-2.79 (m, 1H), 2.70-2.45 (m, 4H), 2.15-1.95 (m, 1H), 1.79-1.72 (m, 2H), 1.49-1.40 (m, 2H), 1.19 (s, 3H).

Intermediate 243

N-(1-Benzyl-5-hydroxy-4-methylazepan-4-yl)-2,2,2-trifluoroacetamide

To a solution 5-amino-1-benzyl-5-methylazepan-4-ol (1.2 g, 5.12 mmol) and Et$_3$N (0.77 g, 7.68 mmol) in THF (20 mL) at 0° C. was added dropwise trifluoroacetic anhydride (1.18 g, 5.63 mmol, 0.78 mL). The reaction mixture was allowed to warm to room temperature and stirred for 3 hr. The mixture was partitioned between EtOAc (10 mL) and water (10 mL) and the aqueous layer was extracted with EtOAc (3×25 mL). The combined organic layers were washed with brine (30 mL), dried over MgSO$_4$ and concentrated under reduced pressure. Purification via silica gel column chromatography (1-5% (7 M NH$_3$ in MeOH)/DCM) gave N-(1-benzyl-5-hydroxy-4-methylazepan-4-yl)-2,2,2-trifluoroacetamide (0.8 g, 47%) as a yellow gum. $^1$H NMR (400 MHz, CDCl$_3$) δ 7.34-7.28 (m, 5H), 6.65 (br s, 1H), 4.22-4.15 (m, 1H), 3.60 (dd, J=9.6, 9.7 Hz, 2H), 2.90-2.75 (m, 1H), 2.70-2.65 (m, 1H), 2.60-2.49 (m, 2H), 2.20-2.10 (m, 1H), 1.95-1.80 (m, 2H), 1.75-1.55 (m, 2H), 1.58 (s, 3H).

Intermediate 244

2,2,2-Trifluoro-N-(5-hydroxy-4-methylazepan-4-yl)acetamide

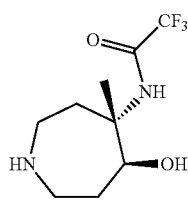 [SMILES: C[C@]1(NC(=O)C(F)(F)F)CCNCC[C@@H]1O]

To a solution of N-(1-benzyl-5-hydroxy-4-methylazepan-4-yl)-2,2,2-trifluoroacetamide (1.7 g, 5.0 mmol) in MeOH (30 mL) was added 1M HCl (1 mL) and palladium hydroxide on carbon (0.25 g). The mixture was shaken under an atmosphere of hydrogen gas (40 psi) for 72 hr. The mixture was filtered through Celite® washing with MeOH (30 mL). The solvent was removed under reduced pressure and the residue passed through an SCX column eluting with (1-10% (7 M NH$_3$ in MeOH)/DCM) to give 2,2,2-trifluoro-N-(5-hydroxy-4-methylazepan-4-yl)acetamide as a yellow gum (0.8 g, 66%). $^1$H (400 MHz, CDCl$_3$) δ 6.90 (br s, 1H), 4.22-4.16 (m, 1H), 3.70-3.60 (m, 1H), 3.40-3.35 (m, 1H), 3.15-2.99 (m, 1H), 2.90-2.75 (m, 2H), 2.20-2.05 (m, 1H), 1.99-1.75 (m, 4H), 1.53 (s, 3H).

Intermediate 245

2,2,2-Trifluoro-N-(5-hydroxy-4-methyl-1-(1-methyl-4-nitro-1H-pyrazol-5-yl)azepan-4-yl)acetamide

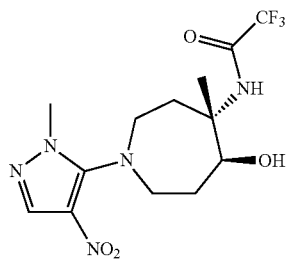 [SMILES: Cn1ncc([N+](=O)[O-])c1N1CC[C@H](O)[C@@](C)(NC(=O)C(F)(F)F)CC1]

Following the procedure for Intermediate 213 starting from 2,2,2-trifluoro-N-(5-hydroxy-4-methylazepan-4-yl)acetamide gave 2,2,2-trifluoro-N-(5-hydroxy-4-methyl-1-(1-methyl-4-nitro-1H-pyrazol-5-yl)azepan-4-yl)acetamide as a white solid (400 mg, 88%). $^1$H NMR (400 MHz, CDCl$_3$) δ 8.03 (s, 1H), 3.77 (s, 2H), 3.54 (dd, J=10.2, 3.2 Hz, 1H), 3.49 (s, 3H), 3.41-3.32 (m, 1H), 3.30-3.22 (m, 1H), 3.13 (dt, J=13.1, 4.7 Hz, 2H), 2.22-2.00 (m, 1H), 1.95-1.72 (m, 2H), 1.24-1.15 (m, 3H), 1.08 (d, J=7.0 Hz, 1H).

Intermediate 246 tert-Butyl 1-(4-(5-(tert-butoxycabonyl-amino)-2-bromothiazole-4-carboxamido)-1-methyl-1H-pyrazol-5-yl)-6,6-difluoroazepan-4-ylcarbamate

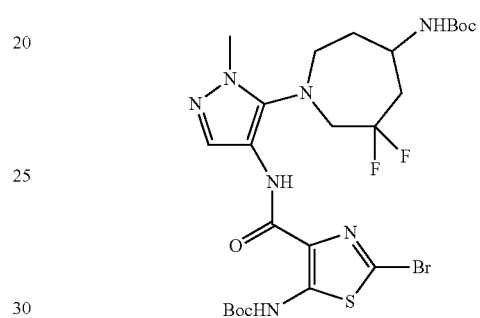

To a solution of tert-butyl 6,6-difluoro-1-(1-methyl-4-nitro-1H-pyrazol-5-yl)azepan-4-ylcarbamate (2.5 g, 6.67 mmol) in ethanol (100 mL) and water (10 mL) was added ammonium chloride (3.5 g, 65.0 mmol) and iron powder (3.0 g, 53.7 mmol). The reaction mixture was heated at 100° C. for 2.5 hr, before being cooled down at room temperature, filtered through Celite®, washed with MeOH and the filtrate concentrated under reduced pressure. The residue was dissolved in DCM (200 mL), quenched with a saturated solution of sodium hydrogencarbonate (300 mL) and a 10% solution of sodium sulfite (100 mL) and the mixture stirred for 30 min. The layers were separated and the aqueous layer extracted with DCM (100 mL). The combined organic layers were dried over MgSO$_4$ and concentrated under reduced pressure. Purification via silica gel column chromatography (0-30% EtOAc/isohexane) gave tert-butyl 1-(4-amino-1-methyl-1H-pyrazol-5-yl)-6,6-difluoroazepan-4-ylcarbamate as an orange foam (2.12 g). A solution of PyBOP (1.92 g, 3.70 mmol) and 2-bromo-5-(tert-butoxycarbonyl-amino)thiazole-4-carboxylic acid (795 mg, 2.46 mmol) in DCM (50 mL) was stirred at room temperature for 15 min. tert-Butyl 1-(4-amino-1-methyl-1H-pyrazol-5-yl)-6,6-difluoroazepan-4-ylcarbamate (850 mg, 2.46 mmol) and DIPEA (2.0 mL, 11.4 mmol) were added and the mixture stirred at room temperature for 18 hr. The reaction mixture was diluted with DCM (50 mL) and washed with a saturated solution of sodium hydrogencarbonate (100 mL). The organic layer was passed through a phase separation cartridge and concentrated under reduced pressure. Purification of the residue via silica gel column chromatography (0-100% EtOAc/isohexane) gave tert-butyl 1-(4-(5-(tert-butoxycabonyl-amino)-2-bromothiazole-4-carboxamido)-1-methyl-1H-pyrazol-5-yl)-6,6-difluoroazepan-4-ylcarbamate as a pale yellow foam (1.35 g, 77% over two steps). $^1$H NMR (400 MHz, CDCl$_3$) δ 10.24 (s, 1H), 8.37 (s, 1H), 7.65 (s, 1H), 4.88 (s, 1H), 4.04 (s, 1H), 3.77

(s, 3H), 3.63-3.43 (m, 2H), 3.38-3.24 (m, 2H), 2.52-2.40 (m, 2H), 2.13-2.05 (m, 1H), 1.99 (s, 1H), 1.53 (s, 9H), 1.43 (s, 9H).

Intermediate 247 tert-Butyl 1-(4-(5-(tert-butoxy-carbonyl-amino)-2-bromothiazole-4-carboxamido)-1-methyl-1H-pyrazol-5-yl)-6-methoxy-6-methylazepan-4-ylcarbamate

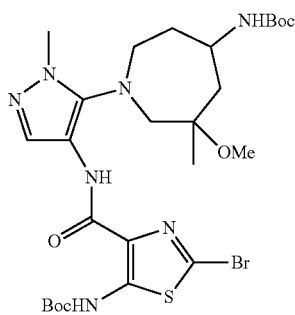 [SMILES: COC1(C)CC(NC(=O)OC(C)(C)C)CCN(c2c(NC(=O)c3nc(Br)sc3NC(=O)OC(C)(C)C)cnn2C)C1]

Following the procedure for Intermediate 245 starting from tert-butyl 6-methoxy-6-methyl-1-(1-methyl-4-nitro-1H-pyrazol-5-yl)azepan-4-ylcarbamate gave tert-butyl 1-(4-(5-(tert-butoxy-carbonyl-amino)-2-bromothiazole-4-carboxamido)-1-methyl-1H-pyrazol-5-yl)-6-methoxy-6-methylazepan-4-ylcarbamate as a pale yellow foam (530 mg, 79% over two steps). $^1$H NMR (400 MHz, CDCl$_3$) δ 10.43 (s, 1H), 9.25 (s, 1H), 7.92 (s, 1H), 4.60 (s, 1H), 4.03 (d, J=10.5 Hz, 1H), 3.71 (s, 3H), 3.38 (s, 3H), 3.39-3.19 (m, 4H), 3.06 (d, J=14.5 Hz, 1H), 2.36 (d, J=14.2 Hz, 1H), 2.16 (d, J=13.4 Hz, 1H), 1.77 (d, J=12.1 Hz, 1H), 1.52 (s, 9H), 1.43 (s, 9H), 1.12 (s, 3H).

Intermediate 248

(E)-3-(1-Methyl-4-nitro-1H-pyrazol-5-yl)cyclohept-2-enone

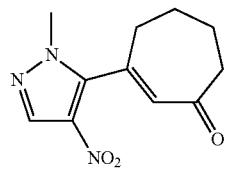

To a solution of cycloheptane-1,3-dione (10 g, 79.3 mmol) in DCM (500 mL) was added pyridine (12.8 mL, 158.6 mmol). The solution was cooled at −78° C. before triflic anhydride (13.2 mL, 95.1 mmol) was added dropwise. The mixture was warmed to 0° C. and left stirring for 4 hr before being quenched with 1 M HCl (150 mL). The organic layer was washed with a saturated solution of sodium hydrogencarbonate (200 mL), passed through a phase separation cartridge and concentrated under reduced pressure to give (E)-3-oxocyclohept-1-enyl trifluoromethanesulfonate as a brown oil. To a solution of this oil (1.8 g, 6.97 mmol) in degassed dioxane (200 mL) was added potassium acetate (15.6 g, 158.6 mmol), bis(pinacolato)diboron (24.2 g, 95.1 mmol) and [1,1'-bis(diphenylphosphino)-ferrocene]dichloropalladium(II) complex with dichloromethane (3.24 g, 3.97 mmol) and the mixture was heated at 90° C. for 18 hr. The mixture was cooled to room temperature, filtered through Celite®, washed with MeOH (50 mL) and the solvents were removed under reduced pressure. The residue was dissolved in degassed dioxane (200 mL) before 5-chloro-1-methyl-4-nitro-1H-pyrazole (15.4 g, 95.1 mmol) was added followed by [1,1'-bis(diphenylphosphino)ferrocene]dichloropalladium(II), complex with dichloromethane (3.24 mg, 3.97 mmol) and a 1/1 aqueous solution of sodium carbonate/potassium acetate (63 mL, 3.8 M). The mixture was heated at 105° C. for 3 hr. The mixture was allowed to cool to room temperature, filtered through Celite® and washed with MeOH (50 mL). The filtrate was concentrated under reduced pressure. The residue was dissolved in EtOAc (50 mL) and washed with water (50 mL). The organic layer was separated, dried over MgSO$_4$ and concentrated under reduced pressure. Purification via silica gel column chromatography (0-50% EtOAc/isohexane) gave (E)-3-(1-methyl-4-nitro-1H-pyrazol-5-yl)cyclohept-2-enone as a light brown solid (7.2 g, 39% over three steps). $^1$H NMR (400 MHz, CDCl$_3$) δ 8.08 (s, 1H), 6.09 (s, 1H), 3.83 (s, 3H), 2.81-2.77 (m, 2H), 2.71-2.67 (m, 2H), 2.07-1.97 (m, 4H).

Intermediate 249

(2E,6Z)-3-(1-Methyl-4-nitro-1H-pyrazol-5-yl)cyclohepta-2,6-dienone

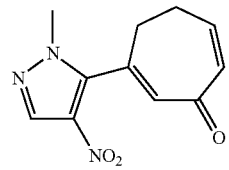

To a solution of LiHMDS (1 M in THF, 1.28 mL, 1.28 mmol) at −78° C. was added (E)-3-(1-methyl-4-nitro-1H-pyrazol-5-yl)cyclohept-2-enone (150 mg, 0.64 mmol) and the mixture was stirred at −78° C. for 1 hr. A solution of phenylselenium bromide (453 mg, 1.92 mmol) in THF (0.5 mL) was added and the reaction mixture was warmed to 0° C. and stirred for 45 min before being quenched with a saturated aqueous solution of ammonium chloride (2 mL). The mixture was extracted with EtOAc (3×5 mL) and the combined organic layers were dried over MgSO$_4$ and concentrated under reduced pressure to give (E)-3-(1-methyl-4-nitro-1H-pyrazol-5-yl)-7-(phenylselanyl)cyclohept-2-enone as an oil. This oil was dissolved in DCM (3 mL) and pyridine (0.1 mL, 1.28 mmol) was added, followed by hydrogen peroxide (30% wt in water, 0.37 mL, 3.34 mmol). The reaction mixture was stirred at room temperature for 18 hr. 1 M HCl (10 mL) was added and the mixture was extracted with DCM (2×5 mL). The combined organic layers were washed with 1 M HCl (5 mL), water (5 mL) and brine (5 mL), separated, dried over MgSO$_4$ and concentrated under reduced pressure. Purification via silica gel column chromatography (0-100% EtOAc/isohexane) gave (2E,6Z)-3-(1-methyl-4-nitro-1H-pyrazol-5-yl)cyclohepta-2,6-dienone as a yellow oil (26 mg, 17% over three steps). $^1$H NMR (400 MHz, CDCl$_3$) δ 8.11 (s, 1H), 6.88-6.82 (m, 1H), 6.26-6.23 (dd, J=12.0, 1.6 Hz, 1H), 6.19 (d, J=2.0 Hz, 1H), 3.87 (s, 3H), 2.82-2.73 (m, 4H).

Intermediate 250

(E)-tert-Butyl 5-(1-methyl-4-nitro-1H-pyrazol-5-yl)-3-oxocyclohept-4-enylcarbamate

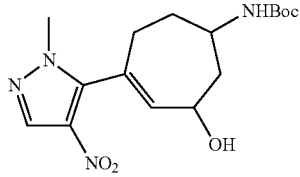 [SMILES: Cn1ncc([N+](=O)[O-])c1C1=CC(O)CC(NC(=O)OC(C)(C)C)CC1]

To a solution of (2E,6Z)-3-(1-methyl-4-nitro-1H-pyrazol-5-yl)cyclohepta-2,6-dienone (690 mg, 2.95 mmol) in acetonitrile (10 mL) was added trimethylsilyl azide (1 mL, 7.57 mmol) and Amberlite™ IRA900F resin (590 mg, 1.47 mmol). The reaction mixture was stirred at 40° C. for 5 hr, cooled to room temperature, filtered and concentrated under reduced pressure to give (E)-6-azido-3-(1-methyl-4-nitro-1H-pyrazol-5-yl)cyclohept-2-enone as a yellow oil. To a solution of this oil (810 mg, 2.93 mmol) in THF (20 mL) and water (6 mL) was added sodium borohydride (166 mg, 4.40 mmol). The mixture was stirred at room temperature for 18 hr before being diluted with water (50 mL). The mixture was extracted with EtOAc (100 mL) and the organic layer was separated, dried over MgSO$_4$ and concentrated under reduced pressure. Purification via silica gel column chromatography (0-100% EtOAc/isohexane) gave (E)-6-azido-3-(1-methyl-4-nitro-1H-pyrazol-5-yl)cyclohept-2-enol as a yellow oil. This oil (810 mg, 2.91 mmol) was dissolved in THF (15 mL) and added to a suspension of polymer-supported triphenylphosphine (3.1 g, 5.76 mmol) in THF (45 mL) and water (1.5 mL). The mixture was gently stirred at 60° C. for 18 hr, cooled to room temperature and concentrated under reduced pressure. The residue was diluted in DCM (30 mL) and di-tert-butyl dicarbonate (754 mg, 3.46 mmol) and DIPEA (1.51 mL, 8.64 mmol) were added. The mixture was stirred at room temperature for 5 hr, diluted with DCM (50 mL) and quenched with a saturated solution of sodium hydrogencarbonate (50 mL). The organic layer was washed with water (50 mL), separated, dried over MgSO$_4$ and concentrated under reduced pressure. Purification via silica gel column chromatography (0-100% EtOAc/isohexane) gave (E)-tert-butyl 5-(1-methyl-4-nitro-1H-pyrazol-5-yl)-3-oxocyclohept-4-enylcarbamate as a white foam (620 mg, 59% over three steps). $^1$H NMR (400 MHz, CDCl$_3$) δ 8.05 (s, 1H), 6.03-5.99 (m, 1H), 4.82-4.60 (m, 2H), 3.86-3.82 (m, 4H), 2.82-2.34 (m, 1H), 2.29-2.35 (m, 1H), 2.34-2.20 (m, 2H), 2.15-2.04 (m, 1H), 1.85-1.51 (m, 2H), 1.45 (s, 9H).

Intermediate 251

(Z)-tert-Butyl 2-(2,6-difluorophenyl)-4-(1-methyl-5-(2,3,6,7-tetrahydro-1H-azepin-1-yl)-1H-pyrazol-4-ylcarbamoyl)thiazol-5-ylcarbamate

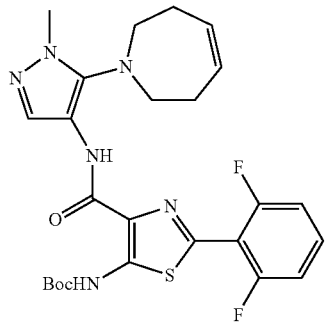 [SMILES: Cn1ncc(NC(=O)c2nc(-c3c(F)cccc3F)sc2NC(=O)OC(C)(C)C)c1N1CCC=CCC1]

To a solution of (Z)-2,3,6,7-tetrahydro-1H-azepine hydrochloride (32.3 g, 0.24 mmol) in DMSO (650 mL) was added 3-chloro-1-methyl-4-nitro-1H-pyrazole (37.2 g, 0.23 mmol) followed by DIPEA (64 mL, 0.36 mmol) and potassium fluoride (56.2 g, 0.96 mmol). The reaction mixture was heated at 75° C. for 25 hr before being cooled to room temperature, poured into water (1.5 L) and extracted with EtOAc (4×500 mL). The combined organic layers were washed with water (400 mL) and brine (300 mL), separated, dried over MgSO$_4$ and concentrated under reduced pressure to give (Z)-1-(1-methyl-4-nitro-1H-pyrazol-3-yl)-2,3,6,7-tetrahydro-1H-azepine as a light brown solid (50.7 g). To a solution of this solid (1.80 g, 8.1 mmol) in ethanol (80 mL) and water (8 mL) was added ammonium chloride (2.15 g, 40.1 mmol) and iron powder (1.77 g, 31.8 mmol). The reaction mixture was heated at 80° C. for 1.5 hr, before being cooled to room temperature, filtered through Celite® and concentrated under reduced pressure. The residue was dissolved in DCM (200 mL) and washed with water (200 mL). The aqueous layer was extracted with DCM (100 mL) and the combined organic layers were dried over MgSO$_4$ and concentrated under reduced pressure to give (Z)-1-methyl-3-(2,3,6,7-tetrahydro-1H-azepin-1-yl)-1H-pyrazol-4-amine as a brown oil (1.36 g, 87%). A solution of HATU (3.22 g, 8.47 mmol), 5-(tert-butoxycarbonylamino)-2-(2,6-difluorophenyl)-thiazole-4-carboxylic acid (2.52 g, 7.07 mmol), (Z)-1-methyl-3-(2,3,6,7-tetrahydro-1H-azepin-1-yl)-1H-pyrazol-4-amine (1.36 g, 7.07 mmol) and DIPEA (2.48 mL, 14.2 mmol) in DMF (30 mL) was stirred at room temperature for 18 hr. The reaction mixture was diluted with DCM (50 mL) and washed with water (100 mL). The organic layer was passed through a phase separation cartridge and concentrated under reduced pressure. Purification of the residue via silica gel column chromatography (5-80% 10% MeOH in DCM/DCM) gave (Z)-tert-butyl 2-(2,6-difluorophenyl)-4-(1-methyl-5-(2,3,6,7-tetrahydro-1H-azepin-1-yl)-1H-pyrazol-4-ylcarbamoyl)thiazol-5-ylcarbamate as a brown solid (2.71 g, 72% over two steps). $^1$H NMR (400 MHz, CDCl$_3$) δ 10.39 (s, 1H), 8.82 (s, 1H), 7.85 (s, 1H), 7.40-7.30 (m, 1H), 7.08-6.99 (m, 2H), 5.93-5.84 (m, 2H), 3.77 (s, 3H), 3.19 (t, J=5.1 Hz, 4H), 2.42-2.37 (m, 4H), 1.58-1.48 (m, 9H).

Intermediate 252

1-(1-Methyl-4-nitro-1H-pyrazol-5-yl)piperidin-4-one

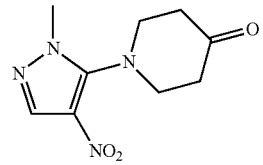

To a solution of 3-chloro-1-methyl-4-nitro-1H-pyrazole (1.0 g, 6.17 mmol) in ethanol (10 mL) was added DIPEA (2 mL, 11.4 mmol) followed by 4-hydroxypyridine (686 mg, 6.79 mmol). The reaction mixture was heated at 130° C. in the microwave for 60 min before the solvents were removed under reduced pressure. Purification of the residue via silica gel column chromatography (75-100% EtOAc/isohexane) gave 1-(1-methyl-4-nitro-1H-pyrazol-5-yl)piperidin-4-ol as a bright yellow oil (1.46 g). To a solution of this oil (1.40 g, 6.17 mmol) in DCM (40 mL) was added portionwise Dess-Martin periodinane (3.1 g, 7.41 mmol). The reaction mixture was stirred at room temperature for 3 hr, diluted with DCM (100 mL) and washed with saturated aqueous sodium hydrogencarbonate (30 mL), followed by saturated aqueous sodium thiosulphate (30 mL), saturated aqueous sodium hydrogencarbonate (30 mL) and brine (30 mL). The organic layer was separated, dried over MgSO$_4$ and concentrated under reduced pressure. Purification via silica gel column chromatography (50-75% EtOAc/isohexane) gave 1-(1-methyl-4-nitro-1H-pyrazol-5-yl)piperidin-4-one as a yellow solid (1.32 g, 95% over two steps). $^1$H NMR (400 MHz, CDCl$_3$) δ 8.06 (s, 1H), 3.86 (s, 3H), 3.54 (t, J=6.0 Hz, 4H), 2.65 (t, J=6.0 Hz, 4H).

Intermediate 253

4-(Azidomethyl)-1-(1-methyl-4-nitro-1H-pyrazol-5-yl)piperidin-4

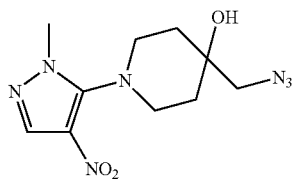 [SMILES: Cn1ncc([N+](=O)[O-])c1N1CCC(O)(CN=[N+]=[N-])CC1]

Sodium hydride (255 mg, 6.38 mmol) was added portionwise to DMSO (15 mL) at 0° C. The reaction mixture was warmed to room temperature and stirred for 15 min before trimethyl sulfoxonium iodide (1.34 g, 6.09 mmol) was added. After stirring at 90 min at room temperature, a solution of 1-(1-methyl-4-nitro-1H-pyrazol-5-yl)piperidin-4-one (1.3 g, 5.80 mmol) in DMSO (15 mL) was added. The mixture was heated at 55° C. for 2 hr, then poured into water (200 mL) and extracted with EtOAc (3×80 mL). The combined organic layers were dried over MgSO$_4$ and concentrated under reduced pressure to give 6-(1-methyl-4-nitro-1H-pyrazol-5-yl)-1-oxa-6-azaspiro[2.5]octane as an orange liquid. To a solution of this liquid (1.38 g, 5.80 mmol) in MeOH (25 mL) and water (5 mL) was added ammonium chloride (768 mg, 14.4 mmol) followed by sodium azide (1.9 g, 29.2 mmol). The reaction mixture was heated at 70° C. for 18 hr, allowed to cool to room temperature and the MeOH removed under reduced pressure. The residue was diluted with water (20 mL) and extracted with EtOAc (150 mL). The organic layer was washed with water (20 mL) and brine (20 mL), separated, dried over MgSO$_4$ and concentrated under reduced pressure. Purification via silica gel column chromatography (50-75% EtOAc/isohexane) gave 4-(azidomethyl)-1-(1-methyl-4-nitro-1H-pyrazol-5-yl)piperidin-4-ol as yellow oil (1.03 g, 63% over two steps). $^1$H NMR (400 MHz, CDCl$_3$) δ 8.03 (s, 1H), 3.76 (s, 3H), 3.64-3.54 (m, 2H), 3.42 (s, 2H), 3.05-2.96 (m, 2H), 1.92 (s, 1H), 1.81-1.77 (m, 4H).

Intermediate 254 tert-Butyl (4-methoxy-1-(1-methyl-4-nitro-1H-pyrazol-5-yl)piperidin-4-yl)methylcarbamate

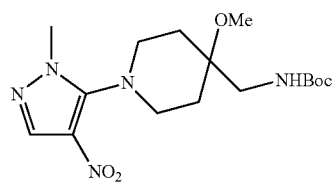 [SMILES: COC1(CNC(=O)OC(C)(C)C)CCN(c2c([N+](=O)[O-])cnn2C)CC1]

Following the procedure for Intermediate 120 starting from 4-(azidomethyl)-1-(1-methyl-4-nitro-1H-pyrazol-5-yl)piperidin-4-ol gave tert-butyl (4-methoxy-1-(1-methyl-4-nitro-1H-pyrazol-5-yl)piperidin-4-yl)methylcarbamate as a yellow oil (330 mg, 88% over three steps). $^1$H NMR (400 MHz, CDCl$_3$) δ 8.01 (s, 1H), 4.72 (s, 1H), 3.74 (s, 3H), 3.51 (t, J=11.8 Hz, 2H), 3.28 (d, J=5.9 Hz, 2H), 3.25 (s, 3H), 2.92 (d, J=11.8 Hz, 2H), 1.91 (d, J=13.5 Hz, 2H), 1.66 (t, J=13.5 Hz, 2H), 1.45 (s, 9H).

Intermediate 255

2,2,2-Trifluoro-N-(5-fluoro-2-hydroxy-5-(2-methyl-4-nitro-pyrazol-3-yl)cycloheptyl)acetamide

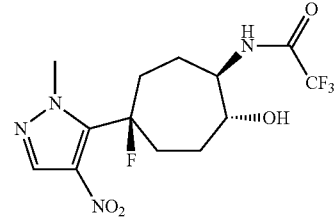 [SMILES: Cn1ncc([N+](=O)[O-])c1[C@@]1(F)CC[C@@H](O)[C@H](NC(=O)C(F)(F)F)CC1]

A solution of 2-azido-5-fluoro-5-(1-methyl-4-nitro-1H-pyrazol-5-yl)cycloheptanol (280 mg, 094 mmol) in THF/water (20 mL/4 mL) was treated with triphenylphosphine (270 g, 1.03 mmol) and the mixture was heated at 60° C. behind a blast screen for 18 hr. The solvents were removed under reduced pressure and the residue was purified via a SCX cartridge washing with MeOH and eluting with 3 N NH$_3$ in MeOH to give 2-amino-5-fluoro-5-(2-methyl-4-nitro-pyrazol-3-yl)cycloheptanol as a colourless oil. To a solution of this oil (256 mg, 0.94 mmol) in dry DCM (20 mL) at 0° C. was added slowly DIPEA (0.49 mL, 2.82 mmol) followed by trifluoroacetic anhydride (0.16 ml, 1.13 mmol) dropwise. The reaction mixture was allowed to warm to room temperature and stirred for 18 hr. Water (20 mL) was added and the mixture was extracted with DCM (100 mL). The organic layer was passed through a phase separation cartridge and concentrated under reduced pressure. Purification via silica gel column chromatography (30-50% EtOAc/isohexane) gave 2,2,2-trifluoro-N-(5-fluoro-2-hydroxy-5-(2-methyl-4-nitro-pyrazol-3-yl)cycloheptyl)acetamide as a pale yellow oil (130 mg, 38% over two steps). $^1$H NMR (400 MHz, CDCl$_3$) δ 8.07 and 8.06 (2s, 1H), 6.53 (s, 1H), 4.08 and 4.06 (2s, 3H), 4.05-3.92 (m, 2H), 3.06-2.69 (m, 3H), 2.32-1.89 (m, 6H).

Intermediate 257

4-(Aminomethyl)-1-(2-methyl-4-nitro-pyrazol-3-yl)piperidin-4-ol

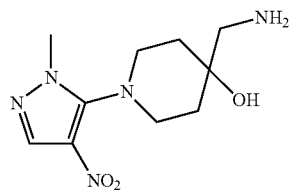

Sodium hydride (60% in mineral oil, 200 mg, 4.9 mmol) was added portionwise to DMSO (15 mL) at 0° C. The reaction mixture was warmed to room temperature and stirred for 15 min before trimethyl sulfoxonium iodide (1.0 g, 4.6 mmol) was added. After stirring for 90 min at room temperature, a solution of 1-(1-methyl-4-nitro-1H-pyrazol-5-yl)piperidin-4-one (1.0 g, 4.45 mmol) in DMSO (15 mL) was added. The mixture was heated at 55° C. for 3 hr, then poured into water (50 mL) and extracted with EtOAc (3×50 mL). The combined organic layers were dried over MgSO₄ and concentrated under reduced pressure to give 6-(1-methyl-4-nitro-1H-pyrazol-5-yl)-1-oxa-6-azaspiro[2.5]octane as an orange liquid. To a solution of this liquid (0.4 g, 1.67 mmol) in a reaction tube was added a 7 M solution of NH₃ in MeOH (20 mL) and the mixture stirred in a sealed tube at room temperature for 24 hr. The reaction mixture was concentrated under reduced pressure and the residue purified via silica gel chromatography (1-10% 7 M NH₃ in MeOH/DCM) to give 4-(aminomethyl)-1-(2-methyl-4-nitro-pyrazol-3-yl)piperidin-4-ol as a yellow solid, (350 mg, 60% over two steps). ¹H NMR (400 MHz, CDCl₃) δ 8.02 (s, 1H), 3.76 (s, 3H), 3.64-3.54 (m, 2H), 3.09-3.03 (m, 2H), 2.72 (s, 2H), 1.73-1.62 (m, 4H). Exchangeables not observed.

Intermediate 258 tert-Butyl N-((4-hydroxy-1-(2-methyl-4-nitro-pyrazol-3-yl)-4-piperidyl)methyl)carbamate

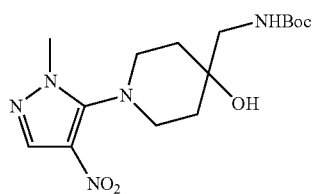 [SMILES: Cn1ncc([N+](=O)[O-])c1N1CCC(O)(CNC(=O)OC(C)(C)C)CC1]

To a solution of 4-(aminomethyl)-1-(2-methyl-4-nitropyrazol-3-yl)piperidin-4-ol (150 mg, 0.58 mml), triethylamine (0.12 mL, 0.88 mmol) and DMAP (17 mg, 0.15 mmol) in DCM (10 mL) cooled to 0° C. was added slowly a solution of di-tert-butyl dicarbonate (140 mg, 0.65 mmol) in DCM (2 mL). The reaction mixture was stirred at room temperature for 16 hr. Water (10 mL) was added and the aqueous layer extracted with DCM (3×15 mL). The combined organic layers were washed with brine (15 mL), passed through a phase separation cartridge and concentrated under reduced pressure. Purification via silica gel column chromatography (1-10% MeOH/DCM) gave tert-butyl N-((4-hydroxy-1-(2-methyl-4-nitro-pyrazol-3-yl)-4-piperidyl)methyl)carbamate as a yellow solid (140 mg, 68%). ¹H NMR (400 MHz, CDCl₃) δ 8.02 (s, 1H), 5.10-5.03 (m, 1H), 3.76 (s, 3H), 3.61-3.49 (m, 2H), 3.25 (d, J=6.3 Hz, 2H), 3.08-2.96 (m, 2H), 1.77-1.72 (m, 4H), 1.46 (s, 9H). OH not observed.

Intermediate 259 tert-Butyl 3-(2-methyl-4-nitro-pyrazol-3-yl)-11-oxa-3,8-diazaspiro[5.5]undecane-8-carboxylate

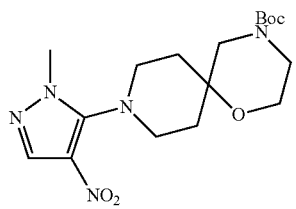 [SMILES: Cn1ncc([N+](=O)[O-])c1N1CCC2(CC1)CN(C(=O)OC(C)(C)C)CCO2]

To a solution of 4-(aminomethyl)-1-(2-methyl-4-nitropyrazol-3-yl)piperidin-4-01 (0.5 g, 1.95 mmol) in THF (25 mL) was added K₂CO₃ (0.68 g, 4.98 mmol) dissolved in water (10 mL). After cooling to 0° C., chloroacetyl chloride (0.19 mL, 2.45 mmol) was added slowly. The mixture was allowed to warm to room temperature and stirred for 16 hr, partitioned between water (15 mL) and EtOAc (15 mL) and the aqueous layer extracted with EtOAc (3×30 mL). The combined organic layers were washed with brine (20 mL), dried over MgSO₄ and concentrated under reduced pressure to give a yellow solid. This was dissolved in tert-butanol (15 mL) and THF (3 mL) and potassium tert-butoxide (0.34 g, 2.9 mmol) was added. The mixture was heated at 85° C. for 16 hr. After cooling to room temperature, the mixture was partitioned between water (20 mL) and EtOAc (20 mL) and the aqueous layer extracted with EtOAc (3×30 mL). The combined organic layers were dried over MgSO₄ and concentrated under reduced pressure. Purification via silica gel column chromatography (1-10%, MeOH/DCM) gave a yellow solid (0.47 g). This solid was dissolved in THF (15 mL) and a solution of borane (1 M in THF, 10 mL) added. The reaction mixture was heated at 66° C. for 72 hr before cooling to room temperature. The reaction was quenched with 1 M hydrocholoric acid (5 mL) and extracted with EtOAc (3×20 mL). The combined organic layers were washed with brine (20 mL), dried over MgSO₄ and concentrated under reduced pressure. To a solution of the intermediate obtained (200 mg) in DCM (10 mL) was added triethylamine (0.12 mL, 0.85 mmol) and DMAP (20 mg, 0.14 mmol). The mixture was cooled to 0° C. and a solution of di-tert-butyl dicarbonate (0.18 g, 0.85 mmol) in DCM (2 mL) was added slowly. The mixture was allowed to warm to room temperature and stirred for 16 hr. Water (5 mL) was added and the mixture was extracted with DCM (3×10 mL). The combined organic layers were passed through a phase separation cartridge and concentrated under reduced pressure. Purification via silica gel column chromatography (10-100%, EtOAc/isohexane) gave tert-butyl 3-(2-methyl-4-nitro-pyrazol-3-yl)-11-oxa-3,8-diazaspiro[5.5]undecane-8-carboxylate as an off-white solid (110 mg, 44% over 3 steps). ¹H NMR (400 MHz, CDCl₃) δ 8.02 (s, 1H), 3.82-3.59 (m, 5H), 3.50-3.32 (m, 4H), 2.00-1.85 (m, 4H), 1.82-1.69 (m, 4H), 1.44 (s, 9H).

Intermediate 265

5-((4-Methoxyphenyl)methoxy)-1-(2-methyl-4-nitropyrazol-3-yl)azepan-4-ol

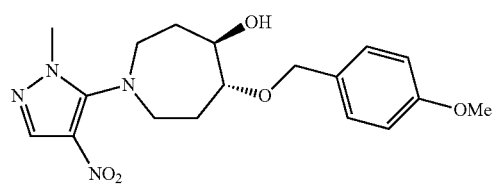 [SMILES: COc1ccc(CO[C@@H]2CCN(c3c([N+](=O)[O-])cnn3C)CC[C@H]2O)cc1]

To a solution of (Z)-2,3,6,7-tetrahydro-1H-azepine hydrochloride (5.0 g, 25.38 mmol) in MeOH (25 mL) at 0° C. was added HCl in dioxane (4 M, 0.10 mol, 25 mL). The reaction mixture was stirred at 0° C. for 5 min, warmed to room temperature and stirred for a further 3.5 hr. The mixture was concentrated under reduced pressure and the crude residue was dissolved in DMSO (90 mL). DIPEA (8.80 mL, 50.52 mmol) was added followed by 5-chloro-1-methyl-4-nitropyrazole (4.1 g, 25.37 mmol) and potassium fluoride (5.9 g, 101.54 mmol) and the mixture was heated at 70° C. for 18 hr. After cooling to room temperature, the reaction was quenched with water (500 mL) and extracted with EtOAc (3×200 mL). The combined organic layers were washed with water (200 mL) and brine (200 mL), separated, dried over MgSO₄ and concentrated under reduced pressure. Purification via silica gel chromatography (0-100% EtOAc/isohexane) gave a pale yellow solid (5.22 g). To a solution of this solid (3.13 g, 14.10 mmol) in DCM (50 mL) was added 3-chloroperbenzoic acid (7.30 g, 21.10 mmol) and the mixture stirred at room temperature for 1.5 hr. The mixture was diluted with DCM (250 mL), washed with saturated aqueous NaHCO₃ (250 mL) and 1 M aqueous NaOH (150 mL). The organic layer was passed through a phase separation cartridge and concentrated under reduced pressure. Purification via silica gel column chromatography (0-100% EtOAc/isohexane) gave a pale yellow solid (3.03 g). To a solution of this solid (1.29 g, 5.42 mmol) and para-methoxybenzylalcohol (3.74 g, 27.10 mmol) in DCM (30 mL) was added copper(II) trifluoromethanesulfonate (0.20 g, 0.54 mmol) and the mixture was stirred at room temperature for 18 hr. Additional copper(II) trifluoromethanesulfonate (0.10 g, 0.26 mmol) was added and the mixture was stirred for a further 48 hr. The mixture was quenched with water (250 mL) and extracted with DCM (2×250 mL). The combined organic layers were passed through a phase separation cartridge and concentrated under reduced pressure. Purification via silica gel column chromatography (20-90% EtOAc/isohexane then 0-20% EtOAc/DCM) gave 5-((4-methoxyphenyl)methoxy)-1-(2-methyl-4-nitro-pyrazol-3-yl)azepan-4-ol as a pale yellow gum (800 mg, 8% over four steps). ¹H NMR (400 MHz, CDCl₃) δ 8.03 (t, J=3.4 Hz, 1H), 7.31-7.25 (m, 2H), 6.92-6.87 (m, 2H), 4.65 (d, J=11.0 Hz, 1H), 4.49-4.38 (m, 1H), 3.98-3.67 (m, 4H), 3.73 (s, 3H), 3.57-3.44 (m, 1H), 3.34-3.23 (m, 2H), 3.22-3.12 (m, 2H), 2.95 (d, J=1.3 Hz, 1H), 2.25-2.10 (m, 2H), 1.91-1.75 (m, 2H).

Intermediate 266 tert-Butyl N-(2-(2,6-difluorophenyl)-4-((5-(4-hydroxy-5-[((4-methoxyphenyl)methoxy)azepan-1-yl)-1-methyl-pyrazol-4-yl)carbamoyl)thiazol-5-yl]carbamate

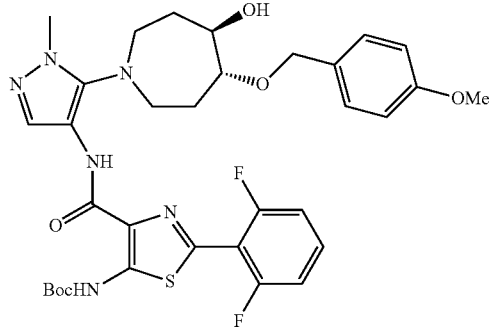 [SMILES: COc1ccc(CO[C@@H]2CCN(c3c(NC(=O)c4nc(-c5c(F)cccc5F)sc4NC(=O)OC(C)(C)C)cnn3C)CC[C@H]2O)cc1]

To a solution of 5-((4-methoxyphenyl)methoxy)-1-(2-methyl-4-nitro-pyrazol-3-yl)azepan-4-ol (0.80 g, 2.18 mmol) in EtOH (30 mL) and water (3 mL) was added iron powder (0.90 g, 16.11 mmol) The reaction mixture was heated at 100° C. for 2 hr, cooled to room temperature, filtered through Celite® and the filtrate concentrated under reduced pressure. The residue was dissolved in DCM (50 mL) and washed with water (50 mL). The aqueous layer was re-extracted with DCM (50 mL) and the combined organic layers passed through a phase separation cartridge and concentrated under reduced pressure to give a pale orange gum. To a solution of this gum (0.55 g, 1.60 mmol) in DMF (5 mL) was added 5-(tert-butoxycarbonylamino)-2-(2,6-difluorophenyl)thiazole-4-carboxylic acid (0.62 g, 1.76 mmol), HATU (0.85 g, 2.40 mmol) and DIPEA (0.56 mL, 3.20 mmol). The reaction mixture was stirred at room temperature for 66 hr, quenched with a saturated aqueous NaHCO₃ (200 mL) and extracted with EtOAc (3×150 mL). The combined organic layers were washed with brine (100 mL), separated, dried over MgSO₄ and concentrated under reduced pressure. Purification via silica gel column chromatography (0-10% MeOH/EtOAc) gave tert-butyl N-(2-(2,6-difluorophenyl)-4-((5-(4-hydroxy-5-((4-methoxyphenyl)methoxy)azepan-1-yl)-1-methyl-pyrazol-4-yl)carbamoyl)thiazol-5-yl]carbamate as a pale pink solid (530 mg, 35% over two steps). ¹H NMR (400 MHz, CDCl₃) δ 10.44 (s, 1H), 9.02 (s, 1H), 7.91 (s, 1H), 7.38-7.28 (m, 1H), 7.25 (d, J=8.2 Hz, 2H), 7.00 (t, J=8.7 Hz, 2H), 6.92-6.84 (m, 2H), 4.61 (d, J=11.1 Hz, 1H), 4.40 (d, J=11.1 Hz, 1H), 3.91 (t, J=8.6 Hz, 1H), 3.81 (s, 3H), 3.73 (s, 3H), 3.55 (td, J=8.4, 3.4 Hz, 1H), 3.34-3.13 (m, 4H), 3.10 (s, 1H), 2.22-2.14 (m, 2H), 1.93-1.77 (m, 2H), 1.62-1.50 (m, 9H).

Intermediate 267

5-Azido-4-methoxy-4-methyl-1-(2-methyl-4-nitro-pyrazol-3-yl)azepane

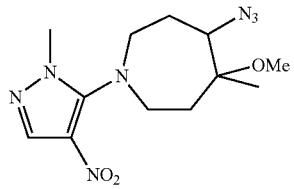 [SMILES: COC1(C)CCN(c2c([N+](=O)[O-])cnn2C)CCC1N=[N+]=[N-]]

To a stirred solution of tert-butyl 4-azido-5-hydroxy-azepane-1-carboxylate (2.4 g, 9.38 mmol) in DCM (100 mL) was added in a single portion Dess Martin periodinane (5.16 g, 12.19 mmol) and the mixture was stirred at room temperature for 2 hr. Further DCM (100 mL) was added followed by saturated NaHCO₃ (100 mL) and 10% Na₂S₂O₃ (30 mL). Stirring continued for 30 min. The layers were separated and the aqueous extracted with DCM (100 mL). The combined organic layers were passed through a phase separation cartridge and the solvent removed under reduced pressure. Purification via silica gel column chromatography (0-100% EtOAc/isohexane) gave a colourless oil (1.99 g). To an ice-cooled solution of this oil in anhydrous Et₂O (30 mL) under nitrogen was added a solution of methyllithium lithium bromide complex in Et₂O (1.5 M, 5.8 mL, 8.62 mmol) slowly over 15 min. The mixture was stirred with ice cooling for 1 hr, allowed to warm to room temperature and stirred for 18 hr. After cooling in ice, saturated brine (100 mL) was added. The mixture was extracted with EtOAc (3×100 mL) and the combined extracts were dried over MgSO₄ and concentrated under reduced pressure. Purification via silica gel column chromatography (20-40% EtOAc/isohexane) gave a colourless oil (0.92 g). The oil was dissolved in anhydrous DMF (5 mL) under nitrogen, cooled in ice and sodium hydride (60% dispersion in mineral oil, 203 mg, 5.08 mmol) added portionwise over 15 min. After stirring with ice cooling for 15 min, iodomethane (1.06 mL, 16.94 mmol) was added dropwise and the mixture stirred with ice cooling for 30 min. The reaction mixture was allowed to warm to room temperature and stirred for 4 hr. Saturated brine (100 mL) was added and the mixture was extracted with Et₂O (3×100 mL). The combined organic layers were dried over MgSO₄ and the solvent removed under reduced pressure to afford a pale green oil (1.05 g). This oil was dissolved in MeOH (10 mL) and a solution of HCl in dioxane (4 M, 10 mL) added. The solution was warmed to 40° C. and stirred for 2.5 hr. Concentration under reduced pressure gave a light brown gum (1.03 g) which was dissolved in DMSO (10 mL). To this solution was added 5-chloro-1-methyl-4-nitro-pyrazole (712 mg, 4.41 mmol), potassium fluoride (720 mg, 13.56 mmol) and DIPEA (1.2 mL, 6.78 mmol) and the mixture heated at 70° C. under nitrogen for 19 hr. The mixture was cooled, poured into water (300 mL) and extracted with EtOAc (3×150 mL). The combined organic layers were washed with water (150 mL) and brine (150 mL), separated, dried over MgSO$_4$ and the solvent removed under reduced pressure. Purification via silica gel column chromatography (0-100% EtOAc/isohexane) gave 5-azido-4-methoxy-4-methyl-1-(2-methyl-4-nitro-pyrazol-3-yl)azepane as a pale yellow solid (830 mg, 11% over four steps). $^1$H NMR (400 MHz, CDCl$_3$) δ 8.03 (s, 1H), 3.79 (s, 3H), 3.47-3.35 (m, 2H), 3.32-3.20 (m, 5H), 3.06-2.95 (m, 1H), 2.60-2.40 (m, 1H), 2.18-2.08 (m, 1H), 2.06-1.92 (m, 1H), 1.80-1.65 (m, 1H), 1.39 (s, 3H).

Intermediate 268 tert-Butyl N-(5-methoxy-5-methyl-1-(2-methyl-4-nitro-pyrazol-3-yl)azepan-4-yl)carbamate

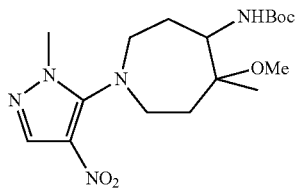 [SMILES: COC1(C)CCN(c2c([N+](=O)[O-])cnn2C)CCC1NC(=O)OC(C)(C)C]

Following the procedure for Intermediate 122 starting from 5-azido-4-methoxy-4-methyl-1-(2-methyl-4-nitro-pyrazol-3-yl)azepane gave tert-butyl N-(5-methoxy-5-methyl-1-(2-methyl-4-nitro-pyrazol-3-yl)azepan-4-yl)carbamate as a yellow gum (780 mg, 75% over two steps). $^1$H NMR (400 MHz, CDCl$_3$) δ 8.02 (s, 1H), 5.25-5.15 (m, 1H), 3.75 (s, 3H), 3.74-3.65 (m, 1H), 3.65-3.50 (m, 1H), 3.48-3.35 (m, 1H), 3.20 (s, 3H), 3.19-3.10 (m, 1H), 3.00-2.85 (m, 1H), 2.45-2.30 (m, 1H), 2.20-2.05 (m, 1H), 1.90-1.70 (m, 2H), 1.46 (s, 9H), 1.28 (s, 3H).

Intermediate 269

G02693495 tert-Butyl N-(1-(4-((5-(tert-butoxycarbonylamino)-2-(2,6-difluorophenyl)thiazole-4-carbonyl)amino)-2-methyl-pyrazol-3-yl)-5-methoxy-5-methyl-azepan-4-yl]carbamate

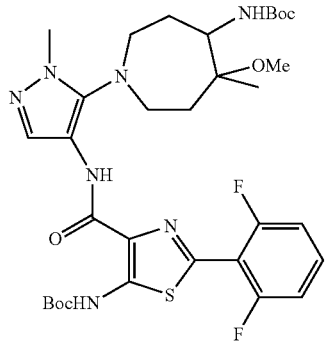 [SMILES: COC1(C)CCN(c2c(NC(=O)c3nc(-c4c(F)cccc4F)sc3NC(=O)OC(C)(C)C)cnn2C)CCC1NC(=O)OC(C)(C)C]

10% Palladium on carbon (0.2 g) was added to a stirred solution of tert-butyl N-(5-methoxy-5-methyl-1-(2-methyl-4-nitro-pyrazol-3-yl)azepan-4-yl)carbamate (0.77 g, 2.01 mmol) and ammonium formate (1.6 g, 25 mmol) in MeOH (30 mL) under nitrogen and the mixture heated at reflux for 2 hr. After cooling to room temperature the mixture was filtered through Celite® and the filtrate concentrated under reduced pressure. The residue was partitioned between DCM (100 mL) and saturated aqueous NaHCO$_3$ (150 mL) and the aqueous layer was extracted with DCM (100 mL). The combined organics were passed through a phase separation cartridge and the solvent removed under reduced pressure to give a light brown gum (700 mg). This gum was dissolved in DCM (10 mL) and DMF (10 mL) and 5-(tert-butoxycarbonylamino)-2-(2,6-difluorophenyl)thiazole-4-carboxylic acid (0.84 g, 2.2 mmol), HATU (1.14 g, 3 mmol) and DIPEA (0.7 mL, 4 mmol) were added. The mixture was stirred at room temperature for 18 hr. The DCM was removed under reduced pressure and saturated NaHCO$_3$ (300 mL) added. The mixture was extracted with EtOAc (3×200 mL), the combined organic layers were passed through a phase separation cartridge and the solvent was removed under reduced pressure. Purification via silica gel column chromatography (0-100% EtOAc/isohexane) gave tert-butyl N-(1-(4-((5-(tert-butoxycarbonylamino)-2-(2,6-difluorophenyl)thiazole-4-carbonyl)amino)-2-methyl-pyrazol-3-yl)-5-methoxy-5-methyl-azepan-4-yl]carbamate as a pale yellow solid (540 mg, 39% over two steps). $^1$H NMR (400 MHz, CDCl$_3$) δ 10.39 (s, 1H), 8.77 (s, 1H), 7.89 (s, 1H), 7.45-7.30 (m, 1H), 7.12-6.95 (m, 2H), 5.30-5.20 (m, 1H), 3.73 (s, 3H), 3.72-3.65 (m, 1H), 3.50-3.28 (m, 2H), 3.25-3.15 (m, 1H), 3.14 (s, 3H), 3.05-2.95 (m, 1H), 2.40-2.20 (m, 1H), 2.18-2.05 (m, 1H), 1.95-1.70 (m, 2H), 1.55 (s, 9H), 1.45 (s, 9H), 1.22 (s, 3H).

Intermediate 270 tert-Butyl N-((4R,5S)-5-hydroxy-1-(2-methyl-4-nitro-pyrazol-3-yl)azepan-4-yl)carbamate

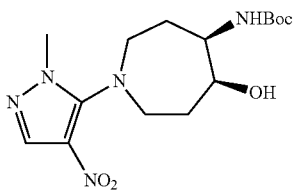 [SMILES: Cn1ncc([N+](=O)[O-])c1N1CC[C@H](O)[C@H](NC(=O)OC(C)(C)C)CC1]

The racemic mixture of tert-butyl 5-hydroxy-1-(1-methyl-4-nitro-1H-pyrazol-5-yl)azepan-4-ylcarbamate (5.13 g, 14.13 mmol) was submitted for chiral SFC separation of enantiomers and gave tert-butyl N-((4R,5S)-5-hydroxy-1-(2-methyl-4-nitro-pyrazol-3-yl)azepan-4-yl)carbamate as a yellow gum (2.08 g, 98.3% ee, 40%). $^1$H NMR (400 MHz, CDCl$_3$) δ 8.03 (s, 1H), 5.12 (s, 1H), 4.19 (s, 1H), 3.93 (t, J=8.6 Hz, 1H), 3.79 (s, 3H), 3.52-3.44 (m, 1H), 3.33-3.26 (m, 1H), 3.22-3.08 (m, 2H), 2.53 (s, 1H), 2.19-2.11 (m, 1H), 2.02-1.95 (m, 2H), 1.92-1.82 (m, 1H), 1.46 (s, 9H).

Intermediate 271 tert-Butyl N-((4S,5R)-5-hydroxy-1-(2-methyl-4-nitro-pyrazol-3-yl)azepan-4-yl)carbamate

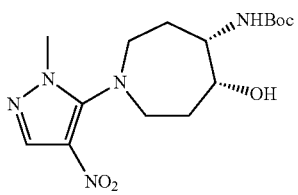 [SMILES: Cn1ncc([N+](=O)[O-])c1N1CC[C@@H](O)[C@@H](NC(=O)OC(C)(C)C)CC1]

The racemic mixture of tert-butyl 5-hydroxy-1-(1-methyl-4-nitro-1H-pyrazol-5-yl)azepan-4-ylcarbamate (5.13 g, 14.13 mmol) was submitted for chiral SFC separation of enantiomers and gave tert-butyl N-((4S,5R)-5-hydroxy-1-(2-methyl-4-nitro-pyrazol-3-yl)azepan-4-yl)carbamate as yellow gum (2.02 g, 97.6% ee, 39%). $^1$H NMR (400 MHz, CDCl$_3$) δ 8.03 (s, 1H), 5.12 (s, 1H), 4.19 (s, 1H), 3.93 (t, J=8.6 Hz, 1H), 3.79 (s, 3H), 3.52-3.44 (m, 1H), 3.33-3.26 (m, 1H), 3.22-3.08 (m, 2H), 2.53 (s, 1H), 2.19-2.11 (m, 1H), 2.02-1.95 (m, 2H), 1.92-1.82 (m, 1H), 1.46 (s, 9H).

Intermediate 272 tert-Butyl N-((4R,5S)-1-(4-((5-(tert-butoxycarbonylamino)-2-(2,6-difluorophenyl)thiazole-4-carbonyl)amino)-2-methyl-pyrazol-3-yl)-5-hydroxy-azepan-4-yl]carbamate

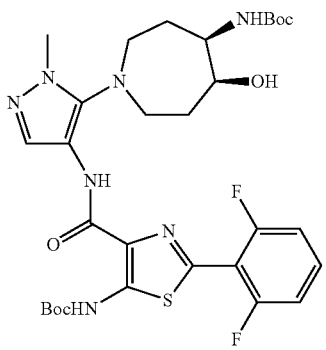 [SMILES: Cn1ncc(NC(=O)c2nc(-c3c(F)cccc3F)sc2NC(=O)OC(C)(C)C)c1N1CC[C@H](O)[C@H](NC(=O)OC(C)(C)C)CC1]

To a solution of tert-butyl N-((4R,5S)-5-hydroxy-1-(2-methyl-4-nitro-pyrazol-3-yl)azepan-4-yl)carbamate (1.92 g, 5.40 mmol) in methanol (40 mL) was added 10% palladium on carbon (37 mg, 0.35 mmol) and the reaction mixture stirred for 6 hr at room temperature under a 600 psi atmosphere of hydrogen. The mixture was filtered through Celite® and the filtrate concentrated under reduced pressure to give the crude amino-pyrazole (1.5 g). A solution of PyBOP (3.35 g, 6.44 mmol) and 5-(tert-butoxycarbonylamino)-2-(2,6-difluorophenyl)thiazole-4-carboxylic acid (1.8 g, 5.06 mmol) in DCM (50 mL) was stirred at room temperature for 30 minutes. A solution of the crude amino-pyrazole (1.5 g, 4.60 mmol) and DIPEA (1.28 mL, 7.36 mmol) in DCM (50 mL) was added and the mixture stirred at room temperature for 70 hr. The reaction mixture was diluted with DCM (50 mL) and washed with water (3×50 mL). The organic layer was passed through a phase separation cartridge and concentrated under reduced pressure. Purification via silica gel chromatography (0-3% MeOH/DCM) and trituration with hot Et$_2$O then with hot MeCN gave tert-butyl N-((4R,5S)-1-(4-(5-(tert-butoxycarbonylamino)-2-(2,6-difluorophenyl)thiazole-4-carbonyl)amino)-2-methyl-pyrazol-3-yl)-5-hydroxy-azepan-4-yl]carbamate as an off-white solid (1.85 g, 51% over two steps). $^1$H NMR (400 MHz, CDCl$_3$) δ 10.67 (s, 1H), 9.76 (s, 1H), 8.03 (s, 1H), 7.41-7.34 (m, 1H), 7.09 (t, J=8.8 Hz, 2H), 5.00 (d, J=8.4 Hz, 1H), 4.25 (s, 1H), 3.83 (s, 1H), 3.72 (s, 3H), 3.45-3.25 (m, 4H), 3.20-3.12 (m, 1H), 2.20-1.84 (m, 3H), 1.84-1.78 (m, 1H), 1.55 (s, 9H), 1.42 (s, 9H).

Intermediate 273 tert-Butyl N-((4S,5R)-1-(4-(5-(tert-butoxycarbonylamino)-2-(2,6-difluorophenyl)thiazole-4-carbonyl)amino)-2-methyl-pyrazol-3-yl)-5-hydroxy-azepan-4-yl]carbamate

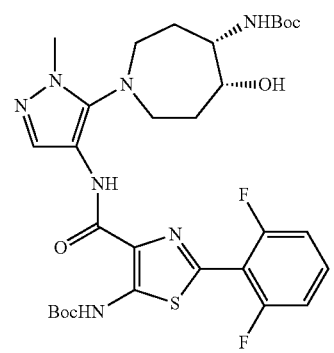 [SMILES: Cn1ncc(NC(=O)c2nc(-c3c(F)cccc3F)sc2NC(=O)OC(C)(C)C)c1N1CC[C@@H](O)[C@@H](NC(=O)OC(C)(C)C)CC1]

Following the procedure for Intermediate 272 starting from tert-butyl N-((4S,5R)-5-hydroxy-1-(2-methyl-4-nitro-pyrazol-3-yl)azepan-4-yl)carbamate gave tert-butyl N-((4S,5R)-1-(4-((5-(tert-butoxycarbonylamino)-2-(2,6-difluorophenyl)thiazole-4-carbonyl)amino)-2-methyl-pyrazol-3-yl)-5-hydroxy-azepan-4-yl]carbamate as a white solid (1.34 g, 37% over two steps). $^1$H NMR (400 MHz, CDCl$_3$) δ 10.67 (s, 1H), 9.76 (s, 1H), 8.03 (s, 1H), 7.41-7.34 (m, 1H), 7.09 (t, J=8.8 Hz, 2H), 5.00 (d, J=8.4 Hz, 1H), 4.25 (s, 1H), 3.83 (s, 1H), 3.72 (s, 3H), 3.45-3.25 (m, 4H), 3.20-3.12 (m, 1H), 2.20-1.84 (m, 3H), 1.84-1.78 (m, 1H), 1.55 (s, 9H), 1.42 (s, 9H).

Intermediate 274 anti-7-Azido-4-(2-methyl-4-nitro-pyrazol-3-yl)cyclohept-3-en-1-ol

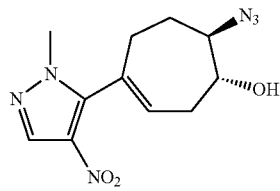 [SMILES: Cn1ncc([N+](=O)[O-])c1C1=CC[C@@H](O)[C@H](N=[N+]=[N-])CC1]

Following the procedure for Intermediate 221 also gave anti-7-azido-4-(2-methyl-4-nitro-pyrazol-3-yl)cyclohept-3-en-1-ol as a pale yellow oil (294 mg, 42% yield). $^1$H NMR (400 MHz, CDCl$_3$) δ 8.06 (s, 1H), 5.96 (dd, J=8.3, 4.9 Hz, 1H), 3.82 (s, 3H), 3.80-3.73 (m, 1H), 3.56-3.48 (m, 1H), 2.71 (ddd, J=15.5, 8.3, 2.3 Hz, 1H), 2.58-2.39 (m, 4H), 2.24-2.14 (m, 1H), 1.86-1.73 (m, 1H).

Intermediate 275 syn-7-Azido-4-(2-methyl-4-nitro-pyrazol-3-yl)cyclohept-3-en-1-ol

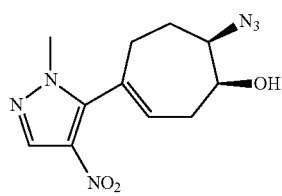 [SMILES: Cn1ncc([N+](=O)[O-])c1C1=CC[C@H](O)[C@H](N=[N+]=[N-])CC1]

Following the procedure for Intermediate 119 starting from anti-7-azido-4-(2-methyl-4-nitro-pyrazol-3-yl)cyclohept-3-en-1-ol gave syn-7-azido-4-(2-methyl-4-nitro-pyrazol-3-yl)cyclohept-3-en-1-ol as a yellow oil (346 mg, 67% over two steps). $^1$H NMR (400 MHz, CDCl$_3$) δ 8.06 (s, 1H), 5.93-5.85 (m, 1H), 3.94-3.88 (m, 1H), 3.85 (s, 3H), 2.98 (ddd, J=15.2, 9.5, 6.4 Hz, 1H), 2.65 (dd, J=15.7, 9.0 Hz, 1H), 2.41 (dd, J=15.2, 6.9 Hz, 1H), 2.30 (dd, J=15.9, 9.4 Hz, 1H), 2.04-1.87 (m, 4 H).

Intermediate 276 tert-Butyl N-(-2-methoxy-5-(2-methyl-4-nitro-pyrazol-3-yl)cyclohept-4-en-1-yl)carbamate

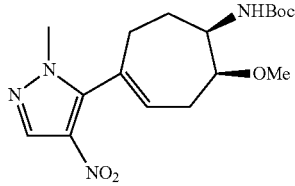 [SMILES: CO[C@H]1CC=C(c2c([N+](=O)[O-])cnn2C)CC[C@H]1NC(=O)OC(C)(C)C]

Following the procedure for Intermediate 120 starting from syn-7-azido-4-(2-methyl-4-nitro-pyrazol-3-yl)cyclohept-3-en-1-ol gave tert-butyl N-(-2-methoxy-5-(2-methyl-4-nitro-pyrazol-3-yl)cyclohept-4-en-1-yl)carbamate as a colourless oil (189 mg, 89% over three steps). $^1$H NMR (400 MHz, CDCl$_3$) δ 8.05 (s, 1H), 5.92 (ddd, J=8.4, 4.7, 1.6 Hz, 1H), 5.23 (s, 1H), 3.91-3.81 (m, 1H), 3.80 (s, 3H), 3.66-3.62 (m, 1H), 3.41 (s, 3H), 2.93 (ddd, J=15.1, 11.1, 4.7 Hz, 1H), 2.78 (t, J=12.9 Hz, 1H), 2.23 (dd, J=15.1, 8.5 Hz, 1H), 2.15-1.82 (m, 3H), 1.46 (s, 9H).

Intermediate 277

G02693497 tert-Butyl N-(5-(4-((5-(tert-butoxycarbonylamino)-2-(2,6-difluorophenyl)thiazole-4-carbonyl)amino)-2-methyl-pyrazol-3-yl]-2-methoxy-cycloheptyl]carbamate

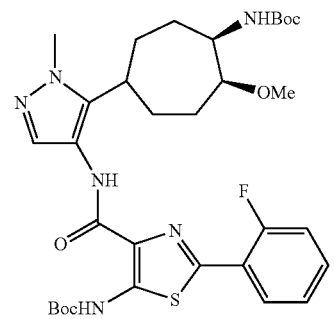 [SMILES: CO[C@H]1CCC(c2c(NC(=O)c3nc(-c4ccccc4F)sc3NC(=O)OC(C)(C)C)cnn2C)CC[C@H]1NC(=O)OC(C)(C)C]

A solution of tert-butyl N-(-2-methoxy-5-(2-methyl-4-nitro-pyrazol-3-yl)cyclohept-4-en-1-yl)carbamate (180 mg, 0.49 mmol) in MeOH (30 mL) was passed through the H-Cube® (full H$_2$, 70° C., flow rate: 1 mL/min, 30 mm 20% Pd/C cartridge). The solvent was removed under reduced pressure to give a colourless oil. To a solution of this oil in DCM (30 mL) was added DIPEA (2.00 mL, 11.48 mmol) and 5-(tert-butoxycarbonylamino)-2-(2-fluorophenyl)thiazole-4-carboxylic acid (171 mg, 0.50 mmol) followed by PyBOP (596 mg, 1.15 mmol) and the mixture was stirred at room temperature for 16 hr. The reaction was quenched with water (20 mL) and extracted with DCM (80 mL). The organic layer was separated, dried over MgSO$_4$ and concentrated under reduced pressure. Purification via silica gel chromatography (70-80% EtOAc/isohexane) gave tert-butyl N-(5-(4-((5-(tert-butoxycarbonylamino)-2-(2,6-difluorophenyl)thiazole-4-carbonyl)amino)-2-methyl-pyrazol-3-yl]-2-methoxy-cycloheptyl]carbamate as a mixture of four diastereomers as an off-white solid (175 mg, 54% over two steps). $^1$H NMR (400 MHz, CDCl$_3$) δ 10.39 and 10.36 (2s, 1H), 8.69 and 8.62 (2s, 1H), 8.32-8.28 and 8.21-8.14 (2 m, 1H), 7.85 and 7.75 (2s, 1H), 7.43-7.36 (m, 1H), 7.32 (t, J=7.6 Hz, 1H), 7.25-7.17 (m, 1H), 5.19 and 5.08 (2d, J=8.8 Hz, 1H), 3.84 (s, 3H), 3.78-3.54 (m, 2H), 3.37 and 3.27 (2s, 3H), 3.11-2.94 (m, 1H), 2.32-1.30 (m, 8H), 1.55 (s, 9H), 1.43 (s, 9H).

Intermediate 278 tert-Butyl 4-methyl-6-oxo-3,7-dihydro-2H-azepine-1-carboxylate

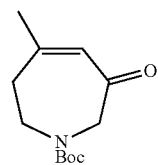

A solution of n-butyllithium in hexanes (2.5 M, 5.1 mL, 12.75 mmol) was added dropwise over 10 min to a stirred solution of N-(3-methyl-3-buten-1-yl)-1,1-dimethylethyl ester (2.14 g, 11.57 mmol) in anhydrous THF (30 mL) at room temperature under nitrogen. After 1.25 hr, 1-chloro-3-(triphenyl-$\lambda^5$-phosphanylidene)propan-2-one (4.07 g, 11.57 mmol) was added portionwise over 15 min and stirring continued at room temperature for 18 hr. Water (100 mL) was carefully added and the reaction mixture extracted with EtOAc (3×150 mL). The combined organic layers were dried over MgSO$_4$ and the solvent removed under reduced pressure. Purification via silica gel column chromatography (0-10% MeOH/DCM) gave a pale orange gum (5.7 g). This was dissolved in anhydrous THF (60 mL) and acetaldehyde (6.4 mL) was added. The reaction mixture was stirred at room temperature for 20 hr. The solvent was removed under reduced pressure. Purification via silica gel column chromatography (0-100% EtOAc/isohexane) gave a pale orange oil (2.18 g). This oil was dissolved in DCM (30 mL) deoxygenated with nitrogen and Grubbs 2nd generation catalyst (335 mg, 0.34 mmol) added. The mixture was heated at reflux under nitrogen for 20 hr. The mixture was allowed to cool to room temperature and the solvent removed under reduced pressure. Purification via silica gel column chromatography (0-30% EtOAc/isohexane) gave tert-butyl 4-methyl-6-oxo-3,7-dihydro-2H-azepine-1-carboxylate as a dark brown oil (1.23 g, 47% over three steps). $^1$H NMR (400 MHz, CDCl$_3$) δ 5.30 (s, 1H), 4.30-4.10 (m, 2H), 3.65-3.50 (m, 2H), 2.70-2.55 (m, 2H), 2.05-1.90 (m, 3H), 1.48 and 1.44 (2s, 9H).

Intermediate 279

5-Azido-5-methyl-1-(2-methyl-4-nitro-pyrazol-3-yl)azepan-3-ol

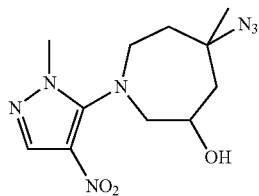 [SMILES: Cn1ncc([N+](=O)[O-])c1N1CCC(C)(N=[N+]=[N-])CC(O)C1]

Following the procedure for Intermediate 18 starting from tert-butyl 4-methyl-6-oxo-3,7-dihydro-2H-azepine-1-carboxylate gave 5-azido-5-methyl-1-(2-methyl-4-nitro-pyrazol-3-yl)azepan-3-ol as a pale green gum (720 mg, 64% over three steps). $^1$H NMR (400 MHz, CDCl$_3$) δ 8.04-8.03 (m, 1H), 4.25-3.90 (m, 1H), 3.88 and 3.84 (2s, 3H), 3.75-3.45 (m, 1H), 3.45-2.90 (m, 3H), 2.30-2.18 (m, 1H), 2.15-1.75 (m, 4H), 1.55 (2s, 3H).

Intermediate 280 tert-Butyl N-(6,6-difluoro-4-methyl-1-(2-methyl-4-nitro-pyrazol-3-yl)azepan-4-yl)carbamate

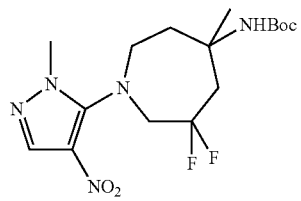 [SMILES: Cn1ncc([N+](=O)[O-])c1N1CCC(C)(NC(=O)OC(C)(C)C)CC(F)(F)C1]

To a solution of 5-azido-5-methyl-1-(2-methyl-4-nitro-pyrazol-3-yl)azepan-3-ol (720 mg, 2.44 mmol) in DCM (100 mL) was added in a single portion Dess-Martin periodinane (1.35 g, 3.17 mmol). The reaction mixture was stirred at room temperature for 1 hr, diluted with DCM (100 mL) and quenched with saturated aqueous NaHCO$_3$ (200 mL) followed by 20% aqueous Na$_2$S$_2$O$_3$ (100 mL). The resulting mixture was stirred for 15 min, the organic layer separated and the aqueous layer extracted with DCM (100 mL). The combined organic layers were passed through a phase separation cartridge and the solvent removed under reduced pressure to afford a pale green gum (720 mg). To a solution of this gum in DCM (50 mL) was added deoxo-Fluor® (50% in THF, 3.12 mL, 8.6 mmol) and the mixture was stirred at room temperature for 20 hr. More deoxo-Fluor® (3.1 mL) was added and the mixture heated at 40° C. for 28 hr. The mixture was cooled and quenched by dropwise addition of saturated aqueous NaHCO$_3$ (200 mL) and diluted with DCM (100 mL). The organic layer was separated and the aqueous extracted with DCM (100 mL). The combined organic layers were passed through a phase separation cartridge and the solvent removed under reduced pressure. Purification via silica gel column chromatography (0-100% EtOAc/isohexane) gave a pale yellow gum (626 mg). This gum was dissolved in THF (20 mL) and water (4 mL) and triphenylphosphine (522 mg, 2 mmol) added. The mixture was heated at 70° C. behind a blast screen for 16 hr. More triphenylphosphine (500 mg) was added and heating continued for a further 5 hr. The solvents were removed under reduced pressure and the residue dissolved in DCM (30 mL). To this solution was added di-tert-butyl dicarbonate (1.08 g, 5 mmol) and DIPEA (0.7 mL, 4 mmol) and the mixture was stirred at room temperature for 66 hr. The solvent was removed under reduced pressure and the residue purified via silica gel column chromatography (0-100% EtOAc/isohexane) to give tert-butyl N-(6,6-difluoro-4-methyl-1-(2-methyl-4-nitro-pyrazol-3-yl)azepan-4-yl)carbamate as a colourless solid (540 mg, 57% over four steps). $^1$H NMR (400 MHz, CDCl$_3$) δ 8.04 (s, 1H), 4.92 (s, 1H), 3.84 (s, 3H), 3.82-3.55 (m, 1H), 3.52-3.05 (m, 3H), 2.70-2.45 (m, 2H), 2.30-2.05 (m, 1H), 2.04-1.85 (m, 1H), 1.52 (s, 3H), 1.45 (s, 9H).

Intermediate 281 tert-Butyl N-(4-((5-(5-(tert-butoxycarbonylamino)-3,3-difluoro-5-methyl-azepan-1-yl)-1-methyl-pyrazol-4-yl)carbamoyl)-2-(2,6-difluorophenyl)thiazol-5-yl]carbamate

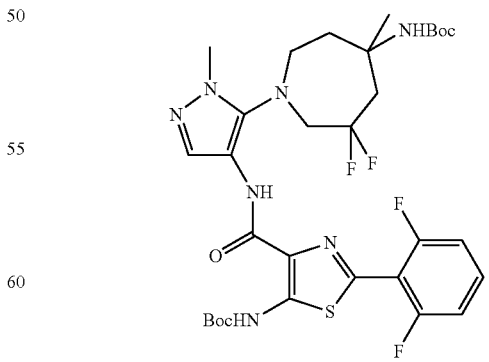

Following the procedure for Intermediate 269 starting from tert-butyl N-(6,6-difluoro-4-methyl-1-(2-methyl-4-nitro-pyrazol-3-yl)azepan-4-yl)carbamate gave tert-butyl N-(4-

((5-(5-(tert-butoxycarbonylamino)-3,3-difluoro-5-methyl-azepan-1-yl)-1-methyl-pyrazol-4-yl)carbamoyl)-2-(2,6-difluorophenyl)thiazol-5-yl)carbamate as a yellow solid (409 mg, 58% over two steps). $^1$H NMR (400 MHz, CDCl$_3$) δ 10.39 (s, 1H), 8.79 (s, 1H), 7.88 (s, 1H), 7.45-7.30 (m, 1H), 7.15-7.00 (m, 2H), 5.12 (br s, 1H), 3.78 (s, 3H), 3.75-3.42 (m, 2H), 3.40-3.10 (m, 2H), 2.70-2.45 (m, 2H), 2.40-2.15 (m, 1H), 1.95-1.70 (m, 1H), 1.55 (s, 9H), 1.46 (s, 3H), 1.33 (s, 9H).

Intermediate 285

3-Ethyl-1-(2-methyl-4-nitro-pyrazol-3-yl)piperidin-4-one

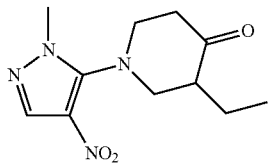 [SMILES: CCC1CN(c2c([N+](=O)[O-])cnn2C)CCC1=O]

To a solution of tert-butyl 3-ethyl-4-oxo-piperidine-1-carboxylate (380 mg, 1.67 mmol) in DCM (15 mL) at room temperature was added TFA (3 mL) and the reaction mixture stirred at room temperature for 4 hr. The mixture was concentrated under reduced pressure to give the ethyl piperidinone as its trifluoroacetate salt. A mixture of this salt (410 mg, 1.7 mmol), 5-chloro-1-methyl-4-nitro-pyrazole (330 mg, 2.0 mmol) and DIPEA (0.75 mL, 4.2 mmol) in EtOH (15 mL) was heated at 130° C. for 2 hr under microwave conditions. The reaction mixture was concentrated under reduced pressure. Purification via silica gel column chromatography (10-50% EtOAc/isohexane) gave 3-ethyl-1-(2-methyl-4-nitro-pyrazol-3-yl)piperidin-4-one as a light yellow solid, (250 mg, 58% over two steps). $^1$H NMR (400 MHz, CDCl$_3$) δ 8.05 (s, 1H), 3.87 (s, 3H), 3.65-3.54 (m, 1H), 3.53-3.41 (m, 2H), 3.36-3.21 (m, 1H), 2.78-2.64 (m, 1H), 2.64-2.49 (m, 2H), 2.01-1.87 (m, 1H), 1.44-1.29 (m, 1H), 0.94 (t, J=7.5 Hz, 3H).

Intermediate 286

4-(Azidomethyl)-3-ethyl-1-(2-methyl-4-nitro-pyrazol-3-yl)piperidin-4-ol

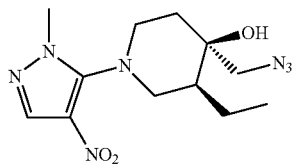 [SMILES: CC[C@H]1CN(c2c([N+](=O)[O-])cnn2C)CC[C@]1(O)CN=[N+]=[N-]]

Following the procedure for Intermediate 253 starting from 3-ethyl-1-(2-methyl-4-nitro-pyrazol-3-yl)piperidin-4-one gave 4-(azidomethyl)-3-ethyl-1-(2-methyl-4-nitro-pyrazol-3-yl)piperidin-4-ol as a yellow gum (170 mg, 66% over two steps). $^1$H NMR (400 MHz, CDCl$_3$) δ 8.03 (s, 1H), 3.76 (s, 3H), 3.62-3.53 (m, 2H), 3.40 (d, J=12.2 Hz, 1H), 3.34-3.15 (m, 1H), 3.06-2.94 (m, 2H), 1.97-1.77 (m, 3H), 1.37-1.15 (m, 2H), 0.92 (t, J=7.4 Hz, 3H). OH not observed.

Intermediate 287 tert-Butyl N-((3-ethyl-4-methoxy-1-(2-methyl-4-nitro-pyrazol-3-yl)-4-piperidyl)methyl)carbamate

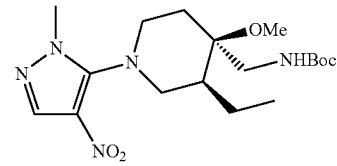 [SMILES: CC[C@H]1CN(c2c([N+](=O)[O-])cnn2C)CC[C@@]1(CNC(=O)OC(C)(C)C)OC]

Following the procedure for Intermediate 120 starting from 4-(azidomethyl)-3-ethyl-1-(2-methyl-4-nitro-pyrazol-3-yl)piperidin-4-ol gave tert-butyl N-((3-ethyl-4-methoxy-1-(2-methyl-4-nitro-pyrazol-3-yl)-4-piperidyl)methyl)carbamate as a light yellow solid (110 mg, 70% over three steps). $^1$H NMR (400 MHz, CDCl$_3$) δ 8.02 (s, 1H), 4.95-4.35 (m, 1H), 3.76 (s, 3H), 3.53-3.43 (m, 2H), 3.36-3.09 (m, 7H), 2.07-1.93 (m, 1H), 1.44-1.10 (m, 4H), 0.96-0.81 (m, 12H).

Intermediate 292

3-(2-Methyl-4-nitro-pyrazol-3-yl)-8-oxa-3-azabicyclo[3.2.1]octan-6-ol

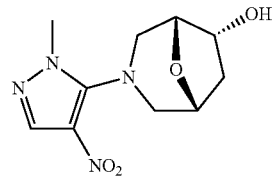

A solution of 7-oxabicyclo[2.2.1]hept-2-en-5-ol (0.7 g, 6.2 mmol) in MeOH/DCM (25 mL/5 mL) cooled to −78° C. was degassed by bubbling nitrogen through it for 5 min. Ozone was bubbled through the reaction mixture until a greyish-blue colour persisted. Nitrogen was again bubbled through the cold reaction mixture until only a pale colour persisted. A solution of benzylamine (0.67 g, 6.2 mmol) dissolved in MeOH (5 mL) was added followed by NaCNBH$_3$ (1.6 g, 25 mmol) in MeOH (10 mL). The mixture was allowed to warm to room temperature and stirred for 16 hr. The solvents were removed under reduced pressure and the residue partitioned between EtOAc (30 mL) and water (30 mL). The aqueous layer was further extracted with EtOAc (3×50 mL) and the combined organic layers were washed with brine (20 mL), dried over MgSO$_4$ and concentrated under reduced pressure to give the benzyl protected amine. This was dissolved in EtOH (40 mL) and 2 M aqueous HCl (1 mL) and Pd(OH)$_2$/C (0.2 g) were then added. The mixture was stirred under a 600 psi atmosphere of hydrogen at 70° C. for 18 hr. The reaction mixture was cooled to room temperature, filtered through celite washing with EtOH (40 mL). The filtrate was concentrated under reduced pressure to give the debenzylated product, as the hydrochloride salt. To a suspension of the hydrochloride salt (1.1 g, 6.6 mmol) in DMSO (15 mL) was added 5-chloro-1-methyl-4-nitro-pyrazole (1.2 g, 7.3 mmol), DIPEA (1.7 mL, 9.7 mmol) and potassium fluoride (1.1 g, 20 mmol) and the reaction was heated at 85° C. for 16 hr. The mixture was cooled to room temperature, partitioned between water (25 mL) and EtOAc (25 mL) and the aqueous layer extracted with EtOAc (3×25 mL). The combined organic layers were washed with brine (25 mL), separated, dried over MgSO$_4$ and concentrated under reduced pressure. Purification via silica gel column chromatography (10-50% EtOAc/isohexane) gave 3-(2-methyl-4-nitro-pyrazol-3-yl)-8-oxa-3-azabicyclo[3.2.1]octan-6-ol as an off-white solid, (550 mg, 62% over three steps). $^1$H NMR (400 MHz, CDCl$_3$) δ 8.06 (s, 1H), 4.66-4.57 (m, 1H), 4.38 (d, J=7.6 Hz, 1H), 4.19 (d, J=6.3 Hz, 1H), 3.94 (s, 3H), 3.82-3.73 (m, 1H), 3.68 (dd, J=11.1, 2.8 Hz, 1H), 3.12 (d, J=11.1 Hz, 1H), 2.71-2.59 (m, 2H), 2.38 (d, J=7.0 Hz, 1H), 1.97 (dd, J=12.9, 3.9 Hz, 1H).

Intermediate 293

6-Azido-3-(2-methyl-4-nitro-pyrazol-3-yl)-8-oxa-3-azabicyclo[3.2.1]octane

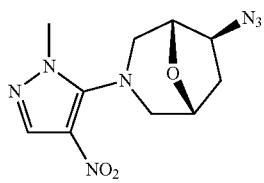 [SMILES: Cn1ncc([N+](=O)[O-])c1N1C[C@H]2C[C@H](N=[N+]=[N-])[C@@H](C1)O2]

3-(2-Methyl-4-nitro-pyrazol-3-yl)-8-oxa-3-azabicyclo[3.2.1]octan-6-ol (500 mg, 1.96 mmoL) was dissolved in DCM (15 mL) and triethylamine (0.41 mL, 2.95 mmol) was added. After cooling to 0° C., methanesulfonyl chloride (0.19 mL, 2.45 mmol) was added slowly and the reaction mixture was allowed to warm to room temperature and stirred for 18 hr. The mixture was diluted with DCM (10 mL), quenched with water (10 mL) and the aqueous layer extracted with DCM (3×20 mL). The combined organic layers were washed with brine (10 mL), passed through a phase separation cartridge and concentrated under reduced pressure to give a light brown solid. This solid (450 mg, 1.35 mmol) was dissolved in DMF (20 mL), sodium azide (450 mg, 6.8 mmol) was added and the mixture heated at 150° C. for 18 hr, behind a blast shield. The mixture was allowed to cool to room temperature, the mixture partitioned between water (20 mL) and EtOAc (20 mL) and the aqueous layer extracted with EtOAc (3×25 mL). The combined organic layers were washed with brine (20 mL), dried over MgSO$_4$ and concentrated under reduced pressure. Purification via silica gel column chromatography (10-50%, EtOAc/isohexane) gave 6-azido-3-(2-methyl-4-nitro-pyrazol-3-yl)-8-oxa-3-azabicyclo[3.2.1]octane as brown gum (25 mg, 68% over two steps). $^1$H NMR (400 MHz, CDCl$_3$) δ 8.05 (s, 1H), 4.65 (d, J=7.4 Hz, 1H), 4.34 (s, 1H), 4.28 (dd, J=8.0, 3.2 Hz, 1H), 3.82 (s, 3H), 3.75-3.70 (m, 2H), 2.83-2.73 (m, 1H), 2.64-2.49 (m, 2H), 2.20 (ddd, J=13.4, 7.3, 3.2 Hz, 1H).

Intermediate 294 tert-Butyl N-(3-(2-methyl-4-nitro-pyrazol-3-yl)-8-oxa-3-azabicyclo[3.2.1]octan-6-yl)carbamate

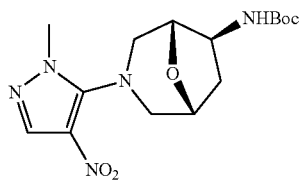 [SMILES: Cn1ncc([N+](=O)[O-])c1N1C[C@H]2C[C@H](NC(=O)OC(C)(C)C)[C@@H](C1)O2]

To a solution of 6-azido-3-(2-methyl-4-nitro-pyrazol-3-yl)-8-oxa-3-azabicyclo[3.2.1]octane (250 g, 0.8 mmol) in THF (10 mL) and water (2 mL), was added trimethylphosphine (1 M solution in toluene, 5 mL, 4.47 mmol) and the mixture was heated at 65° C. for 16 hr. The solvents were removed under reduced pressure and the resulting residue was dissolved in (2 M, 15 mL) and washed with EtOAc (2×10 mL). The aqueous layer was basified to pH 14 with 5 M aqueous NaOH solution and extracted with DCM (3×20 mL). The combined DCM layers were passed through a phase separation cartridge and concentrated under reduced pressure to afford a cream solid, (220 mg). To a solution of this amine in DCM (10 mL) was added triethylamine (0.18 mL 1.3 mmol) and DMAP (26 mg, 0.22 mmol). The mixture was cooled to 0° C. and a solution of di-tert-butyl dicarbonate (0.28 g, 1.3 mmol) in DCM (2 mL) was added slowly. The reaction mixture was stirred at room temperature for 18 hr. The mixture was diluted with DCM (10 mL) and washed with water (10 mL). The organic layer was passed through a phase separation cartridge and concentrated under reduced pressure. Purification via silica gel column chromatography (1-10% MeOH/DCM) gave tert-butyl N-(3-(2-methyl-4-nitro-pyrazol-3-yl)-8-oxa-3-azabicyclo[3.2.1]octan-6-yl)carbamate as an off-white solid (110 mg, 66% over two steps). $^1$H NMR (400 MHz, CDCl$_3$) δ 8.03 (s, 1H), 4.64-4.52 (m, 1H), 4.20 (s, 1H), 3.85 (s, 3H), 3.50-3.41 (m, 4H), 2.69-2.46 (m, 3H), 1.84-1.76 (m, 1H), 1.45 (s, 9H).

Intermediate 295 tert-Butyl N-(5-fluoro-2-hydroxy-5-(2-methyl-4-nitro-pyrazol-3-yl)cycloheptyl)carbamate

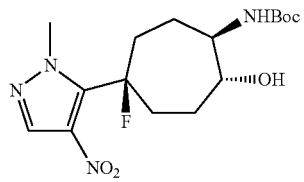

Following the procedure for Intermediate 294 starting from 2-azido-5-fluoro-5-(1-methyl-4-nitro-1H-pyrazol-5-yl)cycloheptanol gave tert-butyl N-(5-fluoro-2-hydroxy-5-(2-methyl-4-nitro-pyrazol-3-yl)cycloheptyl)carbamate as a colourless solid (572 mg, 61% over two steps). $^1$H NMR (400 MHz, CDCl$_3$) δ 8.06 and 8.05 (2s, 1H), 4.70 (br s, 1H), 4.07 and 4.06 (2s, 3H), 3.86-3.67 (m, 3H), 2.96 (ddd, J=40.6, 15.3, 10.4 Hz, 1H), 2.74 (dt, J=44.6, 13.8 Hz, 1H), 2.25-2.04 (m, 2H), 2.01-1.79 (m, 3H), 1.72-1.63 (m, 1H), 1.47 (s, 9H).

Intermediate 302

O1-Benzyl O4-ethyl 5-hydroxy-4-methyl-azepane-1,4-dicarboxylate

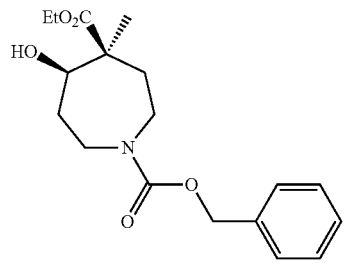 [SMILES: CCOC(=O)[C@@]1(C)CCN(C(=O)OCc2ccccc2)CC[C@H]1O]

To a solution of 1-(benzyloxycarbonyl)-4-piperidinone (20.0 g, 85.80 mmol) in Et$_2$O (200 mL) at 0° C. was added boron trifluoride etherate (12.0 mL, 94.40 mmol) followed by the addition of ethyl diazoacetate (11.7 mL, 94.40 mmol) maintaining the temperature below 7° C. The reaction mixture was stirred for 1 hr, quenched with a 2 M aqueous solution of sodium carbonate (150 mL) and extracted with EtOAc (3×150 mL). The combined organic layers were dried over MgSO$_4$ and concentrated under reduced pressure. Purification via silica gel column chromatography (0-50% EtOAc/isohexane) gave a light yellow oil. This oil (10 g, 31.30 mmol) was dissolved in DMF (75 mL) at 0° C. and sodium hydride (60% dispersion in mineral oil, 1.38 g, 34.50 mmol) was added portionwise. The reaction mixture was stirred at 0° C. for 1 hr before iodomethane (2.15 mL, 34.50 mmol) was added. The reaction was allowed to warm to room temperature and stirred for 18 hr. The mixture was diluted with Et$_2$O (100 mL) and quenched with water (100 mL). The aqueous layer was extracted with Et$_2$O (3×75 mL) and the combined organic layers were washed with water (2×100 mL) and brine (2×100 mL), separated, dried over MgSO$_4$ and concentrated under reduced pressure. Purification via silica gel column chromatography (50% Et$_2$O/isohexane) gave a light yellow oil. A portion of this oil (0.90 g, 2.70 mmol) was dissolved in MeOH (4 mL) and added to a stirred suspension of NaBH$_4$ (0.12 g, 3.24 mmol) in MeOH (5 mL) at 0° C. The reaction mixture was stirred at 0° C. for 3 hr, before being quenched with a 1 M aqueous solution of HCl (5 mL). The aqueous layer was extracted with DCM (3×10 mL) and the combined organic layers were passed through a phase separation cartridge and concentrated under reduced pressure. Purification via silica gel column chromatography (25-100% EtOAc/isohexane) gave O1-benzyl O4-ethyl 5-hydroxy-4-methyl-azepane-1,4-dicarboxylate as a colourless oil (480 mg, 1% over three steps). $^1$H NMR (400 MHz, CDCl$_3$) δ 7.37-7.28 (m, 5H), 5.17-5.10 (m, 2H), 4.20-4.07 (m, 2H), 3.78-3.20 (m, 7H), 2.32-2.24 (m, 1H), 2.07-1.86 (m, 3H), 1.73-1.62 (m, 1H), 1.30-1.19 (m, 3H). Exchangeable OH not observed.

Intermediate 303

Benzyl 3a-methyl-2-oxo-3,4,5,7,8,8a-hexahydrooxazolo[4,5-d]azepine-6-carboxylate

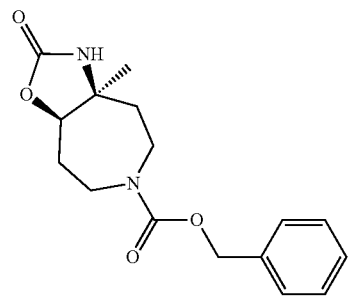 [SMILES: C[C@]12CCN(C(=O)OCc3ccccc3)CC[C@H]1OC(=O)N2]

To a solution of O1-benzyl O4-ethyl 5-hydroxy-4-methyl-azepane-1,4-dicarboxylate (0.48 g, 1.43 mmol) in dioxane (5 mL) was added a 1 M aqueous solution of NaOH (2.9 mL, 2.87 mmol) and the reaction was stirred at room temperature for 16 hr. The mixture was acidified to pH 3 with 2 M aqueous HCl and extracted with Et$_2$O (10 mL) and DCM (10 mL). The combined organic layers were passed through a phase separation cartridge and concentrated under reduced pressure. Purification via silica gel column chromatography (0-100% EtOAc/isohexane) gave a colourless oil (0.42 g). A portion of this oil (0.21 g, 0.68 mmol), diphenyl phosphoryl azide (0.17 mL, 0.82 mmol) and triethylamine (0.12 mL, 0.88 mmol) were dissolved in toluene (7 mL) and the reaction mixture was stirred at room temperature for 40 min and heated at 90° C. behind a blast shield for 40 min. tert-Butanol (0.05 mL, 0.56 mmol) was added and the reaction mixture was heated at reflux for 16 hr behind a blast shield. The reaction mixture was cooled to room temperature and quenched with saturated aqueous NaHCO$_3$ (10 mL). The mixture was extracted with EtOAc (15 mL) and the organic layer was washed with water (10 mL) and brine (10 mL), separated, dried over MgSO$_4$ and concentrated under reduced pressure. Purification via silica gel column chromatography (0-100% EtOAc/isohexane) gave benzyl 3a-methyl-2-oxo-3,4,5,7,8,8a-hexahydrooxazolo[4,5-d]azepine-6-carboxylate as a yellow oil (100 mg, 22% over two steps). $^1$H NMR (400 MHz, CDCl$_3$) δ 7.38-7.28 (m, 5H), 5.26-4.97 (m, 3H), 4.51 (s, 1H), 3.98-3.76 (m, 1H), 3.43-3.06 (m, 2H), 2.17 (s, 1H), 1.96-1.77 (m, 3H), 1.58 (s, 3H). Exchangeable not observed.

Intermediate 304

3a-Methyl-6-(2-methyl-4-nitro-pyrazol-3-yl)-3,4,5,7,8,8a-hexahydrooxazolo[4,5-d]azepin-2-one

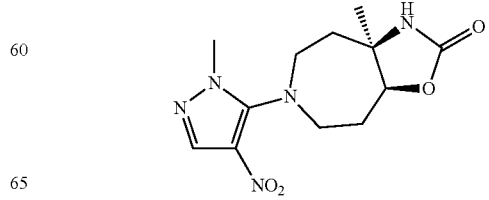

To a solution of benzyl 3a-methyl-2-oxo-3,4,5,7,8,8a-hexahydrooxazolo[4,5-d]azepine-6-carboxylate (305 mg, 1.0 mmol) and 1-methyl-1,4-cyclohexadiene (1.1 mL, 10.00 mmol) in EtOH (10 mL) was added 10% palladium on carbon (53 mg, 0.50 mmol) under nitrogen and the mixture was heated at 60° C. for 2 hr. The mixture was cooled to room temperature, filtered through Celite® and concentrated under reduced pressure. To a solution of the residue (170 mg, 1.00 mmol) in DMSO (5 mL) was added 5-chloro-1-methyl-4-nitro-pyrazole (178 mg, 1.10 mmol) and potassium fluoride (232 mg, 4.00 mmol) and the mixture was heated in the microwave at 110° C. for 4 hr. The reaction was quenched with water (20 mL) and extracted with EtOAc (3×5 mL). The combined organic layers were passed through a phase separation cartridge and concentrated under reduced pressure. Purification via silica gel chromatography (0-5% MeOH/DCM) gave a yellow solid (220 mg, 74% over two steps). The material was combined with another batch to give 350 mg for separation of the diastereoisomers by reverse-phase preparative HPLC. The major diastereomer was isolated as a yellow solid (196 mg, 67% over two steps) $^1$H NMR (400 MHz, $d_6$-DMSO) δ 8.11 (s, 1H), 7.72 (s, 1H), 4.48 (dd, J=6.6, 2.7 Hz, 1H), 3.74 (s, 3H), 3.10-3.01 (m, 2H), 2.20-1.96 (m, 3H), 1.85 (dd, J=15.2, 7.8 Hz, 1H), 1.32 (s, 3H). Two protons under water peak. LCMS (ES+) m/z 296 (M+1).

Intermediate 305

8-(2-Methyl-4-nitro-pyrazol-3-yl)-1,4-dioxaspiro[4.5]decan-8-ol

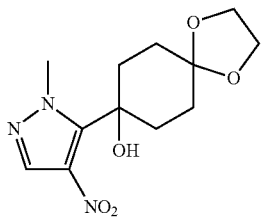 [SMILES: Cn1ncc([N+](=O)[O-])c1C1(O)CCC2(CC1)OCCO2]

Following the procedure for Intermediate 218 starting from 1-methyl-4-nitro-1H-pyrazole and 1,4-cyclohexanedione monoethylene acetal gave 8-(2-methyl-4-nitro-pyrazol-3-yl)-1,4-dioxaspiro[4.5]decan-8-ol as a light beige solid (3.68 g, 83%). $^1$H NMR (400 MHz, CDCl$_3$) δ 8.06 (s, 1H), 4.45 (s, 1H), 4.12 (s, 3H), 4.04-3.93 (m, 4H), 2.44-2.34 (m, 2H), 2.23-1.95 (m, 4H), 1.75-1.67 (m, 2H).

Intermediate 306

4-Fluoro-4-(2-methyl-4-nitro-pyrazol-3-yl)cyclohexanone

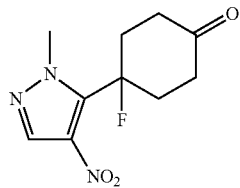 [SMILES: Cn1ncc([N+](=O)[O-])c1C1(F)CCC(=O)CC1]

To a solution of 8-(2-methyl-4-nitro-pyrazol-3-yl)-1,4-dioxaspiro[4.5]decan-8-ol (3.68 g, 13.0 mmol) in dry DCM (80 mL) under nitrogen was added dropwise a solution of deoxo-Fluor® (50% in THF, 14.1 mL, 39.0 mmol). The reaction mixture was stirred at room temperature for 1 hr. After cooling to 0° C., saturated aqueous NaHCO$_3$ (100 mL) was added, dropwise initially, and the mixture was extracted with DCM (2×75 mL). The combined organic layers were dried over MgSO$_4$, and concentrated under reduced pressure. Purification via silica gel column chromatography (30-50% EtOAc/isohexane) gave a pale yellow oil. A portion of this oil (780 mg, 2.74 mmol) was dissolved in THF (20 mL) and treated with 2 M aqueous HCl (3 mL). The reaction mixture was stirred at room temperature for 4 hr, heated at 60° C. for 7 hr and stirred at room temperature for 18 hr. Water (10 mL) was added and the mixture extracted with EtOAc (100 mL). The organic layer was washed with brine (20 mL), separated, dried over MgSO$_4$ and concentrated under reduced pressure. Purification via silica gel column chromatography (25-40% EtOAc/isohexane) gave 4-fluoro-4-(2-methyl-4-nitro-pyrazol-3-yl)cyclohexanone as a white solid (490 mg, 30% over two steps). $^1$H NMR (400 MHz, CDCl$_3$) δ 8.10 and 8.09 (2s, 1H), 4.17 and 4.15 (2s, 3H), 3.16-2.94 (m, 2H), 2.84-2.72 (m, 2H), 2.51 (dd, J=15.4, 5.6 Hz, 2H), 2.43-2.33 (m, 2H).

Intermediate 307 tert-Butyl N-[[4-fluoro-1-hydroxy-4-(2-methyl-4-nitro-pyrazol-3-yl)cyclohexyl]methyl]carbamate

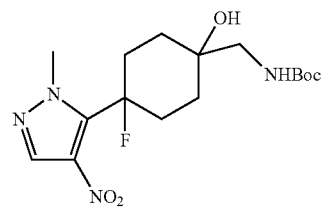

Sodium hydride (60% dispersion in mineral oil, 183 mg, 4.56 mmol) was added portionwise to dry DMSO (15 mL) under nitrogen at 0° C. The reaction mixture was warmed to room temperature and stirred for 15 min before trimethyl sulfoxonium iodide (0.96 g, 4.36 mmol) was added portionwise. After stirring for 90 min at room temperature, a solution of 4-fluoro-4-(2-methyl-4-nitro-pyrazol-3-yl)cyclohexanone (1.0 g, 4.15 mmol) in DMSO (15 mL) was added dropwise. The mixture was heated at 55° C. for 2 hr, cooled to room temperature, poured into water (200 mL) and extracted with EtOAc (3×60 mL). The combined organic layers were dried over MgSO$_4$ and concentrated under reduced pressure to give a gum. A solution of this gum (1.1 g, 4.15 mmol) in 7 M NH$_3$ in MeOH (30 mL) and DCM (10 mL) was stirred at room temperature for 4 days. The solvent was removed under reduced pressure and the resulting yellow oil (1.1 g, 4.15 mmol) was dissolved in DCM (30 mL) and DIPEA (3.6 mL), 20.7 mmol). The solution was treated with a solution of di-tert-butyl-dicarbonate (1.1 g, 4.98 mmol) in DCM (20 mL) and the reaction mixture was stirred at room temperature for 18 hr. Water (20 mL) was added and the mixture was extracted with DCM (100 mL). The organic layer was passed through a phase separation cartridge and concentrated under reduced pressure. Purification via silica gel column chromatography (50% EtOAC/Petrol 40-60) gave tert-butyl N-[[4-fluoro-1-hydroxy-4-(2-methyl-4-nitro-pyrazol-3-yl)cyclohexyl]methyl]carbamate as a cream foam (858 mg, 56% over three steps). $^1$H NMR (400 MHz, CDCl$_3$) δ 8.07 and 8.06 (2s, 1H), 5.05-4.95 (m, 1H), 4.09 and 4.07 (2s, 3H), 3.21 (d, J=6.3 Hz, 2H), 2.95-2.72 (m, 2H), 2.54 (s, 1H), 1.99-1.87 (m, 2H), 1.85-1.65 (m, 4H), 1.45 (s, 9H).

Intermediate 308 tert-Butyl N-[(4R)-6,6-difluoro-4-methyl-1-(2-methyl-4-nitro-pyrazol-3-yl)azepan-4-yl]carbamate

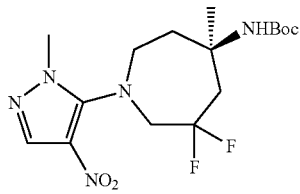 [SMILES: Cn1ncc([N+](=O)[O-])c1N1CC[C@@](C)(NC(=O)OC(C)(C)C)CC(F)(F)C1]

Intermediate 280 was further purified via chiral SFC to give tert-butyl N-[(4R)-6,6-difluoro-4-methyl-1-(2-methyl-4-nitro-pyrazol-3-yl)azepan-4-yl]carbamate (first eluting isomer) (440 mg) ee 100%. LCMS (ES+) m/z 412 (M+23).

Intermediate 309 tert-Butyl N-[(4S)-6,6-difluoro-4-methyl-1-(2-methyl-4-nitro-pyrazol-3-yl)azepan-4-yl]carbamate

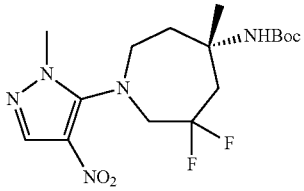 [SMILES: Cn1ncc([N+](=O)[O-])c1N1CC[C@](C)(NC(=O)OC(C)(C)C)CC(F)(F)C1]

Following the procedure of Intermediate 308, further elution gave tert-butyl N-[(4S)-6,6-difluoro-4-methyl-1-(2-methyl-4-nitro-pyrazol-3-yl)azepan-4-yl]carbamate (second eluting isomer) (430 mg) ee 93%. LCMS (ES+) m/z 412 (M+23).

Intermediate 310 tert-Butyl N-[4-[[5-[(5R)-5-(tert-butoxycarbonylamino)-3,3-difluoro-5-methyl-azepan-1-yl]-1-methyl-pyrazol-4-yl]carbamoyl]-2-(2,6-difluorophenyl)thiazol-5-yl]carbamate

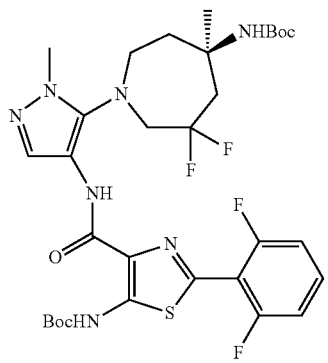 [SMILES: Cn1ncc(NC(=O)c2nc(-c3c(F)cccc3F)sc2NC(=O)OC(C)(C)C)c1N1CC[C@@](C)(NC(=O)OC(C)(C)C)CC(F)(F)C1]

Following the procedure for Intermediate 269 starting from tert-butyl N-[(4R)-6,6-difluoro-4-methyl-1-(2-methyl-4-nitro-pyrazol-3-yl)azepan-4-yl]carbamate gave tert-butyl N-[4-[[5-[(5R)-5-(tert-butoxycarbonylamino)-3,3-difluoro-5-methyl-azepan-1-yl]-1-methyl-pyrazol-4-yl]carbamoyl]-2-(2,6-difluorophenyl)thiazol-5-yl]carbamate as a pale brown solid (210 mg, 57%) ee 98.6%. $^1$H NMR (400 MHz, CDCl$_3$) δ 10.39 (s, 1H), 8.79 (s, 1H), 7.88 (s, 1H), 7.45-7.30 (m, 1H), 7.15-7.00 (m, 2H), 5.12 (br s, 1H), 3.78 (s, 3H), 3.75-3.40 (m, 2H), 3.35-3.10 (m, 2H), 2.70-2.45 (m, 2H), 2.40-2.15 (m, 1H), 1.95-1.70 (m, 1H), 1.55 (s, 9H), 1.46 (s, 3H), 1.33 (s, 9H).

Intermediate 311 tert-Butyl N-[4-[[5-[(5S)-5-(tert-butoxycarbonylamino)-3,3-difluoro-5-methyl-azepan-1-yl]-1-methyl-pyrazol-4-yl]carbamoyl]-2-(2,6-difluorophenyl)thiazol-5-yl]carbamate Following the procedure for Intermediate 269 starting from tert-butyl N-[(4S)-6,6-difluoro-4-methyl-1-(2-methyl-4-nitro-pyrazol-3-yl)azepan-4-yl]carbamate (Intermediate 309) gave a pale brown solid (246 mg). This was further purified via chiral SFC to give tert-butyl N-[4-[[5-[(5S)-5-(tert-butoxycarbonylamino)-3,3-difluoro-5-methyl-azepan-1-yl]-1-methyl-pyrazol-4-yl]carbamoyl]-2-(2,6-difluorophenyl)thiazol-5-yl]carbamate as a pale brown solid (190 mg, 51%) ee 98.5%. $^1$H NMR (400 MHz, CDCl$_3$) δ 10.39 (s, 1H), 8.79 (s, 1H), 7.88 (s, 1H), 7.45-7.30 (m, 1H), 7.15-7.00 (m, 2H), 5.12 (br s, 1H), 3.78 (s, 3H), 3.75-3.40 (m, 2H), 3.35-3.10 (m, 2H), 2.70-2.45 (m, 2H), 2.40-2.15 (m, 1H), 1.95-1.70 (m, 1H), 1.55 (s, 9H), 1.46 (s, 3H), 1.33 (s, 9H).

Intermediate 312

5-(2-Methyl-4-nitro-pyrazol-3-yl)-5-azaspiro[2.6]non-8-ene

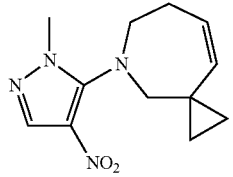

To a solution of zirconocene chloride (20.8 g, 71 mmol) in THF (300 mL) at −78° C. was added slowly ethyl magnesium bromide (1 M in THF, 142 mL, 142 mmol) and the mixture was stirred at −78° C. for 30 min before warming to 0° C. Stirring continued until a red solution was obtained. The mixture was stirred for a further 30 min. tert-Butyl 6-oxo-3, 7-dihydro-2H-azepine-1-carboxylate (15 g, 71 mmol) in THF (100 mL) was added slowly and the mixture was allowed to warm to room temperature and stirred for 3 hr. The solvent was removed under reduced pressure and the residue dissolved in DCM (150 mL). Titanium tetrachloride (8 mL, 71 mmol) was added and the mixture stirred at room temperature for 16 hr. Saturated ammonium chloride solution (100 mL) was slowly added to the reaction mixture, giving a white suspension. The layers were separated and aqueous layer extracted with DCM (3×200 mL). The combined organic layers were washed with saturated aqueous NaHCO$_3$ (200 mL) and brine (200 mL), dried over MgSO$_4$ and concentrated under reduced pressure. Purification via silica gel column chromatography (10-50% Et$_2$O/isohexane) gave the desired Boc protected material. This was dissolved in DCM (50 mL), TFA (10 mL) was added and the mixture stirred at 40° C. for 4 hr. Removal of solvent under reduced pressure gave the amine as the trifluoroacetate salt. This was dissolved in DMSO (50 mL) and DIPEA (6.2 mL, 35 mmol), potassium fluoride (3.1 g, 19.1 mmol) and 5-chloro-1-methyl-4-nitropyrazole (3.0 g, 19.1 mmol) were added. The mixture was heated at 85° C. for 16 hr before cooling to room temperature. The mixture was partitioned between water (50 mL) and EtOAc (50 mL), the aqueous layer was extracted with EtOAc (3×50 mL) and the combined organics were washed with brine (50 mL), separated, dried over MgSO$_4$ and concentrated under reduced pressure. Purification via silica gel column chromatography (10-50% EtOAc/isohexane) gave 5-(2-methyl-4-nitro-pyrazol-3-yl)-5-azaspiro[2.6]non-8-ene as an off-white solid (2.0 g, 56% over three steps). $^1$H NMR (400 MHz, CDCl$_3$) δ 8.00 (s, 1H), 5.69 (dt, J=11.2, 5.4 Hz, 1H), 5.22-5.11 (m, 1H), 3.82 (s, 3H), 3.47-3.38 (m, 2H), 3.18 (s, 2H), 2.55-2.48 (m, 2H), 0.72-0.61 (m, 4H).

Intermediate 313

8-Azido-5-(2-methyl-4-nitro-pyrazol-3-yl)-5-azaspiro[2.6]nonan-9-ol

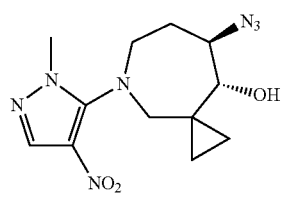 [SMILES: Cn1ncc([N+](=O)[O-])c1N1CC[C@@H](N=[N+]=[N-])[C@H](O)C2(CC2)C1]

To a solution of 5-(2-methyl-4-nitro-pyrazol-3-yl)-5-azaspiro[2.6]non-8-ene (1.0 g, 4.1 mmol) in DCM (25 mL) was added m-CPBA (1.1 g, 4.8 mmol) and the resulting mixture stirred at room temperature for 16 hr. Saturated aqueous NaHCO$_3$ (15 mL) was added and the aqueous layer extracted with DCM (3×20 mL). The combined organic layers were passed through a phase separation cartridge and concentrated under reduced pressure. Purification via silica gel column chromatography (10-50%, EtOAc/isohexane) gave the intermediate epoxide as a yellow solid. This was dissolved in DMSO (30 mL) and acetic acid (3 mL) and sodium azide was added. The mixture was heated at 110° C. for 16 hr behind a blast shield. After cooling to room temperature, the mixture was partitioned between saturated aqueous NaHCO$_3$ (10 mL) and EtOAc (10 mL). The aqueous layer was extracted with EtOAc (3×20 mL) and the combined organic layers were washed with brine (20 mL), separated, dried over MgSO$_4$ and concentrated under reduced pressure. Purification via silica gel column chromatography (10-50%, EtOAc/isohexane) gave 8-azido-5-(2-methyl-4-nitro-pyrazol-3-yl)-5-azaspiro[2.6]nonan-9-ol as a yellow gum (160 mg, 54% over two steps). $^1$H NMR (400 MHz, CDCl$_3$) δ 8.01 (s, 1H), 3.80 (s, 3H), 3.79-3.72 (m, 1H), 3.55 (dd, J=7.4, 2.4 Hz, 1H), 3.51-3.34 (m, 1H), 3.31-3.18 (m, 2H), 2.92 (d, J=13.4 Hz, 1H), 2.33-2.24 (m, 1H), 2.20 (d, J=2.7 Hz, 1H), 2.09-1.98 (m, 1H), 1.00-0.94 (m, 1H), 0.81-0.71 (m, 1H), 0.53-0.44 (m, 2 H).

Intermediate 314

9-Azido-5-(2-methyl-4-nitro-pyrazol-3-yl)-5-azaspiro[2.6]nonan-8-ol

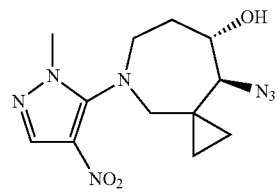

Following the procedure for Intermediate 313 also gave 9-azido-5-(2-methyl-4-nitro-pyrazol-3-yl)-5-azaspiro[2.6]nonan-8-ol as a yellow gum (350 mg, 68% over two steps). $^1$H NMR (400 MHz, CDCl$_3$) δ 8.02 (s, 1H), 3.99-3.92 (m, 1H), 3.79 (s, 3H), 3.53-3.20 (m, 4H), 2.76 (d, J=13.7 Hz, 1H), 2.61 (d, J=5.9 Hz, 1H), 2.35-2.15 (m, 1H), 2.17-1.82 (m, 1H), 0.94-0.73 (m, 2H), 0.61-0.51 (m, 2H).

Intermediate 315

8-Azido-9-methoxy-5-(2-methyl-4-nitro-pyrazol-3-yl)-5-azaspiro[2.6]nonane

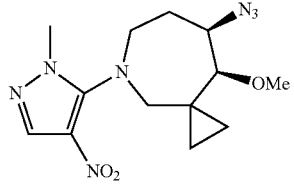 [SMILES: CO[C@@H]1[C@H](N=[N+]=[N-])CCN(c2c([N+](=O)[O-])cnn2C)CC12CC2]

To a solution of 8-azido-5-(2-methyl-4-nitro-pyrazol-3-yl)-5-azaspiro[2.6]nonan-9-ol (200 mg, 0.67 mmol) in DCM (10 mL) was added portionwise Dess-Martin periodinane (340 mg, 0.80 mmol). The reaction mixture was stirred at room temperature for 18 hr. The mixture was diluted with DCM (50 mL), saturated aqueous NaHCO$_3$ (50 mL) added and the mixture extracted with DCM (50 mL). The combined organic layers were washed with brine (20 mL) passed through a phase separation cartridge and concentrated under reduced pressure. Purification via silica gel column chromatography (10-50% EtOAc/isohexane) gave the intermediate ketone. To a solution of this ketone (190 mg, 0.62 mmol) in dry THF (7 mL) under nitrogen cooled to −78° C. was added dropwise a solution of L-selectride (1 M in THF, 0.8 mL, 0.78 mmol) and the reaction mixture was stirred at −78° C. for 2 hr. The mixture was allowed to warm to room temperature and water (10 mL) was added. The mixture was extracted with EtOAc (2×30 mL) and the combined organic layers were washed with brine (20 mL), dried over MgSO$_4$ and concentrated under reduced pressure to give the intermediate alcohol. To a solution of this alcohol (160 mg, 0.52 mmol) in dry DMF (5 mL) cooled to 0° C. was added sodium hydride (60% in mineral oil, 25 mg, 0.62 mmol). After stirring for 15 min, iodomethane (0.05 mL, 0.78 mmol) was added and the reaction mixture was allowed to warm to room temperature and stirred for 18 hr. The mixture was concentrated under reduced pressure and the residue partitioned between water (30 mL) and EtOAc (30 mL). The aqueous layer was extracted with EtOAc (30 mL) and the combined organic layers were washed with brine (20 mL), separated, dried over MgSO$_4$, and concentrated under reduced pressure. Purification via silica gel column chromatography (10-50% EtOAc/isohexane) gave 8-azido-9-methoxy-5-(2-methyl-4-nitro-pyrazol-3-yl)-5-azaspiro[2.6]nonane as an off-white solid (120 mg, 55% over three steps). $^1$H NMR (400 MHz, CDCl$_3$) δ 8.02 (s, 1H), 3.84 (s, 3H), 3.84-3.72 (m, 1H), 3.58 (s, 3H), 3.57-3.47 (m, 2 H), 3.22-3.15 (m, 1H), 2.93 (s, 1H), 2.40-2.28 (m, 1H), 2.24 (d, J=12.5 Hz, 1H), 2.07-1.91 (m, 1H), 0.79-0.72 (m, 1H), 0.67-0.46 (m, 3H).

Intermediate 316

9-Azido-8-methoxy-5-(2-methyl-4-nitro-pyrazol-3-yl)-5-azaspiro[2.6]nonane

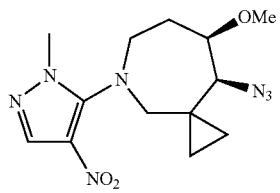 [SMILES: CO[C@@H]1CCN(c2c([N+](=O)[O-])cnn2C)CC2(CC2)[C@@H]1N=[N+]=[N-]]

Following the procedure for Intermediate 315 starting from 9-azido-5-(2-methyl-4-nitro-pyrazol-3-yl)-5-azaspiro[2.6]nonan-8-ol gave 9-azido-8-methoxy-5-(2-methyl-4-nitro-pyrazol-3-yl)-5-azaspiro[2.6]nonane as a yellow gum (170 mg, 62% over three steps). $^1$H NMR (400 MHz, CDCl$_3$) δ 8.02 (s, 1H), 3.90 (d, J=13.4 Hz, 1H), 3.84 (s, 2H), 3.73-3.67 (m, 1H), 3.45-3.36 (m, 1H), 3.41 (s, 3H), 3.28 (s, 1H), 3.21-3.14 (m, 2H), 2.32-2.15 (m, 2H), 2.09-1.99 (m, 1H), 0.82-0.74 (m, 1H), 0.69-0.51 (m, 3H).

Intermediate 317 tert-Butyl N-[9-methoxy-5-(2-methyl-4-nitro-pyrazol-3-yl)-5-azaspiro[2.6]nonan-8-yl]carbamate

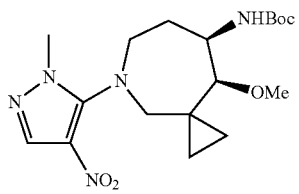 [SMILES: CO[C@@H]1[C@H](NC(=O)OC(C)(C)C)CCN(c2c([N+](=O)[O-])cnn2C)CC12CC2]

A solution of 8-azido-9-methoxy-5-(2-methyl-4-nitro-pyrazol-3-yl)-5-azaspiro[2.6]nonane (120 mg, 0.37 mmol) in THF/water (5 mL/1 mL) was treated with trimethylphosphine (1.0 M in toluene, 1.8 mL, 1.8 mmol) and the reaction mixture was heated at 70° C. behind a blast screen for 4 hr. The reaction was cooled to room temperature and concentrated under reduced pressure. The residue was acidified with 1 M aqueous HCl and washed with EtOAc (2×20 mL). The aqueous layer was basified to pH 14 with aqueous 6 M NaOH and extracted with DCM (2×30 mL). The combined organic layers were passed through a phase separation cartridge and concentrated under reduced pressure to give a light brown gum. To a solution of this gum (80 mg, 0.27 mmol) in dry DCM (5 mL) at 0° C. was added DIPEA (0.1 mL, 0.54 mmol) followed by a solution of di-tert-butyl-dicarbonate (90 mg, 0.41 mmol) in DCM (5 mL). The reaction mixture was allowed to warm to room temperature and stirred for 4 hr. Water (5 mL) was added and the mixture extracted with DCM (2×30 mL). The combined organic layers were washed with brine (10 mL), passed through a phase separation cartridge and concentrated under reduced pressure. Purification via silica gel column chromatography (10-50% EtOAc/isohexane) gave tert-butyl N-[9-methoxy-5-(2-methyl-4-nitro-pyrazol-3-yl)-5-azaspiro[2.6]nonan-8-yl]carbamate as a yellow gum (110 mg, 72% over three steps). $^1$H NMR (400 MHz, CDCl$_3$) δ 8.00 (s, 1H), 5.08 (d, J=8.9 Hz, 1H), 3.97-3.86 (m, 2H), 3.81 (s, 3H), 3.60 (ddd, J=13.6, 10.5, 2.8 Hz, 1H), 3.51 (s, 3H), 3.12-3.04 (m, 1H), 2.74 (s, 1H), 2.16 (d, J=12.6 Hz, 1H), 2.25-1.86 (m, 1H), 1.95-1.85 (m, 1H), 1.45 (s, 9H), 0.77-0.57 (m, 4H).

Intermediate 318 tert-Butyl N-[8-methoxy-5-(2-methyl-4-nitro-pyrazol-3-yl)-5-azaspiro[2.6]nonan-9-yl]carbamate

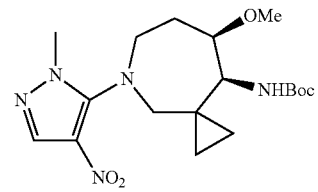 [SMILES: CO[C@@H]1CCN(c2c([N+](=O)[O-])cnn2C)CC2(CC2)[C@@H]1NC(=O)OC(C)(C)C]

Following the procedure for Intermediate 317 starting from 9-azido-8-methoxy-5-(2-methyl-4-nitro-pyrazol-3-yl)-5-azaspiro[2.6]nonane gave tert-butyl N-[8-methoxy-5-(2-methyl-4-nitro-pyrazol-3-yl)-5-azaspiro[2.6]nonan-9-yl]carbamate as a yellow gum (160 mg, 67% over two steps). $^1$H NMR (400 MHz, CDCl$_3$) δ 8.01 (s, 1H), 5.12 (d, J=8.8 Hz, 1 H), 3.82 (s, 3H), 3.68-3.57 (m, 2H), 3.52-3.38 (m, 1H), 3.36 (s, 3H), 3.32 (d, J=12.7 Hz, 1H), 3.21-3.14 (m, 1H), 2.74 (d, J=12.8 Hz, 1H), 2.13-1.88 (m, 2H), 1.47 (s, 9H), 0.91-0.81 (m, 1H), 0.68-0.53 (m, 2H), 0.43-0.36 (m, 1H).

TABLES 1A AND 1B FORMULA I COMPOUNDS 101-529

Example 101

5-Amino-2-(2,6-difluorophenyl)-N-(1-methyl-5-(4-((methylamino)methyl)piperidin-1-yl)-1H-pyrazol-4-yl)thiazole-4-carboxamide 101

A solution of Intermediate 1, tert-butyl methyl((1-(1-methyl-4-nitro-1H-pyrazol-5-yl)piperidin-4-yl)methyl)carbamate (145 mg, 0.41 mmol) in MeOH (40 mL) was passed through the H-Cube® (full H$_2$, 50° C., flow rate: 1 mL/min, 30 mm 10% Pd/C cartridge). The solvent was removed under reduced pressure to afford crude tert-butyl (1-(4-amino-1-methyl-1H-pyrazol-5-yl)piperidin-4-yl)methyl(methyl)carbamate as a red-brown oil (117 mg). To a solution of this amine (115 mg, 0.36 mmol) in DCM (20 mL) was added DIPEA (1.0 mL), PyBOP (0.46 g, 0.89 mmol) and 5-(tert-butoxycarbonylamino)-2-(2,6-difluorophenyl)thiazole-4-carboxylic acid from Example 25 (127 mg, 0.36 mmol) and the mixture was stirred at room temperature for 18 hr. The mixture was diluted with DCM (80 mL) and washed with water (20 mL). The organic layer was separated, dried over $MgSO_4$ and the solvent removed under reduced pressure. Purification via silica gel column chromatography (75% EtOAc/isohexane) gave tert-butyl (1-(4-(5-tert-butoxycarbonylamino-2-(2,6-difluorophenyl)thiazole-4-carboxamido)-1-methyl-1H-pyrazol-5-yl)piperidin-4-yl)methyl(methyl) carbamate as a lilac foam (200 mg). This foam (200 mg, 0.30 mmol) was stirred with HCl in 1,4-dioxane (4 M, 3.8 mL, 15.1 mmol) in MeOH (5 mL) at room temperature for 3 days. The solvents were removed under reduced pressure and the crude residue was re-dissolved in MeOH and loaded onto an SCX column. The column was washed with MeOH and eluted with 7 N ammonia in MeOH to yield 101 as a beige solid (99 mg, 53% over three steps). $^1$H NMR (400 MHz, $d_6$-DMSO) δ 8.75 (s, 1H), 7.59-7.49 (m, 3H), 7.44 (s, 1H), 7.32-7.22 (m, 2H), 6.90 (br s, 1H), 3.63 (s, 3H), 3.14-2.96 (m, 4H), 2.66 (d, J=6.8 Hz, 2H), 2.45 (s, 3H), 1.77 (d, J=12.6 Hz, 2H), 1.78-1.55 (m, 1H), 1.36-1.22 (m, 2H). LCMS (ES+) m/z 462 (M+1).

Example 102

(R)-5-amino-2-(2,6-difluorophenyl)-N-(1-methyl-5-(3-methylpiperazin-1-yl)-1H-pyrazol-4-yl)thiazole-4-carboxamide 102

Step A. tert-Butyl (±)-2-Methyl-4-(1-methyl-4-nitro-1H-pyrazol-5-yl)piperazine-1-carboxylate

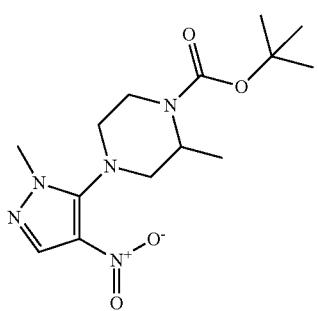 [SMILES: CC1CN(c2c([N+](=O)[O-])cnn2C)CCN1C(=O)OC(C)(C)C]

A mixture of 2-methylpiperazine (1 g, 6.2 mmol), 5-chloro-1-methyl-4-nitro-1H-pyrazole from Example 1 (2.48 g, 12.4 mmol), DIPEA (2.4 g, 18.6 mmol) in EtOH (10 mL) was heated in a microwave oven at 140° C. for 5 hours. The solvent was removed under reduced pressure to give a residue. The residue was purified by silica gel chromatography using MeOH/DCM (10:1) as eluting solvents to afford tert-butyl (±)-2-methyl-4-(1-methyl-4-nitro-1H-pyrazol-5-yl)piperazine-1-carboxylate (1.0 g, 40%) as yellow solid. $^1$H NMR (500 MHz, CDCl$_3$) δ (ppm): 8.03 (s, 1H), 4.38 (s, 1H), 3.99-3.68 (m, 1H), 3.83 (s, 3H), 3.67-3.65 (m, 1H), 3.46-3.41 (m, 1H), 3.31-3.25 (m, 1H), 2.90-2.88 (d, J=9.6 Hz, 1H), 2.71-2.68 (d, J=9.2 Hz, 1H), 1.49 (s, 9H), 1.36-1.34 (d, J=5.2 Hz, 3H).

Step B. tert-Butyl (±)-4-(4-Amino-1-methyl-1H-pyrazol-5-yl)-2-methylpiperazine-1-carboxylate To a solution of tert-butyl (±)-2-methyl-4-(1-methyl-4-nitro-1H-pyrazol-5-yl)piperazine-1-carboxylate (500 mg, 1.54 mmol) in MeOH (20 mL) and H$_2$O (5 mL) was added zinc (845 mg, 13 mmol) and NH$_4$Cl (1.4 g, 26 mmol). The reaction mixture was stirred at ambient temperature for 2 hours and filtered through Celite. The filtrate was concentrated under reduced pressure to give a residue. The residue was purified by silica gel chromatography PE/EtOAc (10/1~1/10) as eluting solvents to give tert-butyl (±)-4-(4-amino-1-methyl-1H-pyrazol-5-yl)-2-methylpiperazine-1-carboxylate (650 mg, ~100%) as red solid. $^1$H NMR (500 MHz, CD$_3$OD) δ (ppm): 7.22 (s, 1H), 4.35-4.33 (m, 1H), 4.12-4.11 (m, 1H), 3.94 (s, 3H), 3.43-3.46 (m, 1H), 3.25-3.30 (m, 2H), 3.01-3.00 (m, 1H), 2.89-2.87 (d, J=12 Hz, 1H), 1.49 (s, 9H), 1.34-1.36 (d, J=5.6 Hz, 3H); MS (ESI) m/z=296 (M+H$^+$).

Step C. tert-Butyl (±)-4-(4-(5-(tert-Butoxycarbonylamino)-2-(2,6-difluorophenyl)thiazole-4-carboxamido)-1-methyl-1H-pyrazol-5-yl)-2-methylpiperazine-1-carboxylate To a solution of tert-butyl (±)-4-(4-amino-1-methyl-1H-pyrazol-5-yl)-2-methylpiperazine-1-carboxylate (400 mg, 2.05 mmol), 5-(tert-butoxycarbonylamino)-2-(2,6-difluorophenyl)thiazole-4-carboxylic acid (630 mg, 2.46 mmol), HATU (0.83 g, 8.19 mmol) in DMF (15 mL) was added TEA (1.5 mL). The reaction mixture was stirred at 25° C. for 20 hours and poured into water (100 mL). The mixture was extracted with EtOAc (50 mL×2). The combined organic layers was washed with water (50 mL×2) and brine (30 mL×2), dried over Na$_2$SO$_4$, filtered, and concentrated under reduced pressure to give a residue. The residue was purified by silica gel chromatography using DCM/MeOH (1:1) as eluting solvents to afford tert-butyl (±)-4-(4-(5-(tert-butoxycarbonylamino)-2-(2,6-difluorophenyl)thiazole-4-carboxamido)-1-methyl-1H-pyrazol-5-yl)-2-methylpiperazine-1-carboxylate (280 mg, 52%) as white solid. $^1$H NMR (500 MHz, CDCl$_3$) δ (ppm): 10.32 (s, 1H), 8.70 (s, 1H), 7.80 (s, 1H), 7.38-7.35 (m, 1H), 7.06-7.03 (m, 2H), 4.34 (s, 1H), 3.94-3.97 (m, 1H), 3.81 (s, 3H), 3.67-3.40 (m, 1H), 3.20-3.25 (m, 2H), 3.04-3.06 (m, 1H), 2.88-2.90 (m, 1H), 1.55 (s, 9H), 1.47 (s, 9H), 1.34-1.36 (d, J=6.4 Hz, 3H); MS (ESI) m/z=434 (M+H$^+$).

Step D. tert-Butyl (R)-4-(4-(5-(tert-Butoxycarbonylamino)-2-(2,6-difluorophenyl)-thiazole-4-carboxamido)-1-methyl-1H-pyrazol-5-yl)-2-methylpiperazine-1-carboxylate and tert-Butyl (S)-4-(4-(5-(tert-Butoxycarbonylamino)-2-(2,6-difluorophenyl)thiazole-4-carboxamido)-1-methyl-1H-pyrazol-5-yl)-2-methylpiperazine-1-carboxylate Chiral separation by using preparative HPLC of tert-butyl (±)-4-(4-(5-(tert-Butoxycarbonylamino)-2-(2,6-difluorophenyl)thiazole-4-carboxamido)-1-methyl-1H-pyrazol-5-yl)-2-methyl-piperazine-1-carboxylate (280 mg) afforded tert-Butyl (S)-4-(4-(5-(tert-Butoxycarbonylamino)-2-(2,6-difluorophenyl)thiazole-4-carboxamido)-1-methyl-1H-pyrazol-5-yl)-2-methylpiperazine-1-carboxylate (80 mg) and tert-Butyl (R)-4-(4-(5-(tert-Butoxycarbonylamino)-2-(2,6-difluorophenyl)thiazole-4-carboxamido)-1-methyl-1H-pyrazol-5-yl)-2-methylpiperazine-1-carboxylate (80 mg).

Step E. A solution of tert-butyl (R)-4-(4-(5-(tert-butoxycarbonylamino)-2-(2,6-difluorophenyl)thiazole-4-carboxamido)-1-methyl-1H-pyrazol-5-yl)-2-methylpiperazine-1-carboxylate (80 mg, 0.126 mmol) in TFA (1 mL) and DCM (4 mL) was stirred at ambient temperature for 3 hours. The pH of the mixture was adjusted to about 8~9 by addition of ammonia and concentrated under reduced pressure to give a residue. The residue was purified by preparative HPLC to afford 102 (40 mg, 73%). $^1$H NMR (500 MHz, CDCl$_3$) δ (ppm): 8.48 (s, 1H), 8.33 (s, 1H), 7.69 (s, 1H), 7.30-7.36 (m, 1H), 7.03-7.07 (m, 2H), 6.14-6.17 (m, 2H), 3.78 (s, 3H), 3.53-3.48 (m, 1H), 2.90-3.34 (m, 6H), 1.32 (d, J=6.5 Hz, 3H); MS (ESI) m/z=434 (M+1$^+$).

Example 103

(S)-5-amino-N-(5-(3-aminoazepan-1-yl)-1-(2,2-difluoroethyl)-1H-pyrazol-4-yl)-2-(2,6-difluorophenyl)thiazole-4-carboxamide 103

Chiral separation by SFC of the racemic mixture gave 103 as a single enantiomer. $^1$H NMR (400 MHz, DMSO) δ 7.77 (s, 1H), 7.60-7.43 (m, 3H), 7.27 (dd, J=14.5, 5.8 Hz, 2H), 6.39 (tt, J=55.3, 4.2 Hz, 1H), 4.54-4.28 (m, 2H), 3.23-3.02 (m, 4H), 3.00-2.90 (m, 2H), 1.85-1.40 (m, 6H). MS (ESI) m/z: 498.2 [M+H$^+$].

Example 104

(R)-5-amino-N-(5-(3-aminoazepan-1-yl)-1-(2,2-difluoroethyl)-1H-pyrazol-4-yl)-2-(2,6-difluorophenyl)thiazole-4-carboxamide 104

Chiral separation by SFC of the racemic mixture gave 104 as a single enantiomer. $^1$H NMR (400 MHz, DMSO) δ 7.78 (s, 1H), 7.60-7.42 (m, 3H), 7.34-7.21 (m, 2H), 6.39 (tt, J=55.3, 4.1 Hz, 1H), 4.54-4.29 (m, 2H), 3.25-3.02 (m, 4H), 3.00-2.90 (m, 2H), 1.87-1.36 (m, 8H). MS (ESI) m/z: 498.2 [M+H$^+$].

Example 105

5-Amino-N-(5-(6,6-difluoro-1,4-diazepan-1-yl)-1-methyl-1H-pyrazol-4-yl)-2-(2-fluoro-5-methylphenyl)thiazole-4-carboxamide 105

A mixture of Intermediate 3, tert-butyl 4-(4-(2-bromo-5-(tert-butoxycarbonylamino)thiazole-4-carboxamido)-1-methyl-1H-pyrazol-5-yl)-6,6-difluoro-1,4-diazepane-1-carboxylate (283 mg, 0.44 mmol), Na$_2$CO$_3$ (93 mg, 0.88 mmol) and 2-fluoro-5-methylphenylboronic acid (95 mg, 0.62 mmol) in DME (4.9 mL) and water (1.6 mL) was degassed by gently bubbling nitrogen through the mixture for 10 min. [1,1'-Bis(diphenylphosphino)ferrocene]dichloro-palladium (II) (36 mg, 0.04 mmol) was then added and the mixture degassed for a further 10 min before being heated in a microwave at 120° C. for 1 hr. The solvents were removed under reduced pressure and the residue dissolved in DCM (50 mL) and washed with water (2×20 mL). The organic layer was separated, dried over MgSO$_4$ and the solvent removed under reduced pressure. The residue was purified via silica gel column chromatography (0-80% EtOAc/isohexane) to yield tert-butyl 4-(4-(5-tert-butoxycarbonylamino-2-(2-fluoro-5-methylphenyl)thiazole-4-carboxamido)-1-methyl-1H-pyrazol-5-yl)-6,6-difluoro-1,4-diazepane-1-carboxylate (179 mg) and tert-butyl 4-(4-(5-amino-2-(2-fluoro-5-methylphenyl)thiazole-4-carboxamido)-1-methyl-1H-pyrazol-5-yl)-6,6-difluoro-1,4-diazepane-1-carboxylate (50 mg). The isolated intermediates were combined and suspended in MeOH (2 mL) and to this was added a solution of HCl in 1,4-dioxane (4 M, 1.7 mL, 6.75 mmol) and stirred at room temperature for 16 hr. The solvent was removed under reduced pressure and the residue dissolved in EtOAc (50 mL) and washed with 1 M NaOH solution (20 mL). The residue was purified via silica gel column chromatography (0-10% MeOH/DCM) to yield 105 as a beige solid (59 mg, 30% over two steps). $^1$H NMR (400 MHz, CDCl$_3$) δ 8.98 (s, 1H), 7.90 (dd, J=7.0, 2.5 Hz, 1H), 7.80 (s, 1H), 7.16-7.11 (m, 1H), 7.09-7.01 (m, 1H), 6.09 (s, 2H), 3.77 (s, 3H), 3.63 (t, J=13.5 Hz, 2H), 3.46-3.29 (m, 4H), 3.06 (t, J=5.5 Hz, 2H), 2.39 (s, 3H), 1.95 (s, 1H). LCMS (ES+) m/z 466 (M+1).

Example 106

5-Amino-N-(5-(6,6-difluoro-1,4-diazepan-1-yl)-1-methyl-1H-pyrazol-4-yl)-2-(2,5-difluorophenyl)thiazole-4-carboxamide 106

Following the procedure for Example 105, reacting tert-butyl 4-(4-(2-bromo-5-(tert-butoxycarbonylamino)thiazole-4-carboxamido)-1-methyl-1H-pyrazol-5-yl)-6,6-difluoro-1,4-diazepane-1-carboxylate and 2,5-difluorophenylboronic acid gave 106 as a beige solid (57 mg, 28% over two steps). $^1$H NMR (400 MHz, CDCl$_3$) δ 8.90 (s, 1H), 7.88-7.81 (m, 2H), 7.18-7.10 (m, 1H), 7.06-6.99 (m, 1H), 6.16 (s, 2H), 3.78 (s, 3H), 3.70-3.56 (m, 2H), 3.44 (t, J=14.0 Hz, 2H), 3.35 (t, J=5.5 Hz, 2H), 3.11-3.05 (m, 2H), 1.95 (s, 1H). LCMS (ES+) m/z 470 (M+1).

Example 107

(R)-5-Amino-N-(1-(2,2-difluoroethyl)-5-(4-(methylamino)azepan-1-yl)-1H-pyrazol-4-yl)-2-(2,6-difluorophenyl)thiazole-4-carboxamide 107

To a solution of (R)—N-(1-(4-amino-1-(2,2-difluoroethyl)-1H-pyrazol-5-yl)azepan-4-yl)-2,2,2-trifluoro-N-methylacetamide (100 mg, 0.28 mmol) in DCM (10 mL) was added DIPEA (0.5 mL, 2.87 mmol), PyBOP (293 mg, 0.56 mmol) and 5-(tert-butoxycarbonylamino)-2-cyclopropylthiazole-4-carboxylic acid (125 mg, 0.35 mmol) and the mixture was stirred at room temperature for 20 hr. The mixture was diluted with DCM (50 mL) and washed with water (10 mL). The organic layer was separated by passing through a phase separation cartridge and the solvent removed under reduced pressure. Purification via silica gel column chromatography (0-100% EtOAc/isohexane) gave (R)-tert-butyl 4-(1-(2,2-difluoroethyl)-5-(4-(2,2,2-trifluoro-N-methylacetamido)azepan-1-yl)-1H-pyrazol-4-ylcarbamoyl)-2-(2,6-difluorophenyl)thiazol-5-ylcarbamate as a pale yellow solid (172 mg). This gum (170 mg, 0.24 mmol) was stirred in HCl in 1,4-dioxane (4 M, 5 mL) and MeOH (5 mL) at 50° C. for 4 hr. The solvents were removed under reduced pressure and the residue purified by preparative HPLC to afford 107 as the mono formate salt as a white solid (62 mg, 41% over two steps). $^1$H NMR (400 MHz, d$_4$-MeOD) δ 8.56 (s, 1H), 7.72 (s, 1H), 7.49 (tt, J=8.5, 6.2 Hz, 1H), 7.20-7.12 (m, 2H), 6.24 (tt, J=55.5, 4.2 Hz, 1H), 4.48 (td, J=14.0, 4.2 Hz, 2H), 3.40-3.20 (m, 5H), 2.68 (s, 3H), 2.28-1.74 (m, 6H). LCMS (ES+) m/z 512 (M+1).

Example 108

(R)-5-Amino-N-(1-(2,2-difluoroethyl)-5-(4-(methylamino)azepan-1-yl)-1H-pyrazol-4-yl)-2-(2,5-difluorophenyl)thiazole-4-carboxamide 108

A mixture of (R)-tert-butyl 2-bromo-4-(1-(2,2-difluoroethyl)-5-(4-(2,2,2-trifluoro-N-methylacetamido)azepan-1-yl)-

1H-pyrazol-4-ylcarbamoyl)thiazol-5-ylcarbamate (200 mg, 0.29 mmol), Na$_2$CO$_3$ (62 mg, 0.59 mmol) and 2,5-difluorobenzeneboronic acid (66 mg, 0.41 mmol) in DME (3 mL) and water (1 mL) was degassed by gently bubbling nitrogen through the mixture for 5 min. [1,1'-Bis(diphenylphosphino)ferrocene]dichloro-palladium(II) (30 mg, 0.037 mmol) was then added and the mixture heated in a microwave at 120° C. for 60 min. The solvents were removed under reduced pressure and the residue dissolved in a solution of HCl in 1,4-dioxane (4 M, 5 mL) and MeOH (5 mL) and stirred at 70° C. for 48 hr. The solvent was removed under reduced pressure and the residue dissolved in MeOH/DCM and passed through an SCX cartridge washing with DCM and MeOH and eluting with 1 N ammonia in MeOH. The solvent was removed under reduced pressure and the residue purified by preparative HPLC to yield 108 as the mono formate salt as a pale brown solid (21 mg, 14% over two steps). $^1$H NMR (400 MHz, d$_4$-MeOD) δ 8.53 (s, 1H), 8.15-7.95 (m, 1H), 7.58 (s, 1H), 7.35-7.05 (m, 2H), 6.25 (tt, J=55.6, 4.1 Hz, 1H), 4.54-4.43 (m, 2H), 3.43-3.22 (m, 5H), 2.68 (s, 3H), 2.28-1.74 (m, 6H). LCMS (ES+) m/z 512 (M+1).

Example 109

(R)-5-Amino-N-(1-(2,2-difluoroethyl)-5-(4-(methylamino)azepan-1-yl)-1H-pyrazol-4-yl)-2-(2-fluoro-5-methylphenyl)thiazole-4-carboxamide 109

Following the procedure for Example 108, reacting (R)-tert-butyl 2-bromo-4-(1-(2,2-difluoroethyl)-5-(4-(2,2,2-trifluoro-N-methylacetamido)azepan-1-yl)-1H-pyrazol-4-ylcarbamoyl)thiazol-5-ylcarbamate (200 mg, 0.29 mmol) and 2-fluoro-5-methylbenzeneboronic acid (63 mg, 0.41 mmol) gave 109 as the mono formate salt as a pale brown solid (67 mg, 45% over two steps). $^1$H NMR (400 MHz, d$_4$-MeOD) δ 8.56 (s, 1H), 8.07 (dd, J=7.3, 2.2 Hz, 1H), 7.61 (s, 1H), 7.26-7.20 (m, 1H), 7.12 (dd, J=11.4, 8.4 Hz, 1H), 6.25 (tt, J=55.6, 4.2 Hz, 1H), 4.48 (td, J=13.9, 4.2 Hz, 2H), 3.41-3.33 (m, 3H), 3.30-3.13 (m, 2H), 2.58 (s, 3H), 2.40 (s, 3H), 2.23-1.72 (m, 6H). LCMS (ES+) m/z 508 (M+1).

Example 110

5-Amino-N-(1-(2,2-difluoroethyl)-5-(4-hydroxyazepan-1-yl)-1H-pyrazol-4-yl)-2-(2,6-difluorophenyl)thiazole-4-carboxamide 110

To a solution of 1-(4-amino-1-(2,2-difluoroethyl)-1H-pyrazol-5-yl)azepan-4-ol (100 mg, 0.39 mmol) in DCM (20 mL) was added DIPEA (0.5 mL, 2.87 mmol), PyBOP (300 mg, 0.58 mmol) and 5-(tert-butoxycarbonylamino)-2-cyclopropylthiazole-4-carboxylic acid (164 mg, 0.46 mmol) and the mixture was stirred at room temperature for 18 hr. The mixture was diluted with DCM (100 mL) and washed with water (20 mL). The organic layer was separated by passing through a phase separation cartridge and the solvent was removed under reduced pressure. Purification via silica gel column chromatography (0-100% EtOAc/isohexane) gave tert-butyl 4-(1-(2,2-difluoroethyl)-5-(4-hydroxyazepan-1-yl)-1H-pyrazol-4-ylcarbamoyl)-2-(2,6-difluorophenyl)thiazol-5-ylcarbamate as a colorless solid (145 mg). This solid (145 mg, 0.24 mmol) was stirred in HCl in 1,4-dioxane (4 M, 5 mL) at room temperature for 20 hr. The solvents were removed under reduced pressure and the residue purified by preparative HPLC to afford 110 as a cream solid (80 mg, 44% over two steps). $^1$H NMR (400 MHz, d$_4$-MeOD) δ 7.81 (s, 1H), 7.46 (tt, J=8.5, 6.2 Hz, 1H), 7.19-7.11 (m, 2H), 6.22 (tt, J=55.6, 4.2 Hz, 1H), 4.45 (td, J=13.9, 4.2 Hz, 2H), 4.01-3.93 (m, 1H), 3.32-3.15 (m, 5H), 2.10-1.90 (m, 3H), 1.87-1.65 (m, 3H). LCMS (ES+) m/z 499 (M+1).

Example 111

5-Amino-N-(1-(2,2-difluoroethyl)-5-(4-hydroxyazepan-1-yl)-1H-pyrazol-4-yl)-2-(2-fluoro-5-methylphenyl)thiazole-4-carboxamide 111

Following the procedure for Example 105 starting with tert-butyl 2-bromo-4-(1-(2,2-difluoroethyl)-5-(4-hydroxyazepan-1-yl)-1H-pyrazol-4-ylcarbamoyl)thiazol-5-ylcarbamate (0.13 g, 0.23 mmol) and 2-fluoro-5-methylbenzeneboronic acid (53 mg, 0.35 mmol) gave 111 as a black solid (56 mg, 50% over two steps). $^1$H NMR (400 MHz, d$_6$-DMSO) δ 8.93 (s, 1H), 8.08 (d, J=7.4 Hz, 1H), 7.66 (s, 1H), 7.42 (s, 2H), 7.24 (d, J=8.7 Hz, 2H), 6.39 (tt, J=55.3, 4.2 Hz, 1H), 4.55 (d, J=3.8 Hz, 1H), 4.42 (td, J=14.5, 4.2 Hz, 2H), 3.86-3.80 (m, 1H), 3.29-3.03 (m, 4H), 2.37 (s, 3H), 1.94-1.84 (m, 3H), 1.77-1.55 (m, 3H). LCMS (ES+) m/z 495 (M+1).

Example 112

(R)-5-Amino-2-(2,6-difluorophenyl)-N-(1-methyl-5-(2-methylpiperazin-1-yl)-1H-pyrazol-4-yl)thiazole-4-carboxamide 112

A solution of PyBOP (313 mg, 0.60 mmol) and 5-(tert-butoxycarbonylamino)-2-(2,6-difluorophenyl)thiazole-4-carboxylic acid from Example 25 (153 mg, 0.43 mmol) in DCM (10 mL) was stirred at room temperature for 30 min. A solution of (R)-tert-butyl 4-(4-amino-1-methyl-1H-pyrazol-5-yl)-3-methylpiperazine-1-carboxylate (133 mg, 0.45 mmol) and DIPEA (0.12 mL, 0.68 mmol) in DCM (10 mL) were added and the mixture stirred at room temperature for 16 hr. The mixture was diluted with DCM (50 mL) and washed with water (20 mL). The organic layer was separated, passed through a phase separation cartridge and concentrated under reduced pressure. The isolated intermediate was re-dissolved in DCM (6 mL) and TFA (2 mL) added. The mixture was stirred at room temperature for 4 hr. The mixture was concentrated under reduced pressure and the residue re-dissolved in DCM (50 mL) and washed with saturated aqueous NaHCO$_3$ (2×10 mL). The organic layer was separated, passed through a phase separation cartridge and concentrated under reduced pressure. Purification by preparative HPLC gave 112 as a white solid (41 mg, 22% over two steps). $^1$H NMR (400 MHz, CDCl$_3$) δ 8.66 (s, 1H), 7.92 (s, 1H), 7.38-7.25 (m, 1H), 7.03 (t, J=9.0 Hz, 2H), 6.20 (s, 2H), 3.77 (s, 3H), 3.27-3.15 (m, 2H), 3.10-2.93 (m, 4H), 2.59 (dd, J=12.5, 9.5 Hz, 1H), 0.88 (d, J=6.3 Hz, 3H). Alkyl NH not observed. LCMS (ES+) m/z 434 (M+1).

Example 113

(S)-5-Amino-2-(2,6-difluorophenyl)-N-(5-(2-ethylpiperazin-1-yl)-1-methyl-1H-pyrazol-4-yl)thiazole-4-carboxamide 113

Following the procedure for Example 112, reacting (S)-tert-butyl 4-(4-amino-1-methyl-1H-pyrazol-5-yl)-3-ethylpiperazine-1-carboxylate and 5-(tert-butoxycarbonylamino)-2-(2,6-difluorophenyl)thiazole-4-carboxylic acid from Example 25 gave 113 as a white solid (27 mg, 19% over two steps). $^1$H NMR (400 MHz, CDCl$_3$) δ 8.68 (s, 1H), 7.91 (s, 1H), 7.31 (t, J=7.7 Hz, 1H), 7.03 (t, J=9.2 Hz, 2H), 6.20 (s, 2H), 3.77 (s, 3H), 3.24-3.14 (m, 2H), 3.12-2.93 (m, 4H), 2.60 (t, J=10.8 Hz, 1H), 1.48-1.28 (m, 1H), 1.28-1.16 (m, 1H), 0.79 (t, J=7.6 Hz, 3H). Alkyl NH not observed. LCMS (ES+) m/z 448 (M+1).

Example 114

(R)-5-Amino-2-(2,6-difluorophenyl)-N-(5-(2-ethylpiperazin-1-yl)-1-methyl-1H-pyrazol-4-yl)thiazole-4-carboxamide 114

Following the procedure for Example 112, reacting (R)-tert-butyl 4-(4-amino-1-methyl-1H-pyrazol-5-yl)-3-ethylpiperazine-1-carboxylate and 5-(tert-butoxycarbonylamino)-2-(2,6-difluorophenyl)thiazole-4-carboxylic acid from Example 25 gave 114 as a white solid (30 mg, 21% over two steps). $^1$H NMR (400 MHz, CDCl$_3$) δ 8.68 (s, 1H), 7.91 (s, 1H), 7.36-7.27 (m, 1H), 7.02 (t, J=8.9 Hz, 2H), 6.24 (s, 2H), 3.76 (s, 3H), 3.25-3.15 (m, 2H), 3.11-2.90 (m, 4H), 2.58 (t, J=5.5 Hz, 1H), 1.41-1.31 (m, 1H), 1.28-1.14 (m, 1H), 0.79 (t, J=7.5 Hz, 3H). Alkyl NH not observed. LCMS (ES+) m/z 448 (M+1).

Example 115

(R)-5-amino-N-(5-(4-aminoazepan-1-yl)-1-methyl-1H-pyrazol-4-yl)-2-(3-cyclopropyl-2,6-difluorophenyl)thiazole-4-carboxamide 115

Step A. tert-butyl 2-(5-cyclopropyl-2-fluorophenyl)-4-(1-methyl-5-(4-(benzyloxycarbonylamino)azepan-1-yl)-1H-pyrazol-4-ylcarbamoyl)thiazol-5-ylcarbamate

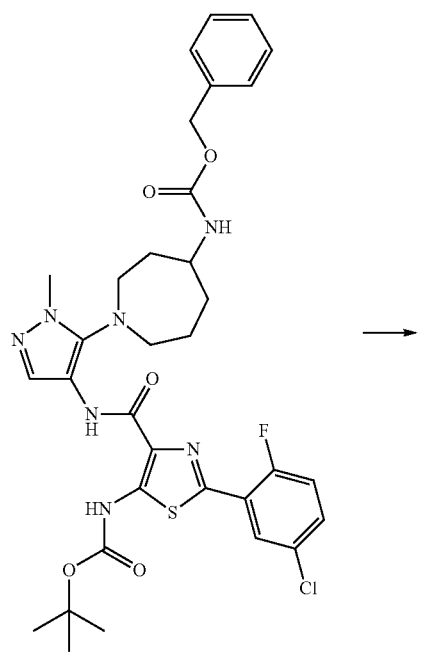

→

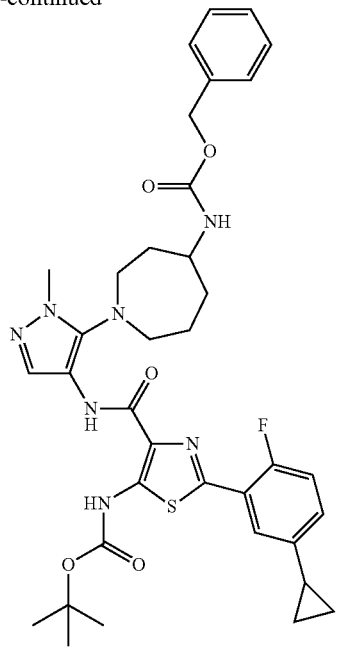

tert-butyl 2-(5-chloro-2-fluorophenyl)-4-(1-methyl-5-(4-(benzyloxycarbonylamino)azepan-1-yl)-1H-pyrazol-4-ylcarbamoyl)thiazol-5-ylcarbamate (309 mg, 0.44 mmol), potassium cyclopropyltrifluoroborate (98 mg, 0.66 mmol), palladium acetate (20.0 mg, 0.088 mmol), butyl-di-1-adamantylphosphine (50.1 mg, 0.133 mmol) and cesium carbonate (437 mg, 1.33 mmol) were charged in a 40 mL reaction vial and vacuum purged with nitrogen three times. Toluene (10.8 mL) and water (1.2 mL) were added and the mixture was heated at 105° C. for four days, monitoring with LCMS. The reaction was filtered through Celite and washed thoroughly with methanol. The filtrate was concentrated under reduced pressure and the residue was purified via flash chromatography, eluted with 0 to 100% ethyl acetate in heptane to give tert-butyl 2-(5-cyclopropyl-2-fluorophenyl)-4-(1-methyl-5-(4-(benzyloxycarbonylamino)azepan-1-yl)-1H-pyrazol-4-ylcarbamoyl)thiazol-5-ylcarbamate (192 mg, 62%).

Step B. The Cbz and Boc groups were deprotected from tert-butyl 2-(5-cyclopropyl-2-fluorophenyl)-4-(1-methyl-5-(4-(benzyloxycarbonylamino)azepan-1-yl)-1H-pyrazol-4-ylcarbamoyl)thiazol-5-ylcarbamate to give 115

$^1$H NMR (400 MHz, DMSO) δ 8.83 (br, 1H), 7.59 (s, 1H), 7.48 (br, 2H), 7.20-7.05 (m, 2H), 3.65 (d, J=4.6 Hz, 3H), 3.18-3.04 (m, 4H), 3.3.05-2.95 (m, 1H), 2.1-2.02 (m, 1H), 1.85-1.75 (m, 3H), 1.68-1.43 (m, 3H), 0.98 (dt, J=8.4, 3.1 Hz, 2H), 0.79-0.68 (m, 2H). MS (ESI) m/z: 488.2 [M+H$^+$]

Example 116

(R)-5-amino-N-(5-(4-aminoazepan-1-yl)-1-methyl-1H-pyrazol-4-yl)-2-(2,6-difluoro-3-methylphenyl)thiazole-4-carboxamide 116

Compound 116 was prepared according to the procedures described in Example 115. $^1$H NMR (400 MHz, DMSO) δ 8.81 (s, 1H), 7.58 (s, 1H), 7.47 (s, 2H), 7.40 (dd, J=15.0, 8.5

Hz, 1H), 7.17 (t, J=9.3 Hz, 1H), 3.64 (s, 3H), 3.19-2.93 (m, 5H), 2.27 (s, 3H), 1.93-1.72 (m, 3H), 1.67-1.43 (m, 3H). MS (ESI) m/z: 462.2 [M+H$^+$].

Example 117

(S)-5-Amino-2-(2,6-difluorophenyl)-N-(1-methyl-5-(3-methylpiperazin-1-yl)-1H-pyrazol-4-yl)thiazole-4-carboxamide 117

Following the procedure for Example 102, (S)-4-(4-(5-(tert-butoxycarbonylamino)-2-(2,6-difluorophenyl)thiazole-4-carboxamido)-1-methyl-1H-pyrazol-5-yl)-2-methylpiperazine-1-carboxylate was reacted to give 117 as a white solid (40 mg, 73%). $^1$H NMR (500 MHz, DMSO-d$_6$) δ (ppm): 8.81 (s, 1H), 8.17 (s, 1H), 7.51-7.57 (m, 3H), 7.36 (s, 1H), 7.25-7.29 (m, 2H), 3.65 (s, 3H), 3.17-3.19 (m, 3H), 2.91-3.14 (m, 4H), 1.10 (d, J=5.2 Hz, 3H); MS (ESI) m/z=434 (M+1$^+$).

Example 118

5-Amino-N-(1-(2,2-difluoroethyl)-5-(4-hydroxyazepan-1-yl)-1H-pyrazol-4-yl)-2-(2,5-difluorophenyl)thiazole-4-carboxamide 118

Following the procedure for Example 105, tert-butyl 2-bromo-4-(1-(2,2-difluoroethyl)-5-(4-hydroxyazepan-1-yl)-1H-pyrazol-4-ylcarbamoyl)thiazol-5-ylcarbamate (130 mg, 0.23 mmol) and 2,5-difluorobenzeneboronic acid (55 mg, 0.35 mmol) were reacted to give 118 as a dark green solid (66 mg, 57% over two steps). $^1$H NMR (400 MHz, d$_4$-MeOD) δ 8.10-8.00 (m, 1H), 7.68 (s, 1H), 7.30-7.20 (m, 1H), 7.19-7.11 (m, 1H), 6.24 (tt, J=55.6, 4.2 Hz, 1H), 4.51-4.40 (m, 2H), 4.01-3.92 (m, 1H), 3.45-3.30 (m, 2H), 3.31-3.16 (m, 3H), 2.13-1.91 (m, 2H), 1.90-1.67 (m, 2H). LCMS (ES+) m/z 499 (M+1).

Example 119

(S)-5-Amino-N-(1-(2,2-difluoroethyl)-5-(4-(methylamino)azepan-1-yl)-1H-pyrazol-4-yl)-2-(2-fluoro-5-methylphenyl)thiazole-4-carboxamide 119

Following the procedure for Example 108, (R)-tert-butyl 2-bromo-4-(1-(2,2-difluoroethyl)-5-(4-(2,2,2-trifluoro-N-methylacetamido)azepan-1-yl)-1H-pyrazol-4-ylcarbamoyl)thiazol-5-ylcarbamate (80 mg, 0.12 mmol) and 2-fluoro-5-methylbenzeneboronic acid (30 mg, 0.20 mmol) were reacted to give 119 as the mono formate salt as a pale pink solid (11 mg, 19% over two steps). $^1$H NMR (400 MHz, d$_4$-MeOD) δ 8.56 (s, 1H), 8.08 (dd, J=7.3, 2.2 Hz, 1H), 7.60 (s, 1H), 7.26-7.20 (m, 1H), 7.12 (dd, J=11.4, 8.4 Hz, 1H), 6.41-6.08 (m, 1H), 4.54-4.43 (m, 2H), 3.40-3.33 (m, 3H), 3.32-3.24 (m, 2H), 2.64 (s, 3H), 2.41 (s, 3H), 2.33-1.94 (m, 3H), 1.91-1.76 (m, 3H). LCMS (ES+) m/z 508 (M+1).

Example 120

5-Amino-N-(5-(4-Amino-3-fluoroazepan-1-yl)-1-methyl-1H-pyrazol-4-yl)-2-(2,6-difluorophenyl)thiazole-4-carboxamide 120

To a solution of Intermediate 17, 2,2,2-trifluoro-N-(3-fluoro-1-(1-methyl-4-nitro-1H-pyrazol-5-yl)azepan-4-yl)acetamide (70 mg, 0.20 mmol) and ammonium formate (101 mg, 1.60 mmol) in MeOH (5 mL) under nitrogen was added 10% palladium on carbon (21 mg, 0.20 mmol). The mixture was heated at 70° C. for 3 hr before being cooled, filtered and concentrated under reduced pressure. The residue was partitioned between water (10 mL) and DCM (50 mL). The organic layer was separated, passed through a phase separation cartridge and concentrated under reduced pressure to give N-(1-(4-amino-1-methyl-1H-pyrazol-5-yl)-3-fluoroazepan-4-yl)-2,2,2-trifluoroacetamide as a red gum (64 mg). A solution of PyBOP (146 mg, 0.28 mmol) and 5-(tert-butoxycarbonylamino)-2-(2,6-difluorophenyl)thiazole-4-carboxylic acid from Example 25 (78 mg, 0.22 mmol) in DCM (3 mL) was stirred at room temperature for 30 min. A solution of N-(1-(4-amino-1-methyl-1H-pyrazol-5-yl)-3-fluoroazepan-4-yl)-2,2,2-trifluoroacetamide (65 mg, 0.20 mmol) and DIPEA (56 μL, 0.32 mmol) in DCM (2 mL) was added and the mixture was stirred at room temperature for 30 hr. Additional DCM (50 mL) was added and the mixture washed with water (20 mL). The organic layer was passed through a phase separation cartridge and concentrated under reduced pressure. Purification via silica gel column chromatography (0-100% Et$_2$O/DCM) gave tert-butyl 2-(2,6-difluorophenyl)-4-(5-(3-fluoro-4-(2,2,2-trifluoroacetamido)azepan-1-yl)-1-methyl-1H-pyrazol-4-ylcarbamoyl)thiazol-5-ylcarbamate as a racemic mixture of four diastereoisomers in the form of a white solid (82 mg). This solid was re-dissolved in a mixture of DCM (12 mL) and TFA (2 mL) and the mixture was stirred at room temperature for 4 hr. The solvent was removed under reduced pressure. The residue was then re-dissolved in 7 N ammonia in MeOH (20 mL) and heated at 55° C. for 24 hr. The solvent was removed under reduced pressure and purification via silica gel column chromatography (0-5% 7 N ammonia in MeOH/DCM) gave two separate pairs of enantiomers of tert-butyl difluorophenyl)-4-(5-(3-fluoro-4-(2,2,2-trifluoroacetamido)azepan-1-yl)-1-methyl-1H-pyrazol-4-ylcarbamoyl)thiazol-5-ylcarbamate. One pair of enantiomers 120 was obtained as a white solid (41 mg). $^1$H NMR (400 MHz, d$_4$-MeOD) δ 7.60 (s, 1H), 7.53-7.43 (m, 1H), 7.15 (t, J=8.8 Hz, 2H), 4.48-4.30 (m, 1H), 3.83-3.72 (m, 3H), 3.57 (d, J=4.4 Hz, 1H), 3.59-3.45 (m, 1H), 3.37-3.29 (m, 2H), 3.14 (td, J=11.4, 5.2 Hz, 1H), 1.95-1.84 (m, 3H), 1.82-1.71 (m, 1H). LCMS (ES+) m/z 466 (M+1).

Example 121

5-Amino-N-(5-(5-amino-3,3-difluoroazepan-1-yl)-1-methyl-1H-pyrazol-4-yl)-2-(2,6-difluorophenyl)thiazole-4-carboxamide 121

Following the procedure for Example 101, Intermediate 19, tert-butyl 6,6-difluoro-1-(1-methyl-4-nitro-1H-pyrazol-5-yl)azepan-4-ylcarbamate gave after dissolving in 5% MeOH/DCM (350 mL), washing with saturated NaHCO$_3$ (50 mL) and water (4×50 mL) and removal of the solvent under reduced pressure, 121 as a beige solid (1.1 g, 34% over 3 steps). $^1$H NMR (400 MHz, d$_6$-DMSO) δ 8.83 (s, 1H), 7.57-7.47 (m, 4H), 7.31-7.22 (m, 2H), 3.78-3.45 (m, 4H), 3.45-3.02 (m, 3H), 2.25-2.06 (m, 2H), 1.92-1.55 (m, 5H). LCMS (ES+) m/z 484 (M+1).

Example 122

5-amino-N-(5-((3S,5S)-5-amino-3-fluoroazepan-1-yl)-1-methyl-1H-pyrazol-4-yl)-2-(2,6-difluorophenyl)thiazole-4-carboxamide 122

Following the procedure for Example 101, Intermediate 20, tert-butyl 6-fluoro-1-(1-methyl-4-nitro-1H-pyrazol-5-yl)azepan-4-ylcarbamate and 5-(tert-butoxycarbonylamino)-2-

(2,6-difluorophenyl)thiazole-4-carboxylic acid from Example 25 gave, after silica gel column chromatography (0-10% MeOH/DCM, 1% 7 N ammonia in MeOH), a white solid (93 mg, 7% over three steps). Compound 122 was obtained as a single enantiomer from SFC chiral separation of the racemic mixture. $^1$H NMR (400 MHz, CDCl$_3$) δ 8.51 (s, 1H), 7.88 (s, 1H), 7.38-7.28 (m, 2H), 7.08-6.98 (m, 3H), 6.18-6.07 (m, 2H), 4.83-4.66 (m, 1H), 4.30-4.21 (m, 1H), 4.16-4.09 (m, 1H), 3.74 (s, 3H), 3.40-3.16 (m, 3H), 3.11 (m, 1H), 2.98-2.89 (m, 1H), 1.95-1.76 (m, 2H). LCMS (ES+) m/z 466 (M+1).

Example 123

(S)-5-Amino-2-(2,6-difluorophenyl)-N-(1-methyl-5-(2-methylpiperazin-1-yl)-1H-pyrazol-4-yl)thiazole-4-carboxamide 123

Following the procedure for Example 112, starting with (S)-tert-butyl 4-(4-amino-1-methyl-1H-pyrazol-5-yl)-3- and 5-(tert-butoxycarbonylamino)-2-(2,6-difluorophenyl)-thiazole-4-carboxylic acid gave 123 as a white solid (61 mg, 32% over two steps). $^1$H NMR (400 MHz, CDCl$_3$) δ 8.66 (s, 1H), 7.92 (s, 1H), 7.34-7.27 (m, 1H), 7.03 (t, J=8.8 Hz, 2H), 6.11 (s, 2H), 3.77 (s, 3H), 3.28-3.16 (m, 2H), 3.08-2.93 (m, 4H), 2.59 (dd, J=12.4, 9.5 Hz, 1H), 0.88 (d, J=6.3 Hz, 3H). Alkyl NH not observed. LCMS (ES+) m/z 434 (M+1).

Example 124

5-Amino-2-(2,6-difluorophenyl)-N-(1-methyl-5-(2,8-diazaspiro[4.5]decan-8-yl)-1H-pyrazol-4-yl)thiazole-4-carboxamide 124

Following the procedure for Example 101, starting with tert-butyl 8-(1-methyl-4-nitro-1H-pyrazol-5-yl)-2,8-diazaspiro[4.5]decane-2-carboxylate gave 124 as a beige solid (140 mg, 47% over 3 steps). $^1$H NMR (400 MHz, d$_6$-DMSO) $^1$H NMR δ 8.85 (br s, 1H), 8.81 (s, 1H), 7.61-7.45 (m, 4H), 7.29 (t, J=8.8 Hz, 2H), 3.64 (s, 3H), 3.22 (t, J=7.5 Hz, 2H), 3.14-2.96 (m, 6H), 1.81 (t, J=7.5 Hz, 2H), 1.73-1.60 (m, 4H). LCMS (ES+) m/z 474 (M+1).

Example 125

5-Amino-N-(5-(4-amino-3-fluoroazepan-1-yl)-1-methyl-1H-pyrazol-4-yl)-2-(2,6-difluorophenyl)thiazole-4-carboxamide 125

Following the procedure for Example 121, also gave one pair of enantiomers 125 as an off-white solid (37 mg). $^1$H NMR (400 MHz, d$_4$-MeOD) δ 7.73 (s, 1H), 7.53-7.41 (m, 1H), 7.14 (t, J=8.8 Hz, 2H), 4.78-4.56 (m, 1H), 3.75 (s, 3H), 3.55 (t, J=15.3 Hz, 1H), 3.51-3.31 (m, 2H), 3.20-2.97 (m, 2H), 2.14 (q, J=12.2 Hz, 1H), 2.05-1.83 (m, 1H), 1.78-1.69 (m, 2H). LCMS (ES+) m/z 466 (M+1).

Example 126

5-amino-N-(5-((3R,5R)-5-amino-3-fluoroazepan-1-yl)-1-methyl-1H-pyrazol-4-yl)-2-(2,6-difluorophenyl)thiazole-4-carboxamide 126

Following the procedure for Example 101, starting with Intermediate 20, tert-butyl 6-fluoro-1-(1-methyl-4-nitro-1H-pyrazol-5-yl)azepan-4-ylcarbamate and 5-(tert-butoxycarbonylamino)-2-(2,6-difluorophenyl)thiazole-4-carboxylic acid from Example 25 gave, after silica gel column chromatography (0-10% MeOH/DCM, 1% 7 N ammonia in MeOH), a white solid (273 mg, 19% over three steps). Compound 126 was obtained as a single enantiomer from SFC chiral separation of the racemic mixture. $^1$H NMR (400 MHz, CDCl$_3$) δ 8.52 (s, 1H), 7.80 (s, 1H), 7.37-7.28 (m, 2H), 7.08-6.98 (m, 3H), 6.13 (s, 2H), 4.83-4.78 and 4.72-4.68 (2 m, 1H), 3.79-3.72 (m, 3H), 3.54-3.30 (m, 3H), 3.24-3.12 (m, 2H), 2.31-2.22 (m, 1H), 2.18-2.07 (m, 1H), 1.93-1.76 (m, 2H). LCMS (ES+) m/z 466 (M+1).

Example 127

5-Amino-N-(5-((3S,5R)-3-amino-5-fluoropiperidin-1-yl)-1-methyl-1H-pyrazol-4-yl)-2-(2,6-difluorophenyl)thiazole-4-carboxamide 127

A mixture of tert-butyl (3S,5R)-1-(4-(5-(tert-butoxycarbonylamino)-2-(2,6-difluorophenyl)-thiazole-4-carboxamido)-1-methyl-1H-pyrazol-5-yl)-5-fluoropiperidin-3-ylcarbamate (100 mg, 0.15 mmol) in HCl/MeOH (10 mL) was stirred at ambient temperature for 20 hours and concentrated reduced pressure to give a residue. The residue was diluted with MeOH (10 mL), neutralized with 28% ammonia solution, and concentrated to give a crude product. The crude product was purified by preparative HPLC to give 127 (40 mg, 59%). $^1$H-NMR (500 MHz, CD$_3$OD) δ (ppm): 7.51-7.49 (m, 2H), 7.17-7.12 (m, 2H), 4.95-4.86 (m, 2H), 3.75 (s, 3H), 3.31-3.25 (m, 3H), 2.97-2.90 (m, 1H), 2.31-2.23 (m, 1H), 1.64-1.48 (m, 1H); MS (ESI) m/z: 452 [M+H$^+$].

Example 128

N-(5-(1,4-diazepan-1-yl)-1-(oxetan-3-ylmethyl)-1H-pyrazol-4-yl)-5-amino-2-(2,6-difluorophenyl)thiazole-4-carboxamide 128

Removal of the Boc group from tert-butyl 4-(4-(5-amino-2-(2,6-difluorophenyl)thiazole-4-carboxamido)-1-(oxetan-3-ylmethyl)-1H-pyrazol-5-yl)-1,4-diazepane-1-carboxylate in 1:1 methylene chloride: TFA gave 128. $^1$H NMR (400 MHz, DMSO) δ 11.57 (s, 1H), 8.57 (s, 1H), 7.65 (s, 2H), 7.61-7.43 (m, 1H), 7.29 (t, J=8.7 Hz, 2H), 5.21-5.03 (m, 1H), 4.58-4.36 (m, 2H), 4.26-4.04 (m, 2H), 3.59 (s, 2H), 3.46-3.36 (m, 2H), 2.98 (t, J=6.1 Hz, 2H), 2.79 (t, J=5.7 Hz, 2H), 1.60-1.40 (m, 2H). MS (ESI) m/z: 490.2 [M+H$^+$].

Example 129

N-(5-(1,4-diazepan-1-yl)-1-(oxetan-3-ylmethyl)-1H-pyrazol-4-yl)-5-amino-2-(2-fluoro-5-methylphenyl)thiazole-4-carboxamide 129

Removal of the Boc group from tert-butyl 4-(4-(5-amino-2-(2-fluoro-5-methylphenyl)thiazole-4-carboxamido)-1-(oxetan-3-ylmethyl)-1H-pyrazol-5-yl)-1,4-diazepane-1-carboxylate in 1:1 methylene chloride: TFA gave 129. $^1$H NMR (400 MHz, DMSO) δ 10.78 (s, 1H), 8.49 (s, 1H), 8.41 (s, 2H), 7.90 (d, J=7.4 Hz, 1H), 7.55 (s, 2H), 7.26 (d, J=9.0 Hz, 2H), 4.61-4.42 (m, 2H), 4.27-4.11 (m, 2H), 3.70-3.54 (m, 2H), 3.00 (t, J=5.4 Hz, 2H), 2.84 (t, J=5.5 Hz, 2H), 2.36 (s, 3H), 1.71-1.57 (m, 2H). MS (ESI) m/z: 486.2 [M+H⁺].

Example 130

N-(5-(1,4-diazepan-1-yl)-1-(oxetan-3-ylmethyl)-1H-pyrazol-4-yl)-5-amino-2-(2,5-difluorophenyl)thiazole-4-carboxamide 130

Removal of the Boc group from tert-butyl 4-(4-(5-amino-2-(2,5-difluorophenyl)thiazole-4-carboxamido)-1-(oxetan-3-ylmethyl)-1H-pyrazol-5-yl)-1,4-diazepane-1-carboxylate in 1:1 methylene chloride: TFA gave 130. ¹H NMR (400 MHz, DMSO) δ 10.43 (s, 1H), 8.42 (s, 1H), 8.36 (s, 2H), 8.06-7.94 (m, 1H), 7.60 (s, 2H), 7.51-7.37 (m, 1H), 7.36-7.24 (m, 1H), 4.56 (dd, J=10.5, 8.2 Hz, 1H), 4.47 (dd, J=11.2, 8.1 Hz, 1H), 4.25 (dd, J=10.7, 5.5 Hz, 1H), 4.18 (dd, J=11.2, 5.7 Hz, 1H), 3.60-3.36 (m, 7H), 2.94 (t, J=5.5 Hz, 2H), 2.83-2.74 (m, 2H), 1.75-1.56 (m, 2H). MS (ESI) m/z: 486.2 [M+H⁺].

Example 131

(R)-5-amino-2-(2-fluorophenyl)-N-(5-(4-hydroxy-4-methylazepan-1-yl)-1-methyl-1H-pyrazol-4-yl)thiazole-4-carboxamide 131

Chiral separation of the racemic mixture by SFC gave 131 as a single enantiomer. ¹H NMR (400 MHz, DMSO) δ 8.85 (s, 1H), 8.33-8.20 (m, 1H), 7.53 (s, 1H), 7.50-7.24 (m, 5H), 4.24 (s, 1H), 3.65 (s, 3H), 3.43-3.32 (m, 1H), 3.28-3.17 (m, 1H), 3.11-2.98 (m, 1H), 2.96-2.83 (m, 1H), 2.05-1.88 (m, 1H), 1.84-1.64 (m, 4H), 1.63-1.45 (m, 1H), 1.17 (s, 3H). MS (ESI) m/z: 445.2 [M+H⁺].

Example 132

(S)-5-amino-2-(2-fluorophenyl)-N-(5-(4-hydroxy-4-methylazepan-1-yl)-1-methyl-1H-pyrazol-4-yl)thiazole-4-carboxamide 132

Chiral separation of the racemic mixture by SFC gave 132 as a single enantiomer. ¹H NMR (400 MHz, DMSO) δ 8.85 (s, 1H), 8.33-8.22 (m, 1H), 7.53 (s, 1H), 7.50-7.23 (m, 5H), 4.24 (s, 1H), 3.65 (s, 3H), 3.42-3.33 (m, 1H), 3.27-3.19 (m, 1H), 3.11-2.98 (m, 1H), 2.96-2.80 (m, 1H), 2.06-1.89 (m, 1H), 1.80-1.63 (m, 4H), 1.63-1.47 (m, 1H), 1.17 (s, 3H). MS (ESI) m/z: 445.2 [M+H⁺].

Example 133

(R)-5-amino-2-(2,6-difluorophenyl)-N-(1-methyl-5-(5-(trifluoromethyl)-1,4-diazepan-1-yl)-1H-pyrazol-4-yl)thiazole-4-carboxamide 133

Chiral separation of the racemic mixture by SFC gave 133 as a single enantiomer. ¹H NMR (400 MHz, DMSO) δ 11.98 (s, 1H), 7.90 (s, 1H), 7.64-7.39 (m, 3H), 7.37-7.21 (m, 2H), 3.62 (s, 3H), 3.22-2.97 (m, 6H), 2.89 (dd, J=14.6, 10.5 Hz, 1H), 2.79-2.60 (m, 1H), 2.25 (dd, J=12.4, 10.6 Hz, 1H), 1.83-1.59 (m, 1H), 0.68 (d, J=6.7 Hz, 3H). MS (ESI) m/z: 448.2 [M+H⁺].

Example 134

(S)-5-amino-2-(2,6-difluorophenyl)-N-(1-methyl-5-(5-(trifluoromethyl)-1,4-diazepan-1-yl)-1H-pyrazol-4-yl)thiazole-4-carboxamide 134

Chiral separation of the racemic mixture by SFC gave 134 as a single enantiomer. ¹H NMR (400 MHz, DMSO) δ 11.98 (s, 1H), 7.90 (s, 1H), 7.64-7.39 (m, 3H), 7.37-7.21 (m, 2H), 3.62 (s, 3H), 3.22-2.97 (m, 6H), 2.89 (dd, J=14.6, 10.5 Hz, 1H), 2.79-2.60 (m, 1H), 2.25 (dd, J=12.4, 10.6 Hz, 1H), 1.83-1.59 (m, 1H), 0.68 (d, J=6.7 Hz, 3H). MS (ESI) m/z: 448.2 [M+H⁺].

Example 135

(S)-5-amino-N-(1-(2,2-difluoroethyl)-5-(4-hydroxyazepan-1-yl)-1H-pyrazol-4-yl)-2-(2,6-difluorophenyl)thiazole-4-carboxamide 135

Chiral separation of the racemic mixture by SFC gave 135 as a single enantiomer. ¹H NMR (400 MHz, DMSO) δ 8.69 (s, 1H), 7.69 (s, 1H), 7.59-7.43 (m, 3H), 7.27 (t, J=8.7 Hz, 2H), 6.37 (tt, J=55.3, 4.1 Hz, 1H), 4.41 (td, J=14.5, 4.1 Hz, 2H), 3.79 (d, J=7.8 Hz, 1H), 3.24-2.94 (m, 4H), 1.96-1.75 (m, 3H), 1.73-1.48 (m, 3H). MS (ESI) m/z: 499.1 [M+H⁺].

Example 136

(R)-5-amino-N-(1-(2,2-difluoroethyl)-5-(4-hydroxyazepan-1-yl)-1H-pyrazol-4-yl)-2-(2,6-difluorophenyl)thiazole-4-carboxamide 136

Chiral separation of the racemic mixture by SFC gave 136 as a single enantiomer. ¹H NMR (400 MHz, DMSO) δ 8.69 (s, 1H), 7.69 (s, 1H), 7.58-7.42 (m, 3H), 7.27 (t, J=8.7 Hz, 2H), 6.37 (tt, J=55.3, 4.0 Hz, 1H), 4.47 (d, J=3.8 Hz, 1H), 4.40 (td, J=14.5, 4.1 Hz, 2H), 3.87-3.72 (m, 1H), 3.23-2.94 (m, 4H), 1.92-1.76 (m, 3H), 1.73-1.46 (m, 3H). MS (ESI) m/z: 499.1 [M+H⁺].

Example 137

(S)-5-amino-N-(1-(2,2-difluoroethyl)-5-(4-hydroxyazepan-1-yl)-1H-pyrazol-4-yl)-2-(2-fluoro-5-methylphenyl)thiazole-4-carboxamide 137

Chiral separation of the racemic mixture by SFC gave 137 as a single enantiomer. ¹H NMR (400 MHz, DMSO) δ 8.91 (s, 1H), 8.07 (d, J=7.5 Hz, 1H), 7.65 (s, 1H), 7.41 (s, 2H), 7.23 (d, J=9.0 Hz, 2H), 6.38 (tt, J=55.4, 4.1 Hz, 1H), 4.53 (s, 1H), 4.42 (td, J=14.5, 4.1 Hz, 2H), 3.89-3.76 (m, 1H), 3.27-2.98 (m, 4H), 2.36 (s, 3H), 1.95-1.79 (m, 3H), 1.79-1.48 (m, 3H). MS (ESI) m/z: 495.2 [M+H⁺].

Example 138

(R)-5-amino-N-(1-(2,2-difluoroethyl)-5-(4-hydroxyazepan-1-yl)-1H-pyrazol-4-yl)-2-(2-fluoro-5-methylphenyl)thiazole-4-carboxamide 138

Chiral separation of the racemic mixture by SFC gave 138 as a single enantiomer. ¹H NMR (400 MHz, DMSO) δ 8.91 (s, 1H), 8.07 (d, J=7.5 Hz, 1H), 7.66 (s, 1H), 7.41 (s, 2H), 7.23 (d, J=9.0 Hz, 2H), 6.38 (tt, J=55.4, 4.1 Hz, 1H), 4.53 (d, J=3.8 Hz, 1H), 4.42 (td, J=14.5, 4.1 Hz, 2H), 3.93-3.74 (m, 1H), 3.27-3.00 (m, 4H), 2.37 (s, 3H), 1.97-1.78 (m, 3H), 1.78-1.49 (m, 3H). MS (ESI) m/z: 495.2 [M+H⁺].

Example 139

5-amino-N-(5-((4R,5R)-4-amino-5-fluoroazepan-1-yl)-1-methyl-1H-pyrazol-4-yl)-2-(2,6-difluorophenyl)thiazole-4-carboxamide 139

Step A: To a solution of benzyl 4-azido-5-hydroxyazepane-1-carboxylate (1.0 g, 3.45 mmol) in dry DCM (10 ml) was added deoxo-Fluor® (1.6 mL, 8.62 mmol, 50% in THF) and the mixture was stirred at room temperature for 18 hr. Saturated aqueous NaHCO₃ solution was added (20 mL) and the mixture was extracted with DCM (100 mL). The organic layer was washed with saturated aqueous NaHCO₃ solution (20 mL), separated, dried over MgSO₄ and concentrated under reduced pressure. The residue was purified via silica gel column chromatography (20% EtOAc/isohexane) to give benzyl 4-azido-5-fluoroazepane-1-carboxylate as a mixture of syn and anti isomers as a pale yellow oil (0.76 g).

Step B: A solution of benzyl 4-azido-5-fluoroazepane-1-carboxylate (0.5 g, 1.71 mmol) in THF/water (10 mL/2 mL) was treated with triphenylphosphine (0.45 g, 1.71 mmol) and the mixture was heated at 60° C. for 24 hr. The mixture was partitioned between EtOAc (100 mL) and water (20 mL) and washed with brine (20 mL). The organic layer was separated, dried over MgSO₄, and concentrated under reduced pressure to give a colourless oil. This oil was triturated in Et₂O, the resulting solid was filtered off, washed with Et₂O and the filtrate concentrated under reduced pressure to give a colourless oil. The reaction was repeated on half the scale and the combined batches were dissolved in dry DCM (20 mL) and treated with di-tert-butyl dicarbonate (1.1 g, 5.11 mmol) and NEt₃ (1.1 mL, 7.67 mmol). The mixture was stirred at room temperature for 18 hr. Water was added (10 mL) and the mixture was extracted with DCM (100 mL). The organic layer was separated, dried over MgSO₄ and concentrated under reduced pressure. Purification via silica gel column chromatography (40% EtOAc/isohexane) gave benzyl 4-(tert-butoxycarbonylamino)-5-fluoroazepane-1-carboxylate as a mixture of syn and anti isomers as a colourless oil (0.55 g).

Step C: A solution of benzyl 4-(tert-butoxycarbonylamino)-5-fluoroazepane-1-carboxylate (0.55 g, 1.50 mmol) in MeOH (75 mL) was passed through the H-Cube® (full H₂, 50° C., flow rate: 1 mL/min, 30 mm 10% Pd/C cartridge). The solvent was removed under reduced pressure to afford tert-butyl 5-fluoroazepan-4-ylcarbamate as a mixture of syn and anti isomers as a colourless oil (317 mg).

Step D: To a solution of tert-butyl 5-fluoroazepan-4-ylcarbamate (310 mg, 1.34 mmol) in EtOH (4 mL) was added DIPEA (1 ml, 5.7 mmol) and 5-chloro-1-methyl-4-nitro-1H-pyrazole (216 mg, 1.34 mmol). The reaction mixture was heated at 130° C. in a microwave for 8 hr. The solvent was removed under reduced pressure and the residue was purified via silica gel column chromatography (30-40% EtOAc/isohexane) to give the two trans (anti) isomers, tert-butyl 5-fluoro-1-(1-methyl-4-nitro-1H-pyrazol-5-yl)azepan-4-ylcarbamate as a yellow glass (65 mg) contaminated with some of the cis (syn) isomer.

Step E: A solution of tert-butyl 5-fluoro-1-(1-methyl-4-nitro-1H-pyrazol-5-yl)azepan-4-ylcarbamate (65 mg, 0.182 mmol) in MeOH (20 mL) was passed through the H-Cube® (full H₂, 50° C., flow rate: 1 mL/min, 30 mm 10% Pd/C cartridge). The solvent was removed under reduced pressure to give the free amine, 5-fluoro-1-(1-methyl-4-nitro-1H-pyrazol-5-yl)azepan-4-amine, as a pale yellow glass (51 mg).

Step F: To a solution of 5-fluoro-1-(1-methyl-4-nitro-1H-pyrazol-5-yl)azepan-4-amine (51 mg, 0.156 mmol) in DCM (10 mL) was added 5-(tert-butoxycarbonylamino)-2-(2,6-difluorophenyl)thiazol-4-carboxylic acid (56 mg, 0.156 mmol), PyBOP (203 mg, 0.39 mmol) and DIPEA (0.5 mL, 2.9 mmol) and the reaction mixture was stirred at room temperature for 18 hr. Water (10 mL) was added and the mixture was extracted with DCM (40 mL). The organic layer was separated, dried over MgSO₄ and concentrated under reduced pressure. Purification of the residue via silica gel column chromatography (60% EtOAc/isohexane) afforded the two trans isomers of tert-butyl 4-(5-(4-Boc-amino-5-fluoroazepan-1-yl)-1-methyl-1H-pyrazol-4-ylcarbamoyl)-2-(2,6-difluorophenyl)thiazol-5-ylcarbamate as a pale lilac solid (36 mg) contaminated with a small amount of the syn (cis) isomer.

Step G: A solution/suspension of the two trans isomers of tert-butyl 4-(5-(4-Boc-amino-5-fluoroazepan-1-yl)-1-methyl-1H-pyrazol-4-ylcarbamoyl)-2-(2,6-difluorophenyl) thiazol-5-ylcarbamate (35 mg, 0.053 mmol) in MeOH (2 mL) was treated with a solution of HCl in dioxane (4 M, 0.65 mL, 2.63 mmol) and the mixture stirred at room temperature for 18 hr. The solvent was removed under reduced pressure and the residue was purified by preparative HPLC to afford 5-amino-N-(5-(4-amino-5-fluoroazepan-1-yl)-1-methyl-1H-pyrazol-4-yl)-2-(2,6-difluorophenyl)thiazole-4-carboxamide as an off-white solid (3 mg, 0.16% over eight steps). The 4-amino and the 5-fluoro groups are trans. The ¹H NMR (400 MHz, CDCl₃) δ 8.81 (s, 1H), 7.88 (s, 1H), 7.38-7.27 (m, 1H), 7.08-6.98 (m, 2H), 6.14 (s, 2H), 4.92-4.77 (m, 1H), 3.73 (s, 3H), 3.50-3.29 (m, 3H), 3.18-3.05 (m, 2H), 2.29-2.24 (m, 1H), 2.11-1.76 (m, 3H). Alkyl NH₂ not observed. LCMS (ES+) m/z 466 (M+1)

Chiral separation of 5-amino-N-(5-(4-amino-5-fluoroazepan-1-yl)-1-methyl-1H-pyrazol-4-yl)-2-(2,6-difluorophenyl)thiazole-4-carboxamide by SFC gave 139 as a single enantiomer. ¹H NMR (400 MHz, DMSO) δ 8.82 (s, 1H), 7.59-7.42 (m, 4H), 7.26 (t, J=8.7 Hz, 2H), 4.55-4.31 (m, 1H), 3.63 (s, 3H), 3.23-3.03 (m, 5H), 2.20-2.02 (m, 1H), 2.02-1.88 (m, 1H), 1.88-1.76 (m, 1H), 1.67-1.52 (m, 1H). MS (ESI) m/z: 466.1 [M+H⁺].

Example 140

5-amino-N-(5-((4S,5S)-4-amino-5-fluoroazepan-1-yl)-1-methyl-1H-pyrazol-4-yl)-2-(2,6-difluorophenyl)thiazole-4-carboxamide 140

The procedures of Example 139 were followed to give 5-amino-N-(5-(4-amino-5-fluoroazepan-1-yl)-1-methyl-1H-pyrazol-4-yl)-2-(2,6-difluorophenyl)thiazole-4-carboxamide where the 4-amino and the 5-fluoro groups are cis. Chiral separation of the racemic mixture by SFC gave 140 as a single enantiomer. ¹H NMR (400 MHz, DMSO) δ 8.82 (s, 1H), 7.59-7.42 (m, 4H), 7.26 (t, J=8.7 Hz, 2H), 4.55-4.31 (m, 1H), 3.63 (s, 3H), 3.23-3.03 (m, 5H), 2.20-2.02 (m, 1H), 2.02-1.88 (m, 1H), 1.88-1.76 (m, 1H), 1.67-1.52 (m, 1H). MS (ESI) m/z: 466.1 [M+H⁺].

Example 141

(S)-5-Amino-2-(2,6-difluorophenyl)-N-(1-methyl-5-(2-methylpiperazin-1-yl)-1-methyl-1H-pyrazol-4-yl)thiazole-4-carboxamide 141

Following the procedure for Example 112, (S)-5-(2,4-dimethylpiperazin-1-yl)-1-methyl-1H-pyrazol-4-amine and 5-(tert-butoxycarbonylamino)-2-(2,6-difluorophenyl)thiazole-4-carboxylic acid from Example 25 was reacted to give 141 as a pink solid (86 mg, 46% over two steps). ¹H NMR (400 MHz, CDCl₃) δ 8.59 (s, 1H), 7.88 (s, 1H), 7.35-7.28 (m, 1H), 7.02 (t, J=8.7 Hz, 2H), 6.13 (s, 2H), 3.77 (s, 3H), 3.43-3.31 (m, 2H), 2.98 (d, J=11.6 Hz, 1H), 2.83 (t, J=11.4 Hz, 2H), 2.35 (s, 3H), 2.32-2.25 (m, 1H), 1.96 (t, J=10.2 Hz, 1H), 0.90 (d, J=6.3 Hz, 3H). LCMS (ES+) m/z 448 (M+1).

Example 142

(R)-5-Amino-2-(2,6-difluorophenyl)-N-(1-methyl-5-(2-methylpiperazin-1-yl)-1-methyl-1H-pyrazol-4-yl)thiazole-4-carboxamide 142

Following the procedure for Example 110, (R)-5-(2,4-dimethylpiperazin-1-yl)-1-methyl-1H-pyrazol-4-amine and 5-(tert-butoxycarbonylamino)-2-(2,6-difluorophenyl)thiazole-4-carboxylic acid from Example 25 was reacted to give 142 as a white solid (54 mg, 29% over two steps). $^1$H NMR (400 MHz, CDCl$_3$) δ 8.59 (s, 1H), 7.88 (s, 1H), 7.36-7.25 (m, 1H), 7.02 (t, J=8.7 Hz, 2H), 6.12 (s, 2H), 3.77 (s, 3H), 3.43-3.30 (m, 2H), 2.98 (dt, J=11.5, 2.8 Hz, 1H), 2.83 (t, J=11.4 Hz, 2H), 2.35 (s, 3H), 2.42-2.20 (m, 1H), 1.96 (t, J=10.2 Hz, 1H), 0.92 (d, J=8.6 Hz, 3H). LCMS (ES+) m/z 448 (M+1).

Example 143

5-Amino-N-(1-cyclopropyl-5-(6,6-difluoro-1,4-diazepan-1-yl)-1H-pyrazol-4-yl)-2-(2,5-difluorophenyl)thiazole-4-carboxamide 143

Following the procedure for Example 105, tert-butyl 4-(4-(2-bromo-5-(tert-butoxycarbonylamino)thiazole-4-carboxamido)-1-cyclopropyl-1H-pyrazol-5-yl)-6,6-difluoro-1,4-diazepane-1-carboxylate and 2,5-difluoro-phenylboronic acid was reacted to give 143 as a beige foam (60 mg, 42% over two steps). $^1$H NMR (400 MHz, CDCl$_3$) δ 8.92 (s, 1H), 7.92-7.84 (m, 2H), 7.17-7.08 (m, 1H), 7.07-6.99 (m, 1H), 6.15 (s, 2H), 3.68 (t, J=13.2 Hz, 2H), 3.52-3.32 (m, 5H), 3.11 (t, J=5.4 Hz, 2H), 1.95 (s, 1H), 1.26-1.20 (m, 2H), 1.08-1.00 (m, 2H). LCMS (ES+) m/z 496 (M+1).

Example 144

5-Amino-N-(1-cyclopropyl-5-(6,6-difluoro-1,4-diazepan-1-yl)-1H-pyrazol-4-yl)-2-(2-fluoro-5-methylphenyl)thiazole-4-carboxamide 144

Following the procedure for Example 105, tert-butyl 4-(4-(2-bromo-5-(tert-butoxycarbonylamino)thiazole-4-carboxamido)-1-cyclopropyl-1H-pyrazol-5-yl)-6,6-difluoro-1,4-diazepane-1-carboxylate and 2-fluoro-5-methylphenylboronic acid was reacted to give 144 as a beige foam (75 mg, 53% over two steps). $^1$H NMR (400 MHz, CDCl$_3$) δ 8.99 (s, 1H), 7.92 (dd, J=7.2, 2.2 Hz, 1H), 7.84-7.79 (m, 1H), 7.16-7.11 (m, 1H), 7.10-7.00 (m, 1H), 6.09 (s, 2H), 3.69 (t, J=13.3 Hz, 2H), 3.51-3.35 (m, 5H), 3.09 (t, J=5.5 Hz, 2H), 2.39 (s, 3H), 2.05-1.80 (m, 1H), 1.29-1.19 (m, 2H), 1.09-0.98 (m, 2H). LCMS (ES+) m/z 492 (M+1).

Example 145

5-Amino-N-(1-cyclopropyl-5-(6,6-difluoro-1,4-diazepan-1-yl)-1H-pyrazol-4-yl)-2-(2,6-difluorophenyl)thiazole-4-carboxamide 145

A mixture of tert-butyl 4-(4-(2-bromo-5-(tert-butoxycarbonylamino)thiazole-4-carboxamido)-1-cyclopropyl-1H-pyrazol-5-yl)-6,6-difluoro-1,4-diazepane-1-carboxylate (191 mg, 0.29 mmol), potassium fluoride dihydrate (90 mg, 0.96 mmol) and 2,6-difluoro-phenylboronic acid (137 mg, 0.87 mmol) in THF (3 mL) was degassed by gently bubbling nitrogen through the mixture for 15 min. Tris(dibenzylideneacetone)dipalladium/tri-tert-butyl phosphonium tetrafluoroborate mixture (mole ratio: 1/1.2) (35 mg, 0.029 mmol) was then added and the mixture degassed was heated in a microwave at 100° C. for 2 hr. The solvent was removed under reduced pressure. Water (5 mL) was added and the mixture extracted with EtOAc (2×20 mL). The combined organic layers were dried over MgSO$_4$ and concentrated under reduced pressure. The residue was purified via silica gel column chromatography (0-60% EtOAc/isohexane) to give tert-butyl 4-(4-(5-tert-butoxycarbonylamino-2-(2,6-difluorophenyl)thiazole-4-carboxamido)-1-cyclopropyl-1H-pyrazol-5-yl)-6,6-difluoro-1,4-diazepane-1-carboxylate as an orange solid (95 mg, 0.13 mmol) which was dissolved in a solution of HCl in 1,4-dioxane (4 M, 0.7 mL, 2.73 mmol) and MeOH (0.2 mL) and stirred at 70° C. for 48 hr. The solvent was removed under reduced pressure and the residue dissolved in MeOH/DCM and passed through an SCX cartridge washing with DCM and MeOH and eluting with 1 N ammonia in MeOH. Purification by silica gel column chromatography (0-10% MeOH/DCM) gave 145 as a beige solid (35 mg, 25% over two steps). $^1$H NMR (400 MHz, CDCl$_3$) δ 9.42 (s, 1H), 7.87 (s, 1H), 7.38-7.28 (m, 1H), 7.08-6.97 (m, 2H), 6.20 (s, 2H), 3.71-3.56 (m, 3H), 3.46-3.35 (m, 4H), 3.12-3.06 (m, 2H), 1.25-1.19 (m, 2H), 1.06-0.97 (m, 2H). Alkyl NH not observed. LCMS (ES+) m/z 496 (M+1).

Example 146

5-Amino-2-(2,6-difluorophenyl)-N-(5-(4-hydroxy-4-methylazepan-1-yl)-1-methyl-1H-pyrazol-4-yl)thiazole-4-carboxamide 146

To a solution of 4-methyl-1-(1-methyl-4-nitro-1H-pyrazol-5-yl)azepan-4-ol (212 mg, 0.83 mmol) and ammonium formate (386 mg, 6.6 mmol) in MeOH (15 mL) under nitrogen was added 10% palladium on carbon (88 mg, 0.83 mmol). The mixture was heated at 80° C. for 16 hr before being cooled, filtered through Celite® and concentrated under reduced pressure. The residue was partitioned between water (20 mL) and DCM (40 mL) and the organic layer was separated, passed through a phase separation cartridge and concentrated under reduced pressure to give 1-(4-amino-1-methyl-1H-pyrazol-5-yl)-4-methylazepan-4-ol as a red oil which was used without further purification. To a solution of DIPEA (0.06 mL, 0.33 mmol), PyBOP (151 mg, 0.29 mmol) and 5-(tert-butoxycarbonylamino)-2-(2,6-difluorophenyl)thiazole-4-carboxylic acid (89 mg, 0.25 mmol) in DCM (10 mL) (pre-stirred for 30 min) was added 1-(4-amino-1-methyl-1H-pyrazol-5-yl)-4-methylazepan-4-ol (47 mg, 0.21 mmol) and the mixture was stirred at room temperature for 16 hr. The mixture was diluted with DCM (30 mL) and water (20 mL). The organic layer was passed through a phase separation cartridge and the solvent removed under reduced pressure. Purification via silica gel column chromatography (0-100% EtOAc/isohexane) gave tert-butyl 2-(2,6-difluorophenyl)-4-(5-(4-hydroxy-4-methylazepan-1-yl)-1-methyl-1H-pyrazol-4-ylcarbamoyl)thiazol-5-ylcarbamate as an off-white solid (109 mg). This solid was stirred with HCl in 1,4-dioxane (4 M, 5 mL, 20 mmol) in MeOH (5 mL) at room temperature for 16 h. The solvent was removed under reduced pressure, the residue re-dissolved in MeOH and passed through an SCX column, washing with DCM and MeOH and eluting with 3-10% 7 N ammonia in MeOH/DCM. Purification via silica gel column chromatography (0-5% MeOH/DCM) gave 146 as an off-white solid (36 mg, 37% over 3 steps). $^1$H NMR (400 MHz, d$_4$-MeOD) δ 7.68 (s, 1H), 7.52-7.43 (m, 1H), 7.17-7.10 (m, 2H), 3.74 (s, 3H), 3.56-3.44 (m, 1H), 3.19-3.10 (m, 1H), 3.04-2.96 (m, 1H), 2.14-2.02 (m, 1H), 1.94-1.80 (m, 4H), 1.74-1.64 (m, 1H), 1.23 (s, 3H) (1 proton coincident with solvent peak). LCMS (ES+) m/z 463 (M+1).

Example 147

5-amino-N-(5-((4S,5R)-4-amino-5-fluoroazepan-1-yl)-1-methyl-1H-pyrazol-4-yl)-2-(2,6-difluorophenyl)thiazole-4-carboxamide 147

Step A: To a solution of 5-(tert-butoxycarbonylamino)-2-(2,6-difluorophenyl)thiazole-4-carboxylic acid (784 mg, 2.2 mmol) in DCM (40 mL) was added PyBOP (1.46 g, 2.8 mmol) and the mixture stirred at room temperature for 30 min. A solution of N-(1-(4-Amino-1-methyl-1H-pyrazol-5-yl)-5-fluoroazepan-4-yl)-2,2,2-trifluoroacetamide (647 mg, 2.0 mmol) and DIPEA (0.59 mL, 3.4 mmol) in DCM (40 mL) was then added and the mixture was stirred at room temperature for 16 hr. The mixture was diluted with DCM (60 mL) and washed with water (30 mL). The organic layer was separated, passed through a phase separation cartridge and the solvent removed under reduced pressure. Purification via silica gel column chromatography (0-100% EtOAc/isohexane) gave tert-butyl 2-(2,6-difluorophenyl)-4-(5-(4-fluoro-5-(2,2,2-trifluoroacetamido)azepan-1-yl)-1-methyl-1H-pyrazol-4-ylcarbamoyl)thiazol-5-ylcarbamate as an off-white solid (1.32 g).

Step B: tert-Butyl 2-(2,6-difluorophenyl)-4-(5-(4-fluoro-5-(2,2,2-trifluoroacetamido)azepan-1-yl)-1-methyl-1H-pyrazol-4-ylcarbamoyl)thiazol-5-ylcarbamate was suspended in MeOH (20 mL) in a pressure vessel and to this was added a solution of HCl in 1,4-dioxane (4 M, 20 mL, 80.0 mmol). The vessel was sealed and the mixture heated at 60° C. for 16 hr. The solvent was removed under reduced pressure and the residue was purified via silica gel column chromatography (0-10% 7 N ammonia in MeOH/DCM) to yield 5-amino-N-(5-(4-amino-5-fluoroazepan-1-yl)-1-methyl-1H-pyrazol-4-yl)-2-(2,6-difluorophenyl)thiazole-4-carboxamide as a pale brown solid (653 mg, 70% over two steps). The 4-amino and the 5-fluoro groups are cis. $^1$H NMR (400 MHz, CDCl$_3$) δ 8.63 (s, 1H), 7.84 (s, 1H), 7.37-7.29 (m, 1H), 7.03 (t, J=8.7 Hz, 2H), 6.13 (s, 2H), 4.48 (dtd, J=47.9, 8.6, 3.6 Hz, 1H), 3.72 (s, 3H), 3.37-3.15 (m, 5H), 2.23-1.92 (m, 3H), 1.75-1.67 (m, 1H). Alkyl NH$_2$ not observed. LCMS (ES+) m/z 466 (M+1). Chiral separation of the racemic mixture by SFC gave 147 as a single enantiomer. $^1$H NMR (400 MHz, DMSO) δ 9.04 (s, 1H), 7.59 (s, 1H), 7.56-7.43 (m, 3H), 7.26 (dd, J=14.5, 5.9 Hz, 2H), 4.82 (dd, J=47.0, 7.4 Hz, 1H), 3.63 (s, 3H), 3.29-3.15 (m, 4H), 3.08-2.91 (m, 2H), 2.24-2.06 (m, 1H), 1.91-1.76 (m, 2H), 1.74-1.59 (m, 1H). MS (ESI) m/z: 466.1 [M+H$^+$].

Example 148

(S)-5-amino-N-(1-(2,2-difluoroethyl)-5-(4-hydroxyazepan-1-yl)-1H-pyrazol-4-yl)-2-(2,5-difluorophenyl)thiazole-4-carboxamide 148

Chiral separation of the racemic mixture by SFC gave 148 as a single enantiomer. $^1$H NMR (400 MHz, DMSO) δ 9.10 (s, 1H), 8.15 (ddd, J=9.3, 5.7, 3.3 Hz, 1H), 7.55 (s, 1H), 7.51-7.36 (m, 3H), 7.27 (tt, J=7.4, 3.6 Hz, 1H), 6.38 (tt, J=55.4, 4.1 Hz, 1H), 4.50 (d, J=3.8 Hz, 1H), 4.42 (td, J=14.5, 4.1 Hz, 2H), 3.87-3.71 (m, 1H), 3.25-2.97 (m, 4H), 1.92-1.76 (m, 3H), 1.73-1.47 (m, 3H). MS (ESI) m/z: 499.1 [M+H$^+$].

Example 149

(R)-5-amino-N-(1-(2,2-difluoroethyl)-5-(4-hydroxyazepan-1-yl)-1H-pyrazol-4-yl)-2-(2,5-difluorophenyl)thiazole-4-carboxamide 149

Chiral separation of the racemic mixture by SFC gave 149 as a single enantiomer. $^1$H NMR (400 MHz, DMSO) δ 9.10 (s, 1H), 8.15 (ddd, J=9.3, 5.7, 3.3 Hz, 1H), 7.55 (s, 1H), 7.51-7.36 (m, 3H), 7.27 (tt, J=7.4, 3.6 Hz, 1H), 6.38 (tt, J=55.4, 4.1 Hz, 1H), 4.50 (d, J=3.8 Hz, 1H), 4.42 (td, J=14.5, 4.1 Hz, 2H), 3.87-3.71 (m, 1H), 3.25-2.97 (m, 4H), 1.92-1.76 (m, 3H), 1.73-1.47 (m, 3H). MS (ESI) m/z: 499.1 [M+H$^+$].

Example 150

5-amino-N-(5-((4R,5S)-4-amino-5-fluoroazepan-1-yl)-1-methyl-1H-pyrazol-4-yl)-2-(2,6-difluorophenyl)thiazole-4-carboxamide 150

The procedures of Example 147 were followed to give 5-amino-N-(5-(4-amino-5-fluoroazepan-1-yl)-1-methyl-1H-pyrazol-4-yl)-2-(2,6-difluorophenyl)thiazole-4-carboxamide where the 4-amino and the 5-fluoro groups are cis. Chiral separation of the racemic mixture by SFC gave 150 as a single enantiomer. $^1$H NMR (400 MHz, DMSO) δ 9.05 (s, 1H), 7.59 (s, 1H), 7.57-7.47 (m, 3H), 7.27 (t, J=8.7 Hz, 2H), 4.82 (dd, J=47.0, 7.2 Hz, 1H), 3.63 (s, 3H), 3.30-3.15 (m, 4H), 3.08-2.94 (m, 2H), 2.26-2.09 (m, 1H), 1.93-1.74 (m, 2H), 1.74-1.60 (m, 1H). MS (ESI) m/z: 466.1 [M+H$^+$].

Example 151

5-amino-2-(2,6-difluorophenyl)-N-(5-(6-fluoro-1,4-diazepan-1-yl)-1-methyl-1H-pyrazol-4-yl)thiazole-4-carboxamide 151

Compound 151 was prepared according to the procedures described in Example 102, using 6-fluoro-1,4-diazepane. $^1$H NMR (400 MHz, DMSO) δ 8.74 (s, 1H), 8.17 (s, 1H), 7.59-7.46 (m, 3H), 7.43 (s, 1H), 7.27 (t, J=8.7 Hz, 2H), 4.47-4.37 (m, 1H), 4.30 (dd, J=5.2, 2.3 Hz, 1H), 3.64 (s, 3H), 3.08-2.73 (m, 8H). MS (ESI) m/z: 452.1 [M+H$^+$].

Example 152

(R)-5-amino-N-(5-(4-aminoazepan-1-yl)-1-(2,2-difluoroethyl)-1H-pyrazol-4-yl)-2-(2,6-difluorophenyl)thiazole-4-carboxamide 152

Compound 152 was prepared according to the procedures described herein.

Example 153

5-amino-N-(5-((3S,5R)-5-amino-3-fluoroazepan-1-yl)-1-methyl-1H-pyrazol-4-yl)-2-(2,6-difluorophenyl)thiazole-4-carboxamide 153

Following the procedure for Example 101, Intermediate 20, tert-butyl 6-fluoro-1-(1-methyl-4-nitro-1H-pyrazol-5-yl)azepan-4-ylcarbamate and 5-(tert-butoxycarbonylamino)-2-(2,6-difluorophenyl)thiazole-4-carboxylic acid from Example 25 gave, after silica gel column chromatography (0-10% MeOH/DCM, 1% 7 N ammonia in MeOH), a white solid (273 mg, 19% over three steps). Compound 153 was obtained as a single enantiomer from SFC chiral separation of the racemic mixture. ¹H NMR (400 MHz, DMSO) δ 8.77 (s, 1H), 7.61-7.41 (m, 4H), 7.27 (dd, J=14.5, 5.8 Hz, 2H), 4.84-4.56 (m, 1H), 3.67 (d, J=7.4 Hz, 3H), 3.44-3.34 (m, 2H), 3.21-2.86 (m, 3H), 2.22-2.07 (m, 1H), 1.87 (ddt, J=34.3, 21.1, 7.4 Hz, 3H), 1.70-1.53 (m, 1H). MS (ESI) m/z: 466.1 [M+H⁺].

Example 154

5-amino-N-(5-(5-amino-3-fluoroazepan-1-yl)-1-methyl-1H-pyrazol-4-yl)-2-(2,6-difluorophenyl)thiazole-4-carboxamide 154

Following the procedure for Example 101, Intermediate 20, tert-butyl 6-fluoro-1-(1-methyl-4-nitro-1H-pyrazol-5-yl)azepan-4-ylcarbamate and 5-(tert-butoxycarbonylamino)-2-(2,6-difluorophenyl)thiazole-4-carboxylic acid from Example 25 gave, after silica gel column chromatography (0-10% MeOH/DCM, 1% 7 N ammonia in MeOH), a white solid (273 mg, 19% over three steps). Compound 154 was obtained as a single enantiomer from SFC chiral separation of the racemic mixture. ¹H NMR (400 MHz, DMSO) δ 8.77 (s, 1H), 7.61-7.41 (m, 4H), 7.27 (dd, J=14.5, 5.8 Hz, 2H), 4.84-4.56 (m, 1H), 3.67 (d, J=7.4 Hz, 3H), 3.44-3.34 (m, 2H), 3.21-2.86 (m, 3H), 2.22-2.07 (m, 1H), 1.87 (ddt, J=34.3, 21.1, 7.4 Hz, 3H), 1.70-1.53 (m, 1H). MS (ESI) m/z: 466.1 [M+H⁺].

Example 155

5-amino-N-(5-((3R,4S)-4-amino-3-fluoroazepan-1-yl)-1-methyl-1H-pyrazol-4-yl)-2-(2,6-difluorophenyl)thiazole-4-carboxamide 155

Following the procedures of Example 101 or 112, compound 155 was obtained as a single enantiomer from SFC chiral separation of the racemic mixture. ¹H NMR (400 MHz, DMSO) δ 8.77 (s, 1H), 7.60-7.44 (m, 4H), 7.26 (dd, J=14.4, 5.8 Hz, 2H), 4.34-4.10 (m, 1H), 3.66 (s, 3H), 3.54-3.33 (m, 2H), 3.17-2.93 (m, 3H), 1.96-1.50 (m, 5H). MS (ESI) m/z: 466.1 [M+H⁺].

Example 156

5-amino-N-(5-((3S,4R)-4-amino-3-fluoroazepan-1-yl)-1-methyl-1H-pyrazol-4-yl)-2-(2,6-difluorophenyl)thiazole-4-carboxamide 156

Following the procedures of Example 101 or 112, compound 156 was obtained as a single enantiomer from SFC chiral separation of the racemic mixture. ¹H NMR (400 MHz, DMSO) δ 8.77 (s, 1H), 7.60-7.44 (m, 4H), 7.26 (dd, J=14.4, 5.8 Hz, 2H), 4.34-4.10 (m, 1H), 3.66 (s, 3H), 3.54-3.33 (m, 2H), 3.17-2.93 (m, 3H), 1.96-1.50 (m, 5H). MS (ESI) m/z: 466.1 [M+H⁺].

Example 157

5-amino-N-(5-((3R,4R)-4-amino-3-fluoroazepan-1-yl)-1-methyl-1H-pyrazol-4-yl)-2-(2,6-difluorophenyl)thiazole-4-carboxamide 157

Following the procedures of Example 101 or 112, compound 157 was obtained as a single enantiomer from SFC chiral separation of the racemic mixture. ¹H NMR (400 MHz, DMSO) δ 8.77 (s, 1H), 7.61-7.41 (m, 4H), 7.26 (dd, J=14.4, 5.8 Hz, 2H), 4.33-4.09 (m, 1H), 3.66 (s, 3H), 3.51-3.32 (m, 2H), 3.06 (m, 3H), 1.87-1.49 (m, 4H). MS (ESI) m/z: 466.2 [M+H⁺].

Example 158

5-amino-N-(5-((3S,4S)-4-amino-3-fluoroazepan-1-yl)-1-methyl-1H-pyrazol-4-yl)-2-(2,6-difluorophenyl)thiazole-4-carboxamide 158

Following the procedures of Example 101 or 112, compound 158 was obtained as a single enantiomer from SFC chiral separation of the racemic mixture. ¹H NMR (400 MHz, DMSO) δ 8.77 (s, 1H), 7.61-7.41 (m, 4H), 7.26 (dd, J=14.4, 5.8 Hz, 2H), 4.33-4.09 (m, 1H), 3.66 (s, 3H), 3.51-3.32 (m, 2H), 3.06 (m, 3H), 1.87-1.49 (m, 4H). MS (ESI) m/z: 466.2 [M+H⁺].

Example 159

5-Amino-N-(5-((3R,5R)-3-amino-5-fluoropiperidin-1-yl)-1-methyl-1H-pyrazol-4-yl)-2-(2,6-difluorophenyl)thiazole-4-carboxamide 159

A mixture of tert-butyl (3R,5R)-1-(4-(5-(tert-butoxycarbonylamino)-2-(2,6-difluorophenyl)-thiazole-4-carboxamido)-1-methyl-1H-pyrazol-5-yl)-5-fluoropiperidin-3-ylcarbamate (150 mg, 0.23 mmol) in HCl/MeOH (10 mL) was stirred at ambient temperature for 20 hours and concentrated under reduced pressure to afford a residue. The residue was diluted with MeOH (10 mL), neutralized with 28% ammonia solution, and concentrated to give a crude product. The crude product was purified by preparative HPLC to give 159 as pale solid (77 mg, 74%). ¹H NMR (500 MHz, CD₃OD) δ (ppm): 7.74 (s, 1H), 7.48-7.42 (m, 1H), 7.14-7.11 (m, 2H), 5.36-5.24 (m, 1H), 4.00-3.94 (m, 1H), 3.83-3.72 (m, 4H), 3.42-3.37 (m, 1H), 2.74-2.62 (m, 2H), 2.50-5.42 (m, 1H), 2.02-1.88 (m, 1H); MS (ESI) m/z: 452 [M+H⁺].

Example 160

5-amino-N-(5-(6,6-difluoro-1,4-diazepan-1-yl)-1-(oxetan-3-ylmethyl)-1H-pyrazol-4-yl)-2-(2,6-difluorophenyl)thiazole-4-carboxamide 160

Following Example 162, compound 160 was prepared. ¹H NMR (400 MHz, DMSO) δ 10.13 (s, 1H), 9.14 (s, 1H), 8.51 (s, 1H), 7.60-7.45 (m, 1H), 7.27 (t, J=8.4 Hz, 2H), 5.17 (s, 1H), 4.55 (t, J=8.2 Hz, 2H), 4.33-4.10 (m, 2H), 3.77 (t, J=12.8 Hz, 2H), 3.69-3.51 (m, 2H), 3.47-3.36 (m, 2H), 3.19 (t, J=14.3 Hz, 2H), 3.03-2.81 (m, 3H). MS (ESI) m/z: 526.2 [M+H⁺].

Example 161

(R)-5-amino-N-(5-(4-aminoazepan-1-yl)-1-(2,2-difluoroethyl)-1H-pyrazol-4-yl)-2-(2,5-difluorophenyl)thiazole-4-carboxamide 161

Following Example 101, 5-chloro-1-(2,2-difluoroethyl)-4-nitro-pyrazole and (R)-benzyl azepan-4-ylcarbamate were reacted to give 161. ¹H NMR (400 MHz, DMSO) δ 9.12 (s, 1H), 8.18-8.06 (m, 1H), 7.57 (s, 1H), 7.52-7.35 (m, 3H), 7.34-7.18 (m, 1H), 6.39 (tt, J=55.3, 4.2 Hz, 1H), 4.42 (td, J=14.5, 4.2 Hz, 2H), 3.21-3.03 (m, 4H), 3.03-2.91 (m, 1H), 1.91-1.71 (m, 3H), 1.64-1.36 (m, 3H). MS (ESI) m/z: 498.2 [M+H⁺].

Example 162

5-amino-2-(2,6-difluorophenyl)-N-(5-(4-hydroxyazepan-1-yl)-1-(oxetan-3-ylmethyl)-1H-pyrazol-4-yl)thiazole-4-carboxamide 162

Step A. oxetan-3-ylmethyl methanesulfonate

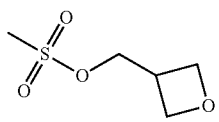

Oxetan-3-ylmethanol (1.85 g, 21.0 mmol) was dissolved in methylene chloride and cooled to 0° C. Triethylamine (5.31 g, 52.2 mmol) was added followed by slow addition of methanesulfonyl chloride (2.89 g, 25.2 mmol). The mixture was allowed to warm to ambient temperature for 2 h and quenched with sat. sodium bicarbonate (14 mL). The aqueous solution was extracted with methylene chloride 3×. The combined organic layers were dried over sodium sulfate, filtered and concentrated to give crude oxetan-3-ylmethyl methanesulfonate (quant.).

Step B. 4-nitro-1-(oxetan-3-ylmethyl)pyrazole

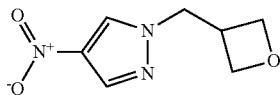

A mixture of 4-nitropyrazole (1000 mg, 8.80 mmol), oxetan-3-ylmethyl methanesulfonate (1.90 g, 11.0 mmol), cesium carbonate (8.70 g, 27.0 mmol) and acetonitrile (13 mL) was heated at 100° C. for 3 h. The mixture was cooled to room temperature, saturated ammonium chloride was added. The mixture was extracted with methylene chloride 3×. Combined organics were dried ($Na_2SO_4$) and the solvent removed under reduced pressure. The crude product was purified by flash chromatography eluting with 0 to 70% ethyl acetate in heptane to give 4-nitro-1-(oxetan-3-ylmethyl)pyrazole (1.60 g, 99%).

Step C. 5-chloro-4-nitro-1-(oxetan-3-ylmethyl)-1H-pyrazole

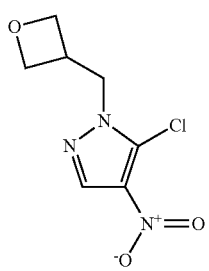

To a solution of 4-nitro-1-(oxetan-3-ylmethyl)pyrazole (3200 mg, 17.47 mmol) in THF (80 mL) was added LHMDS (1M solution in THF, 22.7 mL, 22.7 mmol) dropwise at −78° C. over a period of 15 min. The resulting mixture was stirred at −78° C. for 30 min. Hexachloroethane (5.38 g, 22.7 mmol.) in THF (20 mL) was added at −78° C. dropwise. The resulting mixture was stirred at −78° C. for another 40 min. The reaction mixture was quenched with aqueous ammonium chloride and extracted with Ethyl acetate (×3). Combined organic layers were dried over $Na_2SO_4$ and concentrated under reduced pressure. The crude material was purified by column chromatography with 0 to 75% ethyl acetate in heptane as eluent to give 5-chloro-4-nitro-1-(oxetan-3-ylmethyl)-1H-pyrazole (3.60 g, 95%).

Step D. Following Example 101, starting from 5-chloro-4-nitro-1-(oxetan-3-ylmethyl)-1H-pyrazole and azepan-4-ol, using TFA in place of 4N HCl in dioxane in the last step deprotection, 162 was obtained. $^1$H NMR (400 MHz, DMSO) δ 9.25 (s, 1H), 8.27 (s, 1H), 7.65-7.48 (m, 3H), 7.26 (dd, J=14.3, 5.8 Hx, 2H), 5.18 (t, J=5.2 Hz, 1H), 4.65-4.52 (m, 2H), 4.41 (dd, J=11.0, 8.2 Hz, 1H), 4.27 (dd, J=10.5, 5.8 hZ, 1H), 4.10 (dd, J=11.1, 6.1 Hz, 1H), 3.80-3.66 (m, 1H), 3.63-3.43 (m, 5H), 3.43-3.32 (m, 1H), 1.95-1.78 (m, 2H), 1.77-1.52 (m, 4H). MS (ESI) m/z: 505.1 [M+H$^+$].

Example 163

5-amino-2-(2-fluoro-5-methylphenyl)-N-(5-(4-hydroxyazepan-1-yl)-1-(oxetan-3-ylmethyl)-1H-pyrazol-4-yl)thiazole-4-carboxamide 163

Following the procedures of Example 162, 163 was obtained. $^1$H NMR (400 MHz, DMSO) δ 8.85 (s, 1H), 8.05 (d, J=7.6 Hz, 1H), 7.56 (s, 1H), 7.40 (s, 2H), 7.23 (d, J=9.1 Hz, 2H), 4.72-4.61 (m, 2H), 4.53 (d, J=3.8 Hz, 1H), 4.46 (t, J=6.2 Hz, 2H), 4.25 (d, J=7.4 Hz, 2H), 3.90-3.76 (m, 1H), 3.49-3.36 (m, 1H), 3.28-2.97 (m, 4H), 2.37 (s, 3H), 1.99-1.81 (m, 3H), 1.78-1.53 (m, 3H). MS (ESI) m/z: 501.1 [M+H$^+$].

Example 164

(R)-5-amino-N-(5-(4-aminoazepan-1-yl)-1-(oxetan-3-ylmethyl)-1H-pyrazol-4-yl)-2-(2,6-difluorophenyl)thiazole-4-carboxamide 164

Following the procedures of Example 162, 164 was obtained. $^1$H NMR (400 MHz, DMSO) δ 9.09 (s, 1H), 8.31 (s, 1H), 8.29 (s, 1H), 7.66-7.45 (m, 2H), 7.27 (td, J=8.4, 5.9 Hz, 2H), 5.17 (s, 1H), 4.59 (dd, J=18.0, 7.8 Hz, 1H), 4.48-4.35 (m, 1H), 4.32-4.18 (m, 1H), 4.16-4.02 (m, 1H), 3.67-3.38 (m, 6H), 2.97-2.84 (m, 1H), 1.91-1.30 (m, 6H). MS (ESI) m/z: 504.1 [M+H$^+$].

Example 165

5-amino-2-(2,6-difluorophenyl)-N-(5-(6-fluoro-1,4-diazepan-1-yl)-1-(oxetan-3-ylmethyl)-1H-pyrazol-4-yl)thiazole-4-carboxamide Following the procedures of Example 162, 165 was obtained. MS (ESI) m/z: 508.2 [M+H$^+$].

Example 166

(S)-5-amino-N-(5-(5-amino-3,3-difluoroazepan-1-yl)-1-methyl-1H-pyrazol-4-yl)-2-(2,6-difluorophenyl)thiazole-4-carboxamide 166

Following the procedures of Example 101 and 112, compound 166 was obtained as a single enantiomer from SFC chiral separation of the racemic mixture. ¹H NMR (400 MHz, DMSO) δ 8.83 (s, 1H), 7.59-7.43 (m, 4H), 7.28 (t, J=8.6 Hz, 2H), 3.75-3.54 (m, 4H), 3.25-3.01 (m, 4H), 2.29-2.09 (m, 2H), 1.90-1.77 (m, 1H), 1.77-1.62 (m, 1H). MS (ESI) m/z: 484.1 [M+H⁺].

Example 167

(R)-5-amino-N-(5-(5-amino-3,3-difluoroazepan-1-yl)-1-methyl-1H-pyrazol-4-yl)-2-(2,6-difluorophenyl)thiazole-4-carboxamide 167

Following the procedures of Example 101 and 112, compound 167 was obtained as a single enantiomer from SFC chiral separation of the racemic mixture. ¹H NMR (400 MHz, DMSO) δ 8.84 (s, 1H), 7.59-7.44 (m, 4H), 7.28 (t, J=8.7 Hz, 2H), 3.73-3.57 (m, 4H), 3.26-2.96 (m, 4H), 2.30-2.09 (m, 2H), 1.91-1.79 (m, 1H), 1.79-1.60 (m, 1H). MS (ESI) m/z: 484.1 [M+H⁺].

Example 168

(R)-5-Amino-2-(2,6-difluorophenyl)-N-(1-methyl-5-(3-(trifluoromethyl)piperazin-1-yl)-1H-pyrazol-4-yl)thiazole-4-carboxamide 168

Example 169

(S)-5-amino-2-(2,6-difluorophenyl)-N-(1-methyl-5-(3-(trifluoromethyl)piperazin-1-yl)-1H-pyrazol-4-yl)thiazole-4-carboxamide 169

Step A. (±)-1-(1-Methyl-4-nitro-1H-pyrazol-5-yl)-3-(trifluoromethyl)piperazine

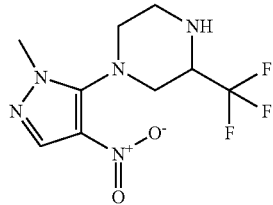 [SMILES: Cn1ncc([N+](=O)[O-])c1N1CCNC(C(F)(F)F)C1]

A mixture of (±)-2-(trifluoromethyl)piperazine (1 g, 6.2 mmol), 5-chloro-1-methyl-4-nitro-1H-pyrazole (2.1 g, 13 mmol), DIPEA (2.4 g, 18.6 mmol) in EtOH (10 mL) was heated in a microwave oven at 140° C. for 5 hours. The reaction mixture was concentrated under reduced pressure to give a residue. The residue was purified by silica gel chromatography using DCM/MeOH (10:1) as eluting solvents to afford (±)-1-(1-methyl-4-nitro-1H-pyrazol-5-yl)-3-(trifluoromethyl)piperazine as a yellow oil (1.8 g, 99%). MS (ESI) m/z: 280 [M+H⁺].

Step B. (±)-1-Methyl-5-(3-(trifluoromethyl)piperazin-1-yl)-1H-pyrazol-4-amine

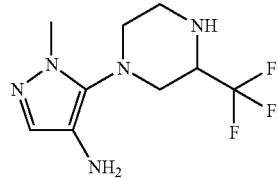 [SMILES: Cn1ncc(N)c1N1CCNC(C(F)(F)F)C1]

To a solution of (±)-1-(1-methyl-4-nitro-1H-pyrazol-5-yl)-3-(trifluoromethyl)piperazine (420 mg, 1.5 mmol) in MeOH (20 mL) and H₂O (5 mL) was added zinc (590 mg, 4 mmol) and NH₄Cl (805 mg, 10 mmol). The reaction mixture was stirred at ambient temperature for 2 hours and filtered through Celite. The filtrate was concentrated under reduced pressure to give a residue. The residue was purified by silica gel chromatography using PE/EtOAc (10/1~1/10) as eluting solvents to afford (±)-1-methyl-5-(3-(trifluoromethyl)piperazin-1-yl)-1H-pyrazol-4-amine (340 mg, 90%) as red solid. ¹H NMR (500 MHz, DMSO-d₆) δ (ppm): 6.84 (s, 1H), 3.38-3.52 (m, 5H), 3.13-3.17 (m, 2H), 2.94-3.00 (m, 2H), 2.50-2.78 (s, 3H), 1.98 (m, 1H); MS (ESI) m/z: 250 (M+1⁺).

Step C. tert-butyl (±)-2-(2,6-difluorophenyl)-4-(1-methyl-5-(3-(trifluoromethyl)piperazin-1-yl)-1H-pyrazol-4-ylcarbamoyl)thiazol-5-ylcarbamate

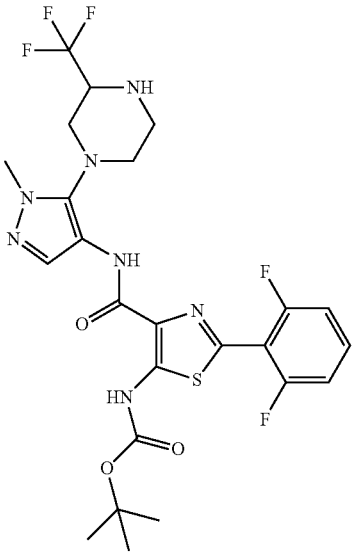 [SMILES: Cn1ncc(NC(=O)c2nc(-c3c(F)cccc3F)sc2NC(=O)OC(C)(C)C)c1N1CCNC(C(F)(F)F)C1]

To a solution of (±)-1-methyl-5-(3-(trifluoromethyl)piperazin-1-yl)-1H-pyrazol-4-amine (300 mg, 2.05 mmol), 5-(tert-butoxycarbonylamino)-2-(2,6-difluorophenyl)thiazole-4-carboxylic acid from Example 25 (516 mg, 1.73 mmol), HATU (0.54 g, 1.73 mmol) in DMF (15 mL) was added TEA (1.1 mL). The reaction mixture was stirred at 25° C. for 20 hours, poured into water (100 mL), and extracted with EtOAc (50 mL×2). The combined organic layers was washed with water (50 mL×2) and brine (30 mL×2), dried over Na₂SO₄, filtered, and concentrated under reduced pressure to give a residue. The residue was purified by silica gel chromatography using DCM/MeOH (1:1) as eluting solvents to afford tert-butyl (±)-2-(2,6-difluorophenyl)-4-(1-methyl-5-(3-(trifluoromethyl)piperazin-1-yl)-1H-pyrazol-4-ylcarbamoyl)thiazol-5-ylcarbamate (380 mg, 52%) as white solid. MS (ESI) m/z: 588 (M+1⁺).

Step D. Chiral separation by using preparative HPLC of tert-butyl (±)-2-(2,6-difluorophenyl)-4-(1-methyl-5-(3-(trifluoromethyl)piperazin-1-yl)-1H-pyrazol-4-ylcarbamoyl)thiazol-5-ylcarbamate (380 mg) afforded tert-Butyl (S)-2-(2,6-difluorophenyl)-4-(1-methyl-5-(3-(trifluoromethyl)piperazin-1-yl)-1H-pyrazol-4-ylcarbamoyl)thiazol-5-ylcarbamate (123 mg) and tert-Butyl (R)-2-(2,6-difluorophenyl)-4-(1-methyl-5-(3-(trifluoromethyl)piperazin-1-yl)-1H-pyrazol-4-ylcarbamoyl)thiazol-5-ylcarbamate (120 mg).

Step E. A mixture of tert-Butyl (S)-2-(2,6-difluorophenyl)-4-(1-methyl-5-(3-(trifluoromethyl)piperazin-1-yl)-1H-pyrazol-4-ylcarbamoyl)thiazol-5-ylcarbamate (80 mg, 0.126 mmol) in TFA (1 mL) and DCM (4 mL) was stirred at ambient temperature for 3 hours. The pH of the mixture was adjusted to about 8~9 by addition of ammonia and concentrated under reduced pressure to give a residue. The residue was purified by preparative HPLC to afford 168 formic acid salt (40 mg, 73%) as a white solid. ¹H NMR (500 MHz, DMSO-d₆) δ (ppm): 8.85 (s, 1H), 7.50-7.56 (m, 3H), 7.37 (s, 1H), 7.25-7.28 (m, 2H), 3.65 (s, 3H), 3.46-3.48 (m, 1H), 3.02-3.14 (m, 3H), 2.92-2.97 (m, 2H), 2.78 (m, 1H), 1.23 (s, 1H); MS (ESI) m/z=488.1 (M+1⁺).

Step F. A mixture of tert-Butyl (R)-2-(2,6-difluorophenyl)-4-(1-methyl-5-(3-(trifluoromethyl)piperazin-1-yl)-1H-pyrazol-4-ylcarbamoyl)thiazol-5-ylcarbamate (80 mg, 0.126 mmol) in TFA (1 mL) and DCM (4 mL) was stirred at ambient temperature for 3 hours. The pH of the mixture was adjusted to about 8~9 by addition of ammonia and concentrated under reduced pressure to give a residue. The residue was purified by preparative HPLC to afford 169 formic acid salt (40 mg, 73%) as white solid. ¹H NMR (500 MHz, DMSO-d₆) δ (ppm): 8.84 (s, 1H), 7.50-7.55 (m, 3H), 7.37 (s, 1H), 7.25-7.28 (m, 2H), 3.47 (s, 3H), 3.36-3.48 (m, 1H), 3.07-3.16 (m, 3H), 2.94-2.96 (m, 2H), 2.78-2.80 (m, 1H), 1.24 (s, 1H); MS (ESI) m/z=488.1 (M+1⁺).

Example 170

(S)-5-amino-N-(1-(2,2-difluoroethyl)-5-(3-hydroxyazepan-1-yl)-1H-pyrazol-4-yl)-2-(2,6-difluorophenyl)thiazole-4-carboxamide 170

Following the procedures of Example 101 or 112, compound 170 was obtained as a single enantiomer from SFC chiral separation of the racemic mixture. ¹H NMR (400 MHz, DMSO) δ 8.84 (s, 1H), 7.71 (s, 1H), 7.56-7.52 (m, 1H), 7.51 (s, 2H), 7.27 (m, 2H), 6.39 (tt, J=55.4, 4.1 Hz, 1H), 4.63 (d, J=3.9 Hz, 1H), 4.60-4.50 (m, 1H), 4.42-4.31 (m, 1H), 3.70 (d, J=3.8 Hz, 1H), 3.18 (ddd, J=17.8, 12.9, 4.7 Hz, 2H), 3.11-3.02 (m, 2H), 1.91-1.82 (m, 1H), 1.77 (dd, J=17.4, 10.6 Hz, 1H), 1.67 (m, 2H), 1.60-1.47 (m, 2H). ESIMS m/z=499.1 (M+1).

Example 171

(R)-5-amino-N-(1-(2,2-difluoroethyl)-5-(3-hydroxyazepan-1-yl)-1H-pyrazol-4-yl)-2-(2,6-difluorophenyl)thiazole-4-carboxamide 171

Following the procedures of Example 101 or 112, compound 171 was obtained as a single enantiomer from SFC chiral separation of the racemic mixture. ¹H NMR (400 MHz, DMSO) δ 8.84 (s, 1H), 7.72 (s, 1H), 7.56-7.52 (m, 1H), 7.51 (s, 2H), 7.27 (m, 2H), 6.39 (tt, J=55.4, 4.1 Hz, 1H), 4.63 (d, J=3.9 Hz, 1H), 4.52 (m, 1H), 4.43-4.32 (m, 1H), 3.75-3.66 (m, 1H), 3.18 (ddd, J=17.8, 12.9, 4.7 Hz, 2H), 3.11-3.02 (m, 2H), 1.91-1.82 (m, 1H), 1.77 (dd, J=17.4, 10.6 Hz, 1H), 1.67 (m, 2H), 1.45 (m, 2H). ESIMS m/z=499.1 (M+1).

Example 172

5-Amino-N-(5-(6,6-difluoro-1,4-diazepan-1-yl)-1-(2,2-difluoroethyl)-1H-pyrazol-4-yl)-2-(2,6-difluorophenyl)thiazole-4-carboxamide 172

Following the procedure for Example 149 and starting from tert-butyl 4-(4-nitro-1-(2,2-difluoroethyl)-1H-pyrazol-5-yl)-6,6-difluoro-1,4-diazepane-1-carboxylate (64 mg, 0.16 mmol), compound 172 was obtained as a pale orange solid (13 mg, 16% over three steps). ¹H NMR (400 MHz, d₆-DMSO) δ 9.45 (s, 1H), 7.72 (s, 1H), 7.60-7.47 (m, 3H), 7.29 (t, J=8.7 Hz, 2H), 6.53-6.21 (m, 1H), 4.45 (td, J=14.5, 4.0 Hz, 2H), 3.56 (t, J=13.6 Hz, 2H), 3.31-3.14 (m, 3H), 2.89 (s, 3H). Alkyl NH not observed. LCMS (ES+) m/z 520 (M+1).

Example 173

5-Amino-N-(5-(6-hydroxy-1,4-diazepan-1-yl)-1-(2,2-difluoroethyl)-1H-pyrazol-4-yl)-2-(2,6-difluorophenyl)thiazole-4-carboxamide 173

Following the procedure for Example 149, starting from tert-butyl 4-(4-nitro-1-(2,2-difluoroethyl)-1H-pyrazol-5-yl)-6-hydroxy-1,4-diazepane-1-carboxylate (18 mg, 0.46 mmol) gave 173 as a colorless solid (78 mg, 34% over three steps). ¹H NMR (400 MHz, d₆-DMSO) δ 11.42 (s, 1H), 8.01 (s, 1H), 7.60 (s, 2H), 7.59-7.48 (m, 1H), 7.30 (t, J=8.7 Hz, 2H), 6.37 (tt, J=55.4, 4.2 Hz, 1H), 4.72 (s, 1H), 4.55-4.30 (m, 2H), 3.65-3.50 (m, 1H), 3.10-2.93 (m, 4H), 2.73-2.63 (m, 2H), 2.45 (dd, J=12.7, 8.8 Hz, 1H). Alkyl NH and OH not observed. LCMS (ES+) m/z 500 (M+1).

Example 174

(S)-5-Amino-2-(2,6-difluorophenyl)-N-(5-(2-methylpiperazin-1-yl)-1-methyl-1H-pyrazol-4-yl)thiazole-4-carboxamide 174

A solution of PyBOP (328 mg, 0.63 mmol) and 5-(tert-butoxycarbonylamino)-2-(2,6-difluorophenyl)thiazole-4-carboxylic acid from Example 25 (176 mg, 0.50 mmol) in DCM (5 mL) was stirred at room temperature for 30 min. A solution of Intermediate 33 (S)-tert-butyl 4-(4-amino-1-(4-methoxybenzyl)-1H-pyrazol-5-yl)-3-methylpiperazine-1-carboxylate (181 mg, 0.45 mmol) and DIPEA (0.13 mL, 0.72 mmol) in DCM (5 mL) was added and the mixture stirred at room temperature for 65 hr. The mixture was diluted with DCM (40 mL) and washed with water (15 mL). The organic layer was separated, passed through a phase separation cartridge and concentrated under reduced pressure. Purification via silica gel column chromatography (0-100% EtOAc/isohexane) gave (S)-tert-butyl 4-(4-(5-(tert-butoxycarbonylamino)-2-(2,6-difluorophenyl)thiazole-4-carboxamido)-1-(4-methoxybenzyl)-1H-pyrazol-5-yl)-3-methylpiperazine-1-carboxylate as a yellow solid (150 mg). This solid was re-dissolved in DCM (10 mL) and TFA (2 mL) was added before being heated at 65° C. for 2.5 hr. The mixture was concentrated under reduced pressure before being re-dissolved in 7 N ammonia in MeOH (20 mL) and heated in a sealed pressure vessel behind a blast shield at 55° C. for 16 hr. The mixture was concentrated under reduced pressure, redissolved in MeOH and passed through an SCX column, washing with DCM and MeOH and eluting with 3-10% 7 N ammonia in MeOH/DCM to give 174 as an off-white solid (60 mg, 32% over two steps). $^1$H NMR (400 MHz, d$_4$-MeOD) δ 8.03 (s, 1H), 7.51-7.41 (m, 1H), 7.16 (t, J=8.9 Hz, 2H), 3.20-3.14 (m, 1H), 3.08-2.98 (m, 5H), 2.64 (dd, J=12.7, 9.4 Hz, 1H), 0.93 (d, J=6.2 Hz, 3H). LCMS (ES+) m/z 420 (M+1).

Example 175

(R)-5-Amino-2-(2,6-difluorophenyl)-N-(5-(2-methylpiperazin-1-yl)-1-methyl-1H-pyrazol-4-yl)thiazole-4-carboxamide 175

Following the procedure for Example 174, tert-butyl 4-(4-amino-1-(4-methoxybenzyl)-1H-pyrazol-5-yl)piperazine-1-carboxylate and 5-(tert-butoxycarbonyl-amino)-2-(2,6-difluorophenyl)thiazole-4-carboxylic acid gave 175 as a white solid (29 mg, 15% over two steps). $^1$H NMR (400 MHz, d$_4$-MeOD) δ 8.03 (s, 1H), 7.50-7.44 (m, 1H), 7.16 (t, J=8.9 Hz, 2H), 3.20-3.14 (m, 1H), 3.09-2.99 (m, 5H), 2.64 (dd, J=12.6, 9.3 Hz, 1H), 0.93 (d, J=6.2 Hz, 3H). LCMS (ES+) m/z 420 (M+1).

Example 176

(S)-5-Amino-2-(2,6-difluorophenyl)-N-(5-(2-ethyl-4-methylpiperazin-1-yl)-1-methyl-1H-pyrazol-4-yl)thiazole-4-carboxamide 176

Following the procedure for Example 110 starting from (S)-5-(2-ethyl-4-methylpiperazin-1-yl)-1-methyl-1H-pyrazol-4-amine and 5-(tert-butoxycarbonylamino)-2-(2,6-difluorophenyl)thiazole-4-carboxylic acid from Example 25 gave 176 as a lilac solid (53 mg, 31%). $^1$H NMR (400 MHz, CDCl$_3$) δ 8.58 (s, 1H), 7.88 (s, 1H), 7.37-7.27 (m, 1H), 7.01 (t, J=8.8 Hz, 2H), 6.16 (s, 2H), 3.76 (s, 3H), 3.32 (t, J=11.3 Hz, 1H), 3.22 (t, J=9.3 Hz, 1H), 2.96 (t, J=12.9 Hz, 2H), 2.79 (d, J=11.0 Hz, 1H), 2.42-2.22 (m, 4H), 1.96 (t, J=10.2 Hz, 1H), 1.41-1.33 (m, 1H), 1.29-1.15 (m, 1H), 0.80 (t, J=7.5 Hz, 3H). LCMS (ES+) m/z 462 (M+1).

Example 176

(R)-5-Amino-2-(2,6-difluorophenyl)-N-(5-(2-ethyl-4-methylpiperazin-1-yl)-1-methyl-1H-pyrazol-4-yl)thiazole-4-carboxamide 176

Following the procedure for Example 110, (R)-5-(2-ethyl-4-methylpiperazin-1-yl)-1-methyl-1H-pyrazol-4-amine and 5-(tert-butoxycarbonylamino)-2-(2,6-difluorophenyl)thiazole-4-carboxylic acid from Example 25 gave 176 as a white solid (47 mg, 28% over two steps). $^1$H NMR (400 MHz, CDCl$_3$) δ 8.58 (s, 1H), 7.87 (s, 1H), 7.37-7.25 (m, 1H), 7.01 (t, J=8.8 Hz, 2H), 6.17 (s, 2H), 3.76 (s, 3H), 3.33 (t, J=11.3 Hz, 1H), 3.22 (t, J=9.2 Hz, 1H), 2.97 (t, J=12.7 Hz, 2H), 2.79 (d, J=11.0 Hz, 1H), 2.41-2.22 (m, 4H), 1.96 (t, J=10.2 Hz, 1H), 1.41-1.33 (m, 1H), 1.28-1.13 (m, 1H), 0.80 (t, J=7.5 Hz, 3H). LCMS (ES+) m/z 462 (M+1).

Example 178

5-Amino-2-(2-fluoro-5-methylphenyl)-N-(5-(4-hydroxy-4-methylazepan-1-yl)-1-methyl-1H-pyrazol-4-yl)thiazole-4-carboxamide 178

Following the procedure for Example 105, starting from tert-butyl 2-bromo-4-(5-(4-hydroxy-4-methylazepan-1-yl)-1-methyl-1H-pyrazol-4-ylcarbamoyl)thiazol-5-ylcarbamate gave 178 as an off-white solid (60 mg, 25% over two steps) $^1$H NMR (400 MHz, d$_4$-MeOD) δ 8.06 (d, J=7.3 Hz, 1H), 7.59 (s, 1H), 7.24-7.19 (m, 1H), 7.11 (dd, J=11.4, 8.4 Hz, 1H), 3.75 (s, 3H), 3.51-3.48 (m, 1H), 3.26-3.17 (m, 1H), 3.09-3.01 (m, 1H), 2.41 (s, 3H), 2.16-2.04 (m, 1H), 1.96-1.83 (m, 4H), 1.78-1.68 (m, 1H), 1.26 (s, 3H) (1 proton coincident with solvent peak). LCMS (ES+) m/z 459 (M+1).

Example 179

5-Amino-N-(5-(6-fluoro-1,4-diazepan-1-yl)-1-(2,2-difluoroethyl)-1H-pyrazol-4-yl)-2-(2,6-difluorophenyl)thiazole-4-carboxamide 179

Following the procedure for Example 149, starting from tert-butyl 4-(4-amino-1-(2,2-difluoroethyl)-1H-pyrazol-5-yl)-6-fluoro-1,4-diazepane-1-carboxylate (366 mg, 0.93 mmol) gave 179 as a pale yellow solid (40 mg, 10% over three steps). $^1$H NMR (400 MHz, d$_6$-DMSO) δ 10.26 (s, 1H), 7.88 (s, 1H), 7.66-7.52 (m, 3H), 7.34 (t, J=8.9 Hz, 2H), 6.42 (t, J=55.3 Hz, 1H), 4.71 (d, J=47.8 Hz, 1H), 3.61-3.41 (m, 2H), 3.42-3.04 (m, 4H), 3.05 (t, J=16.5 Hz, 1H), 2.83-2.57 (m, 3H). Alkyl NH not observed. LCMS (ES+) m/z 502 (M+1).

Example 180

(R)-3-amino-N-(5-(4-aminoazepan-1-yl)-1-(2,2-difluoroethyl)-1H-pyrazol-4-yl)-6-(2-fluorophenyl)picolinamide 180

Following the procedures of Examples 101 or 112, (R)-3-amino-6-bromo-N-(1-(2,2-difluoroethyl)-5-(4-(2,2,2-trifluoroacetamido)azepan-1-yl)-1H-pyrazol-4-yl)picolinamide was prepared. In a microwave reaction tube, (R)-3-amino-6-bromo-N-(1-(2,2-difluoroethyl)-5-(4-(2,2,2-trifluoroacetamido)azepan-1-yl)-1H-pyrazol-4-yl)picolinamide (284 mg, 0.51 mmol), (2-fluorophenyl)boronic acid (215 mg, 1.54 mmol), and Pd(dppf)$_2$Cl$_2$ (37 mg, 0.051 mmol) were dissolved in acetonitrile (4 mL). 1.0M potassium acetate (0.77 mL, 0.77 mmol) and 1.0 M sodium carbonate (0.77 mL, 0.77 mmol) were added. The mixture was irradiated under microwave at 120° C. for 30 min. It was cooled and filtered through Celite and washed with methanol. The filtrate was concentrated and purified by flash chromatography eluting with 0 to 10% methanol in methylene chloride to give (R)-3-amino-N-(1-(2,2-difluoroethyl)-5-(4-(2,2,2-trifluoroacetamido)azepan-1-yl)-1H-pyrazol-4-yl)-6-(2-fluorophenyl)picolinamide (98 mg, 33%).

(R)-3-amino-N-(1-(2,2-difluoroethyl)-5-(4-(2,2,2-trifluoroacetamido)azepan-1-yl)-1H-pyrazol-4-yl)-6-(2-fluorophenyl)picolinamide (98 mg, 0.17 mmol) was stirred with potassium carbonate (144 mg, 1.03 mmol) in methanol (5 mL) at 50° C. overnight. The mixture was filtered and the filtrate was purified on reversed phase HPLC to give 180. $^1$H NMR (400 MHz, DMSO) δ 9.81 (s, 1H), 8.00 (td, J=8.3, 1.8 Hz, 1H), 7.86 (s, 1H), 7.74 (dd, J=8.7, 2.2 Hz, 1H), 7.43 (dt, J=7.2, 3.8 Hz, 1H), 7.38-7.20 (m, 4H), 7.08 (s, 2H), 6.38 (tt, J=55.3, 4.1 Hz, 1H), 4.43 (td, J=14.5, 4.1 Hz, 2H), 3.55 (s, 1H), 3.21-3.07 (m, 4H), 2.92 (dd, J=19.4, 10.4 Hz, 1H), 1.89-1.69 (m, 3H), 1.69-1.37 (m, 3H). MS (ESI) m/z: 474.2 [M+H$^+$].

Example 181

(S)-5-amino-2-(2,6-difluorophenyl)-N-(5-(3-hydroxyazepan-1-yl)-1-methyl-1H-pyrazol-4-yl)thiazole-4-carboxamide 181

Following the procedures described herein, compound 181 was prepared. $^1$H NMR (400 MHz, DMSO) δ 8.78 (s, 1H), 7.59 (s, 1H), 7.51 (d, J=12.3 Hz, 3H), 7.27 (t, J=8.7 Hz, 2H), 4.55 (d, J=4.1 Hz, 1H), 3.68 (m, 1H), 3.66 (s, 3H), 3.20-3.10 (m, 2H), 3.05 (dd, J=13.6, 7.4 Hz, 2H), 2.07-1.55 (m, 6H). ESIMS m/z=449.1 (M+1).

Example 182

(R)-5-amino-2-(2,6-difluorophenyl)-N-(5-(3-hydroxyazepan-1-yl)-1-methyl-1H-pyrazol-4-yl)thiazole-4-carboxamide 182

Following the procedures described herein, compound 182 was prepared. $^1$H NMR (400 MHz, DMSO) δ 8.78 (s, 1H), 7.59 (s, 1H), 7.49 (m, 3H), 7.28 (d, J=8.8 Hz, 2H), 4.55 (d, J=4.0 Hz, 1H), 3.68 (m, 1H) 3.66 (s, 3H), 3.23-3.11 (m, 2H), 3.05 (dd, J=13.6, 7.4 Hz, 2H), 1.95-1.82 (m, 1H), 1.81-1.61 (m, 3H), 1.61-1.47 (m, 2H). ESIMS m/z=449.1 (M+1).

Example 183

5-Amino-N-(5-(3,3-difluoro-5-(methylamino)azepan-1-yl)-1-methyl-1H-pyrazol-4-yl)-2-(2,6-difluorophenyl)thiazole-4-carboxamide 183

Following the procedure for Example 101, starting from tert-butyl 6,6-difluoro-1-(1-methyl-4-nitro-1H-pyrazol-5-yl)azepan-4-yl(methyl)carbamate gave, after silica gel column chromatography (0-10% MeOH/DCM, 1% 7 N ammonia in MeOH), 183 as a white solid (122 mg, 48% over three steps). $^1$H NMR (400 MHz, d$_6$-DMSO) δ 8.85 (s, 1H), 7.59-7.49 (m, 4H), 7.33-7.23 (m, 2H), 3.80-3.57 (m, 4H), 3.48-3.24 (m, 2H), 3.14-3.03 (m, 1H), 2.90-2.80 (m, 1H), 2.50-2.04 (m, 5H), 1.95 (d, J=13.9 Hz, 1H), 1.77-1.65 (m, 1H). Alkyl NH not observed. LCMS (ES+) m/z 498 (M+1).

Example 184

5-Amino-N-(5-((3R,5S)-3-amino-5-fluoropiperidin-1-yl)-1-methyl-1H-pyrazol-4-yl)-2-(2,6-difluorophenyl)thiazole-4-carboxamide 184

A mixture of tert-butyl (3R,5S)-1-(4-(5-(tert-butoxycarbonylamino)-2-(2,6-difluorophenyl)thiazole-4-carboxamido)-1-methyl-1H-pyrazol-5-yl)-5-fluoropiperidin-3-ylcarbamate (200 mg, 0.31 mmol) in HCl/MeOH (10 mL) was stirred at ambient temperature for 20 hours and concentrated under reduced pressure to give a residue. The residue was diluted with MeOH (10 mL), neutralized with 28% ammonia solution, and concentrated to give a crude product. The crude product was purified by preparative HPLC to afford 184 as pale solid (138 mg, 99%). $^1$H NMR (500 MHz, CD$_3$OD) δ (ppm): 7.60 (s, 1H), 7.50-7.45 (m, 1H), 7.14-7.11 (m, 2H), 5.36-5.23 (m, 1H), 3.84-3.74 (m, 2H), 3.63-3.49 (m, 2H), 2.72-2.62 (m, 2H), 2.54-5.41 (m, 1H), 2.16-2.05 (m, 1H); MS (ESI) m/z: 452 [M+H$^+$].

Example 185

(R)-5-amino-N-(5-(4-aminoazepan-1-yl)-1-(2,2,2-trifluoroethyl)-1H-pyrazol-4-yl)-2-(2,6-difluorophenyl)thiazole-4-carboxamide 185

Following the procedure for Example 107, starting from (R)-tert-butyl 2-(2,6-difluorophenyl)-4-(5-(4-(2,2,2-trifluoroacetamido)azepan-1-yl)-1-(2,2,2-trifluoroethyl)-1H-pyrazol-4-ylcarbamoyl)thiazol-5-ylcarbamate (148 mg, 0.21 mmol) gave 185 as an orange solid (69 mg, 65% over two steps). $^1$H NMR (400 MHz, d$_6$-DMSO) δ 9.0 (br s, 1H), 7.79 (s, 1H), 7.60-7.48 (m, 3H), 7.33-7.25 (m, 2H), 4.84 (q, J=9.1 Hz, 2H), 3.15-3.10 (m, 4H), 3.04-2.97 (m, 1H), 1.88-1.73 (m, 3H), 1.65-1.45 (m, 3H). Alkyl NH$_2$ not observed. LCMS (ES+) m/z 516 (M+1).

Example 186

N-(5-(1,4-Diazepan-1-yl)-1-(2,2,2-trifluoroethyl)-1H-pyrazol-4-yl)-5-amino-2-(2,6-difluorophenyl)thiazole-4-carboxamide 186

Following the procedure for Example 145, starting from tert-butyl 4-(4-nitro-1-(2,2,2-trifluoroethyl)-1H-pyrazol-5-yl)-1,4-diazepane-1-carboxylate (197 mg, 0.5 mmol) gave, after trituration in 5% MeOH in Et$_2$O, 186 as the bis-hydrochloride salt and orange solid (48 mg, 19% over three steps). $^1$H NMR (400 MHz, d$_6$-DMSO) δ 9.22 (br s, 2H), 8.91 (s, 1H), 7.60 (s, 1H), 7.60-7.52 (m, 3H), 7.34-7.24 (m, 2H), 5.02 (q, J=9.1 Hz, 2H), 3.43-3.12 (m, 8H), 2.02-1.95 (m, 2H). LCMS (ES+) m/z 502 (M+1). Alkyl NH not observed.

Example 187

5-Amino-N-(5-(4-amino-5-hydroxyazepan-1-yl)-1-methyl-1H-pyrazol-4-yl)-2-(2,6-difluorophenyl)thiazole-4-carboxamide 187

Following the procedure for Example 107, starting from N-(1-(4-amino-1-methyl-1H-pyrazol-5-yl)-5-hydroxyazepan-4-yl)-2,2,2-trifluoroacetamide gave 187 as a beige solid (119 mg, 49% over two steps). $^1$H NMR (400 MHz, d$_6$-DMSO) δ 8.83 (s, 1H), 7.60-7.47 (m, 4H), 7.28 (t, J=8.8 Hz, 2H), 3.64 (s, 3H), 3.50-3.05 (m, 8H), 2.81 (t, J=8.7 Hz, 1H), 2.00-1.84 (m, 2H), 1.78-1.67 (m, 1H), 1.65-1.56 (m, 1H). LCMS (ES+) m/z 464 (M+1).

Example 188

5-amino-N-(5-(3,3-difluoroazepan-1-yl)-1-methyl-1H-pyrazol-4-yl)-2-(2,6-difluorophenyl)thiazole-4-carboxamide 188

Following the procedures described herein, compound 188 was prepared. $^1$H NMR (400 MHz, DMSO) δ 8.74 (s, 1H), 7.56 (s, 1H), 7.52-7.46 (m, 2H), 7.31-7.23 (m, 2H), 3.67 (s, 3H), 3.52 (t, J=13.2 Hz, 2H), 3.16 (t, J=6.0 Hz, 2H), 2.23-2.09 (m, 2H), 1.82-1.68 (m, 4H). ESIMS m/z=469.1 (M+1)

Example 189

5-Amino-N-(5-((3S,5S)-3-amino-5-fluoropiperidin-1-yl)-1-methyl-1H-pyrazol-4-yl)-2-(2,6-difluorophenyl)thiazole-4-carboxamide 189

A mixture of tert-butyl (3S,5S)-1-(4-(5-(tert-butoxycarbonylamino)-2-(2,6-difluorophenyl)thiazole-4-carboxamido)-1-methyl-1H-pyrazol-5-yl)-5-fluoropiperidin-3-ylcarbamate (208 mg, 0.32 mmol) in HCl/MeOH (10 mL) was stirred at ambient temperature for 20 hours and concentrated reduced pressure to give a residue. The residue was diluted with MeOH (10 mL), neutralized with 28% ammonia solution, and concentrated to give a crude product. The crude product was purified by preparative HPLC to afford 189 (130 mg, 90%) as solid. $^1$H NMR (500 MHz, DMSO) δ (ppm): 8.82 (s, 1H), 7.56-7.51 (m, 3H), 7.41 (s, 1H), 7.30-7.26 (m, 2H), 4.80-4.65 (m, 1H), 3.64 (s, 3H), 3.06-2.98 (m, 2H), 2.89-2.84 (m, 1H), 2.70-2.66 (m, 1H), 2.23-2.18 (m, 1H), 1.72 (br s, 3H), 1.41-1.32 (m, 1H); MS (ESI) m/z: 452 [M+H$^+$].

Example 190

5-Amino-2-(2,6-difluorophenyl)-N-(5-(6-hydroxy-6-methyl-1,4-diazepan-1-yl)-1-methyl-1H-pyrazol-4-yl)thiazole-4-carboxamide 190

To a solution of Intermediate 44, tert-butyl 6-hydroxy-6-methyl-4-(1-methyl-4-nitro-1H-pyrazol-5-yl)-1,4-diazepane-1-carboxylate (70 mg, 0.20 mmol) in MeOH (5 mL), was added 10% palladium on carbon (10 mg) and the mixture was stirred under an atmosphere of H$_2$ (60 psi) for 16 hr. The mixture was filtered through Celite® and the solvent was removed under reduced pressure to afford tert-butyl 4-(4-amino-1-methyl-1H-pyrazol-5-yl)-6-hydroxy-6-methyl-1,4-diazepane-1-carboxylate as an oil. To a solution of this amine in DCM (5 mL), DIPEA (0.1 mL, 9.6 mmol), PyBOP (0.16 g, 0.3 mmol) and 5-(tert-butoxycarbonylamino)-2-(2,6-difluorophenyl)-thiazole-4-carboxylic acid (78 mg, 0.22 mmol) were added and the mixture was stirred at room temperature for 18 hr. The mixture was diluted with DCM (30 mL) and washed with water (10 mL). The organic layer was separated, dried over MgSO$_4$ and the solvent removed under reduced pressure. Purification via silica gel column chromatography (0-60% EtOAc/isohexane) gave tert-butyl 4-(4-(5-(tert-butoxycarbonylamino)-2-(2,6-difluorophenyl)thiazole-4-carboxamido)-1-methyl-1H-pyrazol-5-yl)-6-hydroxy-6-methyl-1,4-diazepane-1-carboxylate as a solid (122 mg). To this solid (122 mg, 0.18 mmol) in MeOH (1 mL), a solution of HCl (4 M in 1,4-dioxane, 3.2 mL, 12.9 mmol) was added and the resulting solution was stirred at room temperature for 16 hr. The solvents were removed under reduced pressure and the crude residue was dissolved in MeOH and loaded onto an SCX column. The column was washed with MeOH and eluted with 7 N ammonia in MeOH. Purification by preparative HPLC gave 190 as an off-white solid (40 mg, 44% over three steps). $^1$H NMR (400 MHz, d$_6$-DMSO) δ 9.19 (s, 1H), 8.24 (s, 1H), 7.59-7.48 (m, 3H), 7.33-7.23 (m, 2H), 3.69 (s, 3H), 3.26-3.02 (m, 4H), 2.98-2.73 (m, 4H), 1.01 (s, 3H). Alkyl NH and OH not observed. LCMS (ES+) m/z 464 (M+1).

Example 191

5-Amino-2-(2,6-difluorophenyl)-N-(5-(6-fluoro-6-methyl-1,4-diazepan-1-yl)-1-methyl-1H-pyrazol-4-yl)thiazole-4-carboxamide 191

Following the procedure for Example 101, starting from tert-butyl 6-fluoro-6-methyl-4-(1-methyl-4-nitro-1H-pyrazol-5-yl)-1,4-diazepane-1-carboxylate, after silica gel column chromatography (0-10% MeOH/DCM, 1% 7 N ammonia in MeOH), gave 191 as a beige solid (51 mg, 39% over three steps). $^1$H NMR (400 MHz, d$_6$-DMSO) δ 9.37 (s, 1H), 7.62-7.48 (m, 4H), 7.34-7.24 (m, 2H), 3.68 (s, 3H), 3.16 (t, J=6.4 Hz, 4H), 3.03-2.79 (m, 4H), 1.21 (d, J=21.2 Hz, 3H). LCMS (ES+) m/z 466 (M+1).

Example 192

5-Amino-2-(2,6-difluorophenyl)-N-(5-(6-methoxy-6-methyl-1,4-diazepan-1-yl)-1-methyl-1H-pyrazol-4-yl)thiazole-4-carboxamide 192

To a cooled (ice-water bath) solution of Intermediate 44, tert-butyl 6-hydroxy-6-methyl-4-(1-methyl-4-nitro-1H-pyrazol-5-yl)-1,4-diazepane-1-carboxylate (70 mg, 0.20 mmol) in DMF (1 mL) under nitrogen, was added sodium hydride (60% in mineral oil, 9.5 mg, 0.24 mmol) and the mixture stirred for 10 min. Iodomethane (0.04 mL, 0.6 mmol) was added and the mixture stirred at room temperature for 16 hr. Additional sodium hydride (60% in mineral oil, 9.5 mg, 0.24 mmol) was added and the mixture stirred for 30 min before the addition of more iodomethane (0.04 mL, 0.6 mmol). After 5 hr, water (30 mL) was added and the mixture extracted with EtOAc (2×5 mL). The combined organic layers were dried over Na$_2$SO$_4$ and the solvent removed under reduced pressure to afford tert-butyl 6-methoxy-6-methyl-4-(1-methyl-4-nitro-1H-pyrazol-5-yl)-1,4-diazepane-1-carboxylate as an oil. A solution of this oil in MeOH (4 mL) was passed through the H-Cube® (full H$_2$, 60° C., flow rate: 1 mL/min, 30 mm 10% Pd/C cartridge). The solvent was removed under reduced pressure to afford tert-butyl 4-(4-amino-1-methyl-1H-pyrazol-5-yl)-6-methoxy-6-methyl-1,4-diazepane-1-carboxylate as an oil. To a solution of this amine in DCM (10 mL) was added DIPEA (0.1 mL, 9.6 mmol), PyBOP (160 mg, 0.30 mmol) and 5-(tert-butoxycarbonylamino)-2-(2,6-difluorophenyl)thiazole-4-carboxylic acid from Example 25 (78 mg, 0.22 mmol) and the mixture was stirred at room temperature for 18 hr. The mixture was diluted with DCM (30 mL) and washed with water (20 mL). The organic layer was separated, dried over MgSO$_4$ and the solvent removed under reduced pressure. Purification via silica gel column chromatography (75% EtOAc/isohexane) gave tert-butyl 4-(4-(5-(tert-butoxycarbonylamino)-2-(2,6-difluorophenyl)thiazole-4-carboxamido)-1-methyl-1H-pyrazol-5-yl)-6-methoxy-6-methyl-1,4-diazepane-1-carboxylate as a beige solid (123 mg). This solid (120 mg, 0.30 mmol) was stirred with HCl in 1,4-dioxane (4 M, 2.3 mL, 9.1 mmol) in MeOH (1 mL) at room temperature for 16 hr. The solvents were removed under reduced pressure and the crude residue was re-dissolved in MeOH and loaded onto an SCX column. The column was washed with MeOH and eluted with 7 N ammonia in MeOH and the residue was purified via silica gel column chromatography (0-10% MeOH/DCM, 1% 7 N ammonia in MeOH). Further purification by preparative HPLC gave 192 as the monoformate salt as an off-white solid (19 mg, 20% over four steps). $^1$H NMR (400 MHz, d$_6$-DMSO) δ 9.38 (s, 1H), 8.21 (s, 1H), 7.66 (s, 1H), 7.60-7.48 (m, 3H), 7.33-7.23 (m, 2H), 3.67 (t, J=4.9 Hz, 3H), 3.29-2.69 (m, 11H), 0.97 (s, 3H). Alkyl NH not observed. LCMS (ES+) m/z 477 (M+1).

Example 193

5-Amino-N-(5-(6,6-difluoro-1,4-diazepan-1-yl)-1H-pyrazol-4-yl)-2-(2,6-difluorophenyl)thiazole-4-carboxamide 193

Following the procedure for Example 101, starting from tert-butyl 6,6-difluoro-4-(4-nitro-1-(2-(trimethylsilyl)

ethoxy)methyl)-1H-pyrazol-5-yl)-1,4-diazepane-1-carboxylate gave, after silica gel column chromatography (0-10% MeOH/DCM, 1% 7 N ammonia in MeOH) and preparative HPLC, 193 as an off-white solid (86 mg, 25% over three steps). $^1$H NMR (400 MHz, d$_6$-DMSO) δ 11.99 (s, 1H), 8.53 (s, 1H), 7.85 (s, 1H), 7.59-7.47 (m, 3H), 7.32-7.24 (m, 2H), 3.70 (t, J=13.9 Hz, 2H), 3.22-3.10 (m, 4H), 2.96-2.91 (m, 2H), 2.80-2.73 (s, 1H). LCMS (ES+) m/z 456 (M+1).

Example 194

5-Amino-2-(2,6-difluorophenyl)-N-(5-(6-methoxy-1,4-diazepan-1-yl)-1-methyl-1H-pyrazol-4-yl)thiazole-4-carboxamide 194

A solution of Intermediate 47, tert-butyl 6-methoxy-4-(1-methyl-4-nitro-1H-pyrazol-5-yl)-1,4-diazepane-1-carboxylate (114 mg, 0.32 mmol) in MeOH (15 mL) was passed through the H-Cube® (full H$_2$, 70° C., flow rate: 1 mL/min, 30 mm 10% Pd/C cartridge). The solvent was removed under reduced pressure to afford tert-butyl 4-(4-amino-1-methyl-1H-pyrazol-5-yl)-6-methoxy-1,4-diazepane-1-carboxylate as a pink solid (100 mg). To a solution of this solid in DCM (5 mL) was added DIPEA (0.84 mL, 48 mmol), PyBOP (219 mg, 0.42 mmol) and 5-(tert-butoxycarbonylamino)-2-(2,6-difluorophenyl)thiazole-4-carboxylic acid from Example 25 (118 mg, 0.33 mmol) and the mixture was stirred at room temperature for 65 hr. The mixture was diluted with DCM (50 mL) and washed with water (10 mL). The organic layer was separated, passed through a phase separation cartridge and concentrated under reduced pressure. Purification via silica gel column chromatography (0-5% MeOH/DCM) gave tert-butyl 4-(4-(5-(tert-butoxycarbonylamino)-2-(2,6-difluorophenyl)thiazole-4-carboxamido)-1-methyl-1H-pyrazol-5-yl)-6-methoxy-1,4-diazepane-1-carboxylate as a pink solid (160 mg). This solid (159 mg, 0.24 mmol) was dissolved in HCl in 1,4-dioxane (4 M, 3 mL, 12.0 mmol) and MeOH (3 mL) and heated in a sealed pressure vessel behind a blast shield at 60° C. for 16 hr. The solvents were removed under reduced pressure and the crude residue re-dissolved in MeOH and loaded onto an SCX column. The column was washed with MeOH and eluted with 0-10% 7 N ammonia in MeOH/DCM to give 194 as a pale brown solid (53 mg, 36% over three steps). $^1$H NMR (400 MHz, CDCl$_3$) δ 11.35 (s, 1H), 8.13 (s, 1H), 7.39-7.29 (m, 1H), 7.04 (t, J=8.6 Hz, 2H), 6.33 (s, 2H), 3.74 (s, 3H), 3.41-3.28 (m, 4H), 3.36-3.00 (m, 6H), 2.88-2.77 (m, 1H), 2.69 (dd, J=12.7, 7.6 Hz, 1H). Alkyl NH not observed. LCMS (ES+) m/z 464 (M+1).

Example 195

5-Amino-N-(5-(4-amino-5-fluoroazepan-1-yl)-1-methyl-1H-pyrazol-4-yl)-2-(2-fluorophenyl)thiazole-4-carboxamide 195

Following the procedures described herein, Intermediate 49, N-(1-(4-Amino-1-methyl-1H-pyrazol-5-yl)-5-fluoroazepan-4-yl)-2,2,2-trifluoroacetamide and 5-(tert-butoxycarbonyl-amino)-2-(2-fluorophenyl)thiazole-4-carboxylic acid gave 195 as a brown solid (368 mg, 69% over two steps). $^1$H NMR (400 MHz, CDCl$_3$) δ 8.49 (s, 1H), 8.13 (td, J=7.7, 1.8 Hz, 1H), 7.79 (s, 1H), 7.39-7.31 (m, 1H), 7.33-7.17 (m, 1H), 7.17 (dd, J=11.4, 8.3 Hz, 1H), 6.09 (s, 2H), 4.50 (dtd, J=48.0, 8.7, 3.8 Hz, 1H), 3.73 (s, 3H), 3.36-3.19 (m, 5H), 2.34-2.23 (m, 1H), 2.14-2.05 (m, 1H), 2.01-1.93 (m, 1H), 1.78-1.67 (m, 1H). Alkyl NH$_2$ not observed. LCMS (ES+) m/z 448 (M+1).

Example 196

5-Amino-N-(5-(4-amino-5-fluoroazepan-1-yl)-1-methyl-1H-pyrazol-4-yl)-2-(2-fluoro-5-methylphenyl)thiazole-4-carboxamide 196

A solution of PyBOP (1.82 g, 3.5 mmol) and 2-bromo-5-(tert-butoxycarbonyl-amino)thiazole-4-carboxylic acid (889 mg, 2.75 mmol) in DCM (40 mL) was stirred at room temperature for 30 min. A solution of N-(1-(4-amino-1-methyl-1H-pyrazol-5-yl)-5-fluoroazepan-4-yl)-2,2,2-trifluoroacetamide (808 mg, 2.50 mmol) and DIPEA (0.74 mL, 4.25 mmol) in DCM (40 mL) was added and the mixture stirred at room temperature for 16 hr. The mixture was diluted with DCM (50 mL) and washed with water (10 mL). The organic layer was separated, passed through a phase separation cartridge and concentrated under reduced pressure. Purification via silica gel column chromatography (0-5% MeOH/DCM) gave tert-butyl 2-bromo-4-(5-(4-fluoro-5-(tert-butoxycarbonylamino) azepan-1-yl)-1-methyl-1H-pyrazol-4-ylcarbamoyl)thiazol-5-ylcarbamate as a pale brown solid (1.57 g). A mixture of this solid (786 mg, 1.25 mmol), Na$_2$CO$_3$ (265 mg, 2.50 mmol) and 2-fluoro-5-methylbenzeneboronic acid (250 mg, 1.63 mmol) in DME (12 mL) and water (4 mL) was degassed by gently bubbling nitrogen through the mixture for 30 min. [1,1'-Bis(diphenylphosphino)ferrocene]dichloro-palladium (II) (102 mg, 0.125 mmol) was then added and the mixture degassed for a further 10 min before being heated in a microwave at 100° C. for 4 hr. Water (10 mL) was added and the mixture extracted with EtOAc (2×50 mL). The combined organic layers were passed through a phase separation cartridge and concentrated under reduced pressure. Purification via silica gel column chromatography (0-5% MeOH/DCM) gave tert-butyl 4-(5-(4-fluoro-5-(tert-butoxycarbonylamino) azepan-1-yl)-1-methyl-1H-pyrazol-4-ylcarbamoyl)-2-(2-fluoro-5-methylphenyl)thiazol-5-ylcarbamate as a brown solid (600 mg). This solid (591 mg, 0.9 mmol) was dissolved in HCl in 1,4-dioxane (4 M, 10 mL, 40.0 mmol) and MeOH (10 mL) and heated in a sealed pressure vessel behind a blast shield at 60° C. for 16 hr. The solvents were removed under reduced pressure and the residue re-dissolved in MeOH and loaded onto an SCX column. The column was washed with MeOH and eluted with 0-10% 7 N ammonia in MeOH/DCM to give 196 as a pale brown solid (235 mg, 41% over three steps). $^1$H NMR (400 MHz, CDCl$_3$) δ 8.44 (s, 1H), 7.87 (dd, J=7.2, 2.2 Hz, 1H), 7.74 (s, 1H), 7.18-7.12 (m, 1H), 7.05 (dd, J=11.0, 8.4 Hz, 1H), 6.08 (s, 2H), 4.49 (dtd, J=48.0, 8.5, 3.7 Hz, 1H), 3.74 (s, 3H), 3.38-3.19 (m, 5H), 2.40 (s, 3H), 2.31-2.20 (m, 1H), 2.15-2.09 (m, 1H), 2.01-1.94 (m, 1H), 1.74-1.68 (m, 1H). Alkyl NH$_2$ not observed. LCMS (ES+) m/z 462 (M+1).

Example 197

(R)-5-amino-2-(2,6-difluorophenyl)-N-(1-methyl-5-(4-(2,2,2-trifluoroethylamino)azepan-1-yl)-1H-pyrazol-4-yl)thiazole-4-carboxamide 197

(R)-tert-butyl 4-(5-(4-aminoazepan-1-yl)-1-methyl-1H-pyrazol-4-ylcarbamoyl)-2-(2,6-difluorophenyl)thiazol-5-ylcarbamate (112 mg, 0.204 mmol) and 2,2,2-trifluoroethyl trifluoromethanesulfonate (95 mg, 0.409 mmol) were dissolved in methylene chloride/DMF (1.5 mL/1.5 mL). N,N-diisopropylethylamine (132 mg, 1.02 mmol) was added and the reaction mixture was stirred at room temperature overnight. The reaction mixture was concentrated to remove DMF, redissolved in ethyl acetate and washed with brine. The aqueous layer was extracted with ethyl acetate 3×. Combined organic layers were concentrated and purified by flash chromatography eluted with 0 to 100% ethyl acetate in heptane to give (R)-tert-butyl 2-(2,6-difluorophenyl)-4-(1-methyl-5-(4-(2,2,2-trifluoroethylamino)azepan-1-yl)-1H-pyrazol-4-ylcarbamoyl)thiazol-5-ylcarbamate (96 mg, 75%), which was deprotected by 4N HCl in dioxane and purified on reversed phase HPLC to give 197. $^1$H NMR (400 MHz, DMSO) δ 8.65 (s, 1H), 7.59-7.43 (m, 4H), 7.25 (t, J=8.7 Hz, 2H), 3.64 (s, 3H), 3.24-3.01 (m, 6H), 2.81 (s, 1H), 2.14 (d, J=6.1 Hz, 1H), 1.96-1.74 (m, 3H), 1.65-1.48 (m, 3H). MS (ESI) m/z: 530.2 [M+H$^+$].

Example 198

3-amino-N-(5-(6,6-difluoro-1,4-diazepan-1-yl)-1-methyl-1H-pyrazol-4-yl)-6-(2-fluorophenyl)picolinamide 198

Following the procedures of Example 180, compound 198 was prepared. $^1$H NMR (400 MHz, DMSO) δ 9.81 (s, 1H), 8.03 (dd, J=11.2, 4.9 Hz, 1H), 7.72 (dd, J=8.7, 2.3 Hz, 1H), 7.64 (s, 1H), 7.42 (ddd, J=7.4, 6.1, 1.8 Hz, 1H), 7.36-7.24 (m, 3H), 7.07 (s, 2H), 3.70 (s, 3H), 3.59 (t, J=13.8 Hz, 2H), 3.17 (dt, J=18.1, 9.7 Hz, 4H), 2.89 (s, 2H), 2.78 (s, 1H). MS (ESI) m/z: 446.2 [M+H$^+$].

Example 199

(R)-5-amino-2-(2,6-difluorophenyl)-N-(5-(3-fluoroazepan-1-yl)-1-methyl-1H-pyrazol-4-yl)thiazole-4-carboxamide 199

Following the procedures described herein, compound 199 was prepared. $^1$H NMR (400 MHz, DMSO) δ 8.72 (s, 1H), 7.55 (s, 1H), 7.55-7.50 (m, 1H), 7.48 (s, 2H), 7.28 (d, J=8.8 Hz, 2H), 4.85-4.64 (m, 1H), 3.66 (s, 3H), 3.50-3.33 (m, 2H), 3.18-3.05 (m, 2H), 1.96 (ddd, J=23.4, 9.2, 4.8 Hz, 2H), 1.74 (ddt, J=20.0, 14.0, 7.3 Hz, 3H), 1.60-1.46 (m, 1H). ESIMS m/z=451.1 (M+1)

Example 200

(S)-5-amino-2-(2,6-difluorophenyl)-N-(5-(3-fluoroazepan-1-yl)-1-methyl-1H-pyrazol-4-yl)thiazole-4-carboxamide 200

Following the procedures described herein, compound 200 was prepared. $^1$H NMR (400 MHz, DMSO) δ 8.72 (s, 1H), 7.55 (s, 1H), 7.55-7.50 (m, 1H), 7.48 (s, 2H), 7.30-7.23 (m, 2H), 4.91-4.60 (m, 1H), 3.66 (s, 3H), 3.50-3.33 (m, 2H), 3.17-3.08 (m, 2H), 2.01-1.89 (m, 2H), 1.89-1.72 (m, 2H), 1.67 (dd, J=15.2, 9.1 Hz, 1H), 1.60-1.47 (m, 1H). ESIMS m/z=451.1 (M+1)

Example 201

5-amino-2-(2,6-difluorophenyl)-N-(5-(3-hydroxy-3-methylazepan-1-yl)-1-methyl-1H-pyrazol-4-yl)thiazole-4-carboxamide 201

Following the procedures described herein, compound 201 was prepared. $^1$H NMR (400 MHz, DMSO) δ 8.85 (s, 1H), 7.60 (s, 1H), 7.56-7.50 (m, 1H), 7.48 (s, 2H), 7.26 (m, 2H), 4.19 (s, 1H), 3.66 (s, 3H), 3.09 (t, J=6.1 Hz, 2H), 3.03 (s, 2H), 1.85-1.57 (m, 5H), 1.50 (dd, J=14.0, 8.1 Hz, 1H), 1.05 (s, 3H). ESIMS m/z=463.2 (M+1)

Example 202

5-Amino-N-(5-(4-amino-5-fluoroazepan-1-yl)-1-methyl-1H-pyrazol-4-yl)-2-(2,5-difluorophenyl)thiazole-4-carboxamide 202

Following the procedures described herein, compound 202 was prepared as an off-white solid (212 mg, 36% over three steps). $^1$H NMR (400 MHz, CDCl$_3$) δ 8.41 (s, 1H), 7.84 (ddd, J=9.1, 5.8, 3.2 Hz, 1H), 7.78 (s, 1H), 7.13 (td, J=9.7, 4.4 Hz, 1H), 7.07-7.00 (m, 1H), 6.15 (s, 2H), 4.50 (dtd, J=47.9, 8.7, 3.8 Hz, 1H), 3.74 (s, 3H), 3.37-3.21 (m, 5H), 2.32-2.21 (m, 1H), 2.15-1.96 (m, 2H), 1.76-1.70 (m, 1H). Alkyl NH$_2$ not observed. LCMS (ES+) m/z 466 (M+1).

Example 203

5-Amino-N-(5-(4-amino-5-fluoroazepan-1-yl)-1-(2,2-difluoroethyl)-1H-pyrazol-4-yl)-2-(2,6-difluorophenyl)thiazole-4-carboxamide 203

A solution of PyBOP (692 mg, 1.33 mmol) and 5-(tert-butoxycarbonylamino)-2-(2,6-difluorophenyl)thiazole-4-carboxylic acid from Example 25 (372 mg, 1.05 mmol) in DCM (40 mL) was stirred at room temperature for 30 min. A solution of Intermediate 51, N-(1-(4-amino-1-(2,2-difluoroethyl)-1H-pyrazol-5-yl)-5-fluoroazepan-4-yl)-2,2,2-trifluoroacetamide (354 mg, 0.95 mmol) and DIPEA (0.28 mL, 1.62 mmol) in DCM (40 mL) was added and the mixture stirred at room temperature for 16 hr. The mixture was diluted with DCM (50 mL) and washed with water (20 mL). The organic layer was separated, passed through a phase separation cartridge and concentrated under reduced pressure. Purification via silica gel column chromatography (0-5% MeOH/DCM) gave tert-butyl 4-(1-(2,2-difluoroethyl)-5-(4-fluoro-5-(2,2,2-trifluoroacetamido)azepan-1-yl)-1H-pyrazol-4-ylcarbamoyl)-2-(2,6-difluorophenyl)thiazol-5-ylcarbamate as an off-white solid (600 mg, 0.84 mmol) which was dissolved in HCl in 1,4-dioxane (4 M, 10 mL, 40.0 mmol) and MeOH (10 mL) and heated in a sealed pressure vessel behind a blast shield at 60° C. for 16 hr. The solvents were removed under reduced pressure and the residue re-dissolved in MeOH and loaded onto an SCX column. The column was washed with MeOH and eluted with 0-10% 7 N ammonia in MeOH/DCM to give 203 as an off-white solid (197 mg, 40% over two steps). $^1$H NMR (400 MHz, CDCl$_3$) δ 8.75 (s, 1H), 8.00 (s, 1H), 7.37-7.29 (m, 1H), 7.09-6.99 (m, 2H), 6.31-6.01 (m, 3H), 4.56-4.28 (m, 3H), 3.39-3.13 (m, 5H), 2.32-2.17 (m, 1H), 2.14-1.94 (m, 2H), 1.77-1.64 (m, 1H). Alkyl NH$_2$ not observed. LCMS (ES+) m/z 516 (M+1).

Example 204

(R)-5-amino-N-(5-(4-(2,2-difluoroethylamino)azepan-1-yl)-1-methyl-1H-pyrazol-4-yl)-2-(2,6-difluorophenyl)thiazole-4-carboxamide 204

Following the procedures of Example 197, compound 204 was prepared. $^1$H NMR (400 MHz, DMSO) δ 8.66 (s, 1H), 7.61-7.40 (m, 4H), 7.25 (dd, J=14.5, 5.8 Hz, 2H), 5.89 (tt, J=56.6, 4.3 Hz, 1H), 3.64 (s, 3H), 3.22-3.01 (m, 4H), 2.91-2.73 (m, 3H), 1.97-1.75 (m, 3H), 1.64-1.46 (m, 3H). MS (ESI) m/z: 512.2 [M+H$^+$].

Example 205

5-amino-2-(2,6-difluorophenyl)-N-(1-methyl-5-(5-methyl-1,4-diazepan-1-yl)-1H-pyrazol-4-yl)thiazole-4-carboxamide 205

Following the procedures described herein, racemic compound 205 was prepared. $^1$H NMR (400 MHz, DMSO) δ

12.03 (s, 1H), 7.91 (s, 1H), 7.63-7.46 (m, 3H), 7.35-7.21 (m, 2H), 3.60 (s, 3H), 3.22-2.99 (m, 5H), 2.85-2.64 (m, 3H), 1.52-1.35 (m, 1H), 1.31-1.11 (m, 1H), 0.89 (d, J=6.3 Hz, 3H). MS (ESI) m/z: 448.2 [M+H$^+$].

Example 206

(R)-5-amino-2-(2,6-difluorophenyl)-N-(5-(6-fluoro-6-methyl-1,4-diazepan-1-yl)-1-methyl-1H-pyrazol-4-yl)thiazole-4-carboxamide 206

Following the procedures described herein, compound 206 was prepared by chiral separation from its racemic mixture on SFC. $^1$H NMR (400 MHz, DMSO) δ 9.37 (s, 1H), 7.62 (s, 1H), 7.56-7.52 (m, 1H), 7.51 (s, 2H), 7.26 (dd, J=14.5, 5.8 Hz, 2H), 3.66 (s, 3H), 3.34 (s, 1H), 3.12 (dd, J=13.6, 3.1 Hz, 3H), 2.99-2.87 (m, 2H), 2.87-2.73 (m, 2H), 1.19 (d, J=21.2 Hz, 4H). ESIMS m/z=466.1 (M+1)

Example 207

(R)-5-amino-2-(2,6-difluorophenyl)-N-(5-(6-hydroxy-6-methyl-1,4-diazepan-1-yl)-1-methyl-1H-pyrazol-4-yl)thiazole-4-carboxamide 207

Following the procedures described herein, compound 207 was prepared by chiral separation from its racemic mixture on SFC. $^1$H NMR (400 MHz, DMSO) δ 9.20 (s, 1H), 7.60 (s, 1H), 7.54 (dd, J=8.3, 6.3 Hz, 1H), 7.49 (s, 2H), 7.27 (m, 2H), 4.30 (s, 1H), 3.67 (s, 3H), 3.08 (m, 5H), 2.89 (dt, J=11.7, 5.7 Hz, 1H), 2.84-2.76 (m, 1H), 2.74 (s, 2H), 0.99 (s, 3H). ESIMS m/z=464.2 (M+1)

Example 208

(S)-5-amino-2-(2,6-difluorophenyl)-N-(5-(6-hydroxy-6-methyl-1,4-diazepan-1-yl)-1-methyl-1H-pyrazol-4-yl)thiazole-4-carboxamide 208

Following the procedures described herein, compound 208 was prepared by chiral separation from its racemic mixture on SFC. $^1$H NMR (400 MHz, DMSO) δ 9.20 (s, 1H), 7.60 (s, 1H), 7.53 (m, 1H) 7.50 (s, 2H), 7.27 (m, 2H), 4.30 (s, 1H), 3.67 (s, 3H), 3.16-3.00 (m, 5H), 2.89 (dt, J=11.8, 5.8 Hz, 1H), 2.83-2.77 (m, 1H), 2.74 (s, 2H), 0.99 (s, 3H). ESIMS m/z=464.2 (M+1)

Example 209

(S)-5-amino-2-(2,6-difluorophenyl)-N-(5-(6-fluoro-6-methyl-1,4-diazepan-1-yl)-1-methyl-1H-pyrazol-4-yl)thiazole-4-carboxamide 209

Following the procedures described herein, compound 209 was prepared by chiral separation from its racemic mixture on SFC. $^1$H NMR (400 MHz, DMSO) δ 9.37 (s, 1H), 7.62 (s, 1H), 7.56-7.52 (m, 1H), 7.52 (s, 2H), 7.26 (dd, J=14.5, 5.8 Hz, 2H), 3.66 (s, 3H), 3.34 (s, 1H), 3.11 (dd, J=13.6, 3.1 Hz, 3H), 2.98-2.87 (m, 2H), 2.87-2.73 (m, 2H), 1.18 (d, J=21.2 Hz, 4H). ESIMS m/z=466.1 (M+1)

Example 210

5-amino-N-(5-((4S,5S)-4-amino-5-fluoroazepan-1-yl)-1-(2,2-difluoroethyl)-1H-pyrazol-4-yl)-2-(2,6-difluorophenyl)thiazole-4-carboxamide 210

Following the procedures described herein, compound 210 was prepared by chiral separation from its racemic mixture on SFC. $^1$H NMR (400 MHz, DMSO) δ 8.91 (s, 1H), 8.22 (s, 1H), 7.68 (s, 1H), 7.53 (m, 1H), 7.50 (s, 2H), 7.27 (t, J=8.7 Hz, 2H), 6.36 (m, 1H), 4.42 (dd, J=14.3, 4.0 Hz, 2H), 3.25-3.07 (m, 6H), 2.21-2.04 (m, 1H), 1.94 (ddd, J=41.1, 22.7, 8.9 Hz, 2H), 1.75-1.53 (m, 1H). ESIMS m/z=516.1 (M+1)

Example 211

5-amino-N-(5-((4R,5R)-4-amino-5-fluoroazepan-1-yl)-1-(2,2-difluoroethyl)-1H-pyrazol-4-yl)-2-(2,6-difluorophenyl)thiazole-4-carboxamide 211

Following the procedures described herein, compound 211 was prepared by chiral separation from its racemic mixture on SFC. $^1$H NMR (400 MHz, DMSO) δ 8.90 (s, 1H), 8.22 (s, 1H), 7.68 (s, 1H), 7.53 (m, 1H), 7.51 (s, 2H), 7.27 (t, J=8.7 Hz, 2H), 6.36 (m, 1H), 4.42 (dd, J=14.3, 4.0 Hz, 2H), 3.25-3.09 (m, 6H), 2.21-2.04 (m, 1H), 1.94 (ddd, J=41.1, 22.7, 8.9 Hz, 2H), 1.75-1.55 (m, 1H). ESIMS m/z=516.1 (M+1)

Example 212

5-amino-N-(5-((4S,5S)-4-amino-5-fluoroazepan-1-yl)-1-methyl-1H-pyrazol-4-yl)-2-(2-fluoro-5-methylphenyl)thiazole-4-carboxamide 212

Following the procedures described herein, compound 212 was prepared by chiral separation from its racemic mixture on SFC. $^1$H NMR (400 MHz, DMSO) δ 8.95 (s, 1H), 8.07 (d, J=7.7 Hz, 1H), 7.46 (s, 1H), 7.39 (s, 2H), 7.23 (d, J=9.3 Hz, 2H), 4.48 (dtd, J=48.1, 8.3, 3.6 Hz, 1H), 3.65 (s, 3H), 3.15 (ddd, J=13.5, 8.5, 3.3 Hz, 5H), 2.36 (s, 3H), 2.22-2.06 (m, 1H), 2.06-1.92 (m, 1H), 1.91-1.78 (m, 1H), 1.64 (m, 1H). ESIMS m/z=462.2 (M+1)

Example 213

5-amino-N-(5-((4R,5R)-4-amino-5-fluoroazepan-1-yl)-1-methyl-1H-pyrazol-4-yl)-2-(2-fluoro-5-methylphenyl)thiazole-4-carboxamide 213

Following the procedures described herein, compound 213 was prepared by chiral separation from its racemic mixture on SFC. $^1$H NMR (400 MHz, DMSO) δ 8.95 (s, 1H), 8.07 (d, J=7.7 Hz, 1H), 7.45 (s, 1H), 7.39 (s, 2H), 7.23 (d, J=9.3 Hz, 2H), 4.51 (dtd, J=48.1, 8.3, 3.6 Hz, 1H), 3.65 (s, 3H), 3.15 (ddd, J=13.5, 8.5, 3.3 Hz, 5H), 2.36 (s, 3H), 2.22-2.06 (m, 1H), 2.06-1.92 (m, 1H), 1.91-1.78 (m, 1H), 1.64 (m, 1H). ESIMS m/z=462.2 (M+1)

Example 214

3-amino-N-(5-(6,6-difluoro-1,4-diazepan-1-yl)-1-methyl-1H-pyrazol-4-yl)-6-(2-fluorophenyl)pyrazine-2-carboxamide 214

Following the procedures in Example 180, compound 214 was prepared. $^1$H NMR (400 MHz, DMSO) δ 9.93 (s, 1H), 8.67 (s, 1H), 8.12 (t, J=7.9 Hz, 1H), 7.73 (s, 2H), 7.58 (s, 1H), 7.52-7.40 (m, 1H), 7.35 (dd, J=13.3, 5.6 Hz, 2H), 3.70 (s, 3H), 3.58 (t, J=13.8 Hz, 3H), 2.89 (s, 2H), 2.78 (s, 1H). MS (ESI) m/z: 447.2 [M+H$^+$].

Example 215

5-Amino-2-(2,6-difluorophenyl)-N-(5-(5-(dimethylamino)-3,3-difluoroazepan-1-yl)-1-methyl-1H-pyrazol-4-yl)thiazole-4-carboxamide 215

Following the procedure for Example 101, starting from 6,6-difluoro-N,N-dimethyl-1-(1-methyl-4-nitro-1H-pyrazol-5-yl)azepan-4-amine gave, after purification by preparative HPLC, 215 as a white solid (119 mg, 12%). $^1$H NMR (400 MHz, d$_6$-DMSO) δ 8.72 (s, 1H), 7.58-7.48 (m, 4H), 7.31-7.21 (m, 2H), 3.75-3.50 (m, 3H), 3.53-3.22 (m, 2H), 3.16-3.06 (m, 1H), 2.89-2.81 (m, 1H), 2.37-2.19 (m, 2H), 2.10-2.05 (m, 6H), 1.89-1.74 (m, 3H). LCMS (ES+) m/z 512 (M+1).

Example 216

5-Amino-N-(5-(5-amino-3-methoxyazepan-1-yl)-1-methyl-1H-pyrazol-4-yl)-2-(2,6-difluorophenyl)thiazole-4-carboxamide 216

Following the procedure for Example 101, starting from tert-butyl 6-methoxy-1-(1-methyl-4-nitro-1H-pyrazol-5-yl)azepan-4-ylcarbamate gave, after purification by preparative HPLC the monoformate salt of 216 as a white solid (480 mg, 39% over three steps). $^1$H NMR (400 MHz, d$_6$-DMSO) δ 8.92 and 8.79 (2 br s, 1H), 8.43 (s, 1H), 7.61-7.46 (m, 4H), 7.36-7.25 (m, 2H), 3.67 and 3.66 (2s, 3H), 3.54-2.99 (m, 9H), 2.26-2.18 (m, 1H), 2.05-1.91 (m, 1H), 1.86-1.69 (m, 2H). Alkyl NH$_2$ not seen. LCMS (ES+) m/z 478 (M+1).

Example 217

5-amino-N-(5-((4S,5S)-4-amino-5-methoxyazepan-1-yl)-1-methyl-1H-pyrazol-4-yl)-2-(2,6-difluorophenyl)thiazole-4-carboxamide 217

To a solution of Intermediate 54, N-(1-(4-amino-1-methyl-1H-pyrazol-5-yl)-5-methoxyazepan-4-yl)-2,2,2-trifluoroacetamide (150 mg, 0.45 mmol) in DCM (20 mL) was added DIPEA (1.0 mL), PyBOP (580 mg, 1.12 mmol) and 5-(tert-butoxycarbonylamino)-2-(2,6-difluorophenyl)-thiazole-4-carboxylic acid (159 mg, 0.45 mmol) and the mixture was stirred at room temperature for 18 hr. The mixture was diluted with DCM (100 mL) and washed with water (20 mL). The organic layer was separated, dried over MgSO$_4$ and the solvent removed under reduced pressure. Purification via silica gel column chromatography (70-80% EtOAc/isohexane) gave tert-butyl 2-(2,6-difluorophenyl)-4-(5-(4-methoxy-5-(2,2,2-trifluoroacetamido)azepan-1-yl)-1-methyl-1H-pyrazol-4-ylcarbamoyl)thiazol-5-ylcarbamate as an off-white solid (260 mg, 0.39 mmol) which was stirred with HCl in 1,4-dioxane (4 M, 4.8 mL, 19.3 mmol) in MeOH (5 mL) at room temperature for 3 days. The solvent was removed under reduced pressure and the resulting solid was dissolved in MeOH/water (10 mL/10 mL) and to this was added K$_2$CO$_3$ (267 mg, 19.3 mmol). The reaction mixture was heated at 65° C. for 3 hr. The MeOH was removed under reduced pressure and the aqueous residue was diluted with water (5 mL) and extracted with 5% MeOH in DCM (2×75 mL). The organic layers were combined, dried over MgSO$_4$ and concentrated under reduced pressure to give 217 as a beige solid (144 mg, 67% over 3 steps). $^1$H NMR (400 MHz, CDCl$_3$) δ 8.62 (s, 1H), 7.84 (s, 1H), 7.38-7.28 (m, 1H), 7.02 (t, J=8.8 Hz, 2H), 6.15 (s, 2H), 3.72 (s, 3H), 3.37 (s, 3H), 3.36-3.25 (m, 2H), 3.22-3.08 (m, 3H), 3.07-2.99 (m, 1H), 2.17-2.10 (m, 1H), 2.02-1.93 (m, 1H), 1.88-1.65 (m, 2H). Alkyl NH$_2$ not observed. LCMS (ES+) m/z 478 (M+1).

Example 218

5-Amino-N-(5-(5-amino-3,3-difluoroazepan-1-yl)-1-methyl-1H-pyrazol-4-yl)-2-(2-fluorophenyl)thiazole-4-carboxamide 218

Following the procedure for Example 145, starting from Intermediate 19, tert-butyl 6,6-difluoro-1-(1-methyl-4-nitro-1H-pyrazol-5-yl)azepan-4-ylcarbamate gave 218 as a yellow solid (560 mg, 60% over two steps). $^1$H NMR (400 MHz, CDCl$_3$) δ 8.54 (s, 1H), 8.18 (td, J=3.9, 1.8 Hz, 1H), 7.74 (s, 1H), 7.39-7.33 (m, 1H), 7.33-7.17 (m, 1H), 7.17 (ddd, J=11.4, 8.2, 1.2 Hz, 1H), 6.09 (s, 2H), 3.76 (s, 3H), 3.73-3.61 (m, 1H), 3.53-3.36 (m, 3H), 3.26 (td, J=11.6, 4.9 Hz, 1H), 2.41-2.25 (m, 2H), 2.02-1.91 (m, 1H), 1.88-1.78 (m, 1H). Alkyl NH$_2$ not observed. LCMS (ES+) m/z 466 (M+1).

Example 219

5-Amino-N-(5-(5-amino-3,3-difluoroazepan-1-yl)-1-methyl-1H-pyrazol-4-yl)-2-(2-fluoro-5-methylphenyl)thiazole-4-carboxamide 219

Following the procedure for Example 145, starting from Intermediate 19, tert-butyl 6,6-difluoro-1-(1-methyl-4-nitro-1H-pyrazol-5-yl)azepan-4-ylcarbamate gave 219 as a yellow solid (665 mg, 70% over two steps). $^1$H NMR (400 MHz, CDCl$_3$) δ 8.52 (s, 1H), 7.95 (d, J=7.3 Hz, 1H), 7.72 (s, 1H), 7.14 (s, 1H), 7.04 (dd, J=11.1, 8.5 Hz, 1H), 6.09 (s, 2H), 3.86-3.51 (m, 4H), 3.57-3.37 (m, 3H), 3.33-3.23 (m, 1H), 2.53-2.15 (m, 5H), 2.02-1.90 (m, 1H), 1.87-1.74 (m, 1H). Alkyl NH$_2$ not observed. LCMS (ES+) m/z 480 (M+1).

Example 220

5-Amino-N-(5-(5-amino-3,3-difluoroazepan-1-yl)-1-methyl-1H-pyrazol-4-yl)-2-(2,5-difluorophenyl)thiazole-4-carboxamide 220

Following the procedure for Example 145, starting from Intermediate 19, tert-butyl 6,6-difluoro-1-(1-methyl-4-nitro-1H-pyrazol-5-yl)azepan-4-ylcarbamate gave 220 as a yellow solid (570 mg, 59% over two steps). $^1$H NMR (400 MHz, CDCl$_3$) δ 8.62 (s, 1H), 7.95-7.88 (m, 1H), 7.85 (s, 1H), 7.13 (td, J=9.7, 4.4 Hz, 1H), 7.07-6.98 (m, 1H), 6.15 (s, 2H), 3.81-3.58 (m, 4H), 3.56-3.36 (m, 3H), 3.30-3.20 (m, 1H), 2.51-2.39 (m, 1H), 2.38-2.21 (m, 1H), 2.05-1.94 (m, 1H), 1.91-1.79 (m, 1H). Alkyl NH$_2$ not observed. LCMS (ES+) m/z 484 (M+1).

Example 221

5-amino-N-(5-((4S,5S)-4-amino-5-fluoroazepan-1-yl)-1-methyl-1H-pyrazol-4-yl)-2-(2,5-difluorophenyl)thiazole-4-carboxamide 221

Following the procedures described herein, compound 221 was prepared by chiral separation from its racemic mixture on SFC. $^1$H NMR (400 MHz, DMSO) δ 9.08 (s, 1H), 8.15 (s, 1H), 7.45 (d, J=11.0 Hz, 2H), 7.43 (s, 2H), 7.27 (t, J=8.3 Hz, 1H), 4.45 (dtd, J=48.2, 8.4, 3.6 Hz, 1H), 3.65 (s, 3H), 3.15

(ddd, J=25.1, 17.1, 8.5 Hz, 5H), 2.20-2.03 (m, 1H), 2.02-1.90 (m, 1H), 1.88-1.77 (m, 1H), 1.71-1.53 (m, 1H). ESIMS m/z=466.1 (M+1)

Example 222

5-amino-N-(5-((4R,5R)-4-amino-5-fluoroazepan-1-yl)-1-methyl-1H-pyrazol-4-yl)-2-(2,5-difluorophenyl)thiazole-4-carboxamide 222

Following the procedures described herein, compound 222 was prepared by chiral separation from its racemic mixture on SFC. $^1$H NMR (400 MHz, DMSO) δ 9.08 (s, 1H), 8.15 (s, 1H), 7.46 (d, J=11.0 Hz, 2H), 7.43 (s, 2H), 7.28 (t, J=8.3 Hz, 1H), 4.45 (dtd, J=48.2, 8.4, 3.6 Hz, 1H), 3.66 (s, 3H), 3.15 (ddd, J=25.1, 17.1, 8.5 Hz, 5H), 2.20-2.03 (m, 1H), 2.02-1.90 (m, 1H), 1.89-1.78 (m, 1H), 1.71-1.53 (m, 1H). ESIMS m/z=466.1 (M+1)

Example 223

5-amino-N-(5-(6,6-difluoro-1,4-diazepan-1-yl)-1-methyl-1H-pyrazol-4-yl)-2-(pyridin-2-yl)thiazole-4-carboxamide 223

Following the procedures described herein, compound 223 was prepared. $^1$H NMR (400 MHz, DMSO) δ 9.12 (s, 1H), 8.54 (d, J=4.7 Hz, 1H), 8.08 (d, J=8.0 Hz, 1H), 7.92 (td, J=7.8, 1.5 Hz, 1H), 7.56 (s, 2H), 7.47 (s, 1H), 7.38 (dd, J=7.0, 5.3 Hz, 1H), 3.68 (s, 3H), 3.59 (t, J=13.9 Hz, 2H), 3.24-3.16 (m, 2H), 2.97-2.86 (m, 2H). MS (ESI) m/z: 435.1 [M+H$^+$].

Example 224

5-amino-N-(5-(6,6-difluoro-1,4-diazepan-1-yl)-1-methyl-1H-pyrazol-4-yl)-2-(3-fluoropyridin-2-yl)thiazole-4-carboxamide 224

Following the procedures described herein, compound 224 was prepared. $^1$H NMR (400 MHz, DMSO) δ 9.37 (s, 1H), 8.44 (d, J=4.6 Hz, 1H), 7.86 (dd, J=11.1, 8.5 Hz, 1H), 7.68 (d, J=2.8 Hz, 3H), 7.48 (dt, J=8.4, 4.2 Hz, 1H), 3.68 (s, 3H), 3.57 (t, J=13.4 Hz, 2H), 3.27-3.18 (m, 3H), 3.07-2.89 (m, 3H), 2.07 (s, 2H). MS (ESI) m/z: 453.1 [M+H$^+$].

Example 225

(S)-5-amino-2-(2,6-difluorophenyl)-N-(1-methyl-5-(5-methyl-1,4-diazepan-1-yl)-1H-pyrazol-4-yl)thiazole-4-carboxamide 225

Following the procedures described herein, compound 225 was prepared as a single enantiomer by chiral separation from its racemic mixture of 205 on SFC. $^1$H NMR (400 MHz, DMSO) δ 11.81 (s, 1H), 8.20 (s, 1H), 7.88 (s, 1H), 7.62-7.46 (m, 3H), 7.35-7.21 (m, 2H), 3.60 (s, 3H), 3.21-3.01 (m, 5H), 2.90-2.69 (m, 3H), 1.48 (d, J=11.6 Hz, 1H), 1.35-1.17 (m, 1H), 0.92 (d, J=6.3 Hz, 3H). MS (ESI) m/z: 448.1 [M+H$^+$].

Example 226

(R)-5-amino-2-(2,6-difluorophenyl)-N-(1-methyl-5-(5-methyl-1,4-diazepan-1-yl)-1H-pyrazol-4-yl)thiazole-4-carboxamide 226

Following the procedures described herein, compound 226 was prepared as a single enantiomer by chiral separation from its racemic mixture of 205 on SFC. $^1$H NMR (400 MHz, DMSO) δ 11.83 (s, 1H), 8.23 (s, 1H), 7.88 (s, 1H), 7.61-7.47 (m, 3H), 7.33-7.23 (m, 2H), 3.60 (s, 3H), 3.26-2.98 (m, 6H), 2.84-2.67 (m, 3H), 1.48 (d, J=11.9 Hz, 1H), 1.32-1.12 (m, 1H), 0.92 (d, J=6.3 Hz, 3H). MS (ESI) m/z: 448.1 [M+H$^+$].

Example 227

(R)-5-amino-2-(2,6-difluorophenyl)-N-(5-(3-hydroxy-3-methylazepan-1-yl)-1-methyl-1H-pyrazol-4-yl)thiazole-4-carboxamide 227

Following the procedures described herein, compound 227 was prepared. $^1$H NMR (400 MHz, DMSO) δ 8.85 (s, 1H), 7.61 (s, 1H), 7.56-7.50 (m, 1H), 7.48 (s, 2H), 7.26 (m, 2H), 4.19 (s, 1H), 3.67 (s, 3H), 3.09 (t, J=6.1 Hz, 2H), 3.03 (s, 2H), 1.85-1.58 (m, 5H), 1.50 (dd, J=14.0, 8.1 Hz, 1H), 1.05 (s, 3H). ESIMS m/z=463.2 (M+1)

Example 228

(S)-5-amino-2-(2,6-difluorophenyl)-N-(5-(3-hydroxy-3-methylazepan-1-yl)-1-methyl-1H-pyrazol-4-yl)thiazole-4-carboxamide 228

Following the procedures described herein, compound 228 was prepared. $^1$H NMR (400 MHz, DMSO) δ 8.85 (s, 1H), 7.61 (s, 1H), 7.56-7.50 (m, 1H), 7.48 (s, 2H), 7.26 (m, 2H), 4.19 (s, 1H), 3.67 (s, 3H), 3.09 (t, J=6.1 Hz, 2H), 3.03 (s, 2H), 1.85-1.57 (m, 5H), 1.50 (dd, J=14.0, 8.1 Hz, 1H), 1.05 (s, 3H). ESIMS m/z=463.2 (M+1)

Example 229

5-amino-N-(5-((4S,5S)-4-amino-5-fluoroazepan-1-yl)-1-methyl-1H-pyrazol-4-yl)-2-(2-fluorophenyl)thiazole-4-carboxamide 229

Following the procedures described herein, compound 229 was prepared as a single enantiomer by chiral separation from its racemic mixture on SFC. $^1$H NMR (400 MHz, DMSO) δ 8.93 (s, 1H), 8.29 (m, 1H), 7.48 (s, 1H), 7.43 (m, 1H), 7.41 (s, 2H), 7.33 (d, J=7.9 Hz, 2H), 4.48 (dtd, J=47.9, 8.5, 3.5 Hz, 1H), 3.65 (s, 3H), 3.23-3.10 (m, 5H), 2.14 (ddd, J=19.7, 8.6, 3.1 Hz, 1H), 1.98 (ddd, J=18.3, 9.4, 4.9 Hz, 1H), 1.86 (dd, J=18.4, 13.0 Hz, 1H), 1.63 (dtd, J=14.3, 9.5, 4.6 Hz, 1H). ESIMS m/z=448.2 (M+1)

Example 230

5-amino-N-(5-((4R,5R)-4-amino-5-fluoroazepan-1-yl)-1-methyl-1H-pyrazol-4-yl)-2-(2-fluorophenyl)thiazole-4-carboxamide 230

Following the procedures described herein, compound 230 was prepared as a single enantiomer by chiral separation from its racemic mixture on SFC. $^1$H NMR (400 MHz, DMSO) δ 8.94 (s, 1H), 8.29 (m, 1H), 7.47 (s, 1H), 7.43 (m, 1H), 7.41 (s, 2H), 7.34 (d, J=7.9 Hz, 2H), 4.48 (dtd, J=47.9, 8.5, 3.5 Hz, 1H), 3.65 (s, 3H), 3.23-3.10 (m, 5H), 2.14 (ddd, J=19.7, 8.6, 3.1 Hz, 1H), 1.98 (ddd, J=18.3, 9.4, 4.9 Hz, 1H), 1.86 (dd, J=18.4, 13.0 Hz, 1H), 1.65 (dtd, J=14.3, 9.5, 4.6 Hz, 1H). ESIMS m/z=448.2 (M+1)

Example 231

3-amino-N-(5-(4-amino-5-fluoroazepan-1-yl)-1-methyl-1H-pyrazol-4-yl)-6-(2-fluorophenyl)picolinamide 231

Following the procedures described herein, racemic compound 231 was prepared. $^1$H NMR (400 MHz, DMSO) δ 9.73 (s, 1H), 8.01 (dd, J=11.3, 4.8 Hz, 1H), 7.73 (dd, J=8.7, 2.1 Hz, 1H), 7.67 (s, 1H), 7.43 (ddd, J=7.2, 6.2, 1.7 Hz, 1H), 7.37-7.24 (m, 3H), 7.06 (s, 2H), 4.40 (dtd, J=48.0, 8.2, 3.6 Hz, 1H), 3.67 (s, 3H), 3.28-3.00 (m, 5H), 2.21-2.04 (m, 1H), 2.04-1.89 (m, 1H), 1.83 (dd, J=9.3, 5.6 Hz, 1H), 1.76-1.54 (m, 3H). MS (ESI) m/z: 442.2 [M+H$^+$].

Example 232

3-amino-N-(5-(4-amino-5-fluoroazepan-1-yl)-1-methyl-1H-pyrazol-4-yl)-6-(2-fluorophenyl)pyrazine-2-carboxamide 232

Following the procedures described herein, racemic compound 232 was prepared. $^1$H NMR (400 MHz, DMSO) δ 9.76 (s, 1H), 8.68 (d, J=2.4 Hz, 1H), 8.12 (td, J=8.2, 1.8 Hz, 1H), 7.73 (s, 2H), 7.57 (s, 1H), 7.46 (dt, J=7.2, 3.7 Hz, 1H), 7.41-7.27 (m, 2H), 4.39 (dtd, J=48.0, 8.2, 3.6 Hz, 1H), 3.66 (s, 3H), 3.26-2.97 (m, 5H), 2.19-1.87 (m, 2H), 1.87-1.74 (m, 1H), 1.69-1.51 (m, 3H). MS (ESI) m/z: 443.2 [M+H$^+$].

Example 233

(R)-5-Amino-2-(2,6-difluorophenyl)-N-(5-(3-methylpiperazin-1-yl)-1-(2,2,2-trifluoroethyl)-1H-pyrazol-4-yl)thiazole-4-carboxamide 233

Step A. tert-Butyl (±)-2-Methyl-4-(4-nitro-1-(2,2,2-trifluoroethyl)-1H-pyrazol-5-yl)piperazine-1-carboxylate

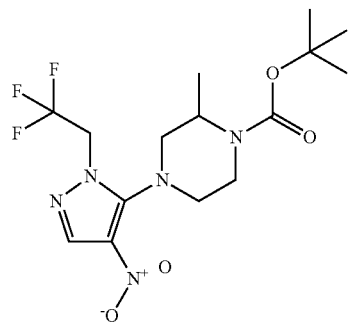

A solution of Intermediate 39, 5-bromo-4-nitro-1-(2,2,2-trifluoroethyl)-1H-pyrazole (550 mg, 2.01 mmol), (±) tert-butyl 2-methylpiperazine-1-carboxylate (403 mg, 2.01 mmol), DIPEA (2 mL) in EtOH (6 mL) was stirred at 130° C. for 2 hours in a microwave oven. The reaction mixture was concentrated under reduced pressure to give a residue. The residue was purified by silica gel chromatography using PE:EtOAc (1:1) as eluting solvents to afford tert-butyl (±)-2-methyl-4-(4-nitro-1-(2,2,2-trifluoroethyl)-1H-pyrazol-5-yl)piperazine-1-carboxylate as yellow solid (377 mg, 48%). MS (ESI) m/z: 394 [M+H$^+$].

Step B. tert-Butyl (±)-4-(4-Amino-1-(2,2,2-trifluoroethyl)-1H-pyrazol-5-yl)-2-methyl-piperazine-1-carboxylate

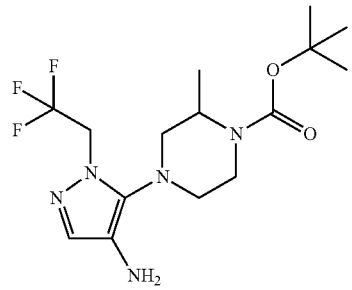 [SMILES: CC1CN(c2c(N)cnn2CC(F)(F)F)CCN1C(=O)OC(C)(C)C]

To a solution of (±) tert-butyl 2-methyl-4-(4-nitro-1-(2,2,2-trifluoroethyl)-1H-pyrazol-5-yl)piperazine-1-carboxylate (370 mg, 0.94 mmol) in MeOH (15 mL) and H$_2$O (3 mL) was added zinc (362 mg, 5.6 mmol) and NH$_4$Cl (400 mg, 7.5 mmol). The reaction mixture was stirred at ambient temperature for 4 hours, filtered through Celite, and evaporated under reduced pressure to afford tert-butyl (±)-4-(4-amino-1-(2,2,2-trifluoroethyl)-1H-pyrazol-5-yl)-2-methylpiperazine-1-carboxylate as yellow solid (300 mg, 88%). MS (ESI) m/z: 364 [M+H$^+$].

Step C. tert-Butyl (±)-4-(4-(5-(tert-Butoxycarbonylamino)-2-(2,6-difluorophenyl)thiazole-4-carboxamido)-1-(2,2,2-trifluoroethyl)-1H-pyrazol-5-yl)-2-methylpiperazine-1-carboxylate To a solution of tert-butyl (±)-4-(4-amino-1-(2,2,2-trifluoroethyl)-1H-pyrazol-5-yl)-2-methylpiperazine-1-carboxylate (300 mg, 0.83 mmol), 5-(tert-butoxycarbonylamino)-2-(2,6-difluorophenyl)thiazole-4-carboxylic acid (294 mg, 0.83 mmol), HATU (410 mg, 1.08 mmol) in DMF (15 mL) was added TEA (2 mL). The mixture was stirred at 30° C. for 20 hours, poured into water (100 mL), and extracted with EtOAc (40 mL×3). The combined organic layers was washed with water (50 mL×2) and brine (30 mL×2), dried over Na$_2$SO$_4$, filtered, and concentrated under reduced pressure to afford a residue. The residue was purified by preparative HPLC to give tert-butyl (±)-4-(4-(5-(tert-butoxycarbonylamino)-2-(2,6-difluorophenyl)thiazole-4-carboxamido)-1-(2,2,2-trifluoroethyl)-1H-pyrazol-5-yl)-2-methylpiperazine-1-carboxylate as white solid (190 mg, 33%). MS (ESI) m/z: 702 [M+H$^+$].

Step D. Chiral separation by preparative HPLC of tert-butyl (±)-4-(4-(5-(tert-butoxy-carbonylamino)-2-(2,6-difluorophenyl)thiazole-4-carboxamido)-1-(2,2,2-trifluoroethyl)-1H-pyrazol-5-yl)-2-methylpiperazine-1-carboxylate (190 mg) afforded about 80 mg each of the (R) enantiomer and (S) enantiomer.

Step E. A mixture of tert-butyl (R)-4-(4-(5-(tert-butoxycarbonylamino)-2-(2,6-difluorophenyl)thiazole-4-carboxamido)-1-(2,2,2-trifluoroethyl)-1H-pyrazol-5-yl)-2-methylpiperazine-1-carboxylate (82 mg, 0.12 mmol) in HCl/MeOH (10 mL) was stirred at ambient temperature for 20 hours. The reaction mixture was concentrated under reduced pressure to give a residue. The residue was diluted with MeOH (30 mL), neutralized with 28% ammonia solution, concentrated, and purified by preparative HPLC to afford 233 as a white solid (32 mg, 56%). $^1$H-NMR (500 MHz, CD$_3$OD) δ (ppm): 7.69 (s, 1H), 7.51-7.45 (m, 1H), 7.17-7.12 (m, 2H), 4.84-4.78 (m, 2H), 3.22-3.17 (m, 1H), 3.05-2.86 (m, 6H), 1.08 (d, J=6 Hz, 3H); MS (ESI) m/z: 502 [M+H$^+$].

Example 234

5-Amino-N-(5-(5-amino-3,3-difluoroazepan-1-yl)-1-(2,2-difluoroethyl)-1H-pyrazol-4-yl)-2-(2,6-difluorophenyl)thiazole-4-carboxamide 234

Following the procedure for Example 145, starting from Intermediate 56, tert-butyl 1-(1-(2,2-difluoroethyl)-4-nitro-1H-pyrazol-5-yl)-6,6-difluoroazepan-4-ylcarbamate (1.33 g, 3.13 mmol) gave 234 as a pale yellow solid (300 mg, 36% over three steps). $^1$H NMR (400 MHz, d$_6$-DMSO) δ 8.95 (s, 1H), 7.67 (s, 1H), 7.59-7.48 (m, 3H), 7.29 (t, J=8.7 Hz, 2H), 6.38 (tt, J=55.2, 4.2 Hz, 1H), 4.44 (td, J=14.4, 4.2 Hz, 2H), 3.75-3.58 (m, 1H), 3.50-3.05 (m, 6H), 2.29-2.06 (m, 2H), 1.92-1.80 (m, 1H), 1.77-1.63 (m, 1H). LCMS (ES+) m/z 534 (M+1).

Example 235

5-amino-N-(5-(4-amino-5-fluoroazepan-1-yl)-1-methyl-1H-pyrazol-4-yl)-2-(2-fluorophenyl)pyrimidine-4-carboxamide 235

Following the procedures of Example 237, compound 235 was prepared. $^1$H NMR (400 MHz, DMSO) δ 9.78 (s, 1H), 8.61 (s, 1H), 8.13-8.00 (m, 1H), 7.67 (s, 1H), 7.53-7.39 (m, 1H), 7.35-7.23 (m, 2H), 7.00 (s, 2H), 4.51-4.29 (m, 1H), 3.29-2.98 (m, 5H), 2.23-2.04 (m, 1H), 2.04-1.87 (m, 1H), 1.87-1.72 (m, 1H), 1.72-1.51 (m, 1H). MS (ESI) m/z: 447.1 [M+H$^+$].

Example 236

5-amino-N-(5-(6,6-difluoro-1,4-diazepan-1-yl)-1-methyl-1H-pyrazol-4-yl)-2-(2-fluorophenyl)pyrimidine-4-carboxamide 236

Following the procedures provided in Example 237, compound 236 was prepared. $^1$H NMR (400 MHz, DMSO) δ 9.95 (s, 1H), 8.61 (s, 1H), 8.08-7.94 (m, 2H), 7.66 (s, 1H), 7.55-7.40 (m, 1H), 7.35-7.21 (m, 2H), 7.00 (s, 2H), 3.58-3.44 (m, 2H), 3.23-3.10 (m, 4H), 2.96-2.81 (m, 2H). MS (ESI) m/z: 447.1 [M+H$^+$].

Example 237

5-amino-N-(5-(5-amino-3,3-difluoroazepan-1-yl)-1-methyl-1H-pyrazol-4-yl)-2-(2-fluorophenyl)pyrimidine-4-carboxamide 237

Sodium ethoxide (21 mass % in ethanol; 8.69 mL, 23.268 mmol) was added to an ice-bath cooled mixture of 2-fluorobenzamidine (2.71 g, 15.512 mmol) in ethanol (100 mL). The resulting mixture was allowed to warm to room temperature and stirred at rt (room temperature) under nitrogen for 30 min. To the reaction mixture was added a solution of (E)-2,3-dibromo-4-oxo-but-2-enoic acid (2.00 g, 7.7561 mmol) in ethanol (20 ml). The mixture was heated at 50° C. for 3 h. After cooling to RT, the reaction was concentrated in vacuo. Water and 1M NaOH (~50 ml) were added and the aqueous mixture was extracted with EtOAc. The aqueous phase was acidified to pH4 with 1N HCl (about 30 ml), then extracted with EtOAc 3x. Combined organic extracts were dried over sodium sulfate, filtered and concentrated to gave 5-bromo-2-(2-fluorophenyl)pyrimidine-4-carboxylic acid, 770 mg.

CuSO4 (with 5H$_2$O, 65 mg) was added to a mixture of the above made 5-bromo-2-(2-fluorophenyl)pyrimidine-4-carboxylic acid (770 mg, 2.59 mmol) and 28% aqueous ammonium hydroxide (12 ml). The reaction was heated in a microwave reactor at 110° C. for 30 min. It was cooled to RT and concentrated in vacuo. The residue was diluted with 1N HCl (20 mL) and extracted with EtOAc 3x. Combined organic extracts were dried over sodium sulfate and filtered and concentrated to give 5-amino-2-(2-fluorophenyl)pyrimidine-4-carboxylic acid (320 mg, 53%).

1-(4-amino-1-methyl-1H-pyrazol-5-yl)-6,6-difluoroazepan-4-amine (99 mg, 0.29 mmol), 5-amino-2-(2-fluorophenyl)pyrimidine-4-carboxylic acid (87 mg, 0.37 mmol), PyBop (304 mg, 0.57 mmol), and diisopropylethylamine (222 mg, 1.72 mmol) were dissolved in methylene chloride (10 mL) and stirred at room temperature overnight. The reaction mixture was concentrated and purified by flash chromatography eluting with 0 to 100% ethyl acetate in heptane to give tert-butyl 1-(4-(5-amino-2-(2-fluorophenyl)pyrimidine-4-carboxamido)-1-methyl-1H-pyrazol-5-yl)-6,6-difluoroazepan-4-ylcarbamate (157 mg, 97%).

tert-butyl 1-(4-(5-amino-2-(2-fluorophenyl)pyrimidine-4-carboxamido)-1-methyl-1H-pyrazol-5-yl)-6,6-difluoroazepan-4-ylcarbamate (157 mg) was stirred with 4N HCl in dioxane (6 mL) at room temperature for 1 h. The reaction mixture was concentrated to dryness, basified with saturated aqueous sodium bicarbonate, and extracted with ethyl acetate 3x. Combined organic phase was dried over sodium sulfate, filtered and concentrated. The crude product was purified on reversed phase HPLC to give 237. MS (ESI) m/z: 461.1 [M+H$^+$].

Example 241

(S)-5-amino-2-(2,6-difluorophenyl)-N-(1-methyl-5-(3-(trifluoromethyl)piperidin-1-yl)-1H-pyrazol-4-yl)thiazole-4-carboxamide 241

Following the procedures of Example 101, compound 241 was obtained as a single enantiomer starting from enantiomerically pure 1-methyl-5-(3-(trifluoromethyl)piperidin-1-yl)-1H-pyrazol-4-amine and 5-(tert-butoxycarbonylamino)-2-(2,6-difluorophenyl)thiazole-4-carboxylic acid from Example 25. $^1$H NMR (400 MHz, DMSO) δ 8.80 (s, 1H), 7.62-7.47 (m, 1H), 7.45 (s, 1H), 7.32-7.14 (m, 2H), 3.65 (s, 3H), 3.23 (dd, J=11.5, 3.8 Hz, 1H), 3.15-2.91 (m, 3H), 2.71-2.55 (m, 1H), 1.95 (dd, J=12.8, 3.3 Hz, 1H), 1.79 (d, J=13.2 Hz, 1H), 1.70-1.51 (m, 1H), 1.39 (ddd, J=24.5, 12.2, 4.1 Hz, 1H). MS (ESI) m/z: 487.3 [M+H$^+$].

Example 242

(R)-5-Amino-2-(2,6-difluoro-phenyl)-thiazole-4-carboxylic acid [1-methyl-5-(3-trifluoromethyl-piperidin-1-yl)-1H-pyrazol-4-yl]-amide 242

Following the procedures of Example 101, compound 242 was obtained as a single enantiomer starting from enantiomerically pure 1-methyl-5-(3-(trifluoromethyl)piperidin-1-yl)-1H-pyrazol-4-amine and 5-(tert-butoxycarbonylamino)-2-(2,6-difluorophenyl)thiazole-4-carboxylic acid from Example 25. ¹H NMR (400 MHz, DMSO) δ 8.80 (s, 1H), 7.62-7.47 (m, 1H), 7.45 (s, 1H), 7.32-7.14 (m, 2H), 3.65 (s, 3H), 3.23 (dd, J=11.5, 3.8 Hz, 1H), 3.15-2.91 (m, 3H), 2.71-2.55 (m, 1H), 1.95 (dd, J=12.8, 3.3 Hz, 1H), 1.79 (d, J=13.2 Hz, 1H), 1.70-1.51 (m, 1H), 1.39 (ddd, J=24.5, 12.2, 4.1 Hz, 1H). MS (ESI) m/z: 487.3 [M+H⁺].

Example 243

3-amino-N-(5-(4-amino-5-fluoroazepan-1-yl)-1-methyl-1H-pyrazol-4-yl)-6-(2-fluorophenyl)pyrazine-2-carboxamide 243

SFC chiral separation of parent racemic compound 232 gave chiral diastereomer 243 as peak 2. ¹H NMR (400 MHz, DMSO) δ 9.76 (s, 1H), 8.68 (d, J=2.5 Hz, 1H), 8.22 (s, 1H), 8.13 (td, J=8.2, 1.9 Hz, 1H), 7.71 (s, 2H), 7.55 (s, 1H), 7.50-7.40 (m, 1H), 7.40-7.24 (m, 2H), 4.58-4.35 (m, 1H), 3.67 (s, 3H), 3.28-3.02 (m, 5H), 2.23-2.05 (m, 1H), 2.05-1.92 (m, 1H), 1.92-1.77 (m, 1H), 1.71-1.57 (m, 1H). MS (ESI) m/z: 443.1 [M+H⁺].

Example 244

3-amino-N-(5-(4-amino-5-fluoroazepan-1-yl)-1-methyl-1H-pyrazol-4-yl)-6-(2-fluorophenyl)pyrazine-2-carboxamide 244

SFC chiral separation of parent racemic compound 232 gave chiral diastereomer 244 as peak 1. ¹H NMR (400 MHz, DMSO) δ 9.75 (s, 1H), 8.68 (d, J=2.5 Hz, 1H), 8.12 (td, J=8.1, 1.9 Hz, 1H), 7.72 (s, 2H), 7.56 (s, 1H), 7.52-7.40 (m, 1H), 7.40-7.27 (m, 2H), 4.53-4.28 (m, 2H), 3.67 (s, 3H), 3.23-2.97 (m, 5H), 2.19-2.03 (m, 1H), 2.03-1.90 (m, 1H), 1.90-1.74 (m, 1H), 1.67-1.52 (m, 1H). MS (ESI) m/z: 443.1 [M+H⁺].

Example 245

3-amino-N-(5-(4-amino-5-fluoroazepan-1-yl)-1-methyl-1H-pyrazol-4-yl)-6-(2-fluorophenyl)picolinamide 245

SFC chiral separation of parent racemic compound 231 gave chiral diastereomer 245 as peak 2. ¹H NMR (400 MHz, DMSO) δ 9.72 (s, 1H), 8.01 (td, J=8.0, 1.8 Hz, 1H), 7.73 (dd, J=8.7, 2.2 Hz, 1H), 7.67 (s, 1H), 7.48-7.37 (m, 1H), 7.37-7.21 (m, 3H), 7.05 (s, 2H), 4.39 (dtd, J=48.0, 8.2, 3.7 Hz, 1H), 3.67 (s, 3H), 3.24-2.98 (m, 5H), 2.19-2.04 (m, 1H), 1.97 (dtd, J=19.7, 9.8, 4.8 Hz, 1H), 1.89-1.77 (m, 1H), 1.73-1.53 (m, 2H). MS (ESI) m/z: 442.1 [M+H⁺].

Example 246

3-amino-N-(5-(4-amino-5-fluoroazepan-1-yl)-1-methyl-1H-pyrazol-4-yl)-6-(2-fluorophenyl)picolinamide 246

SFC chiral separation of parent racemic compound 231 gave chiral diastereomer 246 as peak 1. ¹H NMR (400 MHz, DMSO) δ 9.72 (s, 1H), 8.01 (td, J=8.0, 1.8 Hz, 1H), 7.73 (dd, J=8.7, 2.2 Hz, 1H), 7.67 (s, 1H), 7.47-7.37 (m, 1H), 7.38-7.22 (m, 3H), 7.05 (s, 2H), 4.39 (dtd, J=48.0, 8.2, 3.7 Hz, 1H), 3.67 (s, 3H), 3.25-2.97 (m, 5H), 2.21-2.03 (m, 1H), 2.03-1.88 (m, 1H), 1.88-1.75 (m, 1H), 1.75-1.52 (m, 2H). MS (ESI) m/z: 442.1 [M+H⁺].

Example 247

(S)-3-amino-N-(5-(5-amino-3,3-difluoroazepan-1-yl)-1-methyl-1H-pyrazol-4-yl)-6-(2-fluorophenyl)pyrazine-2-carboxamide 247

SFC chiral separation of parent racemic compound 293 gave enantiomer 247 as peak 2. ¹H NMR (400 MHz, DMSO) δ 9.78 (s, 1H), 8.68 (d, J=2.5 Hz, 1H), 8.15 (dd, J=11.3, 4.9 Hz, 1H), 7.73 (s, 2H), 7.54 (s, 1H), 7.51-7.41 (m, 1H), 7.35 (dd, J=16.1, 7.7 Hz, 2H), 3.79-3.59 (m, 4H), 3.53-3.37 (m, 2H), 3.19-3.10 (m, 1H), 2.37-2.15 (m, 2H), 1.98-1.67 (m, 2H). MS (ESI) m/z: 461.1 [M+H⁺].

Example 248

(R)-3-amino-N-(5-(5-amino-3,3-difluoroazepan-1-yl)-1-methyl-1H-pyrazol-4-yl)-6-(2-fluorophenyl)pyrazine-2-carboxamide 248

SFC chiral separation of parent racemic compound 293 gave enantiomer 248 as peak 1. ¹H NMR (400 MHz, DMSO) δ 9.76 (s, 1H), 8.68 (d, J=2.5 Hz, 1H), 8.17-8.04 (m, 1H), 7.73 (s, 2H), 7.59 (s, 1H), 7.54-7.41 (m, 1H), 7.41-7.25 (m, 2H), 3.77-3.55 (m, 4H), 3.50-3.34 (m, 1H), 3.21-3.04 (m, 2H), 2.27-2.03 (m, 2H), 1.92-1.64 (m, 3H). MS (ESI) m/z: 461.1 [M+H⁺].

Example 249

3-amino-N-(5-(5-amino-3,3-difluoroazepan-1-yl)-1-methyl-1H-pyrazol-4-yl)-6-(2-fluorophenyl)picolinamide 249

SFC chiral separation of parent racemic compound 292 gave enantiomer 249 as peak 2. ¹H NMR (400 MHz, DMSO) δ 9.71 (s, 1H), 8.07-7.96 (m, 1H), 7.71 (dd, J=8.7, 2.3 Hz, 1H), 7.66 (s, 1H), 7.48-7.38 (m, 1H), 7.38-7.23 (m, 3H), 7.06 (s, 2H), 3.78-3.58 (m, 4H), 3.50-3.33 (m, 1H), 3.19-3.02 (m, 2H), 2.24-1.97 (m, 2H), 1.88-1.78 (m, 1H), 1.78-1.63 (m, 1H), 1.63-1.42 (m, 1H). MS (ESI) m/z: 460.1 [M+H⁺].

Example 250

(R)-3-amino-N-(5-(5-amino-3,3-difluoroazepan-1-yl)-1-methyl-1H-pyrazol-4-yl)-6-(2-fluorophenyl)picolinamide 250

SFC chiral separation of parent racemic compound 292 gave enantiomer 250 as peak 1. ¹H NMR (400 MHz, DMSO) δ 9.71 (s, 1H), 8.06-7.96 (m, 1H), 7.71 (dd, J=8.7, 2.3 Hz, 1H), 7.66 (s, 1H), 7.48-7.37 (m, 1H), 7.37-7.25 (m, 3H), 7.06 (s, 2H), 3.76-3.59 (m, 4H), 3.51-3.33 (m, 1H), 3.18-3.04 (m, 2H), 2.25-2.01 (m, 2H), 1.91-1.77 (m, 1H), 1.77-1.64 (m, 1H), 1.64-1.43 (m, 2H). MS (ESI) m/z: 460.1 [M+H⁺].

Example 252

5-Amino-2-(2,6-difluoro-phenyl)-thiazole-4-carboxylic acid [5-(5-amino-3-methoxy-3-methylazepan-1-yl)-1-methyl-1H-pyrazol-4-yl]-amide 252

Following the procedure for Example 145 starting from tert-butyl 6-methoxy-6-methyl-1-(1-methyl-4-nitro-1H-pyrazol-5-yl)azepan-4-ylcarbamate (more polar pair of diastereoisomers) gave, after purification via preparative HPLC, 252 as the monoformate salt as a pale yellow solid (116 mg, 53% over three steps). ¹H NMR (400 MHz, d₆-DMSO) δ 8.83 (br s, 1H), 8.43 (s, 1H), 7.60-7.45 (m, 4H), 7.35-7.20 (m, 2H), 3.68 (s, 3H), 3.30-3.15 (m, 5H), 3.10-2.85 (m, 5H), 2.15-1.65 (m, 4H), 1.02 (s, 3H). LCMS (ES+) m/z 492 (M+1)

Example 253

5-Amino-2-(2,6-difluoro-phenyl)-thiazole-4-carboxylic acid [5-(5-amino-3-hydroxy-3-methyl-azepan-1-yl)-1-methyl-1H-pyrazol-4-yl]-amide 253

Following the procedure for Example 145 starting from tert-butyl 6-hydroxy-6-methyl-1-(1-methyl-4-nitro-1H-pyrazol-5-yl)azepan-4-ylcarbamate (more polar pair of diastereoisomers) gave, after purification via preparative HPLC, 253 as the monoformate salt as a pale yellow solid (37 mg, 19% over three steps). ¹H NMR (400 MHz, d₆-DMSO) δ 8.70 (br s, 1H), 8.44 (s, 1H), 7.58-7.45 (m, 4H), 7.35-7.20 (m, 2H), 3.70 (s, 3H), 3.60-2.80 (m, 8H), 2.05-1.60 (m, 4H), 1.14 (s, 3H). LCMS (ES+) m/z 478 (M+1)

Example 254

5-Amino-2-(2,6-difluoro-phenyl)-thiazole-4-carboxylic acid [5-(5-amino-3-methoxy-3-methyl-azepan-1-yl)-1-methyl-1H-pyrazol-4-yl]-amide 254

Following the procedure for Example 145 starting from tert-butyl 6-methoxy-6-methyl-1-(1-methyl-4-nitro-1H-pyrazol-5-yl)azepan-4-ylcarbamate (less polar pair of diastereoisomers) gave, after purification via preparative HPLC, 254 as the monoformate salt as a pale yellow solid (78 mg, 34%). ¹H NMR (400 MHz, d₆-DMSO) δ 8.84 (s, 1H), 8.44 (s, 1H), 7.63 (s, 1H), 7.60-7.45 (m, 3H), 7.35-7.20 (m, 2H), 3.67 (s, 3H), 3.60-3.15 (m, 5H), 3.15-2.90 (m, 5H), 2.15-1.55 (m, 4H), 1.01 (s, 3H). LCMS (ES+) m/z 492 (M+1)

Example 255

5-Amino-2-(2,6-difluoro-phenyl)-thiazole-4-carboxylic acid [5-(5-amino-3-hydroxy-3-methyl-azepan-1-yl)-1-methyl-1H-pyrazol-4-yl]-amide 255

Following the procedure for Example 145 starting from tert-butyl 6-hydroxy-6-methyl-1-(1-methyl-4-nitro-1H-pyrazol-5-yl)azepan-4-ylcarbamate (less polar pair of diastereoisomers) gave, after purification via preparative HPLC, 255 as the monoformate salt as a pale yellow solid (39 mg, 18% over three steps). ¹H NMR (400 MHz, d₆-DMSO) δ 8.88 (s, 1H), 8.42 (s, 1H), 7.60-7.45 (m, 4H), 7.35-7.20 (m, 2H), 3.68 (s, 3H), 3.67-3.55 (m, 2H), 3.30-2.80 (m, 6H), 2.05-1.60 (m, 4H), 1.06 (s, 3H). LCMS (ES+) m/z 478 (M+1)

Example 256

5-Amino-2-(2,6-difluoro-phenyl)-thiazole-4-carboxylic acid [5-(5-amino-3-fluoro-3-methyl-azepan-1-yl)-1-methyl-1H-pyrazol-4-yl]-amide 256

Following the procedure for Example 145 starting from tert-butyl 6-fluoro-6-methyl-1-(1-methyl-4-nitro-1H-pyrazol-5-yl)azepan-4-ylcarbamate gave 256 as a pale brown solid (110 mg, 27% over three steps). ¹H NMR (400 MHz, CDCl₃) δ 8.64-8.56 (m, 1H), 7.89 and 7.80 (2s, 1H), 7.40-7.26 (m, 1H), 7.06-6.99 (m, 2H), 6.22 (br s, 2H), 3.77 and 3.64 (2s, 3H), 3.67-2.99 (m, 5H), 2.45-2.05 (m, 1H), 2.05-1.60 (m, 5H), 1.45-1.25 (m, 3H). LCMS (ES+) m/z 480 (M+1)

Example 257

5-Amino-2-(2,6-difluoro-phenyl)-thiazole-4-carboxylic acid [5-(3-fluoro-5-hydroxy-azepan-1-yl)-1-methyl-1H-pyrazol-4-yl]-amide 257

Following the procedure for Example 145 starting from 1-(1-methyl-4-nitro-1H-pyrazol-5-yl)-3-(trifluoromethyl)piperidine gave, after purification via preparative HPLC, 257 as a beige solid (222 mg, 41% over three steps). ¹H NMR (400 MHz, CDCl₃) δ 9.08 and 8.66 (2s, 1H), 7.93 and 7.83 (s, 1H), 7.33 (ddd, J=8.6, 5.9, 2.7 Hz, 1H), 7.07-6.99 (m, 2H), 6.22 and 6.16 (2s, 2H), 4.96-4.73 (m, 1H), 4.45 and 4.12 (2s, 1H), 3.76 and 3.74 (2s, 3H), 3.60-3.17 (m, 4H), 2.44-1.90 (m, 4H). OH not observed. LCMS (ES+) m/z 467 (M+1)

Example 258

5-Amino-2-(2,6-difluoro-phenyl)-thiazole-4-carboxylic acid [1-methyl-5-(3-trifluoromethyl-piperidin-1-yl)-1H-pyrazol-4-yl]-amide 258

Following the procedure for Example 101 starting from 1-(1-methyl-4-nitro-1H-pyrazol-5-yl)-3-(trifluoromethyl)piperidine gave, after purification via silica gel column chromatography (20-100% EtOAc/isohexane), 258 as an off-white foam (415 mg, 48% over three steps). ¹H NMR (400 MHz, CDCl₃) δ 8.52 (s, 1H), 7.77 (s, 1H), 7.37-7.26 (m, 1H), 7.07-6.97 (m, 2H), 6.13 (s, 2H), 3.73 (s, 3H), 3.32 (dd, J=11.5, 3.8 Hz, 1H), 3.17-3.04 (m, 3H), 2.54-2.40 (m, 1H), 2.10-2.04 (m, 1H), 1.94-1.84 (m, 1H), 1.84-1.43 (m, 2H). LCMS (ES+) m/z 487 (M+1)

Example 261

(S)-5-amino-N-(5-(5-amino-3,3-difluoroazepan-1-yl)-1-methyl-1H-pyrazol-4-yl)-2-(pyridin-2-yl)thiazole-4-carboxamide 261

SFC chiral separation of the parent racemic compound gave enantiomer 261. ¹H NMR (400 MHz, DMSO) δ 8.92 (s, 1H), 8.54 (d, J=4.7 Hz, 1H), 8.12 (d, J=8.0 Hz, 1H), 7.93 (t, J=7.7 Hz, 1H), 7.53 (d, J=14.5 Hz, 3H), 7.42-7.35 (m, 1H), 3.68 (s, 3H), 3.50-3.37 (m, 2H), 3.20-3.09 (m, 2H), 2.36-2.16 (m, 3H), 1.90 (d, J=18.9 Hz, 1H), 1.83-1.68 (m, 1H). ESIMS m/z=449.1 (M+1)

Example 262

(R)-5-amino-N-(5-(5-amino-3,3-difluoroazepan-1-yl)-1-methyl-1H-pyrazol-4-yl)-2-(pyridin-2-yl)thiazole-4-carboxamide 262

SFC chiral separation of the parent racemic compound gave enantiomer 262. ¹H NMR (400 MHz, DMSO) δ 8.92 (s, 1H), 8.54 (d, J=4.7 Hz, 1H), 8.12 (d, J=8.0 Hz, 1H), 7.93 (t, J=7.7 Hz, 1H), 7.53 (d, J=14.5 Hz, 3H), 7.42-7.35 (m, 1H), 3.68 (s, 3H), 3.50-3.37 (m, 2H), 3.20-3.09 (m, 2H), 2.36-2.16 (m, 3H), 1.90 (d, J=18.9 Hz, 1H), 1.83-1.68 (m, 1H). ESIMS m/z=449.1 (M+1)

Example 263

5-amino-N-(5-((4S,5S)-4-amino-5-fluoroazepan-1-yl)-1-methyl-1H-pyrazol-4-yl)-2-(pyridin-2-yl)thiazole-4-carboxamide 263

SFC chiral separation of the parent racemic compound gave enantiomer 263. $^1$H NMR (400 MHz, DMSO) δ 8.88 (s, 1H), 8.53 (d, J=4.7 Hz, 1H), 8.14 (d, J=7.9 Hz, 1H), 7.89 (d, J=1.4 Hz, 1H), 7.54 (s, 2H), 7.49 (s, 1H), 7.40-7.35 (m, 1H), 4.49 (dtd, J=48.0, 8.5, 3.6 Hz, 1H), 3.65 (s, 3H), 3.22-3.11 (m, 5H), 2.22-2.08 (m, 1H), 2.08-1.95 (m, 1H), 1.93-1.79 (m, 1H), 1.63 (dtd, J=14.3, 9.5, 4.5 Hz, 1H). ESIMS m/z=431.1 (M+1)

Example 264

(S)-5-amino-N-(5-(5-amino-3,3-difluoroazepan-1-yl)-1-methyl-1H-pyrazol-4-yl)-2-(3-fluoropyridin-2-yl)thiazole-4-carboxamide 264

SFC chiral separation of the parent racemic compound gave enantiomer 264. $^1$H NMR (400 MHz, DMSO) δ 8.69 (s, 1H), 8.43 (d, J=4.5 Hz, 1H), 8.27 (s, 2H), 7.88 (dd, J=10.9, 8.6 Hz, 1H), 7.67 (s, 2H), 7.61 (s, 1H), 7.48 (dt, J=8.3, 4.1 Hz, 1H), 3.68 (s, 3H), 3.20-2.99 (m, 3H), 2.32 (t, J=19.9 Hz, 3H), 1.93 (d, J=13.3 Hz, 1H), 1.82 (dd, J=14.8, 9.4 Hz, 2H). ESIMS m/z=467.1 (M+1)

Example 265

5-amino-N-(5-((4R,5S)-4-amino-5-fluoroazepan-1-yl)-1-methyl-1H-pyrazol-4-yl)-2-(2-fluoro-5-methylphenyl)thiazole-4-carboxamide 265

SFC chiral separation of the parent racemic compound gave enantiomer 265. $^1$H NMR (400 MHz, DMSO) δ 9.16 (s, 1H), 8.05 (s, 1H), 7.51 (s, 1H), 7.40 (s, 2H), 7.23 (d, J=9.0 Hz, 2H), 4.88 (dd, J=47.4, 7.4 Hz, 1H), 3.65 (s, 3H), 3.09 (m, 3H), 2.36 (s, 3H), 2.20 (ddd, J=10.8, 7.3, 3.4 Hz, 1H), 2.00-1.80 (m, 3H), 1.78-1.67 (m, 1H). ESIMS m/z=462.1 (M+1)

Example 266

5-amino-N-(5-((4S,5R)-4-amino-5-fluoroazepan-1-yl)-1-methyl-1H-pyrazol-4-yl)-2-(2,5-difluorophenyl)thiazole-4-carboxamide 266

SFC chiral separation of the parent racemic compound gave enantiomer 266. $^1$H NMR (400 MHz, DMSO) δ 9.21 (s, 1H), 8.28 (s, 2H), 8.12 (ddd, J=9.3, 5.7, 3.3 Hz, 1H), 7.47 (s, 2H), 7.40 (m, 2H), 7.27 (tt, J=7.4, 3.5 Hz, 1H), 4.88 (d, J=40.8 Hz, 2H), 3.67 (s, 3H), 3.09 (d, J=4.0 Hz, 1H), 2.25-2.09 (m, 2H), 2.06-1.82 (m, 3H), 1.82-1.66 (m, 2H). ESIMS m/z=466.1 (M+1)

Example 267

5-amino-N-(5-((4R,5S)-4-amino-5-fluoroazepan-1-yl)-1-methyl-1H-pyrazol-4-yl)-2-(2-fluorophenyl)thiazole-4-carboxamide 267

SFC chiral separation of the parent racemic compound gave enantiomer 267. $^1$H NMR (400 MHz, DMSO) δ 9.11 (s, 1H), 8.26 (dd, J=14.8, 6.9 Hz, 1H), 7.51 (s, 1H), 7.41 (s, 3H), 7.39-7.29 (m, 2H), 4.88 (dd, J=47.4, 7.1 Hz, 1H), 3.65 (s, 3H), 3.12-3.03 (m, 5H), 2.26-2.12 (m, 1H), 2.00-1.80 (m, 2H), 1.79-1.67 (m, 1H). ESIMS m/z=448.1 (M+1)

Example 268

5-amino-N-(5-((4R,5R)-4-amino-5-fluoroazepan-1-yl)-1-methyl-1H-pyrazol-4-yl)-2-(3-fluoropyridin-2-yl)thiazole-4-carboxamide 268

SFC chiral separation of the parent racemic compound gave enantiomer 268. $^1$H NMR (400 MHz, DMSO) δ 8.79 (s, 1H), 8.43 (d, J=4.6 Hz, 1H), 7.85 (dd, J=11.0, 8.6 Hz, 1H), 7.63 (d, J=13.0 Hz, 3H), 7.47 (dt, J=8.3, 4.1 Hz, 1H), 4.49 (dtd, J=47.9, 8.1, 3.6 Hz, 1H), 3.65 (s, 3H), 3.18-3.07 (m, 4H), 2.21-2.04 (m, 1H), 1.98 (dt, J=9.5, 7.4 Hz, 1H), 1.94-1.83 (m, 1H), 1.76-1.50 (m, 1H), 1.72-1.57 (m, 1H). ESIMS m/z=449.1 (M+1)

Example 269

5-amino-N-(5-((4S,5S)-4-amino-5-fluoroazepan-1-yl)-1-methyl-1H-pyrazol-4-yl)-2-(3-fluoropyridin-2-yl)thiazole-4-carboxamide 269

SFC chiral separation of the parent racemic compound gave enantiomer 269. $^1$H NMR (400 MHz, DMSO) δ 8.79 (s, 1H), 8.43 (d, J=4.6 Hz, 1H), 7.85 (dd, J=11.0, 8.6 Hz, 1H), 7.63 (d, J=13.0 Hz, 3H), 7.47 (dt, J=8.3, 4.1 Hz, 1H), 4.49 (dtd, J=47.9, 8.1, 3.6 Hz, 1H), 3.65 (s, 3H), 3.18-3.07 (m, 4H), 2.21-2.04 (m, 1H), 1.98 (dt, J=9.5, 7.4 Hz, 1H), 1.94-1.83 (m, 1H), 1.76-1.50 (m, 1H), 1.72-1.57 (m, 1H). ESIMS m/z=449.1 (M+1)

Example 270

5-amino-N-(5-((4S,5R)-4-amino-5-fluoroazepan-1-yl)-1-methyl-1H-pyrazol-4-yl)-2-(2-fluorophenyl)thiazole-4-carboxamide 270

SFC chiral separation of the parent racemic compound gave enantiomer 270. $^1$H NMR (400 MHz, DMSO) δ 9.11 (s, 1H), 8.26 (dd, J=14.8, 6.9 Hz, 1H), 7.51 (s, 1H), 7.41 (s, 3H), 7.39-7.29 (m, 2H), 4.88 (dd, J=47.4, 7.1 Hz, 1H), 3.65 (s, 3H), 3.12-3.03 (m, 5H), 2.26-2.12 (m, 1H), 2.00-1.80 (m, 2H), 1.79-1.67 (m, 1H). ESIMS m/z=448.1 (M+1)

Example 271

5-amino-N-(5-((4R,5S)-4-amino-5-fluoroazepan-1-yl)-1-methyl-1H-pyrazol-4-yl)-2-(2,5-difluorophenyl)thiazole-4-carboxamide 271

SFC chiral separation of the parent racemic compound gave enantiomer 271. $^1$H NMR (400 MHz, DMSO) δ 9.21 (s, 1H), 8.28 (s, 2H), 8.12 (ddd, J=9.3, 5.7, 3.3 Hz, 1H), 7.47 (s, 2H), 7.40 (m, 2H), 7.27 (tt, J=7.4, 3.5 Hz, 1H), 4.88 (d, J=40.8 Hz, 2H), 3.67 (s, 3H), 3.09 (d, J=4.0 Hz, 1H), 2.25-2.09 (m, 2H), 2.06-1.82 (m, 3H), 1.82-1.66 (m, 2H). ESIMS m/z=466.1 (M+1)

Example 272

5-amino-N-(5-((4S,5R)-4-amino-5-fluoroazepan-1-yl)-1-methyl-1H-pyrazol-4-yl)-2-(2-fluoro-5-methylphenyl)thiazole-4-carboxamide 272

SFC chiral separation of the parent racemic compound gave enantiomer 272. $^1$H NMR (400 MHz, DMSO) δ 9.16 (s, 1H), 8.05 (s, 1H), 7.51 (s, 1H), 7.40 (s, 2H), 7.23 (d, J=9.0 Hz, 2H), 4.88 (dd, J=47.4, 7.4 Hz, 1H), 3.65 (s, 3H), 3.09 (m, 3H), 2.36 (s, 3H), 2.20 (ddd, J=10.8, 7.3, 3.4 Hz, 1H), 2.00-1.80 (m, 3H), 1.78-1.67 (m, 1H). ESIMS m/z=462.1 (M+1)

Example 273

(R)-5-amino-N-(5-(5-amino-3,3-difluoroazepan-1-yl)-1-methyl-1H-pyrazol-4-yl)-2-(3-fluoropyridin-2-yl)thiazole-4-carboxamide 273

SFC chiral separation of the parent racemic compound gave enantiomer 273. $^1$H NMR (400 MHz, DMSO) δ 8.69 (s, 1H), 8.43 (d, J=4.5 Hz, 1H), 8.27 (s, 2H), 7.88 (dd, J=10.9, 8.6 Hz, 1H), 7.67 (s, 2H), 7.61 (s, 1H), 7.48 (dt, J=8.3, 4.1 Hz, 1H), 3.68 (s, 3H), 3.20-2.99 (m, 3H), 2.32 (t, J=19.9 Hz, 3H), 1.93 (d, J=13.3 Hz, 1H), 1.82 (dd, J=14.8, 9.4 Hz, 2H). ESIMS m/z=467.1 (M+1)

Example 274

5-amino-N-(5-((4R,5R)-4-amino-5-fluoroazepan-1-yl)-1-methyl-1H-pyrazol-4-yl)-2-(pyridin-2-yl)thiazole-4-carboxamide 274

SFC chiral separation of the parent racemic compound gave enantiomer 274. $^1$H NMR (400 MHz, DMSO) δ 8.88 (s, 1H), 8.53 (d, J=4.7 Hz, 1H), 8.14 (d, J=7.9 Hz, 1H), 7.89 (d, J=1.4 Hz, 1H), 7.54 (s, 2H), 7.49 (s, 1H), 7.40-7.35 (m, 1H), 4.49 (dtd, J=48.0, 8.5, 3.6 Hz, 1H), 3.65 (s, 3H), 3.22-3.11 (m, 5H), 2.22-2.08 (m, 1H), 2.08-1.95 (m, 1H), 1.93-1.79 (m, 1H), 1.63 (dtd, J=14.3, 9.5, 4.5 Hz, 1H). ESIMS m/z=431.1 (M+1)

Example 275

5-Amino-2-(2,6-difluoro-3-iodo-phenyl)-thiazole-4-carboxylic acid [5-(5-amino-3,3-difluoro-azepan-1-yl)-1-methyl-1H-pyrazol-4-yl]-amide 275

Following the procedure for Example 145 starting from tert-butyl 6,6-difluoro-1-(1-methyl-4-nitro-1H-pyrazol-5-yl)azepan-4-ylcarbamate gave 275 as an off-white solid (220 mg, 34% over three steps). $^1$H NMR (400 MHz, d$_4$-MeOD) δ 7.93-7.85 (m, 1H), 7.64 (s, 1H), 7.04 (ddd, J=10.3, 8.8, 1.4 Hz, 1H), 3.77 (s, 3H), 3.74-3.62 (m, 1H), 3.55-3.36 (m, 3H), 3.30-3.23 (m, 1H), 2.41-2.22 (m, 2H), 2.06-1.95 (m, 1H), 1.91-1.80 (m, 1H). LCMS (ES+) m/z 610 (M+1)

Example 276

5-amino-N-(5-((4S,5S)-4-amino-5-fluoroazepan-1-yl)-1-cyclopropyl-1H-pyrazol-4-yl)-2-(2,5-difluorophenyl)thiazole-4-carboxamide 276

Following the procedure for Example 107 starting from N-(1-(4-amino-1-cyclopropyl-1H-pyrazol-5-yl)-5-fluoroazepan-4-yl)-2,2,2-trifluoroacetamide and 5-(tert-butoxycarbonyl-amino)-2-(2,5-difluorophenyl)thiazole-4-carboxylic acid gave 276 as the monoformate salt as an off-white solid (170 mg, 40% over two steps). $^1$H NMR (400 MHz, d$_4$-MeOD) δ 8.54 (s, 1H), 8.06 (ddd, J=9.4, 5.8, 3.2 Hz, 1H), 7.39 (s, 1H), 7.28 (td, J=9.9, 4.4 Hz, 1H), 7.19-7.11 (m, 1H), 4.86 (dtd, J=49.0, 9.3, 3.6 Hz, 1H), 3.62-3.49 (m, 2H), 3.50-3.38 (m, 4H), 2.45-2.31 (m, 1H), 2.26-2.06 (m, 2H), 1.99-1.86 (m, 1H), 1.21-1.12 (m, 2H), 1.15-1.05 (m, 2H). LCMS (ES+) m/z 492 (M+1)

Example 277

5-amino-N-(5-((4S,5S)-4-amino-5-fluoroazepan-1-yl)-1-cyclopropyl-1H-pyrazol-4-yl)-2-(2-fluoro-5-methylphenyl)thiazole-4-carboxamide 277

Following the procedure for Example 107 starting from N-(1-(4-amino-1-cyclopropyl-1H-pyrazol-5-yl)-5-fluoroazepan-4-yl)-2,2,2-trifluoroacetamide and 5-(tert-butoxycarbonyl-amino)-2-(2-fluoro-5-methylphenyl)thiazole-4-carboxylic acid gave 277 as a yellow solid (228 mg, 55% over two steps). $^1$H NMR (400 MHz, d$_4$-MeOD) δ 8.07 (dd, J=7.3, 2.3 Hz, 1H), 7.48 (s, 1H), 7.24-7.19 (m, 1H), 7.11 (dd, J=11.4, 8.4 Hz, 1H), 4.49 (dtd, J=48.3, 8.8, 3.8 Hz, 1H), 3.56-3.48 (m, 1H), 3.47-3.34 (m, 4H), 3.23-3.13 (m, 1H), 2.41 (s, 3H), 2.35-2.21 (m, 1H), 2.19-2.06 (m, 1H), 2.01-1.91 (m, 1H), 1.84-1.72 (m, 1H), 1.19-1.10 (m, 2H), 1.11-1.04 (m, 2H). LCMS (ES+) m/z 488 (M+1)

Example 278

5-amino-N-(5-((4S,5S)-4-amino-5-fluoroazepan-1-yl)-1-cyclopropyl-1H-pyrazol-4-yl)-2-(2,6-difluorophenyl)thiazole-4-carboxamide 278

Following the procedure for Example 107 starting from N-(1-(4-amino-1-cyclopropyl-1H-pyrazol-5-yl)-5-fluoroazepan-4-yl)-2,2,2-trifluoroacetamide and 5-(tert-butoxycarbonyl-amino)-2-(2,6-difluorophenyl)thiazole-4-carboxylic acid gave, after purification via preparative HPLC, 278 as the monoformate salt as an off-white solid (209 mg, 50% over two steps). $^1$H NMR (400 MHz, d$_4$-MeOD) δ 8.54 (s, 1H), 7.52 (s, 1H), 7.51-7.44 (m, 1H), 7.19-7.12 (m, 2H), 4.86 (dtd, J=48.0, 9.3, 3.0 Hz, 1H), 3.61-3.47 (m, 2H), 3.48-3.36 (m, 4H), 2.46-2.32 (m, 1H), 2.26-2.05 (m, 2H), 1.99-1.86 (m, 1H), 1.23-1.11 (m, 2H), 1.13-1.05 (m, 2H). LCMS (ES+) m/z 492 (M+1)

Example 279

5-Amino-2-(2,6-difluoro-phenyl)-thiazole-4-carboxylic acid [5-(5-amino-3,3-difluoro-azepan-1-yl)-1-cyclopropyl-1H-pyrazol-4-yl]-amide 279

Following the procedure for Example 145 starting from N-(1-(1-cyclopropyl-4-nitro-1H-pyrazol-5-yl)-6,6-difluoroazepan-4-yl)-2,2,2-trifluoroacetamide gave 279 as the monoformate salt as an off-white solid (166 mg, 16% over three steps). $^1$H NMR (400 MHz, d$_4$-MeOD) δ 8.55 (s, 1H), 7.55-7.43 (m, 2H), 7.19-7.12 (m, 2H), 3.87-3.71 (m, 1H), 3.69-3.45 (m, 4H), 3.44-3.39 (m, 1H), 2.70-2.45 (m, 2H), 2.24-2.13 (m, 1H), 2.08-1.95 (m, 1H), 1.24-1.11 (m, 2H), 1.14-1.05 (m, 2H). LCMS (ES+) m/z 510 (M+1)

Example 280

(R)-5-amino-N-(5-(5-amino-3,3-difluoroazepan-1-yl)-1-methyl-1H-pyrazol-4-yl)-2-(2,5-difluorophenyl)thiazole-4-carboxamide 280

SFC chiral separation of the parent racemic compound gave enantiomer 280. $^1$H NMR (400 MHz, DMSO) δ 8.92 (s, 1H), 7.66 (s, 1H), 7.52 (d, J=8.0 Hz, 3H), 7.28 (t, J=8.6 Hz, 2H), 6.37 (m, 2H), 4.43 (d, J=4.1 Hz, 3H), 3.64 (dt, J=27.0, 13.5 Hz, 2H), 2.26 (s, 3H), 1.92-1.80 (m, 1H), 1.71 (tt, J=19.7, 10.0 Hz, 1H), 1.49 (dd, J=8.3, 6.7 Hz, 1H), 0.98 (d, J=2.4 Hz, 1H). ESIMS m/z=534.1 (M+1)

Example 281

(S)-5-amino-N-(5-(5-amino-3,3-difluoroazepan-1-yl)-1-methyl-1H-pyrazol-4-yl)-2-(2,5-difluorophenyl)thiazole-4-carboxamide 281

SFC chiral separation of the parent racemic compound gave enantiomer 281. $^1$H NMR (400 MHz, DMSO) δ 8.92 (s, 1H), 7.66 (s, 1H), 7.52 (d, J=8.0 Hz, 3H), 7.28 (t, J=8.6 Hz, 2H), 6.37 (m, 2H), 4.43 (d, J=4.1 Hz, 3H), 3.64 (dt, J=27.0, 13.5 Hz, 2H), 2.26 (s, 3H), 1.92-1.80 (m, 1H), 1.71 (tt, J=19.7, 10.0 Hz, 1H), 1.49 (dd, J=8.3, 6.7 Hz, 1H), 0.98 (d, J=2.4 Hz, 1H). ESIMS m/z=534.1 (M+1)

Example 282

(S)-5-amino-N-(5-(5-amino-3,3-difluoroazepan-1-yl)-1-methyl-1H-pyrazol-4-yl)-2-(2,5-difluorophenyl)thiazole-4-carboxamide 282

SFC chiral separation of the parent racemic compound gave enantiomer 282. $^1$H NMR (400 MHz, DMSO) δ 9.11 (s, 1H), 8.13 (s, 1H), 7.48 (s, 2H), 7.44 (s, 1H), 7.43 (m, 1H), 7.28 (tt, J=7.5, 3.6 Hz, 1H), 3.68 (s, 3H), 3.67-3.62 (m, 1H), 3.48-3.35 (m, 2H), 3.19-3.06 (m, 2H), 2.23 (ddd, J=35.9, 24.1, 14.0 Hz, 3H), 1.92-1.82 (m, 1H), 1.73 (ddd, J=20.0, 12.7, 8.0 Hz, 1H). ESIMS m/z=484.1 (M+1)

Example 283

(R)-5-amino-N-(5-(5-amino-3,3-difluoroazepan-1-yl)-1-methyl-1H-pyrazol-4-yl)-2-(2,5-difluorophenyl)thiazole-4-carboxamide 283

SFC chiral separation of the parent racemic compound gave enantiomer 283. $^1$H NMR (400 MHz, DMSO) δ 9.11 (s, 1H), 8.13 (s, 1H), 7.48 (s, 2H), 7.44 (s, 1H), 7.43 (m, 1H), 7.28 (tt, J=7.5, 3.6 Hz, 1H), 3.68 (s, 3H), 3.67-3.62 (m, 1H), 3.48-3.35 (m, 2H), 3.19-3.06 (m, 2H), 2.23 (ddd, J=35.9, 24.1, 14.0 Hz, 3H), 1.92-1.82 (m, 1H), 1.73 (ddd, J=20.0, 12.7, 8.0 Hz, 1H). ESIMS m/z=484.1 (M+1)

Example 284

(S)-5-amino-N-(5-(5-amino-3,3-difluoroazepan-1-yl)-1-methyl-1H-pyrazol-4-yl)-2-(2-fluoro-5-methylphenyl)thiazole-4-carboxamide 284

SFC chiral separation of the parent racemic compound gave enantiomer 284. $^1$H NMR (400 MHz, DMSO) δ 8.98 (s, 1H), 8.31 8.08 (d, J=7.4 Hz, 1H), 7.49 (s, 1H), 7.41 (s, 2H), 7.23 (d, J=9.0 Hz, 2H), 3.68 (s, 3H), 3.64 (d, J=14.5 Hz, 1H), 3.45 (ddd, J=19.7, 15.1, 9.3 Hz, 2H), 3.21-3.11 (m, 2H), 2.37 (s, 3H), 2.28 (dd, J=31.2, 15.2 Hz, 2H), 1.88 (d, J=15.3 Hz, 1H), 1.81-1.66 (m, 1H). ESIMS m/z=480.1 (M+1)

Example 285

((R)-5-amino-N-(5-(5-amino-3,3-difluoroazepan-1-yl)-1-methyl-1H-pyrazol-4-yl)-2-(2-fluoro-5-methylphenyl)thiazole-4-carboxamide 285

SFC chiral separation of the parent racemic compound gave enantiomer 285. $^1$H NMR (400 MHz, DMSO) δ 8.98 (s, 1H), 8.31 8.08 (d, J=7.4 Hz, 1H), 7.49 (s, 1H), 7.41 (s, 2H), 7.23 (d, J=9.0 Hz, 2H), 3.68 (s, 3H), 3.64 (d, J=14.5 Hz, 1H), 3.45 (ddd, J=19.7, 15.1, 9.3 Hz, 2H), 3.21-3.11 (m, 2H), 2.37 (s, 3H), 2.28 (dd, J=31.2, 15.2 Hz, 2H), 1.88 (d, J=15.3 Hz, 1H), 1.81-1.66 (m, 1H). ESIMS m/z=480.1 (M+1)

Example 286

(S)-5-amino-N-(5-(5-amino-3,3-difluoroazepan-1-yl)-1-methyl-1H-pyrazol-4-yl)-2-(2-fluorophenyl)thiazole-4-carboxamide 286

SFC chiral separation of the parent racemic compound gave enantiomer 286. $^1$H NMR (400 MHz, DMSO) δ 8.99 (s, 1H), 8.30 (dd, J=14.7, 6.9 Hz, 1H), 7.51 (s, 1H), 7.48-7.40 (m, 3H), 7.40-7.32 (m, 2H), 3.68 (s, 3H), 3.50-3.37 (m, 3H), 3.16 (m, 2H), 2.35-2.17 (m, 2H), 1.87 (m, 1H), 1.76 (m, 1H). ESIMS m/z=466.1 (M+1)

Example 287

(R)-5-amino-N-(5-(5-amino-3,3-difluoroazepan-1-yl)-1-methyl-1H-pyrazol-4-yl)-2-(2-fluorophenyl)thiazole-4-carboxamide 287

SFC chiral separation of the parent racemic compound gave enantiomer 287. $^1$H NMR (400 MHz, DMSO) δ 8.99 (s, 1H), 8.30 (dd, J=14.7, 6.9 Hz, 1H), 7.51 (s, 1H), 7.48-7.40 (m, 3H), 7.40-7.32 (m, 2H), 3.68 (s, 3H), 3.50-3.37 (m, 3H), 3.16 (m, 2H), 2.35-2.17 (m, 2H), 1.87 (m, 1H), 1.76 (m, 1H). ESIMS m/z=466.1 (M+1)

Example 288

5-amino-N-(5-((4S,5S)-4-amino-5-methoxyazepan-1-yl)-1-methyl-1H-pyrazol-4-yl)-2-(2,6-difluorophenyl)thiazole-4-carboxamide 288

SFC chiral separation of the parent racemic compound gave enantiomer 288. $^1$H NMR (400 MHz, DMSO) δ 8.79 (s, 1H), 8.31 (s, 1H), 7.53-7.49 (m, 4H), 7.26 (t, J=8.7 Hz, 2H), 3.63 (s, 3H), 3.25 (s, 3H), 3.24-3.13 (m, 4H), 3.06 (m, 2H), 1.69 (m, 2H). ESIMS m/z=478.2 (M+1)

Example 289

5-amino-N-(5-((4R,5R)-4-amino-5-methoxyazepan-1-yl)-1-methyl-1H-pyrazol-4-yl)-2-(2,6-difluorophenyl)thiazole-4-carboxamide 289

SFC chiral separation of the parent racemic compound gave enantiomer 289. $^1$H NMR (400 MHz, DMSO) δ 8.79 (s, 1H), 8.31 (s, 1H), 7.53-7.49 (m, 4H), 7.26 (t, J=8.7 Hz, 2H), 3.63 (s, 3H), 3.25 (s, 3H), 3.24-3.13 (m, 4H), 3.06 (m, 2H), 1.69 (m, 2H). ESIMS m/z=478.2 (M+1)

Example 290

(S)-5-amino-2-(2,6-difluorophenyl)-N-(5-(5-(dimethylamino)-3,3-difluoroazepan-1-yl)-1-methyl-1H-pyrazol-4-yl)thiazole-4-carboxamide 290

SFC chiral separation of the parent racemic compound gave enantiomer 290. $^1$H NMR (400 MHz, DMSO) δ 8.70 (s, 1H), 8.18 (s, 1H), 7.54 (s, 1H), 7.50 (m, 2H), 7.25 (t, J=8.6 Hz, 2H), 3.68 (s, 3H), 3.65-3.51 (m, 2H), 2.84 (s, 1H), 2.24 (m, 4H), 2.07 (s, 6H), 1.96-1.76 (m, 2H). ESIMS m/z=512.1 (M+1)

Example 292

3-amino-N-(5-(5-amino-3,3-difluoroazepan-1-yl)-1-methyl-1H-pyrazol-4-yl)-6-(2-fluorophenyl)picolinamide 292

Following the procedures of Example 180, compound 292 was prepared. $^1$H NMR (400 MHz, DMSO) δ 9.72 (s, 1H), 8.02 (t, J=7.3 Hz, 1H), 7.72 (dd, J=8.7, 2.1 Hz, 1H), 7.66 (s, 1H), 7.49-7.38 (m, 1H), 7.38-7.25 (m, 3H), 7.07 (s, 2H), 3.80-3.58 (m, 4H), 3.51-3.33 (m, 2H), 3.20-3.03 (m, 2H), 2.25-2.09 (m, 1H), 1.90-1.76 (m, 1H), 1.76-1.61 (m, 1H), 1.54-1.37 (m, 1H). MS (ESI) m/z: 460.2 [M+H$^+$].

Example 293

3-amino-N-(5-(5-amino-3,3-difluoroazepan-1-yl)-1-methyl-1H-pyrazol-4-yl)-6-(2-fluorophenyl)pyrazine-2-carboxamide 293

Following the procedures of Example 180, compound 293 was prepared. $^1$H NMR (400 MHz, DMSO) δ 9.79 (s, 1H), 8.68 (d, J=2.3 Hz, 1H), 8.25 (s, 1H), 8.12 (t, J=8.1 Hz, 1H), 7.74 (s, 2H), 7.60-7.52 (m, 1H), 7.52-7.41 (m, 1H), 7.41-7.28 (m, 2H), 3.77-3.57 (m, 5H), 3.18-2.96 (m, 3H), 2.31-2.15 (m, 2H), 1.94-1.81 (m, 1H), 1.81-1.62 (m, 1H). MS (ESI) m/z: 461.2 [M+H$^+$].

Example 291

(R)-5-amino-2-(2,6-difluorophenyl)-N-(5-(5-(dimethylamino)-3,3-difluoroazepan-1-yl)-1-methyl-1H-pyrazol-4-yl)thiazole-4-carboxamide 291

SFC chiral separation of the parent racemic compound gave enantiomer 291. $^1$H NMR (400 MHz, DMSO) δ 8.70 (s, 1H), 8.18 (s, 1H), 7.54 (s, 1H), 7.50 (m, 2H), 7.25 (t, J=8.6 Hz, 2H), 3.68 (s, 3H), 3.65-3.51 (m, 2H), 2.84 (s, 1H), 2.24 (m, 4H), 2.07 (s, 6H), 1.96-1.76 (m, 2H). ESIMS m/z=512.1 (M+1)

Example 294

5-amino-N-(5-((4S,5R)-4-amino-5-fluoroazepan-1-yl)-1-methyl-1H-pyrazol-4-yl)-2-(2-fluoro-5-methylphenyl)thiazole-4-carboxamide 294

Following the procedure for Example 221 starting from N-(1-(4-amino-1-methyl-1H-pyrazol-5-yl)-5-fluoroazepan-4-yl)-2,2,2-trifluoroacetamide and 5-(tert-butoxycarbonylamino)-2-(2-fluoro-5-methylphenyl)thiazole-4-carboxylic acid gave, after purification via silica gel column chromatography (5% MeOH/DCM with 1% 7 N ammonia in MeOH), 294 as a cream solid (107 mg, 48%). $^1$H NMR (400 MHz, CDCl$_3$) δ 8.73 (s, 1H), 7.90-7.84 (m, 1H), 7.82 (s, 1H), 7.17-7.11 (m, 1H), 7.04 (dd, J=11.1, 8.4 Hz, 1H), 6.10 (s, 2H), 4.95-4.78 (m, 1H), 3.74 (s, 3H), 3.49-3.33 (m, 3H), 3.24-3.11 (m, 2H), 2.40 (s, 3H), 2.40-2.26 (m, 1H), 2.09-1.91 (m, 2H), 1.87-1.77 (m, 1H). Alkyl NH$_2$ not seen. LCMS (ES+) m/z 462 (M+1)

Example 295

5-amino-N-(5-((4S,5R)-4-amino-5-fluoroazepan-1-yl)-1-methyl-1H-pyrazol-4-yl)-2-(2,5-difluorophenyl)thiazole-4-carboxamide 295

Following the procedure for Example 221 starting from N-(1-(4-amino-1-methyl-1H-pyrazol-5-yl)-5-fluoroazepan-4-yl)-2,2,2-trifluoroacetamide and 5-(tert-butoxycarbonylamino)-2-(2,5-difluorophenyl)thiazole-4-carboxylic acid gave 295 as a dark cream solid (166 mg, 73% over three steps. $^1$H NMR (400 MHz, CDCl$_3$) δ 8.65 (s, 1H), 7.87-7.81 (m, 2H), 7.17-7.09 (m, 1H), 7.07-7.01 (m, 1H), 6.16 (s, 2H), 4.90 (dd, J=47.1, 6.7 Hz, 1H), 3.74 (s, 3H), 3.49-3.32 (m, 3H), 3.23-3.09 (m, 2H), 2.36-2.28 (m, 1H), 2.18-1.81 (m, 3H). Alkyl NH$_2$ not seen. LCMS (ES+) m/z 466 (M+1)

Example 296

5-amino-N-(5-((4S,5R)-4-amino-5-fluoroazepan-1-yl)-1-methyl-1H-pyrazol-4-yl)-2-(2-fluorophenyl)thiazole-4-carboxamide 296

Following the procedure for Example 221 starting from N-(1-(4-amino-1-methyl-1H-pyrazol-5-yl)-5-fluoroazepan-4-yl)-2,2,2-trifluoroacetamide and 5-(tert-butoxycarbonylamino)-2-(2-fluorophenyl)thiazole-4-carboxylic acid gave, after purification via silica gel column chromatography (5-7% MeOH/DCM with 1% 7 N ammonia in MeOH), 296 as a cream solid (128 mg, 59% over three steps). $^1$H NMR (400 MHz, CDCl$_3$) δ 8.72 (s, 1H), 8.13-8.08 (m, 1H), 7.84 (s, 1H), 7.40-7.32 (m, 1H), 7.29-7.20 (m, 1H), 7.17 (dd, J=11.4, 8.3 Hz, 1H), 6.10 (s, 2H), 4.89 (dd, J=47.0, 7.0 Hz, 1H), 3.74 (s, 3H), 3.50-3.31 (m, 3H), 3.22-3.09 (m, 2H), 2.37-2.27 (m, 1H), 2.12-1.89 (m, 2H), 1.86-1.78 (m, 1H). Alkyl NH$_2$ not seen. LCMS (ES+) m/z 448 (M+1)

Example 297

5-amino-N-(5-((4S,5S)-4-amino-5-fluoroazepan-1-yl)-1-methyl-1H-pyrazol-4-yl)-2-(3-fluoropyridin-2-yl)thiazole-4-carboxamide 297

Following the procedure for Example 107 starting from N-(1-(4-amino-1-methyl-1H-pyrazol-5-yl)-5-fluoroazepan-4-yl)-2,2,2-trifluoroacetamide and 5-(tert-butoxycarbonylamino)-2-(3-fluoropyridin-2-yl)thiazole-4-carboxylic acid gave 297 as a pale brown solid (424 mg, 72% over 2 steps). $^1$H NMR (400 MHz, CDCl$_3$) δ 8.70 (s, 1H), 8.39 (dt, J=4.6, 1.4 Hz, 1H), 7.86 (s, 1H), 7.52 (ddd, J=10.8, 8.3, 1.4 Hz, 1H), 7.32-7.26 (m, 1H), 6.32 (s, 2H), 4.51 (dtd, J=47.9, 8.5, 3.6 Hz, 1H), 3.73 (s, 3H), 3.40-3.17 (m, 5H), 2.34-2.19 (m, 1H), 2.16-1.96 (m, 2H), 1.79-1.66 (m, 1H). Alkyl NH$_2$ not seen. LCMS (ES+) m/z 449 (M+1)

Example 298

5-amino-N-(5-((4S,5S)-4-amino-5-fluoroazepan-1-yl)-1-methyl-1H-pyrazol-4-yl)-2-(pyridin-2-yl)thiazole-4-carboxamide 298

Following the procedure for Example 107 starting from N-(1-(4-amino-1-methyl-1H-pyrazol-5-yl)-5-fluoroazepan-4-yl)-2,2,2-trifluoroacetamide and 5-(tert-butoxycarbonylamino)-2-(pyridin-2-yl)thiazole-4-carboxylic acid gave 298 as a pale yellow solid (418 mg, 74% over 2 steps). $^1$H NMR (400 MHz, CDCl$_3$) δ 8.54 (d, J=4.9 Hz, 1H), 8.40 (s, 1H), 8.06 (d, J=8.0 Hz, 1H), 7.78-7.73 (m, 2H), 7.28-7.23 (m, 1H), 6.26 (s, 2H), 4.51 (dtd, J=48.0, 8.8, 3.8 Hz, 1H), 3.73 (s, 3H), 3.37-3.20 (m, 5H), 2.35-2.21 (m, 1H), 2.18-2.04 (m, 1H), 2.02-1.92 (m, 1H), 1.79-1.66 (m, 1H). Alkyl NH₂ not seen. LCMS (ES+) m/z 431 (M+1)

Example 299

5-Amino-2-(3-fluoro-pyridin-2-yl)-thiazole-4-carboxylic acid [5-(5-amino-3,3-difluoro-azepan-1-yl)-1-methyl-1H-pyrazol-4-yl]-amide 299

Following the procedure for Example 145 starting from tert-butyl 6,6-difluoro-1-(1-methyl-4-nitro-1H-pyrazol-5-yl) azepan-4-ylcarbamate gave 299 as a pale yellow solid (350 mg, 43% over 3 steps). $^1$H NMR (400 MHz, CDCl$_3$) δ 8.56 (s, 1H), 8.39 (dt, J=4.6, 1.4 Hz, 1H), 7.81 (s, 1H), 7.52 (ddd, J=10.8, 8.3, 1.4 Hz, 1H), 7.32-7.26 (m, 1H), 6.32 (s, 2H), 3.76 (s, 3H), 3.71-3.57 (m, 1H), 3.54-3.35 (m, 3H), 3.33-3.24 (m, 1H), 2.41-2.26 (m, 2H), 2.03-1.92 (m, 1H), 1.90-1.78 (m, 1H), 1.34 (br s, 2H). LCMS (ES+) m/z 467 (M+1)

Example 300

5-Amino-2-pyridin-2-yl-thiazole-4-carboxylic acid [5-(5-amino-3,3-difluoro-azepan-1-yl)-1-methyl-1H-pyrazol-4-yl]-amide 300

Following the procedure for Example 145 starting from tert-butyl 6,6-difluoro-1-(1-methyl-4-nitro-1H-pyrazol-5-yl) azepan-4-ylcarbamate gave 300 as a pale yellow solid (519 mg, 66% over 3 steps). $^1$H NMR (400 MHz, CDCl$_3$) δ 8.55 (d, J=4.9 Hz, 1H), 8.41 (s, 1H), 8.07 (d, J=8.0 Hz, 1H), 7.76 (t, J=7.8 Hz, 1H), 7.69 (s, 1H), 7.33-7.20 (m, 1H), 6.25 (s, 2H), 3.77 (s, 3H), 3.74-3.59 (m, 1H), 3.55-3.36 (m, 3H), 3.33-3.23 (m, 1H), 2.43-2.28 (m, 2H), 2.03-1.92 (m, 1H), 1.88-1.77 (m, 1H). Alkyl NH₂ not seen. LCMS (ES+) m/z 449 (M+1).

Example 301

(S)-5-Amino-2-(2,6-difluorophenyl)-N-(5-(3-methylpiperazin-1-yl)-1-(2,2,2-trifluoroethyl)-1H-pyrazol-4-yl)thiazole-4-carboxamide 301

Following the procedure for Example 233 starting from tert-butyl (S)-4-(4-(5-(tert-butoxycarbonylamino)-2-(2,6-difluorophenyl)thiazole-4-carboxamido)-1-(2,2,2-trifluoroethyl)-1H-pyrazol-5-yl)-2-methylpiperazine-1-carboxylate gave 301 as a white solid (25 mg, 50%). $^1$H-NMR (500 MHz, CD$_3$OD) δ (ppm): 7.69 (s, 1H), 7.51-7.45 (m, 1H), 7.16-7.12 (m, 2H), 4.90-4.78 (m, 2H), 3.22-3.17 (m, 1H), 3.05-2.86 (m, 6H), 1.08 (d, J=6 Hz, 3H); MS (ESI) m/z: 502 [M+H⁺]

Example 304

5-Amino-2-(2,6-difluoro-phenyl)-thiazole-4-carboxylic acid [5-(3,3-difluoro-5-hydroxy-azepan-1-yl)-1-methyl-1H-pyrazol-4-yl]-amide 304

Following the procedure for Example 101 starting from benzaldehyde O-6,6-difluoro-1-(1-methyl-4-nitro-1H-pyrazol-5-yl)azepan-4-yloxime from Example 85a gave, after purification via preparative HPLC 304 as a white solid (37 mg, 27% over three steps). $^1$H NMR (400 MHz, CDCl$_3$) δ 8.77 (s, 1H), 7.84 (s, 1H), 7.39-7.29 (m, 1H), 7.09-6.99 (m, 2H), 6.19 (s, 2H), 4.30 (s, 1H), 3.75 (s, 3H), 3.66-3.36 (m, 3H), 3.34-3.24 (m, 1H), 2.57-2.40 (m, 2H), 2.10-2.02 (m, 3H). LCMS (ES+) m/z 485 (M+1)

Example 305

5-amino-N-(5-((4S,5R)-4-amino-5-methoxyazepan-1-yl)-1-methyl-1H-pyrazol-4-yl)-2-(2,6-difluorophenyl)thiazole-4-carboxamide 305

Following the procedure for Example 101 starting from tert-butyl 5-methoxy-1-(1-methyl-4-nitro-1H-pyrazol-5-yl) azepan-4-ylcarbamate from Example 49c gave 305 as an apricot foam (286 mg, 66% over three steps). $^1$H NMR (400 MHz, CDCl$_3$) δ 8.94 (s, 1H), 7.90 (s, 1H), 7.38-7.28 (m, 1H), 7.02 (t, J=8.7 Hz, 2H), 6.16 (s, 2H), 3.72 (s, 3H), 3.49-3.44 (m, 1H), 3.45-3.18 (m, 6H), 3.20-3.06 (m, 2H), 2.17-2.06 (m, 1H), 2.06-1.96 (m, 1H), 1.85-1.65 (m, 2H). Alkyl NH₂ not observed. LCMS (ES+) m/z 478 (M+1)

Example 306

5-amino-N-(5-((3R,5R)-5-amino-3-fluoroazepan-1-yl)-1-cyclopropyl-1H-pyrazol-4-yl)-2-(2,6-difluorophenyl)thiazole-4-carboxamide 306

Following the procedure for Example 107 starting from N-(1-(4-amino-1-cyclopropyl-1H-pyrazol-5-yl)-6-fluoroazepan-4-yl)-2,2,2-trifluoroacetamide from Example 53a gave, after purification via chiral preparative HPLC, 306 as an off-white solid (7.6 mg, 2% over 2 steps). $^1$H NMR (400 MHz, d$_4$-MeOD) δ 7.63 (s, 1H), 7.51-7.42 (m, 1H), 7.20-7.11 (m, 2H), 4.89-4.85 (m, 1H), 3.63-3.46 (m, 4H), 3.45-3.27 (m, 2H), 2.34-2.18 (m, 1H), 2.10-1.90 (m, 2H), 1.80-1.66 (m, 1H), 1.25-1.15 (m, 2H), 1.17-1.00 (m, 3H). LCMS (ES+) m/z 492 (M+1)

Example 307

5-amino-N-(5-((3S,5S)-5-amino-3-fluoroazepan-1-yl)-1-cyclopropyl-1H-pyrazol-4-yl)-2-(2,6-difluorophenyl)thiazole-4-carboxamide 307

Following the procedure for Example 107 starting from N-(1-(4-amino-1-cyclopropyl-1H-pyrazol-5-yl)-6-fluoroazepan-4-yl)-2,2,2-trifluoroacetamide from Example 53a gave, after purification via chiral preparative HPLC, 307 as an off-white solid (7.8 mg, 2% over 2 steps). $^1$H NMR (400 MHz, d$_4$-MeOD) δ 7.63 (s, 1H), 7.51-7.42 (m, 1H), 7.20-7.11 (m, 2H), 4.89-4.85 (m, 1H), 3.63-3.46 (m, 4H), 3.45-3.27 (m, 2H), 2.34-2.18 (m, 1H), 2.10-1.90 (m, 2H), 1.80-1.66 (m, 1H), 1.25-1.15 (m, 2H), 1.17-1.00 (m, 3H). LCMS (ES+) m/z 492 (M+1)

Example 308

5-amino-N-(5-((3S,5R)-5-amino-3-fluoroazepan-1-yl)-1-cyclopropyl-1H-pyrazol-4-yl)-2-(2,6-difluorophenyl)thiazole-4-carboxamide 308

Following the procedure for Example 107 starting from N-(1-(4-amino-1-cyclopropyl-1H-pyrazol-5-yl)-6-fluoroazepan-4-yl)-2,2,2-trifluoroacetamide from Example 53a gave, after purification via chiral preparative HPLC, 308 as an off-white solid (2.6 mg, 1% over 2 steps). $^1$H NMR (400 MHz, d$_4$-MeOD) δ 7.58 (s, 1H), 7.52-7.44 (m, 1H), 7.21-7.11 (m, 2H), 4.87-4.86 (m, 1H), 3.61-3.49 (m, 4H), 3.38-3.30 (m, 1H), 3.12 (t, J=5.8 Hz, 1H), 2.32-2.23 (m, 1H), 2.21-2.07 (m, 1H), 2.03-1.93 (m, 1H), 1.93-1.83 (m, 1H), 1.22-1.04 (m, 4H). LCMS (ES+) m/z 492 (M+1)

Example 309

5-amino-N-(5-((3R,5S)-5-amino-3-fluoroazepan-1-yl)-1-cyclopropyl-1H-pyrazol-4-yl)-2-(2,6-difluorophenyl)thiazole-4-carboxamide 309

Following the procedure for Example 107 starting from N-(1-(4-amino-1-cyclopropyl-1H-pyrazol-5-yl)-6-fluoroazepan-4-yl)-2,2,2-trifluoroacetamide from Example 53a gave, after purification via chiral preparative HPLC, 309 as an off-white solid (2.5 mg, 1% over 2 steps). $^1$H NMR (400 MHz, d$_4$-MeOD) δ 7.58 (s, 1H), 7.52-7.44 (m, 1H), 7.21-7.11 (m, 2H), 4.87-4.86 (m, 1H), 3.61-3.49 (m, 4H), 3.38-3.30 (m, 1H), 3.12 (t, J=5.8 Hz, 1H), 2.32-2.23 (m, 1H), 2.21-2.07 (m, 1H), 2.03-1.93 (m, 1H), 1.93-1.83 (m, 1H), 1.22-1.04 (m, 4H). LCMS (ES+) m/z 492 (M+1)

Example 310

5-amino-N-(5-((4S,5R)-4-amino-5-hydroxyazepan-1-yl)-1-methyl-1H-pyrazol-4-yl)-2-(2,6-difluorophenyl)thiazole-4-carboxamide 310

Following the procedure for Example 101 starting from tert-butyl 5-hydroxy-1-(1-methyl-4-nitro-1H-pyrazol-5-yl)azepan-4-ylcarbamate from Example 49d gave 310 as a light beige solid (106 mg, 68% over three steps). $^1$H NMR (400 MHz, d$_6$-DMSO) δ 9.05 (br s, 1H), 7.60-7.47 (m, 4H), 7.28 (t, J=8.8 Hz, 2H), 3.90-3.82 (s, 1H), 3.70-3.58 (m, 3H), 3.40-3.20 (m, 3H), 3.08-2.92 (m, 2H), 1.99-1.83 (m, 2H), 1.70-1.55 (m, 2H). Alkyl NH$_2$ and OH not observed. LCMS (ES+) m/z 464 (M+1)

Example 313

5-amino-N-[5-(5,8-diazaspiro[2.6]nonan-8-yl)-1-methyl-pyrazol-4-yl]-2-(2,6-difluorophenyl)thiazole-4-carboxamide 313

Following the procedures in Example 101, starting from tert-butyl 8-(1-methyl-4-nitro-1H-pyrazol-5-yl)-5,8-diazaspiro[2.6]nonane-5-carboxylate gave 313 as a pale yellow solid (90 mg, 35% over three steps). $^1$H NMR (400 MHz, CDCl$_3$) δ 12.25 (s, 1H), 8.15 (s, 1H), 7.41-7.22 (m, 1H), 7.02 (t, J=8.6 Hz, 2H), 6.34 (s, 2H), 3.66 (s, 3H), 3.38 (t, J=6.3 Hz, 2H), 3.11 (t, J=6.3 Hz, 2H), 2.97 (s, 2H), 2.74 (s, 2H), 0.33 (t, J=5.3 Hz, 2H), 0.13 (t, J=5.3 Hz, 2H). Exchangeable NH not observed. LCMS (ES+) m/z 460 (M+1)

Example 314

5-amino-N-[5-(4-amino-5-methoxy-azepan-1-yl)-1-methyl-pyrazol-4-yl]-2-(2,6-difluorophenyl)thiazole-4-carboxamide 314

Chiral separation by SFC of racemic 5-amino-N-[5-(4-amino-5-methoxy-azepan-1-yl)-1-methyl-pyrazol-4-yl]-2-(2,6-difluorophenyl)thiazole-4-carboxamide gave 314. $^1$H NMR (400 MHz, DMSO) δ 9.28 (s, 1H), 7.64 (s, 1H), 7.61-7.40 (m, 4H), 7.32-7.17 (m, 2H), 3.62 (s, 3H), 3.40 (d, J=8.4 Hz, 1H), 3.20 (s, 3H), 3.18-3.07 (m, 2H), 3.07-2.92 (m, 3H), 2.13-1.93 (m, 1H), 1.83-1.74 (m, 1H), 1.74-1.56 (m, 2H). LCMS (ES+) m/z 478 (M+1)

Example 315

5-amino-N-(5-((4S,5R)-4-amino-5-hydroxyazepan-1-yl)-1-methyl-1H-pyrazol-4-yl)-2-(2,6-difluorophenyl)thiazole-4-carboxamide 315

Chiral separation by SFC of racemic 5-amino-N-[5-(4-amino-5-methoxy-azepan-1-yl)-1-methyl-pyrazol-4-yl]-2-(2,6-difluorophenyl)thiazole-4-carboxamide gave 315. $^1$H NMR (400 MHz, DMSO) δ 9.28 (s, 1H), 7.64 (s, 1H), 7.60-7.42 (m, 4H), 7.31-7.20 (m, 2H), 3.62 (s, 3H), 3.44-3.36 (m, 1H), 3.19 (s, 3H), 3.18-3.07 (m, 2H), 3.02 (dt, J=13.0, 3.8 Hz, 3H), 2.12-1.95 (m, 1H), 1.86-1.73 (m, 1H), 1.73-1.57 (m, 2H). LCMS (ES+) m/z 478 (M+1)

Example 318

5-amino-2-(2,6-difluorophenyl)-N-[1-methyl-5-(2-oxoazepan-1-yl)pyrazol-4-yl]thiazole-4-carboxamide 318

Following the procedures in Example 101, starting from 1-(1-methyl-4-nitro-1H-pyrazol-5-yl)azepan-2-one gave 318 as a white solid (51 mg, 26% over three steps). $^1$H NMR (400 MHz, CDCl$_3$) δ 8.40 (s, 1H), 7.95 (s, 1H), 7.35-7.28 (m, 1H), 7.01 (t, J=8.9 Hz, 2H), 6.14 (s, 2H), 3.78-3.58 (m, 5H), 2.76 (d, J=7.4 Hz, 2H), 1.92-1.75 (m, 6H). LCMS (ES+) m/z 447 (M+1)

Example 319

5-amino-2-(2,6-difluorophenyl)-N-[1-methyl-5-(7-oxo-1,4-diazepan-1-yl)pyrazol-4-yl]thiazole-4-carboxamide 319

Following the procedures in Example 101, starting from tert-butyl 4-(1-methyl-4-nitro-1H-pyrazol-5-yl)-3-oxo-1,4-diazepane-1-carboxylate gave 319 as a white solid (35 mg, 20% over three steps). $^1$H NMR (400 MHz, CDCl$_3$) δ 8.70 (s, 1H), 7.96 (s, 1H), 7.36-7.28 (m, 1H), 7.02 (t, J=8.7 Hz, 2H), 6.16 (s, 2H), 3.83 (ddd, J=15.2, 8.3, 2.4 Hz, 1H), 3.72 (s, 3H), 3.64 (ddd, J=15.2, 6.1, 2.5 Hz, 1H), 3.22-3.02 (m, 4H), 2.96-2.84 (m, 2H). Exchangeable NH not observed. LCMS (ES+) m/z 448 (M+1)

Example 322

5-amino-N-[5-(4-amino-5-methoxy-azepan-1-yl)-1-methyl-pyrazol-4-yl]-2-(2-pyridyl)thiazole-4-carboxamide 322

Following the procedure Example 101, reacting tert-butyl ((4R,5R)-1-(4-amino-1-methyl-1H-pyrazol-5-yl)-5-methoxyazepan-4-yl)carbamate and 5-((tert-butoxycarbonyl)amino)-2-(pyridin-2-yl)thiazole-4-carboxylic acid gave racemic 322 (58.4 mg, 41% over two steps). $^1$H NMR (400 MHz, DMSO) δ 8.89 (s, 1H), 8.54 (d, J=4.7 Hz, 1H), 8.17 (d, J=8.0 Hz, 1H), 7.89 (t, J=7.7 Hz, 1H), 7.62-7.47 (m, 3H), 7.43-7.31 (m, 1H), 3.64 (s, 3H), 3.27 (s, 3H), 3.23-2.91 (m, 6H), 2.15-2.00 (m, 1H), 1.92-1.80 (m, 1H), 1.79-1.55 (m, 2H). LCMS (ES+) m/z 443 (M+1)

Example 323

5-amino-N-[5-(4-amino-5-methoxy-azepan-1-yl)-1-methyl-pyrazol-4-yl]-2-(3-fluoro-2-pyridyl)thiazole-4-carboxamide 323

Following the procedure Example 101, reacting tert-butyl ((4R,5R)-1-(4-amino-1-methyl-1H-pyrazol-5-yl)-5-methoxyazepan-4-yl)carbamate and 5-((tert-butoxycarbonyl)amino)-2-(3-fluoro-pyridin-2-yl)thiazole-4-carboxylic acid gave racemic 323 (35.8 mg, 24% over two steps). $^1$H NMR (400 MHz, DMSO) δ 8.84 (s, 1H), 8.43 (d, J=4.6 Hz, 1H), 7.89-7.78 (m, 1H), 7.66 (s, 2H), 7.62 (s, 1H), 7.48 (dt, J=8.3, 4.1 Hz, 1H), 3.65 (s, 3H), 3.28 (d, J=7.5 Hz, 5H), 3.26-2.95 (m, 8H), 2.07 (dd, J=10.6, 4.4 Hz, 1H), 1.92 (dd, J=10.6, 7.4 Hz, 1H), 1.79-1.55 (m, 2H). LCMS (ES+) m/z 461 (M+1)

Example 324

5-amino-N-[5-(4-amino-5-methoxy-azepan-1-yl)-1-methyl-pyrazol-4-yl]-2-(2-fluorophenyl)thiazole-4-carboxamide 324

Following the procedure Example 101, reacting tert-butyl ((4R,5R)-1-(4-amino-1-methyl-1H-pyrazol-5-yl)-5-methoxyazepan-4-yl)carbamate and 5-((tert-butoxycarbonyl)amino)-2-(2-fluorophenyl)thiazole-4-carboxylic acid gave 324 (118 mg, 63% over two steps). $^1$H NMR (400 MHz, DMSO) δ 8.94 (s, 1H), 8.30 (t, J=8.2 Hz, 1H), 7.51 (s, 1H), 7.48-7.39 (m, 3H), 7.39-7.27 (m, 2H), 3.64 (s, 3H), 3.27 (s, 4H), 3.24-2.90 (m, 7H), 2.14-2.01 (m, 1H), 1.91-1.81 (m, 1H), 1.77-1.54 (m, 2H). LCMS (ES+) m/z 460 (M+1)

Example 325

5-amino-N-[5-(4-amino-5-methoxy-azepan-1-yl)-1-methyl-pyrazol-4-yl]-2-(2-fluoro-5-methyl-phenyl)thiazole-4-carboxamide 325

Following the procedure Example 101, reacting tert-butyl ((4R,5R)-1-(4-amino-1-methyl-1H-pyrazol-5-yl)-5-methoxyazepan-4-yl)carbamate and 5-((tert-butoxycarbonyl)amino)-2-(2-fluoro-5-methylphenyl)thiazole-4-carboxylic acid gave 325 (70.8 mg, 40% over two steps). $^1$H NMR (400 MHz, DMSO) δ 8.98 (s, 1H), 8.07 (d, J=7.4 Hz, 1H), 7.48 (s, 1H), 7.40 (s, 2H), 7.23 (d, J=9.0 Hz, 2H), 3.64 (s, 3H), 3.24 (s, 4H), 3.23-2.86 (m, 8H), 2.37 (s, 3H), 2.11-1.95 (m, 1H), 1.91-1.79 (m, 1H), 1.79-1.53 (m, 2H). LCMS (ES+) m/z 474 (M+1).

Example 326

5-amino-N-[5-(4-amino-5-methoxy-azepan-1-yl)-1-methyl-pyrazol-4-yl]-2-(2,5-difluorophenyl)thiazole-4-carboxamide 326

Following the procedure Example 101, reacting tert-butyl ((4R,5R)-1-(4-amino-1-methyl-1H-pyrazol-5-yl)-5-methoxyazepan-4-yl)carbamate and 5-((tert-butoxycarbonyl)amino)-2-(2,5-difluorophenyl)thiazole-4-carboxylic acid gave 326 (64.2 mg, 33.6% over two steps). $^1$H NMR (400 MHz, DMSO) δ 9.08 (s, 1H), 8.22-8.10 (m, 1H), 7.46 (d, J=9.7 Hz, 2H), 7.45-7.35 (m, 2H), 7.34-7.18 (m, 1H), 3.64 (s, 3H), 3.23 (d, J=12.0 Hz, 4H), 3.21-2.89 (m, 6H), 2.10-1.97 (m, 1H), 1.89-1.79 (m, 1H), 1.78-1.53 (m, 2H). LCMS (ES+) m/z 478 (M+1)

Example 327

5-amino-N-[5-(4-amino-5-hydroxy-azepan-1-yl)-1-methyl-pyrazol-4-yl]-2-(2,6-difluorophenyl)thiazole-4-carboxamide 327

Chiral separation by SFC of racemic 5-amino-N-[5-(4-amino-5-hydroxy-azepan-1-yl)-1-methyl-pyrazol-4-yl]-2-(2,6-difluorophenyl)thiazole-4-carboxamide gave single enantiomer 327. $^1$H NMR (400 MHz, DMSO) δ 9.14 (s, 1H), 7.60 (s, 1H), 7.57-7.41 (m, 3H), 7.27 (t, J=8.7 Hz, 2H), 3.77 (d, J=7.1 Hz, 1H), 3.62 (s, 3H), 3.25-2.91 (m, 5H), 1.96-1.78 (m, 2H), 1.72-1.55 (m, 2H). LCMS (ES+) m/z 464 (M+1)

Example 328

5-amino-N-[5-(4-amino-5-hydroxy-azepan-1-yl)-1-methyl-pyrazol-4-yl]-2-(2,6-difluorophenyl)thiazole-4-carboxamide 328

Following the procedures of Example 333, and starting from 5-azido-1-(1-methyl-4-nitro-1H-pyrazol-5-yl)azepan-4-ol which is the second eluting peak on chiral separation, 328 was obtained (18%). $^1$H NMR (400 MHz, DMSO) δ 8.85 (s, 1H), 7.60-7.39 (m, 4H), 7.27 (t, J=8.7 Hz, 2H), 3.63 (s, 3H), 3.22-3.01 (m, 5H), 2.81-2.68 (m, 1H), 1.97-1.78 (m, 2H), 1.76-1.62 (m, 1H), 1.62-1.45 (m, 1H). LCMS (ES+) m/z 464 (M+1)

Example 331

5-amino-N-[5-(4-amino-5-fluoro-azepan-1-yl)-1-cyclopropyl-pyrazol-4-yl]-2-(2,6-difluorophenyl)thiazole-4-carboxamide 331

Racemic trans-tert-butyl N-[1-(2-cyclopropyl-4-nitro-pyrazol-3-yl)-5-fluoro-azepan-4-yl]carbamate was chirally separated on AD column with 20% methanol w/0.1% NH4OH. Following the procedures in Example 369, the second eluting peak was converted to 331. $^1$H NMR (400 MHz, DMSO) δ 8.83 (s, 1H), 7.59-7.40 (m, 4H), 7.26 (t, J=8.7 Hz, 2H), 4.44 (dtd, J=47.9, 8.3, 3.7 Hz, 1H), 3.54 (tt, J=7.5, 3.9 Hz, 1H), 3.27-3.05 (m, 5H), 2.23-2.09 (m, 1H), 2.01-1.77 (m, 4H), 1.70-1.53 (m, 1H), 1.03 (dd, J=7.4, 3.8 Hz, 2H), 0.94 (dd, J=6.8, 4.6 Hz, 2H). LCMS (ES+) m/z 492 (M+1)

Example 332

5-amino-N-[5-(4-amino-5-fluoro-azepan-1-yl)-1-cyclopropyl-pyrazol-4-yl]-2-(2,6-difluorophenyl)thiazole-4-carboxamide 332

Following the preparation of 331, the first eluting peak was converted to single enantiomer 332. $^1$H NMR (400 MHz, DMSO) δ 8.81 (s, 1H), 8.25 (s, 1H), 7.95 (s, 1H), 7.60-7.42 (m, 3H), 7.27 (t, J=8.7 Hz, 2H), 4.64-4.42 (m, 1H), 3.59-3.49 (m, 1H), 3.32-3.10 (m, 5H), 2.24-2.07 (m, 1H), 2.03-1.85 (m, 2H), 1.74-1.59 (m, 1H), 1.04 (dd, J=8.3, 4.1 Hz, 2H), 0.96 (dd, J=10.3, 5.8 Hz, 2H). LCMS (ES+) m/z 492 (M+1)

Example 333

5-amino-N-[5-(4-amino-5-hydroxy-azepan-1-yl)-1-methyl-pyrazol-4-yl]-2-(2,6-difluorophenyl)thiazole-4-carboxamide 333

Step A: A solution of 5-azido-1-(1-methyl-4-nitro-1H-pyrazol-5-yl)azepan-4-ol (502 mg, 1.78 mmol) (first eluting peak on chiral separation) in THF/water (15 mL/3 mL) was treated with triphenylphosphine (476 mg, 1.78 mmol) and the reaction mixture was heated at 60° C. for 5 hr. EtOAc (100 mL) was added and the mixture was washed with saturated aqueous NaHCO$_3$ solution (20 mL). The aqueous layer was extracted with EtOAc (50 mL) and the combined organic layers were dried over MgSO$_4$ and concentrated under reduced pressure to give an oil. To a solution of this oil in dry DCM (20 mL) at 0° C. was added DIPEA (0.85 mL, 4.88 mmol) and trifluoroacetic anhydride (0.29 mL, 2.05 mmol). The reaction mixture was allowed to warm to room temperature and stirred for 4 hr. Water (20 mL) was added and the mixture extracted with DCM (100 mL). The organic layer was separated, dried over MgSO$_4$ and concentrated under reduced pressure. Purification via silica gel column chromatography (0 to 100% EtOAc/heptane) gave 2,2,2-trifluoro-N-(5-hydroxy-1-(1-methyl-4-nitro-1H-pyrazol-5-yl)azepan-4-yl)acetamide as a yellow oil (626 mg, 88%). A solution of this oil (554 mg, 1.57 mmol) in MeOH (20 mL) was treated with ammonium formate (1002 mg, 15.7 mmol) and 10% palladium on carbon (50 mg). The mixture was heated at 65° C. for 1 hr. After cooling to room temperature the catalyst was filtered off and the filtrate concentrated under reduced pressure. The residue was partitioned between saturated aqueous NaHCO$_3$ solution (20 mL) and DCM (50 mL). The aqueous layer was extracted with DCM (3×50 mL) and the combined organic layers were dried over MgSO$_4$ and concentrated under reduced pressure to give N-(1-(4-amino-1-methyl-1H-pyrazol-5-yl)-5-hydroxyazepan-4-yl)-2,2,2-trifluoroacetamide as an orange form.

Step B: To a solution of N-(1-(4-amino-1-methyl-1H-pyrazol-5-yl)-5-hydroxyazepan-4-yl)-2,2,2-trifluoroacetamide (504 mg, 1.57 mmol) in DCM (20 mL) was added DIPEA (1.65 mL, 9.42 mmol), PyBOP (1.17 mg, 2.20 mmol) and 5-(tert-butoxycarbonylamino)-2-(2,6-difluorophenyl)-thiazole-4-carboxylic acid (559 mg, 1.57 mmol) and the mixture was stirred at room temperature for 18 hr. The mixture was diluted with DCM (100 mL) and washed with water (20 mL). The organic layer was separated, dried over MgSO$_4$ and the solvent removed under reduced pressure. Purification via silica gel column chromatography (0 to 100% EtOAc/heptane) gave tert-butyl 2-(2,6-difluorophenyl)-4-(5-(4-hydroxy-5-(2,2,2-trifluoroacetamido)azepan-1-yl)-1-methyl-1H-pyrazol-4-ylcarbamoyl)thiazol-5-ylcarbamate as an off-white solid (240 mg, 23%). This solid (240 mg, 0.36 mmol) was stirred with HCl in 1,4-dioxane (4 M, 6 mL, 24 mmol) in MeOH (5 mL) at room temperature for 18 h. The solvent was removed under reduced pressure, basified with saturated NaHCO$_3$, and extracted with ethyl acetate (3×). The combined organic layers were dried over MgSO$_4$ and the solvent removed under reduced pressure and the residue purified by preparative HPLC to afford 333. LCMS (ES+) m/z 464 (M+1)

Example 334

5-amino-2-(2,6-difluorophenyl)-N-[1-methyl-5-[(4S)-4-[(3-methyloxetan-3-yl)methylamino]azepan-1-yl]pyrazol-4-yl]thiazole-4-carboxamide 334

To a solution of (S)-tert-butyl (4-((5-(4-aminoazepan-1-yl)-1-methyl-1H-pyrazol-4-yl)carbamoyl)-2-(2,6-difluorophenyl)thiazol-5-yl)carbamate (103 mg, 0.19 mmol) in acetonitrile (2 mL) and THF (2 mL) was added 3-(iodomethyl)-3-methyl-oxetane (78 mg, 0.38 mmol) and potassium carbonate (130 mg, 0.94 mmol). The mixture was heated at 65° C. for 3 days. After cooling to room temperature, water (20 mL) was added and the mixture extracted with DCM (50 mL×3). The organic layer was separated, dried over MgSO$_4$ and concentrated under reduced pressure. Purification via silica gel column chromatography (0 to 15% methanol/DCM) gave tert-butyl N-[2-(2,6-difluorophenyl)-4-[[1-methyl-5-[(4R)-4-[(3-methyloxetan-3-yl)methylamino]azepan-1-yl]pyrazol-4-yl]carbamoyl]thiazol-5-yl]carbamate (130 mg, quantitative). This solid (130 mg, 0.21 mmol) was stirred with TFA (3 mL) and DCM (3 mL) at room temperature for 1 h. The solvent was removed under reduced pressure, basified with saturated NaHCO$_3$, and extracted with ethyl acetate (3×). The combined organic layers were dried over MgSO$_4$ and the solvent removed under reduced pressure and the residue purified by preparative HPLC to afford 334 (55.7 mg, 51%). $^1$H NMR (400 MHz, DMSO) δ 8.66 (s, 1H), 8.18 (s, 1H), 7.56 (s, 1H), 7.55-7.41 (m, 3H), 7.26 (t, J=8.7 Hz, 2H), 4.28 (d, J=5.6 Hz, 2H), 4.12 (d, J=5.5 Hz, 2H), 3.65 (s, 3H), 3.23-3.00 (m, 4H), 2.83-2.70 (m, 1H), 2.70-2.58 (m, 2H), 1.99-1.77 (m, 3H), 1.68-1.51 (m, 3H), 1.17 (s, 3H). LCMS (ES+) m/z 532 (M+1)

Example 335

5-amino-2-(2,6-difluorophenyl)-N-[5-[(4S)-4-(2-hydroxyethylamino)azepan-1-yl]-1-methyl-pyrazol-4-yl]thiazole-4-carboxamide 335

Following the procedures in Example 334, except for replacing 3-(iodomethyl)-3-methyl-oxetane with 2-iodoethanol, gave tert-butyl N-[2-(2,6-difluorophenyl)-4-[[5-[(4R)-4-(2-hydroxyethylamino)azepan-1-yl]-1-methyl-pyrazol-4-yl]carbamoyl]thiazol-5-yl]carbamate (37 mg, 38%) and tert-butyl N-[4-[[5-[(4R)-4-[bis(2-hydroxyethyl)amino]azepan-1-yl]-1-methyl-pyrazol-4-yl]carbamoyl]-2-(2,6-difluorophenyl)thiazol-5-yl]carbamate (10 mg, 9.6%). Following the deprotection procedure in Example 334, tert-butyl N-[2-(2,6-difluorophenyl)-4-[[5-[(4R)-4-(2-hydroxyethylamino)azepan-1-yl]-1-methyl-pyrazol-4-yl]carbamoyl]thiazol-5-yl]carbamate was converted to 335 (16.7 mg, 31%). $^1$H NMR (400 MHz, DMSO) δ 8.69 (s, 1H), 8.27 (s, 1H), 7.59-7.41 (m, 4H), 7.27 (t, J=8.7 Hz, 2H), 3.65 (s, 3H), 3.50-3.42 (m, 2H), 3.24-3.03 (m, 5H), 2.98-2.83 (m, 1H), 2.73-2.57 (m, 2H), 1.89 (m, 3H), 1.68-1.49 (m, 3H). LCMS (ES+) m/z 492 (M+1)

Example 336

5-amino-N-[5-[(4S)-4-[bis(2-hydroxyethyl)amino]azepan-1-yl]-1-methyl-pyrazol-4-yl]-2-(2,6-difluorophenyl)thiazole-4-carboxamide 336

In the preparation of 335, tert-butyl N-[4-[[5-[(4R)-4-[bis(2-hydroxyethyl)amino]azepan-1-yl]-1-methyl-pyrazol-4-yl]carbamoyl]-2-(2,6-difluorophenyl)thiazol-5-yl]carbamate was deprotected following the procedure in Example 334 to give 336 (6 mg, 71%). $^1$H NMR (400 MHz, DMSO) δ 8.63 (s, 1H), 8.24 (s, 1H), 7.56 (s, 1H), 7.55-7.41 (m, 3H), 7.27 (t, J=8.7 Hz, 2H), 3.65 (s, 3H), 3.19-3.02 (m, 7H), 2.85-2.71 (m, 2H), 2.46 (t, J=6.2 Hz, 4H), 1.92-1.75 (m, 3H), 1.67-1.50 (m, 3H). LCMS (ES+) m/z 536 (M+1)

Example 337

5-amino-N-[5-(4-amino-5-hydroxy-azepan-1-yl)-1-methyl-pyrazol-4-yl]-2-(2,6-difluorophenyl)thiazole-4-carboxamide 337

Chiral separation by SFC of 5-amino-N-[5-(4-amino-5-hydroxy-azepan-1-yl)-1-methyl-pyrazol-4-yl]-2-(2,6-difluorophenyl)thiazole-4-carboxamide gave single enantiomer 337. LCMS (ES+) m/z 464 (M+1)

Example 340

5-amino-2-(2,6-difluorophenyl)-N-[1-methyl-5-(5-oxo-1,4-oxazepan-4-yl)pyrazol-4-yl]thiazole-4-carboxamide 340

Following the procedure in Example 101, starting from 4-(1-methyl-4-nitro-1H-pyrazol-5-yl)-1,4-oxazepan-5-one gave 340 as a white solid (45 mg, 70% over three steps). $^1$H NMR (400 MHz, CDCl$_3$) δ 8.38 (s, 1H), 7.86 (s, 1H), 7.36-7.27 (m, 1H), 7.06-6.98 (m, 2H), 6.12 (s, 2H), 4.01-3.86 (m, 5H), 3.80-3.62 (m, 4H), 3.03-2.94 (m, 2H). LCMS (ES+) m/z 449 (M+1)

Example 341

5-amino-2-(2,6-difluorophenyl)-N-[1-methyl-5-(8-oxa-3-azabicyclo[3.2.1]octan-3-yl)pyrazol-4-yl]thiazole-4-carboxamide 341

Following the procedure in Example 101, starting from 3-(1-methyl-4-nitro-1H-pyrazol-5-yl)-8-oxa-3-azabicyclo[3.2.1]octane gave 341 as a white solid (49 mg, 40% over three steps). $^1$H NMR (400 MHz, d$_6$-DMSO) δ 8.71 (s, 1H), 7.56-7.52 (m, 3H), 7.47 (s, 1H), 7.30-7.24 (m, 2H), 4.27 (br s, 2H), 3.68 (s, 3H), 3.35-3.32 (m, 2H), 2.68 (d, J=10.9 Hz, 2H), 2.09-1.97 (m, 2H), 1.82-1.79 (m, 2H). LCMS (ES+) m/z 447 (M+1)

Example 342

5-amino-2-(2,6-difluorophenyl)-N-[1-methyl-5-[(4S)-4-(oxetan-3-ylmethylamino)azepan-1-yl]pyrazol-4-yl]thiazole-4-carboxamide 342

Following the procedures of Example 334, except for replacing 3-(iodomethyl)-3-methyl-oxetane with 3-(iodomethyl)oxetane, gave tert-butyl N-[2-(2,6-difluorophenyl)-4-[[1-methyl-5-[(4R)-4-(oxetan-3-ylmethylamino)azepan-1-yl]pyrazol-4-yl]carbamoyl]thiazol-5-yl]carbamate (17 mg, 25.5%) and tert-butyl N-[4-[[5-[(4R)-4-[bis(oxetan-3-ylmethyl)amino]azepan-1-yl]-1-methyl-pyrazol-4-yl]carbamoyl]-2-(2,6-difluorophenyl)thiazol-5-yl]carbamate (19 mg, 25.6%). Following the deprotection procedure in Example 334, tert-butyl N-[2-(2,6-difluorophenyl)-4-[[1-methyl-5-[(4R)-4-(oxetan-3-ylmethylamino)azepan-1-yl]pyrazol-4-yl]carbamoyl]thiazol-5-yl]carbamate was converted to 342 (4.1 mg, 29%). LCMS (ES+) m/z 518 (M+1)

Example 343

5-amino-N-[5-[(4S)-4-[bis(oxetan-3-ylmethyl)amino]azepan-1-yl]-1-methyl-pyrazol-4-yl]-2-(2,6-difluorophenyl)thiazole-4-carboxamide 343

In the preparation of 342, tert-butyl N-[4-[[5-[(4R)-4-[bis(oxetan-3-ylmethyl)amino]azepan-1-yl]-1-methyl-pyrazol-4-yl]carbamoyl]-2-(2,6-difluorophenyl)thiazol-5-yl]carbamate was deprotected following the procedure in Example 334 to give 343. LCMS (ES+) m/z 588 (M+1)

Example 348

5-amino-N-(5-((4S,5S)-4-amino-5-fluoroazepan-1-yl)-1-ethyl-1H-pyrazol-4-yl)-2-(2,6-difluorophenyl)thiazole-4-carboxamide 348

Following the procedures in Example 101, starting from tert-butyl 1-(1-ethyl-4-nitro-1H-pyrazol-5-yl)-5-fluoroazepan-4-ylcarbamate gave 348 as a white solid (37 mg, 23% over three steps). $^1$H NMR (400 MHz, CDCl$_3$) δ 8.64 (s, 1H), 7.88 (s, 1H), 7.39-7.26 (m, 1H), 7.03 (t, J=8.7 Hz, 2H), 6.17 (s, 2H), 4.48 (dtd, J=48.0, 8.7, 3.6 Hz, 1H), 4.02 (q, J=7.2 Hz, 2H), 3.38-3.13 (m, 6H), 2.32-2.18 (m, 1H), 2.14-1.93 (m, 2H), 1.85-1.79 (m, 1H), 1.83-1.57 (m, 1H), 1.43 (t, J=7.2 Hz, 3H). LCMS (ES+) m/z 480 (M+1)

Example 349

5-amino-N-[5-(3-azabicyclo[3.2.1]octan-3-yl)-1-methyl-pyrazol-4-yl]-2-(2,6-difluorophenyl)thiazole-4-carboxamide 349

Following the procedure for Example 101, starting from 3-(1-methyl-4-nitro-1H-pyrazol-5-yl)-3-azabicyclo[3.2.1]octane gave 349 as an off-white solid (80 mg, 30% over three steps). $^1$H NMR (400 MHz, CDCl$_3$) δ 8.57 (s, 1H), 7.86 (s, 1H,) 7.39-7.22 (m, 1H), 7.04-6.99 (m, 2H), 6.12 (br s, 2H), 3.76 (s, 3H), 3.25 (d J=10.4 Hz, 2H), 2.81-2.78 (dd J=10.4, 3.4 Hz, 2H) 2.24 (br s, 2H), 1.86 (d, J=7.7 Hz, 2H), 1.72-1.69 (m, 2H), 1.60 (br s, 2H). LCMS (ES+) m/z 445 (M+1)

Example 350

5-amino-2-(2,6-difluorophenyl)-N-[5-(1,1-dioxo-1,4-thiazepan-4-yl)-1-methyl-pyrazol-4-yl]thiazole-4-carboxamide 350

Following the procedure for Example 101, starting from 4-(1-methyl-4-nitro-1H-pyrazol-5-yl)-1,4-thiazepane 1,1-dioxide gave 350 as an off-white solid (52 mg, 20% over three steps). $^1$H NMR (400 MHz, CDCl$_3$) δ 8.45 (s, 1H), 7.74 (s, 1H), 7.36-7.32 (m, 1H), 7.07-7.01 (m, 2H), 6.12 (br s, 2H), 3.79 (s, 3H), 3.59-3.56 (m, 2H), 3.47-3.43 (m, 2H), 3.38-3.35 (m, 2H), 3.30-3.27 (m, 2H), 2.24-2.18 (m, 2H). LCMS (ES+) m/z 483 (M+1)

Example 352

5-amino-N-[5-(5-amino-3-methoxy-3-methyl-azepan-1-yl)-1-methyl-pyrazol-4-yl]-2-(2,6-difluorophenyl)thiazole-4-carboxamide 352

Chiral separation by SFC of 5-amino-N-[5-(5-amino-3-methoxy-3-methyl-azepan-1-yl)-1-methyl-pyrazol-4-yl]-2-(2,6-difluorophenyl)thiazole-4-carboxamide gave single enantiomer 352. $^1$H NMR (400 MHz, DMSO) δ 8.85 (s, 1H), 8.46 (s, 1H), 7.64 (s, 1H), 7.60-7.44 (m, 3H), 7.29 (t, J=8.7 Hz, 2H), 3.65 (s, 3H), 3.27-3.14 (m, 3H), 3.07 (dd, J=10.9, 5.5 Hz, 1H), 3.02 (s, 3H), 2.97 (d, J=14.4 Hz, 1H), 2.00 (d, J=14.3 Hz, 1H), 1.92-1.82 (m, 1H), 1.71-1.57 (m, 1H), 1.48 (dd, J=14.3, 10.8 Hz, 1H), 0.99 (s, 3H). LCMS (ES+) m/z 492 (M+1)

Example 353

5-amino-N-[5-(5-amino-3-methoxy-3-methyl-azepan-1-yl)-1-methyl-pyrazol-4-yl]-2-(2,6-difluorophenyl)thiazole-4-carboxamide 353

Chiral separation by SFC of 5-amino-N-[5-(5-amino-3-methoxy-3-methyl-azepan-1-yl)-1-methyl-pyrazol-4-yl]-2-(2,6-difluorophenyl)thiazole-4-carboxamide gave single enantiomer 353. $^1$H NMR (400 MHz, DMSO) δ 8.85 (s, 1H), 8.47 (s, 1H), 7.64 (s, 1H), 7.59-7.45 (m, 3H), 7.29 (t, J=8.7 Hz, 2H), 3.65 (s, 3H), 3.28-3.12 (m, 3H), 3.11-3.03 (m, 1H), 3.02 (s, 3H), 2.97 (d, J=14.3 Hz, 1H), 2.00 (d, J=14.2 Hz, 1H), 1.93-1.80 (m, 1H), 1.71-1.57 (m, 1H), 1.48 (dd, J=14.3, 10.8 Hz, 1H), 0.99 (s, 3H). LCMS (ES+) m/z 492 (M+1)

Example 354

5-amino-2-(2,6-difluorophenyl)-N-[1-methyl-5-(9-oxa-3,7-diazabicyclo[3.3.1]nonan-3-yl)pyrazol-4-yl]thiazole-4-carboxamide 354

Step A. To a microwave reaction vial was added 5-chloro-1-methyl-4-nitro-1H-pyrazole (141 mg, 0.88 mmol), tert-butyl 9-oxa-3,7-diazabicyclo[3.3.1]nonane-3-carboxylate (200 mg, 0.88 mmol). Ethanol (8 mL) and diisopropylethylamine (0.92 mL, 5.25 mmol) were added and the mixture was irradiated with a microwave for 60 min at 130° C. The mixture was cooled, concentrated and purified via flash chromatography, ethyl acetate/heptane 0% to 100% to afford yellow oil tert-butyl 7-(2-methyl-4-nitro-pyrazol-3-yl)-9-oxa-3,7-diazabicyclo[3.3.1]nonane-3-carboxylate (202 mg, 65%).

Step B: A solution of the above yellow oil in MeOH (30 mL) was passed through the H-Cube® (60 bar, 60° C., flow rate: 1 mL/min, 30 mm 10% Pd/C cartridge). The solvent was removed under reduced pressure to afford tert-butyl 7-(4-amino-2-methyl-pyrazol-3-yl)-9-oxa-3,7-diazabicyclo[3.3.1]nonane-3-carboxylate as a brown oil. To a solution of this oil in DCM (10 mL) was added 5-(tert-butoxycarbonylamino)-2-(2,6-difluorophenyl)thiazole-4-carboxylic acid (260 mg, 0.74 mmol), PyBOP (480 g, 0.91 mmol) and DIPEA (0.60 mL, 3.40 mmol) and the mixture was stirred at room temperature for 16 hr. Water (20 ml) was added and the mixture was diluted with DCM (100 mL). The organic layer was washed with water (20 mL), separated, dried over MgSO4 and the solvent removed under reduced pressure. Purification via silica gel column chromatography (0-100% EtOAc/heptane) gave tert-butyl 7-[4-[[5-(tert-butoxycarbonylamino)-2-(2,6-difluorophenyl)thiazole-4-carbonyl]amino]-2-methyl-pyrazol-3-yl]-9-oxa-3,7-diazabicyclo[3.3.1]nonane-3-carboxylate (380 mg, quantitative).

Step C: This solid (380 mg, 0.57 mmol) was stirred with TFA (7 mL) and DCM (10 mL) at room temperature for 1 h. The solvent was removed under reduced pressure, basified with saturated NaHCO3, and extracted with ethyl acetate (3×). The combined organic layers were dried over MgSO4 and the solvent removed under reduced pressure and the residue purified by preparative HPLC to afford 354 (82 mg, 29%). $^1$H NMR (400 MHz, DMSO) δ 9.58 (s, 1H), 7.63-7.40 (m, 4H), 7.27 (t, J=8.6 Hz, 2H), 3.66 (s, 3H), 3.62 (d, J=19.8 Hz, 3H), 3.20-2.86 (m, 7H). LCMS (ES+) m/z 462 (M+1)

Example 357

5-amino-N-(5-((4R,5R)-4-amino-5-fluorocycloheptyl)-1-methyl-1H-pyrazol-4-yl)-2-(2,6-difluorophenyl)thiazole-4-carboxamide 357

To a solution/suspension of tert-butyl 2-(2,6-difluorophenyl)-4-(5-(4-fluoro-5-(2,2,2-trifluoroacetamido)cycloheptyl)-1-methyl-1H-pyrazol-4-ylcarbamoyl)thiazol-5-ylcarbamate (Diastereomer 1) (49 mg, 0.074 mmol) in MeOH (2 mL) was added a solution of HCl in dioxane (4 M, 1.9 mL, 7.42 mmol) and the mixture was heated at 60° C. for 72 hr. The solvent was removed under reduced pressure and the residue was dissolved in MeOH/water (5 mL/5 mL) and treated with K$_2$CO$_3$ (51 mg, 0.37 mmol). The mixture was heated at 65° C. for 18 hr. The MeOH was removed under reduced pressure and the aqueous residue was extracted with 5% MeOH/DCM (2×30 mL). The organic layers were combined, dried over MgSO$_4$ and concentrated under reduced pressure. The residue was dissolved in MeOH and loaded onto an SCX column. The column was washed with MeOH, eluted with 3 N ammonia in MeOH and the solvent removed under reduced pressure to give 357 (Diastereomer 1) as a beige solid (10 mg, 29% over two steps). $^1$H NMR (400 MHz, CDCl$_3$) δ 8.44 (s, 1H), 7.76 (s, 1H), 7.35-7.28 (m, 1H), 7.07-6.99 (m, 2H), 6.11 (s, 2H), 4.46-4.29 (m, 1H), 3.83 (s, 3H), 3.23-3.13 (m, 1H), 2.84-2.76 (m, 1H), 2.26-1.81 (m, 6H), 1.60-1.40 (m, 2H). Alkyl NH$_2$ not observed. LCMS (ES+) m/z 465 (M+1)

Example 358

5-amino-N-(5-((4R,5R)-4-amino-5-fluorocycloheptyl)-1-methyl-1H-pyrazol-4-yl)-2-(2,6-difluorophenyl)thiazole-4-carboxamide 358

To a suspension of tert-butyl 2-(2,6-difluorophenyl)-4-(5-(4-fluoro-5-(2,2,2-trifluoroacetamido)cycloheptyl)-1-methyl-1H-pyrazol-4-ylcarbamoyl)thiazol-5-ylcarbamate (Diastereomer 2) (28 mg, 0.042 mmol) in MeOH (2 mL) was added a solution of HCl in dioxane (4 M, 1.1 mL, 4.24 mmol) and the mixture was stirred at room temperature for 18 hr. The solvent was removed under reduced pressure and the residue was dissolved in MeOH/water (3 mL/3 mL), treated with K$_2$CO$_3$ (29 mg, 0.21 mmol) and heated at 60° C. for 18 hr. The MeOH was removed under reduced pressure and the aqueous residue was extracted with 5% MeOH/DCM (2×40 mL). The organic layers were combined, passed through a phase separation cartridge and concentrated under reduced pressure to give 358 (Diastereomer 2) as an off-white solid (17 mg, 86% over two steps). $^1$H NMR (400 MHz, CDCl$_3$) δ 8.44 (s, 1H), 7.76 (s, 1H), 7.34-7.29 (m, 1H), 7.03 (t, J=8.7 Hz, 2H), 6.11 (s, 2H), 4.47-4.29 (m, 1H), 3.83 (s, 3H), 3.23-3.12 (m, 1H), 2.86-2.75 (m, 1H), 2.25-1.84 (m, 6H), 1.60-1.40 (m, 2H). Alkyl NH$_2$ not observed. LCMS (ES+) m/z 465 (M+1)

Example 359

5-amino-N-[5-(2,6-diazaspiro[3.4]octan-6-yl)-1-methyl-pyrazol-4-yl]-2-(2,6-difluorophenyl)thiazole-4-carboxamide 359

Following the procedures in Example 354, replacing tert-butyl 9-oxa-3,7-diazabicyclo[3.3.1]nonane-3-carboxylate with tert-butyl 2,7-diazaspiro[3.4]octane-2-carboxylate, gave 359. $^1$H NMR (400 MHz, DMSO) δ 8.70 (s, 1H), 8.44 (s, 1H), 7.58-7.44 (m, 3H), 7.39 (s, 1H), 7.26 (t, J=8.6 Hz, 2H), 3.61 (s, 5H), 3.56 (d, J=8.2 Hz, 4H), 3.21 (t, J=6.8 Hz, 2H), 2.10 (t, J=6.9 Hz, 2H). LCMS (ES+) m/z 446 (M+1)

Example 360

5-amino-2-(2,6-difluorophenyl)-N-[1-methyl-5-(1-oxo-2,8-diazaspiro[4.5]decan-8-yl)pyrazol-4-yl]thiazole-4-carboxamide 360

Following the procedures in Example 354, replacing tert-butyl 9-oxa-3,7-diazabicyclo[3.3.1]nonane-3-carboxylate with 3,8-diazaspiro[4.5]decan-4-one, gave 360. ¹H NMR (400 MHz, DMSO) δ 8.78 (s, 1H), 7.58-7.43 (m, 4H), 7.26 (t, J=8.7 Hz, 2H), 3.64 (s, 3H), 3.21-3.07 (m, 4H), 3.07-2.92 (m, 2H), 1.97 (t, J=6.8 Hz, 2H), 1.86-1.74 (m, 3H), 1.41 (d, J=12.9 Hz, 2H). LCMS (ES+) m/z 488 (M+1)

Example 361

5-amino-N-[5-(2,7-diazaspiro[3.4]octan-2-yl)-1-methyl-pyrazol-4-yl]-2-(2,6-difluorophenyl)thiazole-4-carboxamide 361

Following the procedures in Example 354, replacing tert-butyl 9-oxa-3,7-diazabicyclo[3.3.1]nonane-3-carboxylate with tert-butyl 2,7-diazaspiro[3.4]octane-7-carboxylate; oxalic acid, gave 361. ¹H NMR (400 MHz, DMSO) δ 8.73 (s, 1H), 7.60-7.43 (m, 3H), 7.27 (t, J=8.6 Hz, 2H), 7.15 (s, 1H), 4.04 (d, J=7.0 Hz, 2H), 3.97 (d, J=7.0 Hz, 2H), 3.57 (s, 3H), 3.11 (t, J=7.3 Hz, 2H), 2.89 (s, 1H), 2.73 (s, 1H), 2.14 (t, J=7.3 Hz, 2H), 2.07 (s, 2H). LCMS (ES+) m/z 446 (M+1)

Example 362

5-amino-N-[5-[4-(azetidin-3-yl)-1,4-diazepan-1-yl]-1-methyl-pyrazol-4-yl]-2-(2,6-difluorophenyl)thiazole-4-carboxamide 362

Step A: To a microwave reaction vial was added 5-chloro-1-methyl-4-nitro-1H-pyrazole (500 mg, 3.10 mmol), tert-butyl 1,4-diazepane-1-carboxylate (744 mg, 3.72 mmol). Ethanol (15 mL) and diisopropylethylamine (3.23 mL, 18.57 mmol) were added and the mixture was irradiated with a microwave for 60 min at 130° C. The mixture was cooled, concentrated and purified via flash chromatography, ethyl acetate/heptane 0% to 100% to afford yellow oil tert-butyl 4-(2-methyl-4-nitro-pyrazol-3-yl)-1,4-diazepane-1-carboxylate (690 mg, 69%).

Step B: A solution of tert-butyl 4-(2-methyl-4-nitro-pyrazol-3-yl)-1,4-diazepane-1-carboxylate (200 mg, 0.61 mmol) in DCM (4 mL) and TFA (4 mL) was stirred at room temperature for 1 h. The solvent was removed under reduced pressure, basified with saturated NaHCO3, and extracted with ethyl acetate (3×). The combined organic layers were dried over MgSO4 and the solvent removed under reduced pressure and the residue purified via silica gel column chromatography (0-10% methanol/DCM) to gave 1-(2-methyl-4-nitro-pyrazol-3-yl)-1,4-diazepane (88 mg, 64%). This was dissolved in acetonitrile (3 mL). tert-Butyl 3-iodoazetidine-1-carboxylate (221 mg, 0.78 mmol) and DIPEA (5 eq) were added and the mixture was heated at 75° C. for 7 days, with additional iodide and DIPEA added on days 2 and 3. The reaction mixture was cooled to room temperature, water (20 ml) was added and the mixture was extracted with DCM (50 mL). The organic layer was washed with water (20 mL), separated, dried over MgSO4 and the solvent removed under reduced pressure. Purification via silica gel column chromatography (0-10% methanol/DCM) to gave tert-butyl 3-[4-(2-methyl-4-nitro-pyrazol-3-yl)-1,4-diazepan-1-yl]azetidine-1-carboxylate (144 mg, 97%).

Step C: Following the procedures of Example 354, tert-butyl 3-[4-(2-methyl-4-nitro-pyrazol-3-yl)-1,4-diazepan-1-yl]azetidine-1-carboxylate was converted to 362. ¹H NMR (400 MHz, DMSO) δ 8.71 (s, 1H), 8.36 (s, 1H), 7.62-7.41 (m, 4H), 7.29 (t, J=8.7 Hz, 2H), 4.12-3.96 (m, 1H), 3.89-3.75 (m, 1H), 3.66 (s, 3H), 3.59 (dd, J=17.1, 10.1 Hz, 4H), 3.41 (dd, J=14.3, 7.1 Hz, 2H), 3.21 (t, J=5.4 Hz, 4H), 2.68-2.54 (m, 2H), 1.91-1.73 (m, 2H). LCMS (ES+) m/z 489 (M+1)

Example 363

5-amino-N-[5-(3,3-difluorocycloheptyl)-1-methyl-pyrazol-4-yl]-2-(2,6-difluorophenyl)thiazole-4-carboxamide 363

A solution of (E)-5-(6,6-difluorocyclohept-1-enyl)-1-methyl-4-nitro-1H-pyrazole (0.14 g, 0.54 mmol) in MeOH (10 mL) was passed through the H-Cube® (full H2, 65° C., flow rate: 1 mL/min, 30 mm 10% Pd/C cartridge). The solvent was removed under reduced pressure to afford an oil. This was dissolved in DCM (20 mL) and DIPEA (0.28 mL) and PyBOP (0.42 g, 0.81 mmol) and 5-(tert-butoxycarbonylamino)-2-(2,6-difluorophenyl)thiazole-4-carboxylic acid (211 mg, 0.59 mmol) were added. The mixture was stirred at room temperature for 18 hr, diluted with DCM (30 mL) and washed with water (10 mL). The organic layer was separated and the solvent removed under reduced pressure. Purification via silica gel column chromatography (0-50% EtOAc/isohexane) gave a foam (210 mg). A solution of this foam (200 mg) in MeOH (2 mL) was treated with a solution of HCl in dioxane (4 M, 2.7 mL, 10.8 mmol) and the mixture stirred at room temperature for 5 hr. The solvents were removed under reduced pressure and the residue was dissolved in EtOAC (25 mL) and washed with saturated aqueous NaHCO3 (2×20 mL) and water (20 mL). The organic layer was passed through a phase separation cartridge and the solvents removed under reduced pressure. Purification via chiral prep HPLC gave 363 (Enantiomer 1) as a white solid (6.3 mg, 5% over three steps). ¹H NMR (400 MHz, CDCl3) δ 8.49 (s, 1H), 7.79 (s, 1H), 7.40-7.30 (m, 1H), 7.10-7.00 (m, 2H), 6.13 (s, 2H), 3.88 (s, 3H), 3.19-3.07 (m, 1H), 2.68-2.37 (m, 2H), 2.30-1.94 (m, 6H), 1.89-1.57 (m, 2H)

Example 364

5-amino-N-(5-((4S,5S)-4-amino-5-methoxyazepan-1-yl)-1-ethyl-1H-pyrazol-4-yl)-2-(2,6-difluorophenyl)thiazole-4-carboxamide 364

Following the procedures in Example 101, starting from tert-butyl 1-(1-ethyl-4-nitro-1H-pyrazol-5-yl)-5-methoxyazepan-4-ylcarbamate gave 364 as the monoformate salt as a white solid (70 mg, 64% over three steps). ¹H NMR (400 MHz, d6-DMSO) δ 8.41 (s, 1H), 7.59-7.45 (m, 2H), 7.27 (t, J=8.8 Hz, 2H), 3.96 (q, J=7.2 Hz, 2H), 3.33-3.27 (m, 4H), 3.23-3.04 (m, 5H), 2.13 (d, J=14.4 Hz, 1H), 1.96 (d, J=14.4 Hz, 1H), 1.75-1.67 (m, 2H), 1.32 (t, J=7.2 Hz, 3H). Exchangeables not seen. LCMS (ES+) m/z 492 (M+1)

Example 365

5-amino-N-(5-((4S,5S)-4-amino-5-methoxyazepan-1-yl)-1-cyclopropyl-1H-pyrazol-4-yl)-2-(2,6-difluorophenyl)thiazole-4-carboxamide 365

Following the procedures in Example 101, starting from tert-butyl 1-(1-cyclopropyl-4-nitro-1H-pyrazol-5-yl)-5-methoxyazepan-4-ylcarbamate gave 365 as the monoformate salt as a white solid (68 mg, 64% over three steps). ¹H NMR (400 MHz, d6-DMSO) δ 8.40 (s, 1H), 7.58-7.47 (m, 1H), 7.43 (s, 1H), 7.26 (t, J=8.7 Hz, 2H), 3.55-3.47 (m, 1H), 3.36-3.08

(m, 9H), 2.15 (d, J=14.4 Hz, 1H), 2.02-1.94 (m, 1H), 1.83-1.66 (m, 2H), 1.07-0.94 (m, 4H). Exchangeables not seen. LCMS (ES+) m/z 504 (M+1)

Example 366

5-amino-N-[5-(3,3-difluorocycloheptyl)-1-methyl-pyrazol-4-yl]-2-(2,6-difluorophenyl)thiazole-4-carboxamide 366

Following the procedure in Example 363 gave 366 (Enantiomer 2) as a white solid (6.6 mg, 5%). $^1$H NMR (400 MHz, CDCl$_3$) δ 8.49 (s, 1H), 7.80 (s, 1H), 7.39-7.30 (m, 1H), 7.10-7.00 (m, 2H), 6.13 (s, 2H), 3.88 (s, 3H), 3.17-3.06 (m, 1H), 2.64-2.33 (m, 2H), 2.30-1.94 (m, 6H), 1.85-1.57 (m, 2H)

Example 367

(S)-5-amino-2-(2,6-difluorophenyl)-N-[1-methyl-5-(2-oxo-1,9-diazaspiro[4.6]undecan-9-yl)pyrazol-4-yl]thiazole-4-carboxamide 367

Following procedures in Example 508, 367 was prepared as a single enantiomer. $^1$H NMR (400 MHz, DMSO-d6) δ 8.64 (s, 1H), 7.99 (s, 1H), 7.59-7.50 (m, 2H), 7.48 (s, 2H), 7.27 (t, J=8.7 Hz, 2H), 3.65 (s, 2H), 3.30 (s, 3H), 3.31-3.15 (m, 2H), 3.11-2.96 (m, 2H), 2.15-2.05 (m, 2H), 1.80 (m, 6H). MS (ESI) m/z: 502.1 [M+H$^+$]

Example 368

(R)-5-amino-2-(2,6-difluorophenyl)-N-[1-methyl-5-(2-oxo-1,9-diazaspiro[4.6]undecan-9-yl)pyrazol-4-yl]thiazole-4-carboxamide 368

Following procedures in Example 508, 368 was prepared as a single enantiomer. $^1$H NMR (400 MHz, DMSO-d6) δ 8.64 (s, 1H), 7.99 (s, 1H), 7.59-7.50 (m, 2H), 7.48 (s, 2H), 7.27 (t, J=8.7 Hz, 2H), 3.65 (s, 2H), 3.30 (s, 3H), 3.31-3.15 (m, 2H), 3.11-2.96 (m, 2H), 2.15-2.05 (m, 2H), 1.80 (m, 6H). MS (ESI) m/z: 502.1 [M+H$^+$]

Example 369

5-amino-N-[5-(4-amino-5-fluoro-azepan-1-yl)-1-ethyl-pyrazol-4-yl]-2-(2,6-difluorophenyl)thiazole-4-carboxamide 369

Racemic trans-tert-butyl (1-(1-ethyl-4-nitro-1H-pyrazol-5-yl)-5-fluoroazepan-4-yl)carbamate was chirally separated on AD column with 20% methanol w/0.1% NH4OH. Following the procedures of Example 354, the first eluting peak was converted to 369. $^1$H NMR (400 MHz, DMSO) δ 8.82 (s, 1H), 7.60 (s, 1H), 7.57-7.43 (m, 3H), 7.26 (t, J=8.7 Hz, 2H), 4.42 (dtd, J=47.8, 8.2, 3.6 Hz, 1H), 3.95 (q, J=7.2 Hz, 2H), 3.24-3.04 (m, 5H), 2.18-1.76 (m, 3H), 1.66-1.51 (m, 1H), 1.32 (t, J=7.2 Hz, 3H). LCMS (ES+) m/z 480 (M+1)

Example 370

5-amino-N-[5-(4-amino-5-fluoro-azepan-1-yl)-1-ethyl-pyrazol-4-yl]-2-(2,6-difluorophenyl)thiazole-4-carboxamide 370

In the preparation of 369, the second eluting peak was converted to 370. $^1$H NMR (400 MHz, DMSO) δ 8.82 (s, 1H), 7.60 (s, 1H), 7.57-7.44 (m, 3H), 7.26 (t, J=8.7 Hz, 2H), 4.42 (dd, J=47.9, 3.6 Hz, 1H), 3.95 (q, J=7.2 Hz, 2H), 3.24-3.02 (m, 5H), 2.19-2.03 (m, 1H), 2.00-1.77 (m, 2H), 1.67-1.52 (m, 1H), 1.32 (t, J=7.2 Hz, 3H). LCMS (ES+) m/z 480 (M+1)

Example 371

5-amino-N-[5-(3,3-difluoro-5-hydroxy-azepan-1-yl)-1-methyl-pyrazol-4-yl]-2-(2,6-difluorophenyl)thiazole-4-carboxamide 371

Racemic N-[6,6-difluoro-1-(2-methyl-4-nitro-pyrazol-3-yl)azepan-4-yl]oxy-1-phenyl-methanimine was chirally separated on AD column with 35% methanol w/0.1% NH4OH. Following the procedures in Example 369, the first eluting peak was converted to 371. $^1$H NMR (400 MHz, DMSO) δ 8.76 (s, 1H), 7.61-7.40 (m, 4H), 7.26 (t, J=8.6 Hz, 2H), 4.90 (d, J=3.8 Hz, 1H), 4.06-3.90 (m, 1H), 3.74-3.57 (m, 4H), 3.47-3.34 (m, 1H), 3.34-3.20 (m, 1H), 3.17-3.01 (m, 1H), 2.43-2.23 (m, 2H), 2.00-1.73 (m, 2H). LCMS (ES+) m/z 485 (M+1)

Example 372

5-amino-N-[5-(3,3-difluoro-5-hydroxy-azepan-1-yl)-1-methyl-pyrazol-4-yl]-2-(2,6-difluorophenyl)thiazole-4-carboxamide 372

In the preparation of 371, the second eluting peak of converted to single enantiomer 372. $^1$H NMR (400 MHz, DMSO) δ 8.76 (s, 1H), 7.60-7.42 (m, 4H), 7.26 (t, J=8.6 Hz, 2H), 4.90 (d, J=3.9 Hz, 1H), 4.00 (s, 1H), 3.75-3.54 (m, 4H), 3.46-3.34 (m, 1H), 3.34-3.23 (m, 1H), 3.16-3.03 (m, 1H), 2.45-2.23 (m, 2H), 2.01-1.70 (m, 2H). LCMS (ES+) m/z 485 (M+1)

Example 373

5-amino-N-[5-(4-amino-5-fluoro-azepan-1-yl)-1-ethyl-pyrazol-4-yl]-2-(2-fluorophenyl)thiazole-4-carboxamide 373

Following the procedures in Example 369, the first eluting peak was converted to single enantiomer 373. $^1$H NMR (400 MHz, DMSO) δ 8.92 (s, 1H), 8.28 (t, J=7.9 Hz, 1H), 7.56 (s, 1H), 7.51-7.27 (m, 5H), 4.56-4.32 (m, 1H), 3.96 (q, J=7.2 Hz, 2H), 3.24-3.06 (m, 5H), 2.20-2.04 (m, 1H), 2.04-1.90 (m, 1H), 1.90-1.77 (m, 1H), 1.77-1.54 (m, 3H), 1.33 (t, J=7.2 Hz, 3H). LCMS (ES+) m/z 462 (M+1)

Example 374

5-amino-N-[5-(4-amino-5-fluoro-azepan-1-yl)-1-ethyl-pyrazol-4-yl]-2-(2-fluorophenyl)thiazole-4-carboxamide 374

In the preparation of 373, the second eluting peak of converted to single enantiomer 374. $^1$H NMR (400 MHz, DMSO) δ 8.92 (s, 1H), 8.28 (t, J=7.7 Hz, 1H), 7.56 (s, 1H), 7.50-7.23 (m, 5H), 4.56-4.33 (m, 1H), 3.96 (q, J=7.2 Hz, 2H), 3.25-3.04 (m, 5H), 2.21-2.05 (m, 1H), 2.05-1.90 (m, 1H), 1.90-1.79 (m, 1H), 1.79-1.50 (m, 3H), 1.33 (t, J=7.2 Hz, 3H). LCMS (ES+) m/z 462 (M+1)

Example 375

5-amino-N-(5-((4S,5R)-4-amino-5-hydroxyazepan-1-yl)-1-(2,2-difluoroethyl)-1H-pyrazol-4-yl)-2-(2,6-difluorophenyl)thiazole-4-carboxamide 375

Following the procedure for Example 101, starting from tert-butyl 1-(1-(2,2-difluoroethyl)-4-nitro-1H-pyrazol-5-yl)-

5-hydroxyazepan-4-ylcarbamate gave 375 as the monoformate salt as a pale brown solid (58 mg, 47% over three steps). $^1$H NMR (400 MHz, d$_6$-DMSO) δ 8.42 (s, 1H), 7.65 (s, 1H), 7.58-7.48 (m, 1H), 7.28 (t, J=8.8 Hz, 2H), 6.36 (tt, J=55.3, 4.1 Hz, 1H), 4.43 (td, J=14.5, 4.2 Hz, 2H), 4.04 (s, 1H), 3.40-3.29 (m, 2H), 3.26-3.18 (m, 1H), 3.12-3.02 (m, 1H), 2.95 (dt, J=13.7, 4.7 Hz, 1H), 2.14-2.02 (m, 1H), 1.93-1.66 (m, 2H), 1.77-1.67 (m, 1H). Exchangeables not observed. LCMS (ES+) m/z 514 (M+1)

Example 376

5-amino-N-(5-((4S,5R)-4-amino-5-methoxyazepan-1-yl)-1-ethyl-1H-pyrazol-4-yl)-2-(2,6-difluorophenyl)thiazole-4-carboxamide 376

Following the procedure for Example 101, starting from tert-butyl 1-(1-ethyl-4-nitro-1H-pyrazol-5-yl)-5-methoxyazepan-4-ylcarbamate gave 376 as the monoformate salt as a pale brown solid (60 mg, 51% over three steps). $^1$H NMR (400 MHz, d$_6$-DMSO) δ 8.41 (s, 1H), 7.59 (s, 1H), 7.58-7.45 (m, 1H), 7.27 (t, J=8.8 Hz, 2H), 3.96 (q, J=7.2 Hz, 2H), 3.42 (dt, J=9.8, 3.0 Hz, 1H), 3.70-3.60 (m, 1H), 3.50-2.94 (m, 5H), 3.09-3.00 (m, 1H), 3.00-2.91 (m, 1H), 2.13-2.04 (m, 1H), 2.03-1.91 (m, 1H), 1.79-1.65 (m, 2H), 1.31 (t, J=7.2 Hz, 3H). Exchangeables not observed. LCMS (ES+) m/z 492 (M+1)

Example 377

5-amino-N-(5-((4R,5S)-4-amino-5-fluorocycloheptyl)-1-methyl-1H-pyrazol-4-yl)-2-(2,6-difluorophenyl)thiazole-4-carboxamide 377

Following the procedure in Example 358, starting from tert-butyl 2-(2,6-difluorophenyl)-4-(5-(4-fluoro-5-(2,2,2-trifluoroacetamido)cycloheptyl)-1-methyl-1H-pyrazol-4-ylcarbamoyl)thiazol-5-ylcarbamate (Diastereomer 5) gave 377 (Diastereomer 5) as an off-white solid (16 mg, 79% over two steps). $^1$H NMR (400 MHz, CDCl$_3$) δ 8.46 (s, 1H), 7.79 (s, 1H), 7.38-7.28 (m, 1H), 7.03 (t, J=8.8 Hz, 2H), 6.14 (s, 2H), 4.88-4.71 (m, 1H), 3.82 (s, 3H), 3.25-3.14 (m, 1H), 3.06-2.96 (m, 1H), 2.20-1.83 (m, 7H), 1.78-1.63 (m, 1H). Alkyl NH$_2$ not observed. LCMS (ES+) m/z 465 (M+1)

Example 378

N-[5-(4-acetamido-4-methyl-azepan-1-yl)-1-methyl-pyrazol-4-yl]-5-amino-2-(2,6-difluorophenyl)thiazole-4-carboxamide 378

To a stirred solution of N-(4-methyl-1-(1-methyl-4-nitro-1H-pyrazol-5-yl)azepan-4-yl)acetamide (330 mg, 1.11 mmol) in a mixture of EtOH (25 mL) and water (2.5 mL) was added ammonium chloride (300 mg, 5.55 mmol) and iron powder (250 mg, 4.44 mmol). The reaction mixture was heated at 100° C. for 2 hr before being cooled, filtered through Celite® and concentrated under reduced pressure. The residue was partitioned between water (20 mL) and DCM (40 mL) and the organic layer was separated, washed with brine (20 mL), passed through a phase separation cartridge and concentrated under reduced pressure to give N-(1-(4-amino-1-methyl-1H-pyrazol-5-yl)-4-methylazepan-4-yl)acetamide as a brown solid which was used without further purification. Following the procedure for Example 149 using this intermediate and 5-(tert-butoxycarbonylamino)-2-(2,6-difluorophenyl)-thiazole-4-carboxylic acid gave 378 as an off-white foam (54 mg, 19% over three steps). $^1$H NMR (400 MHz, CDCl$_3$) δ 8.52 (s, 1H), 7.86 (s, 1H), 7.39-7.29 (m, 1H), 7.07-6.99 (m, 2H), 6.15 (s, 2H), 5.38 (s, 1H), 3.74 (s, 3H), 3.30-3.18 (m, 4H), 3.12 (ddd, J=13.6, 6.6, 3.1 Hz, 1H), 2.30-2.19 (m, 2H), 2.00-1.72 (m, 6H), 1.45 (s, 3H). LCMS (ES+) m/z 504 (M+1)

Example 379

5-amino-N-(5-((4R,5R)-4-amino-5-fluorocycloheptyl)-1-methyl-1H-pyrazol-4-yl)-2-(2,6-difluorophenyl)thiazole-4-carboxamide 379

Following the procedure in Example 358, starting from tert-butyl 2-(2,6-difluorophenyl)-4-(5-(4-fluoro-5-(2,2,2-trifluoroacetamido)cycloheptyl)-1-methyl-1H-pyrazol-4-ylcarbamoyl)thiazol-5-ylcarbamate (Diastereomer 3 and Diastereomer 4) gave, after purification via preparative HPLC, 379 (Diastereomer 3 and Diastereomer 4) as a racemic pair of enantiomers and as an off-white solid (4 mg, 7% over two steps). $^1$H NMR (400 MHz, CDCl$_3$) δ 8.41 (s, 1H), 7.76 (s, 1H), 7.38-7.28 (m, 1H), 7.03 (t, J=8.7 Hz, 2H), 6.12 (s, 2H), 4.33-4.18 (m, 1H), 3.83 (s, 3H), 3.14-3.05 (m, 1H), 2.96-2.88 (m, 1H), 2.32-2.20 (m, 1H), 2.00-1.69 (m, 7H). Alkyl NH$_2$ not observed. LCMS (ES+) m/z 465 (M+1)

Example 380

5-amino-N-(5-((4R,5S)-4-amino-5-fluorocycloheptyl)-1-methyl-1H-pyrazol-4-yl)-2-(2,6-difluorophenyl)thiazole-4-carboxamide 380

Following the procedures in Example 358, starting from tert-butyl 2-(2,6-difluorophenyl)-4-(5-(4-fluoro-5-(2,2,2-trifluoroacetamido)cycloheptyl)-1-methyl-1H-pyrazol-4-ylcarbamoyl)thiazol-5-ylcarbamate (Diastereomer 6, Diastereomer 7 and Diastereomer 8) gave, after purification via preparative HPLC, 380 (Diastereomer 6 and Diastereomer 7) as a white foam (8 mg, 15% over two steps). $^1$H NMR (400 MHz, CDCl$_3$) δ 8.47 (s, 1H), 7.75 (s, 1H), 7.38-7.29 (m, 1H), 7.02 (t, J=8.9 Hz, 2H), 6.13 (s, 2H), 4.77 (dd, J=47.1, 6.6 Hz, 1H), 3.83 (s, 3H), 3.18 (dd, J=23.9, 8.0 Hz, 1H), 2.93-2.85 (m, 1H), 2.42-2.32 (m, 1H), 2.18-1.55 (m, 7H). Alkyl NH$_2$ not observed. LCMS (ES+) m/z 465 (M+1)

Example 381

5-amino-N-(5-((4R,5S)-4-amino-5-fluorocycloheptyl)-1-methyl-1H-pyrazol-4-yl)-2-(2,6-difluorophenyl)thiazole-4-carboxamide 381

Following the procedures in Example 358, starting from tert-butyl 2(2,6-difluorophenyl)-4-(5-(4-fluoro-5-(2,2,2-trifluoroacetamido)cycloheptyl)-1-methyl-1H-pyrazol-4-ylcarbamoyl)thiazol-5-ylcarbamate (Diastereomer 6, Diastereomer 7 and Diastereomer 8) gave, after purification via preparative HPLC, 381 (Diastereomer 8) as an off-white solid (9 mg, 17% over two steps). $^1$H NMR (400 MHz, CDCl$_3$) 8.46 (s, 1H), 7.80 (s, 1H), 7.36-7.29 (m, 1H), 7.03 (t, J=8.8 Hz, 2H), 6.11 (s, 2H), 4.88-4.72 (m, 1H), 3.82 (s, 3H), 3.24-3.15 (m, 1H), 3.05-2.97 (m, 1H), 2.13-1.82 (m, 7H), 1.74-1.67 (m, 1H). Alkyl NH$_2$ not observed. LCMS (ES+) m/z 465 (M+1)

Example 383

5-amino-N-(5-cycloheptyl-1-methyl-pyrazol-4-yl)-2-(2,6-difluorophenyl)thiazole-4-carboxamide 383

A solution of (Z)-5-(1-fluorocyclohept-4-enyl)-1-methyl-4-nitro-1H-pyrazole (100 mg, 0.42 mmol) in MeOH (30 mL)

was passed through the H-Cube® (full H$_2$, 70° C., flow rate: 1 mL/min, 10% Pd/C cartridge). The solvent was removed under reduced pressure to give a red gum (81 mg). To a solution of this amine (80 mg, 0.41 mmol) in DCM (20 mL) was added DIPEA (1 mL), PyBOP (606 mg, 1.17 mmol) and 5-(tert-butoxycarbonylamino)-2-(2,6-difluorophenyl)thiazole-4-carboxylic acid (183 mg, 0.51 mmol) and the mixture was stirred at room temperature for 18 hr. The mixture was diluted with DCM (100 mL) and washed with water (20 mL). The organic layer was separated, dried over MgSO$_4$ and the solvent removed under reduced pressure. Purification via silica gel column chromatography (30-40% EtOAc/isohexane) gave tert-butyl 4-(5-cycloheptyl-1-methyl-1H-pyrazol-4-ylcarbamoyl)-2-(2,6-difluorophenyl)thiazol-5-ylcarbamate as a cream solid (140 mg). This solid (130 mg, 0.25 mmol) was stirred with HCl in dioxane (4 M, 3.1 mL, 12.2 mmol) in MeOH (3 mL) at room temperature for 18 hr. The solvents were removed under reduced pressure and the residue was dissolved in MeOH and loaded onto an SCX column. The column was washed with MeOH, eluted with 2 N ammonia in MeOH and the solvent removed under reduced pressure. Purification via preparative HPLC gave 383 as a cream solid (45 mg, 25% over three steps). $^1$H NMR (400 MHz, CDCl$_3$) δ 8.59 (s, 1H), 7.85 (s, 1H), 7.35-7.29 (m, 1H), 7.02 (t, J=8.9 Hz, 2H), 6.10 (s, 2H), 3.83 (s, 3H), 2.92-2.81 (m, 1H), 1.97-1.83 (m, 6H), 1.72-1.50 (m, 6H). LCMS (ES+) m/z 432 (M+1)

Example 384

N-[5-(4-acetamido-4-methyl-azepan-1-yl)-1-methyl-pyrazol-4-yl]-5-amino-2-(3-fluoro-2-pyridyl)thiazole-4-carboxamide 384

Following the procedures in Example 378, starting from N-(4-methyl-1-(1-methyl-4-nitro-1H-pyrazol-5-yl)azepan-4-yl)acetamide and 5-(tert-butoxycarbonylamino)-2-(3-fluoropyridin-2-yl)thiazole-4-carboxylic acid gave 384 as an off-white foam (80 mg, 29% over three steps). $^1$H NMR (400 MHz, CDCl$_3$) δ 8.57 (s, 1H), 8.41 (d, J=4.3 Hz, 1H), 7.90 (s, 1H), 7.52 (t, J=9.7 Hz, 1H), 7.31 (dt, J=8.4, 4.3 Hz, 1H), 6.32 (s, 2H), 5.75 (s, 1H), 3.74 (s, 3H), 3.33-3.15 (m, 4H), 2.38-2.21 (m, 2H), 2.02-1.84 (m, 4H), 1.82-1.74 (m, 3H), 1.51 (s, 3H). LCMS (ES+) m/z 487 (M+1)

Example 385

5-amino-N-[5-(4-amino-5-ethoxy-azepan-1-yl)-1-methyl-pyrazol-4-yl]-2-(2,6-difluorophenyl)thiazole-4-carboxamide 385

Following the procedure for Example 107, starting from N-(1-(4-amino-1-methyl-1H-pyrazol-5-yl)-5-ethoxyazepan-4-yl)-2,2,2-trifluoroacetamide and 5-(tert-butoxycarbonylamino)-2-(2,6-difluorophenyl)-thiazole-4-carboxylic acid gave 385 as a brown solid (127 mg, 60% over two steps). $^1$H NMR (400 MHz, CDCl$_3$) δ 8.61 (s, 1H), 7.85 (s, 1H), 7.42-7.28 (m, 1H), 7.04 (t, J=8.9 Hz, 2H), 6.19 (s, 2H), 3.78-3.58 (m, 4H), 3.47-3.35 (m, 1H), 3.38-3.25 (m, 2H), 3.25-3.16 (m, 3H), 3.09-3.01 (m, 1H), 2.13 (d, J=14.7 Hz, 1H), 2.00 (d, J=14.7 Hz, 1H), 1.92-1.82 (m, 1H), 1.84-1.58 (m, 3H), 1.22 (t, J=7.0 Hz, 3H). LCMS (ES+) m/z 492 (M+1)

Example 386

5-amino-N-(5-((4S,5R)-4-amino-5-methoxyazepan-1-yl)-1-cyclopropyl-1H-pyrazol-4-yl)-2-(2,6-difluorophenyl)thiazole-4-carboxamide 386

Following the procedure for Example 101 starting from tert-butyl 1-(1-cyclopropyl-4-nitro-1H-pyrazol-5-yl)-5-methoxyazepan-4-ylcarbamate and 5-(tert-butoxycarbonylamino)-2-(2,6-difluorophenyl)-thiazole-4-carboxylic acid gave 386 as an off-white solid (29 mg, 23% over three steps). $^1$H NMR (400 MHz, CDCl$_3$) δ 8.96 (s, 1H), 7.86 (s, 1H), 7.36-7.28 (m, 1H), 7.02 (t, J=8.9 Hz, 2H), 6.19-6.10 (m, 2H), 3.50-3.35 (m, 4H), 3.33 (s, 3H), 3.25-3.11 (m, 2H), 2.19-2.05 (m, 1H), 2.03-1.96 (m, 1H), 2.01-1.60 (m, 2H), 1.57 (s, 3H), 1.27-1.12 (m, 2H), 0.97 (d, J=7.1 Hz, 2H). LCMS (ES+) m/z 504 (M+1)

Example 387

5-amino-N-(5-((4S,5R)-4-amino-5-fluoroazepan-1-yl)-1-methyl-1H-pyrazol-4-yl)-2-(pyridin-2-yl)thiazole-4-carboxamide 387

Following the procedure for Example 107 starting from N-(1-(4-amino-1-methyl-1H-pyrazol-5-yl)-5-fluoroazepan-4-yl)-2,2,2-trifluoroacetamide and 5-(tert-butoxycarbonylamino)-2-(pyridin-2-yl)thiazole-4-carboxylic acid gave 387 as an off-white solid (106 mg, 68% over two steps). $^1$H NMR (400 MHz, CDCl$_3$) δ 8.65 (s, 1H), 8.54 (d, J=4.6 Hz, 1H), 8.04 (d, J=7.9 Hz, 1H), 7.81 (s, 1H), 7.76 (t, J=7.9 Hz, 1H), 7.29-7.20 (m, 1H), 6.27 (s, 2H), 4.90 (d, J=47.2 Hz, 1H), 3.73 (s, 3H), 3.58-3.33 (m, 3H), 3.23-3.11 (m, 2H), 2.44-2.22 (m, 1H), 2.11-1.92 (m, 2H), 1.87-1.76 (m, 1H). Exchangeable NH$_2$ not observed. LCMS (ES+) m/z 431 (M+1)

Example 388

5-amino-N-(5-((4S,5R)-4-amino-5-fluoroazepan-1-yl)-1-methyl-1H-pyrazol-4-yl)-2-(3-fluoropyridin-2-yl)thiazole-4-carboxamide 388

Following the procedure for Example 107 starting from N-(1-(4-amino-1-methyl-1H-pyrazol-5-yl)-5-fluoroazepan-4-yl)-2,2,2-trifluoroacetamide and 5-(tert-butoxycarbonylamino)-2-(3-fluoropyridin-2-yl)thiazole-4-carboxylic acid gave 388 as an off-white solid (120 mg, 74% over two steps). $^1$H NMR (400 MHz, d$_6$-DMSO) δ 8.42 (s, 1H), 7.85 (t, J=9.8 Hz, 1H), 7.64 (s, 1H), 7.50-7.44 (m, 1H), 4.85 (d, J=47.3 Hz, 1H), 3.64 (s, 3H), 3.40-3.22 (m, 3H), 3.23-2.83 (m, 2H), 2.31-2.01 (m, 1H), 2.04-1.66 (m, 2H), 1.92-1.48 (m, 1H). Exchangeable NH$_2$ (×2) and NH not observed. LCMS (ES+) m/z 449 (M+1)

Example 389

5-amino-N-[5-(4-amino-5-methoxy-azepan-1-yl)-1-ethyl-pyrazol-4-yl]-2-(2,6-difluorophenyl)thiazole-4-carboxamide 389

Racemic trans-tert-butyl N-[1-(2-ethyl-4-nitro-pyrazol-3-yl)-5-methoxy-azepan-4-yl]carbamate was chirally separation on AD column with 15% methanol. Following the procedures in Example 369, the first eluting peak of trans-tert-butyl N-[1-(2-ethyl-4-nitro-pyrazol-3-yl)-5-methoxy-azepan-4-yl]carbamate was converted to 389. $^1$H NMR (400 MHz, DMSO) δ 8.88 (s, 1H), 7.63 (s, 1H), 7.58-7.40 (m, 3H), 7.26 (t, J=8.7 Hz, 2H), 3.95 (q, J=7.2 Hz, 2H), 3.24 (s, 3H), 3.22-2.97 (m, 5H), 2.94-2.82 (m, 1H), 2.07-1.95 (m, 1H), 1.90-1.49 (m, 3H), 1.32 (t, J=7.2 Hz, 3H). LCMS (ES+) m/z 492 (M+1)

Example 390

5-amino-N-[5-(4-amino-5-methoxy-azepan-1-yl)-1-ethyl-pyrazol-4-yl]-2-(2,6-difluorophenyl)thiazole-4-carboxamide 390

Following the preparation of 389, the second eluting peak of trans-tert-butyl N4'-(2-ethyl-4-nitro-pyrazol-3-yl)-5-methoxy-azepan-4-yl]carbamate off the SFC chiral separation was converted to 390. $^1$H NMR (400 MHz, DMSO) δ 8.88 (s, 1H), 7.63 (s, 1H), 7.59-7.43 (m, 3H), 7.26 (t, J=8.7 Hz, 2H), 3.95 (q, J=7.2 Hz, 2H), 3.24 (s, 3H), 3.22-2.98 (m, 5H), 2.94-2.83 (m, 1H), 2.08-1.95 (m, 1H), 1.90-1.47 (m, 3H), 1.32 (t, J=7.2 Hz, 3H). LCMS (ES+) m/z 492 (M+1)

Example 391

5-amino-N-[5-(4-amino-5-methoxy-azepan-1-yl)-1-ethyl-pyrazol-4-yl]-2-(2,6-difluorophenyl)thiazole-4-carboxamide 391

Following the preparation of 389, the first eluting peak of trans-tert-butyl N-[1-(2-ethyl-4-nitro-pyrazol-3-yl)-5-methoxy-azepan-4-yl]carbamate off the SFC chiral separation was converted to 391. $^1$H NMR (400 MHz, DMSO) δ 8.92 (s, 1H), 8.30 (t, J=8.0 Hz, 1H), 7.60 (s, 1H), 7.49-7.39 (m, 3H), 7.39-7.27 (m, 2H), 3.96 (q, J=7.2 Hz, 2H), 3.26 (s, 3H), 3.24-3.02 (m, 5H), 2.99-2.88 (m, 1H), 2.13-2.01 (m, 1H), 1.91-1.78 (m, 1H), 1.78-1.51 (m, 2H), 1.33 (t, J=7.2 Hz, 3H). LCMS (ES+) m/z 474 (M+1)

Example 392

5-amino-N-[5-(4-amino-5-methoxy-azepan-1-yl)-1-ethyl-pyrazol-4-yl]-2-(2-fluorophenyl)thiazole-4-carboxamide 392

Following the procedure for 390, the second eluting peak of trans-tert-butyl N-[1-(2-ethyl-4-nitro-pyrazol-3-yl)-5-methoxy-azepan-4-yl]carbamate off the SFC chiral separation was converted to 392. $^1$H NMR (400 MHz, DMSO) δ 8.92 (s, 1H), 8.30 (t, J=8.0 Hz, 1H), 7.60 (s, 1H), 7.50-7.38 (m, 3H), 7.33 (t, J=7.7 Hz, 2H), 3.96 (q, J=7.2 Hz, 2H), 3.26 (s, 3H), 3.23-3.03 (m, 5H), 2.98-2.89 (m, 1H), 2.13-2.01 (m, 1H), 1.91-1.50 (m, 3H), 1.33 (t, J=7.2 Hz, 3H). LCMS (ES+) m/z 474 (M+1)

Example 393

5-amino-N-[5-[(4S)-4-aminoazepan-1-yl]-1-methyl-pyrazol-4-yl]-2-(6-hydroxy-2-pyridyl)thiazole-4-carboxamide 393

Step A: In a microwave reaction vial, tert-butyl N-[4-[[5-[(4S)-4-(benzyloxycarbonylamino)azepan-1-yl]-1-methyl-pyrazol-4-yl]carbamoyl]-2-bromo-thiazol-5-yl]carbamate (200 mg, 0.31 mmol), 6-(4,4,5,5-tetramethyl-1,3,2-dioxaborolan-2-yl)pyridin-2-ol (205 mg, 0.93 mmol) and PDCL2 (DPPF) (23 mg, 0.031 mmol) were dissolved in acetonitrile (8 mL). Potassium acetate (1.0M, 0.46 mL, 0.46 mmol) was sodium carbonate (1.0M, 0.46 mL, 0.46 mmol) were added and the mixture was irradiated with a microwave for 30 min at 120° C. The mixture was cooled, filtered through Na2SO4 and Celite, concentrated and purified via flash chromatography, methanol/DCM 0% to 10% to afford tert-butyl N-[4-[[5-[(4S)-4-(benzyloxycarbonylamino)azepan-1-yl]-1-methyl-pyrazol-4-yl]carbamoyl]-2-(6-hydroxy-2-pyridyl)thiazol-5-yl]carbamate.

Step B: In a round bottom flask, the above tert-butyl N-[4-[[5-[(4S)-4-(benzyloxycarbonylamino)azepan-1-yl]-1-methyl-pyrazol-4-yl]carbamoyl]-2-(6-hydroxy-2-pyridyl)thiazol-5-yl] was dissolved in DCM (10 mL). Boron tribromide (1.0 m in DCM, 2.2 mL, 2.21 mmol) was added slowly and the mixture was stirred at room temperature for 4 h. The reaction was concentrated under reduced pressure. Residue was basified with sat. NaHCO3 and extracted with EA 3×. The combined organic layers were dried over MgSO4 and the solvent removed under reduced pressure and the residue purified by preparative HPLC to afford 393 (10.3 mg, 7.6% over two steps). $^1$H NMR (400 MHz, DMSO) δ 8.98 (s, 1H), 7.60 (t, J=7.8 Hz, 1H), 7.50 (s, 2H), 7.47 (s, 1H), 7.16 (d, J=7.2 Hz, 1H), 6.49 (d, J=8.4 Hz, 1H), 3.65 (s, 3H), 3.21-2.98 (m, 5H), 1.96-1.71 (m, 3H), 1.71-1.45 (m, 3H). LCMS (ES+) m/z 429 (M+1)

Example 394

5-amino-N-[5-[4-(2-aminoacetyl)-1,4-diazepan-1-yl]-1-methyl-pyrazol-4-yl]-2-(2,6-difluorophenyl)thiazole-4-carboxamide 394

Step A: In the preparation of 362, 1-(2-methyl-4-nitro-pyrazol-3-yl)-1,4-diazepane (105 mg, 0.47 mmol), 2-(tert-butoxycarbonylamino)acetic acid (106 mg, 0.61 mmol) and PyBOP (396 mg, 0.75 mmol) were dissolved in DCM (6 mL). DIPEA (0.49 ml, 2.80 mmol) was added and the mixture was stirred at room temperature for 18 h. The crude reaction mixture was concentrated and the residue was purified via silica gel column chromatography (0-100% EA/heptane) to gave tert-butyl N-[2-[4-(2-methyl-4-nitro-pyrazol-3-yl)-1,4-diazepan-1-yl]-2-oxo-ethyl]carbamate (qualitative yield).

Step B: Following the procedure for 354, tert-butyl N-[2-[4-(2-methyl-4-nitro-pyrazol-3-yl)-1,4-diazepan-1-yl]-2-oxo-ethyl]carbamate was converted to 394 (85 mg, 24% over three steps). $^1$H NMR (400 MHz, DMSO) δ 8.72 (d, J=8.0 Hz, 1H), 7.59-7.39 (m, 4H), 7.27 (t, J=8.7 Hz, 2H), 3.70-3.58 (m, 5H), 3.58-3.45 (m, 2H), 3.35 (d, J=18.5 Hz, 2H), 3.28-3.22 (m, 1H), 3.22-3.08 (m, 3H), 1.89-1.70 (m, 2H). LCMS (ES+) m/z 491 (M+1)

Example 395

5-amino-N-[5-[4-(2-aminoethyl)-1,4-diazepan-1-yl]-1-methyl-pyrazol-4-yl]-2-(2,6-difluorophenyl)thiazole-4-carboxamide 395

Step A: In the preparation of 362, 1-(2-methyl-4-nitro-pyrazol-3-yl)-1,4-diazepane (105 mg, 0.47 mmol) and tert-butyl N-(2-bromoethyl)carbamate (209 mg, 0.93 mmol) were dissolved in acetonitrile (3 mL). DIPEA (0.41 mL, 2.33 mmol) was added and the mixture was heated at 80° C. for 18 h. The crude reaction mixture was concentrated and the residue was purified via silica gel column chromatography (0-100% EA/heptane) to gave tert-butyl N42-[4-(2-methyl-4-nitro-pyrazol-3-yl)-1,4-diazepan-1-yl]ethyl]carbamate (qualitative yield).

Step B: Following the procedure for 354, tert-butyl N-[2-[4-(2-methyl-4-nitro-pyrazol-3-yl)-1,4-diazepan-1-yl]ethyl] carbamate was converted to 395 (17 mg). $^1$H NMR (400 MHz, DMSO) δ 8.74 (s, 1H), 8.33 (s, 2H), 7.58-7.43 (m, 4H), 7.28 (t, J=8.7 Hz, 2H), 3.66 (s, 3H), 3.21 (t, J=5.4 Hz, 4H), 2.82-2.68 (m, 6H), 2.62 (t, J=6.1 Hz, 2H), 1.91-1.76 (m, 2H). LCMS (ES+) m/z 477 (M+1)

Example 396

N-[5-(3,4,4a,5,6,8,9,9a-octahydro-2H-[1,4]oxazino [2,3-d]azepin-7-yl)-1-methyl-pyrazol-4-yl]-5-amino-2-(2,6-difluorophenyl)thiazole-4-carboxamide 396

In a microwave reaction vial, (4aR,9aR)-2,3,4,4a,5,6,7,8, 9,9a-decahydro-[1,4]oxazino[2,3-d]azepine dihydrochloride (509 mg; 2.22 mmol) and 5-chloro-1-methyl-4-nitro-pyrazole (322 mg, 2.00 mmol) were dissolved in acetonitrile (16 mL). DIPEA (3.11 mL, 17.77 mmol) was added and the mixture was irradiated with microwave at 130° C. for 60 min. The reaction mixture was diluted with water, extracted with EA 3×. Combined organic layers were dried over Na2SO4 and concentrated to give trans-7-(2-methyl-4-nitro-pyrazol-3-yl)-3,4,4a,5,6,8,9,9a-octahydro-2H-[1,4]oxazino[2,3-d] azepine. To a solution of this compound in DCM (15 mL) was added di-tert-butyl-dicarbonate (727 mg, 3.33 mmol) and DIPEA (1.16 mL, 6.66 mmol). The mixture was stirred at room temperature for 18 h. The crude reaction mixture was concentrated and the residue was purified via silica gel column chromatography (0-100% EA/heptane) to gave the racemic trans-tert-butyl-7-(2-methyl-4-nitro-pyrazol-3-yl)-2,3, 4a,5,6,8,9,9a-octahydro-[1,4]oxazino[2,3-d]azepine-4-carboxylate, which was chirally separated on AD column with 20% methanol w/0.1% NH4OH. The first eluting peak of trans-tert-butyl-7-(2-methyl-4-nitro-pyrazol-3-yl)-2,3,4a,5, 6,8,9,9a-octahydro-[1,4]oxazino[2,3-d]azepine-4-carboxylate off the SFC chiral separation was converted to 396 following the procedures of Example 354. $^1$H NMR (400 MHz, DMSO) δ 8.63 (s, 1H), 7.55 (s, 1H), 7.54-7.43 (m, 3H), 7.26 (t, J=8.7 Hz, 2H), 3.64 (s, 3H), 3.24-3.13 (m, 4H), 3.13-2.95 (m, 3H), 2.65 (d, J=5.6 Hz, 2H), 2.60-2.52 (m, 1H), 1.82-1.68 (m, 3H), 1.64-1.53 (m, 2H). LCMS (ES+) m/z 490 (M+1)

Example 397

N-[5-(3,4,4a,5,6,8,9,9a-octahydro-2H-[1,4]oxazino [2,3-d]azepin-7-yl)-1-methyl-pyrazol-4-yl]-5-amino-2-(2,6-difluorophenyl)thiazole-4-carboxamide 397

Following the preparation 396, the second eluting peak of trans-tert-butyl-7-(2-methyl-4-nitro-pyrazol-3-yl)-2,3,4a,5, 6,8,9,9a-octahydro-[1,4]oxazino[2,3-d]azepine-4-carboxylate off the SFC chiral separation was converted to 397. $^1$H NMR (400 MHz, DMSO) δ 8.63 (s, 1H), 7.55 (s, 1H), 7.53-7.40 (m, 3H), 7.26 (t, J=8.7 Hz, 2H), 3.64 (s, 3H), 3.23-3.13 (m, 4H), 3.13-2.94 (m, 3H), 2.65 (d, J=6.8 Hz, 2H), 2.60-2.52 (m, 1H), 1.86-1.65 (m, 3H), 1.65-1.54 (m, 2H). LCMS (ES+) m/z 490 (M+1)

Example 398

5-amino-N-[5-(4-amino-5-hydroxy-azepan-1-yl)-1-(2,2-difluoroethyl)pyrazol-4-yl]-2-(2,6-difluorophenyl)thiazole-4-carboxamide 398

Racemic cis-tert-butyl N-[1-[2-(2,2-difluoroethyl)-4-nitro-pyrazol-3-yl]-5-hydroxy-azepan-4-yl]carbamate was chirally separated on AD column with 30% methanol. Following the procedures in Example 369, the first eluting peak of cis-tert-butyl N-[1-[2-(2,2-difluoroethyl)-4-nitro-pyrazol-3-yl]-5-hydroxy-azepan-4-yl]carbamate off the SFC chiral separation was converted to 398. $^1$H NMR (400 MHz, DMSO) δ 9.30 (s, 1H), 7.76 (s, 1H), 7.59-7.41 (m, 3H), 7.27 (t, J=8.7 Hz, 2H), 6.55-6.17 (m, 1H), 4.56 (s, 1H), 4.45-4.28 (m, 2H), 3.76 (d, J=7.8 Hz, 1H), 3.26-3.13 (m, 2H), 3.13-2.93 (m, 3H), 1.95-1.77 (m, 2H), 1.73-1.55 (m, 2H). LCMS (ES+) m/z 514 (M+1)

Example 399

5-amino-N-[5-(4-amino-5-hydroxy-azepan-1-yl)-1-(2,2-difluoroethyl)pyrazol-4-yl]-2-(2,6-difluorophenyl)thiazole-4-carboxamide 399

Following the preparation of 398, the second eluting peak of cis-tert-butyl N-[1-[2-(2,2-difluoroethyl)-4-nitro-pyrazol-3-yl]-5-hydroxy-azepan-4-yl]carbamate off the SFC chiral separation was converted to 399. $^1$H NMR (400 MHz, DMSO) δ 9.29 (s, 1H), 7.76 (s, 1H), 7.62-7.41 (m, 3H), 7.27 (t, J=8.7 Hz, 2H), 6.55-6.19 (m, 1H), 4.58 (s, 1H), 4.45-4.31 (m, 2H), 3.76 (d, J=7.9 Hz, 1H), 3.25-3.13 (m, 2H), 3.13-2.93 (m, 3H), 1.94-1.77 (m, 2H), 1.71-1.55 (m, 2H). LCMS (ES+) m/z 514 (M+1)

Example 401

5-amino-N-[5-(4-amino-5-methoxy-azepan-1-yl)-1-cyclopropyl-pyrazol-4-yl]-2-(2,6-difluorophenyl) thiazole-4-carboxamide 401

Racemic cis-tert-butyl N-[1-(2-cyclopropyl-4-nitro-pyrazol-3-yl)-5-methoxy-azepan-4-yl]carbamate was chirally separated on AD column with 30% methanol. Following the procedures of Example 369, the first eluting peak of cis-tert-butyl N-[1-(2-cyclopropyl-4-nitro-pyrazol-3-yl)-5-methoxy-azepan-4-yl]carbamate off the SFC chiral separation was converted to 401. $^1$H NMR (400 MHz, DMSO) δ 9.38 (s, 1H), 7.64 (s, 1H), 7.58-7.44 (m, 3H), 7.27 (t, J=8.7 Hz, 2H), 3.58-3.45 (m, 1H), 3.39 (d, J=8.3 Hz, 1H), 3.27-3.20 (m, 1H), 3.27-3.21 (m, 1H), 3.19 (s, 3H), 3.07 (dd, J=11.4, 6.5 Hz, 2H), 2.13-1.96 (m, 1H), 1.85-1.58 (m, 4H), 1.08-0.86 (m, 4H). LCMS (ES+) m/z 504 (M+1)

Example 402

5-amino-N-[5-(4-amino-5-methoxy-azepan-1-yl)-1-cyclopropyl-pyrazol-4-yl]-2-(2,6-difluorophenyl) thiazole-4-carboxamide 402

Following the preparation 401, the second eluting peak of cis-tert-butyl N-[1-(2-cyclopropyl-4-nitro-pyrazol-3-yl)-5-methoxy-azepan-4-yl]carbamate off the SFC chiral separation was converted to 402. $^1$H NMR (400 MHz, DMSO) δ 9.38 (s, 1H), 7.64 (s, 1H), 7.58-7.41 (m, 3H), 7.27 (t, J=8.6 Hz, 2H), 3.60-3.46 (m, 1H), 3.40 (d, J=8.6 Hz, 1H), 3.33-3.27 (m, 1H), 3.27-3.21 (m, 1H), 3.19 (s, 3H), 3.15-2.99 (m, 2H), 2.11-1.97 (m, 1H), 1.85-1.61 (m, 4H), 1.09-0.87 (m, 4H). LCMS (ES+) m/z 504 (M+1)

Example 403

5-amino-N-[5-(4-amino-5-methoxy-azepan-1-yl)-1-cyclopropyl-pyrazol-4-yl]-2-(2,6-difluorophenyl) thiazole-4-carboxamide 403

Racemic trans-tert-butyl N-[1-(2-cyclopropyl-4-nitro-pyrazol-3-yl)-5-methoxy-azepan-4-yl]carbamate was chirally separated on AD column with 15% methanol. Following the procedures in Example 369, the first eluting peak of trans-tert-butyl N-[1-(2-cyclopropyl-4-nitro-pyrazol-3-yl)-5-methoxy-azepan-4-yl]carbamate off the SFC chiral separation was converted to 403. $^1$H NMR (400 MHz, DMSO) δ 8.92 (s, 1H), 7.60-7.39 (m, 4H), 7.27 (t, J=8.7 Hz, 2H), 3.59-3.45 (m, 1H), 3.29-3.02 (m, 8H), 2.96-2.85 (m, 1H), 2.10-1.96 (m, 1H), 1.93-1.83 (m, 1H), 1.78-1.65 (m, 1H), 1.65-1.49 (m, 1H), 1.10-0.85 (m, 4H). LCMS (ES+) m/z 504 (M+1)

Example 404

5-amino-N-[5-(4-amino-5-methoxy-azepan-1-yl)-1-cyclopropyl-pyrazol-4-yl]-2-(2,6-difluorophenyl)thiazole-4-carboxamide 404

Following the preparation of 403, the second eluting peak of trans-tert-butyl N-[1-(2-cyclopropyl-4-nitro-pyrazol-3-yl)-5-methoxy-azepan-4-yl]carbamate off the SFC chiral separation was converted to 404. $^1$H NMR (400 MHz, DMSO) δ 8.92 (s, 1H), 7.62-7.41 (m, 4H), 7.27 (t, J=8.7 Hz, 2H), 3.53 (t, J=5.4 Hz, 1H), 3.28-2.99 (m, 8H), 2.96-2.83 (m, 1H), 2.10-1.97 (m, 1H), 1.92-1.80 (m, 1H), 1.79-1.64 (m, 1H), 1.64-1.46 (m, 1H), 1.10-0.82 (m, 4H). LCMS (ES+) m/z 504 (M+1)

Example 405

5-amino-2-(2,6-difluorophenyl)-N-[5-[4-hydroxy-4-(trifluoromethyl)azepan-1-yl]-1-methyl-pyrazol-4-yl]thiazole-4-carboxamide 405

Following the procedure for Example 101 starting from 1-(1-methyl-4-nitro-1H-pyrazol-5-yl)-4-(trifluoromethyl)azepan-4-ol and 5-(tert-butoxycarbonylamino)-2-(2,6-difluorophenyl)-thiazole-4-carboxylic acid gave 405 as a pale brown solid (53 mg, 29% over three steps). $^1$H NMR (400 MHz, CDCl$_3$) δ 8.95 (s, 1H), 7.94 (s, 1H), 7.39-7.28 (m, 1H), 7.02 (t, J=8.7 Hz, 2H), 6.21 (s, 2H), 3.73 (s, 3H), 3.46 (ddd, J=13.7, 8.5, 5.0 Hz, 1H), 3.29-3.18 (m, 3H), 2.95 (s, 1H), 2.15-1.97 (m, 5H), 1.87-1.77 (m, 1H). LCMS (ES+) m/z 517 (M+1)

Example 406

5-amino-N-[5-(4-amino-5-methoxy-azepan-1-yl)-1-ethyl-pyrazol-4-yl]-2-(2,6-difluorophenyl)thiazole-4-carboxamide 406

Racemic cis-tert-butyl N-[1-(2-ethyl-4-nitro-pyrazol-3-yl)-5-methoxy-azepan-4-yl]carbamate was chirally separated on AD column with 30% methanol. Following the procedures for Example 369, the first eluting peak of cis-tert-butyl N-[1-(2-ethyl-4-nitro-pyrazol-3-yl)-5-methoxy-azepan-4-yl]carbamate off the SFC chiral separation was converted to 406. $^1$H NMR (400 MHz, DMSO) δ 9.20-9.01 (s, 1H), 8.39-8.28 (s, 1H), 7.69-7.60 (s, 1H), 7.60-7.45 (m, 3H), 7.35-7.19 (t, J=8.7 Hz, 2H), 4.01-3.89 (q, J=8.1, 7.7 Hz, 2H), 3.56-3.47 (d, J=6.9 Hz, 1H), 3.26-3.20 (s, 3H), 3.21-2.88 (m, 1H), 2.15-1.98 (s, 0H), 1.96-1.80 (s, 0H), 1.76-1.60 (m, 2H), 1.37-1.27 (t, J=7.2 Hz, 3H). LCMS (ES+) m/z 492 (M+1)

Example 407

5-amino-N-[5-(4-amino-5-methoxy-azepan-1-yl)-1-ethyl-pyrazol-4-yl]-2-(2,6-difluorophenyl)thiazole-4-carboxamide 407

Following the preparation of 406, the second eluting peak of cis-tert-butyl N-[1-(2-ethyl-4-nitro-pyrazol-3-yl)-5-meth-oxy-azepan-4-yl]carbamate off the SFC chiral separation was converted to 407. $^1$H NMR (400 MHz, DMSO) δ 9.23-9.02 (s, 1H), 8.40-8.32 (s, 1H), 7.70-7.61 (s, 1H), 7.59-7.45 (m, 3H), 7.35-7.20 (t, J=8.7 Hz, 2H), 4.01-3.90 (m, 2H), 3.56-3.44 (d, J=7.1 Hz, 1H), 3.27-3.20 (s, 3H), 3.21-2.91 (m, 1H), 2.13-1.99 (m, 1H), 1.94-1.79 (m, 1H), 1.77-1.60 (m, 2H), 1.36-1.27 (t, J=7.2 Hz, 3H). LCMS (ES+) m/z 492 (M+1)

Example 410

5-amino-N-(5-((4S,5S)-5-amino-4-methoxycyclohept-1-enyl)-1-methyl-1H-pyrazol-4-yl)-2-(2,6-difluorophenyl)thiazole-4-carboxamide 410

Following the procedures in Example 378 starting from tert-butyl (E)-2-methoxy-5-(1-methyl-4-nitro-1H-pyrazol-5-yl)cyclohept-4-enylcarbamate and 5-(tert-butoxycarbonylamino)-2-cyclopropylthiazole-4-carboxylic acid gave 410 as the monoformate salt as an off-white foam (13 mg, 4% over three steps). $^1$H NMR (400 MHz, d$_6$-DMSO) δ 8.63 (s, 1H), 8.35 (s, 1H), 7.80 (s, 1H), 7.59-7.43 (m, 3H), 7.26 (t, J=8.8 Hz, 2H), 5.93 (t, J=6.4 Hz, 1H), 3.70 (s, 3H), 3.26 (s, 3H), 3.02-2.96 (m, 1H), 2.91 (t, J=9.3 Hz, 1H), 2.68-2.60 (m, 1H), 2.42-2.24 (m, 4H), 1.98-1.89 (m, 2H), 1.48-1.37 (m, 1H). LCMS (ES+) m/z 475 (M+1)

Example 411

5-amino-N-[5-(4-amino-4-methyl-azepan-1-yl)-1-methyl-pyrazol-4-yl]-2-(2,6-difluorophenyl)thiazole-4-carboxamide 411

Following the procedure for Example 101 starting from tert-butyl 4-methyl-1-(1-methyl-4-nitro-1H-pyrazol-5-yl)azepan-4-ylcarbamate and 5-(tert-butoxycarbonylamino)-2-(2,6-difluorophenyl)-thiazole-4-carboxylic acid gave 411 as a pale brown solid (68 mg, 55% over three steps). $^1$H NMR (400 MHz, CDCl$_3$) δ 8.98 (s, 1H), 7.91 (s, 1H), 7.38-7.25 (m, 1H), 7.02 (t, J=8.7 Hz, 2H), 6.20 (s, 2H), 3.73 (s, 3H), 3.34-3.26 (m, 1H), 3.33-3.08 (m, 2H), 3.17-3.09 (m, 1H), 1.95-1.78 (m, 2H), 1.77-1.66 (m, 4H), 1.19 (s, 3H). Exchangeable NH$_2$ not observed. LCMS (ES+) m/z 462 (M+1)

Example 412

5-amino-N-[5-(4-amino-4-methyl-azepan-1-yl)-1-methyl-pyrazol-4-yl]-2-(2-fluorophenyl)thiazole-4-carboxamide 412

Following the procedure for Example 101 starting from tert-butyl 4-methyl-1-(1-methyl-4-nitro-1H-pyrazol-5-yl)azepan-4-ylcarbamate and 5-(tert-butoxycarbonyl-amino)-2-(2-fluorophenyl)thiazole-4-carboxylic acid gave 412 as a pale brown solid (87 mg, 74% over three steps). $^1$H NMR (400 MHz, CDCl$_3$) δ 8.73 (s, 1H), 8.13 (t, J=7.7 Hz, 1H), 7.85 (s, 1H), 7.39-7.30 (m, 1H), 7.26-7.11 (m, 2H), 6.11 (s, 2H), 3.75 (s, 3H), 3.40-3.18 (m, 3H), 3.17-3.09 (m, 1H), 1.98-1.89 (m, 1H), 1.90-1.71 (m, 5H), 1.23 (s, 3H). Exchangeable NH$_2$ not observed. LCMS (ES+) m/z 444 (M+1)

Example 413

5-amino-N-(5-((4S,5S)-4-amino-5-methoxycycloheptyl)-1-methyl-1H-pyrazol-4-yl)-2-(2-fluorophenyl)thiazole-4-carboxamide 413

A solution of tert-butyl 5-fluoro-2-methoxy-5-(1-methyl-4-nitro-1H-pyrazol-5-yl)cycloheptylcarbamate (430 mg, 1.27 mmol) in MeOH (50 mL) was passed through the H-Cube® (full $H_2$, 70° C., flow rate: 1 mL/min, 30 mm 10% Pd/C cartridge). The solvent was removed under reduced pressure to give an orange foam. This foam was then dissolved in MeOH (70 mL) and 10% palladium on carbon (45 mg) added. The mixture was then stirred under an atmosphere of $H_2$ (400 psi) at room temperature for 3 hr, filtered through Celite® and the solvent removed under reduced pressure to give a complex mixture as an orange foam (378 mg) containing tert-butyl 5-(4-amino-1-methyl-1H-pyrazol-5-yl)-2-methoxycycloheptylcarbamate. To a solution of this mixture (378 mg, 1.13 mmol) in DCM (30 mL) was added DIPEA (1.0 mL, 5.74 mmol), PyBOP (1.5 g, 2.81 mmol) and 5-(tert-butoxycarbonyl-amino)-2-(2-fluorophenyl)thiazole-4-carboxylic acid (418 mg, 1.24 mmol) and the mixture was stirred at room temperature for 18 hr. The mixture was diluted with DCM (150 mL) and washed with water (30 mL). The organic layer was separated, dried over $MgSO_4$ and the solvent removed under reduced pressure. Purification via silica gel column chromatography (70-80% EtOAc/isohexane) gave a mixture of four diastereomers as a peach solid (240 mg) which were separated by preparative HPLC. Each diastereomer (25 mg, 0.03 mmol) was then stirred with HCl in dioxane (4 M, 0.95 mL, 3.80 mmol) in MeOH (1 mL) at room temperature for 18 hr. The solvents were removed under reduced pressure and the crude residue was re-dissolved in MeOH and loaded onto an SCX column. The column was washed with MeOH, eluted with 7 N ammonia in MeOH to give 413 (Diastereomer 1) as an off-white solid (13 mg, 2% over three steps). $^1$H NMR (400 MHz, $CDCl_3$) δ 8.43 (s, 1H), 8.21 (td, J=7.7, 1.9 Hz, 1H), 7.79 (s, 1H), 7.38-7.32 (m, 1H), 7.26-7.21 (m, 1H), 7.16 (dd, J=11.4, 8.3 Hz, 1H), 6.09 (s, 2H), 3.84 (s, 3H), 3.36 (s, 3H), 3.11-2.99 (m, 2H), 2.91-2.84 (m, 1H), 2.13-2.02 (m, 2H), 1.98-1.91 (m, 2H), 1.85 (t, J=12.3 Hz, 4H), 1.58-1.46 (m, 2H). LCMS (ES+) m/z 459 (M+1)

Example 414

5-amino-N-(5-((4S,5S)-4-amino-5-methoxycycloheptyl)-1-methyl-1H-pyrazol-4-yl)-2-(2-fluorophenyl)thiazole-4-carboxamide 414

Following the procedure in Example 413 gave 414 (Diastereomer 2) as a beige solid (16 mg, 2% over three steps). $^1$H NMR (400 MHz, $CDCl_3$) δ 8.39 (s, 1H), 8.22-8.15 (m, 1H), 7.76 (s, 1H), 7.38-7.31 (m, 1H), 7.27-7.20 (m, 1H), 7.15 (dd, J=11.4, 8.3 Hz, 1H), 6.10 (s, 2H), 3.83 (s, 3H), 3.35 (s, 3H), 3.16-3.12 (m, 1H), 3.05 (t, J=9.2 Hz, 1H), 2.95-2.82 (m, 1H), 2.15-2.00 (m, 2H), 1.98-1.80 (m, 5H), 1.64-1.50 (m, 1H). LCMS (ES+) m/z 459 (M+1)

Example 415

5-amino-N-(5-((4S,5S)-4-amino-5-methoxycycloheptyl)-1-methyl-1H-pyrazol-4-yl)-2-(2-fluorophenyl)thiazole-4-carboxamide 415

Following the procedure in Example 413 gave 415 (Diastereomer 3) as a beige solid (15 mg, 2% over three steps). $^1$H NMR (400 MHz, $CDCl_3$) δ 8.37 (s, 1H), 8.17 (t, J=7.8 Hz, 1H), 7.72 (s, 1H), 7.38-7.31 (m, 1H), 7.26-7.12 (m, 2H), 6.11 (s, 2H), 3.84 (s, 3H), 3.36 (s, 3H), 2.99 (d, J=6.6 Hz, 2H), 2.92 (t, J=7.6 Hz, 1H), 2.17 (dd, J=14.1, 7.0 Hz, 1H), 2.13-1.79 (m, 7H), 1.47 (d, J=13.7 Hz, 2H). LCMS (ES+) m/z 459 (M+1).

Example 416

5-amino-N-(5-((4S,5S)-4-amino-5-methoxycycloheptyl)-1-methyl-1H-pyrazol-4-yl)-2-(2-fluorophenyl)thiazole-4-carboxamide 416

Following the procedure in Example 413 gave 416 (Diastereomer 4) as a beige solid (14 mg, 2% over three steps). $^1$H NMR (400 MHz, $CDCl_3$) δ 8.37 (s, 1H), 8.17 (td, J=7.7, 1.9 Hz, 1H), 7.72 (s, 1H), 7.39-7.31 (m, 1H), 7.26-7.12 (m, 2H), 6.10 (s, 2H), 3.84 (s, 3H), 3.36 (s, 3H), 3.02-2.96 (m, 2H), 2.96-2.87 (m, 1H), 2.22-2.11 (m, 1H), 2.13-1.78 (m, 7H), 1.54-1.41 (m, 2H). LCMS (ES+) m/z 459 (M+1)

Example 417

5-amino-N-[5-[(4S)-4-aminoazepan-1-yl]-1-methyl-pyrazol-4-yl]-2-(2-fluoro-4-pyridyl)thiazole-4-carboxamide 417

Step A: In a round bottom flask, N-[(4S)-1-(4-amino-2-methyl-pyrazol-3-yl)azepan-4-yl]-2,2,2-trifluoro-acetamide (733 mg, 2.40 mmol), 2-bromo-5-(tert-butoxycarbonylamino)-1H-imidazole-4-carboxylic acid (955 mg, 3.12 mmol), and PyBOP (2020 mg, 3.84 mmol) were dissolved in DCM (40 mL). DIPEA (2.51 mL, 14.4 mmol) was added and the mixture was stirred at room temperature for 18 h. The mixture was concentrated and purified via flash chromatography, EA/heptane 0% to 100% to afford tert-butyl N-[2-bromo-4-[[1-methyl-5-[(4S)-4-[(2,2,2-trifluoroacetyl)amino]azepan-1-yl]pyrazol-4-yl]carbamoyl]thiazol-5-yl]carbamate (1.39 g, 95%).

Step B: In a microwave reaction vial, tert-butyl N-[2-bromo-4-[[1-methyl-5-[(4S)-4-[(2,2,2-trifluoroacetyl)amino]azepan-1-yl]pyrazol-4-yl]carbamoyl]thiazol-5-yl]carbamate (100 mg, 0.16 mmol), 2-fluoro-4-(4,4,5,5-tetramethyl-1,3,2-dioxaborolan-2-yl)pyridine (110 mg, 0.49 mmol) and PD(DPPF)CL2 (12 mg, 0.016 mmol) were dissolved in acetonitrile (3 mL). 1.0M KOAc (0.25 mL, 0.25 mmol) and 1.0M $Na_2CO_3$ (0.25 mL, 0.25 mmol) were added and the reaction was irradiated with microwave at 120° C. for 30 min. The mixture was cooled, filtered through Celite, concentrated and purified via flash chromatography, EA/heptane 0% to 100% to afford tert-butyl N-[2-(2-fluoro-4-pyridyl)-4-[[1-methyl-5-[(4S)-4-[(2,2,2-trifluoroacetyl)amino]azepan-1-yl]pyrazol-4-yl]carbamoyl]thiazol-5-yl]carbamate (60 mg, 58%). This compound was stirred with 4N HCl in dioxane (3 mL, 12 mmol) and methanol (2 mL) at room temperature for 3 h. Solvent was removed under reduced pressure. The residue was dissolved in methanol (3 mL) and water (1 mL), potassium carbonate (67 mg, 0.48 mmol) was added and the mixture was heated at 60° C. for 1.5 h. After cooling to room temperature, the reaction mixture was diluted with water and extracted with EA 3×. The combined organic layers were dried over MgSO4 and the solvent removed under reduced pressure and the residue purified by preparative HPLC to afford 417. $^1$H NMR (400 MHz, DMSO) δ 9.04 (s, 1H), 8.29 (d, J=5.3 Hz, 1H), 7.74 (d, J=5.3 Hz, 3H), 7.59 (s, 1H), 7.42 (s, 1H), 3.66 (s, 3H), 3.24-3.01 (m, 5H), 1.94-1.73 (m, 3H), 1.67-1.48 (m, 3H). LCMS (ES+) m/z 431 (M+1)

Example 418

5-amino-N-[5-[(4S)-4-aminoazepan-1-yl]-1-methyl-pyrazol-4-yl]-2-(2-methoxy-3-pyridyl)thiazole-4-carboxamide 418

Following the procedure for 417, replacing 2-fluoro-4-(4,4,5,5-tetramethyl-1,3,2-dioxaborolan-2-yl)pyridine with (2-methoxy-3-pyridyl)boronic acid, 418 was prepared. $^1$H NMR (400 MHz, DMSO) δ 8.97 (s, 1H), 8.64 (d, J=7.6 Hz, 1H), 8.22 (d, J=4.6 Hz, 1H), 7.40 (s, 1H), 7.32 (s, 2H), 7.22-7.13 (m, 1H), 4.05 (s, 3H), 3.66 (s, 3H), 3.25-2.98 (m, 5H), 2.04-1.79 (m, 3H), 1.77-1.54 (m, 3H). LCMS (ES+) m/z 443 (M+1)

Example 419

5-amino-N-[5-[(4S)-4-aminoazepan-1-yl]-1-methyl-pyrazol-4-yl]-2-(1-methylpyrazol-4-yl)thiazole-4-carboxamide 419

Following the procedure for 417, replacing 2-fluoro-4-(4,4,5,5-tetramethyl-1,3,2-dioxaborolan-2-yl)pyridine with 1-methyl-4-(4,4,5,5-tetramethyl-1,3,2-dioxaborolan-2-yl)pyrazole, 419 was prepared. $^1$H NMR (400 MHz, DMSO) δ 8.73 (s, 1H), 8.18 (d, J=47.7 Hz, 1H), 7.81 (d, J=11.8 Hz, 1H), 7.53 (d, J=24.5 Hz, 1H), 7.24 (s, 2H), 3.87 (s, 3H), 3.64 (s, 3H), 3.21-3.01 (m, 5H), 1.96-1.77 (m, 3H), 1.72-1.48 (m, 3H). LCMS (ES+) m/z 416 (M+1)

Example 420

5-amino-N-[5-[(4S)-4-aminoazepan-1-yl]-1-methyl-pyrazol-4-yl]-2-(5-fluoro-3-pyridyl)thiazole-4-carboxamide 420

Following the procedure for 417, replacing 2-fluoro-4-(4,4,5,5-tetramethyl-1,3,2-dioxaborolan-2-yl)pyridine with 3-fluoro-5-(4,4,5,5-tetramethyl-1,3,2-dioxaborolan-2-yl)pyridine, 420 was prepared. $^1$H NMR (400 MHz, DMSO) δ 9.01 (s, 1H), 8.90 (s, 1H), 8.58 (d, J=2.4 Hz, 1H), 8.20 (d, J=10.0 Hz, 1H), 7.61 (s, 2H), 7.39 (s, 1H), 3.66 (s, 3H), 3.22-3.03 (m, 5H), 1.99-1.75 (m, 3H), 1.69-1.51 (m, 3H). LCMS (ES+) m/z 431 (M+1)

Example 421

5-amino-N-[5-[(4S)-4-aminoazepan-1-yl]-1-methyl-pyrazol-4-yl]-2-(3,5-dimethylisoxazol-4-yl)thiazole-4-carboxamide 421

Following the procedure for 417, replacing 2-fluoro-4-(4,4,5,5-tetramethyl-1,3,2-dioxaborolan-2-yl)pyridine with (3,5-dimethylisoxazol-4-yl)boronic acid, 421 was prepared. $^1$H NMR (400 MHz, DMSO) δ 8.60 (s, 1H), 8.41 (s, 1H), 7.50 (s, 1H), 7.39 (s, 2H), 3.66 (s, 3H), 3.26-2.98 (m, 5H), 2.65 (s, 3H), 2.47 (s, 3H), 2.04-1.75 (m, 3H), 1.72-1.50 (m, 3H). LCMS (ES+) m/z 431 (M+1)

Example 422

5-amino-N-(5-((4S,5S)-4-amino-5-fluoroazepan-1-yl)-1-methyl-1H-pyrazol-4-yl)-2-(3-fluoropyridin-4-yl)thiazole-4-carboxamide 422

To a solution of tert-butyl 1-(4-(5-(tert-butoxy-carbonyl)-amino-2-bromothiazole-4-carboxamido)-1-methyl-1H-pyrazol-5-yl)-5-fluoroazepan-4-ylcarbamate (100 mg, 0.16 mmol) in dioxane (1.6 mL) was added 3-fluoro-4-(tributylstannyl)pyridine (90 mg, 0.23 mmol), tetrakis(triphenylphosphine)palladium(0) (9 mg, 0.008 mmol), copper(I) iodide (9 mg, 0.05 mmol) and lithium chloride (20 mg, 0.48 mmol). The mixture was degassed for 5 min before being heated in a microwave at 120° C. for 1 hr. The mixture was concentrated under reduced pressure and the residue purified via silica gel column chromatography (0-10% MeOH/DCM) to give a brown oil (100 mg, 96%). To a solution of this oil (100 mg, 0.15 mmol) in dioxane (3 mL) was added HCl in dioxane (4 M, 3 mL, 12.0 mmol) and the mixture was stirred at room temperature for 36 hr. Purification via preparative HPLC gave 422 as the monoformate salt as a yellow solid (24 mg, 35%). $^1$H NMR (d$_6$-DMSO) δ 9.11 (s, 1H), 8.70 (d, J=2.76 Hz, 1H), 8.51 (d, J=5.10 Hz, 1H), 8.33-8.20 (m, 2H), 7.69 (s, 2H), 7.49-7.38 (m, 1H), 4.78-4.44 (m, 1H), 3.66 (s, 3H), 3.30-3.10 (m, 5H), 2.22-2.05 (m, 1H), 2.05-1.96 (m, 1H), 1.95-1.90 (m, 1H), 1.75-1.62 (m, 1H). Exchangeable NH$_2$ not observed. LCMS (ES+) m/z 449 (M+1)

Example 423

5-amino-2-(2-fluorophenyl)-N-[5-(2-methoxy-8-azabicyclo[3.2.1]octan-5-yl)-1-methyl-pyrazol-4-yl]thiazole-4-carboxamide 423

Following the procedure in Example 413 gave 423 as a beige solid (109 mg, 18% over three steps). $^1$H NMR (400 MHz, CDCl$_3$) δ 10.96 (s, 1H), 8.27 (t, J=7.7 Hz, 2H), 7.37-7.29 (m, 1H), 7.22-7.11 (m, 2H), 6.06 (s, 2H), 3.91 (s, 3H), 3.62-3.56 (m, 1H), 3.44 (s, 3H), 2.37-2.28 (m, 1H), 2.19-2.00 (m, 5H), 1.89-1.73 (m, 3H), 1.52-1.39 (m, 1H). LCMS (ES+) m/z 457 (M+1)

Example 424

5-amino-N-(5-((4S,5S)-4-amino-5-hydroxy-4-methylazepan-1-yl)-1-methyl-1H-pyrazol-4-yl)-2-(2,6-difluorophenyl)thiazole-4-carboxamide 424

To a solution of 2,2,2-trifluoro-N-(5-hydroxy-4-methyl-1-(1-methyl-4-nitro-1H-pyrazol-5-yl)azepan-4-yl)acetamide (200 mg, 0.55 mmol) and ammonium formate (700 mg, 2.74 mmol) in MeOH (10 mL) under nitrogen was added 10% palladium on carbon (50 mg, 0.13 mmol). The mixture was heated at 65° C. for 2 hr before being cooled to room temperature, filtered and concentrated under reduced pressure. The residue was partitioned between water (10 mL) and DCM (50 mL). The organic layer was separated, passed through a phase separation cartridge and concentrated under reduced pressure to give N-(1-(4-amino-1-methyl-1H-pyrazol-5-yl)-5-hydroxy-4-methylazepan-4-yl)-2,2,2-trifluoroacetamide as a red gum (140 mg). A solution of PyBOP (330 mg, 0.62 mmol) and 5-(tert-butoxycarbonylamino)-2-(2,6-difluorophenyl)thiazole-4-carboxylic acid (160 mg, 0.45 mmol) in DCM (3 mL) was stirred at room temperature for 30 min. A solution of N-(1-(4-amino-1-methyl-1H-pyrazol-5-yl)-5-hydroxy-4-methylazepan-4-yl)-2,2,2-trifluoroacetamide (140 mg, 0.41 mmol) and DIPEA (140 μL, 0.83 mmol) in DCM (2 mL) was added and the mixture was stirred at room temperature for 18 hr. Additional DCM (50 mL) was added and the mixture washed with water (20 mL). The organic layer was passed through a phase separation cartridge and concentrated under reduced pressure. The residue was dissolved in a mixture of THF (2 mL), MeOH (2 mL) and water (1 mL) and potassium carbonate (200 mg, 1.44 mmol) was added. The reaction mixture was heated at 60° C. for 18 hr, cooled to room temperature, filtered and concentrated under reduced pressure. The residue was then dissolved in DCM (3 mL) and trifluoroacetic acid (1 mL) added. The mixture was stirred at room temperature for 2 hr, concentrated under reduced pressure and purified via preparative HPLC to give 424 as the monoformate salt as a white solid (5 mg, 2% over three steps). $^1$H NMR (400 MHz, d$_4$-MeOD) δ 8.56 (s, 1H), 7.57 (s, 1H), 7.53-7.44 (m, 1H), 7.15 (t, J=8.8 Hz, 2H), 3.86-3.72 (m, 5H), 3.45-3.35 (m, 2H), 3.26-3.14 (m, 1H), 2.15-1.90 (m, 4H), 1.46 (s, 3H). LCMS (ES+) m/z 478 (M+1)

Example 425

5-amino-N-[5-[(4S)-4-aminoazepan-1-yl]-1-methyl-pyrazol-4-yl]-2-(2-fluoro-5-methyl-3-pyridyl)thiazole-4-carboxamide 425

Following the procedure for 417, replacing 2-fluoro-4-(4,4,5,5-tetramethyl-1,3,2-dioxaborolan-2-yl)pyridine with 2-fluoro-5-methyl-3-(4,4,5,5-tetramethyl-1,3,2-dioxaborolan-2-yl)pyridine, 425 was prepared. $^1$H NMR (400 MHz, DMSO) δ 9.00 (s, 1H), 8.55 (d, J=9.7 Hz, 1H), 8.06 (s, 1H), 7.51 (s, 2H), 7.44 (s, 1H), 3.66 (s, 3H), 3.22-2.95 (m, 5H), 2.38 (s, 3H), 1.92-1.77 (m, 3H), 1.67-1.42 (m, 3H). LCMS (ES+) m/z 445 (M+1)

Example 426

5-amino-N-[5-(5-amino-3,3-difluoro-azepan-1-yl)-1-methyl-pyrazol-4-yl]-2-(3-fluoro-4-pyridyl)thiazole-4-carboxamide 426

Following the procedures of Example 422 starting from tert-butyl 1-(4-(5-(tert-butoxycabonyl-amino)-2-bromothiazole-4-carboxamido)-1-methyl-1H-pyrazol-5-yl)-6,6-difluoroazepan-4-ylcarbamate gave 426 as the monoformate salt as a white solid (76 mg, 51% over two steps). $^1$H NMR (400 MHz, d$_6$-DMSO) δ 9.16 (s, 1H), 8.71 (d, J=2.8 Hz, 1H), 8.54 (d, J=5.2 Hz, 1H), 8.32-8.19 (m, 2H), 7.70 (s, 2H), 7.45 (s, 1H), 3.69 (s, 3H, under water peak), 3.56-3.34 (m, 3H, under water peak), 3.37-3.24 (m, 1H), 3.22-3.11 (m, 1H), 2.44-2.31 (m, 2H), 2.03-1.91 (m, 1H), 1.90-1.80 (m, 1H). Exchangeable NH$_2$ not observed. LCMS (ES+) m/z 467 (M+1)

Example 428

5-amino-N-[5-[(4R,5R)-4-amino-5-fluoro-azepan-1-yl]-1-methyl-pyrazol-4-yl]-2-(4-methyl-3-pyridyl)thiazole-4-carboxamide 428

Step A: In a round bottom flask, tert-butyl N-[(4R,5R)-1-(4-amino-2-methyl-pyrazol-3-yl)-5-fluoro-azepan-4-yl]carbamate (1240 mg, 3.80 mmol), 2-bromo-5-(tert-butoxycarbonylamino)-1H-imidazole-4-carboxylic acid (1510 mg, 4.94 mmol), and PyBOP (3.20 g, 6.08 mmol) were dissolved in DCM (50 mL). DIPEA (3.97 mL, 22.8 mmol) was added and the mixture was stirred at room temperature for 18 h. The mixture was concentrated and purified via flash chromatography, EA/heptane 0% to 100% to tert-butyl N-[2-bromo-4-[[5-[(4R,5R)-4-(tert-butoxycarbonylamino)-5-fluoro-azepan-1-yl]-1-methyl-pyrazol-4-yl]carbamoyl]thiazol-5-yl]carbamate (2.23 g, 93%).

Step B: In a microwave reaction vial, tert-butyl N-[2-bromo-4-[[5-[(4R,5R)-4-(tert-butoxycarbonylamino)-5-fluoro-azepan-1-yl]-1-methyl-pyrazol-4-yl]carbamoyl]thiazol-5-yl]carbamate (161 mg, 0.25 mmol), (4-methyl-3-pyridyl)boronic acid (105 mg, 0.76) and PD(DPPF)CL2 (19 mg, 0.025 mmol) were dissolved in acetonitrile (3 mL). 1.0M KOAc (0.38 mL, 0.38 mmol) and 1.0M Na$_2$CO$_3$ (0.38 mL, 0.38 mmol) were added and the reaction was irradiated with microwave at 125° C. for 30 min. The mixture was cooled, filtered through Celite, concentrated and purified via flash chromatography, EA/heptane 0% to 100% to afford tert-butyl N-[4-[[5-[(4R,5R)-4-(tert-butoxycarbonylamino)-5-fluoro-azepan-1-yl]-1-methyl-pyrazol-4-yl]carbamoyl]-2-(4-methyl-3-pyridyl)thiazol-5-yl]carbamate (95 mg, 58%). This compound was stirred with 4N HCl in dioxane (3 mL, 12 mmol) and methanol (2 mL) at room temperature for 3 h. Solvent was removed under reduced pressure. The residue was basified with saturated NaHCO3 and extracted with EA 3×. The combined organic layers were dried over MgSO4 and the solvent removed under reduced pressure and the residue purified by preparative HPLC to afford 428 (38 mg, 58%). $^1$H NMR (400 MHz, DMSO) δ 8.83 (s, 1H), 8.79 (s, 1H), 8.43 (d, J=5.0 Hz, 1H), 7.49 (s, 2H), 7.47 (s, 1H), 7.37 (d, J=4.9 Hz, 1H), 4.42 (dt, J=8.4, 5.0 Hz, 1H), 3.64 (s, 3H), 3.26-3.02 (m, 5H), 2.63 (s, 3H), 2.18-2.02 (m, 1H), 2.02-1.88 (m, 1H), 1.87-1.75 (m, 1H), 1.66-1.53 (m, 1H). LCMS (ES+) m/z 445 (M+1)

Example 429

5-amino-N-[5-[(4R,5R)-4-amino-5-fluoro-azepan-1-yl]-1-methyl-pyrazol-4-yl]-2-(1,5-dimethylpyrazol-4-yl)thiazole-4-carboxamide 429

Following the procedure for 428, replacing (4-methyl-3-pyridyl)boronic acid with 1,5-dimethyl-4-(4,4,5,5-tetramethyl-1,3,2-dioxaborolan-2-yl)pyrazole, 429 was prepared. $^1$H NMR (400 MHz, DMSO) δ 8.61 (s, 1H), 7.69 (s, 1H), 7.54 (s, 1H), 7.23 (s, 2H), 4.46 (dt, J=48.2, 6.6 Hz, 1H), 3.78 (s, 3H), 3.64 (s, 3H), 3.25-3.04 (m, 5H), 2.56 (s, 3H), 2.21-2.03 (m, 1H), 2.03-1.91 (m, 1H), 1.91-1.76 (m, 1H), 1.71-1.55 (m, 1H). LCMS (ES+) m/z 448 (M+1)

Example 430

5-amino-N-[5-[(4R,5R)-4-amino-5-fluoro-azepan-1-yl]-1-methyl-pyrazol-4-yl]-2-(2-methyl-3-pyridyl)thiazole-4-carboxamide 430

Following the procedure for 428, replacing (4-methyl-3-pyridyl)boronic acid with (2-methyl-3-pyridyl)boronic acid, 430 was prepared. $^1$H NMR (400 MHz, DMSO) δ 8.76 (s, 1H), 8.47 (d, J=4.7 Hz, 1H), 8.04 (d, J=7.9 Hz, 1H), 7.49 (s, 2H), 7.40-7.28 (m, 1H), 4.56-4.34 (m, 1H), 3.64 (s, 3H), 3.26-3.02 (m, 5H), 2.82 (s, 3H), 2.22-2.03 (m, 1H), 2.03-1.89 (m, 1H), 1.89-1.76 (m, 1H), 1.70-1.51 (m, 1H). LCMS (ES+) m/z 445 (M+1)

Example 431

5-amino-N-[5-[(4R,5R)-4-amino-5-fluoro-azepan-1-yl]-1-methyl-pyrazol-4-yl]-2-(2-methyl-4-pyridyl)thiazole-4-carboxamide 431

Following the procedure for 428, replacing (4-methyl-3-pyridyl)boronic acid with (2-methyl-4-pyridyl)boronic acid, 431 was prepared. $^1$H NMR (400 MHz, DMSO) δ 8.97 (s, 1H), 8.48 (d, J=5.2 Hz, 1H), 7.64 (d, J=6.5 Hz, 3H), 7.58 (d, J=5.2 Hz, 1H), 7.45 (s, 1H), 4.61-4.37 (m, 1H), 3.65 (s, 3H), 3.26-3.06 (m, 5H), 2.22-2.06 (m, 1H), 2.06-1.93 (m, 1H), 1.93-1.76 (m, 1H), 1.70-1.54 (m, 1H). LCMS (ES+) m/z 445 (M+1)

Example 432

5-amino-N-[5-[(4R,5R)-4-amino-5-fluoro-azepan-1-yl]-1-methyl-pyrazol-4-yl]-2-(6-cyano-2-pyridyl)thiazole-4-carboxamide 432

Following the procedure for 428, replacing (4-methyl-3-pyridyl)boronic acid with 6-(4,4,5,5-tetramethyl-1,3,2-dioxaborolan-2-yl)pyridine-2-carbonitrile, 432 was prepared. $^1$H NMR (400 MHz, DMSO) δ 9.03 (s, 1H), 8.44 (d, J=8.2 Hz, 1H), 8.14 (t, J=7.9 Hz, 1H), 8.00 (d, J=7.6 Hz, 1H), 7.74 (s, 2H), 7.44 (s, 1H), 4.67-4.41 (m, 1H), 3.65 (s, 3H), 3.28-3.05 (m, 5H), 2.23-2.06 (m, 1H), 2.06-1.94 (m, 1H), 1.94-1.77 (m, 1H), 1.75-1.57 (m, 1H). LCMS (ES+) m/z 456 (M+1)

Example 433

5-amino-N-[5-(4-amino-4-methyl-azepan-1-yl)-1-methyl-pyrazol-4-yl]-2-(2-fluorophenyl)thiazole-4-carboxamide 433

Chiral separation of racemic 412 by SFC gave single enantiomer 433. $^1$H NMR (400 MHz, DMSO) δ 9.02 (s, 1H), 8.42 (s, 1H), 8.29 (t, J=7.8 Hz, 1H), 7.45 (d, J=7.2 Hz, 3H), 7.42-7.26 (m, 2H), 3.66 (s, 3H), 3.24-2.95 (m, 4H), 1.95-1.53 (m, 6H), 1.23 (s, 3H). LCMS (ES+) m/z 444 (M+1)

Example 434

5-amino-N-[5-(4-amino-4-methyl-azepan-1-yl)-1-methyl-pyrazol-4-yl]-2-(2-fluorophenyl)thiazole-4-carboxamide 434

Chiral separation of 412 by SFC gave 434. $^1$H NMR (400 MHz, DMSO) δ 9.03 (s, 1H), 8.42 (s, 1H), 8.28 (t, J=7.9 Hz, 1H), 7.45 (d, J=11.1 Hz, 3H), 7.41-7.25 (m, 2H), 3.66 (s, 3H), 3.24-2.98 (m, 4H), 1.96-1.52 (m, 6H), 1.21 (s, 3H). LCMS (ES+) m/z 444 (M+1)

Example 435

5-amino-N-[5-(4-amino-4-methyl-azepan-1-yl)-1-methyl-pyrazol-4-yl]-2-(2,6-difluorophenyl)thiazole-4-carboxamide 435

Chiral separation of racemic 411 by SFC gave single enantiomer 435. $^1$H NMR (400 MHz, DMSO) δ 8.96 (s, 1H), 7.58 (s, 1H), 7.56-7.43 (m, 2H), 7.27 (t, J=8.7 Hz, 2H), 3.65 (s, 3H), 3.23-2.94 (m, 5H), 1.97-1.48 (m, 6H), 1.15 (s, 3H). LCMS (ES+) m/z 462 (M+1)

Example 436

5-amino-N-[5-(4-amino-4-methyl-azepan-1-yl)-1-methyl-pyrazol-4-yl]-2-(2,6-difluorophenyl)thiazole-4-carboxamide 436

Chiral separation of 411 by SFC gave 436. $^1$H NMR (400 MHz, DMSO) δ 8.96 (s, 1H), 7.57 (s, 1H), 7.56-7.44 (m, 2H), 7.27 (t, J=8.7 Hz, 2H), 3.65 (s, 3H), 3.25-2.90 (m, 5H), 1.93-1.51 (m, 6H), 1.15 (s, 3H). LCMS (ES+) m/z 462 (M+1)

Example 437

5-amino-N-[5-[(4R,5R)-4-amino-5-fluoro-azepan-1-yl]-1-methyl-pyrazol-4-yl]-2-(1,3-dimethylpyrazol-4-yl)thiazole-4-carboxamide 437

Following the procedure for Example 428, replacing (4-methyl-3-pyridyl)boronic acid with 1,3-dimethyl-4-(4,4,5,5-tetramethyl-1,3,2-dioxaborolan-2-yl)pyrazole, 437 was prepared. $^1$H NMR (400 MHz, DMSO) δ 8.55 (s, 1H), 8.08 (s, 1H), 7.57 (s, 1H), 7.22 (s, 2H), 4.46 (dt, J=48.3, 6.7 Hz, 1H), 3.78 (s, 3H), 3.65 (s, 3H), 3.26-3.03 (m, 5H), 2.42 (s, 3H), 2.23-2.05 (m, 1H), 2.05-1.92 (m, 1H), 1.92-1.77 (m, 1H), 1.70-1.53 (m, 1H). LCMS (ES+) m/z 448 (M+1)

Example 438

5-amino-N-[5-(5-amino-3,3-difluoro-azepan-1-yl)-1-methyl-pyrazol-4-yl]-2-(3,5-difluoro-4-pyridyl)thiazole-4-carboxamide 438

Following the procedure for Example 422 starting from tert-butyl 1-(4-(5-(tert-butoxycarbonyl-amino)-2-bromothiazole-4-carboxamido)-1-methyl-1H-pyrazol-5-yl)-6,6-difluoroazepan-4-ylcarbamate and 3,5-difluoro-4-(tributylstannyl)pyridine gave 438 as a white solid (68 mg, 43% over two steps). $^1$H NMR (400 MHz, d$_6$-DMSO) δ 8.83 (s, 1H), 8.67 (s, 2H), 7.78 (s, 2H), 7.61-7.56 (m, 1H), 3.79-3.56 (m, 4H), 3.46-3.33 (m, 1H), 3.37-3.16 (m, 2H), 3.16-3.06 (m, 1H), 2.35-2.08 (m, 2H), 1.91-1.78 (m, 1H), 1.81-1.60 (m, 3H). LCMS (ES+) m/z 485 (M+1)

Example 439

5-amino-N-(5-((4S,5S)-4-amino-5-fluoroazepan-1-yl)-1-methyl-1H-pyrazol-4-yl)-2-(3,5-difluoropyridin-4-yl)thiazole-4-carboxamide 439

Following the procedure for Example 422 starting from tert-butyl 1-(4-(5-(tert-butoxy-carbonyl)-amino-2-bromothiazole-4-carboxamido)-1-methyl-1H-pyrazol-5-yl)-5-fluoroazepan-4-ylcarbamate and 3,5-difluoro-4-(tributylstannyl)pyridine gave 439 as a white solid (42 mg, 28% over two steps). $^1$H NMR (400 MHz, d$_6$-DMSO) δ 8.84 (s, 1H), 8.65 (s, 2H), 7.75 (s, 2H), 7.58 (s, 1H), 4.44 (dtd, J=47.9, 8.0, 3.6 Hz, 1H), 3.65 (s, 3H), 3.26-3.08 (m, 5H), 2.19-2.05 (m, 1H), 2.04-1.79 (m, 2H), 1.73-1.50 (m, 3H). LCMS (ES+) m/z 467 (M+1)

Example 440

5-amino-N-[5-(5-amino-3-methoxy-3-methyl-azepan-1-yl)-1-methyl-pyrazol-4-yl]-2-(3,5-difluoro-4-pyridyl)thiazole-4-carboxamide 440

Following the procedure for Example 422 starting from tert-butyl 1-(4-(5-(tert-butoxy-carbonyl-amino)-2-bromothiazole-4-carboxamido)-1-methyl-1H-pyrazol-5-yl)-6-methoxy-6-methylazepan-4-ylcarbamate and 3,5-difluoro-4-(tributylstannyl)pyridine gave 440 as the monoformate salt as a white solid (67 mg, 43% over two steps). $^1$H NMR (400 MHz, d$_6$-DMSO) δ 8.84 (s, 1H), 8.70 (s, 2H), 8.45 (s, 1H), 7.82 (s, 2H), 7.70 (s, 1H), 3.68 (s, 3H), 3.52 (t, J=11.2 Hz, 2H), 3.36-3.19 (m, 3H), 3.13-3.04 (m, 1H), 3.04 (s, 3H), 2.98 (d, J=14.4 Hz, 1H), 2.18 (d, J=14.2 Hz, 1H), 2.12-1.98 (m, 1H), 1.85-1.75 (m, 1H), 1.68-1.57 (m, 1H), 1.03 (s, 3H). LCMS (ES+) m/z 493 (M+1)

Example 441

5-amino-N-[5-(5-amino-3-methoxy-3-methyl-azepan-1-yl)-1-methyl-pyrazol-4-yl]-2-(3-fluoro-4-pyridyl)thiazole-4-carboxamide 441

Following the procedure for Example 422 starting from tert-butyl 1-(4-(5-(tert-butoxy-carbonyl-amino)-2-bromothiazole-4-carboxamido)-1-methyl-1H-pyrazol-5-yl)-6-methoxy-6-methylazepan-4-ylcarbamate gave 441 as the monoformate salt as a white solid (72 mg, 48% over two steps). $^1$H NMR (400 MHz, d$_6$-DMSO) δ 9.15 (s, 1H), 8.71 (d, J=2.7 Hz, 1H), 8.58 (d, J=5.1 Hz, 1H), 8.41 (s, 1H), 8.23 (dd, J=5.2, 6.4 Hz, 1H), 7.72 (s, 2H), 7.59 (s, 1H), 3.69 (s, 3H), 3.54 (t, J=10.6 Hz, 1H), 3.33-3.21 (m, 2H), 3.25-2.91 (m, 5H), 2.22-1.95 (m, 2H), 1.82-1.72 (m, 1H), 1.74-1.61 (m, 1H), 1.05 (s, 3H). Exchangeable NH$_2$ not observed. LCMS (ES+) m/z 475 (M+1)

Example 442

5-amino-N-[5-[(4R,5R)-4-amino-5-fluoro-azepan-1-yl]-1-methyl-pyrazol-4-yl]-2-(5-cyano-2-fluoro-phenyl)thiazole-4-carboxamide 442

Following the procedures for Example 428, replacing (4-methyl-3-pyridyl)boronic acid with (5-cyano-2-fluoro-phenyl)boronic acid, 442 was prepared. $^1$H NMR (400 MHz, DMSO) δ 9.22 (s, 1H), 8.86 (d, J=6.8 Hz, 1H), 7.91 (s, 1H), 7.67-7.57 (m, 1H), 7.53 (s, 2H), 7.35 (s, 1H), 4.56-4.34 (m, 1H), 3.65 (s, 3H), 3.24-3.00 (m, 5H), 2.20-2.03 (m, 1H), 2.03-1.89 (m, 1H), 1.79 (s, 1H), 1.67-1.50 (m, 1H). LCMS (ES+) m/z 473 (M+1)

Example 443

5-amino-N-[5-[(4R,5R)-4-amino-5-fluoro-azepan-1-yl]-1-methyl-pyrazol-4-yl]-2-(2,6-dimethyl-4-pyridyl)thiazole-4-carboxamide 443

Following the procedures for Example 428, replacing (4-methyl-3-pyridyl)boronic acid with 2,6-dimethyl-4-(4,4,5,5-tetramethyl-1,3,2-dioxaborolan-2-yl)pyridine, 443 was prepared. $^1$H NMR (400 MHz, DMSO) δ 8.95 (s, 1H), 7.63 (s, 2H), 7.45 (s, 1H), 7.44 (s, 2H), 4.60-4.35 (m, 1H), 3.65 (s, 3H), 3.27-3.00 (m, 5H), 2.47 (s, 6H), 2.23-2.06 (m, 1H), 2.06-1.90 (m, 1H), 1.90-1.76 (m, 1H), 1.71-1.54 (m, 1H). LCMS (ES+) m/z 459 (M+1).

Example 444

5-amino-N-[5-[(4R,5R)-4-amino-5-fluoro-azepan-1-yl]-1-methyl-pyrazol-4-yl]-2-(5-cyano-3-pyridyl)thiazole-4-carboxamide 444

Following the procedures for Example 428, replacing (4-methyl-3-pyridyl)boronic acid with 5-(4,4,5,5-tetramethyl-1,3,2-dioxaborolan-2-yl)pyridine-3-carbonitrile, 444 was prepared. $^1$H NMR (400 MHz, DMSO) δ 9.29 (s, 1H), 9.03 (s, 1H), 8.97 (s, 1H), 8.74 (s, 1H), 7.64 (s, 2H), 7.41 (s, 1H), 4.44 (dtd, J=11.5, 8.2, 3.2 Hz, 1H), 3.64 (s, 3H), 3.27-3.00 (m, 5H), 2.20-2.04 (m, 1H), 2.04-1.89 (m, 1H), 1.89-1.78 (m, 1H), 1.66-1.52 (m, 1H). LCMS (ES+) m/z 456 (M+1)

Example 445

5-amino-N-[5-[(4R,5R)-4-amino-5-fluoro-azepan-1-yl]-1-methyl-pyrazol-4-yl]-2-(2,5-dimethyl-3-pyridyl)thiazole-4-carboxamide 445

Following the procedures for Example 428, replacing (4-methyl-3-pyridyl)boronic acid with 2,5-dimethyl-3-(4,4,5,5-tetramethyl-1,3,2-dioxaborolan-2-yl)pyridine, 445 was prepared. $^1$H NMR (400 MHz, DMSO) δ 8.70 (s, 1H), 7.92 (d, J=8.0 Hz, 1H), 7.51 (s, 1H), 7.42 (s, 2H), 7.19 (d, J=8.0 Hz, 1H), 4.43 (dt, J=47.9, 6.1 Hz, 1H), 3.64 (s, 3H), 3.27-2.99 (m, 5H), 2.77 (s, 3H), 2.47 (s, 3H), 2.16-2.05 (m, 1H), 2.04-1.89 (m, 1H), 1.87-1.69 (m, 3H), 1.68-1.52 (m, 1H). LCMS (ES+) m/z 459 (M+1)

Example 446

5-amino-N-[5-[(5S)-5-amino-3,3-difluoro-azepan-1-yl]-1-methyl-pyrazol-4-yl]-2-(3-fluoro-4-pyridyl)thiazole-4-carboxamide 446

Chiral separation of racemic 426 by SFC gave single enantiomer 446. $^1$H NMR (400 MHz, DMSO) δ 9.09 (s, 1H), 8.70 (d, J=2.4 Hz, 1H), 8.54 (d, J=5.1 Hz, 1H), 8.22 (t, J=5.9 Hz, 1H), 7.68 (s, 2H), 7.49 (s, 1H), 3.78-3.57 (m, 4H), 3.53-3.35 (m, 1H), 3.29-3.04 (m, 3H), 2.37-2.11 (m, 2H), 1.95-1.67 (m, 4H). LCMS (ES+) m/z 467 (M+1)

Example 447

5-amino-N-[5-[(5R)-5-amino-3,3-difluoro-azepan-1-yl]-1-methyl-pyrazol-4-yl]-2-(3-fluoro-4-pyridyl)thiazole-4-carboxamide 447

Chiral separation of racemic 426 by SFC gave single enantiomer 447. $^1$H NMR (400 MHz, DMSO) δ 9.11 (s, 1H), 8.70 (d, J=2.6 Hz, 1H), 8.53 (d, J=5.1 Hz, 1H), 8.27 (s, 1H), 8.26-8.16 (m, 1H), 7.68 (s, 2H), 7.47 (s, 1H), 3.79-3.62 (m, 4H), 3.51-3.08 (m, 3H), 2.40-2.19 (m, 2H), 2.02-1.86 (m, 1H), 1.86-1.70 (m, 1H). LCMS (ES+) m/z 467 (M+1)

Example 448

5-amino-N-[5-(6-amino-1-oxa-9-azaspiro[3.6]decan-9-yl)-1-methyl-pyrazol-4-yl]-2-(2,6-difluorophenyl)thiazole-4-carboxamide 448

Step A: Methyl triphenylphosphonium bromide (3.09 g, 8.49 mmol) was suspended in toluene (25 mL). Potassium tert-butoxide (1.0 mol/L) in THF (7.07 mL, 7.074 mmol) was added and the mixture turned bright yellow. It was stirred at room temperature for 4 h, then tert-butyl N-[(4S)-1-(2-methyl-4-nitro-pyrazol-3-yl)-6-oxo-azepan-4-yl]carbamate (1000 mg, 2.83 mmol) (second eluting peak in the chiral separation) in 5 mL toluene was added. The mixture was stirred at RT for 30 min, quenched with saturated ammonium chloride, and extracted with EA 3×. The combined organic layers were concentrated and the residue was purified via silica gel column chromatography (0-100% EA/heptane) to give tert-butyl N-[(4R)-6-methylene-1-(2-methyl-4-nitro-pyrazol-3-yl)azepan-4-yl]carbamate (699 mg, 70%).

Step B: MCPBA (335 mg, 1.49 mmol, 77 mass %) was added to a stirred solution of tert-butyl N-[(4R)-6-methylene-1-(2-methyl-4-nitro-pyrazol-3-yl)azepan-4-yl]carbamate (350 mg, 1.00 mmol) in DCM (12 mL). The mixture was stirred at room temperature overnight. The reaction was quenched with sat NaHCO₃ and extracted with DCM 3×. The combined organic layers were concentrated and the residue was purified via silica gel column chromatography (0-100% EA/heptane) to give tert-butyl N-[(5S)-8-(2-methyl-4-nitro-pyrazol-3-yl)-2-oxa-8-azaspiro[2.6]nonan-5-yl]carbamate (316 mg, 86%).

Step C: To a stirred suspension of sodium hydride (115 mg, 2.87 mmol, 60 mass %) in DMSO (5 mL) trimethylsulfoxonium iodide (644 mg, 2.87 mmol) was added and the suspension was stirred at 60° C. for 2 h to give a clear solution. The epoxide tert-butyl N-[(5S)-8-(2-methyl-4-nitro-pyrazol-3-yl)-2-oxa-8-azaspiro[2.6]nonan-5-yl]carbamate (320 mg, 0.87 mmol) was dissolved in DMSO (2 mL) and added to the reaction mixture. The resulting clear solution was stirred at 65° C. for two days. After cooling to room temperature, the reaction was quenched with water and extracted with EA 3×. The combined organic layers were concentrated and the residue was purified via silica gel column chromatography (0-100% EA/heptane) to give tert-butyl ((9S)-6-(1-methyl-4-nitro-1H-pyrazol-5-yl)-1-oxa-6-azaspiro[3.6]decan-9-yl) carbamate (114 mg, 34%).

Step D: A solution of the above compound in MeOH (30 mL) was passed through the H-Cube® (50 bar, 50° C., flow rate: 1 mL/min, 30 mm 10% Pd/C cartridge). The solvent was removed under reduced pressure to afford tert-butyl ((9S)-6-(4-amino-1-methyl-1H-pyrazol-5-yl)-1-oxa-6-azaspiro[3.6]decan-9-yl)carbamate as a brown oil. To a solution of this oil in DCM (10 mL) was added 5-(tert-butoxycarbonylamino)-2-(2,6-difluorophenyl)thiazole-4-carboxylic acid (131 mg, 0.39 mmol), PyBOP (251 g, 0.48 mmol) and DIPEA (0.31 mL, 1.79 mmol) and the mixture was stirred at room temperature for 16 hr. Water (20 ml) was added and the mixture was diluted with DCM (100 mL). The organic layer was washed with water (20 mL), separated, dried over MgSO4 and the solvent removed under reduced pressure. Purification via silica gel column chromatography (0-100% EtOAc/heptane) gave tert-butyl N-[(6S)-9-[4-[[5-(tert-butoxycarbonylamino)-2-(2,6-difluorophenyl)thiazole-4-carbonyl]amino]-2-methyl-pyrazol-3-yl]-3-oxa-9-azaspiro[3.6]decan-6-yl]carbamate (185 mg, 90%).

Step E: The above compound was stirred with TFA (5 mL) and DCM (5 mL) at room temperature for 30 min. The solvent was removed under reduced pressure, basified with saturated NaHCO3, and extracted with ethyl acetate (3×). The combined organic layers were dried over MgSO4 and the solvent removed under reduced pressure and the residue purified by preparative HPLC to afford 448 (11 mg, 8.4%). ¹H NMR (400 MHz, DMSO) δ 7.60 (s, 1H), 7.58-7.43 (m, 3H), 7.30 (t, J=8.7 Hz, 2H), 4.39-4.19 (m, 2H), 3.66 (s, 3H), 3.44 (d, J=13.9 Hz, 1H), 3.24-3.13 (m, 1H), 3.09-2.89 (m, 3H), 2.48-2.38 (m, 1H), 2.34-2.20 (m, 2H), 1.90-1.74 (m, 2H), 1.69-1.51 (m, 1H). LCMS (ES+) m/z 490 (M+1)

Example 449

5-amino-N-[5-[(5R)-5-amino-3-methylene-azepan-1-yl]-1-methyl-pyrazol-4-yl]-2-(2,6-difluorophenyl) thiazole-4-carboxamide 449

In the preparation of 448, tert-butyl N-[(4R)-6-methylene-1-(2-methyl-4-nitro-pyrazol-3-yl)azepan-4-yl]carbamate was converted to 449. ¹H NMR (400 MHz, DMSO) δ 8.73 (s, 1H), 7.56 (s, 1H), 7.55-7.41 (m, 3H), 7.26 (t, J=8.7 Hz, 2H), 4.89 (d, J=9.7 Hz, 2H), 3.86-3.71 (m, 2H), 3.67 (s, 3H), 3.16-3.05 (m, 1H), 3.05-2.92 (m, 1H), 2.85 (s, 1H), 2.44-2.28 (m, 1H), 1.82-1.69 (m, 2H), 1.53-1.35 (m, 1H). LCMS (ES+) m/z 460 (M+1)

Example 450

5-amino-N-[5-[(4S,5S)-4-amino-5-fluoro-azepan-1-yl]-1-(trideuteriomethyl)pyrazol-4-yl]-2-(2,6-difluorophenyl)thiazole-4-carboxamide 450

Following the procedures in Example 147, 5-chloro-1-trideuteriomethyl-4-nitro-1H-pyrazole was converted to 450. ¹H NMR (400 MHz, DMSO) δ 8.83 (s, 1H), 7.62-7.41 (m, 4H), 7.26 (t, J=8.7 Hz, 2H), 4.41 (dtd, J=47.9, 8.2, 3.6 Hz, 1H), 3.24-3.02 (m, 5H), 2.18-2.02 (m, 1H), 2.02-1.89 (m, 1H), 1.89-1.78 (m, 1H), 1.69 (br, 2H), 1.64-1.49 (m, 1H). LCMS (ES+) m/z 469 (M+1)

Example 451

5-amino-N-[5-[(4R,5R)-4-amino-5-fluoro-azepan-1-yl]-1-(trideuteriomethyl)pyrazol-4-yl]-2-(2,6-difluorophenyl)thiazole-4-carboxamide 451

Following the procedures in Example 150, 5-chloro-1-trideuteriomethyl-4-nitro-1H-pyrazole was converted to 451. ¹H NMR (400 MHz, DMSO) δ 8.83 (s, 1H), 7.60-7.40 (m, 4H), 7.26 (t, J=8.7 Hz, 2H), 4.41 (dtd, J=48.0, 8.2, 3.6 Hz, 1H), 3.24-3.02 (m, 5H), 2.19-2.03 (m, 1H), 2.03-1.88 (m, 1H), 1.88-1.77 (m, 1H), 1.69 (br, 2H), 1.66-1.52 (m, 1H). LCMS (ES+) m/z 469 (M+1)

Example 452

5-amino-N-[5-(6-amino-1-oxa-9-azaspiro[3.6]decan-9-yl)-1-methyl-pyrazol-4-yl]-2-(2,6-difluorophenyl) thiazole-4-carboxamide 452

Following the procedures in Example 448, the first eluting peak tert-butyl N-[(4R)-1-(2-methyl-4-nitro-pyrazol-3-yl)-6-oxo-azepan-4-yl]carbamate was converted to 452. LCMS (ES+) m/z 490 (M+1)

Example 453

5-amino-N-[5-(5-amino-3-methyl-azepan-1-yl)-1-methyl-pyrazol-4-yl]-2-(2,6-difluorophenyl)thiazole-4-carboxamide 453

In the preparation of 448, tert-butyl N-[(4R)-6-methylene-1-(2-methyl-4-nitro-pyrazol-3-yl)azepan-4-yl]carbamate was converted to 453. ¹H NMR (400 MHz, DMSO) δ 8.65 (s, 1H), 8.41 (s, 1H), 7.61-7.43 (m, 4H), 7.28 (td, J=8.8, 2.0 Hz, 2H), 3.66 (d, J=3.0 Hz, 4H), 3.33-3.01 (m, 3H), 2.96-2.77 (m, 2H), 2.19-1.58 (m, 4H), 1.49 (dd, J=24.1, 11.2 Hz, 1H), 0.86 (dd, J=15.5, 6.8 Hz, 3H). LCMS (ES+) m/z 462 (M+1)

Example 454

5-amino-N-[5-[(5S)-5-amino-3,3-difluoro-azepan-1-yl]-1-methyl-pyrazol-4-yl]-2-(3,5-difluoro-4-pyridyl) thiazole-4-carboxamide 454

Chiral separation of racemic 438 by SFC gave single enantiomer 454. ¹H NMR (400 MHz, DMSO) δ 8.81 (s, 1H), 8.66 (d, J=1.1 Hz, 2H), 7.76 (s, 2H), 7.60 (s, 1H), 3.76-3.59 (m, 4H), 3.49-3.34 (m, 1H), 3.28-3.02 (m, 3H), 2.37-2.09 (m, 2H), 1.92-1.61 (m, 2H). LCMS (ES+) m/z 485 (M+1)

Example 455

5-amino-N-[5-[(5R)-5-amino-3,3-difluoro-azepan-1-yl]-1-methyl-pyrazol-4-yl]-2-(3,5-difluoro-4-pyridyl)thiazole-4-carboxamide 455

Chiral separation of racemic 438 by SFC gave single enantiomer 455. $^1$H NMR (400 MHz, DMSO) δ 8.79 (s, 1H), 8.66 (s, 2H), 8.28 (s, 1H), 7.76 (s, 2H), 7.58 (s, 1H), 3.78-3.60 (m, 4H), 3.51-3.23 (m, 3H), 3.18-3.05 (m, 1H), 2.42-2.15 (m, 2H), 1.99-1.73 (m, 2H). LCMS (ES+) m/z 485 (M+1)

Example 456

5-amino-N-[5-(5-amino-3-hydroxy-3-methyl-cycloheptyl)-1-methyl-pyrazol-4-yl]-2-(2,6-difluorophenyl)thiazole-4-carboxamide 456

A solution of (E)-tert-butyl 3-hydroxy-5-(1-methyl-4-nitro-1H-pyrazol-5-yl)cyclohept-4-enylcarbamate (620 mg, 1.76 mmol) in MeOH (40 mL) was passed through the H-Cube® (full $H_2$, 70° C., flow rate: 1 mL/min, 30 mm 10% Pd/C cartridge). The solvent was removed under reduced pressure to afford tert-butyl 5-(4-amino-1-methyl-1H-pyrazol-5-yl)-3-hydroxycycloheptylcarbamate as a yellow oil. To a solution of this amine in DCM (50 mL) was added DIPEA (0.92 mL, 5.28 mmol), PyBOP (1.37 g, 2.64 mmol) and 5-(tert-butoxycarbonylamino)-2-(2,6-difluorophenyl)thiazole-4-carboxylic acid (690 mg, 1.94 mmol) and the mixture was stirred at room temperature for 18 hr. The mixture was diluted with DCM (100 mL) and washed with water (50 mL). The organic layer was separated, dried over $MgSO_4$ and the solvent removed under reduced pressure. Purification via silica gel column chromatography (75% EtOAc/isohexane) gave tert-butyl (5-(4-(5-tert-butoxycarbonylamino-2-(2,6-difluorophenyl)thiazole-4-carboxamido)-1-methyl-1H-pyrazol-5-yl)-3-hydroxycycloheptylcarbamate as a yellow foam (890 mg). This foam (890 mg, 1.34 mmol) was dissolved in DCM (50 mL) and Dess-Martin periodinane (684 mg, 1.61 mmol) was added, the mixture was stirred at room temperature for 1.5 hr. The mixture was quenched with a 1/1 aqueous solution of 20% sodium thiosulfate/saturated aqueous $NaHCO_3$ (100 mL), layers extracted, dried over $MgSO_4$ and the solvent removed under reduced pressure. Purification via silica gel column chromatography (0-100% EtOAc/isohexane) gave a light yellow solid (500 mg). A portion of this solid (356 mg, 0.54 mmol) was dissolved in dry THF (5 mL) and cooled at 0° C. before a solution of methylmagnesium bromide (3 M in $Et_2O$, 0.72 mL, 2.15 mmol) was added dropwise. The mixture was stirred at 0° C. for 3 hr, before an additional amount of methylmagnesium bromide (3 M in $Et_2O$, 0.3 mL, 0.9 mmol) was added. The mixture was stirred for a further 6 hr, quenched with a saturated solution of ammonium chloride (30 mL), extracted with EtOAc (50 mL) and washed with water. The combined organic layers were dried over $MgSO_4$ and the solvent removed under reduced pressure. Purification via silica gel column chromatography (0-100% EtOAc/isohexane) gave a light yellow oil. The four diastereomers obtained were separated by preparative HPLC to give Diastereomer 1 as a white solid (22 mg, 2% over five steps). This solid (22 mg, 0.03 mmol) was dissolved in HCl in dioxane (4 M, 1 mL, 4.0 mmol) and MeOH (1 mL) and was stirred at room temperature for 5 hr. The solvents were removed under reduced pressure and the crude residue was purified by preparative HPLC to give 456 as an orange solid (15 mg, 96%). $^1$H NMR (400 MHz, $d_6$-DMSO) δ 8.79 (s, 1H), 8.45 (s, 2H), 7.59-7.50 (m, 2H), 7.33-7.25 (m, 2H), 3.78 (s, 3H), 3.58-3.05 (m, 1H), 3.17 (s, 1H), 2.85-2.77 (m, 1H), 2.08-1.92 (m, 4H), 1.88-1.78 (m, 5H), 1.55-1.44 (m, 1H), 1.17 (s, 3H). LCMS (ES+) m/z 477 (M+1)

Example 457

5-amino-2-(2,6-difluorophenyl)-N-(5-((4R,5S)-4,5-dihydroxyazepan-1-yl)-1-methyl-1H-pyrazol-4-yl)thiazole-4-carboxamide 457

To a solution of (Z)-tert-butyl 2-(2,6-difluorophenyl)-4-(1-methyl-5-(2,3,6,7-tetrahydro-1H-azepin-1-yl)-1H-pyrazol-4-ylcarbamoyl)thiazol-5-ylcarbamate (1.28 g, 2.41 mmol) in tert-butanol (35 mL) was added a solution of N-methylmorpholine-N-oxide (0.80 g, 6.80 mmol) in water (35 mL), followed by a solution of osmium tetroxide 2.5% weight in tert-butanol, 2.5 mL). The reaction mixture was stirred at room temperature for 72 hr before diluted with DCM (100 mL) and quenched with a saturated solution of sodium dithionite (50 mL), the organic layer passed through a phase separation cartridge and concentrated under reduced pressure. Purification via silica gel column chromatography (0-10% MeOH/DCM) gave tert-butyl 2-(2,6-difluorophenyl)-4-(5-(4,5-syn-dihydroxyazepan-1-yl)-1-methyl-1H-pyrazol-4-ylcarbamoyl)thiazol-5-ylcarbamate as a brown gum (0.12 g). This gum (0.12 g, 0.21 mmol) was dissolved in HCl in dioxane (4 M, 10 mL, 40.0 mmol) and MeOH (2 mL) and was stirred at room temperature for 20 hr. The solvents were removed under reduced pressure and the crude residue was purified by preparative HPLC to give 457 as a white solid (36 mg, 3% over two steps). $^1$H NMR (400 MHz, $d_6$-DMSO) δ 8.74 (s, 1H), 7.60-7.50 (m, 4H), 7.34-7.26 (m, 2H), 4.41 (d, J=4.1 Hz, 2H), 3.91 (t, J=4.7 Hz, 2H), 3.67 (s, 3H), 2.96 (ddd, J=12.8, 7.7, 4.4 Hz, 2H), 2.55-2.52 (m, 2H), 2.02-1.92 (m, 2H), 1.72-1.64 (m, 2H). LCMS (ES+) m/z 465 (M+1)

Example 458

5-amino-N-[5-[4-(aminomethyl)-4-methoxy-1-piperidyl]-1-methyl-pyrazol-4-yl]-2-(2,6-difluorophenyl)thiazole-4-carboxamide 458

Following the procedure for Example 101 starting from tert-butyl (4-methoxy-1-(1-methyl-4-nitro-1H-pyrazol-5-yl)piperidin-4-yl)methylcarbamate and 5-(tert-butoxycarbonylamino)-2-(2,6-difluorophenyl)-thiazole-4-carboxylic acid gave 458 as an off-white solid (30 mg, 7% over three steps). $^1$H NMR (400 MHz, $d_4$-MeOD) δ 8.56 (s, 1H), 7.56-7.42 (m, 2H), 7.15 (t, J=8.7 Hz, 2H), 3.74 (s, 3H), 3.42-3.33 (m, 4H), 3.23 (s, 2H), 3.12-2.95 (m, 3H), 1.97 (d, J=13.6 Hz, 2H), 1.76-1.66 (m, 2H). LCMS (ES+) m/z 478 (M+1)

Example 459

5-amino-N-[5-(5-amino-3,3-difluoro-azepan-1-yl)-1-methyl-pyrazol-4-yl]-2-(2,6-difluoro-4-methoxy-phenyl)thiazole-4-carboxamide 459

To a solution of tert-butyl 1-(4-(5-(tert-butoxycabonylamino)-2-bromothiazole-4-carboxamido)-1-methyl-1H-pyrazol-5-yl)-6,6-difluoroazepan-4-ylcarbamate (200 mg, 0.31 mmol) in dimethyl ether (3 mL) was added 2,6-difluoro-4-methoxyphenylboronic acid (101 mg, 0.54 mmol), [1,1'-bis(diphenylphosphino)ferrocene]dichloropalladium(II), complex with dichloromethane (50 mg, 0.06 mmol), sodium carbonate (67 mg, 0.63 mmol) and water (1 mL). The mixture was degassed for 5 minutes before being heated in a microwave at 120° C. for 2.5 hour. The mixture was concentrated under reduced pressure and the residue purified via silica gel column chromatography (0-100% EtOAc/isohexane) to give a brown oil. To a solution of this oil in MeOH (10 mL) was added HCl in dioxane (4 M, 10 mL, 40.0 mmol) and the mixture was heated at 40° C. for 3 hr. Purification via preparative HPLC gave 459 as a white solid (10 mg, 6% over two steps). $^1$H NMR (400 MHz, d$_6$-DMSO) δ 8.82 (s, 1H), 7.54 (s, 1H), 7.43 (s, 2H), 6.99-6.88 (m, 2H), 3.85 (s, 3H), 3.79-3.50 (m, 4H), 3.47-3.33 (m, 1H), 3.29-3.16 (m, 2H), 3.15-3.05 (m, 1H), 2.29-2.09 (m, 2H), 1.90-1.78 (m, 1H), 1.77-1.65 (m, 1H), 1.62 (s, 2H). LCMS (ES+) m/z 514 (M+1)

Example 460

5-amino-N-[5-(5-amino-3,3-difluoro-azepan-1-yl)-1-methyl-pyrazol-4-yl]-2-(1,5-dimethylpyrazol-4-yl)thiazole-4-carboxamide 460

Following the procedure in Example 459, starting from tert-butyl 1-(4-(5-(tert-butoxycarbonyl-amino)-2-bromothiazole-4-carboxamido)-1-methyl-1H-pyrazol-5-yl)-6,6-difluoroazepan-4-ylcarbamate gave 460 as a red solid (13 mg, 8% over two steps). $^1$H NMR (400 MHz, d$_6$-DMSO) δ 8.63 (s, 1H), 7.74-7.65 (m, 1H), 7.59-7.52 (m, 1H), 7.25 (s, 2H), 3.79 (s, 3H), 3.82-3.55 (m, 4H), 3.48-3.34 (m, 1H), 3.29-3.05 (m, 3H), 2.57 (s, 3H), 2.28-2.05 (m, 2H), 1.92-1.80 (m, 1H), 1.84-1.56 (m, 3H). LCMS (ES+) m/z 466 (M+1)

Example 461

5-amino-N-[5-[(5R)-5-amino-3,3-difluoro-azepan-1-yl]-1-methyl-pyrazol-4-yl]-2-(6-cyano-2-pyridyl)thiazole-4-carboxamide 461

Step A: Following the procedures in Example 166, (R)-tert-butyl (6,6-difluoro-1-(1-methyl-4-nitro-1H-pyrazol-5-yl)azepan-4-yl)carbamate was converted to tert-butyl N-[2-bromo-4-[[5-[(5R)-5-(tert-butoxycarbonylamino)-3,3-difluoro-azepan-1-yl]-1-methyl-pyrazol-4-yl]carbamoyl]thiazol-5-yl]carbamate.

Step B: Following the procedures in Example 428, tert-butyl N-[2-bromo-4-[[5-[(5R)-5-(tert-butoxycarbonylamino)-3,3-difluoro-azepan-1-yl]-1-methyl-pyrazol-4-yl]carbamoyl]thiazol-5-yl]carbamate was reacted with 6-(4,4,5,5-tetramethyl-1,3,2-dioxaborolan-2-yl)pyridine-2-carbonitrile to give 461. LCMS (ES+) m/z 474 (M+1)

Example 462

5-amino-N-[5-[(5R)-5-amino-3,3-difluoro-azepan-1-yl]-1-methyl-pyrazol-4-yl]-2-(1,3-dimethylpyrazol-4-yl)thiazole-4-carboxamide 462

Following the procedures in Example 461, 462 was prepared. $^1$H NMR (400 MHz, DMSO) δ 8.57 (s, 1H), 8.07 (s, 1H), 7.57 (s, 1H), 7.22 (s, 2H), 3.79 (s, 3H), 3.74-3.57 (m, 4H), 3.49-3.34 (m, 1H), 3.26-3.04 (m, 3H), 2.43 (d, J=9.1 Hz, 3H), 2.31-2.04 (m, 2H), 1.86 (d, J=14.1 Hz, 1H), 1.82-1.59 (m, 3H). LCMS (ES+) m/z 466 (M+1)

Example 463

5-amino-N-[5-[(5R)-5-amino-3,3-difluoro-azepan-1-yl]-1-methyl-pyrazol-4-yl]-2-(1,5-dimethylpyrazol-4-yl)thiazole-4-carboxamide 463

Following the procedures in Example 461, 463 was prepared. $^1$H NMR (400 MHz, DMSO) δ 8.62 (s, 1H), 8.28 (s, 1H), 7.68 (s, 1H), 7.53 (s, 1H), 7.23 (s, 2H), 3.78 (s, 3H), 3.75-3.58 (m, 4H), 3.52-3.35 (m, 1H), 3.35-3.23 (m, 2H), 3.21-3.06 (m, 1H), 2.56 (s, 3H), 2.37-2.18 (m, 2H), 1.92 (d, J=13.3 Hz, 1H), 1.80 (dd, J=14.9, 9.7 Hz, 1H). LCMS (ES+) m/z 466 (M+1)

Example 464

5-amino-N-[5-[(5R)-5-amino-3,3-difluoro-azepan-1-yl]-1-methyl-pyrazol-4-yl]-2-(2-methyl-4-pyridyl)thiazole-4-carboxamide 464

Following the procedures in Example 461, 464 was prepared. $^1$H NMR (400 MHz, DMSO) δ 8.99 (s, 1H), 8.50 (d, J=5.2 Hz, 1H), 8.27 (s, 1H), 7.64 (d, J=5.6 Hz, 3H), 7.57 (d, J=5.2 Hz, 1H), 7.47 (s, 1H), 3.75-3.60 (m, 4H), 3.54-3.37 (m, 1H), 3.37-3.22 (m, 2H), 3.22-3.05 (m, 1H), 2.53 (s, 3H), 2.41-2.22 (m, 2H), 1.99-1.87 (m, 1H), 1.87-1.70 (m, 1H). LCMS (ES+) m/z 463 (M+1)

Example 465

5-amino-N-[5-(5-amino-3-hydroxy-3-methyl-cycloheptyl)-1-methyl-pyrazol-4-yl]-2-(2,6-difluorophenyl)thiazole-4-carboxamide 465

Chiral separation of the racemic mixture tert-butyl N-[5-[4-[[5-(tert-butoxycarbonylamino)-2-(2,6-difluorophenyl)thiazole-4-carbonyl]amino]-2-methyl-pyrazol-3-yl]-3-hydroxy-3-methyl-cycloheptyl]carbamate by SFC followed by deprotection with 4N HCl in dioxane gave 465 as a single enantiomer. $^1$H NMR (400 MHz, DMSO) δ 8.66 (s, 1H), 8.44 (s, 1H), 7.56 (s, 1H), 7.53 (t, J=8.4 Hz, 1H), 7.47 (s, 2H), 7.27 (t, J=8.8 Hz, 2H), 3.77 (s, 3H), 3.53-3.10 (m, 2H), 2.11-1.99 (m, 1H), 1.99-1.78 (m, 4H), 1.72-1.53 (m, 3H), 1.15 (s, 3H). LCMS (ES+) m/z 477 (M+1)

Example 466

5-amino-N-[5-(5-amino-3-hydroxy-3-methyl-cycloheptyl)-1-methyl-pyrazol-4-yl]-2-(2,6-difluorophenyl)thiazole-4-carboxamide 466

Chiral separation of the racemic mixture tert-butyl N-[5-[4-[[5-(tert-butoxycarbonylamino)-2-(2,6-difluorophenyl)thiazole-4-carbonyl]amino]-2-methyl-pyrazol-3-yl]-3-hydroxy-3-methyl-cycloheptyl]carbamate by SFC followed by deprotection with 4N HCl in dioxane gave 466 as a single enantiomer. LCMS (ES+) m/z 477 (M+1)

Example 467

5-amino-N-[5-(5-amino-3-hydroxy-3-methyl-cycloheptyl)-1-methyl-pyrazol-4-yl]-2-(2,6-difluorophenyl)thiazole-4-carboxamide 467

Chiral separation of the racemic mixture tert-butyl N-[5-[4-[[5-(tert-butoxycarbonylamino)-2-(2,6-difluorophenyl)thiazole-4-carbonyl]amino]-2-methyl-pyrazol-3-yl]-3-hydroxy-3-methyl-cycloheptyl]carbamate by SFC followed by deprotection with 4N HCl in dioxane gave 467 as a single enantiomer. LCMS (ES+) m/z 477 (M+1)

Example 468

5-amino-N-[5-(5-amino-3-hydroxy-3-methyl-cycloheptyl)-1-methyl-pyrazol-4-yl]-2-(2,6-difluorophenyl)thiazole-4-carboxamide 468

Chiral separation of the racemic mixture tert-butyl N-[5-[4-[[5-(tert-butoxycarbonylamino)-2-(2,6-difluorophenyl)thiazole-4-carbonyl]amino]-2-methyl-pyrazol-3-yl]-3-hydroxy-3-methyl-cycloheptyl]carbamate by SFC followed by deprotection with 4N HCl in dioxane gave 468 as a single enantiomer. $^1$H NMR (400 MHz, DMSO) δ 8.70 (s, 1H), 7.85 (s, 2H), 7.60-7.49 (m, 1H), 7.46 (s, 1H), 7.28 (t, J=8.7 Hz, 2H), 3.78 (s, 3H), 3.72-3.42 (m, 1H), 2.99-2.84 (m, 1H), 2.10-1.94 (m, 3H), 1.94-1.74 (m, 4H), 1.65 (d, J=13.6 Hz, 1H), 1.26 (s, 3H). LCMS (ES+) m/z 477 (M+1)

Example 469

5-amino-N-[5-(5-amino-3-hydroxy-3-methyl-cycloheptyl)-1-methyl-pyrazol-4-yl]-2-(2,6-difluorophenyl)thiazole-4-carboxamide 469

Chiral separation of the racemic mixture tert-butyl N-[5-[4-[[5-(tert-butoxycarbonylamino)-2-(2,6-difluorophenyl)thiazole-4-carbonyl]amino]-2-methyl-pyrazol-3-yl]-3-hydroxy-3-methyl-cycloheptyl]carbamate by SFC followed by deprotection with 4N HCl in dioxane gave 469 as a single enantiomer. $^1$H NMR (400 MHz, DMSO) δ 8.70 (s, 1H), 7.85 (s, 2H), 7.60-7.50 (m, 1H), 7.46 (s, 1H), 7.28 (t, J=8.7 Hz, 2H), 3.79 (s, 3H), 3.74-3.43 (m, 1H), 2.99-2.84 (m, 1H), 2.12-1.95 (m, 3H), 1.95-1.71 (m, 4H), 1.65 (d, J=13.5 Hz, 1H), 1.26 (s, 3H). LCMS (ES+) m/z 477 (M+1)

Example 470

5-amino-N-[5-(5-amino-3-hydroxy-3-methyl-cycloheptyl)-1-methyl-pyrazol-4-yl]-2-(2,6-difluorophenyl)thiazole-4-carboxamide 470

Chiral separation of the racemic mixture tert-butyl N-[5-[4-[[5-(tert-butoxycarbonylamino)-2-(2,6-difluorophenyl)thiazole-4-carbonyl]amino]-2-methyl-pyrazol-3-yl]-3-hydroxy-3-methyl-cycloheptyl]carbamate by SFC followed by deprotection with 4N HCl in dioxane gave 470 as a single enantiomer. $^1$H NMR (400 MHz, DMSO) δ 8.66 (s, 1H), 8.43 (s, 1H), 7.56 (s, 1H), 7.53 (dd, J=11.6, 5.2 Hz, 1H), 7.48 (s, 2H), 7.27 (t, J=8.8 Hz, 2H), 3.76 (s, 3H), 3.51-3.29 (m, 2H), 2.13-2.00 (m, 1H), 2.00-1.79 (m, 4H), 1.72-1.54 (m, 3H), 1.16 (s, 3H). LCMS (ES+) m/z 477 (M+1)

Example 471

5-amino-N-[5-[(4S,5S)-4-amino-5-fluoro-azepan-1-yl]-1-methyl-pyrazol-4-yl]-2-(3,5-difluoro-4-pyridyl)thiazole-4-carboxamide 471

Chiral separation of racemic 439 by SFC gave single enantiomer 471. $^1$H NMR (400 MHz, DMSO) δ 8.81 (s, 1H), 8.64 (d, J=0.9 Hz, 2H), 7.73 (s, 2H), 7.58 (s, 1H), 4.57-4.34 (m, 1H), 3.65 (s, 3H), 3.26-3.04 (m, 5H), 2.20-1.78 (m, 5H), 1.71-1.51 (m, 1H). LCMS (ES+) m/z 467 (M+1)

Example 472

5-amino-N-[5-[(4S,5S)-4-amino-5-fluoro-azepan-1-yl]-1-methyl-pyrazol-4-yl]-2-(3,5-difluoro-4-pyridyl)thiazole-4-carboxamide 472

Chiral separation of racemic 439 by SFC gave single enantiomer 472. $^1$H NMR (400 MHz, DMSO) δ 8.82 (s, 1H), 8.64 (d, J=1.1 Hz, 2H), 7.73 (s, 2H), 7.58 (s, 1H), 4.44 (dtd, J=47.9, 8.2, 3.6 Hz, 1H), 3.65 (s, 3H), 3.24-3.04 (m, 5H), 2.23-1.71 (m, 5H), 1.68-1.51 (m, 1H). LCMS (ES+) m/z 467 (M+1)

Example 473

5-amino-N-[5-(5-amino-3-methoxy-3-methyl-azepan-1-yl)-1-methyl-pyrazol-4-yl]-2-(3,5-difluoro-4-pyridyl)thiazole-4-carboxamide 473

Chiral separation of racemic 440 by SFC gave single enantiomer 473. $^1$H NMR (400 MHz, DMSO) δ 8.85 (s, 1H), 8.67 (s, 2H), 7.76 (s, 2H), 7.70 (s, 1H), 3.66 (s, 3H), 3.31-3.23 (m, 2H), 3.24-3.13 (m, 1H), 3.12-2.92 (m, 5H), 2.00 (d, J=14.1 Hz, 1H), 1.88-1.75 (m, 1H), 1.70-1.55 (m, 1H), 1.42 (dd, J=14.3, 10.6 Hz, 1H), 0.99 (s, 3H). LCMS (ES+) m/z 493 (M+1)

Example 474

5-amino-N-[5-(5-amino-3-methoxy-3-methyl-azepan-1-yl)-1-methyl-pyrazol-4-yl]-2-(3,5-difluoro-4-pyridyl)thiazole-4-carboxamide 474

Chiral separation of racemic 440 by SFC gave single enantiomer 474. $^1$H NMR (400 MHz, DMSO) δ 8.85 (s, 1H), 8.67 (s, 2H), 7.76 (s, 2H), 7.70 (s, 1H), 3.66 (s, 3H), 3.29-3.11 (m, 3H), 3.12-2.89 (m, 5H), 2.00 (d, J=14.1 Hz, 1H), 1.89-1.76 (m, 1H), 1.67-1.55 (m, 1H), 1.41 (dd, J=14.4, 10.5 Hz, 1H), 0.99 (s, 3H). LCMS (ES+) m/z 493 (M+1)

Example 475

5-amino-N-[5-(5-amino-3-methoxy-3-methyl-azepan-1-yl)-1-methyl-pyrazol-4-yl]-2-(3-fluoro-4-pyridyl)thiazole-4-carboxamide 475

Chiral separation of racemic 441 by SFC gave single enantiomer 475. $^1$H NMR (400 MHz, DMSO) δ 9.20 (s, 1H), 8.69 (d, J=2.8 Hz, 1H), 8.57 (d, J=5.0 Hz, 1H), 8.31-8.16 (m, 1H), 7.69 (s, 2H), 7.68 (s, 1H), 3.67 (s, 3H), 3.46 (t, J=10.2 Hz, 1H), 3.36-3.18 (m, 2H), 3.09-2.91 (m, 5H), 2.09 (d, J=14.0 Hz, 1H), 1.94-1.81 (m, 1H), 1.77-1.59 (m, 1H), 1.50 (dd, J=14.2, 10.7 Hz, 1H), 1.02 (s, 3H). LCMS (ES+) m/z 475 (M+1)

Example 476

5-amino-N-[5-(5-amino-3-methoxy-3-methyl-azepan-1-yl)-1-methyl-pyrazol-4-yl]-2-(3-fluoro-4-pyridyl)thiazole-4-carboxamide 476

Chiral separation of racemic 441 by SFC gave single enantiomer 476. $^1$H NMR (400 MHz, DMSO) δ 9.20 (s, 1H), 8.69 (d, J=2.8 Hz, 1H), 8.57 (d, J=5.1 Hz, 1H), 8.29-8.21 (m, 1H), 7.69 (s, 2H), 7.68 (s, 1H), 3.67 (s, 3H), 3.46 (t, J=10.3 Hz, 1H), 3.38-3.21 (m, 2H), 3.09-2.94 (m, 5H), 2.09 (d, J=14.2

Hz, 1H), 1.95-1.82 (m, 1H), 1.75-1.63 (m, 1H), 1.50 (dd, J=14.2, 10.7 Hz, 1H), 1.02 (s, 3H). LCMS (ES+) m/z 475 (M+1)

Example 477

5-amino-2-(2-fluorophenyl)-N-[1-methyl-5-(1-oxa-6, 9-diazaspiro[3.6]decan-6-yl)pyrazol-4-yl]thiazole-4-carboxamide 477

Following the procedures in Example 448, tert-butyl 4-(2-methyl-4-nitro-pyrazol-3-yl)-6-oxo-1,4-diazepane-1-carboxylate was converted to racemic 477. ¹H NMR (400 MHz, DMSO) δ 9.46 (s, 1H), 8.35 (t, J=6.9 Hz, 1H), 7.63 (s, 1H), 7.51-7.27 (m, 5H), 4.28 (dt, J=15.1, 6.3 Hz, 2H), 3.67 (s, 3H), 3.45 (q, J=14.5 Hz, 2H), 3.23-3.02 (m, 4H), 2.88-2.74 (m, 2H), 2.42-2.29 (m, 1H), 2.29-2.14 (m, 1H). LCMS (ES+) m/z 458 (M+1).

Example 478

5-amino-2-(2,6-difluorophenyl)-N-[1-methyl-5-(1-oxa-6,9-diazaspiro[3.6]decan-6-yl)pyrazol-4-yl]thiazole-4-carboxamide 478

Following the procedures in Example 448, tert-butyl 4-(2-methyl-4-nitro-pyrazol-3-yl)-6-oxo-1,4-diazepane-1-carboxylate was converted to racemic 478. ¹H NMR (400 MHz, DMSO) δ 9.73 (s, 1H), 7.67 (s, 1H), 7.61-7.41 (m, 3H), 7.29 (t, J=8.7 Hz, 2H), 4.30-4.15 (m, 2H), 3.66 (s, 3H), 3.48-3.33 (m, 2H), 3.21-2.98 (m, 4H), 2.81 (t, J=5.8 Hz, 2H), 2.38-2.25 (m, 1H), 2.25-2.09 (m, 1H). LCMS (ES+) m/z 458 (M+1).

Example 479

5-amino-N-[5-[4-(aminomethyl)-4-hydroxy-1-piperidyl]-1-methyl-pyrazol-4-yl]-2-(2,6-difluorophenyl)thiazole-4-carboxamide 479

Following the procedure for Example 101 starting from tert-butyl N-[[4-hydroxy-1-(2-methyl-4-nitro-pyrazol-3-yl)-4-piperidyl]methyl]carbamate gave 479 as a cream solid (37 mg, 35% over three steps). ¹H NMR (400 MHz, d₄-MeOD) δ 8.55 (s, 1H), 7.52-7.43 (m, 2H), 7.20-7.10 (m, 2H), 3.74 (s, 3H), 3.49-3.38 (m, 2H), 3.09-3.03 (m, 2H), 2.92 (s, 2H), 1.85-1.73 (m, 4H). LCMS (ES+) m/z 464 (M+1)

Example 480

(R)-5-amino-2-(2-fluorophenyl)-N-[1-methyl-5-(1-oxa-6,9-diazaspiro[3.6]decan-6-yl)pyrazol-4-yl]thiazole-4-carboxamide 480

Chiral separation of the racemic 5-amino-2-(2-fluorophenyl)-N-[1-methyl-5-(1-oxa-6,9-diazaspiro[3.6]decan-6-yl)pyrazol-4-yl]thiazole-4-carboxamide 477 by SFC gave 480 (first eluting peak). ¹H NMR (400 MHz, DMSO) δ 9.46 (s, 1H), 8.41-8.32 (m, 1H), 7.63 (s, 1H), 7.51-7.30 (m, 5H), 4.36-4.19 (m, 2H), 3.67 (s, 3H), 3.45 (q, J=14.5 Hz, 2H), 3.26-3.04 (m, 4H), 2.88-2.71 (m, 2H), 2.42-2.29 (m, 1H), 2.29-2.16 (m, 1H). LCMS (ES+) m/z 458 (M+1).

Example 481

(S)-5-amino-2-(2-fluorophenyl)-N-[1-methyl-5-(1-oxa-6,9-diazaspiro[3.6]decan-6-yl)pyrazol-4-yl]thiazole-4-carboxamide 481

Chiral separation of the racemic mixture of 5-amino-2-(2-fluorophenyl)-N-[1-methyl-5-(1-oxa-6,9-diazaspiro[3.6]decan-6-yl)pyrazol-4-yl]thiazole-4-carboxamide 477 by SFC gave 481 (second eluting peak). ¹H NMR (400 MHz, DMSO) δ 9.46 (s, 1H), 8.36 (dd, J=11.1, 4.8 Hz, 1H), 7.63 (s, 1H), 7.52-7.31 (m, 5H), 4.36-4.21 (m, 2H), 3.67 (s, 3H), 3.45 (q, J=14.5 Hz, 2H), 3.21-3.05 (m, 4H), 2.91-2.72 (m, 2H), 2.41-2.31 (m, 1H), 2.26-2.14 (m, 1H). LCMS (ES+) m/z 458 (M+1)

Example 482

(R)-5-amino-2-(2,6-difluorophenyl)-N-(1-methyl-5-(1-oxa-6,9-diazaspiro[3.6]decan-6-yl)-1H-pyrazol-4-yl)thiazole-4-carboxamide 482

Chiral separation of the racemic mixture of 478 by SFC gave 482 (first eluting peak). ¹H NMR (400 MHz, DMSO) δ 9.71 (s, 1H), 7.67 (s, 1H), 7.60-7.44 (m, 3H), 7.28 (dd, J=14.5, 5.9 Hz, 2H), 4.30-4.16 (m, 2H), 3.66 (s, 3H), 3.40 (q, J=14.7 Hz, 2H), 3.19-3.00 (m, 4H), 2.82 (t, J=5.8 Hz, 2H), 2.38-2.26 (m, 1H), 2.23-2.13 (m, 1H). LCMS (ES+) m/z 458 (M+1).

Example 483

(S)-5-amino-2-(2,6-difluorophenyl)-N-(1-methyl-5-(1-oxa-6,9-diazaspiro[3.6]decan-6-yl)-1H-pyrazol-4-yl)thiazole-4-carboxamide 483

Chiral separation of the racemic mixture of 478 by SFC gave 483 (second eluting peak). ¹H NMR (400 MHz, DMSO) δ 9.71 (s, 1H), 8.22 (s, 1H), 7.66 (s, 1H), 7.62-7.44 (m, 3H), 7.29 (t, J=8.7 Hz, 2H), 4.30-4.17 (m, 2H), 3.66 (s, 3H), 3.48-3.31 (m, 2H), 3.20-2.99 (m, 4H), 2.82 (t, J=5.7 Hz, 2H), 2.38-2.25 (m, 1H), 2.25-2.12 (m, 1H). LCMS (ES+) m/z 458 (M+1).

Example 484

5-amino-2-(2,6-difluorophenyl)-N-[1-methyl-5-(1-oxa-4,9-diazaspiro[5.5]undecan-9-yl)pyrazol-4-yl]thiazole-4-carboxamide 484

Following the procedure for Example 121 starting from tert-butyl 3-(2-methyl-4-nitro-pyrazol-3-yl)-11-oxa-3,8-diazaspiro[5.5]undecane-8-carboxylate gave 484 as an off-white solid (15 mg, 30% over three steps). ¹H NMR (400 MHz, CDCl₃) δ 8.56 (s, 1H), 7.80 (s, 1H), 7.39-7.16 (m, 1H), 7.06-6.96 (m, 2H), 6.12 (s, 2H), 3.75 (s, 3H), 3.69 (t, J=4.8 Hz, 2H), 3.40-3.30 (m, 2H), 2.99-2.92 (m, 2H), 2.88-2.83 (m, 2H), 2.79 (s, 2H), 2.11-2.00 (m, 2H), 1.74-1.63 (m, 2H). Alkyl NH not observed. LCMS (ES+) m/z 490 (M+1)

Example 485

5-amino-N-[5-(5-amino-4-methoxy-4-methyl-azepan-1-yl)-1-methyl-pyrazol-4-yl]-2-(2,6-difluorophenyl)thiazole-4-carboxamide 485

To a solution of tert-butyl N-(1-(4-((5-(tert-butoxycarbonylamino)-2-(2,6-difluorophenyl)thiazole-4-carbonyl)amino)-2-methyl-pyrazol-3-yl)-5-methoxy-5-methyl-azepan-4-yl]carbamate (0.12 g, 0.17 mmol) in MeOH (10 mL) was added HCl in dioxane (4 M, 10 mL, 0.04 mol). The reaction mixture was stirred at room temperature for 16 hr and concentrated under reduced pressure. Purification via preparative HPLC gave 485 as a pale yellow solid (64 mg, 74%). ¹H NMR (400 MHz, d₆-DMSO) δ 9.63 (s, 1H), 7.69 (s, 1H), 7.59-7.48 (m, 3H), 7.31-7.22 (m, 2H), 3.61 (s, 3H), 3.31-3.25

(m, 1H), 3.14-3.03 (m, 2H), 3.03 (s, 3H), 2.99-2.89 (m, 1H), 2.11-2.02 (m, 1H), 1.92-1.82 (m, 1H), 1.79-1.59 (m, 4H), 1.47 (dd, J=14.5, 6.2 Hz, 1H), 1.19 (s, 3H). LCMS (ES+) m/z 492 (M+1)

Example 486

N-[5-[(3aR,8aS)-2-oxo-3a,4,5,7,8,8a-hexahydro-3H-oxazolo[4,5-d]azepin-6-yl]-1-methyl-pyrazol-4-yl]-5-amino-2-(2,6-difluorophenyl)thiazole-4-carboxamide 486

To a stirred solution of tert-butyl N-((4R,5S)-1-(4-((5-(tert-butoxycarbonylamino)-2-(2,6-difluorophenyl)thiazole-4-carbonyl)amino)-2-methyl-pyrazol-3-yl)-5-hydroxy-azepan-4-yl)carbamate (199 mg, 0.30 mmol) in DMF (2 mL) at 0° C. was added sodium hydride (60% dispersion in oil, 26 mg, 0.66 mmol). The mixture was allowed to warm to room temperature over 2 hr, quenched with water (3 mL) and the resulting precipitate filtered off and dried under reduced pressure. The aqueous layer was extracted with EtOAc (3×3 mL) and the combined organic layers were passed through a phase separation cartridge, concentrated under reduced pressure and the residue combined with the precipitate collected earlier. A solution of this material (159 mg, 0.27 mmol) in HCl in dioxane (4 M, 10 mL) and MeOH (5 mL) was stirred at room temperature for 16 hr. The solvents were removed under reduced pressure. Purification via preparative HPLC gave 486 as a white solid (55 mg, 41% over two steps). $^1$H NMR (400 MHz, CDCl$_3$) δ 8.50 (s, 1H), 7.79 (s, 1H), 7.37-7.28 (m, 1H), 7.05 (t, J=8.8 Hz, 2H), 6.14 (s, 2H), 5.08-5.00 (m, 1H), 4.87 (s, 1H), 4.26 (td, J=9.3, 3.5 Hz, 1H), 3.75 (s, 3H), 3.45-3.33 (m, 2H), 3.16-3.07 (m, 2H), 2.34-2.27 (m, 2H), 2.20-2.09 (m, 1H), 2.06-1.97 (m, 1H). LCMS (ES+) m/z 490 (M+1)

Example 487

[(4S,5R)-5-amino-1-[4-[[5-amino-2-(2,6-difluorophenyl)thiazole-4-carbonyl]amino]-2-methyl-pyrazol-3-yl]azepan-4-yl]acetate 487

To a solution of tert-butyl N-((4R,5S)-1-(4-((5-(tert-butoxycarbonylamino)-2-(2,6-difluorophenyl)thiazole-4-carbonyl)amino)-2-methyl-pyrazol-3-yl)-5-hydroxy-azepan-4-yl]carbamate (200 mg, 0.3 mmol) and DMAP (55 mg, 0.45 mmol) in DCM (2 mL) was added acetic anhydride (0.43 mL, 0.45 mmol) and the mixture stirred at room temperature for 2 hr. The reaction mixture was quenched with water (3 mL) and extracted with EtOAc (3×3 mL). The combined organic layers were passed through a phase separation cartridge and concentrated under reduced pressure. The residue was purified via silica gel chromatography (0-5% MeOH/DCM) to give an off-white solid. A solution of this solid (176 mg, 0.25 mmol) in HCl in dioxane (4 M, 10 mL) and MeOH (5 mL) was stirred at room temperature for 4 hr. The solvents were removed under reduced pressure and the residue purified via preparative HPLC followed by silica gel chromatography (0-10% 7 M NH$_3$ in MeOH/DCM) to give 487 as a white solid (52 mg, 41% over two steps). $^1$H NMR (400 MHz, d$_4$-MeOD) δ 7.64 (s, 1H), 7.51-7.42 (m, 1H), 7.15 (t, J=8.7 Hz, 2H), 4.19 (dt, J=10.1, 2.6 Hz, 1H), 4.13-4.09 (m, 1H), 3.76 (s, 3H), 3.53 (ddd, J=13.5, 9.7, 3.3 Hz, 1H), 3.35-3.20 (m, 2H), 3.17-3.09 (m, 1H), 2.29-2.18 (m, 1H), 2.09-1.86 (m, 5H), 1.78-1.69 (m, 1H). LCMS (ES+) m/z 506 (M+1)

Example 488

N-[5-[(3aS,8aR)-2-oxo-3a,4,5,7,8,8a-hexahydro-3H-oxazolo[4,5-d]azepin-6-yl]-1-methyl-pyrazol-4-yl]-5-amino-2-(2,6-difluorophenyl)thiazole-4-carboxamide 488

Following the procedures of Example 486 starting from tert-butyl N-((4S,5R)-1-(4-((5-(tert-butoxycarbonylamino)-2-(2,6-difluorophenyl)thiazole-4-carbonyl)amino)-2-methyl-pyrazol-3-yl)-5-hydroxy-azepan-4-yl)carbamate gave 488 as a white solid (69 mg, 52% over two steps). $^1$H NMR (400 MHz, CDCl$_3$) δ 8.50 (s, 1H), 7.79 (s, 1H), 7.37-7.28 (m, 1H), 7.05 (t, J=8.8 Hz, 2H), 6.14 (s, 2H), 5.08-5.00 (m, 1H), 4.87 (s, 1H), 4.26 (td, J=9.3, 3.5 Hz, 1H), 3.75 (s, 3H), 3.45-3.33 (m, 2H), 3.16-3.07 (m, 2H), 2.34-2.27 (m, 2H), 2.20-2.09 (m, 1H), 2.06-1.97 (m, 1H). LCMS (ES+) m/z 490 (M+1)

Example 489

[(4R,5S)-5-amino-1-[4-[[5-amino-2-(2,6-difluorophenyl)thiazole-4-carbonyl]amino]-2-methyl-pyrazol-3-yl]azepan-4-yl]acetate 489

Following the procedure for Example 487 starting from tert-butyl N-((4S,5R)-1-(4-((5-(tert-butoxycarbonylamino)-2-(2,6-difluorophenyl)thiazole-4-carbonyl)amino)-2-methyl-pyrazol-3-yl)-5-hydroxy-azepan-4-yl]carbamate gave 489 as a white solid (40 mg, 31% over two steps). $^1$H NMR (400 MHz, d$_4$-MeOD) δ 7.64 (s, 1H), 7.51-7.42 (m, 1H), 7.15 (t, J=8.7 Hz, 2H), 4.19 (dt, J=10.1, 2.6 Hz, 1H), 4.13-4.09 (m, 1H), 3.76 (s, 3H), 3.53 (ddd, J=13.5, 9.7, 3.3 Hz, 1H), 3.35-3.20 (m, 2H), 3.17-3.09 (m, 1H), 2.29-2.18 (m, 1H), 2.09-1.86 (m, 5H), 1.78-1.69 (m, 1H). LCMS (ES+) m/z 506 (M+1)

Example 490

5-amino-2-(2,6-difluorophenyl)-N-(5-((4R,5R)-4,5-dihydroxyazepan-1-yl)-1-methyl-1H-pyrazol-4-yl)thiazole-4-carboxamide 490

To a solution of tert-butyl N-(2-(2,6-difluorophenyl)-4-((5-(4-hydroxy-5-((4-methoxyphenyl)methoxy)azepan-1-yl)-1-methyl-pyrazol-4-yl)carbamoyl)thiazol-5-yl)carbamate (0.50 g, 0.73 mmol) in MeOH (25 mL) was added 10% Pd/C (0.20 g). The mixture was stirred under a 50 psi atmosphere of hydrogen at room temperature for 18 hr. The reaction mixture was filtered through Celite® and the filtrate concentrated under reduced pressure to give a colourless solid. The crude solid was dissolved in DCM (10 mL) and TFA (10 mL) was added. The reaction mixture was stirred at room temperature for 18 hr, concentrated under reduced pressure and the crude residue was dissolved in a 1/1 mixture of MeOH/2 M aqueous NaOH (40 mL) and heated at 50° C. for 18 hr. The reaction mixture was concentrated under reduced pressure, diluted with water (30 mL) and extracted with DCM (50 mL) and EtOAc (2×50 mL). The combined organic layers were passed through a phase separation cartridge and concentrated under reduced pressure. Purification via preparative HPLC gave 490 as a pale yellow solid (86 mg, 25% over two steps). $^1$H NMR (400 MHz, d$_6$-DMSO) δ 8.72-8.63 (m, 1H), 7.61-7.45 (m, 4H), 7.31-7.23 (m, 2H), 4.57 (s, 2H), 3.63 (s, 3H), 3.52 (d, J=6.5 Hz, 2H), 3.20-3.05 (m, 4H), 1.94-1.86 (m, 2H), 1.74-1.64 (m, 2H). LCMS (ES+) m/z 465 (M+1)

Example 491

5-amino-N-[5-[4-amino-5-(trideuteriomethoxy)azepan-1-yl]-1-methyl-pyrazol-4-yl]-2-(2-fluorophenyl)thiazole-4-carboxamide 491

Following the procedures in Examples 101 and 333, starting from trideuteriomethyl iodide, 491 was yielded. $^1$H NMR (400 MHz, DMSO) δ 8.93 (s, 1H), 8.30 (t, J=7.9 Hz, 1H), 7.52 (s, 1H), 7.50-7.27 (m, 5H), 3.64 (s, 3H), 3.24-3.03 (m, 5H), 3.02-2.87 (m, 1H), 2.13-2.01 (m, 1H), 1.92-1.79 (m, 1H), 1.78-1.53 (m, 2H). LCMS (ES+) m/z 463 (M+1)

Example 492

5-amino-N-[5-[4-amino-5-(trideuteriomethoxy)azepan-1-yl]-1-methyl-pyrazol-4-yl]-2-(2,6-difluorophenyl)thiazole-4-carboxamide 492

Following the procedures in Examples 101 and 333, starting from trideuteriomethyl, 492 was yielded. $^1$H NMR (400 MHz, DMSO) δ 8.87 (s, 1H), 7.63-7.41 (m, 4H), 7.26 (t, J=8.7 Hz, 2H), 3.63 (s, 3H), 3.25-2.98 (m, 5H), 2.98-2.84 (m, 1H), 2.07-1.93 (m, 1H), 1.95-1.80 (m, 1H), 1.79-1.63 (m, 1H), 1.63-1.49 (m, 1H). LCMS (ES+) m/z 481 (M+1)

Example 493

5-amino-N-[5-[(5S)-5-amino-3,3-difluoro-azepan-1-yl]-1-(trideuteriomethyl)pyrazol-4-yl]-2-(2,6-difluorophenyl)thiazole-4-carboxamide 493

Following the procedures in Examples 101 and 112, 5-chloro-1-trideuteriomethyl-4-nitro-1H-pyrazole was converted to 493. $^1$H NMR (400 MHz, DMSO) δ 8.82 (s, 1H), 7.61-7.40 (m, 4H), 7.28 (t, J=8.7 Hz, 2H), 3.72-3.56 (m, 1H), 3.50-3.33 (m, 1H), 3.27-3.03 (m, 3H), 2.29-2.08 (m, 2H), 1.91-1.78 (m, 1H), 1.78-1.46 (m, 3H). LCMS (ES+) m/z 487 (M+1)

Example 494

5-amino-N-[5-[(5R)-5-amino-3,3-difluoro-azepan-1-yl]-1-(trideuteriomethyl)pyrazol-4-yl]-2-(2,6-difluorophenyl)thiazole-4-carboxamide 494

Following the procedures in Examples 101 and 112, 5-chloro-1-trideuteriomethyl-4-nitro-1H-pyrazole was converted to 494. $^1$H NMR (400 MHz, DMSO) δ 8.82 (s, 1H), 7.60-7.40 (m, 4H), 7.28 (t, J=8.7 Hz, 2H), 3.72-3.55 (m, 1H), 3.48-3.33 (m, 1H), 3.27-3.02 (m, 3H), 2.29-2.05 (m, 2H), 1.90-1.78 (m, 1H), 1.78-1.49 (m, 3H). LCMS (ES+) m/z 487 (M+1)

Example 495

5-amino-N-[5-(5-amino-3,3-difluoro-5-methyl-azepan-1-yl)-1-methyl-pyrazol-4-yl]-2-(2,6-difluorophenyl)thiazole-4-carboxamide 495

To a solution of tert-butyl N-(4-((5-(5-(tert-butoxycarbonylamino)-3,3-difluoro-5-methyl-azepan-1-yl)-1-methyl-pyrazol-4-yl)carbamoyl)-2-(2,6-difluorophenyl)thiazol-5-yl)carbamate (0.36 g, 0.51 mmol) in MeOH (5 mL) was added HCl in dioxane (4 M, 0.02 mol, 5 mL). The reaction mixture was stirred at room temperature for 16 hr and concentrated under reduced pressure. Purification via SCX cartridge washing with 1/1 MeOH/DCM (250 mL) followed by MeOH (250 mL) and eluting with 1 N NH$_3$ in MeOH (200 mL) gave 495 as a pale yellow foam (250 mg, 87%). $^1$H NMR (400 MHz, CDCl$_3$) δ 8.92 (s, 1H), 7.85 (s, 1H), 7.33 (tt, J=8.4, 6.1 Hz, 1H), 7.07-6.99 (m, 2H), 6.28-6.06 (m, 2H), 3.78-3.74 (m, 3H), 3.65-3.40 (m, 3H), 3.29-3.20 (m, 1H), 2.41-2.16 (m, 2H), 1.96-1.85 (m, 1H), 1.77 (dt, J=14.7, 4.6 Hz, 1H), 1.26 (s, 3H). Exchangeables not observed. LCMS (ES+) m/z 498 (M+1)

Example 496

5-amino-N-(5-((3S,4R)-4-(aminomethyl)-3-ethyl-4-methoxypiperidin-1-yl)-1-methyl-1H-pyrazol-4-yl)-2-(2,6-difluorophenyl)thiazole-4-carboxamide 496

Following the procedure for Example 101 starting from tert-butyl N-((3-ethyl-4-methoxy-1-(2-methyl-4-nitro-pyrazol-3-yl)-4-piperidyl)methyl)carbamate gave 496 as a white solid (21 mg, 33% over three steps). $^1$H NMR (400 MHz, CDCl$_3$) δ 8.52 (s, 1H), 7.80 (s, 1H), 7.36-7.27 (m, 1H), 7.07-6.97 (m, 2H), 6.15 (s, 2H), 3.75 (s, 3H), 3.18 (s, 3H), 3.20-3.03 (m, 4H), 3.03 (d, J=13.8 Hz, 1H), 2.91 (d, J=13.8 Hz, 1H), 1.89-1.74 (m, 2H), 1.72-1.45 (m, 5H), 0.89 (t, J=7.5 Hz, 3H). LCMS (ES+) m/z 506 (M+1)

Example 497

5-amino-N-[5-(5-amino-1-oxa-8-azaspiro[3.6]decan-8-yl)-1-methyl-pyrazol-4-yl]-2-(2,6-difluorophenyl)thiazole-4-carboxamide 497

Step A: A solution of 5-azido-1-(1-methyl-4-nitro-1H-pyrazol-5-yl)azepan-4-ol (502 mg, 1.78 mmol) (second eluting peak on chiral separation) in THF/water (15 mL/3 mL) was treated with triphenylphosphine (476 mg, 1.78 mmol) and the reaction mixture was heated at 60° C. for 5 hr. EtOAc (100 mL) was added and the mixture was washed with saturated aqueous NaHCO$_3$ solution (20 mL). The aqueous layer was extracted with EtOAc (50 mL) and the combined organic layers were dried over MgSO$_4$ and concentrated under reduced pressure to give an oil. To a solution of this oil in dry DCM (20 mL) at 0° C. was added DIPEA (0.85 mL, 4.88 mmol) and trifluoroacetic anhydride (0.29 mL, 2.05 mmol). The reaction mixture was allowed to warm to room temperature and stirred for 4 hr. Water (20 mL) was added and the mixture extracted with DCM (100 mL). The organic layer was separated, dried over MgSO$_4$ and concentrated under reduced pressure. Purification via silica gel column chromatography (0 to 100% EtOAc/heptane) gave 2,2,2-trifluoro-N-(5-hydroxy-1-(1-methyl-4-nitro-1H-pyrazol-5-yl)azepan-4-yl)acetamide as a yellow oil (626 mg, 88%).

Step B: To a solution of this oil in DCM was added Dess-Martin periodinane (1.0 eq.) and sodium bicarbonate (4.0 eq.). The mixture was stirred at room temperature overnight, then water was added and the mixture extracted with DCM (100 mL). The organic layer was separated, dried over MgSO4 and concentrated under reduced pressure. Purification via silica gel column chromatography (0 to 100% EtOAc/heptane) gave (S)-2,2,2-trifluoro-N-(1-(1-methyl-4-nitro-1H-pyrazol-5-yl)-5-oxoazepan-4-yl)acetamide.

Step C: Following the procedures in Example 448, (S)-2,2,2-trifluoro-N-(1-(1-methyl-4-nitro-1H-pyrazol-5-yl)-5-oxoazepan-4-yl)acetamide was converted to 2,2,2-trifluoro-N-[(10S)-7-(2-methyl-4-nitro-pyrazol-3-yl)-3-oxa-7-azaspiro[3.6]decan-10-yl]acetamide. Chiral separation by SFC gave two peaks as single enantiomers. The second eluting peak was deprotected following the procedure described in Example 417 to give 497. ¹H NMR (400 MHz, DMSO) δ 8.72-8.61 (m, 1H), 7.56 (s, 1H), 7.54-7.40 (m, 2H), 7.25 (t, J=8.6 Hz, 2H), 3.65 (s, 3H), 3.44-3.33 (m, 2H), 3.08-2.86 (m, 4H), 2.73-2.57 (m, 1H), 1.93-1.66 (m, 5H), 1.66-1.53 (m, 1H). LCMS (ES+) m/z 490 (M+1)

Example 498

5-amino-N-[5-(5-amino-1-oxa-8-azaspiro[3.6]decan-8-yl)-1-methyl-pyrazol-4-yl]-2-(2,6-difluorophenyl)thiazole-4-carboxamide 498

In the preparation of 497, the first eluting peak of 2,2,2-trifluoro-N-[(10S)-7-(2-methyl-4-nitro-pyrazol-3-yl)-3-oxa-7-azaspiro[3.6]decan-10-yl]acetamide off the SFC chiral separation was converted to 498. ¹H NMR (400 MHz, DMSO) δ 8.67 (s, 1H), 7.60-7.41 (m, 3H), 7.25 (t, J=8.6 Hz, 2H), 3.65 (s, 3H), 3.44-3.33 (m, 2H), 3.08-2.86 (m, 4H), 2.65-2.54 (m, 1H), 1.91-1.69 (m, 5H), 1.65-1.50 (m, 1H). LCMS (ES+) m/z 490 (M+1)

Example 499

5-amino-N-(5-((1R,5R,6S)-6-amino-8-oxa-3-azabicyclo[3.2.1]octan-3-yl)-1-methyl-1H-pyrazol-4-yl)-2-(2,6-difluorophenyl)thiazole-4-carboxamide 499

Following the procedure for Example 101 starting from tert-butyl N-[3-(2-methyl-4-nitro-pyrazol-3-yl)-8-oxa-3-azabicyclo[3.2.1]octan-6-yl]carbamate gave 499 as the formate salt as an off-white solid (12 mg, 28% over three steps). ¹H NMR (400 MHz, CDCl₃) δ 8.41 (s, 1H), 8.10 (s, 1H), 7.75 (s, 1H), 7.38-7.29 (m, 1H), 7.08-6.97 (m, 2H), 6.14 (s, 2H), 4.53 (d, J=7.2 Hz, 1H), 4.00 (s, 1H), 3.87 (d, J=7.8 Hz, 1H), 3.77 (s, 3H), 3.51-3.40 (m, 2H), 2.86 (d, J=11.2 Hz, 1H), 2.68-2.53 (m, 3H). Alkyl NH₂ not observed. LCMS (ES+) m/z 462 (M+1)

Example 500

5-amino-N-[5-[5-amino-4-hydroxy-4-(2-hydroxyethyl)azepan-1-yl]-1-methyl-pyrazol-4-yl]-2-(2,6-difluorophenyl)thiazole-4-carboxamide 500

Step A: Following the procedures in Example 498, 5-azido-1-(1-methyl-4-nitro-1H-pyrazol-5-yl)azepan-4-ol (502 mg, 1.78 mmol) (first eluting peak on chiral separation) was converted to (R)-2,2,2-trifluoro-N-(1-(1-methyl-4-nitro-1H-pyrazol-5-yl)-5-oxoazepan-4-yl)acetamide.

Step B: Following the procedure described in Example 448, (R)-2,2,2-trifluoro-N-(1-(1-methyl-4-nitro-1H-pyrazol-5-yl)-5-oxoazepan-4-yl)acetamide was converted to 2,2,2-trifluoro-N-[(10R)-7-(2-methyl-4-nitro-pyrazol-3-yl)-3-oxa-7-azaspiro[3.6]decan-10-yl]acetamide. Chiral separation by SFC gave two peaks as single enantiomers. The first eluting peak was converted to 500 (oxetane ring-opened product) following the procedures described in Example 448 and trifluoroacetamide deprotection procedure described in Example 417. ¹H NMR (400 MHz, DMSO) δ 9.14 (s, 1H), 8.21 (s, 1H), 7.61-7.41 (m, 4H), 7.25 (t, J=8.6 Hz, 2H), 3.64 (s, 3H), 3.47-3.37 (m, 2H), 3.22-2.83 (m, 5H), 2.72 (s, 1H), 2.34-2.17 (m, 2H), 1.94-1.82 (m, 1H), 1.82-1.59 (m, 2H), 1.59-1.37 (m, 2H). LCMS (ES+) m/z 508 (M+1)

Example 501

5-amino-N-[5-(5-amino-1-oxa-8-azaspiro[3.6]decan-8-yl)-1-methyl-pyrazol-4-yl]-2-(2,6-difluorophenyl)thiazole-4-carboxamide 501

Following the procedures in Example 498, the second eluting peak of 2,2,2-trifluoro-N-[(10S)-7-(2-methyl-4-nitro-pyrazol-3-yl)-3-oxa-7-azaspiro[3.6]decan-10-yl]acetamide off the SFC chiral separation was converted to 501. ¹H NMR (400 MHz, DMSO) δ 8.67 (s, 1H), 8.39 (s, 1H), 7.61-7.38 (m, 4H), 7.26 (t, J=8.7 Hz, 2H), 3.66 (s, 3H), 3.52-3.17 (m, 2H), 3.12-2.93 (m, 4H), 2.92-2.78 (m, 1H), 2.00-1.77 (m, 5H), 1.72-1.57 (m, 1H). LCMS (ES+) m/z 490 (M+1)

Example 502

5-amino-N-[5-(5-amino-4-methoxy-4-methyl-azepan-1-yl)-1-methyl-pyrazol-4-yl]-2-(2,6-difluorophenyl)thiazole-4-carboxamide 502

Chiral separation of the racemic mixture tert-butyl N-[1-[4-[[5-(tert-butoxycarbonylamino)-2-(2,6-difluorophenyl)thiazole-4-carbonyl]amino]-2-methyl-pyrazol-3-yl]-5-methoxy-5-methyl-azepan-4-yl]carbamate by SFC followed by deprotection with 4N HCl in dioxane gave 502 as a single enantiomer. ¹H NMR (400 MHz, DMSO) δ 9.56 (s, 1H), 7.68 (s, 1H), 7.61-7.43 (m, 3H), 7.26 (t, J=8.6 Hz, 2H), 3.61 (s, 3H), 3.18-3.05 (m, 3H), 3.02 (s, 3H), 2.91 (t, J=8.2 Hz, 1H), 2.15-2.02 (m, 1H), 1.96-1.82 (m, 1H), 1.78-1.63 (m, 1H), 1.55-1.40 (m, 1H), 1.18 (s, 3H). LCMS (ES+) m/z 492 (M+1)

Example 503

5-amino-N-[5-(5-amino-4-methoxy-4-methyl-azepan-1-yl)-1-methyl-pyrazol-4-yl]-2-(2,6-difluorophenyl)thiazole-4-carboxamide 503

Chiral separation of the racemic mixture tert-butyl N-[1-[4-[[5-(tert-butoxycarbonylamino)-2-(2,6-difluorophenyl)thiazole-4-carbonyl]amino]-2-methyl-pyrazol-3-yl]-5-methoxy-5-methyl-azepan-4-yl]carbamate by SFC followed by deprotection with 4N HCl in dioxane gave 503 as a single enantiomer. ¹H NMR (400 MHz, DMSO) δ 9.54 (s, 1H), 7.68 (s, 1H), 7.60-7.41 (m, 3H), 7.26 (t, J=8.6 Hz, 2H), 3.61 (s, 3H), 3.18-3.05 (m, 3H), 3.01 (s, 3H), 2.92 (d, J=7.1 Hz, 1H), 2.13-2.00 (m, 1H), 1.96-1.81 (m, 1H), 1.76-1.62 (m, 1H), 1.56-1.40 (m, 1H), 1.19 (s, 3H). LCMS (ES+) m/z 492 (M+1)

Example 504

5-amino-N-[5-(5-amino-4-methoxy-4-methyl-azepan-1-yl)-1-methyl-pyrazol-4-yl]-2-(2,6-difluorophenyl)thiazole-4-carboxamide 504

Chiral separation of the racemic mixture tert-butyl N-[5-[4-[[5-(tert-butoxycarbonylamino)-2-(2-fluorophenyl)thiazole-4-carbonyl]amino]-2-methyl-pyrazol-3-yl]-2-methoxy-cycloheptyl]carbamate by SFC followed by deprotection with 4N HCl in dioxane gave 504 as a single enantiomer. ¹H NMR (400 MHz, DMSO) δ 8.88 (s, 1H), 8.32 (s, 1H), 7.52 (s, 1H), 7.49-7.26 (m, 4H), 7.03-6.91 (m, 1H), 6.70-6.58 (m, 1H), 3.76 (s, 3H), 3.24 (s, 3H), 3.17-3.10 (m, 1H), 3.02-2.91 (m, 1H), 2.27-2.12 (m, 1H), 2.07-1.84 (m, 3H), 1.76-1.62 (m, 2H), 1.57-1.42 (m, 3H). LCMS (ES+) m/z 459 (M+1)

Example 505

5-amino-N-[5-(5-amino-4-methoxy-4-methyl-azepan-1-yl)-1-methyl-pyrazol-4-yl]-2-(2,6-difluorophenyl)thiazole-4-carboxamide 505

Chiral separation of the racemic mixture tert-butyl N-[5-[4-[[5-(tert-butoxycarbonylamino)-2-(2-fluorophenyl)thiazole-4-carbonyl]amino]-2-methyl-pyrazol-3-yl]-2-methoxy-cycloheptyl]carbamate by SFC followed by deprotection with 4N HCl in dioxane gave 505 as a single enantiomer. $^1$H NMR (400 MHz, DMSO) δ 8.89 (s, 1H), 8.27 (s, 1H), 7.53-7.24 (m, 5H), 7.03-6.91 (m, 1H), 6.67-6.51 (m, 1H), 3.75 (s, 3H), 3.24 (s, 3H), 3.12-2.93 (m, 2H), 2.00-1.61 (m, 7H), 1.58-1.39 (m, 2H). LCMS (ES+) m/z 459 (M+1)

Example 506

5-amino-N-[5-(5-amino-4-methoxy-4-methyl-azepan-1-yl)-1-methyl-pyrazol-4-yl]-2-(2,6-difluorophenyl)thiazole-4-carboxamide 506

Chiral separation of the racemic mixture tert-butyl N-[5-[4-[[5-(tert-butoxycarbonylamino)-2-(2-fluorophenyl)thiazole-4-carbonyl]amino]-2-methyl-pyrazol-3-yl]-2-methoxy-cycloheptyl]carbamate by SFC followed by deprotection with 4N HCl in dioxane gave 506 as a single enantiomer. $^1$H NMR (400 MHz, DMSO) δ 8.89 (s, 1H), 8.27 (s, 1H), 7.55-7.24 (m, 5H), 7.05-6.91 (m, 1H), 6.67-6.54 (m, 1H), 3.75 (s, 3H), 3.24 (s, 3H), 3.12-2.96 (m, 2H), 1.97-1.62 (m, 7H), 1.60-1.36 (m, 2H). LCMS (ES+) m/z 459 (M+1)

Example 507

5-amino-N-[5-(5-amino-4-methoxy-4-methyl-azepan-1-yl)-1-methyl-pyrazol-4-yl]-2-(2,6-difluorophenyl)thiazole-4-carboxamide 507

Chiral separation of the racemic mixture tert-butyl N-[5-[4-[[5-(tert-butoxycarbonylamino)-2-(2-fluorophenyl)thiazole-4-carbonyl]amino]-2-methyl-pyrazol-3-yl]-2-methoxy-cycloheptyl]carbamate by SFC followed by deprotection with 4N HCl in dioxane gave 507 as a single enantiomer. $^1$H NMR (400 MHz, DMSO) δ 8.87 (s, 1H), 8.33 (s, 1H), 7.52 (s, 1H), 7.48-7.26 (m, 4H), 7.02-6.89 (m, 1H), 6.66-6.55 (m, 1H), 3.76 (s, 3H), 3.24 (s, 3H), 3.17-3.07 (m, 1H), 3.02-2.89 (m, 1H), 2.26-2.09 (m, 1H), 2.12-1.86 (m, 3H), 1.77-1.60 (m, 2H), 1.61-1.40 (m, 3H). LCMS (ES+) m/z 459 (M+1)

Example 508

5-amino-N-[5-(2,6-diazaspiro[3.5]nonan-6-yl)-1-methyl-pyrazol-4-yl]-2-(2,6-difluorophenyl)thiazole-4-carboxamide 508

Step A: 5-Chloro-1-methyl-4-nitro-pyrazole (0.16 g; 0.99 mmol) and tert-butyl 2,8-diazaspiro[3.5]nonane-2-carboxylate (0.2 g, 0.88 mmol) were suspended in butan-1-ol (2 mL), followed by the addition of DIPEA (0.7 mL; 3.9616 mmol). The reaction mixture was heated at 120° C. for 2 days. Evaporated all solvent and purified the crude mixture by silica gel eluting with a gradient of 0-30% ethyl acetate in dichloromethane. Tert-butyl 6-(1-methyl-4-nitro-1H-pyrazol-5-yl)-2,6-diazaspiro[3.5]nonane-2-carboxylate (200 mg) was obtained a yellow oil in a 57% yield. MS (ESI) m/z: 352.2 [M+H$^+$].

Step B: Tert-butyl 8-(2-methyl-4-nitro-pyrazol-3-yl)-2,8-diazaspiro[3.5]nonane-2-carboxylate (200 mg, 0.57 mmol) was dissolved in methanol (20 mL). The solution was subjected to hydrogenation using H-Cube through a cartridge of Pd/C at 50° C., with hydrogen pressure at 50 bar and flow rate at 1 mL/min. The reaction was complete after 4 cycles through the system (flow rate at 1 mL/min, 80 min). After evaporation, the desired product tert-butyl 6-(4-amino-1-methyl-1H-pyrazol-5-yl)-2,6-diazaspiro[3.5]nonane-2-carboxylate (184 mg, 100%) was yielded as a light brown solid. MS (ESI) m/z: 322.3 [M+H$^+$].

Step C: 5-(tert-butoxycarbonylamino)-2-(2,6-difluorophenyl)thiazole-4-carboxylic acid (224.4 mg, 0.63 mmol) was suspended in dichloromethane (2 mL) followed by the addition of HATU (269.3 mg, 0.69 mmol), DIPEA (299.0 mg, 2.3 mmol) and tert-butyl 8-(4-amino-2-methyl-pyrazol-3-yl)-2,8-diazaspiro[3.5]nonane-2-carboxylate (184 mg, 0.57 mmol) in dichloromethane (2 mL). The suspension was stirred at room temperature for 16 hr. Saturated NaHCO$_3$ (5 mL) was added to the reaction mixture. After separation, the aqueous layer was extracted with dichloromethane (5 mL×2). The combined organic layers were dried over Na$_2$SO$_4$, filtered and evaporated. The resulting crude mixture was purified on silica gel column eluting with a gradient of 0-6% methanol in dichloromethane. A white solid (336 mg, 89%) was obtained as the desired product, tert-butyl 6-(4-(5-((tert-butoxycarbonyl)amino)-2-(2,6-difluorophenyl)thiazole-4-carboxamido)-1-methyl-1H-pyrazol-5-yl)-2,6-diazaspiro[3.5]nonane-2-carboxylate. MS (ESI) m/z: 674.5 [M+Na$^+$].

Step D: tert-butyl 8-[4-[[5-(tert-butoxycarbonylamino)-2-(2,6-difluorophenyl)thiazole-4-carbonyl]amino]-2-methyl-pyrazol-3-yl]-2,8-diazaspiro[3.5]nonane-2-carboxylate (336 mg, 0.51 mmol) was dissolved in methanol (2 mL) and dichloromethane (2 mL) before the addition of 4 M of hydrogen chloride in 1,4-Dioxane (2 mL). The solution was stirred at room temperature for 16 hr. After evaporation, a crude mixture as an off while solid (345 mg) was obtained. The crude mixture was purified by reverse phase HPLC to give 508 as a white solid (66 mg, 28%). $^1$H NMR (400 MHz, DMSO-d6) δ 8.70 (s, 1H), 7.55-7.45 (m, 4H), 7.26 (t, J=8.8 Hz, 2H), 3.66 (s, 3H), 3.54 (s, 1H), 3.22 (s, 4H), 3.12 (s, 2H), 2.94 (t, J=5.3 Hz, 2H), 1.68-1.60 (m, 2H), 1.58-1.50 (m, 2H). MS (ESI) m/z: 460.2 [M+H$^+$].

Example 509

5-amino-2-(2,6-difluorophenyl)-N-(1-methyl-5-((3aR,8aS)-3a-methyl-2-oxotetrahydro-2H-oxazolo[5,4-d]azepin-6(7H,8H,8aH)-yl)-1H-pyrazol-4-yl)thiazole-4-carboxamide 509

To a solution of 3a-methyl-6-(2-methyl-4-nitro-pyrazol-3-yl)-3,4,5,7,8,8a-hexahydrooxazolo[4,5-d]azepin-2-one (195 mg, 0.66 mmol) and 1-methyl-1,4-cyclohexadiene (0.52 mL, 4.60 mmol) in MeOH (10 mL) was added 10% palladium on carbon (35 mg, 0.33 mmol) under nitrogen and the mixture was heated at 60° C. for 2 hr. TLC indicated mainly starting material so the catalyst was filtered off and fresh 10% palladium on carbon (35 mg, 0.33 mmol) added. The mixture was heated at 65° C. for 16 hr. TLC indicated mainly starting material so the catalyst was filtered off, the volume made up to 14 mL of MeOH and the mixture passed through the H-Cube® (full hydrogen mode, 75° C., flow rate: 1 mL/min, 30 mm 10% Pd/C). The solvent was removed under reduced pressure to give crude amino-pyrazole (175 mg). A solution of HATU (351 mg, 0.92 mmol) and 5-(tert-butoxycarbonylamino)-2-(2,6-difluorophenyl)-thiazole-4-carboxylic acid (259 mg, 0.73 mmol) in DMF (5 mL) was stirred at room temperature for 30 minutes. A solution of the crude aminopyrazole (175 mg, 0.66 mmol) and DIPEA (0.18 mL, 1.06 mmol) in DMF (5 mL) was added and the mixture stirred at room temperature for 16 hr. The solvents were removed under reduced pressure and the residue triturated with DCM then MeOH. The remaining solid was suspended in DMSO (3 mL) and methanol (5 mL), a solution of HCl in dioxane (4 M, 15 mL) was added and the mixture was stirred at 50° C. for 16 hr. The volatile solvents were removed under reduced pressure and the remaining DMSO solution submitted for purification via preparative HPLC to give 509 as a yellow solid (13 mg, 4% over three steps). $^1$H NMR (400 MHz, d$_6$-DMSO) 8.78 (s, 1H), 7.66 (s, 1H), 7.57-7.47 (m, 4H), 7.27 (t, J=8.8 Hz, 2H), 4.45 (dd, J=6.8, 3.8 Hz, 1H), 4.02 (s, 1H), 3.66 (s, 3H), 3.31-3.29 (m, 1H), 3.23-3.15 (m, 1H), 3.07-2.95 (m, 2H), 2.09-2.02 (m, 2H), 1.90 (t, J=5.1 Hz, 2H), 1.30 (s, 3H). LCMS (ES+) m/z 504 (M+1)

Example 510

5-amino-N-[5-(5-amino-1-oxa-8-azaspiro[3.6]decan-8-yl)-1-methyl-pyrazol-4-yl]-2-(2,6-difluorophenyl)thiazole-4-carboxamide 510

To a solution of tert-butyl N-[2-(2,6-difluorophenyl)-4-[[1-methyl-5-[(10R)-10-[(2,2,2-trifluoroacetyl)amino]-3-oxa-7-azaspiro[3.6]decan-7-yl]pyrazol-4-yl]carbamoyl]thiazol-5-yl]carbamate (30 mg, 0.044 mmol) in methanol (2 mL) and water (2 mL) was added potassium carbonate (67 mg, 0.48 mmol). The mixture was heated at 65° C. for 8 h. After cooling to room temperature, the reaction mixture was diluted with water and extracted with EA 3×. Combined organic layers were dried over Na2SO4, filtered and concentrated. The residue was stirred with DCM (4 mL) and TFA (2 mL) for 20 min and concentrated under reduced pressure, basified with saturated NaHCO3, and extracted with ethyl acetate (3×). The combined organic layers were dried over MgSO4 and the solvent removed under reduced pressure and the residue purified by preparative HPLC to afford 510. LCMS (ES+) m/z 490 (M+1).

Example 511

5-amino-N-[5-[4-amino-5-(difluoromethyl)azepan-1-yl]-1-methyl-pyrazol-4-yl]-2-(2,6-difluorophenyl)thiazole-4-carboxamide 511

Step A: (Methoxymethyl)triphenylphosphonium chloride (5.59 g, 15.8 mmol) (dried on vacuum overnight before use) was suspended in ethyl ether (65 mL). The suspension was cooled to −15° C. Potassium tert-butoxide (1.0 mol/L) in THF (12.6 mL, 12.6 mmol) was added slowly and the bright orange suspension was stirred at −25° C. to −10° C. for 1 h while the color persisted. 2,2,2-Trifluoro-N-[(4R)-1-(2-methyl-4-nitro-pyrazol-3-yl)-5-oxo-azepan-4-yl]acetamide (1.38 g, 3.95 mmol) was dissolved in THF (12 mL) and added to the ylide at −15° C. The mixture was slowly allowed to warm to room temperature and stirred overnight then quenched with saturated ammonium chloride, and extracted with EA 3×. The combined organic layers were concentrated and the residue was purified via silica gel column chromatography (0-100% EA/heptane) to give 2,2,2-trifluoro-N-[(4R)-5-(methoxymethylene)-1-(2-methyl-4-nitro-pyrazol-3-yl)azepan-4-yl]acetamide.

Step B: To a solution of 2,2,2-trifluoro-N-[(4R)-5-(methoxymethylene)-1-(2-methyl-4-nitro-pyrazol-3-yl)azepan-4-yl]acetamide (1060 mg, 2.81 mmol) in chloroform (90 mL) was added trichloroacetic acid (1.84 g, 11.24 mmol). The mixture was heated at 70° C. overnight and another portion of trichloroacetic acid (1.84 g, 11.24 mmol) was added and heating continued for 6 h. After cooling to room temperature, the reaction was quenched with saturated sodium bicarbonate and extracted with DCM 3×. The combined organic layers were concentrated and the residue was purified via silica gel column chromatography (0-100% EA/heptane) to give 2,2,2-trifluoro-N-[(4R)-5-formyl-1-(2-methyl-4-nitro-pyrazol-3-yl)azepan-4-yl]acetamide (896 mg, 88%).

Step C: To a solution of 2,2,2-trifluoro-N-[(4R)-5-formyl-1-(2-methyl-4-nitro-pyrazol-3-yl)azepan-4-yl]acetamide (190 mg, 0.52 mmol) in DCM (5 mL) was slowly added DEOXO-FLUOR(R) (1.16 g, 2.62 mmol, 50 mass % in toluene). The mixture was stirred at room temperature for 1.5 h, quenched with sat. NaHCO$_3$ and extracted with DCM 3×. The combined organic layers were concentrated and the residue was purified via silica gel column chromatography (0-100% EA/heptane) to give N-[(4R)-5-(difluoromethyl)-1-(2-methyl-4-nitro-pyrazol-3-yl)azepan-4-yl]-2,2,2-trifluoro-acetamide (121 mg, 60%). Chiral separation of this compound by SFC gave two single enantiomers. The first eluting peak of N-[(4R)-5-(difluoromethyl)-1-(2-methyl-4-nitro-pyrazol-3-yl)azepan-4-yl]-2,2,2-trifluoro-acetamide off the SFC chiral separation was converted to 511 following the procedure described in Example 497. LCMS (ES+) m/z 498 (M+1)

Example 512

5-amino-N-[5-[4-amino-5-(difluoromethyl)azepan-1-yl]-1-methyl-pyrazol-4-yl]-2-(2,6-difluorophenyl)thiazole-4-carboxamide 512

Following the preparation 511, the second eluting peak of N-[(4R)-5-(difluoromethyl)-1-(2-methyl-4-nitro-pyrazol-3-yl)azepan-4-yl]-2,2,2-trifluoro-acetamide off the SFC chiral separation was converted to 512. $^1$H NMR (400 MHz, DMSO) δ 8.72 (s, 1H), 7.60-7.36 (m, 4H), 7.30-7.17 (m, 2H), 6.30 (t, J=58.2 Hz, 1H), 3.64 (s, 3H), 3.29-3.21 (m, 2H), 3.21-3.05 (m, 3H), 2.92-2.79 (m, 1H), 2.05-1.87 (m, 2H), 1.79-1.55 (m, 4H). LCMS (ES+) m/z 498 (M+1)

Example 513

5-amino-N-[5-[4-amino-5-(hydroxymethyl)azepan-1-yl]-1-methyl-pyrazol-4-yl]-2-(2,6-difluorophenyl)thiazole-4-carboxamide 513

Step A: In the preparation of 511, 2,2,2-trifluoro-N-[(4R)-5-formyl-1-(2-methyl-4-nitro-pyrazol-3-yl)azepan-4-yl]acetamide (192 mg, 0.53 mmol) was dissolved in methanol (5 mL) and cooled in an ice bath. Sodium borohydride (41 mg, 1.06 mmol) was added, allowed to warm to room temperature, and stirred for 40 min. The reaction was quenched with sat. NaHCO3 and extracted with EA 3×. The combined organic layers were concentrated and the residue was purified via silica gel column chromatography (0-100% EA/heptane) to give 2,2,2-trifluoro-N-[(4R)-5-(hydroxymethyl)-1-(2-methyl-4-nitro-pyrazol-3-yl)azepan-4-yl]acetamide (120 mg, 62%).

Step B: Following the procedures in Example 497, 2,2,2-trifluoro-N-[(4R)-5-(hydroxymethyl)-1-(2-methyl-4-nitro-pyrazol-3-yl)azepan-4-yl]acetamide was converted to 513. $^1$H NMR (400 MHz, DMSO) δ 8.72 (s, 1H), 7.60-7.36 (m, 4H), 7.30-7.17 (m, 2H), 6.30 (t, J=58.2 Hz, 1H), 3.64 (s, 3H), 3.29-3.21 (m, 2H), 3.21-3.05 (m, 3H), 2.92-2.79 (m, 1H), 2.05-1.87 (m, 2H), 1.79-1.55 (m, 4H). LCMS (ES+) m/z 478 (M+1)

Example 516

5-amino-N-(5-((8R,9S)-8-amino-9-methoxy-5-azaspiro[2.6]nonan-5-yl)-1-methyl-1H-pyrazol-4-yl)-2-(2,6-difluorophenyl)thiazole-4-carboxamide 516

Following the procedure for Example 101 starting from tert-butyl N-[9-methoxy-5-(2-methyl-4-nitro-pyrazol-3-yl)-5-azaspiro[2.6]nonan-8-yl]carbamate gave 516 as a white solid (10 mg, 58% over three steps). $^1$H NMR (400 MHz, CDCl$_3$) δ 8.77 (s, 1H), 7.94 (s, 1H), 7.38-7.28 (m, 1H), 7.08-6.98 (m, 2H), 6.17 (s, 2H), 3.77 (dd, J=12.7, 1.7 Hz, 1H), 3.71 (s, 3H), 3.45 (s, 3H), 3.43-3.37 (m, 1H), 3.19-3.12 (m, 2H), 2.65 (d, J=2.3 Hz, 1H), 2.26 (d, J=12.7 Hz, 1H), 2.12-2.00 (m, 1H), 1.79-1.70 (m, 1H), 0.68-0.62 (m, 1H), 0.60-0.43 (m, 3H). Alkyl NH$_2$ not observed. LCMS (ES+) m/z 504 (M+1)

Example 517

5-amino-N-(5-((8R,9S)-9-amino-8-methoxy-5-azaspiro[2.6]nonan-5-yl)-1-methyl-1H-pyrazol-4-yl)-2-(2,6-difluorophenyl)thiazole-4-carboxamide 517

Following the procedure for Example 101 starting from tert-butyl N-[8-methoxy-5-(2-methyl-4-nitro-pyrazol-3-yl)-5-azaspiro[2.6]nonan-9-yl]carbamate, gave 517 as a white solid (5 mg, 51% over three steps). $^1$H NMR (400 MHz, CDCl$_3$) δ 9.77 (s, 1H), 8.02 (s, 1H), 7.38-7.28 (m, 1H), 7.07-6.97 (m, 2H), 6.24 (s, 2H), 3.97 (d, J=13.2 Hz, 1H), 3.69 (s, 3H), 3.58-3.50 (m, 1H), 3.34-3.25 (m, 1H), 3.22 (s, 3H), 3.23-3.15 (m, 1H), 2.57 (d, J=2.8 Hz, 1H), 2.31-2.16 (m, 2H), 1.85-1.78 (m, 1H), 0.64-0.53 (m, 2H), 0.49-0.41 (m, 1H), 0.39-0.32 (m, 1H). Alkyl NH$_2$ not observed. LCMS (ES+) m/z 504 (M+1)

Example 518

(R)-5-amino-N-(5-(5-amino-3,3-difluoro-5-methylazepan-1-yl)-1-methyl-1H-pyrazol-4-yl)-2-(2,6-difluorophenyl)thiazole-4-carboxamide 518

To a solution of tert-butyl N-(4-((5R-(5-(tert-butoxycarbonylamino)-3,3-difluoro-5-methyl-azepan-1-yl)-1-methyl-pyrazol-4-yl)carbamoyl)-2-(2,6-difluorophenyl)thiazol-5-yl]carbamate (205 mg, 0.294 mmol) in MeOH (10 mL) was added HCl in dioxane (4 M, 0.04 mol, 10 mL). The reaction mixture was stirred at 40° C. for 1 hr and concentrated under reduced pressure to afford 518 as the hydrochloride salt as a pale brown solid (145 mg, 92%). $^1$H NMR (400 MHz, d$_6$-DMSO) δ 8.81 (s, 1H), 8.39 (br s, 3H), 7.65-7.53 (m, 1H), 7.51 (s, 1H), 7.35-7.20 (m, 2H), 3.90-3.75 (m, 1H), 3.74-3.60 (m, 4H), 3.55-3.42 (m, 2H), 3.40-3.30 (m, 1H), 3.25-3.10 (m, 1H), 2.70-2.45 (m, 2H), 2.35-2.15 (m, 1H), 2.00-1.85 (m, 1H), 1.48 (s, 3H). LCMS (ES+) m/z 498 (M+1)

Example 526

(S)-5-amino-N-(5-(5-amino-3,3-difluoro-5-methylazepan-1-yl)-1-methyl-1H-pyrazol-4-yl)-2-(2,6-difluorophenyl)thiazole-4-carboxamide 526

Following the procedure for Example 520 starting from tert-butyl N-(4-((5S-(5-(tert-butoxycarbonylamino)-3,3-difluoro-5-methyl-azepan-1-yl)-1-methyl-pyrazol-4-yl)carbamoyl)-2-(2,6-difluorophenyl)thiazol-5-yl]carbamate gave 526 as the hydrochloride salt as a pale brown solid (147 mg, 98%). $^1$H NMR (400 MHz, d$_6$-DMSO) δ 8.81 (s, 1H), 8.37 (br s, 3H), 7.65-7.53 (m, 1H), 7.52 (s, 1H), 7.35-7.20 (m, 2H), 3.90-3.75 (m, 1H), 3.74-3.65 (m, 4H), 3.60-3.42 (m, 2H), 3.40-3.30 (m, 1H), 3.25-3.10 (m, 1H), 2.70-2.45 (m, 2H), 2.35-2.15 (m, 1H), 2.00-1.85 (m, 1H), 1.46 (s, 3H). LCMS (ES+) m/z 498 (M+1)

Example 901

Pim Kinase Binding Activity

PIM-1, -2, and -3 enzymes were generated as fusion proteins expressed in bacteria and purified by IMAC column chromatography (Sun, X., Chiu, J. F., and He, Q. Y. (2005) Expert Rev. Proteomics, 2:649-657). A fluorescent-labeled Pim-specific peptide substrate, was custom synthesized by American Peptide Company (Sunnyvale, Calif.). Reaction Buffer contained 10 mM HEPES, pH 7.2, 10 mM MgCl$_2$, 0.01% Tween 20, 2 mM DTT. Termination Buffer contained 190 mM HEPES, pH 7.2, 0.015% Brij-35, 0.2% Coating Reagent 3 (Caliper Life Sciences, Hopkinton, Mass.), 20 mM EDTA. Separation Buffer contained 100 mM HEPES, pH 7.2, 0.015% Brij-35, 0.1% Coating Reagent 3, 1:200 Coating Reagent 8 (Caliper Life Sciences, Hopkinton, Mass.), 10 mM EDTA and 5% DMSO.

PIM reactions were carried out in a final volume of 10 µL per well in a 384-well plate. A standard enzymatic reaction, initiated by the addition of 5 µL 2×ATP and test compound to 5 µL of 2× enzyme and FAM-peptide, contained 20 pM PIM1, 50 pM PIM2, or 55 pM PIM3, 1 µM FAM-peptide, and 10 µM ATP, in Reaction Buffer. After 90 minutes of incubation at room temperature, the phosphorylation reaction was stopped by the addition of 10 µL Termination Buffer. The product and substrate in each independent reaction were separated on a 12-sipper microfluidic chip (Caliper Life Sciences, Hopkinton, Mass.) run on a Caliper LC3000® (Caliper Life Sciences, Hopkinton, Mass.). The separation of product and substrate was optimized by choosing voltages and pressure using Caliper's Optimizer software (Hopkinton, Mass.). The separation conditions used a downstream voltage of −500V, an upstream voltage of −2150V, and a screening pressure of −1.2 psi. The product and substrate fluorophore were excited at 488 nm and detected at 530 nm. Substrate conversion was calculated from the electropherogram using HTS Well Analyzer software (Caliper Life Sciences, Hopkinton, Mass.). Ki values for the test compound were calculated. See Table 1 for representative PIM1 LC3K Ki in micromolar values of exemplary compounds.

Example 902

In Vitro Cell Proliferation Potency Assays

BaF3 parental line was obtained from the DSMZ repository. BaF3 lines transfected with PIM 1 or PIM2 were generated. Mouse IL-3 was purchased from R&D Systems. G418 was purchased from Clontech. Media for BaF3 parental line contained RPMI, 10% FBS, 2 mM L-Glutamine, 2 ng/mL mIL-3. Media for BaF3 PIM1 & 2 lines contained RPMI, 10% FBS, 2 mM L-Glutamine, 250 µg/mL. Media for MM1.S (multiple myeloma cells) line contained RPMI, 10% FBS, 2 mM L-Glutamine.

BaF3, a murine interleukin-3 dependent pro-B cell line, parental cells, BaF3 PIM1 cells, BaF3 PIM2 cells, and MM1.S (multiple myeloma) cells were seeded at 2 k/well, 5 k/well, 5 k/well, and 10 k/well respectively, in a 384-well plate, at 45 μL/well. Test compound was added at 5 μL/well. BaF3 cells (parental and transfected) were incubated overnight, while MM1.S cells were incubated for 72 hours at 37° C., 5% $CO_2$. CELL TITER GLO® Reagent (Promega) was added at 50 μL/well, the plates were incubated for 30 minutes, and their luminescence read on an HT Analyst. $IC_{50}/EC_{50}$ values for the test compound were calculated.

Representative compounds of the present invention were tested as described above and found to exhibit a $Ki/IC_{50}/EC_{50}$ as shown below in Tables 2a and 2b.

TABLE 2a

| No. | Prolif BaF3 IL3 (IC50) μM | Prolif BaF3 PIM1 (IC50) μM | Prolif MM1S ATP (EC50) μM |
|---|---|---|---|
| 101 | 19.5 | 0.11 | 17.9 |
| 103 | 8.2 | 4.2 | — |
| 106 | 15.6 | 0.566 | 1.9 |
| 107 | 5.1 | 0.157 | 0.388 |
| 108 | 4.9 | 0.326 | 1.4 |
| 109 | 5.1 | 0.778 | 3.9 |
| 113 | >25 | 0.232 | 19 |
| 115 | 5.8 | 0.0863 | 0.42 |
| 116 | 8.1 | 0.0636 | 0.122 |
| 119 | 5.6 | 0.212 | 3 |
| 121 | 4.8 | 0.021 | 0.0502 |
| 124 | 22.1 | 0.264 | 1.4 |
| 126 | >25 | 0.0387 | 0.11 |
| 139 | 12.7 | 0.0436 | 0.0684 |
| 154 | 24.5 | 0.0535 | 0.0651 |
| 158 | 11.6 | 0.167 | 3 |
| 161 | 6 | 0.404 | 0.16 |
| 166 | 13.4 | 0.0165 | 0.0229 |
| 167 | >25 | 0.0484 | 1.4 |
| 223 | 12.5 | 0.547 | 20.2 |
| 230 | 18.1 | 0.171 | 1.3 |

TABLE 2b

| No. | Prolif BaF3 + IL3 (IC50) uM | Prolif BaF3_PIM1 (IC50) uM | Prolif MM1S ATP (EC50) uM |
|---|---|---|---|
| 313 | 17 | 0.105 | 6.4 |
| 314 | 13.9 | 0.184 | 9 |
| 315 | 17.2+ | 0.133 | 0.424 |
| 316 | >25 | 0.201 | 0.163 |
| 317 | >25 | 0.0452 | 0.663 |
| 320 | 25++ | 0.305 | 0.118 |
| 321 | >25 | 0.0192 | 0.00846 |
| 322 | >25 | 1.4 | 0.123 |
| 323 | >25 | 0.785 | 0.165 |
| 324 | 19.6+ | 0.0336 | 0.032 |
| 325 | 16.6 | 0.191 | 0.752 |
| 326 | 17.4 | 0.0735 | 0.185 |
| 327 | >25 | 2.6 | 14.7 |
| 328 | >25 | 2.3 | 11.5 |
| 329 | 4.6 | 1.3 | 2.8 |
| 331 | 13.4 | 0.152 | 0.167 |
| 333 | >25 | | |
| 337 | 25++ | 0.0612 | 0.0308 |
| 344 | 5.2 | 0.0836 | 1.2 |
| 345 | 8.4 | 0.0813 | 0.136 |
| 346 | 1.2 | 1.5 | |
| 347 | 2.4 | 0.0692 | |
| 348 | 11.2 | 0.825 | |
| 351 | 5.6 | 0.162 | 4.9 |
| 352 | 10.4 | 0.0173 | 0.00869 |
| 353 | 25++ | 0.229 | 0.139 |
| 354 | 14.4 | 0.0396 | 0.168 |
| 365 | | | 0.606 |
| 370 | | | 0.118 |
| 371 | | | 1.3 |
| 375 | | | 0.0706 |
| 381 | | | 3.5 |
| 385 | | | 0.182 |
| 388 | | | 0.396 |
| 390 | | | 0.147 |
| 392 | | | 0.202 |
| 397 | | | 6.4 |
| 398 | | | 5.7 |
| 399 | | | 0.0419 |
| 406 | 12+ | 0.284 | 0.404 |
| 407 | 9.8 | 0.795 | 3.5 |
| 408 | 16.5 | 0.00716 | 2.4 |
| 409 | 10.8+ | 0.0153 | 0.903 |
| 410 | 9.2 | 0.178 | 0.693 |
| 411 | 17.7 | 1.6 | 1.8 |
| 412 | 7.1 | 1.5 | 1.1 |
| 414 | >25 | 0.0786 | 0.0699 |
| 418 | >25 | 1.4 | 7 |
| 422 | >25 | 0.34 | 3.8 |
| 424 | >25 | 2.3 | 6.5 |
| 425 | >25 | 2.5 | |
| 426 | 24.8 | 0.0251 | |
| 428 | >25 | 6.6 | |
| 429 | >25 | 5.3 | |
| 432 | 6.3 | 5.8 | |
| 433 | 11.1 | 1.3 | |
| 434 | 15.5 | 1 | |
| 435 | 9.8 | 0.127 | 1.8 |
| 436 | 8.3 | 0.129 | 4.9 |
| 438 | 20.3 | 0.00303 | 0.0806 |
| 439 | 16.2 | 0.0388 | 3.9 |
| 440 | >25 | 0.0152 | 0.0774 |
| 441 | >25 | 0.0131 | 0.0393 |
| 446 | 23.5+ | 0.00451 | 9.2 |
| 447 | 12.9 | 0.00697 | 0.571 |
| 448 | >25 | 0.469 | 1.4 |
| 449 | 8.5 | 0.0913 | 4.2 |
| 451 | 9.4 | 0.0127 | 0.124 |
| 452 | 24.7 | 0.0795 | 0.0793 |
| 453 | 14.1 | 0.0408 | 3.2 |
| 454 | 17.9 | 0.00217 | 3.7 |
| 455 | 3.9 | 0.00257 | 0.221 |
| 456 | >25 | 5.8 | >25 |
| 457 | >25 | 0.164 | 4 |
| 459 | 7.5 | 0.00684 | 0.492 |
| 460 | >25 | 0.0364 | 0.215 |
| 461 | 16.6 | 0.0397 | 0.211 |
| 462 | 8 | 0.0326 | 1.2 |
| 463 | >25 | 0.0584 | 0.108 |
| 464 | 15.9 | 0.0119 | 0.467 |
| 467 | >25 | 2 | 4.8 |
| 468 | >25 | 1.5 | 0.824 |
| 472 | 18.5+ | 0.0648 | 5.6 |
| 473 | 25++ | 0.0411 | 0.248 |
| 476 | 25++ | 0.0245 | 0.872 |
| 480 | 7.1 | 0.737 | 6.2 |
| 483 | >25 | 1.1 | >25 |
| 484 | 14.3 | 0.15 | 13.7 |
| 485 | 11.6 | 0.0945 | 0.415 |
| 486 | 11.2 | 2.3 | |
| 487 | 20.1 | 4.8 | |
| 488 | 5.4 | 2 | |
| 490 | >25 | 0.596 | 8.8 |
| 491 | >25 | 0.0449 | 0.0679 |
| 492 | 20.4 | 0.0275 | 0.0737 |
| 493 | 7.8 | 0.0177 | 3 |
| 494 | 8.9 | 0.0134 | 0.0546 |
| 495 | 5.4 | 0.436 | 0.888 |
| 496 | 11.6 | 0.835 | 19.6 |
| 502 | 11.9 | 0.255 | 2.2 |
| 503 | 11 | 0.0528 | 0.108 |
| 504 | 15.3 | 0.436 | 10.5 |
| 506 | 17.1 | 0.493 | 11.7 |
| 508 | 25++ | 2 | 3 |
| 509 | >25 | 1.2 | |
| 510 | 22 | 0.623 | 5.6 |
| 511 | 24.3 | 0.964 | |
| 512 | 24.6 | 0.0524 | 2 |

TABLE 2b-continued

| No. | Prolif BaF3 + IL3 (IC50) uM | Prolif BaF3_PIM1 (IC50) uM | Prolif MM1S ATP (EC50) uM |
|---|---|---|---|
| 513 | >25 | 0.379 | 7.2 |
| 514 | 15.4 | 0.342 | 3.1 |
| 515 | 14.7 | 0.0301 | 0.0733 |
| 516 | 10.8 | 0.246 | 5.7 |
| 517 | 11.9 | 0.506 | 9.9 |

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

We claim:
1. A compound selected from
5-amino-2-(2,6-difluorophenyl)-N-(1-methyl-5-(4-((methylamino)methyl)piperidin-1-yl)-1H-pyrazol-4-yl)thiazole-4-carboxamide;
(R)-5-amino-2-(2,6-difluorophenyl)-N-(1-methyl-5-(3-methylpiperazin-1-yl)-1H-pyrazol-4-yl)thiazole-4-carboxamide;
(S)-5-amino-N-(5-(3-aminoazepan-1-yl)-1-(2,2-difluoroethyl)-1H-pyrazol-4-yl)-2-(2,6-difluorophenyl)thiazole-4-carboxamide;
(R)-5-amino-N-(5-(3-aminoazepan-1-yl)-1-(2,2-difluoroethyl)-1H-pyrazol-4-yl)-2-(2,6-difluorophenyl)thiazole-4-carboxamide;
5-amino-N-(5-(6,6-difluoro-1,4-diazepan-1-yl)-1-methyl-1H-pyrazol-4-yl)-2-(2-fluoro-5-methylphenyl)thiazole-4-carboxamide;
5-amino-N-(5-(6,6-difluoro-1,4-diazepan-1-yl)-1-methyl-1H-pyrazol-4-yl)-2-(2,5-difluorophenyl)thiazole-4-carboxamide;
(R)-5-amino-N-(1-(2,2-difluoroethyl)-5-(4-(methylamino)azepan-1-yl)-1H-pyrazol-4-yl)-2-(2,6-difluorophenyl)thiazole-4-carboxamide;
(R)-5-amino-N-(1-(2,2-difluoroethyl)-5-(4-(methylamino)azepan-1-yl)-1H-pyrazol-4-yl)-2-(2,5-difluorophenyl)thiazole-4-carboxamide;
(R)-5-amino-N-(1-(2,2-difluoroethyl)-5-(4-(methylamino)azepan-1-yl)-1H-pyrazol-4-yl)-2-(2-fluoro-5-methylphenyl)thiazole-4-carboxamide;
5-amino-N-(1-(2,2-difluoroethyl)-5-(4-hydroxyazepan-1-yl)-1H-pyrazol-4-yl)-2-(2,6-difluorophenyl)thiazole-4-carboxamide;
5-amino-N-(1-(2,2-difluoroethyl)-5-(4-hydroxyazepan-1-yl)-1H-pyrazol-4-yl)-2-(2-fluoro-5-methylphenyl)thiazole-4-carboxamide;
(R)-5-amino-2-(2,6-difluorophenyl)-N-(1-methyl-5-(2-methylpiperazin-1-yl)-1H-pyrazol-4-yl)thiazole-4-carboxamide;
(S)-5-amino-2-(2,6-difluorophenyl)-N-(5-(2-ethylpiperazin-1-yl)-1-methyl-1H-pyrazol-4-yl)thiazole-4-carboxamide;
(R)-5-amino-2-(2,6-difluorophenyl)-N-(5-(2-ethylpiperazin-1-yl)-1-methyl-1H-pyrazol-4-yl)thiazole-4-carboxamide;
(R)-5-amino-N-(5-(4-aminoazepan-1-yl)-1-methyl-1H-pyrazol-4-yl)-2-(3-cyclopropyl-2,6-difluorophenyl)thiazole-4-carboxamide;
(R)-5-amino-N-(5-(4-aminoazepan-1-yl)-1-methyl-1H-pyrazol-4-yl)-2-(2,6-difluoro-3-methylphenyl)thiazole-4-carboxamide;
(S)-5-Amino-2-(2,6-difluorophenyl)-N-(1-methyl-5-(3-methylpiperazin-1-yl)-1H-pyrazol-4-yl)thiazole-4-carboxamide;
5-amino-N-(1-(2,2-difluoroethyl)-5-(4-hydroxyazepan-1-yl)-1H-pyrazol-4-yl)-2-(2,5-difluorophenyl)thiazole-4-carboxamide;
(S)-5-amino-N-(1-(2,2-difluoroethyl)-5-(4-(methylamino)azepan-1-yl)-1H-pyrazol-4-yl)-2-(2-fluoro-5-methylphenyl)thiazole-4-carboxamide;
5-amino-N-(5-(4-amino-3-fluoroazepan-1-yl)-1-methyl-1H-pyrazol-4-yl)-2-(2,6-difluorophenyl)thiazole-4-carboxamide;
5-amino-N-(5-(5-amino-3,3-difluoroazepan-1-yl)-1-methyl-1H-pyrazol-4-yl)-2-(2,6-difluorophenyl)thiazole-4-carboxamide;
5-amino-N-(5-((3S,5S)-5-amino-3-fluoroazepan-1-yl)-1-methyl-1H-pyrazol-4-yl)-2-(2,6-difluorophenyl)thiazole-4-carboxamide;
(S)-5-amino-2-(2,6-difluorophenyl)-N-(1-methyl-5-(2-methylpiperazin-1-yl)-1H-pyrazol-4-yl)thiazole-4-carboxamide;
5-amino-2-(2,6-difluorophenyl)-N-(1-methyl-5-(2,8-diazaspiro[4.5]decan-8-yl)-1H-pyrazol-4-yl)thiazole-4-carboxamide;
5-amino-N-(5-(4-amino-3-fluoroazepan-1-yl)-1-methyl-1H-pyrazol-4-yl)-2-(2,6-difluorophenyl)thiazole-4-carboxamide;
5-amino-N-(5-((3R,5R)-5-amino-3-fluoroazepan-1-yl)-1-methyl-1H-pyrazol-4-yl)-2-(2,6-difluorophenyl)thiazole-4-carboxamide;
5-amino-N-(5-((3S,5R)-3-amino-5-fluoropiperidin-1-yl)-1-methyl-1H-pyrazol-4-yl)-2-(2,6-difluorophenyl)thiazole-4-carboxamide;
N-(5-(1,4-diazepan-1-yl)-1-(oxetan-3-ylmethyl)-1H-pyrazol-4-yl)-5-amino-2-(2,6-difluorophenyl)thiazole-4-carboxamide;
N-(5-(1,4-diazepan-1-yl)-1-(oxetan-3-ylmethyl)-1H-pyrazol-4-yl)-5-amino-2-(2-fluoro-5-methylphenyl)thiazole-4-carboxamide;
N-(5-(1,4-diazepan-1-yl)-1-(oxetan-3-ylmethyl)-1H-pyrazol-4-yl)-5-amino-2-(2,5-difluorophenyl)thiazole-4-carboxamide;
(R)-5-amino-2-(2-fluorophenyl)-N-(5-(4-hydroxy-4-methylazepan-1-yl)-1-methyl-1H-pyrazol-4-yl)thiazole-4-carboxamide;
(S)-5-amino-2-(2-fluorophenyl)-N-(5-(4-hydroxy-4-methylazepan-1-yl)-1-methyl-1H-pyrazol-4-yl)thiazole-4-carboxamide;
(R)-5-amino-2-(2,6-difluorophenyl)-N-(1-methyl-5-(6-methyl-1,4-diazepan-1-yl)-1H-pyrazol-4-yl)thiazole-4-carboxamide;
(S)-5-amino-2-(2,6-difluorophenyl)-N-(1-methyl-5-(6-methyl-1,4-diazepan-1-yl)-1H-pyrazol-4-yl)thiazole-4-carboxamide;
(S)-5-amino-N-(1-(2,2-difluoroethyl)-5-(4-hydroxyazepan-1-yl)-1H-pyrazol-4-yl)-2-(2,6-difluorophenyl)thiazole-4-carboxamide;
(R)-5-amino-N-(1-(2,2-difluoroethyl)-5-(4-hydroxyazepan-1-yl)-1H-pyrazol-4-yl)-2-(2,6-difluorophenyl)thiazole-4-carboxamide;

(S)-5-amino-N-(1-(2,2-difluoroethyl)-5-(4-hydroxyazepan-1-yl)-1H-pyrazol-4-yl)-2-(2-fluoro-5-methylphenyl)thiazole-4-carboxamide;
(R)-5-amino-N-(1-(2,2-difluoroethyl)-5-(4-hydroxyazepan-1-yl)-1H-pyrazol-4-yl)-2-(2-fluoro-5-methylphenyl)thiazole-4-carboxamide;
5-amino-N-(5-((4R,5R)-4-amino-5-fluoroazepan-1-yl)-1-methyl-1H-pyrazol-4-yl)-2-(2,6-difluorophenyl)thiazole-4-carboxamide;
5-amino-N-(5-((4S,5S)-4-amino-5-fluoroazepan-1-yl)-1-methyl-1H-pyrazol-4-yl)-2-(2,6-difluorophenyl)thiazole-4-carboxamide;
(S)-5-amino-2-(2,6-difluorophenyl)-N-(5-(2,4-dimethylpiperazin-1-yl)-1-methyl-1H-pyrazol-4-yl)thiazole-4-carboxamide;
(R)-5-amino-2-(2,6-difluorophenyl)-N-(5-(2,4-dimethylpiperazin-1-yl)-1-methyl-1H-pyrazol-4-yl)thiazole-4-carboxamide;
5-amino-N-(1-cyclopropyl-5-(6,6-difluoro-1,4-diazepan-1-yl)-1H-pyrazol-4-yl)-2-(2,5-difluorophenyl)thiazole-4-carboxamide;
5-amino-N-(1-cyclopropyl-5-(6,6-difluoro-1,4-diazepan-1-yl)-1H-pyrazol-4-yl)-2-(2-fluoro-5-methylphenyl)thiazole-4-carboxamide;
5-amino-N-(1-cyclopropyl-5-(6,6-difluoro-1,4-diazepan-1-yl)-1H-pyrazol-4-yl)-2-(2,6-difluorophenyl)thiazole-4-carboxamide;
5-amino-2-(2,6-difluorophenyl)-N-(5-(4-hydroxy-4-methylazepan-1-yl)-1-methyl-1H-pyrazol-4-yl)thiazole-4-carboxamide;
5-amino-N-(5-((4S,5R)-4-amino-5-fluoroazepan-1-yl)-1-methyl-1H-pyrazol-4-yl)-2-(2,6-difluorophenyl)thiazole-4-carboxamide;
(S)-5-amino-N-(1-(2,2-difluoroethyl)-5-(4-hydroxyazepan-1-yl)-1H-pyrazol-4-yl)-2-(2,5-difluorophenyl)thiazole-4-carboxamide;
(R)-5-amino-N-(1-(2,2-difluoroethyl)-5-(4-hydroxyazepan-1-yl)-1H-pyrazol-4-yl)-2-(2,5-difluorophenyl)thiazole-4-carboxamide;
5-amino-N-(5-((4R,5S)-4-amino-5-fluoroazepan-1-yl)-1-methyl-1H-pyrazol-4-yl)-2-(2,6-difluorophenyl)thiazole-4-carboxamide;
5-amino-2-(2,6-difluorophenyl)-N-(5-(6-fluoro-1,4-diazepan-1-yl)-1-methyl-1H-pyrazol-4-yl)thiazole-4-carboxamide;
(R)-5-amino-N-(5-(4-aminoazepan-1-yl)-1-(2,2-difluoroethyl)-1H-pyrazol-4-yl)-2-(2,6-difluorophenyl)thiazole-4-carboxamide;
5-amino-N-(5-((3S,5R)-5-amino-3-fluoroazepan-1-yl)-1-methyl-1H-pyrazol-4-yl)-2-(2,6-difluorophenyl)thiazole-4-carboxamide;
5-amino-N-(5-((3R,5S)-5-amino-3-fluoroazepan-1-yl)-1-methyl-1H-pyrazol-4-yl)-2-(2,6-difluorophenyl)thiazole-4-carboxamide;
5-amino-N-(5-((3R,4S)-4-amino-3-fluoroazepan-1-yl)-1-methyl-1H-pyrazol-4-yl)-2-(2,6-difluorophenyl)thiazole-4-carboxamide;
5-amino-N-(5-((3S,4R)-4-amino-3-fluoroazepan-1-yl)-1-methyl-1H-pyrazol-4-yl)-2-(2,6-difluorophenyl)thiazole-4-carboxamide;
5-amino-N-(5-((3R,4R)-4-amino-3-fluoroazepan-1-yl)-1-methyl-1H-pyrazol-4-yl)-2-(2,6-difluorophenyl)thiazole-4-carboxamide;
5-amino-N-(5-((3S,4S)-4-amino-3-fluoroazepan-1-yl)-1-methyl-1H-pyrazol-4-yl)-2-(2,6-difluorophenyl)thiazole-4-carboxamide;
5-amino-N-(5-((3R,5R)-3-amino-5-fluoropiperidin-1-yl)-1-methyl-1H-pyrazol-4-yl)-2-(2,6-difluorophenyl)thiazole-4-carboxamide;
5-amino-N-(5-(6,6-difluoro-1,4-diazepan-1-yl)-1-(oxetan-3-ylmethyl)-1H-pyrazol-4-yl)-2-(2,6-difluorophenyl)thiazole-4-carboxamide;
(R)-5-amino-N-(5-(4-aminoazepan-1-yl)-1-(2,2-difluoroethyl)-1H-pyrazol-4-yl)-2-(2,5-difluorophenyl)thiazole-4-carboxamide;
5-amino-2-(2,6-difluorophenyl)-N-(5-(4-hydroxyazepan-1-yl)-1-(oxetan-3-ylmethyl)-1H-pyrazol-4-yl)thiazole-4-carboxamide;
5-amino-2-(2-fluoro-5-methylphenyl)-N-(5-(4-hydroxyazepan-1-yl)-1-(oxetan-3-ylmethyl)-1H-pyrazol-4-yl)thiazole-4-carboxamide;
(R)-5-amino-N-(5-(4-aminoazepan-1-yl)-1-(oxetan-3-ylmethyl)-1H-pyrazol-4-yl)-2-(2,6-difluorophenyl)thiazole-4-carboxamide;
5-amino-2-(2,6-difluorophenyl)-N-(5-(6-fluoro-1,4-diazepan-1-yl)-1-(oxetan-3-ylmethyl)-1H-pyrazol-4-yl)thiazole-4-carboxamide;
(S)-5-amino-N-(5-(5-amino-3,3-difluoroazepan-1-yl)-1-methyl-1H-pyrazol-4-yl)-2-(2,6-difluorophenyl)thiazole-4-carboxamide;
(R)-5-amino-N-(5-(5-amino-3,3-difluoroazepan-1-yl)-1-methyl-1H-pyrazol-4-yl)-2-(2,6-difluorophenyl)thiazole-4-carboxamide;
(R)-5-amino-2-(2,6-difluorophenyl)-N-(1-methyl-5-(3-(trifluoromethyl)piperazin-1-yl)-1H-pyrazol-4-yl)thiazole-4-carboxamide;
(S)-5-amino-2-(2,6-difluorophenyl)-N-(1-methyl-5-(3-(trifluoromethyl)piperazin-1-yl)-1H-pyrazol-4-yl)thiazole-4-carboxamide;
(S)-5-amino-N-(1-(2,2-difluoroethyl)-5-(3-hydroxyazepan-1-yl)-1H-pyrazol-4-yl)-2-(2,6-difluorophenyl)thiazole-4-carboxamide;
(R)-5-amino-N-(1-(2,2-difluoroethyl)-5-(3-hydroxyazepan-1-yl)-1H-pyrazol-4-yl)-2-(2,6-difluorophenyl)thiazole-4-carboxamide;
5-amino-N-(5-(6,6-difluoro-1,4-diazepan-1-yl)-1-(2,2-difluoroethyl)-1H-pyrazol-4-yl)-2-(2,6-difluorophenyl)thiazole-4-carboxamide;
5-amino-N-(1-(2,2-difluoroethyl)-5-(6-hydroxy-1,4-diazepan-1-yl)-1H-pyrazol-4-yl)-2-(2,6-difluorophenyl)thiazole-4-carboxamide;
(S)-5-amino-2-(2,6-difluorophenyl)-N-(5-(2-methylpiperazin-1-yl)-1H-pyrazol-4-yl)thiazole-4-carboxamide;
(R)-5-amino-2-(2,6-difluorophenyl)-N-(5-(2-methylpiperazin-1-yl)-1H-pyrazol-4-yl)thiazole-4-carboxamide;
(S)-5-amino-2-(2,6-difluorophenyl)-N-(5-(2-ethyl-4-methylpiperazin-1-yl)-1-methyl-1H-pyrazol-4-yl)thiazole-4-carboxamide;
(R)-5-amino-2-(2,6-difluorophenyl)-N-(5-(2-ethyl-4-methylpiperazin-1-yl)-1-methyl-1H-pyrazol-4-yl)thiazole-4-carboxamide;
5-amino-2-(2-fluoro-5-methylphenyl)-N-(5-(4-hydroxy-4-methylazepan-1-yl)-1-methyl-1H-pyrazol-4-yl)thiazole-4-carboxamide;
5-amino-N-(1-(2,2-difluoroethyl)-5-(6-fluoro-1,4-diazepan-1-yl)-1H-pyrazol-4-yl)-2-(2,6-difluorophenyl)thiazole-4-carboxamide;
(R)-3-amino-N-(5-(4-aminoazepan-1-yl)-1-(2,2-difluoroethyl)-1H-pyrazol-4-yl)-6-(2-fluorophenyl)picolinamide;
(S)-5-amino-2-(2,6-difluorophenyl)-N-(5-(3-hydroxyazepan-1-yl)-1-methyl-1H-pyrazol-4-yl)thiazole-4-carboxamide;

(R)-5-amino-2-(2,6-difluorophenyl)-N-(5-(3-hydroxyazepan-1-yl)-1-methyl-1H-pyrazol-4-yl)thiazole-4-carboxamide;

5-amino-N-(5-(3,3-difluoro-5-(methylamino)azepan-1-yl)-1-methyl-1H-pyrazol-4-yl)-2-(2,6-difluorophenyl)thiazole-4-carboxamide;

5-amino-N-(5-((3R,5S)-3-amino-5-fluoropiperidin-1-yl)-1-methyl-1H-pyrazol-4-yl)-2-(2,6-difluorophenyl)thiazole-4-carboxamide;

(R)-5-amino-N-(5-(4-aminoazepan-1-yl)-1-(2,2,2-trifluoroethyl)-1H-pyrazol-4-yl)-2-(2,6-difluorophenyl)thiazole-4-carboxamide;

N-(5-(1,4-diazepan-1-yl)-1-(2,2,2-trifluoroethyl)-1H-pyrazol-4-yl)-5-amino-2-(2,6-difluorophenyl)thiazole-4-carboxamide;

5-amino-N-(5-(4-amino-5-hydroxyazepan-1-yl)-1-methyl-1H-pyrazol-4-yl)-2-(2,6-difluorophenyl)thiazole-4-carboxamide;

5-amino-N-(5-(3,3-difluoroazepan-1-yl)-1-methyl-1H-pyrazol-4-yl)-2-(2,6-difluorophenyl)thiazole-4-carboxamide;

5-amino-N-(5-((3S,5S)-3-amino-5-fluoropiperidin-1-yl)-1-methyl-1H-pyrazol-4-yl)-2-(2,6-difluorophenyl)thiazole-4-carboxamide;

5-amino-2-(2,6-difluorophenyl)-N-(5-(6-hydroxy-6-methyl-1,4-diazepan-1-yl)-1-methyl-1H-pyrazol-4-yl)thiazole-4-carboxamide;

5-amino-2-(2,6-difluorophenyl)-N-(5-(6-fluoro-6-methyl-1,4-diazepan-1-yl)-1-methyl-1H-pyrazol-4-yl)thiazole-4-carboxamide;

5-amino-2-(2,6-difluorophenyl)-N-(5-(6-methoxy-6-methyl-1,4-diazepan-1-yl)-1-methyl-1H-pyrazol-4-yl)thiazole-4-carboxamide;

5-amino-N-(5-(6,6-difluoro-1,4-diazepan-1-yl)-1H-pyrazol-4-yl)-2-(2,6-difluorophenyl)thiazole-4-carboxamide;

5-amino-2-(2,6-difluorophenyl)-N-(5-(6-methoxy-1,4-diazepan-1-yl)-1-methyl-1H-pyrazol-4-yl)thiazole-4-carboxamide;

5-amino-N-(5-(4-amino-5-fluoroazepan-1-yl)-1-methyl-1H-pyrazol-4-yl)-2-(2-fluorophenyl)thiazole-4-carboxamide;

5-amino-N-(5-(4-amino-5-fluoroazepan-1-yl)-1-methyl-1H-pyrazol-4-yl)-2-(2-fluoro-5-methylphenyl)thiazole-4-carboxamide;

(R)-5-amino-2-(2,6-difluorophenyl)-N-(1-methyl-5-(4-(2,2,2-trifluoroethylamino)azepan-1-yl)-1H-pyrazol-4-yl)thiazole-4-carboxamide;

3-amino-N-(5-(6,6-difluoro-1,4-diazepan-1-yl)-1-methyl-1H-pyrazol-4-yl)-6-(2-fluorophenyl)picolinamide;

(R)-5-amino-2-(2,6-difluorophenyl)-N-(5-(3-fluoroazepan-1-yl)-1-methyl-1H-pyrazol-4-yl)thiazole-4-carboxamide;

(S)-5-amino-2-(2,6-difluorophenyl)-N-(5-(3-fluoroazepan-1-yl)-1-methyl-1H-pyrazol-4-yl)thiazole-4-carboxamide;

5-amino-2-(2,6-difluorophenyl)-N-(5-(3-hydroxy-3-methylazepan-1-yl)-1-methyl-1H-pyrazol-4-yl)thiazole-4-carboxamide;

5-amino-N-(5-(4-amino-5-fluoroazepan-1-yl)-1-methyl-1H-pyrazol-4-yl)-2-(2,5-difluorophenyl)thiazole-4-carboxamide;

5-amino-N-(5-(4-amino-5-fluoroazepan-1-yl)-1-(2,2-difluoroethyl)-1H-pyrazol-4-yl)-2-(2,6-difluorophenyl)thiazole-4-carboxamide;

(R)-5-amino-N-(5-(4-(2,2-difluoroethylamino)azepan-1-yl)-1-methyl-1H-pyrazol-4-yl)-2-(2,6-difluorophenyl)thiazole-4-carboxamide;

5-amino-2-(2,6-difluorophenyl)-N-(1-methyl-5-(5-methyl-1,4-diazepan-1-yl)-1H-pyrazol-4-yl)thiazole-4-carboxamide;

(R)-5-amino-2-(2,6-difluorophenyl)-N-(5-(6-fluoro-6-methyl-1,4-diazepan-1-yl)-1-methyl-1H-pyrazol-4-yl)thiazole-4-carboxamide;

(R)-5-amino-2-(2,6-difluorophenyl)-N-(5-(6-hydroxy-6-methyl-1,4-diazepan-1-yl)-1-methyl-1H-pyrazol-4-yl)thiazole-4-carboxamide;

(S)-5-amino-2-(2,6-difluorophenyl)-N-(5-(6-hydroxy-6-methyl-1,4-diazepan-1-yl)-1-methyl-1H-pyrazol-4-yl)thiazole-4-carboxamide;

(S)-5-amino-2-(2,6-difluorophenyl)-N-(5-(6-fluoro-6-methyl-1,4-diazepan-1-yl)-1-methyl-1H-pyrazol-4-yl)thiazole-4-carboxamide;

5-amino-N-(5-((4S,5S)-4-amino-5-fluoroazepan-1-yl)-1-(2,2-difluoroethyl)-1H-pyrazol-4-yl)-2-(2,6-difluorophenyl)thiazole-4-carboxamide;

5-amino-N-(5-((4R,5R)-4-amino-5-fluoroazepan-1-yl)-1-(2,2-difluoroethyl)-1H-pyrazol-4-yl)-2-(2,6-difluorophenyl)thiazole-4-carboxamide;

5-amino-N-(5-((4S,5S)-4-amino-5-fluoroazepan-1-yl)-1-methyl-1H-pyrazol-4-yl)-2-(2-fluoro-5-methylphenyl)thiazole-4-carboxamide;

5-amino-N-(5-((4R,5R)-4-amino-5-fluoroazepan-1-yl)-1-methyl-1H-pyrazol-4-yl)-2-(2-fluoro-5-methylphenyl)thiazole-4-carboxamide;

3-amino-N-(5-(6,6-difluoro-1,4-diazepan-1-yl)-1-methyl-1H-pyrazol-4-yl)-6-(2-fluorophenyl)pyrazine-2-carboxamide;

5-amino-2-(2,6-difluorophenyl)-N-(5-(5-(dimethylamino)-3,3-difluoroazepan-1-yl)-1-methyl-1H-pyrazol-4-yl)thiazole-4-carboxamide;

5-amino-N-(5-(5-amino-3-methoxyazepan-1-yl)-1-methyl-1H-pyrazol-4-yl)-2-(2,6-difluorophenyl)thiazole-4-carboxamide;

5-amino-N-(5-((4S,5S)-4-amino-5-methoxyazepan-1-yl)-1-methyl-1H-pyrazol-4-yl)-2-(2,6-difluorophenyl)thiazole-4-carboxamide;

5-amino-N-(5-(5-amino-3,3-difluoroazepan-1-yl)-1-methyl-1H-pyrazol-4-yl)-2-(2-fluorophenyl)thiazole-4-carboxamide;

5-amino-N-(5-(5-amino-3,3-difluoroazepan-1-yl)-1-methyl-1H-pyrazol-4-yl)-2-(2-fluoro-5-methylphenyl)thiazole-4-carboxamide;

5-amino-N-(5-(5-amino-3,3-difluoroazepan-1-yl)-1-methyl-1H-pyrazol-4-yl)-2-(2,5-difluorophenyl)thiazole-4-carboxamide;

5-amino-N-(5-((4S,5S)-4-amino-5-fluoroazepan-1-yl)-1-methyl-1H-pyrazol-4-yl)-2-(2,5-difluorophenyl)thiazole-4-carboxamide;

5-amino-N-(5-((4R,5R)-4-amino-5-fluoroazepan-1-yl)-1-methyl-1H-pyrazol-4-yl)-2-(2,5-difluorophenyl)thiazole-4-carboxamide;

5-amino-N-(5-(6,6-difluoro-1,4-diazepan-1-yl)-1-methyl-1H-pyrazol-4-yl)-2-(pyridin-2-yl)thiazole-4-carboxamide;

5-amino-N-(5-(6,6-difluoro-1,4-diazepan-1-yl)-1-methyl-1H-pyrazol-4-yl)-2-(3-fluoropyridin-2-yl)thiazole-4-carboxamide;

(S)-5-amino-2-(2,6-difluorophenyl)-N-(1-methyl-5-(5-methyl-1,4-diazepan-1-yl)-1H-pyrazol-4-yl)thiazole-4-carboxamide;

(R)-5-amino-2-(2,6-difluorophenyl)-N-(1-methyl-5-(5-methyl-1,4-diazepan-1-yl)-1H-pyrazol-4-yl)thiazole-4-carboxamide;
(R)-5-amino-2-(2,6-difluorophenyl)-N-(5-(3-hydroxy-3-methylazepan-1-yl)-1-methyl-1H-pyrazol-4-yl)thiazole-4-carboxamide;
(S)-5-amino-2-(2,6-difluorophenyl)-N-(5-(3-hydroxy-3-methylazepan-1-yl)-1-methyl-1H-pyrazol-4-yl)thiazole-4-carboxamide;
5-amino-N-(5-((4S,5S)-4-amino-5-fluoroazepan-1-yl)-1-methyl-1H-pyrazol-4-yl)-2-(2-fluorophenyl)thiazole-4-carboxamide;
5-amino-N-(5-((4R,5R)-4-amino-5-fluoroazepan-1-yl)-1-methyl-1H-pyrazol-4-yl)-2-(2-fluorophenyl)thiazole-4-carboxamide;
3-amino-N-(5-(4-amino-5-fluoroazepan-1-yl)-1-methyl-1H-pyrazol-4-yl)-6-(2-fluorophenyl)picolinamide;
3-amino-N-(5-(4-amino-5-fluoroazepan-1-yl)-1-methyl-1H-pyrazol-4-yl)-6-(2-fluorophenyl)pyrazine-2-carboxamide;
(R)-5-amino-2-(2,6-difluorophenyl)-N-(5-(3-methylpiperazin-1-yl)-1-(2,2,2-trifluoroethyl)-1H-pyrazol-4-yl)thiazole-4-carboxamide;
5-amino-N-(5-(5-amino-3,3-difluoroazepan-1-yl)-1-(2,2-difluoroethyl)-1H-pyrazol-4-yl)-2-(2,6-difluorophenyl)thiazole-4-carboxamide;
5-amino-N-(5-(4-amino-5-fluoroazepan-1-yl)-1-methyl-1H-pyrazol-4-yl)-2-(2-fluorophenyl)pyrimidine-4-carboxamide;
5-amino-N-(5-(6,6-difluoro-1,4-diazepan-1-yl)-1-methyl-1H-pyrazol-4-yl)-2-(2-fluorophenyl)pyrimidine-4-carboxamide;
5-Amino-2-(2-fluoro-phenyl)-pyrimidine-4-carboxylic acid[5-(5-amino-3,3-difluoro-azepan-1-yl)-1-methyl-1H-pyrazol-4-yl]-amide;
(S)-5-amino-2-(2,6-difluorophenyl)-N-(1-methyl-5-(3-(trifluoromethyl)piperidin-1-yl)-1H-pyrazol-4-yl)thiazole-4-carboxamide;
(R)-5-Amino-2-(2,6-difluoro-phenyl)-thiazole-4-carboxylic acid[1-methyl-5-(3-trifluoromethyl-piperidin-1-yl)-1H-pyrazol-4-yl]-amide;
3-amino-N-(5-(4-amino-5-fluoroazepan-1-yl)-1-methyl-1H-pyrazol-4-yl)-6-(2-fluorophenyl)pyrazine-2-carboxamide;
3-amino-N-(5-(4-amino-5-fluoroazepan-1-yl)-1-methyl-1H-pyrazol-4-yl)-6-(2-fluorophenyl)pyrazine-2-carboxamide;
3-amino-N-(5-(4-amino-5-fluoroazepan-1-yl)-1-methyl-1H-pyrazol-4-yl)-6-(2-fluorophenyl)picolinamide;
3-amino-N-(5-(4-amino-5-fluoroazepan-1-yl)-1-methyl-1H-pyrazol-4-yl)-6-(2-fluorophenyl)picolinamide;
(S)-3-amino-N-(5-(5-amino-3,3-difluoroazepan-1-yl)-1-methyl-1H-pyrazol-4-yl)-6-(2-fluorophenyl)pyrazine-2-carboxamide;
(R)-3-amino-N-(5-(5-amino-3,3-difluoroazepan-1-yl)-1-methyl-1H-pyrazol-4-yl)-6-(2-fluorophenyl)pyrazine-2-carboxamide;
(S)-3-amino-N-(5-(5-amino-3,3-difluoroazepan-1-yl)-1-methyl-1H-pyrazol-4-yl)-6-(2-fluorophenyl)picolinamide;
(R)-3-amino-N-(5-(5-amino-3,3-difluoroazepan-1-yl)-1-methyl-1H-pyrazol-4-yl)-6-(2-fluorophenyl)picolinamide;
5-Amino-2-(2,6-difluoro-phenyl)-thiazole-4-carboxylic acid (1-oxetan-3-ylmethyl-5-piperazin-1-yl-1H-pyrazol-4-yl)-amide;
5-Amino-2-(2,6-difluoro-phenyl)-thiazole-4-carboxylic acid[5-(5-amino-3-methoxy-3-methyl-azepan-1-yl)-1-methyl-1H-pyrazol-4-yl]-amide;
5-Amino-2-(2,6-difluoro-phenyl)-thiazole-4-carboxylic acid[5-(5-amino-3-hydroxy-3-methyl-azepan-1-yl)-1-methyl-1H-pyrazol-4-yl]-amide;
5-Amino-2-(2,6-difluoro-phenyl)-thiazole-4-carboxylic acid[5-(5-amino-3-methoxy-3-methyl-azepan-1-yl)-1-methyl-1H-pyrazol-4-yl]-amide;
5-Amino-2-(2,6-difluoro-phenyl)-thiazole-4-carboxylic acid[5-(5-amino-3-hydroxy-3-methyl-azepan-1-yl)-1-methyl-1H-pyrazol-4-yl]-amide;
5-Amino-2-(2,6-difluoro-phenyl)-thiazole-4-carboxylic acid[5-(5-amino-3-fluoro-3-methyl-azepan-1-yl)-1-methyl-1H-pyrazol-4-yl]-amide;
5-Amino-2-(2,6-difluoro-phenyl)-thiazole-4-carboxylic acid[5-(3-fluoro-5-hydroxy-azepan-1-yl)-1-methyl-1H-pyrazol-4-yl]-amide;
5-Amino-2-(2,6-difluoro-phenyl)-thiazole-4-carboxylic acid[1-methyl-5-(3-trifluoromethyl-piperidin-1-yl)-1H-pyrazol-4-yl]-amide;
(S)-5-amino-N-(5-(5-amino-3,3-difluoroazepan-1-yl)-1-methyl-1H-pyrazol-4-yl)-2-(pyridin-2-yl)thiazole-4-carboxamide;
(R)-5-amino-N-(5-(5-amino-3,3-difluoroazepan-1-yl)-1-methyl-1H-pyrazol-4-yl)-2-(pyridin-2-yl)thiazole-4-carboxamide;
5-amino-N-(5-((4S,5S)-4-amino-5-fluoroazepan-1-yl)-1-methyl-1H-pyrazol-4-yl)-2-(pyridin-2-yl)thiazole-4-carboxamide;
(S)-5-amino-N-(5-(5-amino-3,3-difluoroazepan-1-yl)-1-methyl-1H-pyrazol-4-yl)-2-(3-fluoropyridin-2-yl)thiazole-4-carboxamide;
5-amino-N-(5-((4R,5S)-4-amino-5-fluoroazepan-1-yl)-1-methyl-1H-pyrazol-4-yl)-2-(2-fluoro-5-methylphenyl)thiazole-4-carboxamide;
5-amino-N-(5-((4S,5R)-4-amino-5-fluoroazepan-1-yl)-1-methyl-1H-pyrazol-4-yl)-2-(2-fluoro-5-methylphenyl)thiazole-4-carboxamide;
5-amino-N-(5-((4R,5S)-4-amino-5-fluoroazepan-1-yl)-1-methyl-1H-pyrazol-4-yl)-2-(2-fluorophenyl)thiazole-4-carboxamide;
5-amino-N-(5-((4R,5R)-4-amino-5-fluoroazepan-1-yl)-1-methyl-1H-pyrazol-4-yl)-2-(3-fluoropyridin-2-yl)thiazole-4-carboxamide;
5-amino-N-(5-((4S,5S)-4-amino-5-fluoroazepan-1-yl)-1-methyl-1H-pyrazol-4-yl)-2-(3-fluoropyridin-2-yl)thiazole-4-carboxamide;
5-amino-N-(5-((4S,5R)-4-amino-5-fluoroazepan-1-yl)-1-methyl-1H-pyrazol-4-yl)-2-(2-fluorophenyl)thiazole-4-carboxamide;
5-amino-N-(5-((4R,5S)-4-amino-5-fluoroazepan-1-yl)-1-methyl-1H-pyrazol-4-yl)-2-(2,5-difluorophenyl)thiazole-4-carboxamide;
5-amino-N-(5-((4S,5R)-4-amino-5-fluoroazepan-1-yl)-1-methyl-1H-pyrazol-4-yl)-2-(2-fluoro-5-methylphenyl)thiazole-4-carboxamide;
(R)-5-amino-N-(5-(5-amino-3,3-difluoroazepan-1-yl)-1-methyl-1H-pyrazol-4-yl)-2-(3-fluoropyridin-2-yl)thiazole-4-carboxamide;
5-amino-N-(5-((4R,5R)-4-amino-5-fluoroazepan-1-yl)-1-methyl-1H-pyrazol-4-yl)-2-(pyridin-2-yl)thiazole-4-carboxamide;
5-Amino-2-(2,6-difluoro-3-iodo-phenyl)-thiazole-4-carboxylic acid[5-(5-amino-3,3-difluoro-azepan-1-yl)-1-methyl-1H-pyrazol-4-yl]-amide;

5-amino-N-(5-((4S,5S)-4-amino-5-fluoroazepan-1-yl)-1-cyclopropyl-1H-pyrazol-4-yl)-2-(2,5-difluorophenyl)thiazole-4-carboxamide;
5-amino-N-(5-((4S,5S)-4-amino-5-fluoroazepan-1-yl)-1-cyclopropyl-1H-pyrazol-4-yl)-2-(2-fluoro-5-methylphenyl)thiazole-4-carboxamide;
5-amino-N-(5-((4S,5S)-4-amino-5-fluoroazepan-1-yl)-1-cyclopropyl-1H-pyrazol-4-yl)-2-(2,6-difluorophenyl)thiazole-4-carboxamide;
5-Amino-2-(2,6-difluoro-phenyl)-thiazole-4-carboxylic acid[5-(5-amino-3,3-difluoro-azepan-1-yl)-1-cyclopropyl-1H-pyrazol-4-yl]-amide;
(R)-5-amino-N-(5-(5-amino-3,3-difluoroazepan-1-yl)-1-methyl-1H-pyrazol-4-yl)-2-(2,5-difluorophenyl)thiazole-4-carboxamide;
(S)-5-amino-N-(5-(5-amino-3,3-difluoroazepan-1-yl)-1-methyl-1H-pyrazol-4-yl)-2-(2,5-difluorophenyl)thiazole-4-carboxamide;
(S)-5-amino-N-(5-(5-amino-3,3-difluoroazepan-1-yl)-1-methyl-1H-pyrazol-4-yl)-2-(2,5-difluorophenyl)thiazole-4-carboxamide;
(R)-5-amino-N-(5-(5-amino-3,3-difluoroazepan-1-yl)-1-methyl-1H-pyrazol-4-yl)-2-(2,5-difluorophenyl)thiazole-4-carboxamide;
(S)-5-amino-N-(5-(5-amino-3,3-difluoroazepan-1-yl)-1-methyl-1H-pyrazol-4-yl)-2-(2-fluoro-5-methylphenyl)thiazole-4-carboxamide;
((R)-5-amino-N-(5-(5-amino-3,3-difluoroazepan-1-yl)-1-methyl-1H-pyrazol-4-yl)-2-(2-fluoro-5-methylphenyl)thiazole-4-carboxamide;
(S)-5-amino-N-(5-(5-amino-3,3-difluoroazepan-1-yl)-1-methyl-1H-pyrazol-4-yl)-2-(2-fluorophenyl)thiazole-4-carboxamide;
5-Amino-2-(2-fluoro-phenyl)-thiazole-4-carboxylic acid [5-((R)-5-amino-3,3-difluoro-azepan-1-yl)-1-methyl-1H-pyrazol-4-yl]-amide;
5-amino-N-(5-((4S,5S)-4-amino-5-methoxyazepan-1-yl)-1-methyl-1H-pyrazol-4-yl)-2-(2,6-difluorophenyl)thiazole-4-carboxamide;
5-amino-N-(5-((4R,5R)-4-amino-5-methoxyazepan-1-yl)-1-methyl-1H-pyrazol-4-yl)-2-(2,6-difluorophenyl)thiazole-4-carboxamide;
(S)-5-amino-2-(2,6-difluorophenyl)-N-(5-(5-(dimethylamino)-3,3-difluoroazepan-1-yl)-1-methyl-1H-pyrazol-4-yl)thiazole-4-carboxamide;
(R)-5-amino-2-(2,6-difluorophenyl)-N-(5-(5-(dimethylamino)-3,3-difluoroazepan-1-yl)-1-methyl-1H-pyrazol-4-yl)thiazole-4-carboxamide;
3-amino-N-(5-(5-amino-3,3-difluoroazepan-1-yl)-1-methyl-1H-pyrazol-4-yl)-6-(2-fluorophenyl)picolinamide;
3-amino-N-(5-(5-amino-3,3-difluoroazepan-1-yl)-1-methyl-1H-pyrazol-4-yl)-6-(2-fluorophenyl)pyrazine-2-carboxamide;
5-amino-N-(5-((4S,5R)-4-amino-5-fluoroazepan-1-yl)-1-methyl-1H-pyrazol-4-yl)-2-(2-fluoro-5-methylphenyl)thiazole-4-carboxamide;
5-amino-N-(5-((4S,5R)-4-amino-5-fluoroazepan-1-yl)-1-methyl-1H-pyrazol-4-yl)-2-(2,5-difluorophenyl)thiazole-4-carboxamide;
5-amino-N-(5-((4S,5R)-4-amino-5-fluoroazepan-1-yl)-1-methyl-1H-pyrazol-4-yl)-2-(2-fluorophenyl)thiazole-4-carboxamide;
5-amino-N-(5-((4S,5S)-4-amino-5-fluoroazepan-1-yl)-1-methyl-1H-pyrazol-4-yl)-2-(3-fluoropyridin-2-yl)thiazole-4-carboxamide;
5-amino-N-(5-((4S,5S)-4-amino-5-fluoroazepan-1-yl)-1-methyl-1H-pyrazol-4-yl)-2-(pyridin-2-yl)thiazole-4-carboxamide;
5-Amino-2-(3-fluoro-pyridin-2-yl)-thiazole-4-carboxylic acid[5-(5-amino-3,3-difluoro-azepan-1-yl)-1-methyl-1H-pyrazol-4-yl]-amide;
5-Amino-2-pyridin-2-yl-thiazole-4-carboxylic acid[5-(5-amino-3,3-difluoro-azepan-1-yl)-1-methyl-1H-pyrazol-4-yl]-amide;
(S)-5-Amino-2-(2,6-difluorophenyl)-N-(5-(3-methylpiperazin-1-yl)-1-(2,2,2-trifluoroethyl)-1H-pyrazol-4-yl)thiazole-4-carboxamide;
5-Amino-2-(2,6-difluoro-phenyl)-thiazole-4-carboxylic acid[5-(3-amino-azepan-1-yl)-1-(2,2,2-trifluoroethyl)-1H-pyrazol-4-yl]-amide;
5-Amino-2-(2,6-difluoro-phenyl)-thiazole-4-carboxylic acid[5-(3-amino-azepan-1-yl)-1-(2,2,2-trifluoroethyl)-1H-pyrazol-4-yl]-amide;
5-Amino-2-(2,6-difluoro-phenyl)-thiazole-4-carboxylic acid[5-(3,3-difluoro-5-hydroxy-azepan-1-yl)-1-methyl-1H-pyrazol-4-yl]-amide;
5-amino-N-(5-((4S,5R)-4-amino-5-methoxyazepan-1-yl)-1-methyl-1H-pyrazol-4-yl)-2-(2,6-difluorophenyl)thiazole-4-carboxamide;
5-amino-N-(5-((3R,5R)-5-amino-3-fluoroazepan-1-yl)-1-cyclopropyl-1H-pyrazol-4-yl)-2-(2,6-difluorophenyl)thiazole-4-carboxamide;
5-amino-N-(5-((3S,5S)-5-amino-3-fluoroazepan-1-yl)-1-cyclopropyl-1H-pyrazol-4-yl)-2-(2,6-difluorophenyl)thiazole-4-carboxamide;
5-amino-N-(5-((3S,5R)-5-amino-3-fluoroazepan-1-yl)-1-cyclopropyl-1H-pyrazol-4-yl)-2-(2,6-difluorophenyl)thiazole-4-carboxamide;
5-amino-N-(5-((3R,5S)-5-amino-3-fluoroazepan-1-yl)-1-cyclopropyl-1H-pyrazol-4-yl)-2-(2,6-difluorophenyl)thiazole-4-carboxamide;
5-amino-N-(5-((4S,5R)-4-amino-5-hydroxyazepan-1-yl)-1-methyl-1H-pyrazol-4-yl)-2-(2,6-difluorophenyl)thiazole-4-carboxamide;
5-Amino-2-(2,6-difluoro-phenyl)-thiazole-4-carboxylic acid[5-(5-amino-3-methoxy-3-methyl-azepan-1-yl)-1-methyl-1H-pyrazol-4-yl]-amide; and
5-Amino-2-(2,6-difluoro-phenyl)-thiazole-4-carboxylic acid[5-(5-amino-3-hydroxy-3-methyl-azepan-1-yl)-1-methyl-1H-pyrazol-4-yl]-amide.

2. A compound 1 selected from
5-amino-N-[5-(5,8-diazaspiro[2.6]nonan-8-yl)-1-methyl-pyrazol-4-yl]-2-(2,6-difluorophenyl)thiazole-4-carboxamide;
5-amino-N-[5-(4-amino-5-methoxy-azepan-1-yl)-1-methyl-pyrazol-4-yl]-2-(2,6-difluorophenyl)thiazole-4-carboxamide;
5-amino-N-[5-(4-amino-5-methoxy-azepan-1-yl)-1-methyl-pyrazol-4-yl]-2-(2,6-difluorophenyl)thiazole-4-carboxamide;
5-amino-N-[5-(5-amino-3-methoxy-azepan-1-yl)-1-methyl-pyrazol-4-yl]-2-(2,6-difluorophenyl)thiazole-4-carboxamide;
5-amino-N-[5-(5-amino-3-methoxy-azepan-1-yl)-1-methyl-pyrazol-4-yl]-2-(2,6-difluorophenyl)thiazole-4-carboxamide;
5-amino-2-(2,6-difluorophenyl)-N-[1-methyl-5-(2-oxoazepan-1-yl)pyrazol-4-yl]thiazole-4-carboxamide;
5-amino-2-(2,6-difluorophenyl)-N-[1-methyl-5-(7-oxo-1,4-diazepan-1-yl)pyrazol-4-yl]thiazole-4-carboxamide;

5-amino-N-[5-(5-amino-3-methoxy-azepan-1-yl)-1-methyl-pyrazol-4-yl]-2-(2,6-difluorophenyl)thiazole-4-carboxamide;

5-amino-N-[5-(5-amino-3-methoxy-azepan-1-yl)-1-methyl-pyrazol-4-yl]-2-(2,6-difluorophenyl)thiazole-4-carboxamide;

5-amino-N-[5-(4-amino-5-methoxy-azepan-1-yl)-1-methyl-pyrazol-4-yl]-2-(2-pyridyl)thiazole-4-carboxamide;

5-amino-N-[5-(4-amino-5-methoxy-azepan-1-yl)-1-methyl-pyrazol-4-yl]-2-(3-fluoro-2-pyridyl)thiazole-4-carboxamide;

5-amino-N-[5-(4-amino-5-methoxy-azepan-1-yl)-1-methyl-pyrazol-4-yl]-2-(2-fluorophenyl)thiazole-4-carboxamide;

5-amino-N-[5-(4-amino-5-methoxy-azepan-1-yl)-1-methyl-pyrazol-4-yl]-2-(2-fluoro-5-methyl-phenyl)thiazole-4-carboxamide;

5-amino-N-[5-(4-amino-5-methoxy-azepan-1-yl)-1-methyl-pyrazol-4-yl]-2-(2,5-difluorophenyl)thiazole-4-carboxamide;

5-amino-N-[5-(4-amino-5-hydroxy-azepan-1-yl)-1-methyl-pyrazol-4-yl]-2-(2,6-difluorophenyl)thiazole-4-carboxamide;

5-amino-N-[5-(4-amino-5-hydroxy-azepan-1-yl)-1-methyl-pyrazol-4-yl]-2-(2,6-difluorophenyl)thiazole-4-carboxamide;

5-amino-N-[5-(4-amino-5-fluoro-azepan-1-yl)-1-cyclopropyl-pyrazol-4-yl]-2-(2-fluoro-5-methyl-phenyl)thiazole-4-carboxamide;

5-amino-N-[5-(4-amino-5-fluoro-azepan-1-yl)-1-cyclopropyl-pyrazol-4-yl]-2-(2-fluoro-5-methyl-phenyl)thiazole-4-carboxamide;

5-amino-N-[5-(4-amino-5-fluoro-azepan-1-yl)-1-cyclopropyl-pyrazol-4-yl]-2-(2,6-difluorophenyl)thiazole-4-carboxamide;

5-amino-N-[5-(4-amino-5-fluoro-azepan-1-yl)-1-cyclopropyl-pyrazol-4-yl]-2-(2,6-difluorophenyl)thiazole-4-carboxamide;

5-amino-N-[5-(4-amino-5-hydroxy-azepan-1-yl)-1-methyl-pyrazol-4-yl]-2-(2,6-difluorophenyl)thiazole-4-carboxamide;

5-amino-2-(2,6-difluorophenyl)-N-[1-methyl-5-[(4S)-4-[(3-methyloxetan-3-yl)methylamino]azepan-1-yl]pyrazol-4-yl]thiazole-4-carboxamide;

5-amino-2-(2,6-difluorophenyl)-N-[5-[(4S)-4-(2-hydroxyethylamino)azepan-1-yl]-1-methyl-pyrazol-4-yl]thiazole-4-carboxamide;

5-amino-N-[5-[(4S)-4-[bis(2-hydroxyethyl)amino]azepan-1-yl]-1-methyl-pyrazol-4-yl]-2-(2,6-difluorophenyl)thiazole-4-carboxamide;

5-amino-N-[5-(4-amino-5-hydroxy-azepan-1-yl)-1-methyl-pyrazol-4-yl]-2-(2,6-difluorophenyl)thiazole-4-carboxamide;

5-amino-N-[5-(4-amino-5-fluoro-azepan-1-yl)-1-cyclopropyl-pyrazol-4-yl]-2-(2,5-difluorophenyl)thiazole-4-carboxamide;

5-amino-N-[5-(4-amino-5-fluoro-azepan-1-yl)-1-cyclopropyl-pyrazol-4-yl]-2-(2,5-difluorophenyl)thiazole-4-carboxamide;

5-amino-2-(2,6-difluorophenyl)-N-[1-methyl-5-(5-oxo-1,4-oxazepan-4-yl)pyrazol-4-yl]thiazole-4-carboxamide;

5-amino-2-(2,6-difluorophenyl)-N-[1-methyl-5-(8-oxa-3-azabicyclo[3.2.1]octan-3-yl)pyrazol-4-yl]thiazole-4-carboxamide;

5-amino-2-(2,6-difluorophenyl)-N-[1-methyl-5-[(4S)-4-(oxetan-3-ylmethylamino)azepan-1-yl]pyrazol-4-yl]thiazole-4-carboxamide;

5-amino-N-[5-[(4S)-4-[bis(oxetan-3-ylmethyl)amino]azepan-1-yl]-1-methyl-pyrazol-4-yl]-2-(2,6-difluorophenyl)thiazole-4-carboxamide;

5-amino-N-[5-[(5S)-5-amino-3,3-difluoro-azepan-1-yl]-1-cyclopropyl-pyrazol-4-yl]-2-(2,6-difluorophenyl)thiazole-4-carboxamide;

5-amino-N-[5-[(5R)-5-amino-3,3-difluoro-azepan-1-yl]-1-cyclopropyl-pyrazol-4-yl]-2-(2,6-difluorophenyl)thiazole-4-carboxamide;

5-amino-N-[5-[(5R)-5-amino-3,3-difluoro-azepan-1-yl]-1-methyl-pyrazol-4-yl]-2-(2,6-difluoro-3-iodo-phenyl)thiazole-4-carboxamide;

5-amino-N-[5-[(5S)-5-amino-3,3-difluoro-azepan-1-yl]-1-methyl-pyrazol-4-yl]-2-(2,6-difluoro-3-iodo-phenyl)thiazole-4-carboxamide;

5-amino-N-(5-((4S,5S)-4-amino-5-fluoroazepan-1-yl)-1-ethyl-1H-pyrazol-4-yl)-2-(2,6-difluorophenyl)thiazole-4-carboxamide;

5-amino-N-[5-(3-azabicyclo[3.2.1]octan-3-yl)-1-methyl-pyrazol-4-yl]-2-(2,6-difluorophenyl)thiazole-4-carboxamide;

5-amino-2-(2,6-difluorophenyl)-N-[5-(1,1-dioxo-1,4-thiazepan-4-yl)-1-methyl-pyrazol-4-yl]thiazole-4-carboxamide;

5-amino-N-[5-(1,9-diazaspiro[4.6]undecan-9-yl)-1-methyl-pyrazol-4-yl]-2-(2,6-difluorophenyl)thiazole-4-carboxamide;

5-amino-N-[5-(5-amino-3-methoxy-3-methyl-azepan-1-yl)-1-methyl-pyrazol-4-yl]-2-(2,6-difluorophenyl)thiazole-4-carboxamide;

5-amino-N-[5-(5-amino-3-methoxy-3-methyl-azepan-1-yl)-1-methyl-pyrazol-4-yl]-2-(2,6-difluorophenyl)thiazole-4-carboxamide;

5-amino-2-(2,6-difluorophenyl)-N-[1-methyl-5-(9-oxa-3,7-diazabicyclo[3.3.1]nonan-3-yl)pyrazol-4-yl]thiazole-4-carboxamide;

5-amino-2-(2,6-difluorophenyl)-N-[5-[6-(hydroxymethyl)-1,4-diazepan-1-yl]-1-methyl-pyrazol-4-yl]thiazole-4-carboxamide;

5-amino-2-(2,6-difluorophenyl)-N-[5-[6-(hydroxymethyl)-1,4-diazepan-1-yl]-1-methyl-pyrazol-4-yl]thiazole-4-carboxamide;

5-amino-N-(5-((4R,5R)-4-amino-5-fluorocycloheptyl)-1-methyl-1H-pyrazol-4-yl)-2-(2,6-difluorophenyl)thiazole-4-carboxamide;

5-amino-N-(5-((4R,5R)-4-amino-5-fluorocycloheptyl)-1-methyl-1H-pyrazol-4-yl)-2-(2,6-difluorophenyl)thiazole-4-carboxamide;

5-amino-N-[5-(2,6-diazaspiro[3.4]octan-6-yl)-1-methyl-pyrazol-4-yl]-2-(2,6-difluorophenyl)thiazole-4-carboxamide;

5-amino-2-(2,6-difluorophenyl)-N-[1-methyl-5-(1-oxo-2,8-diazaspiro[4.5]decan-8-yl)pyrazol-4-yl]thiazole-4-carboxamide;

5-amino-N-[5-(2,7-diazaspiro[3.4]octan-2-yl)-1-methyl-pyrazol-4-yl]-2-(2,6-difluorophenyl)thiazole-4-carboxamide;

5-amino-N[5-[4-(azetidin-3-yl)-1,4-diazepan-1-yl]-1-methyl-pyrazol-4-yl]-2-(2,6-difluorophenyl)thiazole-4-carboxamide;

5-amino-N-[5-(3,3-difluorocycloheptyl)-1-methyl-pyrazol-4-yl]-2-(2,6-difluorophenyl)thiazole-4-carboxamide;

5-amino-N-(5-((4S,5S)-4-amino-5-methoxyazepan-1-yl)-1-ethyl-1H-pyrazol-4-yl)-2-(2,6-difluorophenyl)thiazole-4-carboxamide;
5-amino-N-(5-((4S,5S)-4-amino-5-methoxyazepan-1-yl)-1-cyclopropyl-1H-pyrazol-4-yl)-2-(2,6-difluorophenyl)thiazole-4-carboxamide;
5-amino-N-[5-(3,3-difluorocycloheptyl)-1-methyl-pyrazol-4-yl]-2-(2,6-difluorophenyl)thiazole-4-carboxamide;
(S)-5-amino-2-(2,6-difluorophenyl)-N-(1-methyl-5-(2-oxo-1,8-diazaspiro[4.6]undecan-8-yl)-1H-pyrazol-4-yl)thiazole-4-carboxamide;
(R)-5-amino-2-(2,6-difluorophenyl)-N-[1-methyl-5-(2-oxo-1,9-diazaspiro[4.6]undecan-9-yl)pyrazol-4-yl]thiazole-4-carboxamide;
5-amino-N-[5-(4-amino-5-fluoro-azepan-1-yl)-1-ethyl-pyrazol-4-yl]-2-(2,6-difluorophenyl)thiazole-4-carboxamide;
5-amino-N-[5-(4-amino-5-fluoro-azepan-1-yl)-1-ethyl-pyrazol-4-yl]-2-(2,6-difluorophenyl)thiazole-4-carboxamide;
5-amino-N-[5-(3,3-difluoro-5-hydroxy-azepan-1-yl)-1-methyl-pyrazol-4-yl]-2-(2,6-difluorophenyl)thiazole-4-carboxamide;
5-amino-N-[5-(3,3-difluoro-5-hydroxy-azepan-1-yl)-1-methyl-pyrazol-4-yl]-2-(2,6-difluorophenyl)thiazole-4-carboxamide;
5-amino-N-[5-(4-amino-5-fluoro-azepan-1-yl)-1-ethyl-pyrazol-4-yl]-2-(2-fluorophenyl)thiazole-4-carboxamide;
5-amino-N-[5-(4-amino-5-fluoro-azepan-1-yl)-1-ethyl-pyrazol-4-yl]-2-(2-fluorophenyl)thiazole-4-carboxamide;
5-amino-N-(5-((4S,5R)-4-amino-5-hydroxyazepan-1-yl)-1-(2,2-difluoroethyl)-1H-pyrazol-4-yl)-2-(2,6-difluorophenyl)thiazole-4-carboxamide;
5-amino-N-(5-((4S,5R)-4-amino-5-methoxyazepan-1-yl)-1-ethyl-1H-pyrazol-4-yl)-2-(2,6-difluorophenyl)thiazole-4-carboxamide;
5-amino-N-(5-((4R,5S)-4-amino-5-fluorocycloheptyl)-1-methyl-1H-pyrazol-4-yl)-2-(2,6-difluorophenyl)thiazole-4-carboxamide;
N-[5-(4-acetamido-4-methyl-azepan-1-yl)-1-methyl-pyrazol-4-yl]-5-amino-2-(2,6-difluorophenyl)thiazole-4-carboxamide;
5-amino-N-(5-((4R,5R)-4-amino-5-fluorocycloheptyl)-1-methyl-1H-pyrazol-4-yl)-2-(2,6-difluorophenyl)thiazole-4-carboxamide;
5-amino-N-(5-((4R,5S)-4-amino-5-fluorocycloheptyl)-1-methyl-1H-pyrazol-4-yl)-2-(2,6-difluorophenyl)thiazole-4-carboxamide;
5-amino-N-(5-((4R,5S)-4-amino-5-fluorocycloheptyl)-1-methyl-1H-pyrazol-4-yl)-2-(2,6-difluorophenyl)thiazole-4-carboxamide;
5-amino-N-[5-(6-cyano-1,4-diazepan-1-yl)-1-methyl-pyrazol-4-yl]-2-(2,6-difluorophenyl)thiazole-4-carboxamide;
5-amino-N-(5-cycloheptyl-1-methyl-pyrazol-4-yl)-2-(2,6-difluorophenyl)thiazole-4-carboxamide;
N-[5-(4-acetamido-4-methyl-azepan-1-yl)-1-methyl-pyrazol-4-yl]-5-amino-2-(3-fluoro-2-pyridyl)thiazole-4-carboxamide;
5-amino-N-[5-(4-amino-5-ethoxy-azepan-1-yl)-1-methyl-pyrazol-4-yl]-2-(2,6-difluorophenyl)thiazole-4-carboxamide;
5-amino-N-(5-((4S,5R)-4-amino-5-methoxyazepan-1-yl)-1-cyclopropyl-1H-pyrazol-4-yl)-2-(2,6-difluorophenyl)thiazole-4-carboxamide;
5-amino-N-(5-((4S,5R)-4-amino-5-fluoroazepan-1-yl)-1-methyl-1H-pyrazol-4-yl)-2-(pyridin-2-yl)thiazole-4-carboxamide;
5-amino-N-(5-((4S,5R)-4-amino-5-fluoroazepan-1-yl)-1-methyl-1H-pyrazol-4-yl)-2-(3-fluoropyridin-2-yl)thiazole-4-carboxamide;
5-amino-N-[5-(4-amino-5-methoxy-azepan-1-yl)-1-ethyl-pyrazol-4-yl]-2-(2,6-difluorophenyl)thiazole-4-carboxamide;
5-amino-N-[5-(4-amino-5-methoxy-azepan-1-yl)-1-ethyl-pyrazol-4-yl]-2-(2,6-difluorophenyl)thiazole-4-carboxamide;
5-amino-N-[5-(4-amino-5-methoxy-azepan-1-yl)-1-ethyl-pyrazol-4-yl]-2-(2-fluorophenyl)thiazole-4-carboxamide;
5-amino-N-[5-(4-amino-5-methoxy-azepan-1-yl)-1-ethyl-pyrazol-4-yl]-2-(2-fluorophenyl)thiazole-4-carboxamide;
5-amino-N-[5-[(4S)-4-aminoazepan-1-yl]-1-methyl-pyrazol-4-yl]-2-(6-hydroxy-2-pyridyl)thiazole-4-carboxamide;
5-amino-N-[5-[4-(2-aminoacetyl)-1,4-diazepan-1-yl]-1-methyl-pyrazol-4-yl]-2-(2,6-difluorophenyl)thiazole-4-carboxamide;
5-amino-N-[5-[4-(2-aminoethyl)-1,4-diazepan-1-yl]-1-methyl-pyrazol-4-yl]-2-(2,6-difluorophenyl)thiazole-4-carboxamide;
N-[5-(3,4,4a,5,6,8,9,9a-octahydro-2H-[1,4]oxazino[2,3-d]azepin-7-yl)-1-methyl-pyrazol-4-yl]-5-amino-2-(2,6-difluorophenyl)thiazole-4-carboxamide;
N-[5-(3,4,4a,5,6,8,9,9a-octahydro-2H-[1,4]oxazino[2,3-d]azepin-7-yl)-1-methyl-pyrazol-4-yl]-5-amino-2-(2,6-difluorophenyl)thiazole-4-carboxamide;
5-amino-N-[5-(4-amino-5-hydroxy-azepan-1-yl)-1-(2,2-difluoroethyl)pyrazol-4-yl]-2-(2,6-difluorophenyl)thiazole-4-carboxamide;
5-amino-N-[5-(4-amino-5-hydroxy-azepan-1-yl)-1-(2,2-difluoroethyl)pyrazol-4-yl]-2-(2,6-difluorophenyl)thiazole-4-carboxamide;
5-amino-N-[5-(4-amino-3-fluoro-azepan-1-yl)-1-methyl-pyrazol-4-yl]-2-(2,6-difluorophenyl)thiazole-4-carboxamide;
5-amino-N-[5-(4-amino-5-methoxy-azepan-1-yl)-1-cyclopropyl-pyrazol-4-yl]-2-(2,6-difluorophenyl)thiazole-4-carboxamide;
5-amino-N-[5-(4-amino-5-methoxy-azepan-1-yl)-1-cyclopropyl-pyrazol-4-yl]-2-(2,6-difluorophenyl)thiazole-4-carboxamide;
5-amino-N-[5-(4-amino-5-methoxy-azepan-1-yl)-1-cyclopropyl-pyrazol-4-yl]-2-(2,6-difluorophenyl)thiazole-4-carboxamide;
5-amino-N-[5-(4-amino-5-methoxy-azepan-1-yl)-1-cyclopropyl-pyrazol-4-yl]-2-(2,6-difluorophenyl)thiazole-4-carboxamide;
5-amino-2-(2,6-difluorophenyl)-N-[5-[4-hydroxy-4-(trifluoromethyl)azepan-1-yl]-1-methyl-pyrazol-4-yl]thiazole-4-carboxamide;
5-amino-N-[5-(4-amino-5-methoxy-azepan-1-yl)-1-ethyl-pyrazol-4-yl]-2-(2,6-difluorophenyl)thiazole-4-carboxamide;
5-amino-N-[5-(4-amino-5-methoxy-azepan-1-yl)-1-ethyl-pyrazol-4-yl]-2-(2,6-difluorophenyl)thiazole-4-carboxamide;

5-amino-N-[5-[3,3-difluoro-5-(methylamino)azepan-1-yl]-1-methyl-pyrazol-4-yl]-2-(2,6-difluorophenyl)thiazole-4-carboxamide;
5-amino-N-[5-[3,3-difluoro-5-(methylamino)azepan-1-yl]-1-methyl-pyrazol-4-yl]-2-(2,6-difluorophenyl)thiazole-4-carboxamide;
5-amino-N-(5-((4S,5S)-5-amino-4-methoxycyclohept-1-enyl)-1-methyl-1H-pyrazol-4-yl)-2-(2,6-difluorophenyl)thiazole-4-carboxamide;
5-amino-N-[5-(4-amino-4-methyl-azepan-1-yl)-1-methyl-pyrazol-4-yl]-2-(2,6-difluorophenyl)thiazole-4-carboxamide;
5-amino-N-[5-(4-amino-4-methyl-azepan-1-yl)-1-methyl-pyrazol-4-yl]-2-(2-fluorophenyl)thiazole-4-carboxamide;
5-amino-N-(5-((4S,5S)-4-amino-5-methoxycycloheptyl)-1-methyl-1H-pyrazol-4-yl)-2-(2-fluorophenyl)thiazole-4-carboxamide;
5-amino-N-(5-((4S,5S)-4-amino-5-methoxycycloheptyl)-1-methyl-1H-pyrazol-4-yl)-2-(2-fluorophenyl)thiazole-4-carboxamide;
5-amino-N-(5-((4S,5S)-4-amino-5-methoxycycloheptyl)-1-methyl-1H-pyrazol-4-yl)-2-(2-fluorophenyl)thiazole-4-carboxamide;
5-amino-N-(5-((4S,5S)-4-amino-5-methoxycycloheptyl)-1-methyl-1H-pyrazol-4-yl)-2-(2-fluorophenyl)thiazole-4-carboxamide;
5-amino-N-[5-[(4S)-4-aminoazepan-1-yl]-1-methyl-pyrazol-4-yl]-2-(2-fluoro-4-pyridyl)thiazole-4-carboxamide;
5-amino-N-[5-[(4S)-4-aminoazepan-1-yl]-1-methyl-pyrazol-4-yl]-2-(2-methoxy-3-pyridyl)thiazole-4-carboxamide;
5-amino-N-[5-[(4S)-4-aminoazepan-1-yl]-1-methyl-pyrazol-4-yl]-2-(1-methylpyrazol-4-yl)thiazole-4-carboxamide;
5-amino-N-[5-[(4S)-4-aminoazepan-1-yl]-1-methyl-pyrazol-4-yl]-2-(5-fluoro-3-pyridyl)thiazole-4-carboxamide;
5-amino-N-[5-[(4S)-4-aminoazepan-1-yl]-1-methyl-pyrazol-4-yl]-2-(3,5-dimethylisoxazol-4-yl)thiazole-4-carboxamide;
5-amino-N-(5-((4S,5S)-4-amino-5-fluoroazepan-1-yl)-1-methyl-1H-pyrazol-4-yl)-2-(3-fluoropyridin-4-yl)thiazole-4-carboxamide;
5-amino-2-(2-fluorophenyl)-N-[5-(2-methoxy-8-azabicyclo[3.2.1]octan-5-yl)-1-methyl-pyrazol-4-yl]thiazole-4-carboxamide;
5-amino-N-(5-((4S,5S)-4-amino-5-hydroxy-4-methylazepan-1-yl)-1-methyl-1H-pyrazol-4-yl)-2-(2,6-difluorophenyl)thiazole-4-carboxamide;
5-amino-N-[5-[(4S)-4-aminoazepan-1-yl]-1-methyl-pyrazol-4-yl]-2-(2-fluoro-5-methyl-3-pyridyl)thiazole-4-carboxamide;
5-amino-N-[5-(5-amino-3,3-difluoro-azepan-1-yl)-1-methyl-pyrazol-4-yl]-2-(3-fluoro-4-pyridyl)thiazole-4-carboxamide;
5-amino-N-[5-[(4S)-4-aminoazepan-1-yl]-1-methyl-pyrazol-4-yl]-2-(2-methoxy-4-methyl-3-pyridyl)thiazole-4-carboxamide;
5-amino-N-[5-[(4R,5R)-4-amino-5-fluoro-azepan-1-yl]-1-methyl-pyrazol-4-yl]-2-(4-methyl-3-pyridyl)thiazole-4-carboxamide;
5-amino-N-[5-[(4R,5R)-4-amino-5-fluoro-azepan-1-yl]-1-methyl-pyrazol-4-yl]-2-(1,5-dimethylpyrazol-4-yl)thiazole-4-carboxamide;
5-amino-N-[5-[(4R,5R)-4-amino-5-fluoro-azepan-1-yl]-1-methyl-pyrazol-4-yl]-2-(2-methyl-3-pyridyl)thiazole-4-carboxamide;
5-amino-N-[5-[(4R,5R)-4-amino-5-fluoro-azepan-1-yl]-1-methyl-pyrazol-4-yl]-2-(2-methyl-4-pyridyl)thiazole-4-carboxamide;
5-amino-N-[5-[(4R,5R)-4-amino-5-fluoro-azepan-1-yl]-1-methyl-pyrazol-4-yl]-2-(6-cyano-2-pyridyl)thiazole-4-carboxamide;
5-amino-N-[5-(4-amino-4-methyl-azepan-1-yl)-1-methyl-pyrazol-4-yl]-2-(2-fluorophenyl)thiazole-4-carboxamide;
5-amino-N-[5-(4-amino-4-methyl-azepan-1-yl)-1-methyl-pyrazol-4-yl]-2-(2-fluorophenyl)thiazole-4-carboxamide;
5-amino-N-[5-(4-amino-4-methyl-azepan-1-yl)-1-methyl-pyrazol-4-yl]-2-(2,6-difluorophenyl)thiazole-4-carboxamide;
5-amino-N-[5-(4-amino-4-methyl-azepan-1-yl)-1-methyl-pyrazol-4-yl]-2-(2,6-difluorophenyl)thiazole-4-carboxamide;
5-amino-N-[5-[(4R,5R)-4-amino-5-fluoro-azepan-1-yl]-1-methyl-pyrazol-4-yl]-2-(1,3-dimethylpyrazol-4-yl)thiazole-4-carboxamide;
5-amino-N-[5-(5-amino-3,3-difluoro-azepan-1-yl)-1-methyl-pyrazol-4-yl]-2-(3,5-difluoro-4-pyridyl)thiazole-4-carboxamide;
5-amino-N-(5-((4S,5S)-4-amino-5-fluoroazepan-1-yl)-1-methyl-1H-pyrazol-4-yl)-2-(3,5-difluoropyridin-4-yl)thiazole-4-carboxamide;
5-amino-N-[5-(5-amino-3-methoxy-3-methyl-azepan-1-yl)-1-methyl-pyrazol-4-yl]-2-(3,5-difluoro-4-pyridyl)thiazole-4-carboxamide;
5-amino-N-[5-(5-amino-3-methoxy-3-methyl-azepan-1-yl)-1-methyl-pyrazol-4-yl]-2-(3-fluoro-4-pyridyl)thiazole-4-carboxamide;
5-amino-N-[5-[(4R,5R)-4-amino-5-fluoro-azepan-1-yl]-1-methyl-pyrazol-4-yl]-2-(5-cyano-2-fluoro-phenyl)thiazole-4-carboxamide;
5-amino-N-[5-[(4R,5R)-4-amino-5-fluoro-azepan-1-yl]-1-methyl-pyrazol-4-yl]-2-(2,6-dimethyl-4-pyridyl)thiazole-4-carboxamide;
5-amino-N-[5-[(4R,5R)-4-amino-5-fluoro-azepan-1-yl]-1-methyl-pyrazol-4-yl]-2-(5-cyano-3-pyridyl)thiazole-4-carboxamide;
5-amino-N-[5-[(4R,5R)-4-amino-5-fluoro-azepan-1-yl]-1-methyl-pyrazol-4-yl]-2-(2,5-dimethyl-3-pyridyl)thiazole-4-carboxamide;
5-amino-N-[5-[(5S)-5-amino-3,3-difluoro-azepan-1-yl]-1-methyl-pyrazol-4-yl]-2-(3-fluoro-4-pyridyl)thiazole-4-carboxamide;
5-amino-N-[5-[(5R)-5-amino-3,3-difluoro-azepan-1-yl]-1-methyl-pyrazol-4-yl]-2-(3-fluoro-4-pyridyl)thiazole-4-carboxamide;
5-amino-N-[5-(6-amino-1-oxa-9-azaspiro[3.6]decan-9-yl)-1-methyl-pyrazol-4-yl]-2-(2,6-difluorophenyl)thiazole-4-carboxamide;
5-amino-N-[5-[(5R)-5-amino-3-methylene-azepan-1-yl]-1-methyl-pyrazol-4-yl]-2-(2,6-difluorophenyl)thiazole-4-carboxamide;
5-amino-N-[5-[(4S,5S)-4-amino-5-fluoro-azepan-1-yl]-1-(trideuteriomethyl)pyrazol-4-yl]-2-(2,6-difluorophenyl)thiazole-4-carboxamide;
5-amino-N-[5-[(4R,5R)-4-amino-5-fluoro-azepan-1-yl]-1-(trideuteriomethyl)pyrazol-4-yl]-2-(2,6-difluorophenyl)thiazole-4-carboxamide;

5-amino-N-[5-(6-amino-1-oxa-9-azaspiro[3.6]decan-9-yl)-1-methyl-pyrazol-4-yl]-2-(2,6-difluorophenyl)thiazole-4-carboxamide;

5-amino-N-[5-(5-amino-3-methyl-azepan-1-yl)-1-methyl-pyrazol-4-yl]-2-(2,6-difluorophenyl)thiazole-4-carboxamide;

5-amino-N-[5-[(5S)-5-amino-3,3-difluoro-azepan-1-yl]-1-methyl-pyrazol-4-yl]-2-(3,5-difluoro-4-pyridyl)thiazole-4-carboxamide;

5-amino-N-[5-[(5R)-5-amino-3,3-difluoro-azepan-1-yl]-1-methyl-pyrazol-4-yl]-2-(3,5-difluoro-4-pyridyl)thiazole-4-carboxamide;

5-amino-N-[5-(5-amino-3-hydroxy-3-methyl-cycloheptyl)-1-methyl-pyrazol-4-yl]-2-(2,6-difluorophenyl)thiazole-4-carboxamide;

5-amino-2-(2,6-difluorophenyl)-N-(5-((4R,5S)-4,5-dihydroxyazepan-1-yl)-1-methyl-1H-pyrazol-4-yl)thiazole-4-carboxamide;

5-amino-N-[5-[4-(aminomethyl)-4-methoxy-1-piperidyl]-1-methyl-pyrazol-4-yl]-2-(2,6-difluorophenyl)thiazole-4-carboxamide;

5-amino-N-[5-(5-amino-3,3-difluoro-azepan-1-yl)-1-methyl-pyrazol-4-yl]-2-(2,6-difluoro-4-methoxy-phenyl)thiazole-4-carboxamide;

5-amino-N-[5-(5-amino-3,3-difluoro-azepan-1-yl)-1-methyl-pyrazol-4-yl]-2-(1,5-dimethylpyrazol-4-yl)thiazole-4-carboxamide;

5-amino-N-[5-[(5R)-5-amino-3,3-difluoro-azepan-1-yl]-1-methyl-pyrazol-4-yl]-2-(6-cyano-2-pyridyl)thiazole-4-carboxamide;

5-amino-N-[5-[(5R)-5-amino-3,3-difluoro-azepan-1-yl]-1-methyl-pyrazol-4-yl]-2-(1,3-dimethylpyrazol-4-yl)thiazole-4-carboxamide;

5-amino-N-[5-[(5R)-5-amino-3,3-difluoro-azepan-1-yl]-1-methyl-pyrazol-4-yl]-2-(1,5-dimethylpyrazol-4-yl)thiazole-4-carboxamide;

5-amino-N-[5-[(5R)-5-amino-3,3-difluoro-azepan-1-yl]-1-methyl-pyrazol-4-yl]-2-(2-methyl-4-pyridyl)thiazole-4-carboxamide;

5-amino-N-[5-(5-amino-3-hydroxy-3-methyl-cycloheptyl)-1-methyl-pyrazol-4-yl]-2-(2,6-difluorophenyl)thiazole-4-carboxamide;

5-amino-N-[5-(5-amino-3-hydroxy-3-methyl-cycloheptyl)-1-methyl-pyrazol-4-yl]-2-(2,6-difluorophenyl)thiazole-4-carboxamide;

5-amino-N-[5-(5-amino-3-hydroxy-3-methyl-cycloheptyl)-1-methyl-pyrazol-4-yl]-2-(2,6-difluorophenyl)thiazole-4-carboxamide;

5-amino-N-[5-(5-amino-3-hydroxy-3-methyl-cycloheptyl)-1-methyl-pyrazol-4-yl]-2-(2,6-difluorophenyl)thiazole-4-carboxamide;

5-amino-N-[5-(5-amino-3-hydroxy-3-methyl-cycloheptyl)-1-methyl-pyrazol-4-yl]-2-(2,6-difluorophenyl)thiazole-4-carboxamide;

5-amino-N-[5-(5-amino-3-hydroxy-3-methyl-cycloheptyl)-1-methyl-pyrazol-4-yl]-2-(2,6-difluorophenyl)thiazole-4-carboxamide;

5-amino-N-[5-[(4S,5S)-4-amino-5-fluoro-azepan-1-yl]-1-methyl-pyrazol-4-yl]-2-(3,5-difluoro-4-pyridyl)thiazole-4-carboxamide;

5-amino-N-[5-[(4R,5R)-4-amino-5-fluoro-azepan-1-yl]-1-methyl-pyrazol-4-yl]-2-(3,5-difluoro-4-pyridyl)thiazole-4-carboxamide;

5-amino-N-[5-(5-amino-3-methoxy-3-methyl-azepan-1-yl)-1-methyl-pyrazol-4-yl]-2-(3,5-difluoro-4-pyridyl)thiazole-4-carboxamide;

5-amino-N-[5-(5-amino-3-methoxy-3-methyl-azepan-1-yl)-1-methyl-pyrazol-4-yl]-2-(3,5-difluoro-4-pyridyl)thiazole-4-carboxamide;

5-amino-N-[5-(5-amino-3-methoxy-3-methyl-azepan-1-yl)-1-methyl-pyrazol-4-yl]-2-(3-fluoro-4-pyridyl)thiazole-4-carboxamide;

5-amino-N-[5-(5-amino-3-methoxy-3-methyl-azepan-1-yl)-1-methyl-pyrazol-4-yl]-2-(3-fluoro-4-pyridyl)thiazole-4-carboxamide;

5-amino-2-(2-fluorophenyl)-N-[1-methyl-5-(1-oxa-6,9-diazaspiro[3.6]decan-6-yl)pyrazol-4-yl]thiazole-4-carboxamide;

5-amino-2-(2,6-difluorophenyl)-N-[1-methyl-5-(1-oxa-6,9-diazaspiro[3.6]decan-6-yl)pyrazol-4-yl]thiazole-4-carboxamide;

5-amino-N-[5-[4-(aminomethyl)-4-hydroxy-1-piperidyl]-1-methyl-pyrazol-4-yl]-2-(2,6-difluorophenyl)thiazole-4-carboxamide;

(R)-5-amino-2-(2-fluorophenyl)-N-(1-methyl-5-(1-oxa-6,9-diazaspiro[3.6]decan-6-yl)-1H-pyrazol-4-yl)thiazole-4-carboxamide;

(S)-5-amino-2-(2-fluorophenyl)-N-(1-methyl-5-(1-oxa-6,9-diazaspiro[3.6]decan-6-yl)-1H-pyrazol-4-yl)thiazole-4-carboxamide;

(R)-5-amino-2-(2,6-difluorophenyl)-N-(1-methyl-5-(1-oxa-6,9-diazaspiro[3.6]decan-6-yl)-1H-pyrazol-4-yl)thiazole-4-carboxamide;

(S)-5-amino-2-(2,6-difluorophenyl)-N-(1-methyl-5-(1-oxa-6,9-diazaspiro[3.6]decan-6-yl)-1H-pyrazol-4-yl)thiazole-4-carboxamide;

5-amino-2-(2,6-difluorophenyl)-N-[1-methyl-5-(1-oxa-4,9-diazaspiro[5.5]undecan-9-yl)pyrazol-4-yl]thiazole-4-carboxamide;

5-amino-N-[5-(5-amino-4-methoxy-4-methyl-azepan-1-yl)-1-methyl-pyrazol-4-yl]-2-(2,6-difluorophenyl)thiazole-4-carboxamide;

N-[5-[(3aR,8aS)-2-oxo-3a,4,5,7,8,8a-hexahydro-3H-oxazolo[4,5-d]azepin-6-yl]-1-methyl-pyrazol-4-yl]-5-amino-2-(2,6-difluorophenyl)thiazole-4-carboxamide;

[(4S,5R)-5-amino-1-[4-[[5-amino-2-(2,6-difluorophenyl)thiazole-4-carbonyl]amino]-2-methyl-pyrazol-3-yl]azepan-4-yl]acetate;

N-[5-[(3aS,8aR)-2-oxo-3a,4,5,7,8,8a-hexahydro-3H-oxazolo[4,5-d]azepin-6-yl]-1-methyl-pyrazol-4-yl]-5-amino-2-(2,6-difluorophenyl)thiazole-4-carboxamide;

[(4R,5S)-5-amino-1-[4-[[5-amino-2-(2,6-difluorophenyl)thiazole-4-carbonyl]amino]-2-methyl-pyrazol-3-yl]azepan-4-yl]acetate;

5-amino-2-(2,6-difluorophenyl)-N-(5-((4R,5R)-4,5-dihydroxyazepan-1-yl)-1-methyl-1H-pyrazol-4-yl)thiazole-4-carboxamide;

5-amino-N-[5-[4-amino-5-(trideuteriomethoxy)azepan-1-yl]-1-methyl-pyrazol-4-yl]-2-(2-fluorophenyl)thiazole-4-carboxamide;

5-amino-N-[5-[4-amino-5-(trideuteriomethoxy)azepan-1-yl]-1-methyl-pyrazol-4-yl]-2-(2,6-difluorophenyl)thiazole-4-carboxamide;

5-amino-N-[5-[(5S)-5-amino-3,3-difluoro-azepan-1-yl]-1-(trideuteriomethyl)pyrazol-4-yl]-2-(2,6-difluorophenyl)thiazole-4-carboxamide;

5-amino-N-[5-[(5R)-5-amino-3,3-difluoro-azepan-1-yl]-1-(trideuteriomethyl)pyrazol-4-yl]-2-(2,6-difluorophenyl)thiazole-4-carboxamide;

5-amino-N-[5-(5-amino-3,3-difluoro-5-methyl-azepan-1-yl)-1-methyl-pyrazol-4-yl]-2-(2,6-difluorophenyl)thiazole-4-carboxamide;

5-amino-N-(5-((3S,4R)-4-(aminomethyl)-3-ethyl-4-methoxypiperidin-1-yl)-1-methyl-1H-pyrazol-4-yl)-2-(2,6-difluorophenyl)thiazole-4-carboxamide;

5-amino-N-[5-(5-amino-1-oxa-8-azaspiro[3.6]decan-8-yl)-1-methyl-pyrazol-4-yl]-2-(2,6-difluorophenyl)thiazole-4-carboxamide;

5-amino-N-[5-(5-amino-1-oxa-8-azaspiro[3.6]decan-8-yl)-1-methyl-pyrazol-4-yl]-2-(2,6-difluorophenyl)thiazole-4-carboxamide;

5-amino-N-(5-((1R,5R,6S)-6-amino-8-oxa-3-azabicyclo[3.2.1]octan-3-yl)-1-methyl-1H-pyrazol-4-yl)-2-(2,6-difluorophenyl)thiazole-4-carboxamide;

5-amino-N-[5-[5-amino-4-hydroxy-4-(2-hydroxyethyl)azepan-1-yl]-1-methyl-pyrazol-4-yl]-2-(2,6-difluorophenyl)thiazole-4-carboxamide;

5-amino-N-[5-(5-amino-1-oxa-8-azaspiro[3.6]decan-8-yl)-1-methyl-pyrazol-4-yl]-2-(2,6-difluorophenyl)thiazole-4-carboxamide;

5-amino-N-[5-(5-amino-4-methoxy-4-methyl-azepan-1-yl)-1-methyl-pyrazol-4-yl]-2-(2,6-difluorophenyl)thiazole-4-carboxamide;

5-amino-N-[5-(5-amino-4-methoxy-4-methyl-azepan-1-yl)-1-methyl-pyrazol-4-yl]-2-(2,6-difluorophenyl)thiazole-4-carboxamide;

5-amino-N-[5-(4-amino-5-methoxy-cycloheptyl)-1-methyl-pyrazol-4-yl]-2-(2-fluorophenyl)thiazole-4-carboxamide;

5-amino-N-[5-(4-amino-5-methoxy-cycloheptyl)-1-methyl-pyrazol-4-yl]-2-(2-fluorophenyl)thiazole-4-carboxamide;

5-amino-N-[5-(4-amino-5-methoxy-cycloheptyl)-1-methyl-pyrazol-4-yl]-2-(2-fluorophenyl)thiazole-4-carboxamide;

5-amino-N-[5-(4-amino-5-methoxy-cycloheptyl)-1-methyl-pyrazol-4-yl]-2-(2-fluorophenyl)thiazole-4-carboxamide;

5-amino-N-[5-(2,6-diazaspiro[3.5]nonan-6-yl)-1-methyl-pyrazol-4-yl]-2-(2,6-difluorophenyl)thiazole-4-carboxamide;

5-amino-2-(2,6-difluorophenyl)-N-(1-methyl-5-((3aR,8aS)-3 a-methyl-2-oxotetrahydro-2H-oxazolo[5,4-d]azepin-6(7H,8H,8aH)-yl)-1H-pyrazol-4-yl)thiazole-4-carboxamide;

5-amino-N-[5-(5-amino-1-oxa-8-azaspiro[3.6]decan-8-yl)-1-methyl-pyrazol-4-yl]-2-(2,6-difluorophenyl)thiazole-4-carboxamide;

5-amino-N-[5-[4-amino-5-(difluoromethyl)azepan-1-yl]-1-methyl-pyrazol-4-yl]-2-(2,6-difluorophenyl)thiazole-4-carboxamide;

5-amino-N-[5-[4-amino-5-(difluoromethyl)azepan-1-yl]-1-methyl-pyrazol-4-yl]-2-(2,6-difluorophenyl)thiazole-4-carboxamide;

5-amino-N-[5-[4-amino-5-(hydroxymethyl)azepan-1-yl]-1-methyl-pyrazol-4-yl]-2-(2,6-difluorophenyl)thiazole-4-carboxamide;

5-amino-N-[5-(4-amino-5-ethoxy-azepan-1-yl)-1-methyl-pyrazol-4-yl]-2-(2,6-difluorophenyl)thiazole-4-carboxamide;

5-amino-N-[5-(4-amino-5-ethoxy-azepan-1-yl)-1-methyl-pyrazol-4-yl]-2-(2,6-difluorophenyl)thiazole-4-carboxamide;

5-amino-N-(5-((8R,9S)-8-amino-9-methoxy-5-azaspiro[2.6]nonan-5-yl)-1-methyl-1H-pyrazol-4-yl)-2-(2,6-difluorophenyl)thiazole-4-carboxamide;

5-amino-N-(5-((8R,9S)-9-amino-8-methoxy-5-azaspiro[2.6]nonan-5-yl)-1-methyl-1H-pyrazol-4-yl)-2-(2,6-difluorophenyl)thiazole-4-carboxamide;

(R)-5-amino-N-(5-(5-amino-3,3-difluoro-5-methylazepan-1-yl)-1-methyl-1H-pyrazol-4-yl)-2-(2,6-difluorophenyl)thiazole-4-carboxamide;

5-amino-N-(5-(4-amino-5-fluoro-4-methylazepan-1-yl)-1-methyl-1H-pyrazol-4-yl)-2-(2,6-difluorophenyl)thiazole-4-carboxamide;

5-amino-N-(5-(8-amino-9-methoxy-5-azaspiro[2.6]nonan-5-yl)-1-methyl-1H-pyrazol-4-yl)-2-(2,6-difluorophenyl)thiazole-4-carboxamide;

5-amino-N-(5-(8-amino-9-methoxy-5-azaspiro[2.6]nonan-5-yl)-1-methyl-1H-pyrazol-4-yl)-2-(2,6-difluorophenyl)thiazole-4-carboxamide;

5-amino-N-(5-(4-(aminomethyl)-4-fluoroazepan-1-yl)-1-methyl-1H-pyrazol-4-yl)-2-(2,6-difluorophenyl)thiazole-4-carboxamide;

5-amino-N-(5-(4-(aminomethyl)-4-fluoroazepan-1-yl)-1-methyl-1H-pyrazol-4-yl)-2-(2,6-difluorophenyl)thiazole-4-carboxamide;

5-amino-N-(5-(4-(aminomethyl)-4-methoxyazepan-1-yl)-1-methyl-1H-pyrazol-4-yl)-2-(2,6-difluorophenyl)thiazole-4-carboxamide;

5-amino-N-(5-(4-(aminomethyl)-4-methoxyazepan-1-yl)-1-methyl-1H-pyrazol-4-yl)-2-(2,6-difluorophenyl)thiazole-4-carboxamide;

(S)-5-amino-N-(5-(5-amino-3,3-difluoro-5-methylazepan-1-yl)-1-methyl-1H-pyrazol-4-yl)-2-(2,6-difluorophenyl)thiazole-4-carboxamide;

5-amino-N-(5-(4-amino-5-(difluoromethoxy)azepan-1-yl)-1-methyl-1H-pyrazol-4-yl)-2-(2-fluorophenyl)thiazole-4-carboxamide;

5-amino-N-(5-(4-amino-5-methoxy-4-methylazepan-1-yl)-1-methyl-1H-pyrazol-4-yl)-2-(2,6-difluorophenyl)thiazole-4-carboxamide; and 5-amino-N-(5-(4-amino-5-(difluoromethoxy)azepan-1-yl)-1-methyl-1H-pyrazol-4-yl)-2-(2-fluorophenyl)thiazole-4-carboxamide.

3. A pharmaceutical composition comprised of a compound of claim 1 or 2, and a pharmaceutically acceptable carrier, glidant, diluent, or excipient.

4. The pharmaceutical composition according to claim 3, further comprising a chemotherapeutic agent.

5. The pharmaceutical composition of claim 3 for use in treating a disease or disorder selected from cancer, immune disorders, cardiovascular disease, viral infection, inflammation, metabolism/endocrine function disorders and neurological disorders, and mediated by Pim kinase.

6. A kit for treating a condition mediated by Pim kinase, comprising:

a) a pharmaceutical composition of claim 3; and b) instructions for use.

7. A compound selected from 5-amino-N-(5-((4R,5R)-4-amino-5-fluoroazepan-1-yl)-1-methyl-1H-pyrazol-4-yl)-2-(2,6-difluorophenyl)thiazole-4-carboxamide;

5-amino-N-(5-((4S,5S)-4-amino-5-fluoroazepan-1-yl)-1-methyl-1H-pyrazol-4-yl)-2-(2,6-difluorophenyl)thiazole-4-carboxamide;

5-amino-N-(5-((4S,5S)-4-amino-5-methoxyazepan-1-yl)-1-ethyl-1H-pyrazol-4-yl)-2-(2,6-difluorophenyl)thiazole-4-carboxamide; and 5-amino-N-(5-((4S,5S)-4-amino-5-methoxyazepan-1-yl)-1-cyclopropyl-1H-pyrazol-4-yl)-2-(2,6-difluorophenyl)thiazole-4-carboxamide.

8. A compound selected from 5-amino-N-(5-((3S,5S)-5-amino-3-fluoroazepan-1-yl)-1-methyl-1H-pyrazol-4-yl)-2-(2,6-difluorophenyl)thiazole-4-carboxamide;

5-amino-N-(5-((3R,5S)-5-amino-3-fluoroazepan-1-yl)-1-methyl-1H-pyrazol-4-yl)-2-(2,6-difluorophenyl)thiazole-4-carboxamide;

5-amino-N-(5-((3S,4S)-4-amino-3-fluoroazepan-1-yl)-1-methyl-1H-pyrazol-4-yl)-2-(2,6-difluorophenyl)thiazole-4-carboxamide; and (R)-5-amino-N-(5-(4-aminoazepan-1-yl)-1-(2,2-difluoroethyl)-1H-pyrazol-4-yl)-2-(2,5-difluorophenyl)thiazole-4-carboxamide.

* * * * *